US011111505B2

(12) United States Patent
Frost et al.

(10) Patent No.: US 11,111,505 B2
(45) Date of Patent: Sep. 7, 2021

(54) METHODS AND COMPOSITIONS FOR TRANSDUCING LYMPHOCYTES AND REGULATING THE ACTIVITY THEREOF

(71) Applicant: Exuma Biotech Corp., West Palm Beach, FL (US)

(72) Inventors: Gregory Ian Frost, West Palm Beach, FL (US); James Joseph Onuffer, Alameda, CA (US); Ghiabe H. Guibinga, San Diego, CA (US); Farzad Haerizadeh, San Diego, CA (US); Anirban Kundu, West-Bay (KY)

(73) Assignee: EXUMA BIOTECH, CORP., West Palm Beach, FL (US)

( * ) Notice: Subject to any disclaimer, the term of this patent is extended or adjusted under 35 U.S.C. 154(b) by 546 days.

(21) Appl. No.: 15/644,778

(22) Filed: Jul. 8, 2017

(65) Prior Publication Data
US 2017/0356010 A1    Dec. 14, 2017

Related U.S. Application Data

(63) Continuation-in-part of application No. PCT/US2017/023112, filed on Mar. 19, 2017, and a
(Continued)

(51) Int. Cl.
| | |
|---|---|
| C12N 15/867 | (2006.01) |
| C12N 15/113 | (2010.01) |
| C12N 15/33 | (2006.01) |
| C12N 15/48 | (2006.01) |
| C07K 16/28 | (2006.01) |
| C12N 15/87 | (2006.01) |
| A61K 35/17 | (2015.01) |
| A61K 48/00 | (2006.01) |
| C12N 15/86 | (2006.01) |
| C07K 14/725 | (2006.01) |
| C07K 14/705 | (2006.01) |
| C07K 16/30 | (2006.01) |
| A61K 39/00 | (2006.01) |
| C07K 14/715 | (2006.01) |
| C07K 14/005 | (2006.01) |

(52) U.S. Cl.
CPC .......... *C12N 15/86* (2013.01); *A61K 39/0011* (2013.01); *C07K 14/005* (2013.01); *C07K 14/7051* (2013.01); *C07K 14/70517* (2013.01); *C07K 14/70521* (2013.01); *C07K 14/70596* (2013.01); *C07K 14/7155* (2013.01); *C07K 16/2803* (2013.01); *C07K 16/30* (2013.01); *C12N 15/113* (2013.01); *C12N 15/1138* (2013.01); *A61K 35/17* (2013.01); *A61K 2039/5158* (2013.01); *A61K 2039/572* (2013.01); *C07K 2319/31* (2013.01); *C07K 2319/32* (2013.01); *C07K 2319/33* (2013.01); *C12N 2310/12* (2013.01); *C12N 2310/16* (2013.01); *C12N 2310/531* (2013.01); *C12N 2510/00* (2013.01); *C12N 2740/10052* (2013.01); *C12N 2740/16043* (2013.01); *C12N 2740/16052* (2013.01); *C12N 2760/18422* (2013.01); *C12N 2800/30* (2013.01); *C12N 2830/008* (2013.01); *C12N 2840/203* (2013.01)

(58) Field of Classification Search
None
See application file for complete search history.

(56) References Cited

U.S. PATENT DOCUMENTS

| | | | |
|---|---|---|---|
| 5,677,425 A | 10/1997 | Bodmer et al. | |
| 8,709,755 B2 | 4/2014 | Short et al. | |

(Continued)

FOREIGN PATENT DOCUMENTS

| | | |
|---|---|---|
| EP | 2019144 A1 | 1/2009 |
| WO | 9303769 A1 | 3/1993 |

(Continued)

OTHER PUBLICATIONS

Frecha et al, Stable transduction of quiescent T cells without induction of cycle progression by a novel lentiviral vector pseudotyped with measles virus glycoproteins, BLOOD, Dec. 15, 2008, vol. 112, No. 13, pp. 4843-4852.*

Blo et al, Enhanced gene expression from retroviral vectors, BMC Biotechnology 2008, 8:19, pp. 1-6.*

Biosettia et al., Lentiviral miRNA Expression pLV-miRNA Expression Vector System , May 2011, pp. 1-14.*

Kloss et al., Combinatorial antigen recognition with balanced signaling promotes selective tumor eradication by engineered T cells, Nature Biotechnology, 2013, pp. 71-76.*

(Continued)

*Primary Examiner* — Maria Marvich
(74) *Attorney, Agent, or Firm* — Double Helix Law; Emanuel Vacchiano; Michael Mand

(57) ABSTRACT

The present disclosure provides methods for genetically modifying lymphocytes and methods for performing adoptive cellular therapy that include transducing T cells and/or NK cells. The methods can include inhibitory RNA molecule(s) and/or engineered signaling polypeptides that can include a lymphoproliferative element, and/or a chimeric antigen receptor (CAR), for example a microenvironment restricted biologic CAR (MRB-CAR). Additional elements of such engineered signaling polypeptides are provided herein, such as those that drive proliferation and regulatory elements therefor, as well as replication incompetent recombinant retroviral particles and packaging cell lines and methods of making the same. Numerous elements and methods for regulating transduced and/or genetically modified T cells and/or NK cells are provided, such as, for example, those including riboswitches, MRB-CARs, recognition domains, and/or pH-modulating agents.

21 Claims, 35 Drawing Sheets
Specification includes a Sequence Listing.

Related U.S. Application Data continuation-in-part of application No. 15/462,855, filed on Mar. 19, 2017, now Pat. No. 10,596,274.

(60) Provisional application No. 62/360,041, filed on Jul. 8, 2016, provisional application No. 62/467,039, filed on Mar. 3, 2017, provisional application No. 62/390,093, filed on Mar. 19, 2016.

(56) References Cited

U.S. PATENT DOCUMENTS

| | | |
|---|---|---|
| 2004/0131637 A1 | 7/2004 | Chatfield |
| 2008/0269258 A1 | 10/2008 | Breaker et al. |
| 2017/0166877 A1 | 6/2017 | Bayle et al. |
| 2017/0246278 A1 | 8/2017 | Valdes et al. |
| 2017/0335281 A1 | 11/2017 | Loew et al. |
| 2018/0057794 A1 | 3/2018 | Rubinstein et al. |

FOREIGN PATENT DOCUMENTS

| | | | |
|---|---|---|---|
| WO | 9309239 | A1 | 5/1993 |
| WO | 9319191 | A1 | 9/1993 |
| WO | 9412649 | A2 | 9/1994 |
| WO | 9428938 | A1 | 12/1994 |
| WO | 9500655 | A1 | 1/1995 |
| WO | 9511984 | A2 | 5/1995 |
| WO | 9523846 | A1 | 9/1995 |
| WO | 9617951 | A2 | 6/1996 |
| WO | 0218609 | A2 | 3/2002 |
| WO | 2004073641 | A2 | 9/2004 |
| WO | 2006007539 | A1 | 1/2006 |
| WO | 2006055351 | A2 | 5/2006 |
| WO | 2008156987 | A2 | 12/2008 |
| WO | 2011059836 | A2 | 5/2011 |
| WO | 2012138858 | A1 | 10/2012 |
| WO | 2012153142 | A2 | 11/2012 |
| WO | 2013045639 | A1 | 4/2013 |
| WO | 2013127964 | A1 | 9/2013 |
| WO | 2013166051 | A1 | 11/2013 |
| WO | 2014011984 | A1 | 1/2014 |
| WO | 2014130657 | A1 | 8/2014 |
| WO | 2014151960 | A2 | 9/2014 |
| WO | 2014186469 | A2 | 11/2014 |
| WO | 2015075195 | A1 | 5/2015 |
| WO | 2016030691 | A1 | 3/2016 |
| WO | 2016033331 | A1 | 3/2016 |
| WO | 2016118857 | A1 | 7/2016 |
| WO | 2016139463 | A1 | 9/2016 |
| WO | 2017011804 | A8 | 1/2017 |
| WO | 2017034615 | A2 | 3/2017 |
| WO | 2017103596 | A1 | 6/2017 |
| WO | 2017165245 | A2 | 9/2017 |
| WO | 2017165245 | A3 | 9/2017 |
| WO | 2018009923 | A1 | 1/2018 |
| WO | 2018033726 | A1 | 2/2018 |
| WO | 2018136570 | A9 | 7/2018 |
| WO | 2018161064 | A1 | 9/2018 |
| WO | 2018175476 | A1 | 9/2018 |
| WO | 2019055946 | A1 | 3/2019 |
| WO | 2019157130 | A1 | 8/2019 |
| WO | 2019169290 | A1 | 9/2019 |
| WO | 2020047527 | A3 | 3/2020 |

OTHER PUBLICATIONS

Geron, The role of TSLP pathway in the development of B-Cell Acute Lymphoblastic Leukemia, Thesis at University of California, 2016, pp. 1-144.*
Keung et al, General Strategy for Decoration of Enveloped Viruses with Functionally Active Lipid-Modified Cytokines, Journal of Virology, Aug. 2007, p. 8666-8676.*
Liu et al, Fc Engineering for Developing Therapeutic Bispecific Antibodies and Novel Scaffolds, Frontiers in Immunology, 2017, pp. 1-15.*

O'Neill LS et al: "Entry kinetics and cell-cell transmission of surface-bound retroviral vector particles", Journal of Gene Medicine, 12(5):463-476, May 2010.
Papapetrou EP et al: "Harnessing endogenous miR-181a to segregate transgenic antigen receptor expression in developing versus post-thymic T cells in murine hematopoietic chimeras", Journal of Clinical Investigation, 119 (1):157-168, Dec. 1, 2008.
Park JW et al: "Immobilization-free screening of aptamers assisted by graphene oxide", Chem. Commun., 48 (15):2071-2073, Dec. 5, 2011.
Pikovskaya O et al: "Structural principles of nucleoside selectivity in a 2'-deoxyguanosine riboswitch", Nature chemical biology, 7(10):748, Aug. 14, 2011.
Poling BC et al: "A lentiviral vector bearing a reverse intron demonstrates superior expression of both proteins and microRNAs", RNA Biology, 14(11):1570-1579, Jul. 21, 2017.
Pulkkinen WS et al: "A *Salmonella typhimurium* virulence protein is similar to a Yersinia enterocolitica invasion protein and a bacteriophage lambda outer membrane protein", Journal of Bacteriology, 173(1):86-93, Jan. 1991.
Reid CA et al: "Development of an inducible anti-VEGF rAAV gene therapy strategy for the treatment of wet AMD", Scientific reports, 8(1):11763, Aug. 6, 2018.
Rolling F et al: "Evaluation of Adeno-Associated Virus-Mediated Gene Transfer into the Rat Retina by Clinical Fluorescence Photography", Human Gene Therapy, 10(4):641-648, Mar. 1999.
Salmon P et al: "Characterization of the human CD4 gene promoter: transcription from the CD4 gene core promoter is tissue-specific and is activated by Ets proteins", Proceedings of the National Academy of Sciences, 90 (16):7739-7743, Aug. 15, 1993.
Samulski RJ et al: "Helper-free stocks of recombinant adeno-associated viruses: normal integration does not require Viral gene expression", Journal of Virology, 63(9):3822-3828, 1989.
Schütze T et al: "Probing the SELEX Process with Next-Generation Sequencing", PLoS ONE, 6(12):e29604, Dec. 29, 2011.
Shaner NC et al: "A guide to choosing fluorescent proteins", Nature Methods, 2(12):905-909, Dec. 2005.
Sharma S et al: "Efficient infection of a human T-cell line and of human primary peripheral blood leukocytes with a pseudotyped retrovirus vector", Proceedings National Academy of Sciences, vol. 93, No. 21, Jan. 1, 1996, pp. 11842-11847.
Shetron-Rama LM et al: "Intracellular Induction of Listeria monocytogenes actA Expression", Infection and Immunity, 70(3):1087-1096, Mar. 2002.
Shochat C et al: "Gain-of-function mutations in interleukin-7 receptor-? (IL7R) in childhood acute lymphoblastic leukemias", Journal of Experimental Medicine, 208(5):901-908, May 2, 2011.
Shochat C et al: "Novel activating mutations lacking cysteine in type I cytokine receptors in acute lymphoblastic leukemia", Blood, 124(1):106-110, May 1, 2014.
Shum T et al: "Constitutive Signaling from an Engineered IL7 Receptor Promotes Durable Tumor Elimination by Tumor-Redirected T Cells", Cancer Discovery, 7(11):1238-1247, Aug. 22, 2017.
Staerk J et al: "Orientation-specific signalling by thrombopoietin receptor dimers: Orientation-specific TpoR signalling", EMBO Journal, 30(21):4398-4413, Sep. 2, 2011.
Strebel K et al: "Human cellular restriction factors that target HIV-1 replication", BMC Medicine, 7:48, Dec. 2009.
Sun J et al: "The quest for spatio-temporal control of CAR T cells", Cell Research, 25(12):1281-1282, Nov. 17, 2015.
Takahashi M et al: "Rescue from Photoreceptor Degeneration in therd Mouse by Human Immunodeficiency Virus Vector-Mediated Gene Transfer", Journal of Virology, 73(9):7812-7816, Sep. 1, 1999.
Till et al: "CD20-specific adoptive immunotherapy for lymphoma using a chimeric antigen receptor with both CD28 and 4-1 BB domains: pilot clinical trial results", Blood, Apr. 25, 2012, vol. 119, No. 17, pp. 3940-3950.
Tone Y et al: "Cell fate conversion by conditionally switching the signal-transducing domain of signalobodies: Cell Fate Conversion by Signalobodies", Biotechnology and Bioengineering, 110(12):3219-3226, Dec. 2013.

(56) References Cited

OTHER PUBLICATIONS

Townshend B et al: "High-throughput cellular RNA device engineering", Nature methods, 12(10):989-994, Aug. 10, 2015.
Unutmaz D et al: "Cytokine Signals Are Sufficient for HIV-1 Infection of Resting Human T Lymphocytes", Journal of Experimental Medicine, 189(11):1735-1746, Jun. 7, 1999.
Valdivia RH et al: "Bacterial genetics by flow cytometry: rapid isolation of *Salmonella typhimurium* acid-inducible promoters by differential fluorescence induction", Molecular Microbiology, 22(2):367-378, Oct. 1996.
Verhoeyen E et al: "Lentiviral vector gene transfer into human T cells", Antibody-Drug Conjugates in: Methods in Molecular Biology , vol. 1045, Jan. 1, 2009, pp. 97-114.
Vigant F et al: "Same day transduction and in vivo expansion of chimeric antigen receptors and synthetic driver constructs for adoptive cellular therapy", Cancer research: Proceedings: AACR Annual Meeting 2019, Mar. 29-Apr. 3, 2019.
Vu MM et al.: "Convergent evolution of adenosine aptamers spanning bacterial, human, and random sequences revealed by structure-based bioinformatics and genomic SELEX", Chemistry & biology, 19(10):1247-1254, Oct. 25, 2012.
Walsh STR: "Structural insights into the common ?-chain family of cytokines and receptors from the interleukin-7 pathway", Immunological Reviews, 250(1):303-316, Nov. 2012.
Wang J et al: "Particle Display: A Quantitative Screening Method for Generating High-Affinity Aptamers*", Angewandte Chemie International Edition, 53(19):4796-4801, Mar. 18, 2014.
Wang X et al: "Phenotypic and Functional Attributes of Lentivirus-modified CD19-specific Human CD8+ Central Memory T Cells Manufactured at Clinical Scale:", Journal of Immunotherapy, 35(9):689-701, Nov. 2012.
Wang Y et al: "An IL-4/21 Inverted Cytokine Receptor Improving CAR-T Cell Potency in Immunosuppressive Solid-Tumor Microenvironment", Frontiers in Immunology, 10:1691, Jul. 19, 2019.
Welz R et al: "Ligand binding and gene control characteristics of tandem riboswitches in Bacillus anthracis", RNA, 13 (4):573-582, Feb. 16, 2007.
Wilkie S et al: "Selective Expansion of Chimeric Antigen Receptor-targeted T-cells with Potent Effector Function using Interleukin-4", Journal of Biological Chemistry, vol. 285, No. 33, Jun. 18, 2010, pp. 25538-25544.
Wu C-Y et al: "Remote control of therapeutic T cells through a small molecule-gated chimeric receptor", Science, 350 (6258):aab4077, Sep. 24, 2015.
Yan B et al: "Engineering Upper Hinge Improves Stability and Effector Function of a Human IgG1", Journal of Biological Chemistry, 287(8):5891-5897, Dec. 27, 2011.
Yang H et al: "Cell type-specific targeting with surface-engineered lentiviral vectors co-displaying OKT3 antibody and fusogenic molecule", Pharmaceutical Research, vol. 26, No. 6, Mar. 4, 2009, pp. 1432-1445.
Yang L et al: "Targeting lentiviral vectors to specific cell types in vivo", Proceedings of the National Academy of Sciences, 103(31):11479-11484, Jul. 24, 2006.
Yokoyama K et al: "In vivo leukemogenic potential of an interleukin 7 receptor ? chain mutant in hematopoietic stem and progenitor cells", Blood, 122(26):4259-4263, Oct. 30, 2013.
Yoon H et al: "An efficient strategy for cell-based antibody library selection using an integrated vector system", BMC Biotechnology, 12:62, Sep. 18, 2012.
Zapata G et al: "Engineering linear F(ab')2 fragments for efficient production in *Escherichia coli* and enhanced antiproliferative activity", "Protein Engineering, Design and Selection", 8(10): 1057-1062, Oct. 1995.
Zenatti PP et al: "Oncogenic IL7R gain-of-function mutations in childhood T-cell acute lymphoblastic leukemia", Nature Genetics, 43(10):932-939, Sep. 4, 2011.
Zeng S et al: "Exploration on the mechanism of DNA adsorption on graphene and graphene oxide via molecular simulations", Journal of Physics D: Applied Physics, 48(27):275402, Oct. 10, 2015.

Zhang X et al: "Tumor pH and Its Measurement", Journal of Nuclear Medicine, 51(8):1167-1170, Jul. 21, 2010.
Zhao Y et al: "Multiple Injections of Electroporated Autologous T Cells Expressing a Chimeric Antigen Receptor Mediate Regression of Human Disseminated Tumor", Cancer Research, 70(22):9053-9061, Nov. 15, 2010.
Zichel R et al: "Aptamers as a sensitive tool to detect subtle modifications in therapeutic proteins", PloS One, 7(2):e31948, Feb. 27, 2012.
Zuker M: "Mfold web server for nucleic acid folding and hybridization prediction", Nucleic Acids Research, 31(13):3406-3415, Jul. 1, 2003.
Adachi K et al.: "IL-7 and CCL19 expression in CAR-T cells improves immune cell infiltration and CAR-T cell survival in the tumor", Nature Biotechnology, 36(4):346-351, Mar. 5, 2018.
Ahn H-J et al: "Requirement for Distinct Janus Kinases and STAT Proteins in T Cell Proliferation Versus IFN-gamma Production Following IL-12 Stimulation", Journal of Immunology, 161(11):5893-5900, Dec. 1, 1998.
Ali RR et al: "Adeno-Associated Virus Gene Transfer to Mouse Retina", Human Gene Therapy, 9(1):81-86, Jan. 1, 1998.
Alpuche Aranda CM et al: "*Salmonella typhimurium* activates virulence gene transcription within acidified macrophage phagosomes", Proceedings of the National Academy of Sciences, 89(21):10079-10083, Nov. 1, 1992.
Anthony PC et al: "Folding energy landscape of the thiamine pyrophosphate riboswitch aptamer", Proceedings of the National Academy of Sciences, 109(5):1485-1489, Jan. 4, 2012.
Armstrong AJ et al: "ATP-Binding Cassette Transporter G1 Negatively Regulates Thymocyte and Peripheral Lymphocyte Proliferation", Journal of Immunology, 184(1):173-183, Jan. 1, 2010.
Beisel CL et al: "Design of small molecule-responsive microRNAs based on structural requirements for Drosha processing", Nucleic acids research, 39(7):2981-2994, Dec. 11, 2010.
Bennett J et al: "Real-time, noninvasive in vivo assessment of adeno-associated virus-mediated retinal transduction", Investigative Ophthalmology & Visual Science, 38(13):2857-2863, Dec. 1, 1997.
Berens C et al: "RNA aptamers as genetic control devices: The potential of riboswitches as synthetic elements for regulating gene expression", Biotechnology Journal, 10(2):246-257, Feb. 10, 2015.
Borrás T et al: "Adenoviral reporter gene transfer to the human trabecular meshwork does not alter aqueous humor outflow. Relevance for potential gene therapy of glaucoma", Gene Therapy, 6(4):515-524, Apr. 7, 1999.
Brown RJ et al: "Model for growth hormone receptor activation based on subunit rotation within a receptor dimer", Nature Structural & Molecular Biology, 12(9):814-821, Aug. 21, 2005.
Budde LE et al: "Combining a CD20 chimeric antigen receptor and an inducible caspase 9 suicide switch to improve the efficacy and safety of T cell adoptive immunotherapy for lymphoma", PLOS One, vol. 8, No. 12, Dec. 17, 2013, e82742, pp. 1-10.
Burns JC et al: "Vesicular Stomatitis Virus G glycoprotein pseudotyped retroviral vectors: concentration to very high titer and efficient gene transfer into mammalian and nonmammalian cells", Proceedings National Academy of Sciences, vol. 90, Sep. 1, 1993, pp. 8033-8037.
Burton DR: "Immunoglobulin G: Functional sites", Molecular Immunology, 22(3):161-206, Mar. 1, 1985.
Carneiro M et al: "Co-expression of chimeric antigen receptor (CAR) and miRNAs to T cell therapy", European Journal of Cancer, 50(5):S219, 2014.
Chen YY et al: "Genetic control of mammalian T-cell proliferation with synthetic RNA regulatory systems", Proceedings of the National Academy of Sciences, 107(19):8531-8536, Apr. 26, 2010.
Chinnasamy D et al: "Lentiviral-mediated gene transfer into human lymphocytes: role of HIV-1 accessory proteins", Blood, 96(4):1309-1316, Aug. 15, 2000.
Chmielewski M et al: "Of CARs and TRUCKs: chimeric antigen receptor (CAR) T cells engineered with an inducible cytokine to modulate the tumor stroma", Immunological Reviews, 257(1):83-90, Jan. 2014.
Colby DW et al: "Engineering Antibody Affinity by Yeast Surface Display", Methods in Enzymology, 388:348-358, 2004.

(56) References Cited

OTHER PUBLICATIONS

Cooper LJN et al: "T-cell clones can be rendered specific for CD19: toward the selective augmentation of the graft-versus-B-lineage leukemia effect", Blood, 101(4):1637-1644, Feb. 15, 2003.

Cruz CR et al: "Adverse events following infusion of T cells for adoptive immunotherapy: a 10-year experience", Cytotherapy, 12(6):743-749, Oct. 2010.

Dambach MD et al: "Expanding roles for metabolite-sensing regulatory RNAs", Current opinion in microbiology, 12(2):161-169, Feb. 26, 2009.

Desai SK et al: "Genetic Screens and Selections for Small Molecules Based on a Synthetic Riboswitch That Activates Protein Translation", Journal of the American Chemical Society, 126(41):13247-13254, Oct. 20, 2004.

Dunstan SJ et al: "Use of In Vivo-Regulated Promoters To Deliver Antigens from Attenuated *Salmonella enterica* var. Typhimurium", Infection and Immunity, 67(10):5133-5141, Oct. 1, 1999.

Durand S et al: "Tailored HIV-1 Vectors for Genetic Modification of Primary Human Dendritic Cells and Monocytes", Journal of Virology, 87(1):234-242, Oct. 17, 2012.

Durum SK: "IL-7 and TSLP receptors: twisted sisters", Blood, 124(1):4-5, Jul. 3, 2014.

Eckelhart E et al: "A novel Ncr1-Cre mouse reveals the essential role of STAT5 for NK-cell survival and development", Blood, 117(5):1565-1573, Dec. 2, 2010.

Edwards A et al: "A structural basis for the recognition of 2'-deoxyguanosine by the purine riboswitch", Journal of molecular biology, 385(3):938-948, Nov. 5, 2008.

Fischer UM et al: "Pulmonary Passage is a Major Obstacle for Intravenous Stem Cell Delivery: The Pulmonary First-Pass Effect", Stem Cells and Development, 18(5):683-692, Jun. 2009.

Flannery JG et al: "Efficient photoreceptor-targeted gene expression in vivo by recombinant adeno-associated virus", Proceedings of the National Academy of Sciences, 94(13):6916-6921, Jun. 24, 1997.

Floss DM et al: "Naturally occurring and synthetic constitutive-active cytokine receptors in disease and therapy", Cytokine & Growth Factor Reviews, 47:1-20, Jun. 2019.

Flotte TR et al: "Stable in vivo expression of the cystic fibrosis transmembrane conductance regulator with an adeno-associated virus vector", Proceedings of the National Academy of Sciences, 90(22):10613-10617, Nov. 15, 1993.

Freitas AA et al: "Population Biology of Lymphocytes: The Flight for Survival", Annual Review of Immunology, 18(1):83-111, Apr. 2000.

Garst AD et al: "Riboswitches: structures and mechanisms", Cold Spring Harbor perspectives in biology, 3(6):a003533, Oct. 18, 2010.

Ghosh A et al: "CAR T-Cell Therapies: Current Limitations & Future Opportunities", Cell & Gene, Sep. 26, 2010.

Grindley NDF et al: "Mechanisms of Site-Specific Recombination", Annual Review of Biochemistry, 75:567-605, Jun. 2006.

Groher F et al: "Synthetic riboswitches—A tool comes of age", Biochimica et Biophysica Acta, 1839(10):964-973, May 17, 2014.

Harborne NR et al: "Transcriptional control, translation and function of the products of the five open reading frames of the *Escherichia coli* nir operon", Molecular Microbiology, 6(19):2805-2813, Oct. 1992.

Harris KA et al: "Biochemical analysis of pistol self-cleaving ribozymes", RNA, 21(11):1852-1858, Sep. 18, 2015.

Hinrichs CS and Rosenberg SA: "Exploiting the curative potential of adoptive T-cell therapy for cancer", Immunological Reviews, vol. 257, No. 1, Jan. 13, 2014, pp. 56-71.

Hoyos V et al: "Engineering CD19-specific T lymphocytes with interleukin-15 and a suicide gene to enhance their anti-lymphoma/leukemia effects and safety", Leukemia, 24(6):1160-1170, Apr. 29, 2010.

Hsieh C et al: "Development of TH1 CD4+ T cells through IL-12 produced by Listeria-induced macrophages", Science, 260(5107):547-549, Apr. 23, 1993.

Hunter MR et al: "Chimeric ?c cytokine receptors confer cytokine independent engraftment of human T lymphocytes", Molecular Immunology, 56(1-2):1-11, Nov. 2013.

Hurton LV et al: "Tethered IL-15 augments antitumor activity and promotes a stem-cell memory subset in tumor-specific T cells", Proceedings of the National Academy of Sciences, 113(48):E7788-E7797, Nov. 14, 2016.

Jensen MC: "Enhancing the IQ of CAR-modified T Cells", International Society & Gene Therapy abstract, Jun. 1, 2012.

Ji Y et al: "Enhancing adoptive T cell immunotherapy with microRNA therapeutics", Seminars in immunology, 28(1):45-53, Dec. 20, 2015.

Jomary C et al: "Rescue of photoreceptor function by AAV-mediated gene transfer in a mouse model of inherited retinal degeneration", Gene Therapy, 4(7):683-690, Jul. 1997.

Jones S et al: "Lentiviral Vector Design for Optimal T Cell Receptor Gene Expression in the Transduction of Peripheral Blood Lymphocytes and Tumor-Infiltrating Lymphocytes", Human Gene Therapy, 20(6):630-640, Jun. 2009.

Kagoya Y et al: "A novel chimeric antigen receptor containing a JAK-STAT signaling domain mediates superior antitumor effects", Nature Medicine, 24(3):352, Feb. 5, 2018.

Kaiser AD et al: "Towards a commercial process for the manufacture of genetically modified T cells for therapy", Cancer Gene Therapy, 22(2):72-78, Jan. 23, 2015.

Kim D-S et al: "An artificial riboswitch for controlling pre-mRNA splicing", RNA, 11(11):1667-1677, Nov. 1, 2005.

Kim DS et al: "Ligand-induced sequestering of branchpoint sequence allows conditional control of splicing", BMC molecular biology, 9(1):23, Feb. 12, 2008.

Kim JN et al: "Design and Antimicrobial Action of Purine Analogues That Bind Guanine Riboswitches", ACS Chemical Biology, 4(11):915-927, Nov. 20, 2009.

Kim JN et al: "Guanine riboswitch variants from Mesoplasma florum selectively recognize 2'-deoxyguanosine", Proceedings of the National Academy of Sciences, 104(41):16092-16097, Oct. 2, 2007.

Kim JN et al: "Purine sensing by riboswitches", Biology of the Cell, 100(1):1-11, Jan. 1, 2008.

Kimura MY et al: "IL-7 signaling must be intermittent, not continuous, during CD8+ T cell homeostasis to promote cell survival instead of cell death", Nature Immunology, 14(2):143-151, Dec. 16, 2012.

Klingemann H: "Are natural killer cells superior CAR drivers?", Oncoimmunology, 3:e28147, Apr. 15, 2014.

Kong S et al: "Suppression of human glioma xenografts with second-generation IL 13R-specific chimeric antigen receptor-modified T cells", Clinical Cancer Research, vol. 18, No. 21, Nov. 1, 2012, pp. 5949-5960.

Korin YD et al: "Progression to the G1b Phase of the Cell Cycle Is Required for Completion of Human Immunodeficiency Virus Type 1 Reverse Transcription in T Cells", Journal of Virology, 72(4):3161-3168, Apr. 1, 1998.

Krishnamurthy J et al: "Targeting an ancient retrovirus expressed in melanoma using adoptive T-cell therapy", Dissertation, Feb. 24, 2012, pp. 1-107.

Lamers CHJ et al: "Treatment of Metastatic Renal Cell Carcinoma With CAIX CAR-engineered T cells: Clinical Evaluation and Management of On-target Toxicity", Molecular Therapy, 21(4):904-912, Feb. 19, 2013.

Leen AM et al: "Reversal of Tumor Immune Inhibition Using a Chimeric Cytokine Receptor", Molecular Therapy: The Journal of The American Society of Gene Therapy, vol. 22, No. 6, Jun. 1, 2014, pp. 1211-1220.

Levay A et al: "Identifying high-affinity aptamer ligands with defined cross-reactivity using high-throughput guided systematic evolution of ligands by exponential enrichment", Nucleic Acids Research, 43(12):e82, May 24, 2015.

Li T et al: "In vivo transfer of a reporter gene to the retina mediated by an adenoviral vector", Investigative Ophthalmology & Visual Science, 35(5):2543-2549, Apr. 1994.

Li T et al: "Phenotype correction in retinal pigment epithelium in murine mucopolysaccharidosis VII by adenovirus-mediated gene

(56) References Cited

OTHER PUBLICATIONS transfer", Proceedings of the National Academy of Sciences, 92(17):7700-7704, Aug. 15, 1995.
Lienert F et al: "Synthetic biology in mammalian cells: next generation research tools and therapeutics", Nature reviews Molecular cell biology, 15(2):95, Jan. 17, 2014.
Lu X et al: "Active Conformation of the Erythropoietin Receptor: Random and Cysteine-Scanning Mutagenesis of the Extracellular Juxtamembrane and Transmembrane Domains", Journal of Biological Chemistry, 281(11):7002-7011, Jan. 12, 2006.
Mandal M et al: "Riboswitches control fundamental biochemical pathways in Bacillus subtilis and other bacteria", Cell, 113(5):577-586, May 29, 2003.
Marin V et al: "Comparison of Different Suicide-Gene Strategies for the Safety Improvement of Genetically Manipulated T Cells", Human Gene Therapy Methods, 23(6):376-386, Nov. 27, 2012.
Marodon G et al: "Specific transgene expression in human and mouse CD4+cells using lentiviral vectors with regulatory sequences from theCD4 gene", Blood, 101(9):3416-3423, Jan. 2, 2003.
Marrack P et al: "Homeostasis of ?? TCR+ T cells", Nature Immunology, 1(2):107-111, Aug. 2000.
Matyjasik MM et al: "Structural basis for 2'-deoxyguanosine recognition by the 2'-dG-11 class of riboswitches", Nucleic Acids Research, 47(20):10931-10941, Oct. 10, 2019.
Matz MV et al: "Fluorescent proteins from nonbioluminescent Anthozoa species", Nature Biotechnology, 17(10):969-973, Oct. 1999.
Maurice M et al: "Efficient gene transfer into human primary blood lymphocytes by surface-engineered lentiviral vectors that display a T cell-activating polypeptide", Blood, vol. 99, No. 7, Apr. 1, 2002, pp. 2342-2350.
McElroy CA et al: "Structural reorganization of the interleukin-7 signaling complex", Proceedings of the National Academy of Sciences, 109(7):2503-2508, Jan. 30, 2012.
McKelvie ND et al: "Expression of heterologous antigens in *Salmonella typhimurium* vaccine vectors using the in vivo-inducible, SPI-2 promoter, ssaG", Vaccine, 22(25-26):3243-3255, Sep. 3, 2004.
Melton DA et al: "Efficient in vitro synthesis of biologically active RNA and RNA hybridization probes from plasmids containing a bacteriophage SP6 promoter", Nucleic Acids Research, 12(18):7035-7056, Sep. 25, 1984.
Mendelson E et al: "Expression and rescue of a nonselected marker from an integrated AAV vector", Virology, 166(1):154-165, Sep. 1988.
Miller AD: "Human gene therapy comes of age", Nature, 357(6378):455-460, Jun. 11, 1992.
Miyoshi H et al: "Stable and efficient gene transfer into the retina using an HIV-based lentiviral vector", Proceedings of the National Academy of Sciences, 94(19):10319-10323, Sep. 16, 1997.
Morgan RA et al: "Case Report of a Serious Adverse Event Following the Administration of T Cells Transduced With a Chimeric Antigen Receptor Recognizing ERBB2", Molecular Therapy, 18(4):843-851, Feb. 23, 2010.
Muhlebach MD et al: "Transduction efficiency of MLV but not of HIV-1 vectors is pseudotype dependent on human primary T lymphocytes", Journal of Molecular Medicine, 81(12):801-810, Oct. 24, 2003.
Nam S et al: "Driving the next wave of innovation in CAR T-cell therapies", McKinsey & Company Pharmaceuticals & Medical Products, Dec. 13, 2019.
Ngo MC et al: "Ex vivo gene transfer for improved adoptive immunotherapy of cancer", Human Molecular Genetics, 20(R1):R93-R99, Mar. 17, 2011.
Nguyen V-T et al: "Multiple GO-SELEX for efficient screening of flexible aptamers", Chemical Communications, 50(72):10513-10516, Jul. 23, 2014.
O'Connor CM et al: "Adoptive T-cell therapy improves treatment of canine non-Hodgkin lymphoma post chemotherapy", Scientific Reports, vol. 2, Feb. 1, 2012.
Ogawa A: "Rational design of artificial riboswitches based on ligand-dependent modulation of internal ribosome entry in wheat germ extract and their applications as label-free biosensors", RNA, 17(3):478-488, Jan. 11, 2011.
Ohno M et al: "Expression of miR-17-92 enhances anti-tumor activity of T-cells transduced with the anti-EGFRvIII chimeric antigen receptor in mice bearing human GBM xenografts", Journal for Immunotherapy of Cancer, 1:21, Dec. 16, 2013.
Okamoto S et al: "A promising vector for TCR gene therapy: differential effect of siRNA, 2A peptide, and disulfide bond on the introduced TCR expression", Molecular Therapy—Nucleic Acids, 1(12):e63, Dec. 18, 2012.
Ali RR et al: "Gene transfer into the mouse retina mediated by an adeno-associated viral vector", Human Molecular Genetics, 5(5):591-594, May 1, 1996.
Cavalieri S et al: "Human T lymphocytes transduced by lentiviral vectors in the absence of TCR activation maintain an intact immune competence", Blood, 102(2):497-505, Mar. 20, 2003.
Chatfield SN et al: "Use of the nirB promoter to direct the stable expression of heterologous antigens in *Salmonella* oral vaccine strains: Development of a single-dose oral tetanus vaccine", Biotechnology (N Y), 10(8):888-892, 1992.
Fuhrmann-Benzakein E et al: "Inducible and irreversible control of gene expression using a single transgene", Nucleic Acids Research, 28(23):E99, Dec. 1, 2000.
Verhoeyen E et al: "IL-7 surface-engineered lentiviral vectors promote survival and efficient gene transfer in resting primary T lymphocytes", Blood, vol. 101, No. 6, Mar. 15, 2003, pp. 2167-2174.

\* cited by examiner

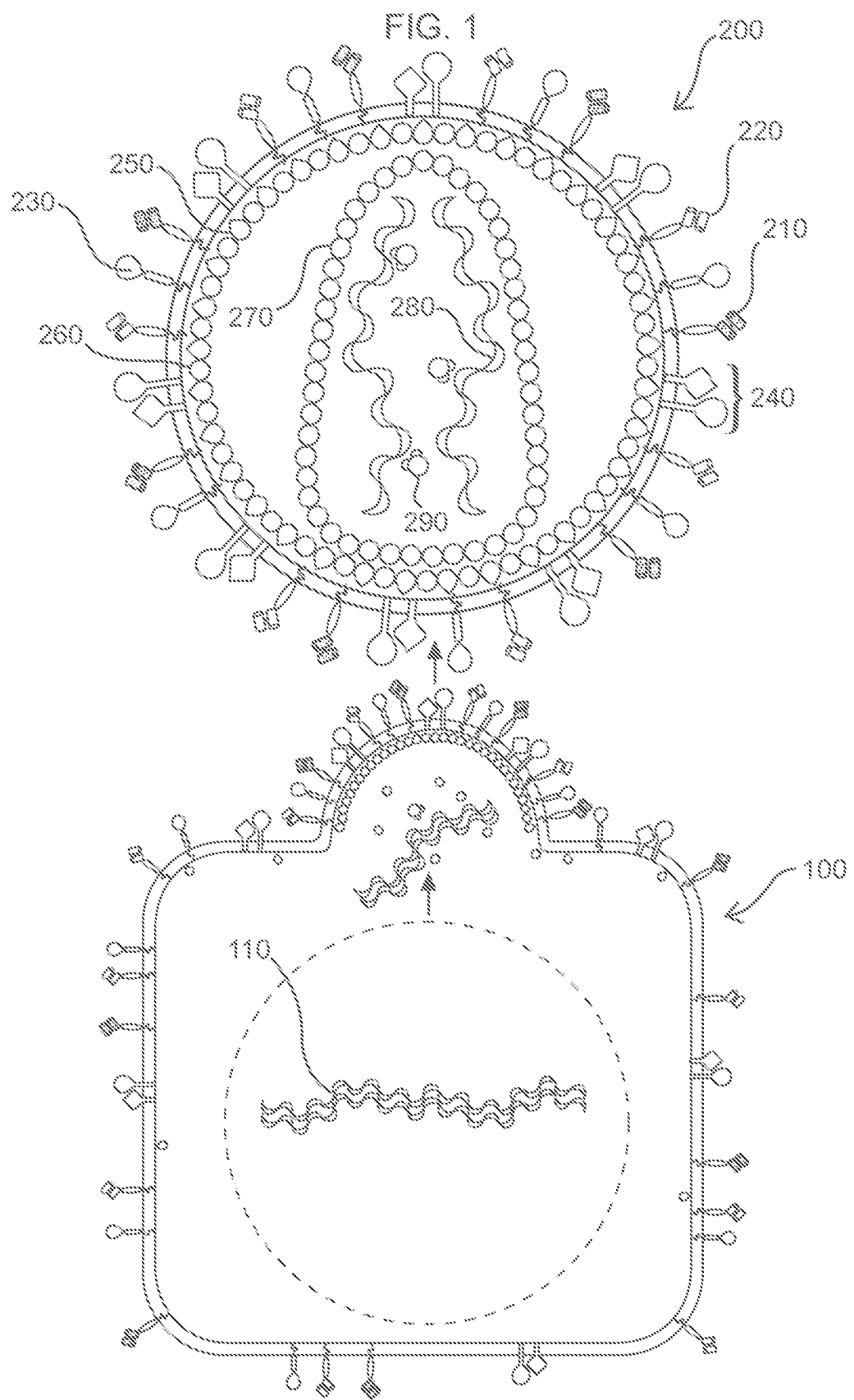

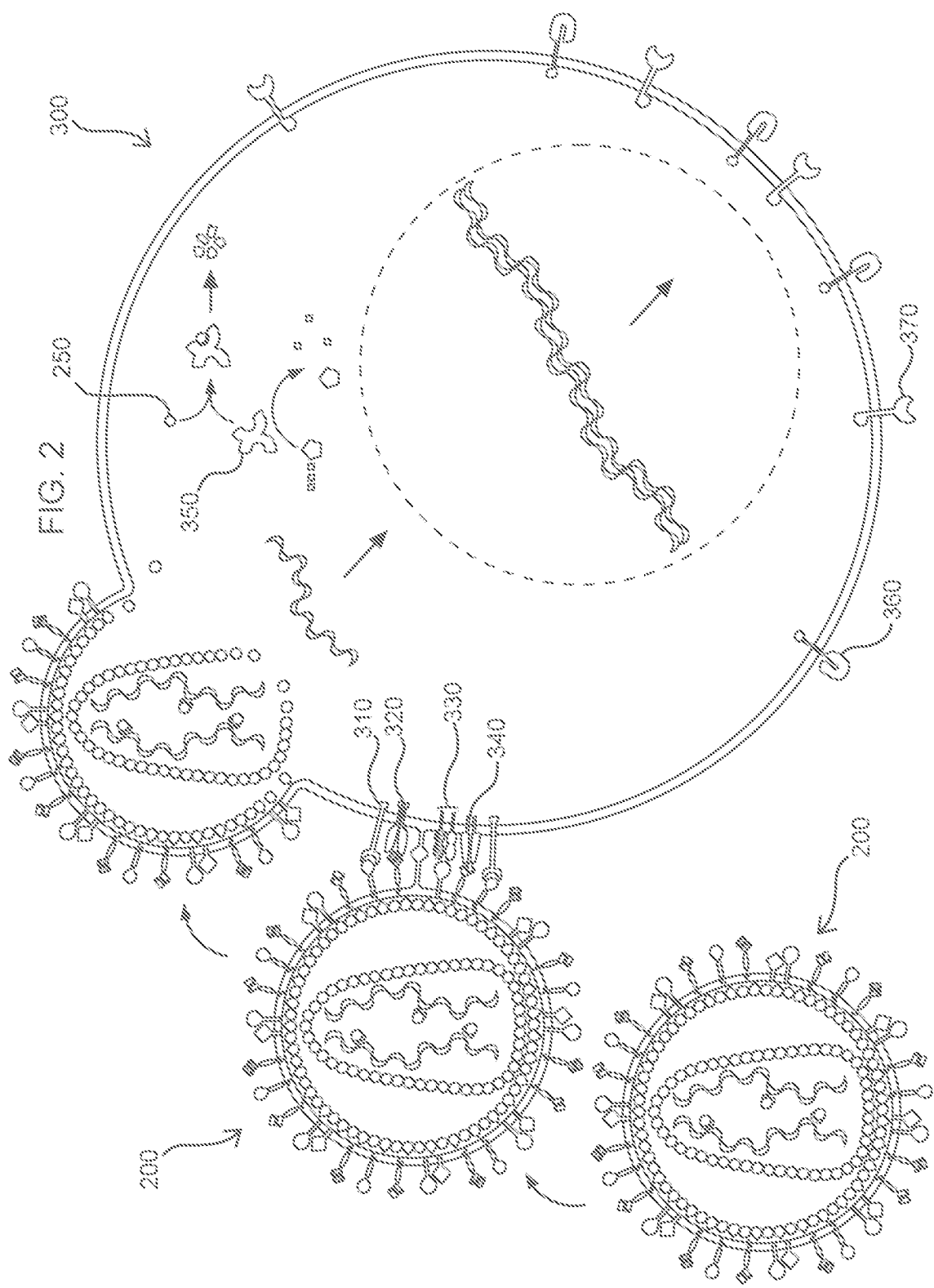

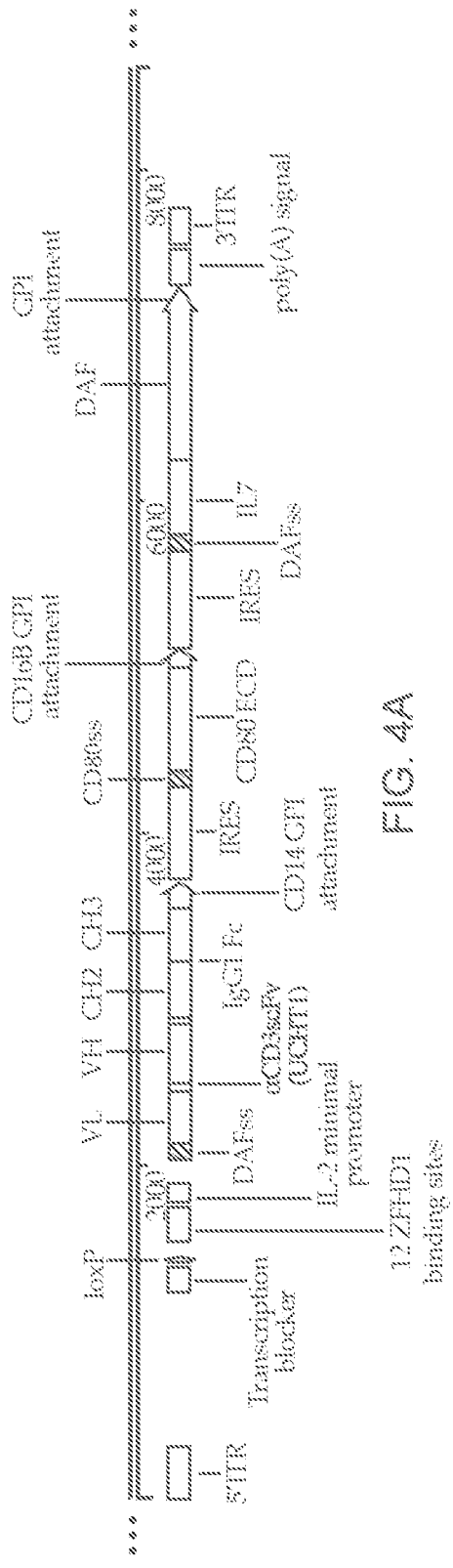
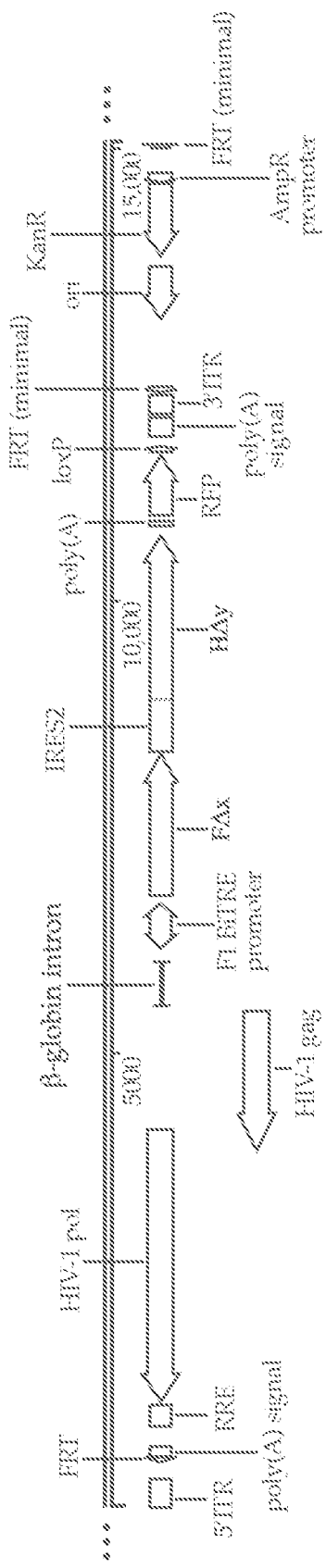
FIG. 4A
FIG. 4B

Acyclovir

Penciclovir

2'-Deoxyguanosine aaaaaaaataaaatcaatagcaaatattaagattttaagaaataaaaaattaatattaatttacaactgaatataaaagaagctta
tacagggtagcataatgggctactgaccccgccttcaaacctatttggagactataagtgaaaaaccactctttaattatta
aagtttcttttatgtccaaaagacaagaagaaacttttttatttagttgaatttataataagagaaaagaaaggatattatATGGC
AAAAATAAAAAACCAATATTACAACGAGTCTGTTTCGCCAATTGAATATGCGCAACAAGGATTTA
AAGGAAAAATGCGTTCAGTAAACTGAAACGTAGTAAATGATGAAAAAGATTTAGAGGTATGAAAT
AGAATTACACAAAACTTCTGATTGCCTGAAAAAATTCCAGTTTCAAATGATTTAACTTCATGAAGA
ACTTTGACACCAGAATGACAAGAATTAATTACAAGAACTTTTACAGGATTAACATTGTTAGATACA
ATTCAAGCTACTGTTGGTGATGTGGCTCAAGTTCCTAACTCATTAACTGACCATGAACAAGTAATT
TACACAAACTTTGCATTTATGGTTGCAGTTCACGCTAGATCATATGGTTCAATCTTTTCAACTTTAT
GTTCAAGTGAACAAATTGAAGAGGCTCATGAATGAGTTATCAATACAGAAACATTACAAGAAAGA
GCTAAAGCATTAATTCCTTATTATGTGAATGATGACCCTTTAAAGTCAAAAGTTGCAGCTGCTTTA
ATGCCAGGCTTCTTATTATATGGAGGCTTCTATTTACCATTTTACCTATCAGCTAGAGGTAAATTACC
AAACACTTCAGATATTATTAGATTAATATTAAGAGATAAAGTTATACATAACTACTATAGTGGTTATA
AATATCAAAAGAAAGTTGCTAAACTTTCTCCAGAAAAACAAGCTGAAATGAAAGAATTTGTTTTT
AAATTATTATATGAATTAATAGATTTAGAAAAAGCTTATTGAAAGAATTGTATGAGGATTTTGGATT
AGCTGATGATGCTATTAGATTTAGTGTTTACAACGCAGGTAAATTTTTACAAAAATTTAGGTTATGAT
TCACCGTTTACAGAAGAAGAAACAAGAATTGAGCCAGAAATATTCACACAATTATCAGCTAGAGC
TGATGAAAACCATGATTTCTTTTCAGGGAATGGCTCATCATATATTATGGGAGTTTCAGAAGAAAC
TGAAGATGACGATTGGGAGTTTaa (SEQ ID NO:236)

Oligo library for screen
CGCGCGACACTTATAGTCNNAAATAGGTTTNNNGGCNNNNNNNNNNCNNNAGCCCATTATGCTNNNNTGTATAAGTGCCGCC
(SEQ ID NO:239)

T7 promoter amplification primer
TAATACGACTCACTATAGGGCGGCCACTTATACA (SEQ ID NO:240)

Reverse amplification primer
CGCGCGACACTTATAGTC (SEQ ID NO:241)

tcaaaagcctggcggcgcggtcgtcagactctttatatcgaatcccttgaaatacgaatgatatctaaaaaaac
aaaattaaagttcgggaattttattttcagcctatgcaagagattagaatcttgatataattattacaatataatagg
aacactcatataatcgcgtggatatggcacgcaagtttctaccgggcaccgtaaatgtccgactatgggtg
agcaatggaaccgcacgtgtacggtttttgtgatatcagcattgcttgctctttatttgagcggcaatgctttttta
ttctcataacggaggtagacaggATGGAAGCACTGAAACGGAAAATAGAGGAAGAAGGCGTC
GTATTATCTGATCAGGTATTGAAAGTGGATTCTTTTTTGAATCACCAAATTGATCCGCTG
CTTATGCAGAGAATTGGTGATGAATTTGCGTCTAGGTTTGCAAAAGACGGTATTACCAA
AATTGTGACAATCGAATCATCAGGTATCGCTCCCGCTGTAATGACGGGCTTGAAGCTG
GGTGTGCCAGTTGTCTTCGCGAGAAAGCATAAATCGTTAACACTCACCGACAACTTGC
TGACAGCGTCTGTTTATTCCTTTACGAAGCAAACAGAAAGCCAAATCGCAGTGTCTGG
GACCCACCTGTCGGATCAGGATCATGTGCTGATTATCGATGATTTTTTGGCAAATGGAC
AGGCAGCGCACGGGCTTGTGTCGATTGTGAAGCAAGCGGGAGCTTCTATTGCGGGAA
TCGGCATTGTTATTGAAAAGTCATTTCAGCCGGGAAGAGATGAACTTGTAAAACTGGG
CTACCGAGTGGAATCTTTGGCAAGAATTCAGTCTTTAGAAGAAGGAAAAGTGTCCTTC
GTACAGGAGGTTCATTCAtga (SEQ ID NO:242)

FIG. 10

CACUCAUAUAUUCGUGAUAUGGCACCAAUUCUIACCGGUAAAUCCUACUAUGGGUG
J1-2    L2                J2-3           L3    J3-1

(SEQ ID NO: 243)

FIG. 12A

CACUCAUAUAUANNNCGUGAUAUGGCACGNNNGNNNNNNNACCNNNUACCGUAAAUGNNNGACUAUGGGUG
J1-2         L2                 J2-3              L3     J3-1

(SEQ ID NO: 244)

Oligo library for screen
CGCGGCGACCCACCCATAGTCWWCATTTACGGTGWWWWGGTWWWWWWWWWCWWCGTGCCATATCCACG
WWWWTATATGAGTGGCGCGCC (SEQ ID NO:245)

T7 promoter amplification primer
TAATACGACTCACTATAGGGCGGCCACTCATATA (SEQ ID NO:246)

Reverse amplification primer
CGCGGCGACCCACCCATAGTC (SEQ ID NO:247)

FIG. 17

| FLP-584 | FLP-710 | FLP-923 | FLP-941 | FLP-837 | FLP-718 | FLP-932 |
|---|---|---|---|---|---|---|
| ΔG = -24.10 kcal/mol | ΔG = -28.90 kcal/mol | ΔG = -23.00 kcal/mol | ΔG = -25.00 kcal/mol | ΔG = -23.70 kcal/mol | ΔG = -25.00 kcal/mol | ΔG = -27.70 kcal/mol |
| Sequence (5'->3'): GGG CGG CAC UAC UAC AGG GGA GCA UAA UGG GCU UUU GAC GCC UUU AAA CCU AUU UGA GGA CGA UAA GGC GCG CGC g | Sequence (5'->3'): GGG CGG CAC UUA UAC AUG GAA GCA UAA UGG GCU GCC GAC GGC CCU UAA CCU UGG GAG ACU AGA AGG GUC CG | Sequence (5'->3'): GGG CGG CAC UUA UAC AGA UUA GCA UAA UGG GCU ACU GAC CCC GCC GGG AAA CCU AUU UGA AGA UGG CGC g | Sequence (5'->3'): GGG CGG CAC UUA UAC AGU GUA GCA UAA UGG GCU ACU GAC GCA UCA AGC GGA UGA UUU UGA GAC UAU GCG g | Sequence (5'->3'): GGG CGG CAC UUA UAC AGU GAA GCA UAA UGG GCU ACU CAC ACC UCU AUU AAA CCU AUU UGC AGA CGA UAA GUC CG | Sequence (5'->3'): GGG CGG CAC UUA UAC AGU GUA GCA UAA UGG GCU ACA CAC GCC GCU AGU AAA CCU AUU UGC UGA CCA GUA GUG CGC g | Sequence (5'->3'): GGG CGG CAC UAC AGG UUA UAC AUG GUG CAU AAU GGG CUA CUG ACC CUA AAG GUA GCA AAG GUA GAG UGU CGC |
| (SEQ ID NO:94) | (SEQ ID NO:95) | (SEQ ID NO:96) | (SEQ ID NO:97) | (SEQ ID NO:98) | (SEQ ID NO:99) | (SEQ ID NO:100) |

FIG. 18

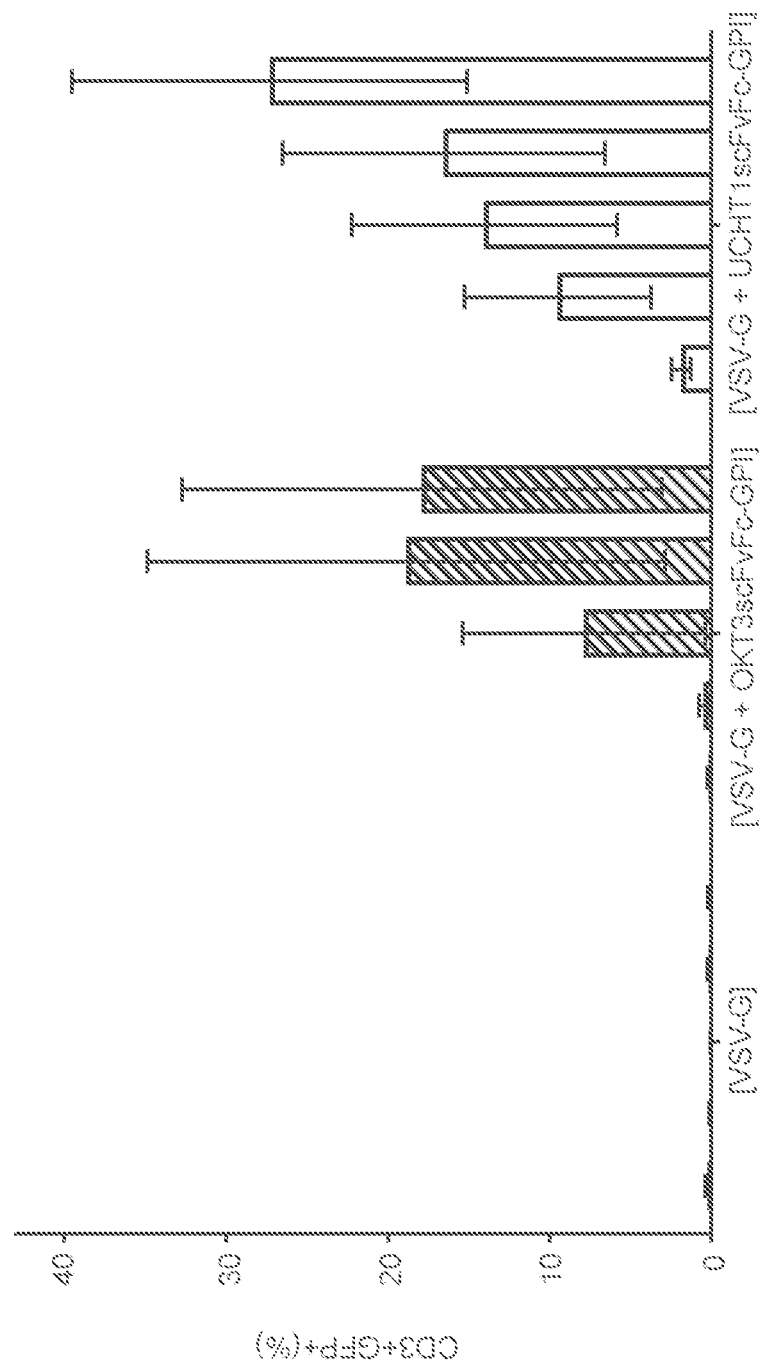

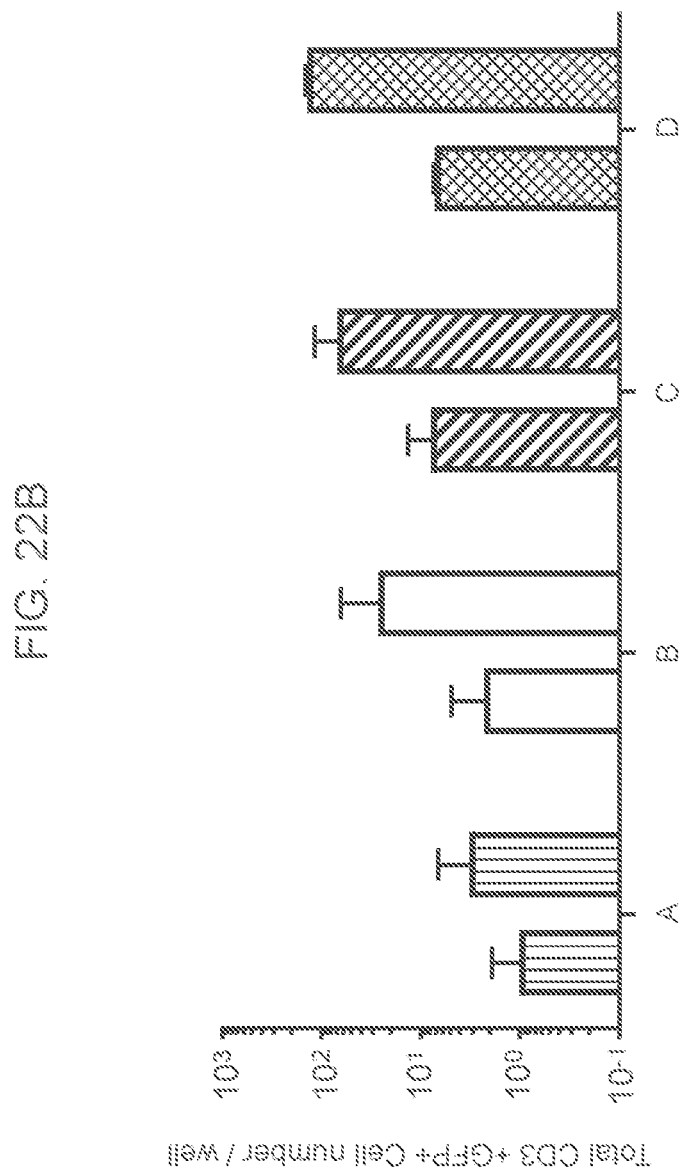

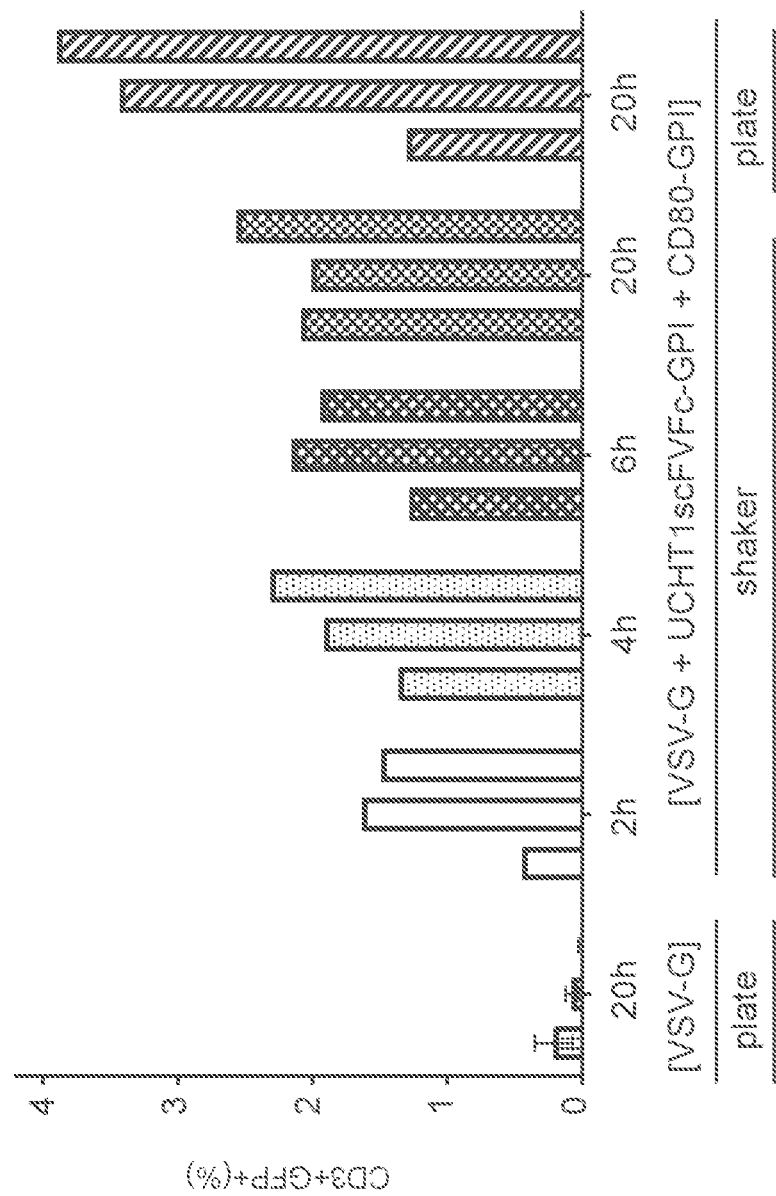

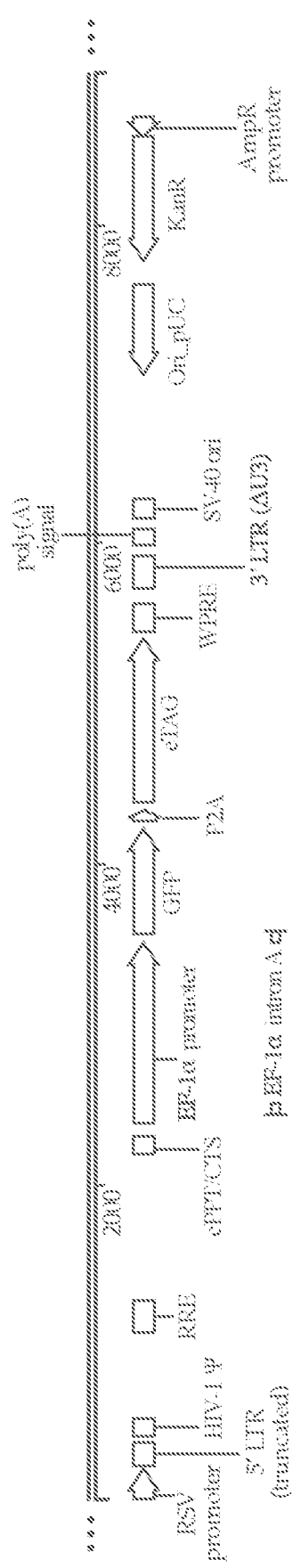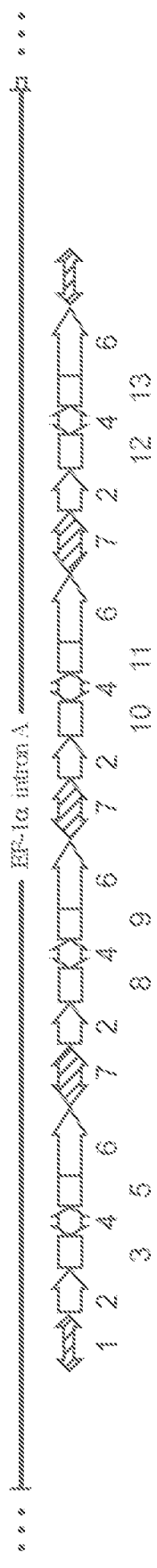
FIG. 24A
FIG. 24B

METHODS AND COMPOSITIONS FOR TRANSDUCING LYMPHOCYTES AND REGULATING THE ACTIVITY THEREOF

CROSS-REFERENCE TO RELATED APPLICATIONS

This application is a continuation-in-part of International Application No. PCT/US2017/023112, filed Mar. 19, 2017, and a continuation-in-part of U.S. patent application Ser. No. 15/462,855, filed Mar. 19, 2017, now U.S. Pat. No. 10,596,274, and claims the benefit of U.S. Provisional Application No. 62/360,041, filed Jul. 8, 2016, and U.S. Provisional Application No. 62/467,039, filed Mar. 3, 2017; International Application No. PCT/US2017/023112 claims the benefit of U.S. Provisional Application No. 62/390,093, filed Mar. 19, 2016, U.S. Provisional Application No. 62/360,041, filed Jul. 8, 2016, and U.S. Provisional Application No. 62/467,039, filed Mar. 3, 2017; U.S. application Ser. No. 15/462,855 claims the benefit of U.S. Provisional Application No. 62/390,093, filed Mar. 19, 2016, U.S. Provisional Application No. 62/360,041, filed Jul. 8, 2016, and U.S. Provisional Application No. 62/467,039, filed Mar. 3, 2017. These applications cited in this paragraph are incorporated by reference herein in their entirety.

SEQUENCE LISTING

This application hereby incorporates by reference the material of the electronic Sequencing Listing filed concurrently herewith. The materials in the electronic Sequence Listing is submitted as a text (.txt) file entitled "F1_001_US_02_Sequence_2017_07_08.txt" created on Jul. 8, 2017, which has a file size of 268 KB, and is herein incorporated by reference in its entirety.

FIELD OF INVENTION

This disclosure relates to the field of immunology, or more specifically, to the genetic modification of T lymphocytes or other immune cells, and methods of making replication incompetent recombinant retroviral particles and controlling the expression of genes therein.

BACKGROUND OF THE DISCLOSURE

Lymphocytes isolated from a subject (e.g. patient) can be activated in vitro and genetically modified to express synthetic proteins that enable redirected engagement with other cells and environments based upon the genetic programs incorporated. An example of such a synthetic protein is a chimeric antigen receptor (CAR). One CAR that is currently used is a fusion of an extracellular recognition domain (e.g., an antigen-binding domain), a transmembrane domain, and one or more intracellular signaling domains encoded by a replication incompetent recombinant retrovirus.

While recombinant retroviruses have shown efficacy in infecting non-dividing cells, resting CD4 and CD8 lymphocytes are refractory to genetic transduction by these vectors. To overcome this difficulty, these cells are typically activated in vitro using stimulation reagents before genetic modification with the CAR gene vector can occur. Following stimulation and transduction, the genetically modified cells are expanded in vitro and subsequently reintroduced into a lymphodepleted patient. Upon antigen engagement in vivo, the intracellular signaling portion of the CAR can initiate an activation-related response in an immune cell and release of cytolytic molecules to induce tumor cell death.

Such current methods require extensive manipulation and manufacturing of proliferating T cells outside the body prior to their reinfusion into the patient, as well as lymphodepleting chemotherapy to free cytokines and deplete competing receptors to facilitate T cell engraftment. Such CAR therapies further cannot be controlled for propagation rate in vivo once introduced into the body, nor safely directed towards targets that are also expressed outside the tumor. As a result, CAR therapies today are typically infused from cells expanded ex vivo from 12 to 28 days using doses from $1 \times 10^5$ to $1 \times 10^8$ cells/kg and are directed towards targets, for example tumor targets, for which off tumor on target toxicity is generally acceptable. These relatively long ex vivo expansion times create issues of cell viability and sterility, as well as sample identity in addition to challenges of scalability. Thus, there are significant needs for a safer, more effective scalable T cell or NK cell therapy.

SUMMARY

Provided herein are methods compositions and kits that help overcome issues related to the effectiveness and safety of methods for transducing and/or genetically modifying lymphocytes such as T cells and/or NK cells and for performing adoptive cell therapy with these cells. Accordingly, in some aspects, provided herein are methods, compositions, and kits for genetically modifying and/or transducing lymphocytes, especially T cell and/or NK cells, and/or for regulating the activity of transduced and/or genetically modified T cells and/or NK cells. Such methods, compositions, and kits provide improved efficacy and safety over current technologies, especially with respect to T cells and/or NK cells that express chimeric antigen receptors (CARs), and in illustrative embodiments microenvironment restricted biologic CARs. Transduced and/or genetically modified T cells and/or NK cells that are produced by and/or used in methods provided herein, include functionality and combinations of functionality, in illustrative embodiments delivered from retroviral (e.g. lentiviral) genomes via retroviral (e.g. lentiviral) particles, that provide improved features for such cells and for methods that utilize such cells, such as adoptive cellular therapy. For example, such cells can be produced in less time ex vivo, and that have improved growth properties that can be better regulated.

Provided herein in some aspects are regulatory elements for regulating the expression of CARs, mRNA, inhibitory RNA(s), and/or lymphoproliferative elements that are not inhibitory RNA(s) in lymphocytes such as T cells and NK cells. Furthermore, provided herein in some aspects are recombinant retroviruses that express various functional elements and that carry various functional elements on their surface, and methods and packaging cell lines for producing the recombinant retroviruses. These recombinant retroviruses and methods and cells for producing the same, overcome prior art limitations with respect to the number and size in a genome, of different functional elements that provide benefits when delivered into a T cell and/or NK cells.

In some aspects, methods are provided for transducing and/or genetically modifying lymphocytes such as T cells and/or NK cells, and in illustrative embodiments, ex vivo methods for transducing and/or genetically modifying resting T cells and/or NK cells. Some of these aspects can be performed much more quickly than previous methods, which can facilitate improved methods of patient care.

Furthermore, provided herein are methods that in some embodiments utilize recombinant retroviruses provided herein in some aspects along with pharmacologic agents, to provide improved safety mechanisms to help modulate the activity of transduced and/or genetically modified lymphocytes such as T cells and/or NK cells. Such methods, compositions, and kits can be used in adoptive cellular therapy with transduced and/or genetically modified T cells and/or NK cells expressing a CAR.

Further details regarding aspects and embodiments of the present disclosure are provided throughout this patent application. Sections and section headers are not intended to limit combinations of methods, compositions, and kits or functional elements therein.

BRIEF DESCRIPTION OF THE DRAWINGS

FIG. 1 shows a schematic of illustrative compositions including a packaging cell (100) and a replication incompetent recombinant retroviral particle (200) of one exemplary, non-limiting embodiment of the present disclosure, produced by the packaging cell (100). In FIG. 1, various vectors (referred to as recombinant polynucleotides (110)) capable of encoding aspects of the invention are packaged into a recombinant retroviral particle (200) that includes in its genome a first engineered signaling polypeptide that includes one or more lymphoproliferative elements and in some embodiments, a second engineered signaling polypeptide that is a chimeric antigen receptor, or a CAR. The replication incompetent recombinant retroviral particle expresses on its membrane, a pseudotyping element (in a non-limiting embodiment, a Measles Virus hemagglutinin (H) polypeptide and a Measles Virus fusion (F) polypeptide, or cytoplasmic domain deletion variants thereof) (240) that allows the replication incompetent recombinant retroviral particle to bind to and fuse with a target cell; an activation element (in non-limiting embodiments an activation element that has a polypeptide capable of binding to CD28 and a polypeptide capable of binding to CD3) (210 and 220, respectively) that is capable of binding to and activating a resting T cell; and a membrane-bound cytokine (in a non-limiting embodiment, an IL-7 DAF fusion polypeptide) (230). Parts labeled as (250), (260), (270), (280), and (290) are the Src-FLAG-Vpx, HIV gag matrix, HIV gag capsid, RNA, and HIV pol, respectively.

FIG. 2 shows a schematic of illustrative compositions including a replication incompetent recombinant retroviral particle (200), produced by a packaging cell (100) and a resting T cell (300) transfected by the replication incompetent recombinant retroviral particle (200). The elements on the surface of the replication incompetent recombinant retroviral particle (200), bind to receptors and/or ligands on the surface of a resting T cell. The pseudotyping element can include, in non-limiting embodiments, a binding polypeptide and a fusogenic polypeptide (in non-limiting embodiments, a Measles Virus hemagglutinin (H) polypeptide and a Measles Virus fusion (F) polypeptide, or cytoplasmic domain deletion variants thereof) that facilitate the binding and fusion of the replication incompetent recombinant retroviral particle (200), to the T cell. In non-limiting embodiments, the replication incompetent recombinant retroviral particle (200), includes on its surface an activation element (in non-limiting embodiments an activation element that has a polypeptide capable of binding to CD28 and a polypeptide capable of binding to CD3) that is capable of activating the resting T cell by engaging the T-cell receptor complex and optionally a co-receptor (320). Furthermore, membrane-bound cytokines (in non-limiting embodiments, an IL-7 DAF fusion polypeptide) present on the surface of the replication incompetent recombinant retroviral particle (200), bind to IL-7Rα (310) on the surface of the resting T cell. The replication incompetent recombinant retroviral particle (200), fuses with the T cell, and polynucleotides that encode the first engineered signaling polypeptide that includes the lymphoproliferative element (in illustrative embodiments, a constitutively active IL-7Rα) (370), are reverse transcribed in the cytosol prior to migrating to the nucleus to be incorporated into the DNA of the activated T cell. Not to be limited by theory, in some non-limiting embodiments, Src-FLAG-Vpx (250) packaged with the virus enters the cytosol of the resting T cells and promotes the degradation of SAMHD1 (350), resulting in an increased pool of cytoplasmic dNTPs available for reverse transcription. In some embodiments, the polynucleotides can also encode a second engineered signaling polypeptide that includes a CAR (360). In some embodiments, the lymphoproliferative element is expressed when a compound binds to a control element that regulates its expression (in non-limiting example, the control element is a riboswitch that binds a nucleoside analog). In some embodiments, expression of the CAR is also regulated by the control element. Part (330) is SLAM and CD46. Part (340) is CD3.

FIG. 3A shows a construct containing a polynucleotide sequence encoding an FRB domain fused to the NFκB p65 activator domain (p65 AD) and ZFHD1 DNA binding domain fused to three FKBP repeats that is constitutively expressed. The construct in FIG. 3A also includes HIV1 REV and Vpx as a SrcFlagVpx fusion under the rapamycin-inducible ZFHD1/p65 AD promoter. FIG. 3B shows a construct containing a polynucleotide encoding an rtTA sequence under the control of the ZFHD1/p65 AD promoter. FIG. 3C shows a construct containing a polynucleotide encoding a puromycin resistance gene flanked by loxP sites and the extracellular MYC tag flanked by lox2272 sites. Both selectable markers are under the control of a BiTRE promoter, which is flanked by FRT sites. FIG. 3D shows a construct that contains a polynucleotide encoding RFP flanked by loxP sites that is under the control of a TRE promoter and a single FRT site between the TRE promoter and the 5' loxP site of RFP. FIG. 3E shows a construct containing a polynucleotide encoding GFP flanked by loxP sites that is under the control of the TRE promoter and a single FRT site between the TRE promoter and the 5' loxP site of GFP. The constructs in FIGS. 3C-3E function as landing pads for other polynucleotide sequences to insert into the genome of the packaging cell line.

FIGS. 4A-4C show schematics of non-limiting, exemplary vector constructs for transfecting packaging cells to produce replication incompetent recombinant retroviral particles described herein. FIG. 4A shows a construct containing a tricistronic polynucleotide encoding anti-CD3 (clone UCHT1) scFvFc with a CD14 GPI anchor attachment site, CD80 extra cellular domain (ECD) capable of binding CD28 with a CD16B GPI anchor attachment site, and IL-7 fused to decay-accelerating factor (DAF) with transposon sequences flanking the polynucleotide region for integration into the HEK293S genome. FIG. 4B shows a construct containing a polynucleotide with a BiTRE promoter and a polynucleotide region encoding the gag and pol polypeptides in one direction and a polynucleotide region encoding the measles virus FΔx and HΔy proteins in the other direction. FIG. 4C shows a construct containing a polynucleotide sequence encoding a CAR and the lymphoproliferative element IL7Rα-insPPCL under the control of a CD3Z promoter which is not active in HEK293S cells, wherein the CAR and IL7Rα-insPPCL are separated by a polynucleotide sequence encoding a T2A ribosomal skip sequence and the IL7Rα-insPPCL has an acyclovir riboswitch controlled ribozyme. The CAR-containing construct further includes cPPT/CTS, an RRE sequence, and a polynucleotide sequence encoding HIV-1 Psi (Ψ). The entire polynucleotide sequence on the CAR-containing construct to be integrated into the genome is flanked by FRT sites.

FIG. 6 represents the *Mesoplasma forum* type I-A deoxyguanosine riboswitch regulatory region and associated gene product. The sequence is the reverse complement of *M. florum* L1 genomic DNA (AE017263.1) nt624396 to nt625670 which is same as *M. florum* W37 genomic DNA (CP006778.1) nt636277 to nt 637550. The deoxyguanosine binding aptamer sequence used for initial screen indicated in bold and underline. The downstream gene product (Ribonucleotide reductase of class Ib (aerobic), beta subunit) is indicated in capital letters.

In FIG. 8A, nucleotides within boxes with solid lines are sequence regions targeted for randomization and nucleotides within boxes with dashed lines are sequence regions targeted for insertion/deletion and randomization. FIG. 8B shows possible sequences generated through mutation ("random nucleotides ("N")") and deletion/insertion.

FIG. 9 represents the *M. florum* type I-A deoxyguanosine riboswitch aptamer oligo library synthesized as a reverse complement with additional base pairs added to allow for PCR amplification and T7 promoter addition for in vitro transcription for library screening. The corresponding T7 promoter amplification primer and reverse amplification primer are also shown.

FIG. 10 represents the *Bacillus subtilis* guanosine xpt riboswitch regulatory region and associated gene product. The sequence is the reverse complement of *B. subtilis* subsp. *subtilis* 6051-HGW genomic DNA (CP003329.1) nt2319439 to nt2320353. The guanosine binding aptamer sequence used for initial screen indicated in bold and underline. The downstream gene product (Xanthine phosphoribosyltransferase xpt) is indicated in capital letters.

FIGS. 12A and 12B represent the *B. subtilis* guanosine xpt riboswitch aptamer screening library. In FIG. 12A, nucleotides within boxes with solid lines are sequence regions targeted for randomization and nucleotides within boxes with dashed lines are sequence regions targeted for insertion/deletion and randomization. FIG. 12B shows possible sequences generated through mutation (random nucleotides ("N")) and deletion/insertion.

FIG. 13 represents the *B. subtilis* guanosine xpt riboswitch aptamer oligo library synthesized as a reverse complement with additional base pairs added to allow for PCR amplification and T7 promoter addition for in vitro transcription for library screening. The corresponding T7 promoter amplification primer and reverse amplification primer are also shown.

Figure 17:
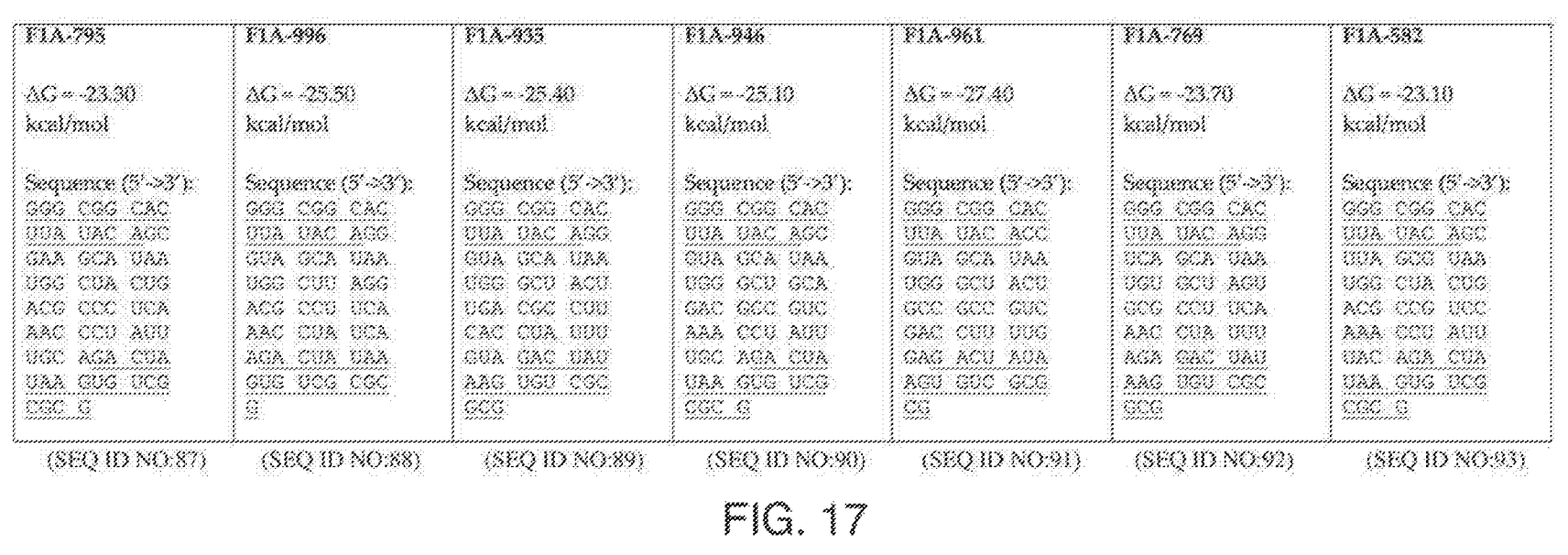

FIG. 17 shows seven aptamer candidates against acyclovir. The free energy for each aptamer was computed at 37° C. and 1 M Na+ by Quikfold 3.0 (Zuker 2003). Sequences were identified using proprietary algorithms. The underlined regions in each sequence are the PCR primer annealing regions.

FIG. 18 shows seven aptamer candidates against penciclovir. The free energy for each aptamer was computed at 37° C. and 1 M Na+ by Quikfold 3.0 (Zuker 2003). Sequences were identified using proprietary algorithms. The underlined regions in each sequence are the PCR primer annealing regions.

FIG. 21A and FIG. 21B show a histogram of the percentage (%) CD3+GFP+ cells in the total CD3+ population and a histogram of the absolute cell count per well of the CD3+GFP+ population, respectively, at 3, 6, 9, 13 and 17 days after transduction of freshly isolated and unstimulated PBMCs from Donor 12M, for 14 h with the indicated lentiviral particles. Each bar represents the mean+/−SD of duplicates.

FIG. 22A and FIG. 22B show a histogram of (%) CD3+ GFP+ cells in the total CD3+ population and a histogram of the absolute cell count per well of the CD3+GFP+ population, respectively, at 3 and 6 days after transduction of freshly isolated and unstimulated PBMCs from Donor 13F, for 14 h, with the indicated lentiviral particles. Please note that "A" shows results using VSV-G pseudotyped lentiviral particles (triplicate experiments); "B" shows results using VSV-G pseudotyped lentiviral particles with OKT3 Ab (1 ug/mL) added to the transduction medium (duplicate experiments); "C" shows results using VSV-G pseudotyped lentiviral particles expressing GPI-anchored UCHT1scFvFc on their surface (triplicate experiments); and "D" shows results using VSV-G pseudotyped lentiviral particles expressing GPI anchored UCHT1scFvFc and GPI-anchored CD80, or a functional extracellular fragment thereof, on their surface (duplicate experiments). Each bar represents the mean+/− SD of duplicates or triplicates, as indicated in FIG. 22A.

FIG. 23A and FIG. 23B show a histogram of percentage (%) CD3+GFP+ cells in the total CD3+ population and a histogram of the absolute cell count per well of the CD3+ GFP+ population, respectively, at 3, 6 and 9 days after transduction of freshly isolated and unstimulated PBMCs from Donor 12M for the indicated time of exposure (2-20 h), with the indicated lentiviral particles. Transduction was performed in a plate or a shaker flask as indicated. Each bar represents the mean+/−SD of duplicates for lentiviral particles pseudotyped with VSV-G ("[VSV-G]"); the other experiments did not have replicates.

FIG. 24A is a schematic of the lentiviral vector backbone F1-0-02 including a transgene expression cassette driving expression of GFP and eTag and a synthetic EF-1alpha promoter and intron A upstream of the GFP. FIG. 24B shows insertion of the miRNAs into EF1alpha intron A of the F1-0-02 backbone. "1" represents the EF1alpha overlap; "2" represents a 5' arm; "3" represents the miRNA1 5' stem; "4" represents a loop; "5" represents the miRNA1 3' stem; "6" represents a 3' arm; "7" represents a linker; "8" represents the miRNA2 5' stem; "9" represents the miRNA2 3' stem; "10" represents the miRNA3 5' stem; "11" represents the miRNA3 3' stem; "12" represents the miRNA4 5' stem; and "13" represents the miRNA4 3' stem.

In FIG. 27A, the CHO-Target 1 cells were initially at pH 6.7 and experimental wells (solid line) and control cells (dashed line) were treated with or without $NaHCO_3$, respectively, at the time indicated by the arrow. In FIG. 27B, the CHO-Target 1 cells were initially at pH 6.7 and experimental wells (solid line) and control cells (dashed line) were treated with or without NaOH, respectively, at the time indicated by the arrow. In FIG. 27C, the CHO-Target 1 cells were initially at pH 7.4 and experimental wells (solid line) and control cells (dashed line) were treated with or without HCl, respectively

DEFINITIONS

Figure 3A:
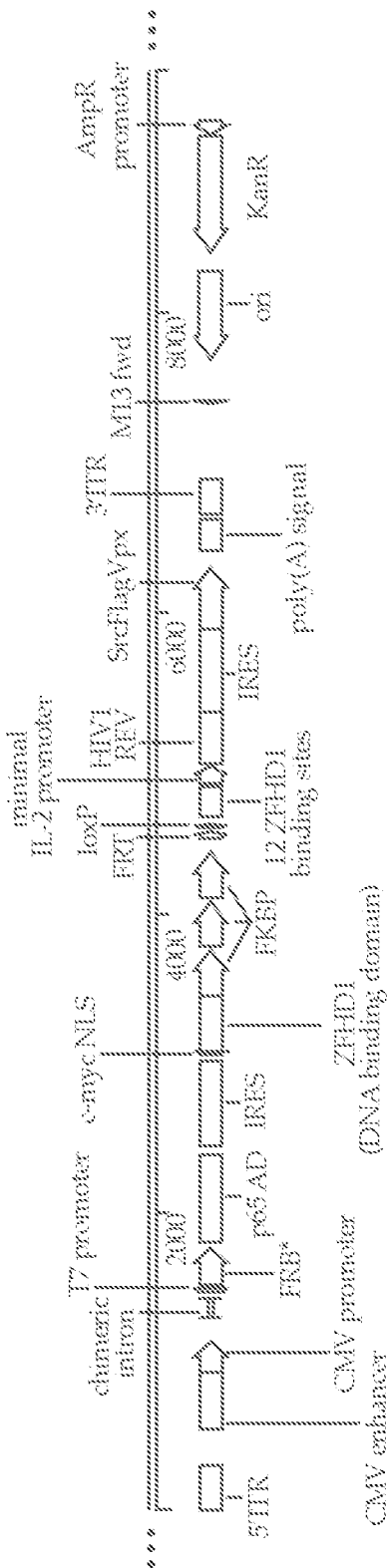
FIGS. 3A-3E show schematics of non-limiting, exemplary vector constructs for transfecting packaging cells to produce replication incompetent recombinant retroviral particles described herein.
Figure 3B:
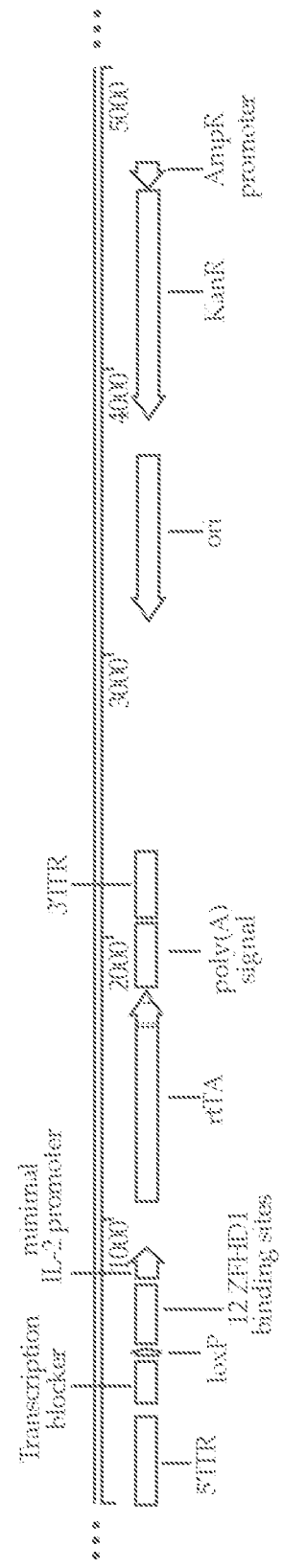
Figures 3C, 3D:
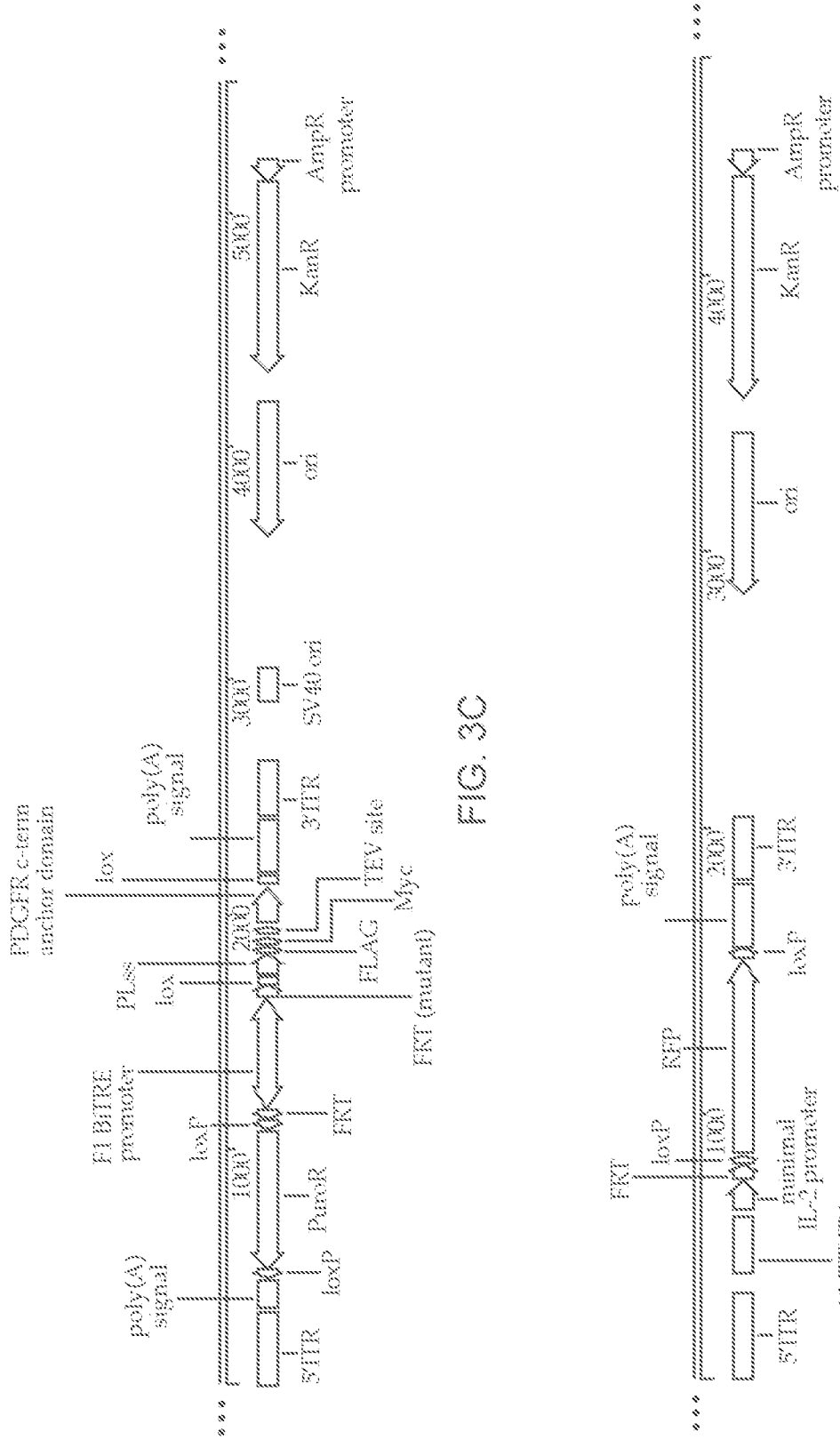
Figure 3E:
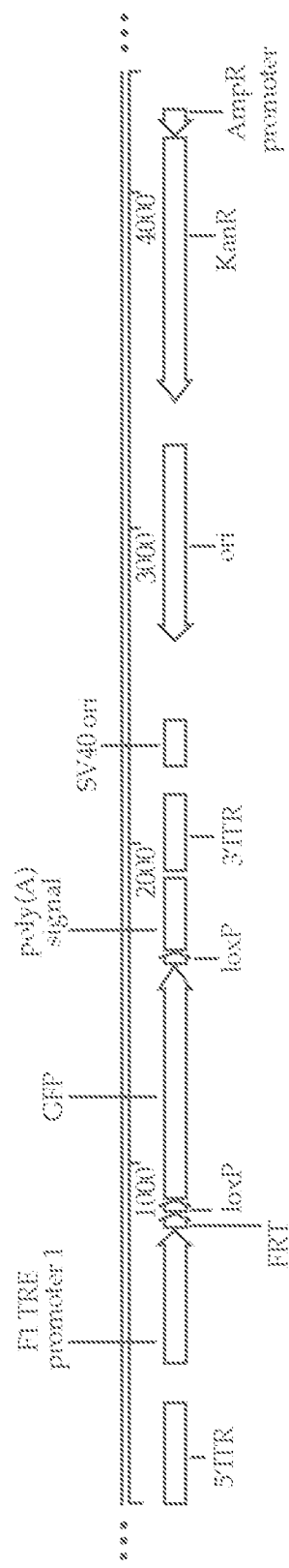

As used herein, the term "chimeric antigen receptor" or "CAR" or "CARs" refers to engineered receptors, which graft an antigen specificity onto cells, for example T cells, NK cells, macrophages, and stem cells. The CARs of the invention include at least one antigen-specific targeting region (ASTR) and an intracellular activating domain (IAD) and can include a stalk, a transmembrane domain (TM), and one or more co-stimulatory domains (CSDs). In another embodiment, the CAR is a bispecific CAR, which is specific to two different antigens or epitopes. After the ASTR binds specifically to a target antigen, the IAD activates intracellular signaling. For example, the IAD can redirect T cell specificity and reactivity toward a selected target in a non-MHC-restricted manner, exploiting the antigen-binding properties of antibodies. The non-MHC-restricted antigen recognition gives T cells expressing the CAR the ability to recognize an antigen independent of antigen processing, thus bypassing a major mechanism of tumor escape. Moreover, when expressed in T cells, CARs advantageously do not dimerize with endogenous T cell receptor (TCR) alpha and beta chains.

As used herein, the term "microenvironment" means any portion or region of a tissue or body that has constant or temporal, physical, or chemical differences from other regions of the tissue or regions of the body. For example, a "tumor microenvironment" as used herein refers to the environment in which a tumor exists, which is the non-cellular area within the tumor and the area directly outside the tumorous tissue but does not pertain to the intracellular compartment of the cancer cell itself. The tumor microenvironment can refer to any and all conditions of the tumor milieu including conditions that create a structural and or functional environment for the malignant process to survive and/or expand and/or spread. For example, the tumor microenvironment can include alterations in conditions such as, but not limited to, pressure, temperature, pH, ionic strength, osmotic pressure, osmolality, oxidative stress, concentration of one or more solutes, concentration of electrolytes, concentration of glucose, concentration of hyaluronan, concentration of lactic acid or lactate, concentration of albumin, levels of adenosine, levels of R-2-hydroxyglutarate, concentration of pyruvate, concentration of oxygen, and/or presence of oxidants, reductants, or co-factors, as well as other conditions a skilled artisan will understand.

As used interchangeably herein, the terms "polynucleotide" and "nucleic acid" refer to a polymeric form of nucleotides of any length, either ribonucleotides or deoxyribonucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases.

As used herein, the term "antibody" includes polyclonal and monoclonal antibodies, including intact antibodies and fragments of antibodies which retain specific binding to antigen. The antibody fragments can be, but are not limited to, fragment antigen binding (Fab) fragments, Fab' fragments, F(ab')$_2$ fragments, Fv fragments, Fab'-SH fragments, (Fab')$_2$ Fv fragments, Fd fragments, recombinant IgG (rIgG) fragments, single-chain antibody fragments, including single-chain variable fragments (scFv), divalent scFv's, trivalent scFv's, and single domain antibody fragments (e.g., sdAb, sdFv, nanobody). The term includes genetically engineered and/or otherwise modified forms of immunoglobulins, such as intrabodies, peptibodies, chimeric antibodies, single-chain antibodies, fully human antibodies, humanized antibodies, fusion proteins including an antigen-specific targeting region of an antibody and a non-antibody protein, heteroconjugate antibodies, multispecific, e.g., bispecific, antibodies, diabodies, triabodies, and tetrabodies, tandem di-scFv's, and tandem tri-scFv's. Unless otherwise stated, the term "antibody" should be understood to include functional antibody fragments thereof. The term also includes intact or full-length antibodies, including antibodies of any class or sub-class, including IgG and sub-classes thereof, IgM, IgE, IgA, and IgD.

As used herein, the term "antibody fragment" includes a portion of an intact antibody, for example, the antigen binding or variable region of an intact antibody. Examples of antibody fragments include Fab, Fab', F(ab')$_2$, and Fv fragments; diabodies; linear antibodies (Zapata et al., Protein Eng. 8(10): 1057-1062 (1995)); single-chain antibody molecules; and multispecific antibodies formed from antibody fragments. Papain digestion of antibodies produces two identical antigen-binding fragments, called "Fab" fragments, each with a single antigen-binding site, and a residual "Fc" fragment, a designation reflecting the ability to crystallize readily. Pepsin treatment yields an F(ab')$_2$ fragment that has two antigen combining sites and is still capable of cross-linking antigen.

As used interchangeably herein, the terms "single-chain Fv," "scFv," or "sFv" antibody fragments include the $V_H$ and $V_L$ domains of antibody, wherein these domains are present in a single polypeptide chain. In some embodiments, the Fv polypeptide further includes a polypeptide linker or spacer between the $V_H$ and $V_L$ domains, which enables the sFv to form the desired structure for antigen binding. For a review of sFv, see Pluckthun in *The Pharmacology of Monoclonal Antibodies*, vol. 113, Rosenburg and Moore eds., Springer-Verlag, New York, pp. 269-315 (1994).

As used herein, "naturally occurring" VH and VL domains refer to VH and VL domains that have been isolated from a host without further molecular evolution to change their affinities when generated in an scFv format under specific conditions such as those disclosed in U.S. Pat. No. 8,709,755 B2 and application WO/2016/033331A1.

As used herein, the term "affinity" refers to the equilibrium constant for the reversible binding of two agents and is expressed as a dissociation constant (Kd). Affinity can be at least 1-fold greater, at least 2-fold greater, at least 3-fold greater, at least 4-fold greater, at least 5-fold greater, at least 6-fold greater, at least 7-fold greater, at least 8-fold greater, at least 9-fold greater, at least 10-fold greater, at least 20-fold greater, at least 30-fold greater, at least 40-fold greater, at least 50-fold greater, at least 60-fold greater, at least 70-fold greater, at least 80-fold greater, at least 90-fold greater, at least 100-fold greater, or at least 1000-fold greater, or more, than the affinity of an antibody for unrelated amino acid sequences. Affinity of an antibody to a target protein can be, for example, from about 100 nanomolar (nM) to about 0.1 nM, from about 100 nM to about 1 picomolar (pM), or from about 100 nM to about 1 femtomolar (fM) or more. As used herein, the term "avidity" refers to the resistance of a complex of two or more agents to dissociation after dilution. The terms "immunoreactive" and "preferentially binds" are used interchangeably herein with respect to antibodies and/or antigen-binding fragments.

As used herein, the term "binding" refers to a direct association between two molecules, due to, for example, covalent, electrostatic, hydrophobic, and ionic and/or hydrogen-bond interactions, including interactions such as salt bridges and water bridges. Non-specific binding would refer to binding with an affinity of less than about $10^{-7}$ M, e.g., binding with an affinity of $10^{-6}$ M, $10^{-5}$ M, $10^{-4}$ M, etc.

As used herein, reference to a "cell surface expression system" or "cell surface display system" refers to the display or expression of a protein or portion thereof on the surface of a cell. Typically, a cell is generated that expresses proteins of interest fused to a cell-surface protein. For example, a protein is expressed as a fusion protein with a transmembrane domain.

As used herein, the term "element" includes polypeptides, including fusions of polypeptides, regions of polypeptides, and functional mutants or fragments thereof and polynucleotides, including microRNAs and shRNAs, and functional mutants or fragments thereof.

As used herein, the term "region" is any segment of a polypeptide or polynucleotide.

As used herein, a "domain" is a region of a polypeptide or polynucleotide with a functional and/or structural property.

As used herein, the terms "stalk" or "stalk domain" refer to a flexible polypeptide connector region providing structural flexibility and spacing to flanking polypeptide regions and can consist of natural or synthetic polypeptides. A stalk can be derived from a hinge or hinge region of an immunoglobulin (e.g., IgG1) that is generally defined as stretching from Glu216 to Pro230 of human IgG1 (Burton (1985) *Molec. Immunol.*, 22:161-206). Hinge regions of other IgG isotypes may be aligned with the IgG1 sequence by placing the first and last cysteine residues forming inter-heavy chain disulfide (S—S) bonds in the same positions. The stalk may be of natural occurrence or non-natural occurrence, including but not limited to an altered hinge region, as disclosed in U.S. Pat. No. 5,677,425. The stalk can include a complete hinge region derived from an antibody of any class or subclass. The stalk can also include regions derived from CD8, CD28, or other receptors that provide a similar function in providing flexibility and spacing to flanking regions.

The term "isolated" as used herein means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

As used herein, a "polypeptide" is a single chain of amino acid residues linked by peptide bonds. A polypeptide does not fold into a fixed structure nor does it have any post-translational modification. A "protein" is a polypeptide that folds into a fixed structure. "Polypeptides" and "proteins" are used interchangeably herein.

As used herein, a polypeptide may be "purified" to remove contaminant components of a polypeptide's natural environment, e.g. materials that would interfere with diagnostic or therapeutic uses for the polypeptide such as, for example, enzymes, hormones, and other proteinaceous or nonproteinaceous solutes. A polypeptide can be purified (1) to greater than 90%, greater than 95%, or greater than 98%, by weight of antibody as determined by the Lowry method, for example, more than 99% by weight, (2) to a degree sufficient to obtain at least 15 residues of N-terminal or internal amino acid sequence by use of a spinning cup sequenator, or (3) to homogeneity by sodium dodecyl sulfate-polyacrylamide gel electrophoresis (SDS-PAGE) under reducing or nonreducing conditions using Coomassie blue or silver stain.

As used herein, the term "immune cells" generally includes white blood cells (leukocytes) which are derived from hematopoietic stem cells (HSC) produced in the bone marrow "Immune cells" includes, e.g., lymphocytes (T cells, B cells, natural killer (NK) cells) and myeloid-derived cells (neutrophil, eosinophil, basophil, monocyte, macrophage, dendritic cells).

As used herein, "T cell" includes all types of immune cells expressing CD3 including T-helper cells (CD4$^+$ cells), cytotoxic T cells (CD8$^+$ cells), T-regulatory cells (Treg) and gamma-delta T cells.

As used herein, a "cytotoxic cell" includes CD8$^+$ T cells, natural-killer (NK) cells, NK-T cells, γδ T cells, a subpopulation of CD4$^+$ cells, and neutrophils, which are cells capable of mediating cytotoxicity responses.

As used herein, the term "stem cell" generally includes pluripotent or multipotent stem cells. "Stem cells" includes, e.g., embryonic stem cells (ES); mesenchymal stem cells (MSC); induced-pluripotent stem cells (iPS); and committed progenitor cells (hematopoeitic stem cells (HSC); bone marrow derived cells, etc.).

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment," as used herein, covers any treatment of a disease in a mammal, e.g., in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease.

As used interchangeably herein, the terms "individual", "subject", "host", and "patient" refer to a mammal, including, but not limited to, humans, murines (e.g., rats, mice), lagomorphs (e.g., rabbits), non-human primates, humans, canines, felines, ungulates (e.g., equines, bovines, ovines, porcines, caprines), etc.

As used herein, the terms "therapeutically effective amount" or "efficacious amount" refers to the amount of an agent, or combined amounts of two agents, that, when administered to a mammal or other subject for treating a disease, is sufficient to affect such treatment for the disease. The "therapeutically effective amount" will vary depending on the agent(s), the disease and its severity and the age, weight, etc., of the subject to be treated.

As used herein, the term "evolution" or "evolving" refers to using one or more methods of mutagenesis to generate a different polynucleotide encoding a different polypeptide, which is itself an improved biological molecule and/or contributes to the generation of another improved biological molecule. "Physiological" or "normal" or "normal physiological" conditions are conditions such as, but not limited to, pressure, temperature, pH, ionic strength, osmotic pressure, osmolality, oxidative stress, concentration of one or more solutes, concentration of electrolytes, concentration of glucose, concentration of hyaluronan, concentration of lactic acid or lactate, concentration of albumin, levels of adenosine, levels of R-2-hydroxyglutarate, concentration of pyruvate, concentration of oxygen, and/or presence of oxidants, reductants, or co-factors, as well as other conditions, that would be considered within a normal range at the site of administration, or at the tissue or organ at the site of action, to a subject.

As used herein, a "genetically modified cell" includes cells that contain exogenous nucleic acids whether or not the exogenous nucleic acids are integrated into the genome of the cell.

A "polypeptide" as used herein can include part of or an entire protein molecule as well as any posttranslational or other modifications.

A pseudotyping element as used herein can include a "binding polypeptide" that includes one or more polypeptides, typically glycoproteins, that identify and bind the target host cell, and one or more "fusogenic polypeptides" that mediate fusion of the retroviral and target host cell membranes, thereby allowing a retroviral genome to enter the target host cell. The "binding polypeptide" as used herein, can also be referred to as a "T cell and/or NK cell binding polypeptide" or a "target engagement element," and the "fusogenic polypeptide" can also be referred to as a "fusogenic element".

A "resting" lymphocyte, such as for example, a resting T cell, is a lymphocyte in the G0 stage of the cell cycle that does not express activation markers such as Ki-67. Resting lymphocytes can include naïve T cells that have never encountered specific antigen and memory T cells that have been altered by a previous encounter with an antigen. A "resting" lymphocyte can also be referred to as a "quiescent" lymphocyte.

As used herein, "lymphodepletion" involves methods that reduce the number of lymphocytes in a subject, for example by administration of a lymphodepletion agent. Lymphodepletion can also be attained by partial body or whole body fractioned radiation therapy. A lymphodepletion agent can be a chemical compound or composition capable of decreasing the number of functional lymphocytes in a mammal when administered to the mammal One example of such an agent is one or more chemotherapeutic agents. Such agents and dosages are known, and can be selected by a treating physician depending on the subject to be treated. Examples of lymphodepletion agents include, but are not limited to, fludarabine, cyclophosphamide, cladribine, denileukin diftitox, or combinations thereof.

RNA interference (RNAi) is a biological process in which RNA molecules inhibit gene expression or translation by neutralizing targeted RNA molecules. The RNA target may be mRNA, or it may be any other RNA susceptible to functional inhibition by RNAi. As used herein, an "inhibitory RNA molecule" refers to an RNA molecule whose presence within a cell results in RNAi and leads to reduced expression of a transcript to which the inhibitory RNA molecule is targeted. An inhibitory RNA molecule as used herein has a 5' stem and a 3' stem that is capable of forming an RNA duplex. The inhibitory RNA molecule can be, for example, a miRNA (either endogenous or artificial) or a shRNA, a precursor of a miRNA (i.e. a Pri-miRNA or Pre-miRNA) or shRNA, or a dsRNA that is either transcribed or introduced directly as an isolated nucleic acid, to a cell or subject.

As used herein, "double stranded RNA" or "dsRNA" or "RNA duplex" refers to RNA molecules that are comprised of two strands. Double-stranded molecules include those comprised of two RNA strands that hybridize to form the duplex RNA structure or a single RNA strand that doubles back on itself to form a duplex structure. Most, but not necessarily all of the bases in the duplex regions are base-paired. The duplex region comprises a sequence complementary to a target RNA. The sequence complementary to a target RNA is an antisense sequence, and is frequently from 18 to 29, from 19 to 29, from 19 to 21, or from 25 to 28 nucleotides long, or in some embodiments between 18, 19, 20, 21, 22, 23, 24, 25 on the low end and 21, 22, 23, 24, 25, 26, 27, 28 29, or 30 on the high end, where a given range always has a low end lower than a high end. Such structures typically include a 5' stem, a loop, and a 3' stem connected by a loop which is contiguous with each stem and which is not part of the duplex. The loop comprises, in certain embodiments, at least 3, 4, 5, 6, 7, 8, 9, or 10 nucleotides. In other embodiments the loop comprises from 2 to 40, from 3 to 40, from 3 to 21, or from 19 to 21 nucleotides, or in some embodiments between 2, 3, 4, 5, 6, 7, 8, 9, 10, 11, 12, 13, 14, 15, 16, 17, 18, 19, or 20 on the low end and 10, 11, 12, 13, 14, 15, 16, 17, 18, 19, 20, 25, 30, 35, or 40 on the high end, where a given range always has a low end lower than a high end.

The term "microRNA flanking sequence" as used herein refers to nucleotide sequences including microRNA processing elements. MicroRNA processing elements are the minimal nucleic acid sequences which contribute to the production of mature microRNA from precursor microRNA. Often these elements are located within a 40 nucleotide sequence that flanks a microRNA stem-loop structure. In some instances the microRNA processing elements are found within a stretch of nucleotide sequences of between 5 and 4,000 nucleotides in length that flank a microRNA stem-loop structure.

The term "linker" when used in reference to a multiplex inhibitory RNA molecule refers to a connecting means that joins two inhibitory RNA molecules.

As used herein, a "recombinant retrovirus" refers to a non-replicable, or "replication incompetent", retrovirus unless it is explicitly noted as a replicable retrovirus. The terms "recombinant retrovirus" and "recombinant retroviral particle" are used interchangeably herein. Such retrovirus/retroviral particle can be any type of retroviral particle including, for example, gamma retrovirus, and In illustrative embodiments, lentivirus. As is known, such retroviral particles, for example lentiviral particles, typically are formed in packaging cells by transfecting the packing cells with plasmids that include packaging components such as Gag, Pol and Rev, an envelope or pseudotyping plasmid that encodes a pseudotyping element, and a transfer, genomic, or retroviral (e.g. lentiviral) expression vector, which is typically a plasmid on which a gene(s) or other coding sequence of interest is encoded. Accordingly, a retroviral (e.g. lentiviral) expression vector includes sequences (e.g. a 5' LTR and a 3' LTR flanking e.g. a psi packaging element and a target heterologous coding sequence) that promote expression and packaging after transfection into a cell. The terms "lentivirus" and "lentiviral particle" are used interchangeably herein.

A "framework" of a miRNA consists of "5' microRNA flanking sequence" and/or "3' microRNA flanking sequence" surrounding a miRNA and, in some cases, a loop sequence that separates the stems of a stem-loop structure in a miRNA. In some examples, the "framework" is derived from naturally occurring miRNAs, such as, for example, miR-155. The terms "5' microRNA flanking sequence" and "5' arm" are used interchangeably herein. The terms "3' microRNA flanking sequence" and "3' arm" are used interchangeably herein.

As used herein, the term "miRNA precursor" refers to an RNA molecule of any length which can be enzymatically processed into an miRNA, such as a primary RNA transcript, a pri-miRNA, or a pre-miRNA.

It is to be understood that the present disclosure and the aspects and embodiments provided herein, are not limited to particular examples disclosed, as such may, of course, vary. It is also to be understood that the terminology used herein is for the purpose of disclosing particular examples and embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention. When multiple low and multiple high values for ranges are given, a skilled artisan will recognize that a selected range will include a low value that is less than the high value. All headings in this specification are for the convenience of the reader and are not limiting.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a chimeric antigen receptor" includes a plurality of such chimeric antigen receptors and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

DETAILED DESCRIPTION

The present disclosure overcomes these prior art challenges by providing methods and compositions for genetically modifying lymphocytes and methods for performing adoptive cellular therapy that include transducing T cells and/or NK cells, that requires far less time ex vivo, for example, 24, 12, or 8 hours or less, and in some embodiments without prior ex vivo stimulation. These methods are well-suited for closed system ex vivo processing of blood from a subject, and can be performed with the subject present in the same room as and/or in some embodiments, within their line of sight of their blood or isolated blood cells thereof at all times during performance of the method. More specifically, the aspects and embodiments of the disclosure herein overcome problems associated with current adoptive cellular therapies by providing methods for transducing resting T cells and/or resting NK cells, that typically utilize a pseudotyping element that facilitates binding and fusion of a replication incompetent recombinant retroviral particle to a resting T cell and/or a resting NK cell, to facilitate genetic modification of the resting T cells and/or NK cells by the replication incompetent recombinant retroviral particles. Furthermore, methods provided herein overcome problems of the art by utilizing in illustrative embodiments, a chimeric antigen receptor and one or more lymphoproliferative elements whose expression is under the control of a control element, such that exposure of the subject to a compound that binds the control element, or termination of such exposure, promotes expansion of the genetically modified T cells and/or NK cells in vivo.

As a result of these and other improvements disclosed in detail herein, in one aspect, provided herein is a method for modifying resting T cells and/or resting NK cells of a subject, such as a patient having a disease or disorder, wherein blood from the subject is collected; resting T cells and/or NK cells are genetically modified by contacting them with a replication incompetent recombinant retroviral particle; and the genetically modified cells are reintroduced into the subject typically within a shorter period of time than prior methods, for example within 24 hours and in some non-limiting embodiments, within 12 hours and/or without further expanding the population of genetically modified T cells and/or NK cells ex vivo, for example such that the genetically modified resting T cells and/or NK cells do not undergo more than 4 cell divisions ex vivo. Thus, methods provided herein can be performed in much less time than current CAR therapies, thereby providing processes by which a subject can remain in a clinic for the entire time of the ex vivo steps. This facilitates performance of the ex vivo steps in a closed system, which reduces the chances for contamination and mixing of patient samples and can be performed more readily by clinical labs.

Accordingly, FIGS. 1 and 2 provide schematic diagrams of illustrative compositions used in methods provided herein. FIG. 1 provides a diagram of a packaging cell (100) and a replication incompetent recombinant retroviral particle, produced by such a packaging cell (200). The packaging cell (100) includes recombinant polynucleotides (110) incorporated into its genome that include recombinant transcriptional elements that express retroviral proteins and various different membrane-bound polypeptides under the control of inducible promoters that are regulated by transactivators, which bind and are activated by ligands. These transactivators, inducible promoters, and ligands are used to induce the sequential expression and accumulation of cell membrane-bound polypeptides that will be incorporated into the membrane of the replication incompetent recombinant retroviral particle as well as retroviral components necessary for packaging and assembly of the replication incompetent recombinant retroviral particles.

As a result of the sequential induced expression of the various polynucleotides as discussed in detail herein below, the illustrative packaging cell (100) illustrated in FIG. 1 is produced, and can be used in illustrative methods to produce replication incompetent recombinant retroviral particles used in methods of transfecting resting T cells and/or NK cells ((300) in FIG. 2) provided herein. The packaging cell (100), in non-limiting illustrative embodiments, includes in its genome nucleic acids encoding a packageable retroviral RNA genome that includes at least some of the elements of a retroviral genome necessary for packaging and assembly of the replication incompetent recombinant retroviral particle (as non-limiting illustrative examples, a retroviral psi element, a retroviral gag polypeptide and a retroviral pol polypeptide).

Some membrane bound polypeptides incorporated or associated with the cell membrane of the packaging cell will become incorporated or associated into the replication incompetent recombinant retroviral particles, but are not encoded by the retroviral genome. For example, the packaging cell and replication incompetent recombinant retroviral particles formed therefrom, can include a retroviral. Vpx polypeptide (250), which in non-limiting illustrative examples can be expressed as a membrane associated fusion protein, for example a Src-Flag-Vpx polypeptide; a pseudotyping element that can include a binding polypeptide and a fusogenic polypeptide (240), which in a non-limiting embodiment includes a Measles Virus hemagglutinin (H) polypeptide and a Measles Virus fusion (F) polypeptide, or cytoplasmic domain deletion variants thereof optionally, one or more activation elements (210, 220), which in a non-limiting embodiment includes a membrane-bound polypeptide capable of binding to CD3 and a membrane-bound polypeptide capable of binding to CD28; and/or optionally a membrane-bound cytokine (230), a non-limiting embodiment of which is a fusion polypeptide that includes IL-7 fused to DAF, or a fragment thereof. Various other specific types of these membrane bound polypeptides are provided herein.

As a result of the sequential expression of the transcriptional elements by the packaging cell, a replication incompetent recombinant retroviral particle is produced. The RNA retroviral genome inside of and typically integrated into the genome of the packaging cell that becomes the genome of the replication incompetent recombinant retroviral particle, includes retroviral components (as non-limiting illustrative examples, retroviral Gag and Pol polynucleotides) that are necessary for retroviral production, infection and integration into the genome of a host cell, which is typically a resting T cell and/or NK cell. Furthermore, the retroviral genome furthermore includes polynucleotides encoding one or typically two engineered signaling polypeptides provided herein. One of the engineered signaling polypeptides typically encodes at least one lymphoproliferative element (in a non-limiting examples a constitutive interleukin 7 receptor mutant) and the other engineered signaling polypeptide typically encodes a chimeric antigen receptor.

The replication incompetent recombinant retroviral particle, (200) is then used to transduce a resting T cell and/or resting NK cell (300) in methods provided herein. As shown in FIG. 2, after the resting cell and/or NK cell (300) is contacted with the replication incompetent recombinant retroviral particle (200), membrane polypeptides discussed above on the surface of the replication incompetent recombinant retroviral particle bind to receptors and/or ligands on the surface of the resting T cell and/or NK cell (300). For example, the pseudotyping element, which as indicated above can include a binding polypeptide that binds to molecules on the surface of resting T cells and/or resting NK cells and a fusogenic polypeptide, facilitates the binding and fusion of replication incompetent recombinant retroviral particle (200) to the T cell and/or NK cell membrane. The activation element(s) (210, 220) activate the resting T cell and/or NK cell (300) by engaging the T-cell receptor complex, a process which occurs over the time course of the contacting or an incubation thereafter. Furthermore, the membrane-bound cytokines (230) can be present on the surface of replication incompetent recombinant retroviral particle and bind cytokine receptors (310) on the surface of the resting T cell and/or NK cell (300), thus further promoting binding and activation. Thus, not to be limited by theory, in illustrative embodiments provided herein, as a result of one or more of these replication incompetent recombinant retroviral particles (200) components, ex vivo stimulation or activation by an element that is not already in or on the replication incompetent recombinant retroviral particle (200) is not required. This in turn, helps to cut down the ex vivo time that is required for completion of the methods in these illustrative methods provided herein.

Upon binding to the T cell and/or NK cell (200), the replication incompetent recombinant retroviral particle then fuses with the T cell and/or NK cell (300), and polypeptides and nucleic acids in the replication incompetent recombinant retroviral particle enter the T cell and/or NK cell (300). As indicated above, one of these polypeptides in the replication incompetent recombinant retroviral particle is the Vpx polypeptide (250). The Vpx polypeptide (250) binds to and induces the degradation of the SAMHD1 restriction factor (350), which degrades free dNTPs in the cytoplasm. Thus, the concentration of free dNTPs in the cytoplasm increases as Vpx degrades SAMHD1, and reverse transcription activity is increased, thus facilitating reverse transcription of the retroviral genome and integration into the T cell and/or NK cell genome.

After integration of the retroviral genome into the T cell and/or NK cell (200), the cell and/or NK cell genome includes nucleic acids encoding the signaling polypeptide encoding the lymphoproliferative element (370) and optionally the signaling polypeptide encoding the CAR (360). Expression of the lymphoproliferative element and optionally the CAR are under the control of a control element. Exposure to a compound that binds the control element, which can occur in vitro or in vivo by administering it to a subject whose T cell and/or NK cell (300) was transduced, promotes proliferation of the T cell and/or NK cell (300) in vitro or in vivo by expressing the lymphoproliferative element and optionally as a result of expression of the CAR and binding of the CAR to its target cell. Thus, T cells and/or NK cells that are transduced with replication incompetent recombinant retroviral particles herein, have one or more signals that drive proliferation and/or inhibit cell death, which in turn in illustrative embodiments, avoids the requirements of prior methods to lymphodeplete a host before returning transduced T cells and/or NK cells back into the subject. This in turn, in illustrative embodiments, further reduces the requirement for days of processing before transduced T cells and/or NK cells are reintroduced into a subject. Thus, in illustrative embodiments, no more than 36 hours, 24 hours, 12 hours, or in some instances even 8 hours, of time is required from collection of blood from the subject to reintroduction of the blood to the subject, which fundamentally changes the CAR-T process from prior methods. Furthermore, the control element provides one of the safety mechanisms provided herein as well. For example, ceasing administration of the compound can down-regulate or even terminate expression of the lymphoproliferative element and optionally the CAR, thus ending a proliferation and/or survival signal to the transduced T cell and/or NK cell and its progeny.

Methods for Performing Adoptive Cell Therapy

In certain aspects, provided herein are methods for performing adoptive cell therapy on a subject. As an illustrative example, the method can include the following:

A. collecting blood from a subject;
B. isolating peripheral blood mononuclear cells (PBMCs) comprising resting T cells and/or resting NK cells;
C. contacting the resting T cells and/or resting NK cells of the subject ex vivo, with replication incompetent recombinant retroviral particles, wherein the replication incompetent recombinant retroviral particles comprise a pseudotyping element on their surface that is capable of binding a resting T cell and/or NK cell and facilitating membrane fusion of the replication incompetent recombinant retroviral particles thereto, wherein said contacting facilitates transduction of the resting T cells and/or NK cells by the replication incompetent recombinant retroviral particles, thereby producing genetically modified T cells and/or NK cells; and
D. reintroducing the genetically modified cells into the subject within 36, 24, 12, or even 8 hours of collecting blood from the subject, thereby performing adoptive cell therapy in the subject.

In some aspects provided herein, methods with similar steps are referred to as methods for genetically modifying and expanding lymphocytes of a subject. A skilled artisan will understand that the discussion herein as it applies to methods and compositions for performing adoptive cell therapy apply to methods for genetically modifying and expanding lymphocytes of a subject as well.

Typically, the adoptive cell therapy methods of the present disclosure are carried out by autologous transfer, in which the cells are isolated and/or otherwise prepared from the subject who is to receive the cell therapy, or from a sample derived from such a subject. Thus, in some aspects, the cells are derived from a subject, e.g., patient, in need of a treatment and the cells, following isolation and processing are administered to the same subject. In some embodiments of the methods and compositions disclosed herein, a subject having a disease or disorder enters a medical facility where the subject's blood is drawn using known methods, such as venipuncture. In certain embodiments, the volume of blood drawn from a subject is between 10, 15, 20, 25, 30, 35, 40, 50, 75, or 100 ml on the low end of the range and 200, 250, 300, 350, 400, 500, 750, 1000, 2000, or 2500 ml on the high end of the range. In some embodiments, between 10 and 400 ml are drawn from the subject. In some embodiments, between 20 and 250 ml of blood are drawn from the subject. In some embodiments, the blood is fresh when it is processed. In any of the embodiments disclosed herein, fresh blood can be blood that was withdrawn from a subject less than 15, 30, 45, 60, 90, 120, 150, or 180 minutes prior. In some embodiments, the blood is processed in the methods provided herein without storage.

Contact between the T cells and/or NK cells and the replication incompetent recombinant retroviral particles typically facilitates transduction of the T cells and/or NK cells by the replication incompetent recombinant retroviral particles. Throughout this disclosure, a transduced T cell and/or NK cell includes progeny of ex vivo transduced cells that retain at least some of the nucleic acids or polynucleotides that are incorporated into the cell during the ex vivo transduction. In methods herein that recite "reintroducing" a transduced cell, it will be understood that such cell is typically not in a transduced state when it is collected from the blood of a subject. A subject in any of the aspects disclosed herein can be for example, an animal, a mammal, and in illustrative embodiments a human.

Not to be limited by theory, in non-limiting illustrative methods, the delivery of a polynucleotide encoding a lymphoproliferative element, such as an IL7 constitutively active mutant, to a resting T cell and/or NK cell ex vivo, which can integrate into the genome of the T cell or NK cell, provides that cell with a driver for in vivo expansion without the need for lymphodepleting the host. Thus, in illustrative embodiments, the subject is not exposed to a lymphodepleting agent within 1, 2, 3, 4, 5, 6, 7, 10, 14, 21, or 28 days, or within 1 month, 2 months, 3 months or 6 months of performing the contacting, during the contacting, and/or within 1, 2, 3, 4, 5, 6, 7, 10, 14, 21, or 28 days, or within 1 month, 2 months, 3 months or 6 months after the modified T cells and/or NK cells are reintroduced back into the subject. Furthermore, in non-limiting illustrative embodiments, methods provided herein can be performed without exposing the subject to a lymphodepleting agent during a step wherein a replication incompetent recombinant retroviral particle is in contact with resting T cells and/or resting NK cells of the subject and/or during the entire ex vivo method.

Hence, methods of expanding genetically modified T cells and/or NK cells in a subject in a vivo is a feature of some embodiments of the present disclosure. In illustrative embodiments, such methods are ex vivo propagation-free or substantially propagation-free.

This entire method/process from blood draw from a subject to reintroduction of blood back into the subject after ex vivo transduction of T cells and/or NK cells, in non-limiting illustrative embodiments herein, can occur over a time period less than 48 hours, less than 36 hours, less than 24 hours, less than 12 hours, less than 11 hours, less than 10 hours, less than 9 hours, less than 8 hours, less than 7 hours, less than 6 hours, less than 5 hours, less than 4 hours, less than 3 hours, 2 hours, or less than 2 hours. In other embodiments, the entire method/process from blood draw/ collection from a subject to reintroduction of blood back into the subject after ex vivo transduction of T cells and/or NK cells, in non-limiting illustrative embodiments herein, occurs over a time period between 1 hour and 12 hours, or between 2 hours and 8 hours, or between 1 hour and 3 hours, or between 2 hours and 4 hours, or between 2 hours and 6 hours, or between 4 hours and 12 hours, or between 4 hours and 24 hours, or between 8 hours and 24 hours, or between 8 hours and 36 hours, or between 8 hours and 48 hours, or between 12 hours and 24 hours, or between 12 hours and 36 hours, or between 12 hours and 48 hours, or over a time period between 15, 30, 60, 90, 120, 180, and 240 minutes on the low end of the range, and 120, 180, and 240, 300, 360, 420, and 480 minutes on the high end of the range. In other embodiments, the entire method/process from blood draw/ collection from a subject to reintroduction of blood back into the subject after ex vivo transduction of T cells and/or NK cells, occurs over a time period between 1, 2, 3, 4, 6, 8, 10, and 12 hours on the low end of the range, and 8, 9, 10, 11, 12, 18, 24, 36, or 48 hours on the high end of the range. In some embodiments, the genetically modified T cells and/or NK cells are separated from the replication incompetent recombinant retroviral particles after the time period in which contact occurs.

In some embodiments of any method herein that includes a step of blood collection and a step of transduction of lymphocytes, in illustrative embodiments T cells and/or NK cells, including resting T cell and NK cells, the method from blood collection through transduction of T cells and/or NK cells does not include a step of removing monocytes by an incubation on an adherent substrate of more than 4 hours in one embodiment, or for more than 6, hours in another embodiment, or for more than 8 hours in another embodiment. In one illustrative embodiment, the method from blood collection through transduction of T cells and/or NK cells does not include an overnight incubation on an adherent substrate to remove monocytes. In another embodiment, the method from blood collection through transduction of T cells and/or NK cells includes a step of removing monocytes by an incubation on an adherent substrate for no more than 30 minutes, 1 hour, or 2 hours. In another embodiment, the method from blood collection from a subject through transduction of lymphocytes, in illustrative embodiments T cells and/or NK cells, including resting T cells and/or NK cells, include no step of removing monocytes by an incubation on an adherent substrate. In another embodiment, In another embodiment, the method from blood collection from a subject through transduction of lymphocytes, in illustrative embodiments T cells and/or NK cells, including resting T cells and/or NK cells, includes, the T cells and/or NK cells are not incubated with or exposed to a bovine serum such as a cell culturing bovine serum, for example fetal bovine serum during the method.

In some embodiments of any method herein that includes a step of blood collection and a step of transduction of lymphocytes, in illustrative embodiments T cells and/or NK cells, including resting T cell and NK cells, the method from blood collection from a subject through reintroduction of T cells and/or NK cells into the subject does not include a step of removing monocytes by an incubation on an adherent substrate of more than 4 hours in one embodiment, or for more than 6, hours in another embodiment, or for more than 8 hours in another embodiment. In one illustrative embodiment, the method from blood collection from a subject through reintroduction of T cells and/or NK cells into the subject does not include an overnight incubation on an adherent substrate to remove monocytes. In another embodiment, the method from blood collection from a subject through reintroduction of T cells and/or NK cells into the subject includes a step of removing monocytes by an incubation on an adherent substrate for no more than 30 minutes, 1 hour, or 2 hours. In another embodiment, the method from blood collection from a subject through reintroduction of T cells and/or NK cells into the subject includes no step of removing monocytes by an incubation on an adherent substrate. In another embodiment, the method from blood collection from a subject through reintroduction of T cells and/or NK cells into the subject, the T cells and/or NK cells are not incubated with or exposed to a bovine serum, such as a cell culturing bovine serum, for example fetal bovine serum during the method.

In some embodiments of any method herein that includes a step of transducing T cells and/or NK cells, in some embodiments, the T cells and/or NK cells have not been exposed to an incubation on a substrate that adheres to monocytes for more than 4 hours in one embodiment, or for more than 6, hours in another embodiment, or for more than 8 hours in another embodiment before the transduction. In one illustrative embodiment, the T cells and/or NK cells have been incubated overnight on an adherent substrate to remove monocytes before the transduction. In another embodiment, the method can include incubating the T cells and/or NK cells on an adherent substrate that binds monocytes for no more than 30 minutes, 1 hour, or 2 hours before the transduction. In another embodiment, the T cells and/or NK cells are exposed to no step of removing monocytes by an incubation on an adherent substrate before said transduction step. In another embodiment, the T cells and/or NK cells are not incubated with or exposed to a bovine serum, such as a cell culturing bovine serum, for example fetal bovine serum before or during the transdcution.

Because methods provided herein for adoptive cell therapy and related methods for modifying resting T cells and/or resting NK cells ex vivo before expanding them in vivo, can be performed in significantly less time than prior methods, fundamental improvements in patient care and safety as well as product manufacturability are made possible. Therefore, such processes are expected to be favorable in the view of regulatory agencies responsible for approving such processes when carried out in vivo for therapeutic purposes. For example, the subject in non-limiting examples, can remain in the same building (e.g. infusion clinic) or room as the instrument processing their blood or sample for the entire time that the sample is being processed before modified T cells and/or NK cells are reintroduced into the patient. In non-limiting illustrative embodiments, a subject remains within line of site and/or within 100, 50, 25, or 12 feet or arm's distance of their blood or cells that are being processed, for the entire method/process from blood draw/collection from the subject to reintroduction of blood to the subject after ex vivo transduction of T cells and/or NK cells. In other non-limiting illustrative embodiments, a subject remains awake and/or at least one person can continue to monitor the blood or cells of the subject that are being processed, throughout and/or continuously for the entire method/process from blood draw/collection from the subject to reintroduction of blood to the subject after ex vivo transduction of T cells and/or NK cells. Because of improvements provided herein, the entire method/process for adoptive cell therapy and/or for transducing resting T cells and/or NK cells from blood draw/collection from the subject to reintroduction of blood to the subject after ex vivo transduction of T cells and/or NK cells can be performed with continuous monitoring by a human. In other non-limiting illustrative embodiments, at no point the entire method/process from blood draw/collection from the subject to reintroduction of blood to the subject after ex vivo transduction of T cells and/or NK cells, are blood cells incubated in a room that does not have a person present. In other non-limiting illustrative embodiments, the entire method/process from blood draw/collection from the subject to reintroduction of blood to the subject after ex vivo transduction of T cells and/or NK cells, is performed next to the subject and/or in the same room as the subject and/or next to the bed or chair of the subject. Thus, sample identity mix-ups can be avoided, as well as long and expensive incubations over periods of days or weeks. This is further provided by the fact that methods provided herein are readily adaptable to closed and automated blood processing systems, where a blood sample and its components that will be reintroduced into the subject, only make contact with disposable, single-use components.

Methods for performing adoptive cell therapy provided herein, typically include 1) methods of transducing lymphocytes, such as T cell(s) or NK cell(s), which in illustrative embodiments are resting T cell(s) and/or NK cell(s), and/or include 2) methods for genetically modifying a lymphocyte such as T cell(s) and/or an NK cell(s), which in illustrative embodiments are resting T cell(s) and/or NK cell(s), both (1 and 2) of which themselves each form distinct aspects of the present disclosure. Such methods can be performed with or without other steps identified herein for performing adoptive cell therapy. A skilled artisan will recognize that details provided herein for transducing and/or genetically modifying T cell(s) and/or NK cell(s) can apply to any aspect that includes such step(s), including aspects that are directed to methods for transducing and/or genetically modifying a lymphocyte such as T cell(s) and/or NK cell(s). Accordingly, provided herein in certain aspects, is a method of transducing and/or genetically modifying a T cell and/or an NK cell, typically a resting T cell and/or resting NK cell, that includes contacting the resting T cell and/or resting NK cell with a replication incompetent recombinant retroviral particle, wherein the replication incompetent recombinant retroviral particle typically comprises a pseudotyping element on its surface that is capable of binding the resting T cell and/or NK cell and typically facilitating membrane fusion on its own or in conjunction with other protein(s)) of the replication incompetent recombinant retroviral particles thereto, wherein said contacting (and incubation under contacting conditions) facilitates transduction of the resting T cell and/or NK cell by the replication incompetent recombinant retroviral particles, thereby producing the genetically modified T cell and/or NK cell. Further embodiments of such a method can include any of the embodiments of replication incompetent recombinant retroviral particles, lymphoproliferative elements, CARs, pseudotyping elements, riboswitches, activation elements, membrane-bound cytokines, miRNAs, and/or other elements disclosed herein. Such a method for transducing a T cell and/or NK cell can be performed in vitro or ex vivo.

Accordingly, provided in one aspect herein is a method for transducing (and/or genetically modifying) lymphocytes, typically resting T cells and/or resting NK cells from isolated blood, comprising:

A. collecting blood from a subject;
  B. isolating peripheral blood mononuclear cells (PBMCs) comprising resting T cells and/or resting NK cells; and
  C. contacting the resting T cells and/or resting NK cells of the subject ex vivo, with replication incompetent recombinant retroviral particles, wherein the replication incompetent recombinant retroviral particles comprise a pseudotyping element on their surface that is capable of binding a resting T cell and/or resting NK cell and facilitating membrane fusion of the replication incompetent recombinant retroviral particles thereto, wherein said contacting facilitates transduction of at least 5% of the resting T cells and/or resting NK cells by the replication incompetent recombinant retroviral particles, thereby producing genetically modified T cells and/or NK cells, thereby transducing resting T cells and/or NK cells.

Accordingly, provided in another aspect herein is a method for genetically modifying or transducing a lymphocyte of a subject, in illustrative embodiments, a T cell and/or and NK cell or a population of T cells or NK cells, that includes contacting the T cell(s) and/or NK cell(s) of, typically of a subject ex vivo, with a replication incompetent recombinant retroviral particle comprising in its genome a polynucleotide comprising one or more nucleic acid sequences operatively linked to a promoter active in T cells and/or NK cells, wherein a first nucleic acid sequence of the one or more nucleic acid sequences encodes two or more inhibitory RNA molecules directed against one or more RNA targets and a second nucleic acid sequence of the one or more nucleic acid sequences encodes a chimeric antigen receptor (CAR) comprising an antigen-specific targeting region (ASTR), a transmembrane domain, and an intracellular activating domain, wherein said contacting facilitates transduction of the, or at least some of the resting T cells and/or NK cells by the replication incompetent recombinant retroviral particle, thereby producing a genetically modified T cell and/or NK cell.

Provided herein in another aspect is a method for genetically modifying or transducing a lymphocyte (e.g. a T cell or an NK cell) or a population thereof, of a subject, comprising contacting the lymphocyte (e.g. the T cell or NK cell) or a population thereof, of the subject ex vivo, with a replication incompetent recombinant retroviral particle comprising in its genome a polynucleotide comprising one or more nucleic acid sequences operatively linked to a promoter active in lymphocytes (e.g. T cells and/or NK cells), wherein a first nucleic acid sequence of the one or more nucleic acid sequences encodes one or more (e.g. two or more) inhibitory RNA molecules directed against one or more RNA targets and a second nucleic acid sequence of the one or more nucleic acid sequences encodes a chimeric antigen receptor (CAR) comprising an antigen-specific targeting region (ASTR), a transmembrane domain, and an intracellular activating domain, wherein said contacting facilitates genetic modification and/or transduction of the lymphocyte (e.g. T cell or NK cell), or at least some of the lymphocytes (e.g. T cells and/or NK cells) by the replication incompetent recombinant retroviral particle, thereby producing a genetically modified and/or transduced lymphocyte (e.g. T cell and/or NK cell).

In some embodiments of the method provided immediately above, the genetically modified and/or transduced lymphocyte (e.g. T cell and/or NK cell) or population thereof, is introduced into the subject. In some embodiments, the genetically modified and/or transduced lymphocyte (e.g. T cell and/or NK cell) or population thereof, undergoes 4 or fewer cell divisions ex vivo prior to being introduced or reintroduced into the subject. In some embodiments, the lymphocyte(s) are resting T cells and/or resting NK cells that are in contact with the replication incompetent recombinant retroviral particles for between 1 hour and 12 hours. In some embodiments, no more than 8 hours pass between the time blood is collected from the subject and the time the genetically modified T cells and/or NK cells are reintroduced into the subject. In some embodiments, all steps after the blood is collected and before the blood is reintroduced, are performed in a closed system in which a person monitors the closed system throughout the processing.

In any of the method aspects provided immediately above that include a polynucleotide comprising one or more nucleic acid sequences operatively linked to a promoter active in T cells and/or NK cells, wherein a first nucleic acid sequence of the one or more nucleic acid sequences encodes one or more (e.g. two or more) inhibitory RNA molecules directed against one or more RNA targets, and a second nucleic acid sequence of the one or more nucleic acid sequences encodes a chimeric antigen receptor (CAR) comprising an antigen-specific targeting region (ASTR), a transmembrane domain, and an intracellular activating domain, the polynucleotide may further include a third nucleic acid sequence that encodes at least one lymphoproliferative element that is not an inhibitory RNA molecule. In some embodiments, the lymphoproliferative element can be a cytokine or cytokine receptor polypeptide, or a fragment thereof comprising a signaling domain. In some embodiments, the lymphoproliferative element is constitutively active. In certain embodiments, the lymphoproliferative element can be an IL-7 receptor or a fragment thereof. In illustrative embodiments, the lymphoproliferative element can be a constitutively active IL-7 receptor or a constitutively active fragment thereof.

In any of the method aspects provided immediately above that include a polynucleotide comprising one or more nucleic acid sequences operatively linked to a promoter active in T cells and/or NK cells, wherein a first nucleic acid sequence of the one or more nucleic acid sequences encodes one or more (e.g. two or more) inhibitory RNA molecules directed against one or more RNA targets, an inhibitory RNA molecule can in some embodiments include a 5' strand and a 3' strand that are partially or fully complementary to one another, wherein said 5' strand and said 3' strand are capable of forming an 18-25 nucleotide RNA duplex. In some embodiments, the 5' strand can be 18, 19, 20, 21, 22, 23, 24, or 25 nucleotides in length, and the 3' strand can be 18, 19, 20, 21, 22, 23, 24, or 25 nucleotides in length. In some embodiments, the 5' strand and the 3' strand can be the same or different lengths. In some embodiments, the RNA duplex can include one or more mismatches. In alternate embodiments, the RNA duplex has no mismatches.

In any of the method aspects provided immediately above that include a polynucleotide comprising one or more nucleic acid sequences operatively linked to a promoter active in T cells and/or NK cells, wherein a first nucleic acid sequence of the one or more nucleic acid sequences encodes one or more (e.g. two or more) inhibitory RNA molecules directed against one or more RNA targets, an inhibitory RNA molecule can be a miRNA or an shRNA. In some embodiments, the inhibitory molecule can be a precursor of a miRNA, such as for example, a Pri-miRNA or a Pre-miRNA, or a precursor of an shRNA. In some embodiments, the inhibitory molecule can be an artificially derived miRNA or shRNA. In other embodiments, the inhibitory RNA molecule can be a dsRNA (either transcribed or artificially introduced) that is processed into an siRNA or the siRNA itself. In some embodiments, the inhibitory RNA molecule can be a miRNA or shRNA that has a sequence that is not found in nature, or has at least one functional segment that is not found in nature, or has a combination of functional segments that are not found in nature. In illustrative embodiments, at least one or all of the inhibitory RNA molecules are miR-155.

In any of the method aspects provided immediately above that include a polynucleotide comprising one or more nucleic acid sequences operatively linked to a promoter active in T cells and/or NK cells, wherein a first nucleic acid sequence of the one or more nucleic acid sequences encodes one or more (e.g. two or more) inhibitory RNA molecules directed against one or more RNA targets, an inhibitory RNA molecule, in some embodiments, can comprises from 5' to 3' orientation: a 5' arm, a 5' stem, a loop, a 3' stem that is partially or fully complementary to said 5' stem, and a 3' arm. In some embodiments, at least one of two or more inhibitory RNA molecules has this arrangement. In other embodiments, all of two or more inhibitory molecules have this arrangement. In some embodiments, the 5' stem can be 18, 19, 20, 21, 22, 23, 24 or 25 nucleotides in length. In some embodiments, the 3' stem can be 18, 19, 20, 21, 22, 23, 24, or 25 nucleotides in length. In some embodiments, the loop can be 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides in length. In some embodiments, the 5' arm, 3' arm, or both, are derived from a naturally occurring miRNA. In some embodiments, the 5' arm, 3' arm, or both, are derived from a naturally occurring miRNA is selected from the group consisting of: miR-155, miR-30, miR-17-92, miR-122, and miR-21. In illustrative embodiments, the 5' arm, 3' arm, or both are derived from miR-155. In some embodiments, the 5' arm, 3' arm, or both are derived from *Mus musculus* miR-155 or *Homo sapiens* miR-155. In some embodiments, the 5' arm has the sequence set forth in SEQ ID NO:256 or is a functional variant thereof, such as, for example, a sequence that is the same length as SEQ ID NO:256, or 95%, 90%, 85%, 80%, 75%, or 50% as long as SEQ ID NO: 256 or is 100 nucleotides or less, 95 nucleotides or less, 90 nucleotides or less, 85 nucleotides or less, 80 nucleotides or less, 75 nucleotides or less, 70 nucleotides or less, 65 nucleotides or less, 60 nucleotides or less, 55 nucleotides or less, 50 nucleotides or less, 45 nucleotides or less, 40 nucleotides or less, 35 nucleotides or less, 30 nucleotides or less, or 25 nucleotides or less; and is at least 50%, 55%, 60%, 65%, 70%, 75%, 80%, 85%, 90%, or 95% identical to SEQ ID NO:256. In some embodiments, the 3' arm has the sequence set forth in SEQ ID NO:260 or is a functional variant thereof, such as, for example, the same length as SEQ ID NO:260, or 95%, 90%, 85%, 80%, 75%, or 50% as long as SEQ ID NO: 260 or is a sequence that is 100 nucleotides or less, 95 nucleotides or less, 90 nucleotides or less, 85 nucleotides or less, 80 nucleotides or less, 75 nucleotides or less, 70 nucleotides or less, 65 nucleotides or less, 60 nucleotides or less, 55 nucleotides or less, 50 nucleotides or less, 45 nucleotides or less, 40 nucleotides or less, 35 nucleotides or less, 30 nucleotides or less, or 25 nucleotides or less; and is at least 50%, 55%, 60%, 65%, 70%, 75%, 80%, 85%, 90%, or 95% identical to SEQ ID NO:260. In some embodiments, the 3' arm comprises nucleotides 221-283 of the *Mus musculus* BIC.

In any of the method aspects provided immediately above that include a polynucleotide comprising one or more nucleic acid sequences operatively linked to a promoter active in T cells and/or NK cells, wherein a first nucleic acid sequence of the one or more nucleic acid sequences encodes two or more inhibitory RNA molecules directed against one or more RNA targets, the two or more inhibitory RNA molecules, in some embodiments, can be positioned in the first nucleic acid sequence in series. In some embodiments, the inhibitory RNA molecules can be adjoined to one another either directly or indirectly by non-functional linker sequence(s). In some embodiments, the linker sequences can be between 5 and 120 nucleotides in length, or between 10 and 40 nucleotides in length.

In any of the method aspects provided immediately above that include a polynucleotide comprising one or more nucleic acid sequences operatively linked to a promoter active in T cells and/or NK cells, wherein a first nucleic acid sequence of the one or more nucleic acid sequences encodes two or more inhibitory RNA molecules directed against one or more RNA targets, in some embodiments, the first nucleic acid sequence encodes two to four inhibitory RNA molecules. In illustrative embodiments, between 2 and 10, 2 and 8, 2 and 6, 2 and 5, 2 and 4, 3 and 5, or 3 and 6 inhibitory RNA molecules are included in the first nucleic acid sequence. In an illustrative embodiment, four inhibitory RNA molecules are included in the first nucleic acid sequence.

In any of the method aspects provided immediately above that include a polynucleotide comprising one or more nucleic acid sequences operatively linked to a promoter active in T cells and/or NK cells, wherein a first nucleic acid sequence of the one or more nucleic acid sequences encodes one or more (e.g. two or more) inhibitory RNA molecules directed against one or more RNA targets, the one or more (e.g. two or more) inhibitory RNA molecules can be in an intron. In some embodiments, the intron is in a promoter. In illustrative embodiments, the intron is EF-1alpha intron A. In some embodiments, the intron is adjacent to and downstream of a promoter, which in illustrative embodiments, is inactive in a packaging cell used to produce the replication incompetent recombinant retroviral particle.

In any of the method aspects provided immediately above that include a polynucleotide comprising one or more nucleic acid sequences operatively linked to a promoter active in T cells and/or NK cells, wherein a first nucleic acid sequence of the one or more nucleic acid sequences encodes two or more inhibitory RNA molecules directed against one or more RNA targets, the two or more inhibitory RNA molecules, in some embodiments, can be directed against different targets. In an alternate embodiment, the two or more inhibitory RNA molecules are directed against the same target. In some embodiments, the RNA targets are mRNAs transcribed from genes that are expressed by T cells such as but not limited to PD-1 (prevent inactivation); CTLA4 (prevent inactivation); TCRa (safety—prevent autoimmunity); TCRb (safety—prevent autoimmunity); CD3Z (safety—prevent autoimmunity); SOCS1 (prevent inactivation); SMAD2 (prevent inactivation); a miR-155 target (promote activation); IFN gamma (reduce CRS); cCBL (prolong signaling); TRAIL2 (prevent death); PP2A (prolong signaling); ABCG1 (increase cholesterol microdomain content by limiting clearance of cholesterol). In some embodiments, the RNA targets are mRNAs transcribed from genes that encode components of the T cell receptor (TCR) complex. In some embodiments, at least one of the two or more of inhibitory RNA molecules can decrease expression of T cell receptors, in illustrative embodiments, one or more endogenous T cell receptor(s) of a T cell. In certain embodiments, the RNA target can be mRNA transcribed from the endogenous TCRα or TCRβ gene of the T cell whose genome comprises the first nucleic acid sequence encoding the one or more miRNAs. In illustrative embodiments, the RNA target is mRNA transcribed from the TCRα gene.

In any of the method aspects provided immediately above that include a polynucleotide comprising one or more nucleic acid sequences operatively linked to a promoter active in T cells and/or NK cells, wherein a first nucleic acid sequence of the one or more nucleic acid sequences encodes one or more (e.g. two or more) inhibitory RNA molecules directed against one or more RNA targets, and a second nucleic acid sequence of the one or more nucleic acid sequences encodes a chimeric antigen receptor (CAR) comprising an antigen-specific targeting region (ASTR), a transmembrane domain, and an intracellular activating domain, in some embodiments, the CAR is a microenvironment restricted biologic (MRB)-CAR. In other embodiments, the ASTR of the CAR binds to a tumor associated antigen. In other embodiments, the ASTR of the CAR is a microenvironment-restricted biologic (MRB)-ASTR.

In any of the method aspects provided immediately above that include a polynucleotide comprising one or more nucleic acid sequences operatively linked to a promoter active in T cells and/or NK cells, wherein a first nucleic acid sequence of the one or more nucleic acid sequences encodes one or more (e.g. two or more) inhibitory RNA molecules directed against one or more RNA targets, and a second nucleic acid sequence of the one or more nucleic acid sequences encodes a chimeric antigen receptor (CAR) comprising an antigen-specific targeting region (ASTR), a transmembrane domain, and an intracellular activating domain, and in some instances a third nucleic acid sequence of the one or more nucleic acid sequences that encodes at least one lymphoproliferative element that is not an inhibitory RNA molecule, in some embodiments, any or all of the first nucleic acid sequence, second nucleic acid sequence, and third nucleic acid sequence is operably linked to a riboswitch. In some embodiments, the riboswitch is capable of binding a nucleoside analog. In some embodiments, the nucleoside analog is an antiviral drug.

In methods for adoptive cell therapy and any method provided herein that include transducing resting T cells and/or resting NK cells ex vivo, typically, neutrophils/granulocytes are separated away from the blood cells before the cells are contacted with replication incompetent recombinant retroviral particles. In some embodiments, peripheral blood mononuclear cells (PBMCs) including peripheral blood lymphocytes (PBLs) such as T cell and/or NK cells, are isolated away from other components of a blood sample using for example, apheresis, and/or density gradient centrifugation. In some embodiments, neutrophils are removed before PBMCs and/or T cells and/or NK cells are processed, contacted with a replication incompetent recombinant retroviral particle, transduced, or transfected. With reference to the subject to be treated, the cells may be allogeneic and/or autologous.

As non-limiting examples, in some embodiments, for performing the PBMCs are isolated using a Sepax or Sepax 2 cell processing system (BioSafe). In some embodiments, the PBMCs are isolated using a CliniMACS Prodigy cell processor (Miltenyi Biotec). In some embodiments, an automated apheresis separator is used which takes blood from the subject, passes the blood through an apparatus that sorts out a particular cell type (such as, for example, PBMCs), and returns the remainder back into the subject. Density gradient centrifugation can be performed after apheresis. In some embodiments, the PBMCs are isolated using a leukoreduction filter device. In some embodiments, magnetic bead activated cell sorting is then used for purifying a specific cell population from PBMCs, such as, for example, PBLs or a subset thereof, according to a cellular phenotype (i.e. positive selection). Other methods for purification can also be used, such as, for example, substrate adhesion, which utilizes a substrate that mimics the environment that a T cell encounters during recruitment, allowing them to adhere and migrate, or negative selection, in which unwanted cells are targeted for removal with antibody complexes that target the unwanted cells. In some embodiments, red blood cell rosetting can be used to purify cells.

In some illustrative embodiments of any of the relevant aspects herein, the PBLs include T cells and/or NK cells. The T cells and/or NK cells that are contacted by replication incompetent recombinant retroviral particles of the present disclosure during certain embodiments herein, for example in methods of modifying lymphocytes and methods of performing adoptive cellular therapy, are mainly resting T cells. In some embodiments, the T cells and/or NK cells consist of between 95 and 100% resting cells (Ki-67$^-$). In some embodiments, the T cell and/or NK cells that are contacted by replication incompetent recombinant retroviral particles include between 90, 91, 92, 93, 94, and 95% resting cells on the low end of the range and 96, 97, 98, 99, or 100% resting cells on the high end of the range. In some embodiments, the T cells and/or NK cells include naïve cells.

In some embodiments of the methods and compositions disclosed herein, T cells and/or NK cells are contacted ex vivo with replication incompetent recombinant retroviral particles to genetically modify T cells and/or NK cells to illicit a targeted immune response in the subject when reintroduced into the subject. During the period of contact, the replication incompetent recombinant retroviral particles identify and bind to T cells and/or NK cells at which point the retroviral and host cell membranes start to fuse. Then, through the process of transduction, genetic material from the replication incompetent recombinant retroviral particles enters the T cells and/or NK cells and is incorporated into the host cell DNA. Methods of lentiviral transduction are known. Exemplary methods are described in, e.g., Wang et al. (2012) J. Immunother. 35(9): 689-701; Cooper et al. (2003) Blood. 101:1637-1644; Verhoeyen et al. (2009) Methods Mol Biol. 506: 97-114; and Cavalieri et al. (2003) Blood. 102(2): 497-505.

Many of the methods provided herein include transduction of T cells and/or NK cells. Methods are known in the art for transducing T cells and/or NK cells ex vivo with replication incompetent recombinant retroviral particles, such as replication incompetent recombinant lentiviral particles. Methods provided herein, in illustrative embodiments, do not require ex vivo stimulation or activation. Thus, this common step in prior methods can be avoided in the present method, although ex vivo stimulatory molecule(s) such as anti-CD3 and/or anti-CD28 beads, can be present during the transduction. However, with illustrative methods provided herein, ex vivo stimulation is not required. In certain exemplary methods, between 3 and 10 multiplicity of infection (MOI), and in some embodiments, between 5 and 10 MOI units of replication incompetent recombinant retroviral particles, for example lentivirus, can be used.

The transduction reaction can be carried out in a closed system, such as a Sepax system, as discussed herein, wherein the transduction reaction can be carried out in disposable bags loaded on the system. Blood cells, such as PBMCs, from the collected blood sample from the subject, can be contacted with replication incompetent recombinant retroviral particles disclosed herein, in a bag as soon as these blood cells are separated, isolated, and/or purified away from granulocytes, including neutrophils, which are typically not present during the contacting step (i.e. the transduction reaction).

The replication incompetent recombinant retroviral particles can be introduced into the bag that contains the isolated PBMCs, thereby contacting the PBMCs. The time from blood collection from the subject to the time when blood cells, such as PBMCs are added to the transduction reaction bag, can be between 30 minutes and 4 hours, between 30 minutes and 2 hours, or around 1 hour, in some examples. Additives such as media, human serum albumin, human AB+ serum, and/or serum derived from the subject can be added to the transduction reaction mixture. Media is typically present, such as those known in the art for ex vivo processes (as non-limiting examples, X-VIVO 15 (Lonza) or CTS media (Thermo Fisher Scientific). Supportive cytokines can be added to the transduction reaction mixture, such as IL2, IL7, or IL15, or those found in HSA.

The transduction reaction mixture can be incubated at between 23 and 39° C., and in some illustrative embodiments at 37° C. In certain embodiments, the transduction reaction can be carried out at 37-39° C. for faster fusion/transduction. dGTP can be added to the transduction reaction. The transduction reaction mixture can be incubated for 1 to 12 hours, and in some embodiments, 6 to 12 hrs. After transduction, before the transduced T cells and/or NK cells are infused back into the subject, the cells are washed out of the transduction reaction mixture. For example, the system, such as a Sepax instrument, can be used to wash cells, for example with 10-50 ml of wash solution, before the transduced cells are infused back into the subject. In some embodiments, neutrophils are removed before PBMCs and/or T cells and/or NK cells are processed, contacted with replication incompetent recombinant retroviral particles, transduced, or transfected.

In an illustrative embodiment for performing adoptive cell therapy, blood is collected from a subject into a blood bag and the blood bag is attached to a cell processing system such as a Sepax cell processing system. PBMCs isolated using the cell processing system are collected into a bag, contacted with the replication incompetent recombinant retroviral particles in conditions sufficient to transduce T cells and/or NK cells, and incubated. After incubation, the bag containing the mixture of PBMCs and replication incompetent recombinant retroviral particles is attached to a cell processing system and the PBMCs are washed. The washed PBMCs are collected into a bag and reinfused into the subject. In some embodiments, the entire method, from collecting blood to reinfusing transduced T and/or NK cells, is performed within 1, 2, 3, 4, 5, 6, 7, 8, 9, 10, 11, 12, 15, 18, or 24 hours. In illustrative embodiments, the entire method is performed within 12 hours.

In some embodiments, the target cells for the replication incompetent recombinant retroviral particles are PBLs. In some embodiments, the target cells are T cells and/or NK cells. In some embodiments, the T cells are helper T cells and/or killer T cells.

In some embodiments, the replication incompetent recombinant retroviral particles provided herein have pseudotyping elements on their surface that are capable of binding to T cells and/or NK cells and facilitating membrane fusion of the replication incompetent recombinant retroviral particles thereto. In other embodiments, the replication incompetent recombinant retroviral particles have activation elements on their surface that are capable of binding to resting T cells and/or NK cells. In still other embodiments, the replication incompetent recombinant retroviral particles have membrane-bound cytokines on their surface. In some embodiments, the replication incompetent recombinant retroviral particles include a polynucleotide having one or more transcriptional units encoding one or more engineered signaling polypeptides, one or more of which includes one or more lymphoproliferative elements. In other embodiments, when two signaling polypeptides are utilized, one includes at least one lymphoproliferative element and the other is typically a chimeric antigen receptor (CAR) that includes an antigen-specific targeting region (ASTR), a transmembrane domain, and an intracellular activating domain. As indicated herein, an activation element(s) that is typically associated with the surface of a replication incompetent recombinant retroviral particle provided herein, is capable of, and as a resulting of contacting resting T cells and/or NK cells for a sufficient period of time and under appropriate conditions, activates resting T cells and/or NK cells. It will be understood that such activation occurs over time during a contacting step of methods herein. Furthermore, it will be understood that in some embodiments where a pseudotyping element is found on the surface of a replication incompetent recombinant retroviral particle, that binds a T cell and/or an NK cell, in methods herein, activation can be induced by binding of the pseudotyping element. An activation element is optional in those embodiments.

Further details regarding a pseudotyping element, an activation element, a membrane-bound cytokine, an engineered signaling polypeptide, a lymphoproliferative element, and a CAR are provided in other sections herein.

In some embodiments of the methods and compositions disclosed herein, between 5% and 90% of the total lymphocytes collected from the blood are transduced. In some embodiments, the percent of lymphocytes that are transduced is between 5, 10, 15, 20, 25, 30, 35, 40, 45, 50, 55, and 60% on the low end of the range, and 50, 55, 60, 65, 70, 75, 80, 85, and 90% on the high end of the range. In some embodiments, the percent of lymphocytes that are transduced is at least 5%, at least 10%, at least 15%, at least 20%, at least 25%, at least 30%, at least 35%, at least 40%, at least 45%, at least 50%, at least 55%, or at least 60%.

In some embodiments of the methods and compositions disclosed herein, the genetically modified T cells and/or NK cells are introduced back, reintroduced, or reinfused into the subject without additional ex vivo manipulation, such as stimulation and/or activation of T cells and/or NKs. In the prior art methods, ex vivo manipulation is used for stimulation/activation of T cells and/or NK cells and for expansion of genetically modified T cells and/or NK cells prior to introducing the genetically modified T cells and/or NK cells into the subject. In prior art methods, this generally takes days or weeks and requires a subject to return to a clinic for a blood infusion days or weeks after an initial blood draw. In some embodiments of the methods and compositions disclosed herein, T cells and/or NK cells are not stimulated ex vivo by exposure to anti-CD3/anti-CD28 solid supports such as, for example, beads coated with anti-CD3/anti-CD28, prior to contacting the T cells and/or NK cells with the replication incompetent recombinant retroviral particles. As such provided herein is an ex vivo propagation-free method. In other embodiments, genetically modified T cells and/or NK cells are not expanded ex vivo, or only expanded for a small number of cell divisions (e.g. 1, 2, 3, 4, 5, 6, 7, 8, 9, or 10 rounds of cell division), but are rather expanded, or predominantly expanded, in vivo, i.e. within the subject. In some embodiments, no additional media is added to allow for further expansion of the cells. In some embodiments, no cell manufacturing of the PBLs occurs while the PBLs are contacted with the replication incompetent recombinant retroviral particles. In illustrative embodiments, no cell manufacturing of the PBLs occurs while the PBLs are ex vivo. In previous methods of adoptive cell therapy, subjects were lymphodepleted prior to reinfusion with genetically modified T cells and or NK cells. In some embodiments, patients or subjects are not lymphodepleted prior to blood being withdrawn. In some embodiments, patients or subjects are not lymphodepleted prior to reinfusion with genetically modified T cells and or NK cells.

In any of the embodiments disclosed herein, the number of T cells and/or NK cells to be reinfused into a subject can be between $1\times10^3$, $2.5\times10^3$, $5\times10^3$, $1\times10^4$, $2.5\times10^4$, $5\times10^4$, $1\times10^5$, $2.5\times10^5$, $5\times10^5$, $1\times10^6$, $2.5\times10^6$, $5\times10^6$, and $1\times10^7$ cells/kg on the low end of the range and $5\times10^4$, $1\times10^5$, $2.5\times10^5$, $5\times10^5$, $1\times10^6$, $2.5\times10^6$, $5\times10^6$, $1\times10^7$, $2.5\times10^7$, $5\times10^7$, and $1\times10^8$ cells/kg on the high end of the range. In illustrative embodiments, the number of T cells and/or NK cells to be reinfused into a subject can be between $1\times10^4$, $2.5\times10^4$, $5\times10^4$, and $1\times10^5$ cells/kg on the low end of the range and $2.5\times10^4$, $5\times10^4$, $1\times10^5$, $2.5\times10^5$, $5\times10^5$, and $1\times10^6$ cells/kg on the high end of the range. In some embodiments, the number of PBLs to be reinfused into a subject can be fewer than $5\times10^5$, $1\times10^6$, $2.5\times10^6$, $5\times10^6$, $1\times10^7$, $2.5\times10^7$, $5\times10^7$, and $1\times10^8$ cells and the low end of the range and $2.5\times10^6$, $5\times10^6$, $1\times10^7$, $2.5\times10^7$, $5\times10^7$, $1\times10^8$, $2.5\times10^8$, $5\times10^8$, and $1\times10^9$ cells on the high end of the range. In some embodiments, the number of T cells and/or NK cells available for reinfusion into a 70 kg subject or patient is between $7\times10^5$ and $2.5\times10^8$ cells. In other embodiments, the number of T cells and/or NK cells available for transduction is approximately $7\times10^6$ plus or minus 10%.

In the methods disclosed herein, the entire adoptive cell therapy procedure, from withdrawing blood to the reinfusion of genetically modified T cells and/or NK cells, can advantageously be performed in a shorter time than previous methods. In some embodiments, the entire adoptive cell therapy procedure can be performed in less than 1, 2, 3, 4, 5, 6, 7, 8, 9, 10, 11, 12, 15, 18, or 24 hours. In illustrative embodiments, the entire adoptive cell therapy procedure can be performed in less than 1, 2, 3, 4, 5, 6, 7, 8, 9, 10, 11, or 12 hours. In some embodiments, the entire adoptive cell therapy procedure can be performed in between 1, 2, 3, 4, 5, 6, 7, 8, 9, 10, 11, 12, or 15 hours on the low end of the range and 1, 2, 3, 4, 5, 6, 7, 8, 9, 10, 11, 12, 15, 18, or 24 hours on the high end of the range.

In some embodiments provided herein, the steps of withdrawing a blood sample from a subject, contacting T cells and/or NK cells with replication incompetent recombinant retroviral particles, and/or introducing genetically modified T cells and/or NK cells into the subject, occur in a closed system. A closed system is a culture process that is generally closed or fully closed to contamination. An advantage of the present invention, is that provided herein are methods for performing CAR therapy in a closed system. One of the greatest risks to safety and regulatory control in the cell processing procedure is the risk of contamination through frequent exposure to the environment as is found in traditional open cell culture systems. To mitigate this risk, particularly in the absence of antibiotics, some commercial processes have been developed that focus on the use of disposable (single-use) equipment. However even with their use under aseptic conditions, there is always a risk of contamination from the opening of flasks to sample or add additional growth media. To overcome this problem, provided herein is a closed-system process, a process that is designed and can be operated such that the product is not exposed to the outside environment. This is important because the outside environment is typically not sterile. Material transfer occurs via sterile connections or tube welding. Air for gas exchange occurs via a gas permeable membrane or like other additions, via 0.2 µm filter to prevent environmental exposure.

In some embodiments, the closed system includes an ex vivo circulating system connected to the in vivo circulatory system of the subject such that blood is drawn and then circulated to the ex vivo circulatory system before being introduced back into the subject. In some embodiments, the ex vivo circulatory system includes a system or apparatus for isolating PBLs and/or a system or apparatus for isolating T cells and/or NK cells, in combination with the system or apparatus for exposing the cells to the replication incompetent recombinant retroviral particles. In some embodiments, the closed system does not allow the T cells and/or NK cells to be exposed to air.

Such closed system methods can be performed with commercially available devices. For example, the method can be carried out in devices adapted for closed system T cell production. Such devices include a G-Rex™, a WAVE Bioreactor™, an OriGen PermaLife™ bags, and a VueLife® bags.

In some embodiments of the methods and compositions disclosed herein, genetically modified T cells and/or NK cells within a subject are exposed to a compound that binds to an in vivo control element present therein, in which the control element is a part of the genetic material introduced by the replication incompetent recombinant retroviral particles. In some embodiments, the control element can be a riboswitch and the compound can bind the aptamer domain of the riboswitch. In some embodiments, the control element can be a molecular chaperone. In any of the embodiments disclosed herein, the compound can be a nucleoside analogue. In some embodiments, the nucleoside analogue can be a nucleoside analogue antiviral drug, wherein an antiviral drug is a compound approved by the Food and Drug Administration for antiviral treatment or a compound in an antiviral clinical trial in the United States. In illustrative embodiments, the compound can be acyclovir or penciclovir. In some embodiments, the compound can be famciclovir, the oral prodrug of penciclovir, or valaciclovir, the oral prodrug of acyclovir. Binding of the compound to the control element affects expression of the introduced genetic material and hence, propagation of genetically modified T cells and/or NK cells.

In some embodiments, the nucleoside analogue antiviral drug or prodrug, for example acyclovir, valaciclovir, penciclovir or famciclovir, is administered to the subject prior to, concurrent with, and/or following PBLs being isolated from the blood of the subject and before T cells and/or NK cells are contacted with replication incompetent recombinant retroviral particles. In some embodiments, the nucleoside analogue antiviral drug or prodrug is administered to the subject for between 5, 10, 15, 30, and 60 minutes on the low end of the range and 1.5, 2, 3, 4, 5, 6, 8, 12, or 24 hours on the high end of the range prior to PBLs being isolated from the blood or prior to T cells and/or NK cells being contacted with replication incompetent recombinant retroviral particles. In other embodiments, the nucleoside analogue antiviral drug or prodrug is administered to the subject for between 1.5, 2, 3, 4, 5, 6, 8, 12, or 24 hours on the low end of the range and ½, 1, 2, 3, 4, 5, 6, 7, 10, 14, 21, or 28 days on the high end of the range after PBLs are isolated from the blood and T cells and/or NK cells are contacted with replication incompetent recombinant retroviral particles in methods provided herein. In some embodiments, the nucleoside analogue antiviral drug or prodrug is administered to the subject for at least 1.5, 2, 3, 4, 5, 6, 8, 12, or 24 hours, or at least 2, 3, 4, 5, 6, 7, 10, 14, 21, or 28 days after PBLs are isolated from the blood and T cells and/or NK cells are contacted with replication incompetent recombinant retroviral particles in methods provided herein. In some embodiments, the nucleoside analogue antiviral drug or prodrug is administered to the subject for at least 1, 2, 3, 4, 5, 7, 10, 14, 21, 28, 30, 60, 90, or 120 days or 5, 6, 9, 12, 24, 36, 48, 60, 72, 84, 96, 120 months or indefinitely after the PBLs have been reinfused into the subject. In any of the embodiments disclosed herein, the nucleoside analogue antiviral drug or prodrug can be administered before and/or during the reinfusion of the PBLs and/or after the PBLs have been reinfused.

In some embodiments, the compound that binds to the control element is administered once, twice, three times, or four times daily to the subject. In some embodiments, daily doses of the compound are provided for 1 week, 2 weeks, 4 weeks, 3 months, 6 months, 1 year, until a subject is disease free, such as cancer free, or indefinitely. The drug, in illustrative embodiments is a nucleoside analogue antiviral drug that binds to a nucleoside analog, such as a riboswitch, as disclosed in further detail herein.

Methods are known in the art for delivering drugs, whether small molecules or biologics, and can be used in methods provided herein. Any such methods can be used to deliver drugs or candidate compounds or antibodies for use in methods of the present invention. For example, common routes of administration include non-invasive peroral (through the mouth), topical (skin), transmucosal (nasal, buccal/sublingual, vaginal, ocular and rectal) and inhalation routes. Many protein and peptide drugs, such as monoclonal antibodies, have to be delivered by injection or a nanoneedle array. For example, many immunizations are based on the delivery of protein drugs and are often done by injection.

Engineered Signaling Polypeptide(s)

In some embodiments, the replication incompetent recombinant retroviral particles used to contact T cells and/or NK cells have a polynucleotide having one or more transcriptional units that encode one or more engineered signaling polypeptides, one or more of which includes at least one lymphoproliferative element. In some embodiments, a signaling polypeptide includes any combination of the following: an extracellular antigen-binding domain (or antigen-specific targeting region or ASTR), a stalk, a transmembrane domain, an intracellular activating domain, a lymphoproliferative element, a modulatory domain (such as a co-stimulatory domain), and a T cell survival motif. In illustrative embodiments, at least one, two, or all of the engineered signaling polypeptides is a CAR. In some embodiments, when two signaling polypeptides are utilized, one encodes one or more lymphoproliferative elements and the other encodes a chimeric antigen receptor (CAR) that includes an antigen-specific targeting region (ASTR), a transmembrane domain, and an intracellular activating domain. In other embodiments, a CAR can include a lymphoproliferative element fused to an antigen-specific targeting region. In other embodiments, when the lymphoproliferative element is a constitutively active interleukin receptor, such as a known variant of IL-7Rα, no antigen-specific targeting region is needed because binding is not dependent on the presence of the ligand. One of ordinary skill in the art would be able to reconfigure the system to put the lymphoproliferative element and the CAR on distinct polynucleotides with similar or dissimilar control elements for the methods and compositions disclosed herein. A skilled artisan will recognize that such engineered polypeptides can also be referred to as recombinant polypeptides.

Antigen-Specific Targeting Region

In some embodiments, an engineered signaling polypeptide includes a member of a specific binding pair, which is typically an ASTR, sometimes called an antigen binding domain herein. Specific binding pairs include, but are not limited to, antigen-antibody binding pairs; ligand-receptor binding pairs; and the like. Thus, a member of a specific binding pair suitable for use in an engineered signaling polypeptide of the present disclosure includes an ASTR that is an antibody, an antigen, a ligand, a receptor binding domain of a ligand, a receptor, a ligand binding domain of a receptor, and an affibody.

An ASTR suitable for use in an engineered signaling polypeptide of the present disclosure can be any antigen-binding polypeptide. In certain embodiments, the ASTR is an antibody such as a full-length antibody, a single-chain antibody, an Fab fragment, an Fab' fragment, an (Fab')2 fragment, an Fv fragment, and a divalent single-chain antibody or a diabody.

In some embodiments, the ASTR is a single chain Fv (scFv). In some embodiments, the heavy chain is positioned N-terminal of the light chain in the engineered signaling polypeptide. In other embodiments, the light chain is positioned N-terminal of the heavy chain in the engineered signaling polypeptide. In any of the disclosed embodiments, the heavy and light chains can be separated by a linker as discussed in more detail herein. In any of the disclosed embodiments, the heavy or light chain can be at the N-terminus of the engineered signaling polypeptide and is typically C-terminal of another domain, such as a signal sequence or peptide.

Other antibody-based recognition domains (cAb VHH (camelid antibody variable domains) and humanized versions, IgNAR VH (shark antibody variable domains) and humanized versions, sdAb VH (single domain antibody variable domains) and "camelized" antibody variable domains are suitable for use with the engineered signaling polypeptides and methods using the engineered signaling polypeptides of the present disclosure. In some instances, T cell receptor (TCR) based recognition domains such as single chain TCR (scTv, single chain two-domain TCR containing VαVβ) are also suitable for use.

In some embodiments, the ASTR can be multispecific, e.g. bispecific antibodies. Multispecific antibodies have binding specificities for at least two different sites. In certain embodiments, one of the binding specificities is for one target antigen and the other is for another target antigen. In certain embodiments, bispecific antibodies may bind to two different epitopes of to target antigen. Bispecific antibodies may also be used to localize cytotoxic agents to cells which express a target antigen. Bispecific antibodies can be prepared as full length antibodies or antibody fragments.

An ASTR suitable for use in an engineered signaling polypeptide of the present disclosure can have a variety of antigen-binding specificities. In some cases, the antigen-binding domain is specific for an epitope present in an antigen that is expressed by (synthesized by) a target cell. In one example, the target cell is a cancer cell associated antigen. The cancer cell associated antigen can be an antigen associated with, e.g., a breast cancer cell, a B cell lymphoma, a Hodgkin lymphoma cell, an ovarian cancer cell, a prostate cancer cell, a mesothelioma, a lung cancer cell (e.g., a small cell lung cancer cell), a non-Hodgkin B-cell lymphoma (B-NHL) cell, an ovarian cancer cell, a prostate cancer cell, a mesothelioma cell, a lung cancer cell (e.g., a small cell lung cancer cell), a melanoma cell, a chronic lymphocytic leukemia cell, an acute lymphocytic leukemia cell, a neuroblastoma cell, a glioma, a glioblastoma, a medulloblastoma, a colorectal cancer cell, etc. A cancer cell associated antigen may also be expressed by a non-cancerous cell.

Non-limiting examples of antigens to which an ASTR of an engineered signaling polypeptide can bind include, e.g., CD19, CD20, CD38, CD30, ERBB2, CA125, MUC-1, prostate-specific membrane antigen (PSMA), CD44 surface adhesion molecule, mesothelin, carcinoembryonic antigen (CEA), epidermal growth factor receptor (EGFR), EGFRvIII, vascular endothelial growth factor receptor-2 (VEGFR2), high molecular weight-melanoma associated antigen (HMW-MAA), MAGE-A1, IL-13R-a2, GD2, Ax1, Ror2, and the like.

In some cases, a member of a specific binding pair suitable for use in an engineered signaling polypeptide is an ASTR that is a ligand for a receptor. Ligands include, but are not limited to, cytokines (e.g., IL-13, etc.); growth factors (e.g., heregulin; vascular endothelial growth factor (VEGF); and the like); an integrin-binding peptide (e.g., a peptide comprising the sequence Arg-Gly-Asp); and the like.

Where the member of a specific binding pair in an engineered signaling polypeptide is a ligand, the engineered signaling polypeptide can be activated in the presence of a second member of the specific binding pair, where the second member of the specific binding pair is a receptor for the ligand. For example, where the ligand is VEGF, the second member of the specific binding pair can be a VEGF receptor, including a soluble VEGF receptor.

As noted above, in some cases, the member of a specific binding pair that is included in an engineered signaling polypeptide is an ASTR that is a receptor, e.g., a receptor for a ligand, a co-receptor, etc. The receptor can be a ligand-binding fragment of a receptor. Suitable receptors include, but are not limited to, a growth factor receptor (e.g., a VEGF receptor); a killer cell lectin-like receptor subfamily K, member 1 (NKG2D) polypeptide (receptor for MICA, MICB, and ULB6); a cytokine receptor (e.g., an IL-13 receptor; an IL-2 receptor; etc.); CD27; a natural cytotoxicity receptor (NCR) (e.g., NKP30 (NCR3/CD337) polypeptide (receptor for HLA-B-associated transcript 3 (BAT3) and B7-H6); etc.); etc.

Stalk

In some embodiments, the engineered signaling polypeptide includes a stalk which is located in the portion of the engineered signaling polypeptide lying outside the cell and interposed between the ASTR and the transmembrane domain. In some cases, the stalk has at least 85, 90, 95, 96, 97, 98, 99, or 100% identity to a wild-type CD8 stalk region (TTTPAPRPPTPAPTIASQPLSLRPEACRPAAGG AVHTRGLDFA (SEQ ID NO:79), has at least 85, 90, 95, 96, 97, 98, 99, or 100% identity to a wild-type CD28 stalk region (FCKIEVMYPPPYLD-NEKSNGTIIHVKGKHLCPSPLFPGPSKP (SEQ ID NO:80)), or has at least 85, 90, 95, 96, 97, 98, 99, or 100% identity to a wild-type immunoglobulin heavy chain stalk region. In an engineered signaling polypeptide, the stalk employed allows the antigen-specific targeting region, and typically the entire engineered signaling polypeptide, to retain increased binding to a target antigen.

The stalk region can have a length of from about 4 amino acids to about 50 amino acids, e.g., from about 4 aa to about 10 aa, from about 10 aa to about 15 aa, from about 15 aa to about 20 aa, from about 20 aa to about 25 aa, from about 25 aa to about 30 aa, from about 30 aa to about 40 aa, or from about 40 aa to about 50 aa.

In some cases, the stalk of an engineered signaling polypeptide includes at least one cysteine. For example, in some cases, the stalk can include the sequence Cys-Pro-Pro-Cys (SEQ ID NO:62). If present, a cysteine in the stalk of a first engineered signaling polypeptide can be available to form a disulfide bond with a stalk in a second engineered signaling polypeptide.

Stalks can include immunoglobulin hinge region amino acid sequences that are known in the art; see, e.g., Tan et al. (1990) Proc. Natl. Acad. Sci. USA 87:162; and Huck et al. (1986) Nucl. Acids Res. 14:1779. As non-limiting examples, an immunoglobulin hinge region can include a domain with at least 50, 60, 70, 75, 80, 85, 90, 95, 96, 97, 98, 99 or 100% sequence identity to a stretch of at least 10, 15, 20, or all of the amino acids of any of the following amino acid sequences: DKTHT (SEQ ID NO:63); CPPC (SEQ ID NO:62); CPEPKSCDTPPPCPR (SEQ ID NO:64) (see, e.g., Glaser et al. (2005) J. Biol. Chem. 280:41494); ELKTPLGDTTHT (SEQ ID NO:65); KSCDKTHTCP (SEQ ID NO:66); KCCVDCP (SEQ ID NO:67); KYGPPCP (SEQ ID NO:68); EPKSCDKTHTCPPCP (SEQ ID NO:69) (human IgG1 hinge); ERKCCVECPPCP (SEQ ID NO:70) (human IgG2 hinge); ELKTPLGDTTHTCPRCP (SEQ ID NO:71) (human IgG3 hinge); SPNMVPHAHHAQ (SEQ ID NO:72) (human IgG4 hinge); and the like. The stalk can include a hinge region with an amino acid sequence of a human IgG1, IgG2, IgG3, or IgG4, hinge region. The stalk can include one or more amino acid substitutions and/or insertions and/or deletions compared to a wild-type (naturally-occurring) hinge region. For example, His229 of human IgG 1 hinge can be substituted with Tyr, so that the stalk includes the sequence EPKSCDKTYTCPPCP (see, e.g., Yan et al. (2012) J. Biol. Chem. 287:5891). The stalk can include an amino acid sequence derived from human CD8; e.g., the stalk can include the amino acid sequence: TTTPAPRPPTPAPTIASQPLSLRPEACRPAAGGAVHTR-GLDFACD (SEQ ID NO:73), or a variant thereof.

Transmembrane Domain

An engineered signaling polypeptide of the present disclosure can include transmembrane domains for insertion into a eukaryotic cell membrane. The transmembrane domain can be interposed between the ASTR and the co-stimulatory domain. The transmembrane domain can be interposed between the stalk and the co-stimulatory domain, such that the chimeric antigen receptor includes, in order from the amino terminus (N-terminus) to the carboxyl terminus (C-terminus): an ASTR; a stalk; a transmembrane domain; and an activating domain.

Any transmembrane (TM) domain that provides for insertion of a polypeptide into the cell membrane of a eukaryotic (e.g., mammalian) cell is suitable for use in aspects and embodiments disclosed herein. Non-limiting examples of TM domains suitable for any of the aspects or embodiments provided herein, include a domain with at least 50, 60, 70, 75, 80, 85, 90, 95, 96, 97, 98, 99 or 100% sequence identity to a stretch of at least 10, 15, 20, or all of the amino acids of any of the following TM domains:

a) CD* alpha
(IYIWAPLAGTCGVLLLSLVITLYC (SEQ ID NO:46));

b) CD8 beta
(LGLLVAGVLVLLVSLGVAIHLCC (SEQ ID NO:47));

c) CD4
(ALIVLGGVAGLLLFIGLGIFFCVRC (SEQ ID NO:48));

d) CD3Z
(LCYLLDGILFIYGVILTALFLRV (SEQ ID NO:49);

-continued e) CD28
(FWVLVVVGGVLACYSLLVTVAFIIFWV (SEQ ID NO:50));

f) CD134 (OX40):
(VAAILGLGLVLGLLGPLAILLALYLL (SEQ ID NO:51));

g) CD7
(ALPAALAVISFLLGLGLGVACVLA (SEQ ID NO:52)), h) CD8
TTTPAPRPPTPAPTIASQPLSLRPEACRPAAGGAVHTRGLDFACDIYIWA

PLAGTCGVLLLSLVITL YC (SEQ ID NO:75),
and i) CD28
IEVMYPPPYLDNEKSNGTIIHVKGKHLCPSPLFPGPSKPFWVLVVVGGVL

ACYSLLVTVAFIIFWV (SEQ ID NO:76).

As non-limiting examples, a transmembrane domain of an aspect of the invention can have at least 80, 90, or 95% sequence identity to the SEQ ID NO:46 transmembrane domain, the CD8 beta transmembrane domain, the CD4 transmembrane domain, the CD3 zeta transmembrane domain, the CD28 transmembrane domain, the CD134 transmembrane domain, or the CD7 transmembrane domain.

Intracellular Activating Domain

Intracellular activating domains suitable for use in an engineered signaling polypeptide of the present disclosure when activated, typically induce the production of one or more cytokines; increased cell death; and/or increased proliferation of CD8$^+$ T cells, CD4$^+$ T cells, natural killer T cells, γδ T cells, and/or neutrophils. Activating domains can also be referred to as activation domains herein.

In some embodiments, the intracellular activating domain includes at least one (e.g., one, two, three, four, five, six, etc.) ITAM motifs as described below. In some embodiments, the intracellular activating domain includes DAP10/CD28 type signaling chains. In some embodiments, the intracellular activating domain is not covalently attached to the membrane bound engineered signaling polypeptide, but is instead diffused in the cytoplasm. As non-limiting examples, an intracellular activating domain of an aspect of the invention can have at least 80%, 90%, or 95% sequence identity to the CD3Z, CD3D, CD3E, CD3G, CD79A, DAP12, FCER1G, DAP10/CD28, or ZAP70 domains as described below.

Intracellular activating domains suitable for use in an engineered signaling polypeptide of the present disclosure include immunoreceptor tyrosine-based activation motif (ITAM)-containing intracellular signaling polypeptides. An ITAM motif is YX$_1$X$_2$L/I, where X$_1$ and X$_2$ are independently any amino acid. In some cases, the intracellular activating domain of an engineered signaling polypeptide includes 1, 2, 3, 4, or 5 ITAM motifs. In some cases, an ITAM motif is repeated twice in an intracellular activating domain, where the first and second instances of the ITAM motif are separated from one another by 6 to 8 amino acids, e.g., (YX$_1$X$_2$L/I)(X$_3$)$_n$(YX$_1$X$_2$L/I), where n is an integer from 6 to 8, and each of the 6-8 X$_3$ can be any amino acid. In some cases, the intracellular activating domain of an engineered signaling polypeptide includes 3 ITAM motifs.

A suitable intracellular activating domain can be an ITAM motif-containing portion that is derived from a polypeptide that contains an ITAM motif. For example, a suitable intracellular activating domain can be an ITAM motif-containing domain from any ITAM motif-containing protein. Thus, a suitable intracellular activating domain need not contain the entire sequence of the entire protein from which it is derived. Examples of suitable ITAM motif-containing polypeptides include, but are not limited to: CD3Z (CD3 zeta); CD3D (CD3 delta); CD3E (CD3 epsilon); CD3G (CD3 gamma); CD79A (antigen receptor complex-associated protein alpha chain); DAP12; and FCER1G (Fc epsilon receptor I gamma chain).

In some cases, the intracellular activating domain is derived from T cell surface glycoprotein CD3 zeta chain (also known as CD3Z, T cell receptor T3 zeta chain, CD247, CD3-ZETA, CD3H, CD3Q, T3Z, TCRZ, etc.). For example, a suitable intracellular activating domain can include a domain with at least 50%, 60%, 70%, 75%, 80%, 85%, 90%, 95%, 96%, 97%, 98%, 99% or 100% sequence identity to a stretch of at least 10, 15, 20, or all amino acids in the following sequences or to a contiguous stretch of from about 100 amino acids to about 110 amino acids (aa), from about 110 aa to about 115 aa, from about 115 aa to about 120 aa, from about 120 aa to about 130 aa, from about 130 aa to about 140 aa, from about 140 aa to about 150 aa, or from about 150 aa to about 160 aa, of either of the following amino acid sequences (2 isoforms): MKWKALFTAAILQAQLPITEAQSFGLLDPKLCYLLDGIL-FIYGVILTALFLRVKFSRSADAPAYQQ GQNQL YNELNLGRREE YDVLDKRRGRDPEMGGKPRRKNPQEGL YNELQKDKMAEAYSEIGM KGERRRGKGHDGL YQGLSTATKDTYDALHMQALPPR (SEQ ID NO:11) or MKWKALFTAAILQAQLPITEAQSFGLLDPKLCYLL-DGILFIYGVILTALFLRVKFSRSADAPAYQQ GQNQL YNELNLGRREE YDVLDKRRGRDPEMGGKPQRRKNPQEGL YNELQKDKMAEAYSEIG MKGERRRGKGHDGL YQGLSTATKDTYDALHMQALPPR (SEQ ID NO:12), where the ITAM motifs are in bold and are underlined.

Likewise, a suitable intracellular activating domain polypeptide can include an ITAM motif-containing a portion of the full length CD3 zeta amino acid sequence. Thus, a suitable intracellular activating domain can include a domain with at least 50%, 60%, 70%, 75%, 80%, 85%, 90%, 95%, 96%, 97%, 98%, 99% or 100% sequence identity to a stretch of at least 10, 15, 20, or all amino acids in the following sequences or to a contiguous stretch of from about 100 amino acids to about 110 amino acids (aa), from about 110 aa to about 115 aa, from about 115 aa to about 120 aa, from about 120 aa to about 130 aa, from about 130 aa to about 140 aa, from about 140 aa to about 150 aa, or from about 150 aa to about 160 aa, of either of the following amino acid sequences: RVKFSRSADAPAYQQGQNQL YNELNLGRREE YDVLDKRRGRDPEMGGKPRRKNPQEGL YNELQKDKMAEAYSEIGMKGERRRGKGHDGL YQGLSTATKDTYDALHMQALPPR (SEQ ID NO:13); RVKFSRSADAPAYQQGQNQLYNELNLGRREE YDVLDKRRGRDPEMGGKPQRRKNPQEGL YNELQKDKMAEAYSEIGMKGERRRGKGHDGL YQGLSTATKDTYDALHMQALPPR (SEQ ID NO:81); NQLYNELNLGRREEYDVLDKR SEQ ID NO:14); EGL YNELQKDKMAEAYSEIGMK (SEQ ID NO:15); or DGL YQGLSTATKDTYDALHMQ (SEQ ID NO:16), where the ITAM motifs are in bold and are underlined.

In some cases, the intracellular activating domain is derived from T cell surface glycoprotein CD3 delta chain (also known as CD3D; CD3-DELTA; T3D; CD3 antigen, delta subunit; CD3 delta; CD3d antigen, delta polypeptide (TiT3 complex); OKT3, delta chain; T cell receptor T3 delta chain; T cell surface glycoprotein CD3 delta chain; etc.).

Thus, a suitable intracellular activating domain can include a domain with at least 50%, 60%, 70%, 75%, 80%, 85%, 90%, 95%, 96%, 97%, 98%, 99% or 100% sequence identity to a stretch of at least 10, 15, 20, or all amino acids in the following sequences or to a contiguous stretch of from about 100 amino acids to about 110 amino acids (aa), from about 110 aa to about 115 aa, from about 115 aa to about 120 aa, from about 120 aa to about 130 aa, from about 130 aa to about 140 aa, from about 140 aa to about 150 aa, or from about 150 aa to about 160 aa, of either of the following amino acid sequences: MEHSTFLSGLV-LATLLSQVSPFKIPIEELEDRVFVNCNTSITWVEG-TVGTLLSDITRLDLGKRILDP RGIYRCNGTDIYKD-KESTVQVHYRMCQSCVELDPATVAGIIVTDVIATL LLALGVFCFAGHETGR LSGAADTQALLRNDQV YQPLRDRDDAQ<u>YSHL</u>GGNWARNK (SEQ ID NO:17) or MEHSTFLSGLVLATLLSQVSPFKIPIEELEDRVFVNCN-TSITWVEGTVGTLLSDITRLDLGKRILDP RGIYRC-NGTDIYKDKESTVQVHYRTADTQALLRNDQV Y<u>QPL</u>RDRDDAQ<u>YSHL</u>GGNWARNK (SEQ ID NO:18), where the ITAM motifs are in bold and are underlined.

Likewise, a suitable intracellular activating domain polypeptide can comprise an ITAM motif-containing portion of the full length CD3 delta amino acid sequence. Thus, a suitable intracellular activating domain can include a domain with at least 50%, 60%, 70%, 75%, 80%, 85%, 90%, 95%, 96%, 97%, 98%, 99% or 100% sequence identity to a stretch of at least 10, 15, 20, or all amino acids in the following sequence: DQV<u>YQPL</u>RDRDDAQ<u>YSHL</u>GGN (SEQ ID NO:19), where the ITAM motifs are in bold and are underlined.

In some cases, the intracellular activating domain is derived from T cell surface glycoprotein CD3 epsilon chain (also known as CD3e, T cell surface antigen T3/Leu-4 epsilon chain, T cell surface glycoprotein CD3 epsilon chain, AI504783, CD3, CD3epsilon, T3e, etc.). Thus, a suitable intracellular activating domain can include a domain with at least 50%, 60%, 70%, 75%, 80%, 85%, 90%, 95%, 96%, 97%, 98%, 99% or 100% sequence identity to a stretch of at least 10, 15, 20, or all amino acids in the following sequences or to a contiguous stretch of from about 100 amino acids to about 110 amino acids (aa), from about 110 aa to about 115 aa, from about 115 aa to about 120 aa, from about 120 aa to about 130 aa, from about 130 aa to about 140 aa, from about 140 aa to about 150 aa, or from about 150 aa to about 160 aa, of the following amino acid sequence: MQSGTH-WRVLGLCLLSVGVWGQDGNEEMGGITQTPYKVSIS-GTTVILTCPQYPGSEILWQHNDK NIGGDEDDKNIGS-DEDHLSLKEFSELEQSGYYVCYPRGSKPEDANFY LYLRARVCENCMEMDMS VATIVIVDICITGGLLLL-VYYWSKNRKAKAKPVTRGAGAGGRQRGQNKER-PPPVPNPD<u>YEPIRK</u> GQRDL<u>YSGL</u>NQRRI (SEQ ID NO:20), where the ITAM motifs are in bold and are underlined.

Likewise, a suitable intracellular activating domain polypeptide can comprise an ITAM motif-containing portion of the full length CD3 epsilon amino acid sequence. Thus, a suitable intracellular activating domain can include a domain with at least 50%, 60%, 70%, 75%, 80%, 85%, 90%, 95%, 96%, 97%, 98%, 99% or 100% sequence identity to a stretch of at least 10, 15, 20, or all amino acids in the following sequence: NPD<u>YEPIRK</u>GQRDL<u>YSGL</u>NQR (SEQ ID NO:21), where the ITAM motifs are in bold and are underlined.

In some cases, the intracellular activating domain is derived from T cell surface glycoprotein CD3 gamma chain (also known as CD3G, T cell receptor T3 gamma chain, CD3-GAMMA, T3G, gamma polypeptide (TiT3 complex), etc.). Thus, a suitable intracellular activating domain can include a domain with at least 50%, 60%, 70%, 75%, 80%, 85%, 90%, 95%, 96%, 97%, 98%, 99% or 100% sequence identity to a stretch of at least 10, 15, 20, or all amino acids in the following sequences or to a contiguous stretch of from about 100 amino acids to about 110 amino acids (aa), from about 110 aa to about 115 aa, from about 115 aa to about 120 aa, from about 120 aa to about 130 aa, from about 130 aa to about 140 aa, from about 140 aa to about 150 aa, or from about 150 aa to about 160 aa, of the following amino acid sequence: MEQGKGLAVLILAIILLQGT-LAQSIKGNHLVKVYDYQEDGSVLLTCDAEAKNIT-WFKDGKMIGF LTEDKKKWNLGSNAKDPRG-MYQCKGSQNKSKPLQVYYRMCQNCIELNAATISGFL-FAEIVSIFV LAVGVYFIAGQDGVRQSR-ASDKQTLLPNDQLYQPLK-DREDDQ<u>YSHL</u>QGNQLRRN (SEQ ID NO:22), where the ITAM motifs are in bold and are underlined.

Likewise, a suitable intracellular activating domain polypeptide can comprise an ITAM motif-containing portion of the full length CD3 gamma amino acid sequence. Thus, a suitable intracellular activating domain can include a domain with at least 50%, 60%, 70%, 75%, 80%, 85%, 90%, 95%, 96%, 97%, 98%, 99% or 100% sequence identity to a stretch of at least 10, 15, 20, or all amino acids in the following sequence: DQL<u>YQPL</u>KDREDDQ<u>YSHL</u>QGN (SEQ ID NO:23), where the ITAM motifs are in bold and are underlined.

In some cases, the intracellular activating domain is derived from CD79A (also known as B-cell antigen receptor complex-associated protein alpha chain; CD79a antigen (immunoglobulin-associated alpha); MB-1 membrane glycoprotein; Ig-alpha; membrane-bound immunoglobulin-associated protein; surface IgM-associated protein; etc.). Thus, a suitable intracellular activating domain can include a domain with at least 50%, 60%, 70%, 75%, 80%, 85%, 90%, 95%, 96%, 97%, 98%, 99% or 100% sequence identity to a stretch of at least 10, 15, 20, or all amino acids in the following sequences or to a contiguous stretch of from about 100 amino acids to about 110 amino acids (aa), from about 110 aa to about 115 aa, from about 115 aa to about 120 aa, from about 120 aa to about 130 aa, from about 130 aa to about 140 aa, from about 140 aa to about 150 aa, or from about 150 aa to about 160 aa, of either of the following amino acid sequences: MPGGPGVLQALPATIFLLFLL-SAVYLGPGCQALWMHKVPASLMVSLGE-DAHFQCPHNSSNNAN VTWWRVLHGNYTWPPE-FLGPGEDPNGTLIIQNVNKSHGGIYVCRVQEGNE SYQQSCGTYLRVR QPPPRPFLDMGEGTKNRIITAE-GIILLFCAVVPGTLLL-FRKRWQNEKLGLDAGDEYEDENL<u>YEGL</u>NLDDCSM <u>YEDI</u>SRGLQGTYQDVGSLNIGDVQLEKP (SEQ ID NO:24) or MPGGPGVLQALPATIFLLFLL-SAVYLGPGCQALWMHKVPASLMVSLGE-DAHFQCPHNSSNNAN VTWWRVLHGNYTWPPE-FLGPGEDPNEPPPRPFLDMGEGTKNRIITAEGIILLF CAVVPGTLLLLFRK RWQNEKLGLDAGDEYEDENLY-EGLNLDDCSMYEDISR-GLQGTYQDVGSLNIGDVQLEKP (SEQ ID NO:25), where the ITAM motifs are in bold and are underlined.

Likewise, a suitable intracellular activating domain polypeptide can comprise an ITAM motif-containing portion of the full length CD79A amino acid sequence. Thus, a suitable intracellular activating domain can include a domain with at least 50%, 60%, 70%, 75%, 80%, 85%, 90%, 95%, 96%, 97%, 98%, 99% or 100% sequence identity to a stretch of at least 10, 15, 20, or all amino acids in the following sequence: ENL<u>YEGL</u>NLDDCSM<u>YEDI</u>SRG (SEQ ID NO:26), where the ITAM motifs are in bold and are underlined.

In some cases, the intracellular activating domain is derived from DAP12 (also known as TYROBP; TYRO protein tyrosine kinase binding protein; KARAP; PLOSL; DNAX-activation protein 12; KAR-associated protein; TYRO protein tyrosine kinase binding protein; killer activating receptor associated protein; killer-activating receptor-associated protein; etc.). For example, a suitable intracellular activating domain can include a domain with at least 50%, 60%, 70%, 75%, 80%, 85%, 90%, 95%, 96%, 97%, 98%, 99% or 100% sequence identity to a stretch of at least 10, 15, 20, or all amino acids in the following sequences or to a contiguous stretch of from about 100 amino acids to about 110 amino acids (aa), from about 110 aa to about 115 aa, from about 115 aa to about 120 aa, from about 120 aa to about 130 aa, from about 130 aa to about 140 aa, from about 140 aa to about 150 aa, or from about 150 aa to about 160 aa, of either of the following amino acid sequences (4 isoforms): MGGLEPCSRLLLLPLLLAVSGLRPVQAQAQSDCSCSTVSPGVLAGIVMGDLVLTVLIALAVYFLG RLVPRGRGAAEAATRKQRITETESP<u>YQEL</u>QGQRSDV<u>YSDL</u>NTQRPYYK (SEQ ID NO:27), MGGLEPCSRLLLLPLLLAVSGLRPVQAQAQSDCSCSTVSPGVLAGIVMGDLVLTVLIALAVYFLG RLVPRGRGAAEATRKQRITETESP<u>YQEL</u>QGQRSDV<u>YSDL</u>NTQ (SEQ ID NO:28), MGGLEPCSRLLLLPLLLAVSDCSCSTVSPGVLAGIVMGDLVLTVLIALAVYFLGRLVPRGRGAAE AATRKQRITETESP<u>YQEL</u>QGQRSDV<u>YSDL</u>NTQRPYYK (SEQ ID NO:29), or MGGLEPCSRLLLLPLLLAVSDCSCSTVSPGVLAGIVMGDLVLTVLIALAVYFLGRLVPRGRGAAE ATRKQRITETESP<u>YQEL</u>QGQRSDV<u>YSDL</u>NTQRPYYK (SEQ ID NO:30), where the ITAM motifs are in bold and are underlined.

Likewise, a suitable intracellular activating domain polypeptide can comprise an ITAM motif-containing portion of the full length DAP12 amino acid sequence. Thus, a suitable intracellular activating domain can include a domain with at least 50%, 60%, 70%, 75%, 80%, 85%, 90%, 95%, 96%, 97%, 98%, 99% or 100% sequence identity to a stretch of at least 10, 15, 20, or all amino acids in the following sequence: ESP<u>YQEL</u>QGQRSDV<u>YSDL</u>NTQ (SEQ ID NO:31), where the ITAM motifs are in bold and are underlined.

In some cases, the intracellular activating domain is derived from FCER1G (also known as FCRG; Fc epsilon receptor I gamma chain; Fc receptor gamma-chain; fc-epsilon RI-gamma; fcRgamma; fceRI gamma; high affinity immunoglobulin epsilon receptor subunit gamma; immunoglobulin E receptor, high affinity, gamma chain; etc.). For example, a suitable intracellular activating domain can include a domain with at least 50%, 60%, 70%, 75%, 80%, 85%, 90%, 95%, 96%, 97%, 98%, 99% or 100% sequence identity to a stretch of at least 10, 15, 20, or all amino acids in the following sequences or to a contiguous stretch of from about 50 amino acids to about 60 amino acids (aa), from about 60 aa to about 70 aa, from about 70 aa to about 80 aa, or from about 80 aa to about 88 aa of the following amino acid sequence: MIPAVVLLLLLLVEQAAALGEPQLCYILDAILFLYGIVLTLLYCRLKIQVRKAAIT-SYEKSDGV<u>YTGL</u>STRNQET<u>YETL</u>KHEKPPQ (SEQ ID NO:32), where the ITAM motifs are in bold and are underlined.

Likewise, a suitable intracellular activating domain polypeptide can comprise an ITAM motif-containing portion of the full length FCER1G amino acid sequence. Thus, a suitable intracellular activating domain can include a domain with at least 50%, 60%, 70%, 75%, 80%, 85%, 90%, 95%, 96%, 97%, 98%, 99% or 100% sequence identity to a stretch of at least 10, 15, 20, or all amino acids in the following sequence: DGV<u>YTGL</u>STRNQET<u>YETL</u>KHE (SEQ ID NO:33), where the ITAM motifs are in bold and are underlined.

Intracellular activating domains suitable for use in an engineered signaling polypeptide of the present disclosure include a DAP10/CD28 type signaling chain. An example of a DAP10 signaling chain is the amino acid sequence is: RPRRSPAQDGKV<u>YINM</u>PGRG (SEQ ID NO:34). In some embodiments, a suitable intracellular activating domain includes a domain with at least 50%, 60%, 70%, 75%, 80%, 85%, 90%, 95%, 96%, 97%, 98%, 99% or 100% sequence identity to a stretch of at least 10, 15, 20, or all amino acids in the following sequence: RPRRSPAQDGKV<u>YINM</u>PGRG (SEQ ID NO:34).

An example of a CD28 signaling chain is the amino acid sequence is FWVLVVVGGVLACYSLLVTVAFIIFWVR-SKRSRLLHSD<u>YMNM</u>TPRRPGPTRKHYQPYAPPRDF AAYRS (SEQ ID NO:35). In some embodiments, a suitable intracellular domain includes a domain with at least 50%, 60%, 70%, 75%, 80%, 85%, 90%, 95%, 96%, 97%, 98%, 99% or 100% sequence identity to a stretch of at least 10, 15, 20, or all amino acids in the following sequence: FWVLVVVGGVLACYSLLVTVAFIIFWVR-SKRSRLLHSD<u>YMNM</u>TPRRPGPTRKHYQPYAPPRDF AAYRS (SEQ ID NO:35).

Intracellular activating domains suitable for use in an engineered signaling polypeptide of the present disclosure include a ZAP70 polypeptide, For example, a suitable intracellular activating domain can include a domain with at least 50%, 60%, 70%, 75%, 80%, 85%, 90%, 95%, 96%, 97%, 98%, 99% or 100% sequence identity to a stretch of at least 10, 15, 20, or all amino acids in the following sequences or to a contiguous stretch of from about 300 amino acids to about 400 amino acids, from about 400 amino acids to about 500 amino acids, or from about 500 amino acids to 619 amino acids, of the following amino acid sequence:

```
                                              (SEQ ID NO: 36)
MPDPAAHLPFFYGSISRAEAEEHLKLAGMADGLFLLRQCLRSLGGYVLSL

VHDVRFHHFPIERQLNGTYAIAGGKAHCGPAELCEFYSRDPDGLPCNLRK

PCNRPSGLEPQPGVFDCLRDAMVRDYVRQTWKLEGEALEQAIISQAPQVE

KLIATTAHERMPWYHSSLTREEAERKLYSGAQTDGKFLLRPRKEQGTYAL

SLIYGKTVYHYLISQDKAGKYCIPEGTKFDTLWQLVEYLKLKADGLIYCL

KEACPNSSASNASGAAAPTLPAHPSTLTHPQRRIDTLNSDGYTPEPARIT

SPDKPRPMPMDTSVYESPYSDPEELKDKKLFLKRDNLLIADIELGCGNFG

SVRQGVYRMRKKQIDVAIKVLKQGTEKADTEEMMREAQIMHQLDNPYIVR

LIGVCQAEALMLVMEMAGGGPLHKFLVGKREEIPVSNVAELLHQVSMGMK

YLEEKNFVHRDLAARNVLLVNRHYAKISDFGLSKALGADDSYYTARSAGK
```

-continued

```
WPLKWYAPECINFRKFSSRSDVWSYGVTMWEALSYGQKPYKKMKGPEVMA
FIEQGKRMECPPECPPELYALMSDCWIYKWEDRPDFLTVEQRMRACYYSL
ASKVEGPPGSTQKAEAACA.
```

Lymphoproliferative Elements

Peripheral T lymphocyte numbers are maintained at remarkably stable levels throughout adulthood, despite the continuing addition of cells, due to emigration from the thymus and proliferation in response to antigen encounter, and loss of cells owing to the removal of antigen-specific effectors after antigen clearance (Marrak, P. et al. 2000. *Nat Immunol* 1:107-111; Freitas, A. A. et al. 2000. *Annu Rev Immunol* 18:83-111). The size of the peripheral T cell compartment is regulated by multiple factors that influence both proliferation and survival. However, in a lymphopenic environment, T lymphocytes divide independently of cognate antigen, due to "acute homeostatic proliferation" mechanisms that maintain the size of the peripheral T cell compartment. Conditions for lymphopenia have been established in subjects or patients during adoptive cell therapy by proliferating T cells in vitro and introducing them into lymphodepleted subjects, resulting in enhanced engraftment and antitumor function of transferred T cells. However, lymphodepletion of a subject is not desirable because it can cause serious side effects, including immune dysfunction and death.

Studies have shown that lymphodepletion removes endogenous lymphocytes functioning as cellular sinks for homeostatic cytokines, thereby freeing cytokines to induce survival and proliferation of adoptively transferred cells. Some cytokines, such as for example, IL-7 and IL-15, are known to mediate antigen-independent proliferation of T cells and are thus capable of eliciting homeostatic proliferation in non-lymphopenic environments. However, these cytokines and their receptors have intrinsic control mechanisms that prevent lymphoproliferative disorders at homeostasis.

Many of the aspects provided herein include a lymphoproliferative element, or a nucleic acid encoding the say, typically as part of an engineered signaling polypeptide. In illustrative embodiments herein, one or more lymphoproliferative elements is introduced into a resting T cell and/or resting NK cell, typically by transducing the resting T cell and/or resting NK cell with replication incompetent recombinant retroviral particles whose genome encodes the lymphoproliferative element as part of an engineered signaling polypeptide. The lymphoproliferative element can be a cytokine or in further illustrative embodiments, a cytokine receptor, or a fragment that includes a signaling domain thereof, that activates a STAT3 pathway, a STAT4 pathway, or in even further illustrative embodiments, a Jak/STAT5 pathway. As such, a lymphoproliferative element, can be, in a non-limiting example, a cytokine receptor, or active fragment that includes a signaling domain thereof, such as an interleukin receptor, or an active fragment that includes a signaling domain thereof, that activates STAT5. Thus, a lymphoproliferative element is a polypeptide that induces proliferation of a T cell and/or NK cell. Illustrative lymphoproliferative elements induce proliferation by activating STAT5. Thus, fragments of such lymphoproliferative elements retain the ability to induce proliferation of T cells and/or NK cells, in illustrative embodiments, by activating STAT5.

In some of the methods and compositions presented herein, a lymphoproliferative element is used to promote proliferation or expansion of genetically modified T cells in vivo without having to lymphodeplete subjects. As such, non-limiting illustrative embodiments of methods provided herein that include inserting a lymphoproliferative element into a resting T cell and/or NK cell of a subject, typically by transducing such T cell and/or NK cell can be performed without lymphodepleting the subject before, during and/or after performing the method, or without lymphodepleting the subject before, during and/or after collecting blood from a subject before performing such method, or without lymphodepleting the subject before, during, and/or after genetically modifying T cells or NK cells ex vivo from the subject, and/or before, during, or after reintroducing the genetically modified T cells and/or NK cells into the subject. Factors that promote proliferation of T cells in vivo include cytokines and their receptors, in which a receptor typically includes a ligand binding domain and a signaling domain. In some embodiments, the lymphoproliferative element used in the methods and compositions disclosed herein is a cytokine and/or a cytokine receptor. The cytokine can be an interleukin, and the cytokine receptor can be an interleukin receptor. The lymphoproliferative element can be a functional fragment of a cytokine and/or a functional fragment of a cytokine receptor, such as a signaling domain thereof, wherein the fragment is capable of promoting proliferation of T cells, for example by activating STAT5.

In some embodiments, the cytokine lymphoproliferative element in the methods and compositions herein include one or more of the following: Interleukin-7 (IL-7) or its receptor (IL-7R), or a signaling domain thereof; Interleukin-12 (IL-12) or its receptor (IL-12R), or a signaling domain thereof; Interleukin-23 (IL-23) or its receptor composed of IL-12Rβ1 and IL-23R, or a signaling domain thereof; Interleukin-27 (IL-27) or its receptor (IL-27R), or a signaling domain thereof; Interleukin-15 (IL-15) or its receptor (IL-15R), or a signaling domain thereof; Interleukin-21 (IL-21) or its receptor (IL-21R), or a signaling domain thereof; or transforming growth factor β (TGFβ) or its receptor (TGFβR) or a signaling domain thereof; or the TGFβ decoy receptor (TGF-β-dominant-negative receptor II (DNRII)). In some embodiments, the lymphoproliferative element is the IL-12R or the TGFβ decoy receptor (TGF-β-dominant-negative receptor II (DNRII)).

IL-7 binds to the IL-7 receptor, a heterodimer consisting of IL-7R alpha and common gamma chain receptor. Binding results in a cascade of signals important for T cell development within the thymus and survival within the periphery. Binding of IL-7 to the IL-7 receptor is known to activate the Jak/STAT5 pathway.

IL-12 is involved in the differentiation of naïve T cells into Th1 cells (Hsieh C S et al. 1993. *Science*. 260(5107): 547-9) and is known as a T cell-stimulating factor. IL-12 binds to the IL-12 receptor, which is a heterodimeric receptor formed by IL-12R-β1 and IL-12R-β2. IL12 can act by activating STAT4, but has been shown to activate STAT5 in T cells as well (Ahn, H., et al. 1998. *J. Immun.* 161:5893-5900). The IL-12 family is composed of the cytokines IL-12, IL-23, and IL-27. The receptor for IL-23 is composed of IL-12R β1 and IL-23R. IL-27 is a heterodimeric cytokine that is composed of two distinct genes, Epstein-Barr virus-induced gene 3 (EBI3) and IL-27p28. IL-27 interacts with IL-27 receptor.

IL-15 is a T and NK cell stimulatory factor that is similar in structure and function to IL-2. Both cytokines induce proliferation of T cells; and their shared functions are thought to result from both receptors using the IL-2/IL-15Rβ and common γ chains. Signaling pathway of IL-15 begins with binding to IL-15Rα receptor, with subsequent presentation to surrounding cells bearing IL-15Rβγc complex on their cell surface. Upon binding IL-15β subunit activates Janus kinase 1 (Jak1) and γc subunit Janus kinase 3 (Jak3), which leads to phosphorylation and activation of STAT3 and STAT5.

IL-21 is expressed in activated human CD4+ T cells and in NK T cells, and IL-21 expression is up-regulated in Th2 and Th17 subsets of T helper cells. The IL-21 receptor (IL-21R) is expressed on the surface of T, B and NK cells and is similar in structure to the receptors for other type I cytokines like IL-2R or IL-15. IL-21R requires dimerization with the common gamma chain (γc) in order to bind IL-21. When bound to IL-21, the IL-21 receptor acts through the Jak/STAT pathway, activating STAT1, STAT3, and STAT5.

TGFβ decoy receptors (TGF-β-dominant-negative receptor II (DNRII)) block TGFβ signaling by competing with the natural receptors for TGFβ binding. TGFβ-DNRII is a kinase-dead truncated form of RII that contains the extracellular TGFβ binding domain and the transmembrane domain of RII. TGFβ-DNRII binds the ligand but does not phosphorylate and activate RI, which thereby diminishes or eliminates Smad phosphorylation.

Gain-of-function mutations in IL-7Rα have been identified in subjects with B and T cell acute lymphoblastic leukemias (B-ALL and T-ALL) (Zenatti P P, et al. 2011. *Nat Genet* 43:932-939; Snochat, C. et al. 2011. *J Exp Med* 208:901-908; McElroy, C. A. et al. 2012. *PNAS* 109(7): 2503-2508). The mutations included insertions and deletions in the N-terminal region of the IL-7Rα TMD, with nearly all of the sequences containing an extra Cys residue, and an S165-to-C165 mutation. The cysteine resulted in constitutive activation of the receptor. Some of the mutations in the T-all group activated JAK1. These gain-of-function IL-7R mutants can be used in any of the aspects provided herein as one of the lymphoproliferative element(s).

Accordingly, in some embodiments, the lymphoproliferative element is a mutated IL-7 receptor. In other embodiments, the mutated IL-7 receptor is constitutively active, activating the JAK-STAT5 pathway in the absence of the cytokine ligand. In still other embodiments, the mutated IL-7 receptor comprises a 1 to 10 amino acid insertion at a position between 237 and 254 that includes a cysteine residue that includes the ability to constitutively activate the STAT5 pathway. In some embodiments, the mutated IL-7 receptor is IL-7Rα-insPPCL (represented by SEQ ID NO:82).

In some embodiments, the lymphoproliferative element is a chimeric cytokine receptor such as but not limited to a cytokine tethered to its receptor that typically constitutively activates the same STAT pathway as a corresponding activated wild-type cytokine receptor such as STAT3, STAT4, and in illustrative embodiments, STAT5. In some embodiments, the chimeric cytokine receptor is an interleukin, or a fragment thereof, tethered to or covalently attached to its cognate receptor, or a fragment thereof, via a linker. In some embodiments, the chimeric cytokine receptor is IL-7 tethered to IL-7Rα. In other embodiments, the chimeric cytokine receptor is IL-7 tethered to a domain of IL-7Rα, such as for example, the extracellular domain of IL-7Rα and/or the transmembrane domain of IL-7Rα. In some embodiments, the lymphoproliferative element is a cytokine receptor that is not tethered to a cytokine, and in fact in illustrative embodiments, provided herein a lymphoproliferative element is a constitutively active cytokine receptor that is not tethered to a cytokine. These chimeric IL-7 receptors typically constitutively activate STAT5 when expressed.

In some embodiments, the lymphoproliferative element is not a cytokine or a cytokine receptor but is an inhibitory RNA such as a miRNA that stimulates the STAT5 pathway typically by potentiating activation of STAT5 by degrading or causing down-regulation of a negative regulator in the SOCS pathway. In some embodiments, the miRNA is directed to mRNA encoding proteins that affect proliferation such as but not limited to ABCG1, SOCS1, TGFbR2, SMAD2, cCBL, and PD1. In illustrative embodiments, as exemplified herein, such inhibitory RNA (e.g. miRNAs) can be located in introns in packaging cells and/or a replication incompetent recombinant retroviral particle genome and/or a retroviral vector, typically with expression driven by a promoter that is active in a T cell and/or NK cell. Not to be limited by theory, inclusion of introns in transcription units are believed to result in higher expression and/or stability of transcripts. As such, the ability to place miRNAs within introns of a retroviral genome adds to the teachings of the present disclosure that overcome challenges in the prior art of trying to get maximum activities into the size restrictions of a retroviral, such as a lentivirus genome. In some embodiments, 1, 2, 3, 4, 5, 6, 7, 8, 9, or 10 miRNAs, in illustrative embodiments between 2 and 5, for example 4 miRNAs, one or more of which each bind nucleic acids encoding one or more of ABCG1, SOCS1, TGFbR2, SMAD2, cCBL, and PD1, can be included in the recombinant retroviral genome and delivered to a target cell, for example T cells and/or NK cells, using methods provided herein. In fact, as provided herein 1, 2, 3, or 4 miRNAs can be delivered in a single intron such as the EF1a intron.

ABCG1 is an ATP-binding cassette transporter that negatively regulates thymocyte and peripheral lymphocyte proliferation (Armstrong et al. 2010. *J Immunol* 184(1):173-183).

SOCS1 is a member of the SOCS (Suppressor of cytokine signaling) family of negative regulators of cytokine signal transduction that inhibit the Jak/Stat pathway such as STAT5. SOCS1 is also known as JAB (Janus Kinase binding protein), SSI-1 (Stat-induced Stat inhibitor-1), and TIP3 (Tec-interacting protein).

TGFbR2 is a member of the serine/threonine protein kinase family that binds TGF-β, forming a complex that phosphorylates proteins that then enter the nucleus and regulate transcription of genes related to proliferation.

SMAD2 mediates the signal of the transforming growth factor (TGF)-β and regulates multiple cellular processes, such as cell proliferation, apoptosis, and differentiation.

cCBL is an E3 ubiquitin ligase that inhibits TCR signaling by dephosphorylation and inactivation of ZAP-70 and through internalization of the TCR.

PD1 (CD279) is a cell surface receptor expressed on T cells and ProB cells. PD-1 binds two ligands, PD-L1 and PD-L2. Signaling through PD-1 functions to prevent activation of cells.

In some of the methods and compositions disclosed herein, expression of the lymphoproliferative element is induced by and can even depend on binding of a compound to a control element (as discussed elsewhere herein), which in non-limiting embodiments is a riboswitch. In some embodiments, the lymphoproliferative element is expressed from a promoter active in a T cell and/or an NK cell. For methods and compositions provided herein, a skilled artisan will recognize that promoters are known that are active in T cells and/or NK cells and can be used to express a first engineered signaling polypeptide or a second engineered signaling polypeptide, or any component thereof. In illustrative embodiments, such a promoter is not active in a packaging cell line, such as the packaging lines disclosed herein. In some embodiments, the promoter is the EF1a promoter or the murine stem cell virus (MSCV) promoter (Jones et al., *Human Gene Therapy* (2009) 20: 630-40). In some embodiments, the promoter is a T cell specific promoter. In illustrative embodiments, the promoter is the T cell specific CD3 zeta promoter.

In some embodiments, the lymphoproliferative element is microenvironment restricted. For example, the lymphoproliferative element can be a mutated receptor that binds its respective cytokine differentially in aberrant versus physiological conditions. For example, an IL-7R that can bind IL7 more strongly in a tumor environment than in a normal physiological environment can be used.

In some embodiments, the lymphoproliferative element is fused to a recognition or elimination domain Such recognition or elimination domains are disclosed in more detail herein. Such fusion provides the advantage, especially when a truncated or other mutated lymphoproliferative element is used, of requiring less polynucleotides in the retroviral genome. This is important in illustrative embodiments provided herein, because it helps to permit more nucleic acids encoding functional elements to be included in the retroviral genome. In other embodiments, the lymphoproliferative element is fused to a co-stimulatory domain and/or an intracellular activating domain. A lymphoproliferative element as disclosed herein, is not a chimeric antigen receptor (CAR) or an intracellular activating domain or co-stimulating domain thereof. However, in some embodiments, a lymphoproliferative element can be fused to an antigen-specific targeting region (ASTR) and activated by binding of the ASTR to its antigen. In still other embodiments, an engineered signaling polypeptide can include an ASTR, an intracellular activation domain (such as a CD3 zeta signaling domain), a co-stimulatory domain, and a lymphoproliferative domain. Further details regarding co-stimulatory domains, intracellular activating domains, ASTRs and other CAR domains, are disclosed elsewhere herein.

In illustrative embodiments herein, a T cell and/or NK cell survival element is introduced into a resting T cell and/or resting NK cell, typically by transducing the resting T cell and/or resting NK cell with a replication incompetent recombinant retroviral particle whose genome encodes the T cell and/or NK cell survival element as part of an engineered signaling polypeptide. In some embodiments, a lymphoproliferative element is also a T cell and/or NK cell survival element. As discussed above, some of the lymphoproliferative elements not only promote proliferation, but they promote cell survival as well. In some embodiments, the T cell and/or NK survival motif is not a lymphoproliferative element. For example, the T cell and/or NK cell survival motif can be a CD28 T cell survival motif or a CD137 cell survival motif. Such T cell survival motifs can be found on engineered signaling polypeptides that include an ASTR, such as an scFV. In an illustrative embodiment, the T cell survival motif is a CD28 T cell survival motif or a CD137 motif connected to an scFv through a CD8a transmembrane domain or a CD28 transmembrane domain. In certain embodiments, said intracellular signaling domain comprises a polypeptide sequence comprising an immunoreceptor tyrosine-based activation motif (ITAM). In a certain embodiment, said polypeptide sequence is a CD3 signaling domain.

Modulatory Domains

Modulatory domains can change the effect of the intracellular activating domain in the engineered signaling polypeptide, including enhancing or dampening the downstream effects of the activating domain or changing the nature of the response. Modulatory domains suitable for use in an engineered signaling polypeptide of the present disclosure include co-stimulatory domains. A modulatory domain suitable for inclusion in the engineered signaling polypeptide can have a length of from about 30 amino acids to about 70 amino acids (aa), e.g., a modulatory domain can have a length of from about 30 aa to about 35 aa, from about 35 aa to about 40 aa, from about 40 aa to about 45 aa, from about 45 aa to about 50 aa, from about 50 aa to about 55 aa, from about 55 aa to about 60 aa, from about 60 aa to about 65 aa, or from about 65 aa to about 70 aa. In other cases, modulatory domain can have a length of from about 70 aa to about 100 aa, from about 100 aa to about 200 aa, or greater than 200 aa.

Co-stimulatory domains typically enhance and/or change the nature of the response to an activation domain. Co-stimulatory domains suitable for use in an engineered signaling polypeptide of the present disclosure are generally polypeptides derived from receptors. In some embodiments, co-stimulatory domains homodimerize. A subject co-stimulatory domain can be an intracellular portion of a transmembrane protein (i.e., the co-stimulatory domain can be derived from a transmembrane protein). Non-limiting examples of suitable co-stimulatory polypeptides include, but are not limited to, 4-1BB (CD137), CD27, CD28, CD28 deleted for Lck binding (ICΔ), ICOS, OX40, BTLA, CD27, CD30, GITR, and HVEM. For example, a co-stimulatory domain of an aspect of the invention can have at least 80%, 90%, or 95% sequence identity to the co-stimulatory domain of 4-1BB (CD137), CD27, CD28, CD28 deleted for Lck binding (ICΔ), ICOS, OX40, BTLA, CD27, CD30, GITR, or HVEM. For example, a co-stimulatory domain of an aspect of the invention can have at least 80%, 90%, or 95% sequence identity to the co-stimulatory domain of Non-limiting examples of suitable co-stimulatory polypeptides include, but are not limited to, 4-1BB (CD137), CD27, CD28, CD28 deleted for Lck binding (ICΔ), ICOS, OX40, BTLA, CD27, CD30, GITR, and HVEM. For example, a co-stimulatory domain of an aspect of the invention can have at least 80%, 90%, or 95% sequence identity to the co-stimulatory domain of 4-1BB (CD137), CD27, CD28, CD28 deleted for Lck binding (ICΔ), ICOS, OX40, BTLA, CD27, CD30, GITR, or HVEM.

A co-stimulatory domain suitable for inclusion in an engineered signaling polypeptide can have a length of from about 30 amino acids to about 70 amino acids (aa), e.g., a co-stimulatory domain can have a length of from about 30 aa to about 35 aa, from about 35 aa to about 40 aa, from about 40 aa to about 45 aa, from about 45 aa to about 50 aa, from about 50 aa to about 55 aa, from about 55 aa to about 60 aa, from about 60 aa to about 65 aa, or from about 65 aa to about 70 aa. In other cases, the co-stimulatory domain can have a length of from about 70 aa to about 100 aa, from about 100 aa to about 200 aa, or greater than 200 aa.

In some cases, the co-stimulatory domain is derived from an intracellular portion of the transmembrane protein CD137 (also known as TNFRSF9; CD137; 4-1BB; CDw137; ILA; etc.). For example, a suitable co-stimulatory domain can include a domain with at least 50%, 60%, 70%, 75%, 80%, 85%, 90%, 95%, 96%, 97%, 98%, 99% or 100% sequence identity to a stretch of at least 10, 15, 20, or all of the amino acids in the following amino acid sequence: KRGRKKL-LYIFKQPFMRPVQTTQEEDGCSCRFPEEEEGGCEL (SEQ ID NO:1). In some of these embodiments, the co-stimulatory domain has a length of from about 30 aa to about 35 aa, from about 35 aa to about 40 aa, from about 40 aa to about 45 aa, from about 45 aa to about 50 aa, from about 50 aa to about 55 aa, from about 55 aa to about 60 aa, from about 60 aa to about 65 aa, or from about 65 aa to about 70 aa.

In some cases, the co-stimulatory domain is derived from an intracellular portion of the transmembrane protein CD28 (also known as Tp44). For example, a suitable co-stimulatory domain can include a domain with at least 50%, 60%, 70%, 75%, 80%, 85%, 90%, 95%, 96%, 97%, 98%, 99% or 100% sequence identity to a stretch of at least 10, 15, 20, or all of the amino acids in the following amino acid sequence: RSKRSRLLHSDYMNMTPRRPGPTRKHYQPYAPPRDFAAYRS (SEQ ID NO:2). In some of these embodiments, the co-stimulatory domain has a length of from about 30 aa to about 35 aa, from about 35 aa to about 40 aa, from about 40 aa to about 45 aa, from about 45 aa to about 50 aa, from about 50 aa to about 55 aa, from about 55 aa to about 60 aa, from about 60 aa to about 65 aa, or from about 65 aa to about 70 aa.

In some cases, the co-stimulatory domain is derived from an intracellular portion of the transmembrane protein CD28 deleted for Lck binding (ICΔ). For example, a suitable co-stimulatory domain can include a domain with at least 50%, 60%, 70%, 75%, 80%, 85%, 90%, 95%, 96%, 97%, 98%, 99% or 100% sequence identity to a stretch of at least 10, 15, 20, or all of the amino acids in the following amino acid sequence: RSKRSRLLHSDYMNMTPRRPGPTRKHYQAYAAARDFAAYRS (SEQ ID NO:3). In some of these embodiments, the co-stimulatory domain has a length of from about 30 aa to about 35 aa, from about 35 aa to about 40 aa, from about 40 aa to about 45 aa, from about 45 aa to about 50 aa, from about 50 aa to about 55 aa, from about 55 aa to about 60 aa, from about 60 aa to about 65 aa, or from about 65 aa to about 70 aa.

In some cases, the co-stimulatory domain is derived from an intracellular portion of the transmembrane protein ICOS (also known as AILIM, CD278, and CVID1). For example, a suitable co-stimulatory domain can include a domain with at least 50%, 60%, 70%, 75%, 80%, 85%, 90%, 95%, 96%, 97%, 98%, 99% or 100% sequence identity to a stretch of at least 10, 15, 20, or all of the amino acids in the following amino acid sequence: TKKKYSSSVHDPNGEYMFMRAVNTAKKSRLTDVTL (SEQ ID NO:4). In some of these embodiments, the co-stimulatory domain has a length of from about 30 aa to about 35 aa, from about 35 aa to about 40 aa, from about 40 aa to about 45 aa, from about 45 aa to about 50 aa, from about 50 aa to about 55 aa, from about 55 aa to about 60 aa, from about 60 aa to about 65 aa, or from about 65 aa to about 70 aa.

In some cases, the co-stimulatory domain is derived from an intracellular portion of the transmembrane protein OX40 (also known as TNFRSF4, RP5-902P8.3, ACT35, CD134, OX-40, TXGP1L). For example, a suitable co-stimulatory domain can include a domain with at least 50%, 60%, 70%, 75%, 80%, 85%, 90%, 95%, 96%, 97%, 98%, 99% or 100% sequence identity to a stretch of at least 10, 15, 20, or all of the amino acids in the following amino acid sequence: RRDQRLPPDAHKPPGGGSFRTPIQEEQADAHSTLAKI (SEQ ID NO:5). In some of these embodiments, the co-stimulatory domain has a length of from about 30 aa to about 35 aa, from about 35 aa to about 40 aa, from about 40 aa to about 45 aa, from about 45 aa to about 50 aa, from about 50 aa to about 55 aa, from about 55 aa to about 60 aa, from about 60 aa to about 65 aa, or from about 65 aa to about 70 aa.

In some cases, the co-stimulatory domain is derived from an intracellular portion of the transmembrane protein CD27 (also known as S 152, T 14, TNFRSF7, and Tp55). For example, a suitable co-stimulatory domain can include a domain with at least 50%, 60%, 70%, 75%, 80%, 85%, 90%, 95%, 96%, 97%, 98%, 99% or 100% sequence identity to a stretch of at least 10, 15, 20, or all of the amino acids in the following amino acid sequence: HQRRKYRSNKGESPVEPAEPCRYSCPREEEGSTIPIQEDYRKPEPACSP (SEQ ID NO:6). In some of these embodiments, the co-stimulatory domain has a length of from about 30 aa to about 35 aa, from about 35 aa to about 40 aa, from about 40 aa to about 45 aa, from about 45 aa to about 50 aa, from about In some cases, the co-stimulatory domain is derived from an intracellular portion of the transmembrane protein BTLA (also known as BTLA1 and CD272). For example, a suitable co-stimulatory domain can include a domain with at least 50%, 60%, 70%, 75%, 80%, 85%, 90%, 95%, 96%, 97%, 98%, 99% or 100% sequence identity to a stretch of at least 10, 15, 20, or all of the amino acids in the following amino acid sequence: CCLRRHQGKQNELSDTAGREINLVDAHLKSEQTEASTRQNSQVLLSETGIYDNDPDLCFRMQEG SEVYSNPCLEENKPGIVYASLNHSVIGPNSRLARNVKEAPTEYASICVRS (SEQ ID NO:7).

In some cases, the co-stimulatory domain is derived from an intracellular portion of the transmembrane protein CD30 (also known as TNFRSF8, D1S166E, and Ki-1). For example, a suitable co-stimulatory domain can include a domain with at least 50%, 60%, 70%, 75%, 80%, 85%, 90%, 95%, 96%, 97%, 98%, 99% or 100% sequence identity to a stretch of from about 100 amino acids to about 110 amino acids (aa), from about 110 aa to about 115 aa, from about 115 aa to about 120 aa, from about 120 aa to about 130 aa, from about 130 aa to about 140 aa, from about 140 aa to about 150 aa, from about 150 aa to about 160 aa, or from about 160 aa to about 185 aa of the following amino acid sequence: RRACRKRIRQKLHLCYPVQTSQPKLELVDSRPRRSSTQLRSGASVTEPVAEERGLMSQPLMETCH SVGAAYLESLPLQDASPAGGPSSPRDLPEPRVSTEHTNNKIEKIYIMKADTVIVGTVKAELPEGRG LAGPAEPELEEELEADHTPHYPEQETEPPLGSCSDVMLSVEEEGKEDPLPTAASGK (SEQ ID NO:8).

In some cases, the co-stimulatory domain is derived from an intracellular portion of the transmembrane protein GITR (also known as TNFRSF18, RP5-902P8.2, AITR, CD357, and GITR-D). For example, a suitable co-stimulatory domain can include a domain with at least 50%, 60%, 70%, 75%, 80%, 85%, 90%, 95%, 96%, 97%, 98%, 99% or 100% sequence identity to a stretch of at least 10, 15, 20, or all of the amino acids in the following amino acid sequence: HIWQLRSQCMWPRETQLLLEVPPSTEDARSCQFPEEERGERSAEEKGRLGDLWV (SEQ ID NO:9). In some of these embodiments, the co-stimulatory domain has a length of from about 30 aa to about 35 aa, from about 35 aa to about 40 aa, from about 40 aa to about 45 aa, from about 45 aa to about 50 aa, from about 50 aa to about 55 aa, from about 55 aa to about 60 aa, from about 60 aa to about 65 aa, or from about 65 aa to about 70 aa.

In some cases, the co-stimulatory domain derived from an intracellular portion of the transmembrane protein HVEM (also known as TNFRSF14, RP3-395M20.6, ATAR, CD270, HVEA, HVEM, LIGHTR, and TR2). For example, a suitable co-stimulatory domain can include a domain with at least 50%, 60%, 70%, 75%, 80%, 85%, 90%, 95%, 96%, 97%, 98%, 99% or 100% sequence identity to a stretch of at least 10, 15, 20, or all of the amino acids in the following amino acid sequence: CVKRRKPRGDVVKVIVSVQRKRQEAEGEAT-VIEALQAPPDVTTVAVEETIPSFTGRSPNH (SEQ ID NO:10). In some of these embodiments, the co-stimulatory domain of both the first and the second polypeptide has a length of from about 30 aa to about 35 aa, from about 35 aa to about 40 aa, from about 40 aa to about 45 aa, from about 45 aa to about 50 aa, from about 50 aa to about 55 aa, from about 55 aa to about 60 aa, from about 60 aa to about 65 aa, or from about 65 aa to about 70 aa.

Linker

In some cases, the engineered signaling polypeptide includes a linker between any two adjacent domains. For example, a linker can be between the transmembrane domain and the first co-stimulatory domain. As another example, the ASTR can be an antibody and a linker can be between the heavy chain and the light chain. As another example, a linker can be between the ASTR and the transmembrane domain and a co-stimulatory domain. As another example, a linker can be between the co-stimulatory domain and the intracellular activating domain of the second polypeptide. As another example, the linker can be between the ASTR and the intracellular signaling domain.

The linker peptide may have any of a variety of amino acid sequences. Proteins can be joined by a spacer peptide, generally of a flexible nature, although other chemical linkages are not excluded. A linker can be a peptide of between about 1 and about 100 amino acids in length, or between about 1 and about 25 amino acids in length. These linkers can be produced by using synthetic, linker-encoding oligonucleotides to couple the proteins. Peptide linkers with a degree of flexibility can be used. The linking peptides may have virtually any amino acid sequence, bearing in mind that suitable linkers will have a sequence that results in a generally flexible peptide. The use of small amino acids, such as glycine and alanine, are of use in creating a flexible peptide. The creation of such sequences is routine to those of skill in the art.

Suitable linkers can be readily selected and can be of any of a suitable of different lengths, such as from 1 amino acid (e.g., Gly) to 20 amino acids, from 2 amino acids to 15 amino acids, from 3 amino acids to 12 amino acids, including 4 amino acids to 10 amino acids, 5 amino acids to 9 amino acids, 6 amino acids to 8 amino acids, or 7 amino acids to 8 amino acids, and may be 1, 2, 3, 4, 5, 6, or 7 amino acids.

Exemplary flexible linkers include glycine polymers $(G)_n$, glycine-serine polymers (including, for example, $(GS)_n$, $GSGGS_n$, $GGGS_n$, and $GGGGS_n$ where n is an integer of at least one), glycine-alanine polymers, alanine-serine polymers, and other flexible linkers known in the art. Glycine and glycine-serine polymers are of interest since both of these amino acids are relatively unstructured, and therefore may serve as a neutral tether between components. Glycine polymers are of particular interest since glycine accesses significantly more phi-psi space than even alanine, and is much less restricted than residues with longer side chains (see Scheraga, Rev. Computational Chem. 11173-142 (1992)). Exemplary flexible linkers include, but are not limited GGGGSGGGGSGGGGS (SEQ ID NO:53), GGGGSGGGGSGGGGSGGGGSGGGGSGGGGS (SEQ ID NO:54), GGGGSGGGSGGGGS (SEQ ID NO:55), GGSG (SEQ ID NO:56), GGSGG (SEQ ID NO:57), GSGSG (SEQ ID NO:58), GSGGG (SEQ ID NO:59), GGGSG (SEQ ID NO:60), GSSSG (SEQ ID NO:61), and the like. The ordinarily skilled artisan will recognize that design of a peptide conjugated to any elements described above can include linkers that are all or partially flexible, such that the linker can include a flexible linker as well as one or more portions that confer less flexible structure.

Chimeric Antigen Receptor

In some aspects of the present invention, an engineered signaling polypeptide is a chimeric antigen receptor (CAR) or a polynucleotide encoding a CAR, which, for simplicity, is referred to herein as "CAR." In some embodiments, a CAR of the present disclosure includes: a) at least one antigen-specific targeting region (ASTR); b) a transmembrane domain; and c) an intracellular activating domain. In illustrative embodiments, the antigen-specific targeting region of the CAR is a scFv portion of an antibody to the target antigen.

A CAR of the present disclosure can be present in the plasma membrane of a eukaryotic cell, e.g., a mammalian cell, where suitable mammalian cells include, but are not limited to, a cytotoxic cell, a T lymphocyte, a stem cell, a progeny of a stem cell, a progenitor cell, a progeny of a progenitor cell, and an NK cell, an NK-T cell, and a macrophage. When present in the plasma membrane of a eukaryotic cell, a CAR of the present disclosure is active in the presence of one or more target antigens that, in certain conditions, binds the ASTR. The target antigen is the second member of the specific binding pair. The target antigen of the specific binding pair can be a soluble (e.g., not bound to a cell) factor; a factor present on the surface of a cell such as a target cell; a factor presented on a solid surface; a factor present in a lipid bilayer; and the like. Where the ASTR is an antibody, and the second member of the specific binding pair is an antigen, the antigen can be a soluble (e.g., not bound to a cell) antigen; an antigen present on the surface of a cell such as a target cell; an antigen presented on a solid surface; an antigen present in a lipid bilayer; and the like.

In some instances, a CAR of the present disclosure, when present in the plasma membrane of a eukaryotic cell, and when activated by one or more target antigens, increases expression of at least one nucleic acid in the cell. For example, in some cases, a CAR of the present disclosure, when present in the plasma membrane of a eukaryotic cell, and when activated by the one or more target antigens, increases expression of at least one nucleic acid in the cell by at least about 10%, at least about 15%, at least about 20%, at least about 25%, at least about 30%, at least about 40%, at least about 50%, at least about 75%, at least about 2-fold, at least about 2.5-fold, at least about 5-fold, at least about 10-fold, or more than 10-fold, compared with the level of transcription of the nucleic acid in the absence of the one or more target antigens.

As an example, the CAR of the present disclosure can include an immunoreceptor tyrosine-based activation motif (ITAM)-containing intracellular signaling polypeptide.

A CAR of the present disclosure, when present in the plasma membrane of a eukaryotic cell, and when activated by one or more target antigens, can, in some instances, result in increased production of one or more cytokines by the cell. For example, a CAR of the present disclosure, when present in the plasma membrane of a eukaryotic cell, and when activated by the one or more target antigens, can increase production of a cytokine by the cell by at least about 10%, at least about 15%, at least about 20%, at least about 25%, at least about 30%, at least about 40%, at least about 50%, at least about 75%, at least about 2-fold, at least about 2.5-fold, at least about 5-fold, at least about 10-fold, or more than 10-fold, compared with the amount of cytokine produced by the cell in the absence of the one or more target antigens. Cytokines whose production can be increased include, but are not limited to interferon gamma (IFN-γ), tumor necrosis factor-alpha (TNF-α), IL-2, IL-15, IL-12, IL-4, IL-5, IL-10; a chemokine; a growth factor; and the like.

In some cases, a CAR of the present disclosure, when present in the plasma membrane of a eukaryotic cell, and when activated by one or more target antigens, can result in both an increase in transcription of a nucleic acid in the cell and an increase in production of a cytokine by the cell.

In some instances, a CAR of the present disclosure, when present in the plasma membrane of a eukaryotic cell, and when activated by one or more target antigens, results in cytotoxic activity by the cell toward a target cell that expresses on its cell surface an antigen to which the antigen-binding domain of the first polypeptide of the CAR binds. For example, where the eukaryotic cell is a cytotoxic cell (e.g., an NK cell or a cytotoxic T lymphocyte), a CAR of the present disclosure, when present in the plasma membrane of the cell, and when activated by the one or more target antigens, increases cytotoxic activity of the cell toward a target cell that expresses on its cell surface the one or more target antigens. For example, where the eukaryotic cell is an NK cell or a T lymphocyte, a CAR of the present disclosure, when present in the plasma membrane of the cell, and when activated by the one or more target antigens, increases cytotoxic activity of the cell by at least about 10%, at least about 15%, at least about 20%, at least about 25%, at least about 30%, at least about 40%, at least about 50%, at least about 75%, at least about 2-fold, at least about 2.5-fold, at least about 5-fold, at least about 10-fold, or more than 10-fold, compared to the cytotoxic activity of the cell in the absence of the one or more target antigens.

In some cases, a CAR of the present disclosure, when present in the plasma membrane of a eukaryotic cell, and when activated by one or more target antigens, can result in other CAR activation related events such as proliferation and expansion (either due to increased cellular division or anti-apoptotic responses).

In some cases, a CAR of the present disclosure, when present in the plasma membrane of a eukaryotic cell, and when activated by one or more target antigens, can result in other CAR activation related events such as intracellular signaling modulation, cellular differentiation, or cell death.

A CAR of the present disclosure can be present in a eukaryotic cell membrane, where the first and second polypeptides of the CAR are not covalently linked to one another. A CAR of the present disclosure can be present in a eukaryotic cell membrane as a single heterodimer that is not covalently linked to any other polypeptide in the membrane. Alternatively, a first CAR of the present disclosure can be present in a eukaryotic cell membrane as a heterodimer that is covalently or non-covalently linked to a second CAR of the present disclosure. In some cases, the first and the second CAR are covalently linked via a disulfide bond formed between cysteines present in a stalk present in both the first polypeptide of the first CAR and the first polypeptide of the second CAR.

In some cases, a CAR of the present disclosure can be present in a eukaryotic cell membrane, where the first polypeptides of the CAR include an antibody fragment and the second polypeptides of the CAR include a signal transducing domain derived from a cytokine receptor, such that, upon dimerization, the CAR may represent a heterodimeric-signalobody CAR, e.g., a signalobody composed of at least two independent polypeptides. A "signalobody", as it is known in the art, is a single chimeric macromolecule composed of an antibody fragment and a signal transduction domain derived from a cytokine receptor. In certain instances, a heterodimeric-signalobody CAR of the present disclosure, when present in the cell membrane of a eukaryotic cell, dimerized by a dimerizer, and activated by an antigen, e.g., an oligomerized antigen, may induce the oligomerization of the heterodimeric-signalobody CAR. Such ligand-induced oligomerization of a heterodimeric-signalobody CAR may activate, e.g., increase, or perpetuate, e.g., maintain, signal transduction, e.g., ligand-induced oligomerization of a heterodimeric-signalobody CAR may transmit a signal eliciting a cellular response. In some instances, a plurality of heterodimeric-signalobody CARs may be utilized combinatorially to elicit a desired cellular response.

In some embodiments, CARs of the present disclosure are microenvironment restricted. This property is typically the result of the microenvironment restricted nature of the ASTR domain of the CAR. Thus, CARs of the present disclosure can have a lower binding affinity or, in illustrative embodiments, can have a higher binding affinity to one or more target antigens under a condition(s) in a microenvironment than under a condition in a normal physiological environment.

Recombination of Sequences

In certain instances, sequences of the engineered signaling polypeptides, which can be referred to herein as recombinant polypeptides, may be rearranged or deleted in a cell through the use of site-specific recombination technology. In certain embodiments, the cellular activation-related response to a particular engineered signaling polypeptide can be changed by site-specific recombination, e.g., a first intracellular activating domain of an engineered signaling polypeptide eliciting a first activation-related response may be exchanged for a second intracellular activating domain eliciting a second activation-related response. As will be clear to one skilled in the art, site-specific recombination can be used in a cell to exchange any domain or sequence of an engineered signaling polypeptide with any other domain or sequence as disclosed herein. As will also be clear to one skilled in the art, site-specific recombination can be used in a cell to delete any domain or sequence of an engineered signaling polypeptide. Such exchange and excision of sequences and domains is known in the art, see, e.g., domain switching in signalobodies as described in Tone et al. (2013) *Biotechnology and Bioengineering*, 3219-3226, the disclosure of which is disclosed herein by reference. Mechanisms and requirements for performing site-specific recombination in vivo are also well known in the art, see, e.g., Grindley et al. (2006) *Annual Review of Biochemistry*, 567-605 and Tropp (2012) Molecular Biology (Jones & Bartlett Publishers, Sudbury, Mass.), the disclosures of which are incorporated herein by reference.

In some embodiments, the engineered signaling polypeptides are generated by fusing all the different domains discussed above together to form a fusion protein. The engineered signaling polypeptide is typically generated by a transcriptional unit comprising polynucleotide sequences that encode the different domains of the engineered signaling polypeptides as discussed herein. In some embodiments, the ASTR of the present invention, which functions to recognize and bind with an antigen on target cells, is microenvironment restricted.

The wild-type or native protein that is suitable to be used in whole or in part for at least its binding domain for the target antigen, as an ASTR in the present invention may be discovered by generating a protein library and screening the library for a protein with a desired binding affinity to the target antigen. The wild-type protein may be discovered by screening a cDNA library. A cDNA library is a combination of cloned cDNA (complementary DNA) fragments inserted into a collection of host cells, which together constitute some portion of the transcriptome of the organism. cDNA is produced from fully transcribed mRNA and therefore contains the coding sequence for expressed proteins of an organism. The information in cDNA libraries is a powerful and useful tool for discovery of proteins with desired properties by screening the libraries for proteins with the desired binding affinity to the target antigen.

Combinations

In some embodiments, a polynucleotide provided by the replication incompetent recombinant retroviral particles has one or more transcriptional units that encode certain combinations of the one or more engineered signaling polypeptides. In some methods and compositions provided herein, genetically modified T cells include the combinations of the one or more engineered signaling polypeptides after transduction of T cells by the replication incompetent recombinant retroviral particles. It will be understood that the reference of a first polypeptide, a second polypeptide, a third polypeptide, etc. is for convenience and elements on a "first polypeptide" and those on a "second polypeptide" means that the elements are on different polypeptides that are referenced as first or second for reference and convention only, typically in further elements or steps to that specific polypeptide.

In some embodiments, the first engineered signaling polypeptide includes an extracellular antigen binding domain, which is capable of binding an antigen, and an intracellular signaling domain. In other embodiments, the first engineered signaling polypeptide also includes a T cell survival motif and/or a transmembrane domain. In some embodiments, the first engineered signaling polypeptide does not include a co-stimulatory domain, while in other embodiments, the first engineered signaling polypeptide does include a co-stimulatory domain.

In some embodiments, a second engineered signaling polypeptide includes a lymphoproliferative gene product and optionally an extracellular antigen binding domain. In some embodiments, the second engineered signaling polypeptide also includes one or more of the following: a T cell survival motif, an intracellular signaling domain, and one or more co-stimulatory domains. In other embodiments, when two engineered signaling polypeptides are used, at least one is a CAR.

In one embodiment, the one or more engineered signaling polypeptides are expressed under a T cell specific promoter or a general promoter under the same transcript wherein in the transcript, nucleic acids encoding the engineered signaling polypeptides are separated by nucleic acids that encode one or more internal ribosomal entry sites (IREs) or one or more protease cleavage peptides.

In certain embodiments, the polynucleotide encodes two engineered signaling polypeptides wherein the first engineered signaling polypeptide includes a first extracellular antigen binding domain, which is capable of binding to a first antigen, and a first intracellular signaling domain but not a co-stimulatory domain, and the second polypeptide includes a second extracellular antigen binding domain, which is capable of binding VEGF, and a second intracellular signaling domain, such as for example, the signaling domain of a co-stimulatory molecule. In a certain embodiment, the first antigen is PSCA, PSMA, or BCMA. In a certain embodiment, the first extracellular antigen binding domain comprises an antibody or fragment thereof (e.g., scFv), e.g., an antibody or fragment thereof specific to PSCA, PSMA, or BCMA. In a certain embodiment, the second extracellular antigen binding domain that binds VEGF is a receptor for VEGF, i.e., VEGFR. In certain embodiments, the VEGFR is VEGFR1, VEGFR2, or VEGFR3. In a certain embodiment, the VEGFR is VEGFR2.

In certain embodiments, the polynucleotide encodes two engineered signaling polypeptides wherein the first engineered signaling polypeptide includes an extracellular tumor antigen binding domain and a CD3 signaling domain, and the second engineered signaling polypeptide includes an antigen-binding domain, wherein the antigen is an angiogenic or vasculogenic factor, and one or more co-stimulatory molecule signaling domains. The angiogenic factor can be, e.g., VEGF. The one or more co-stimulatory molecule signaling motifs can comprise, e.g., co-stimulatory signaling domains from each of CD27, CD28, OX40, ICOS, and 4-1BB.

In certain embodiments, the polynucleotide encodes two engineered signaling polypeptides wherein the first engineered signaling polypeptide includes an extracellular tumor antigen-binding domain and a CD3 signaling domain, the second polypeptide comprises an antigen-binding domain, which is capable of binding to VEGF, and co-stimulatory signaling domains from each of CD27, CD28, OX40, ICOS, and 4-1BB. In a further embodiment, the first signaling polypeptide or second signaling polypeptide also has a T cell survival motif. In some embodiments, the T cell survival motif is, or is derived from, an intracellular signaling domain of IL-7 receptor (IL-7R), an intracellular signaling domain of IL-12 receptor, an intracellular signaling domain of IL-15 receptor, an intracellular signaling domain of IL-21 receptor, or an intracellular signaling domain of transforming growth factor β (TGFβ) receptor or the TGFβ decoy receptor (TGF-β-dominant-negative receptor II (DNRII)).

In certain embodiments, the polynucleotide encodes two engineered signaling polypeptides wherein the first engineered signaling polypeptide includes an extracellular tumor antigen-binding domain and a CD3ξ signaling domain, and the second engineered signaling polypeptide includes an antigen-binding domain, which is capable of binding to VEGF, an IL-7 receptor intracellular T cell survival motif, and co-stimulatory signaling domains from each of CD27, CD28, OX40, ICOS, and 4-1BB.

In some embodiments, more than two signaling polypeptides are encoded by the polynucleotide. In certain embodiments, only one of the engineered signaling polypeptides includes an antigen binding domain that binds to a tumor-associated antigen or a tumor-specific antigen; each of the remainder of the engineered signaling polypeptides comprises an antigen binding domain that binds to an antigen that is not a tumor-associated antigen or a tumor-specific antigen. In other embodiments, two or more of the engineered signaling polypeptides include antigen binding domains that bind to one or more tumor-associated antigens or tumor-specific antigens, wherein at least one of the engineered signaling polypeptides comprises an antigen binding domain that does not bind to a tumor-associated antigen or a tumor-specific antigen.

In some embodiments, the tumor-associated antigen or tumor-specific antigen is Her2, prostate stem cell antigen (PSCA), PSMA (prostate-specific membrane antigen), B cell maturation antigen (BCMA), alpha-fetoprotein (AFP), carcinoembryonic antigen (CEA), cancer antigen-125 (CA-125), CA19-9, calretinin, MUC-1, epithelial membrane protein (EMA), epithelial tumor antigen (ETA), tyrosinase, melanoma-associated antigen (MAGE), CD34, CD45, CD99, CD117, chromogranin, cytokeratin, desmin, glial fibrillary acidic protein (GFAP), gross cystic disease fluid protein (GCDFP-15), HMB-45 antigen, protein melan-A (melanoma antigen recognized by T lymphocytes; MART-1), myo-D1, muscle-specific actin (MSA), neurofilament, neuron-specific enolase (NSE), placental alkaline phosphatase, synaptophysin, thyroglobulin, thyroid transcription factor-1, the dimeric form of the pyruvate kinase isoenzyme type M2 (tumor M2-PK), CD19, CD22, CD27, CD30, CD70, GD2 (ganglioside G2), EphA2, CSPG4, CD138, FAP (Fibroblast Activation Protein), CD171, kappa, lambda, 5T4, $\alpha v \beta 6$ integrin, integrin $\alpha v \beta 3$ (CD61), galactin, K-Ras (V-Ki-ras2 Kirsten rat sarcoma viral oncogene), Ral-B, B7-H3, B7-H6, CAIX, CD20, CD33, CD44, CD44v6, CD44v7/8, CD123, EGFR, EGP2, EGP40, EpCAM, fetal AchR, FR$\alpha$, GD3, HLA-A1+MAGE1, HLA-A1+NY-ESO-1, IL-11R$\alpha$, IL-13R$\alpha$2, Lewis-Y, Muc16, NCAM, NKG2D Ligands, NY-ESO-1, PRAME, ROR1, Survivin, TAG72, TEMs, VEGFR2, EGFRvIII (epidermal growth factor variant III), sperm protein 17 (Sp17), mesothelin, PAP (prostatic acid phosphatase), prostein, TARP (T cell receptor gamma alternate reading frame protein), Trp-p8, STEAP1 (six-transmembrane epithelial antigen of the prostate 1), an abnormal ras protein, or an abnormal p53 protein.

In some embodiments, the first engineered signaling polypeptide includes a first extracellular antigen binding domain that binds a first antigen, and a first intracellular signaling domain; and a second engineered signaling polypeptide includes a second extracellular antigen binding domain that binds a second antigen, or a receptor that binds the second antigen; and a second intracellular signaling domain, wherein the second engineered signaling polypeptide does not comprise a co-stimulatory domain. In a certain embodiment, the first antigen-binding domain and the second antigen-binding domain are independently an antigen-binding portion of a receptor or an antigen-binding portion of an antibody. In a certain embodiment, either or both of the first antigen binding domain or the second antigen binding domain are scFv antibody fragments. In certain embodiments, the first engineered signaling polypeptide and/or the second engineered signaling polypeptide additionally comprises a transmembrane domain. In a certain embodiment, the first engineered signaling polypeptide or the second engineered signaling polypeptide comprises a T cell survival motif, e.g., any of the T cell survival motifs described herein.

In another embodiment, the first engineered signaling polypeptide includes a first extracellular antigen binding domain that binds HER2 and the second engineered signaling polypeptide includes a second extracellular antigen binding domain that binds MUC-1.

In another embodiment, the second extracellular antigen binding domain of the second engineered signaling polypeptide binds an interleukin.

In another embodiment, the second extracellular antigen binding domain of the second engineered signaling polypeptide binds a damage associated molecular pattern molecule (DAMP; also known as an alarmin). In other embodiments, a DAMP is a heat shock protein, chromatin-associated protein high mobility group box 1 (HMGB1), S100A8 (also known as MRP8, or calgranulin A), S100A9 (also known as MRP14, or calgranulin B), serum amyloid A (SAA), deoxyribonucleic acid, adenosine triphosphate, uric acid, or heparin sulfate.

In certain embodiments, said second antigen is an antigen on an antibody that binds to an antigen presented by a tumor cell.

In some embodiments, signal transduction activation through the second engineered signaling polypeptide is non-antigenic, but is associated with hypoxia. In certain embodiments, hypoxia is induced by activation of hypoxia-inducible factor-1$\alpha$ (HIF-1$\alpha$), HIF-1$\beta$, HIF-2$\alpha$, HIF-2$\beta$, HIF-3$\alpha$, or HIF-3$\beta$.

In some embodiments, expression of the one or more engineered signaling polypeptides is regulated by a control element, which is disclosed in more detail herein.

Additional Sequences

The engineered signaling polypeptides, such as CARs, can further include one or more additional polypeptide domains, where such domains include, but are not limited to, a signal sequence; an epitope tag; an affinity domain; and a polypeptide whose presence or activity can be detected (detectable marker), for example by an antibody assay or because it is a polypeptide that produces a detectable signal. Non-limiting examples of additional domains for any of the aspects or embodiments provided herein, include a domain with at least 50%, 60%, 70%, 75%, 80%, 85%, 90%, 95%, 96%, 97%, 98%, 99% or 100% sequence identity to any of the following sequences as described below: a signal sequence, an epitope tag, an affinity domain, or a polypeptide that produces a detectable signal.

Signal sequences that are suitable for use in a subject CAR, e.g., in the first polypeptide of a subject CAR, include any eukaryotic signal sequence, including a naturally-occurring signal sequence, a synthetic (e.g., man-made) signal sequence, etc. In some embodiments, for example, the signal sequence can be the CD8 signal sequence MALPVTALLL-PLALLLHAARP (SEQ ID NO:74).

Suitable epitope tags include, but are not limited to, hemagglutinin (HA; e.g., YPYDVPDYA; SEQ ID NO:37); FLAG (e.g., DYKDDDDK; SEQ ID NO:38); c-myc (e.g., EQKLISEEDL; SEQ ID NO:39), and the like.

Affinity domains include peptide sequences that can interact with a binding partner, e.g., such as one immobilized on a solid support, useful for identification or purification. DNA sequences encoding multiple consecutive single amino acids, such as histidine, when fused to the expressed protein, may be used for one-step purification of the recombinant protein by high affinity binding to a resin column, such as nickel sepharose. Exemplary affinity domains include His5 (HHHHH; SEQ ID NO:40), His×6 (HHHHHH; SEQ ID NO:41), c-myc (EQKLISEEDL; SEQ ID NO:39), Flag (DYKDDDDK; SEQ ID NO:38), Strep Tag (WSHPQFEK; SEQ ID NO:42), hemagglutinin, e.g., HA Tag (YPYDVPDYA; SEQ ID NO:37), GST, thioredoxin, cellulose binding domain, RYIRS (SEQ ID NO:43), Phe-His-His-Thr (SEQ ID NO:44), chitin binding domain, S-peptide, T7 peptide, SH2 domain, C-end RNA tag, WEAAAREAC-CRECCARA (SEQ ID NO:45), metal binding domains, e.g., zinc binding domains or calcium binding domains such as those from calcium-binding proteins, e.g., calmodulin, troponin C, calcineurin B, myosin light chain, recoverin, S-modulin, visinin, VILIP, neurocalcin, hippocalcin, frequenin, caltractin, calpain large-subunit, S100 proteins, parvalbumin, calbindin D9K, calbindin D28K, and calretinin, inteins, biotin, streptavidin, MyoD, Id, leucine zipper sequences, and maltose binding protein.

Suitable detectable signal-producing proteins include, e.g., fluorescent proteins; enzymes that catalyze a reaction that generates a detectable signal as a product; and the like.

Suitable fluorescent proteins include, but are not limited to, green fluorescent protein (GFP) or variants thereof, blue fluorescent variant of GFP (BFP), cyan fluorescent variant of GFP (CFP), yellow fluorescent variant of GFP (YFP), enhanced GFP (EGFP), enhanced CFP (ECFP), enhanced YFP (EYFP), GFPS65T, Emerald, Topaz (TYFP), Venus, Citrine, mCitrine, GFPuv, destabilized EGFP (dEGFP), destabilized ECFP (dECFP), destabilized EYFP (dEYFP), mCFPm, Cerulean, T-Sapphire, CyPet, YPet, mKO, HcRed, t-HcRed, DsRed, DsRed2, DsRed-monomer, J-Red, dimer2, t-dimer2(12), mRFP1, pocilloporin, *Renilla* GFP, Monster GFP, paGFP, Kaede protein and kindling protein, Phycobiliproteins and Phycobiliprotein conjugates including B-Phycoerythrin, R-Phycoerythrin and Allophycocyanin. Other examples of fluorescent proteins include mHoneydew, mBanana, mOrange, dTomato, tdTomato, mTangerine, mStrawberry, mCherry, mGrapel, mRaspberry, mGrape2, mPlum (Shaner et al. (2005) *Nat. Methods* 2:905-909), and the like. Any of a variety of fluorescent and colored proteins from Anthozoan species, as described in, e.g., Matz et al. (1999) *Nature Biotechnol.* 17:969-973, is suitable for use.

Suitable enzymes include, but are not limited to, horse radish peroxidase (HRP), alkaline phosphatase (AP), beta-galactosidase (GAL), glucose-6-phosphate dehydrogenase, beta-N-acetylglucosaminidase, β-glucuronidase, invertase, Xanthine Oxidase, firefly luciferase, glucose oxidase (GO), and the like.

Recognition and/or Elimination Domain

Any of the replication incompetent recombinant retroviral particles provided herein can include nucleic acids that encode a recognition or elimination domain as part of, or separate from, nucleic acids encoding any of the engineered signaling polypeptides provided herein. Thus, any of the engineered signaling polypeptides provided herein, can include a recognition or elimination domain. For example, any of the CARs disclosed herein can include a recognition or elimination domain. Moreover, a recognition or elimination domain can be expressed together with, or even fused with any of the lymphoproliferative elements disclosed herein. The recognition or elimination domains are expressed on the T cell and/or NK cell but are not expressed on the replication incompetent recombinant retroviral particles.

In some embodiments, the recognition or elimination domain can be derived from herpes simplex virus-derived enzyme thymidine kinase (HSV-tk) or inducible caspase-9. In some embodiments, the recognition or elimination domain can include a modified endogenous cell-surface molecule, for example as disclosed in U.S. Pat. No. 8,802,374. The modified endogenous cell-surface molecule can be any cell-surface related receptor, ligand, glycoprotein, cell adhesion molecule, antigen, integrin, or cluster of differentiation (CD) that is modified. In some embodiments, the modified endogenous cell-surface molecule is a truncated tyrosine kinase receptor. In one aspect, the truncated tyrosine kinase receptor is a member of the epidermal growth factor receptor (EGFR) family (e.g., ErbB1, ErbB2, ErbB3, ErbB4. In some embodiments, the recognition domain can be a polypeptide that is recognized by an antibody that recognizes the extracellular domain of an EGFR member. In some embodiments, the recognition domain can be at least 20 contiguous amino acids of an EGFR family member, or for example, between 20 and 50 contiguous amino acids of an EGFR family member. For example, SEQ ID NO:78, is an exemplary polypeptide that is recognized by, and under the appropriate conditions bound by an antibody that recognizes the extracellular domain of an EGFR member. Such extracellular EGFR epitopes are sometimes referred to herein as eTags. In illustrative embodiments, such epitopes are recognized by commercially available anti-EGFR monoclonal antibodies.

Epidermal growth factor receptor, also known as EGFR, ErbB1 and HER1, is a cell-surface receptor for members of the epidermal growth factor family of extracellular ligands. Alterations in EGFR activity have been implicated in certain cancers. In some embodiments, a gene encoding an EGFR polypeptide including human epidermal growth factor receptor (EGFR) is constructed by removal of nucleic acid sequences that encode polypeptides including the membrane distal EGF-binding domain and the cytoplasmic signaling tail, but retains the extracellular membrane proximal epitope recognized by an anti-EGFR antibody. Preferably, the antibody is a known, commercially available anti-EGFR monoclonal antibody, such as cetuximab, matuzumab, necitumumab or panitumumab.

Others have shown that application of biotinylated-cetuximab to immunomagnetic selection in combination with anti-biotin microbeads successfully enriches T cells that have been lentivirally transduced with EGFRt-containing constructs from as low as 2% of the population to greater than 90% purity without observable toxicity to the cell preparation. Furthermore, others have shown that constitutive expression of this inert EGFR molecule does not affect T cell phenotype or effector function as directed by the coordinately expressed chimeric antigen receptor (CAR), CD19R. In addition, others have shown that through flow cytometric analysis, EGFR was successfully utilized as an in vivo tracking marker for T cell engraftment in mice. Furthermore, EGFR was demonstrated to have suicide gene potential through Erbitux® mediated antibody dependent cellular cytotoxicity (ADCC) pathways. The inventors of the present disclosure have successfully expressed eTag in PBMCs using lentiviral vectors, and have found that expression of eTag in vitro by PBMCs exposed to Cetuximab, provided an effective elimination mechanism for PBMCs. Thus, EGFR may be used as a non-immunogenic selection tool, tracking marker, and suicide gene for transduced T cells that have immunotherapeutic potential. The EGFR nucleic acid may also be detected by means well known in the art.

In some embodiments provided herein, EGFR is expressed as part of a single polypeptide that also includes the CAR or as part of a single polypeptide that includes the lymphoproliferative element. In some embodiments, the amino acid sequence encoding the EGFR recognition domain can be separated from the amino acid sequence encoding the chimeric antigen receptor by a cleavage signal and/or a ribosomal skip sequence. The ribosomal skip and/or cleavage signal can be any ribosomal skip and/or cleavage signal known in the art. Not to be limited by theory, the ribosomal skip sequence can be, for example 2A-1 with amino acid sequence GSGEGRGSLLTCGDVEENPGP (SEQ ID NO:77). Not to be limited by theory, other examples of cleavage signals and ribosomal skip sequences include FMDV 2A (F2A); equine rhinitis A virus 2A (abbreviated as E2A); porcine teschovirus-1 2A (P2A); and Thoseaasigna virus 2A (T2A). In some embodiments, the polynucleotide sequence encoding the recognition domain can be on the same transcript as the CAR or lymphoproliferative element but separated from the polynucleotide sequence encoding the CAR or lymphoproliferative element by an internal ribosome entry site.

In other embodiments as exemplified empirically herein, a recognition domain can be expressed as part of a fusion polypeptide, fused to a lymphoproliferative element. Such constructs provide the advantage, especially in combination with other "space saving" elements provided herein, of taking up less genomic space on an RNA genome compared to separate polypeptides. In one illustrative embodiment, an eTag is expressed as a fusion polypeptide, fused to an IL7Rα mutant, as experimentally demonstrated herein.

Pseudotyping Elements

Many of the methods and compositions provided herein include pseudotyping elements. The pseudotyping of replication incompetent recombinant retroviral particles with heterologous envelope glycoproteins typically alters the tropism of a virus and facilitates the transduction of host cells. A pseudotyping element as used herein can include a "binding polypeptide" that includes one or more polypeptides, typically glycoproteins, that identify and bind the target host cell, and one or more "fusogenic polypeptides" that mediate fusion of the retroviral and target host cell membranes, thereby allowing a retroviral genome to enter the target host cell. In some embodiments provided herein, pseudotyping elements are provided as polypeptide(s)/protein(s), or as nucleic acid sequences encoding the polypeptide(s)/protein(s).

In some embodiments, the pseudotyping element is the feline endogenous virus (RD114) envelope protein, the oncoretroviral amphotropic envelope protein, the oncoretroviral ecotropic envelope protein, the vesicular stomatitis virus envelope protein (VSV-G), and/or an envelope or modified envelope protein from the family of Paramyxoviridae, for example the paramyxovirus Measles envelope proteins H and F.

In some embodiments, the pseudotyping elements include a binding polypeptide and a fusogenic polypeptide derived from different proteins. For example, the replication incompetent recombinant retroviral particles of the methods and compositions disclosed herein can be pseudotyped with the fusion (F) and hemagglutinin (H) polypeptides of the measles virus (MV), as non-limiting examples, clinical wildtype strains of MV, and vaccine strains including the Edmonston strain (MV-Edm) or fragments thereof. Not to be limited by theory, both hemagglutinin (H) and fusion (F) polypeptides are believed to play a role in entry into host cells wherein the H protein binds MV to receptors CD46, SLAM, and Nectin-4 on target cells and F mediates fusion of the retroviral and host cell membranes. In an illustrative embodiment, especially where the target cell is a T cell and/or NK cell, the binding polypeptide is a Measles Virus H polypeptide and the fusogenic polypeptide is a Measles Virus F polypeptide.

In some studies, lentiviral particles pseudotyped with truncated F and H polypeptides had a significant increase in titers and transduction efficiency (Funke et al. 2008. *Molecular Therapy.* 16(8):1427-1436), (Frecha et al. 2008. *Blood.* 112(13):4843-4852). The highest titers were obtained when the F cytoplasmic tail was truncated by 30 residues (referred to as MV(Ed)-FΔ30 (SEQ ID NO:105)). For the H variants, optimal truncation occurred when 18 or 19 residues were deleted (MV(Ed)-HΔ18 (SEQ ID NO:106) or MV(Ed)-HΔ19), although variants with a truncation of 24 residues with and without replacement of deleted residues with alanine (MV(Ed)-HΔ24 (SEQ ID NO:235) and MV(Ed)-HΔ24+A) also resulted in optimal titers.

In some embodiments, including those directed to transducing T cells and/or NK cells, the replication incompetent recombinant retroviral particles of the methods and compositions disclosed herein are pseudotyped with mutated or variant versions of the measles virus fusion (F) and hemagglutinin (H) polypeptides, in illustrative examples, cytoplasmic domain deletion variants of measles virus F and H polypeptides. In some embodiments, the mutated F and H polypeptides are "truncated H" or "truncated F" polypeptides, whose cytoplasmic portion has been truncated, i.e. amino acid residues (or coding nucleic acids of the corresponding nucleic acid molecule encoding the protein) have been deleted. "HΔY" and "FΔX" designate such truncated H and F polypeptide, respectively, wherein "Y" refers to 1-34 residues that have been deleted from the amino termini and "X" refers to 1-35 residues that have been deleted from the carboxy termini of the cytoplasmic domains. In a further embodiment, the "truncated F polypeptide" is FΔ24 or FΔ30 and/or the "truncated H protein" is selected from the group consisting of HΔ14, HΔ15, HΔ16, HΔ17, HΔ18, HΔ19, HΔ20, HΔ21+A, HΔ24 and HΔ24+4A, more preferably HΔ18 or HΔ24. In an illustrative embodiment, the truncated F polypeptide is MV(Ed)-FΔ30 and the truncated H polypeptide is MV(Ed)-HΔ18. In some embodiments, the fusogenic polypeptide includes multiple elements expressed as one polypeptide. In some embodiments, the binding polypeptide and fusogenic polypeptide are translated from the same transcript but from separate ribosome binding sites; in other embodiments, the binding polypeptide and fusogenic polypeptide are separated by a cleavage peptide site, which not to be bound by theory, is cleaved after translation, as is common in the literature, or a ribosomal skip sequence. In some embodiments, the translation of the binding polypeptide and fusogenic polypeptide from separate ribosome binding sites results in a higher amount of the fusogenic polypeptide as compared to the binding polypeptide. In some embodiments, the ratio of the fusogenic polypeptide to the binding polypeptide is at least 2:1, at least 3:1, at least 4:1, at least 5:1, at least 6:1, at least 7:1, or at least 8:1. In some embodiments, the ratio of the fusogenic polypeptide to the binding polypeptide is between 1.5:1, 2:1, or 3:1, on the low end of the range, and 3:1, 4:1, 5:1, 6:1, 7:1, 8:1. 9:1 or 10:1 on the high end of the range.

Activation Elements

Many of the methods and composition aspects of the present disclosure include an activation element, or a nucleic acid encoding an activation element. The restrictions associated with lentiviral (LV) transduction into resting T cells are attributed to a series of pre-entry and post-entry barriers as well as cellular restrictive factors (Strebel et al 2009. *BMC Medicine* 7:48). One restriction is the inability for the envelope pseudotyped-LV particles to recognize potential receptors and mediate fusion with the cellular membrane. However, under certain conditions, the transduction of resting T cells with HIV-1-based lentiviral vectors is possible mostly upon T cell receptor (TCR) CD3 complex and CD28 co-stimulation (Korin & Zack. 1998. *Journal of Virology.* 72:3161-8, Maurice et al. 2002. *Blood* 99:2342-50), as well as through exposure to cytokines (Cavalieri et al 2003).

Cells of the immune system such as T lymphocytes recognize and interact with specific antigens through receptors or receptor complexes which, upon recognition or an interaction with such antigens, cause activation of the cell and expansion in the body. An example of such a receptor is the antigen-specific T lymphocyte receptor complex (TCR/CD3). The T cell receptor (TCR) is expressed on the surface of T lymphocytes. One component, CD3, is responsible for intracellular signaling following occupancy of the TCR by ligand. The T lymphocyte receptor for antigen-CD3 complex (TCR/CD3) recognizes antigenic peptides that are presented to it by the proteins of the major histocompatibility complex (MHC). Complexes of MHC and peptide are expressed on the surface of antigen presenting cells and other T lymphocyte targets. Stimulation of the TCR/CD3 complex results in activation of the T lymphocyte and a consequent antigen-specific immune response. The TCR/CD3 complex plays a central role in the effector function and regulation of the immune system.

T lymphocytes also require a second, co-stimulatory signal to become fully active. Without such a signal, T lymphocytes are either non-responsive to antigen binding to the TCR, or become anergic. Such a co-stimulatory signal, for example, is provided by CD28, a T lymphocyte protein, which interacts with CD80 and CD86 on antigen-producing cells. As used herein, a functional extracellular fragment of CD80 retains its ability to interact with CD28. ICOS (Inducible COStimulator), another T lymphocyte protein, provides a co-stimulatory signal when bound to ICOS ligand.

Activation of the T cell receptor (TCR) CD3 complex and co-stimulation with CD28 can occur by ex vivo exposure to solid surfaces (e.g. beads) coated with anti-CD3 and anti-CD28. In some embodiments of the methods and compositions disclosed herein, resting T cells are activated by exposure to solid surfaces coated with anti-CD3 and anti-CD28 ex vivo.

In certain illustrative embodiments of the methods and compositions provided herein, polypeptides that are capable of binding CD3 and/or CD28, are presented as "activation elements" on the surface of replication incompetent recombinant retroviral particles of the methods and compositions disclosed herein, which are also aspects of the invention. Polypeptides that bind CD3 and/or CD28 are referred to as "activation elements" because of their ability to activate resting T cells.

In some embodiments, the activation element is a polypeptide capable of binding to CD3. In some embodiments, the polypeptide capable of binding to CD3 is an anti-CD3 antibody, or a fragment thereof that retains the ability to bind to CD3. In illustrative embodiments, the anti-CD3 antibody or fragment thereof is a single chain anti-CD3 antibody, such as but not limited to, an anti-CD3 scFv. In another illustrative embodiment, the polypeptide capable of binding to CD3 is anti-CD3scFvFc.

A number of anti-human CD3 monoclonal antibodies and antibody fragments thereof are available, and can be used in the present invention, including but not limited to UCHT1, OKT-3, HIT3A, TRX4, X35-3, VIT3, BMA030 (BW264/56), CLB-T3/3, CRIS7, YTH12.5, F111409, CLB-T3.4.2, TR-66, WT31, WT32, SPv-T3b, 11D8, XIII-141, XII146, XIII-87, 12F6, T3/RW2-8C8, T3/RW24B6, OKT3D, M-T301, SMC2 and F101.01.

In some embodiments, the activation element is a polypeptide capable of binding to CD28. In some embodiments, the polypeptide capable of binding to CD28 is an anti-CD28 antibody, or a fragment thereof that retains the ability to bind to CD28. In other embodiments, the polypeptide capable of binding to CD28 is CD80, CD86, or a functional fragment thereof that is capable of binding CD28 and inducing CD28-mediated activation of Akt, such as an external fragment of CD80. In some aspects herein, an external fragment of CD80 means a fragment that is typically present on the outside of a cell in the normal cellular location of CD80, that retains the ability to bind to CD28. In illustrative embodiments, the anti-CD28 antibody or fragment thereof is a single chain anti-CD28 antibody, such as, but not limited to, an anti-CD28 scFv. In another illustrative embodiment, the polypeptide capable of binding to CD28 is CD80, or a fragment of CD80 such as an external fragment of CD80.

Anti-CD28 antibodies are known in the art and can include, as non-limiting examples, monoclonal antibody 9.3, an IgG2a antibody (Dr. Jeffery Ledbetter, Bristol Myers Squibb Corporation, Seattle, Wash.), monoclonal antibody KOLT-2, an IgG1 antibody, 15E8, an IgG1 antibody, 248.23.2, an IgM antibody and EX5.3D10, an IgG2a antibody.

In an illustrative embodiment, an activation element includes two polypeptides, a polypeptide capable of binding to CD3 and a polypeptide capable of binding to CD28.

In certain embodiments, the polypeptide capable of binding to CD3 or CD28 is an antibody, a single chain monoclonal antibody or an antibody fragment, for example a single chain antibody fragment. Accordingly, the antibody fragment can be, for example, a single chain fragment variable region (scFv), an antibody binding (Fab) fragment of an antibody, a single chain antigen-binding fragment (scFab), a single chain antigen-binding fragment without cysteines (scFabΔC), a fragment variable region (Fv), a construct specific to adjacent epitopes of an antigen (CRAb), or a single domain antibody (VH or VL).

In some embodiments, an activation element is fused to a heterologous signal sequence and/or a heterologous membrane attachment sequence, both of which help direct the activation element to the membrane. The heterologous signal sequence targets the activation element to the endoplasmic reticulum, where the heterologous membrane attachment sequence covalently attaches to one or several fatty acids (also known as posttranslational lipid modification) such that the activation elements that are fused to the heterologous membrane attachment sequence are anchored in the lipid rafts of the plasma membrane. In some embodiments, posttranslational lipid modification can occur via myristoylation, palmitoylation, or GPI anchorage. Myristoylation is a post-translational protein modification which corresponds to the covalent linkage of a 14-carbon saturated fatty acid, the myristic acid, to the N-terminal glycine of a eukaryotic or viral protein. Palmitoylation is a post-translational protein modification which corresponds to the covalent linkage of a C16 acyl chain to cysteines, and less frequently to serine and threonine residues, of proteins. GPI anchorage refers to the attachment of glycosylphosphatidylinositol, or GPI, to the C-terminus of a protein during posttranslational modification.

In some embodiments, the heterologous membrane attachment sequence is a GPI anchor attachment sequence. The heterologous GPI anchor attachment sequence can be derived from any known GPI-anchored protein (reviewed in Ferguson M A J, Kinoshita T, Hart G W. Glycosylphosphatidylinositol Anchors. In: Varki A, Cummings R D, Esko J D, et al., editors. *Essentials of Glycobiology*. 2nd edition. Cold Spring Harbor (N.Y.): Cold Spring Harbor Laboratory Press; 2009. Chapter 11). In some embodiments, the heterologous GPI anchor attachment sequence is the GPI anchor attachment sequence from CD14, CD16, CD48, CD55 (DAF), CD59, CD80, and CD87. In some embodiments, the heterologous GPI anchor attachment sequence is derived from CD16. In illustrative embodiments, the heterologous GPI anchor attachment sequence is derived from Fc receptor FcγRIIIb (CD16b) or decay accelerating factor (DAF), otherwise known as complement decay-accelerating factor or CD55.

In some embodiments, one or both of the activation elements include a heterologous signal sequence to help direct expression of the activation element to the cell membrane. Any signal sequence that is active in the packaging cell line can be used. In some embodiments, the signal sequence is a DAF signal sequence. In illustrative embodiments, an activation element is fused to a DAF signal sequence at its N terminus and a GPI anchor attachment sequence at its C terminus.

In an illustrative embodiment, the activation element includes anti-CD3 scFvFc fused to a GPI anchor attachment sequence derived from CD14 and CD80 fused to a GPI anchor attachment sequence derived from CD16b; and both are expressed on the surface of a replication incompetent recombinant retroviral particle provided herein. In some embodiments, the anti-CD3 scFvFc is fused to a DAF signal sequence at its N terminus and a GPI anchor attachment sequence derived from CD14 at its C terminus and the CD80 is fused to a DAF signal sequence at its N terminus and a GPI anchor attachment sequence derived from CD16b at its C terminus; and both are expressed on the surface of a replication incompetent recombinant retroviral particle provided herein. In some embodiments, the DAF signal sequence includes amino acid residues 1-30 of the DAF protein.

Membrane-Bound Cytokines

Some embodiments of the method and composition aspects provided herein, include a membrane-bound cytokine, or polynucleotides encoding a membrane-bound cytokine. Ctyokines are typically, but not always, secreted proteins. Cytokines that are naturally secreted can be engineered as fusion proteins to be membrane-bound. Membrane-bound cytokine fusion polypeptides are included in methods and compositions disclosed herein, and are also an aspect of the invention. In some embodiments, replication incompetent recombinant retroviral particles have a membrane-bound cytokine fusion polypeptide on their surface that is capable of binding a T cell and/or NK cell and promoting proliferation and/or survival thereof. Typically, membrane-bound polypeptides are incorporated into the membranes of replication incompetent recombinant retroviral particles, and when a cell is transduced by the replication incompetent recombinant retroviral particles, the fusion of the retroviral and host cell membranes results in the polypeptide being bound to the membrane of the transduced cell.

In some embodiments, the cytokine fusion polypeptide includes IL-7, IL-15, or an active fragment thereof. The membrane-bound cytokine fusion polypeptides are typically a cytokine fused to heterologous signal sequence and/or a heterologous membrane attachment sequence. In some embodiments, the heterologous membrane attachment sequence is a GPI anchor attachment sequence. The heterologous GPI anchor attachment sequence can be derived from any known GPI-anchored protein (reviewed in Ferguson M A J, Kinoshita T, Hart G W. Glycosylphosphatidylinositol Anchors. In: Varki A, Cummings R D, Esko J D, et al., editors. *Essentials of Glycobiology. 2nd edition*. Cold Spring Harbor (N.Y.): Cold Spring Harbor Laboratory Press; 2009. Chapter 11). In some embodiments, the heterologous GPI anchor attachment sequence is the GPI anchor attachment sequence from CD14, CD16, CD48, CD55 (DAF), CD59, CD80, and CD87. In some embodiments, the heterologous GPI anchor attachment sequence is derived from CD16. In an illustrative embodiment, the heterologous GPI anchor attachment sequence is derived from Fc receptor FcγRIIIb (CD16b). In some embodiments, the GPI anchor is the GPI anchor of DAF.

In illustrative embodiments, the membrane-bound cytokine is a fusion polypeptide of a cytokine fused to DAF. DAF is known to accumulate in lipid rafts that are incorporated into the membranes of replication incompetent recombinant retroviral particles budding from packaging cells. Accordingly, not to be limited by theory, it is believed that DAF fusion proteins are preferentially targeted to portions of membranes of packaging cells that will become part of a recombinant retroviral membrane.

In non-limiting illustrative embodiments, the cytokine fusion polypeptide is an IL-7, or an active fragment thereof, fused to DAF. In a specific non-limiting illustrative embodiment, the fusion cytokine polypeptide includes in order: the DAF signal sequence (residues 1-31 of DAF), IL-7 without its signal sequence, and residues 36-525 of DAF.

Riboswitch Control Element

Riboswitches

Some of the compositions and methods provided herein include one or more riboswitches or polynucleotides that include one or more riboswitch, which themselves form distinct aspects of the present disclosure. Riboswitches are a common feature in bacteria to regulate gene expression and are a means to achieve RNA control of biological functions. Riboswitches are polynucleotides that can be present in the 5'-untranslated region of mRNAs and allow for regulatory control over gene expression through binding of a small molecule ligand that induces or suppresses a riboswitch activity. Typically, the riboswitch controls a gene product involved in the generation of the small molecule ligand, thus forming a feedback loop. Riboswitches typically act in a cis-fashion, although riboswitches have been identified that act in a trans-fashion. Natural riboswitches consist of two domains: an aptamer domain that binds the ligand through a three-dimensional folded RNA structure and a function switching domain that induces or suppresses an activity in the riboswitch based on the absence or presence of the ligand. Thus, there are two ligand sensitive conformations achieved by the riboswitch, representing on and off states (Garst et al., 2011). The function switching domain can affect the expression of a polynucleotide by regulating: an internal ribosome entry site, pre-mRNA splice donor accessibility in the retroviral gene construct, translation, termination of transcription, transcript degradation, miRNA expression, or shRNA expression (Dambach and Winkler 2009). The aptamer and function switching domains can be used as modular components allowing for synthetic RNA devices to control gene expression either as native aptamers, mutated/evolved native aptamers, or totally synthetic aptamers that are identified from screening random RNA libraries (McKeague et al 2016).

The purine riboswitch family represents one of the largest families with over 500 sequences found (Mandal et al 2003; US20080269258; and WO2006055351). The purine riboswitches share a similar structure consisting of three conserved helical elements/stem structures (P1, P2, P3) with intervening loop/junction elements (J1-2, L2, J2-3, L3, J3-1). The aptamer domains of the purine family of riboswitches naturally vary in their affinity/regulation by various purine compounds such as adenine, guanine, adenosine, guanosine, deoxyadenosine, deoxyguanosine (FIG. 5), etc. due to sequence variation (Kim et al. 2007).

In one aspect, provided herein is an isolated polynucleotide for regulating expression of a target polynucleotide, including: a polynucleotide encoding the target polynucleotide operably linked to a promoter and a riboswitch, wherein the riboswitch includes: a.) an aptamer domain capable of binding a nucleoside analogue antiviral drug and having reduced binding to guanine or 2'-deoxyguanosine relative to the nucleoside analogue antiviral drug; and b.) a function switching domain capable of regulating expression of the target polynucleotide, wherein binding of the nucleoside analogue by the aptamer domain induces or suppresses the expression regulating activity of the function switching domain, thereby regulating expression of the target gene. In some embodiments, the target polynucleotide can be a polypeptide encoding region, an miRNA, or an shRNA. In a non-limiting example, the riboswitch is operably linked to a nucleic acid encoding a polypeptide, miRNA, or shRNA with in vivo activity, for example that is effective at treating a disease. For example, in such a non-limiting example, the riboswitch is operably linked to a nucleic acid encoding a chimeric antigen receptor. In non-limiting illustrative examples provided herein, the target polynucleotide encodes one or more engineered signaling polypeptides included in various other aspects of the present disclosure. In these non-limiting illustrative examples, the riboswitch and the target polynucleotide encoding one or more engineered signaling polypeptides can be found in the genome of a packaging cell, in a replication incompetent recombinant retroviral particle, in a T cell and/or in an NK cell.

Figure 5A:
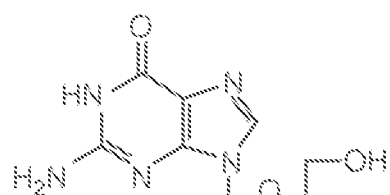
FIGS. 5A-5C show molecular structures of acyclovir (FIG. 5A), penciclovir (FIG. 5B), and 2'-deoxyguanonsine (FIG. 5C) as representative nucleoside analogues for selective riboswitch control.
Figure 5B:
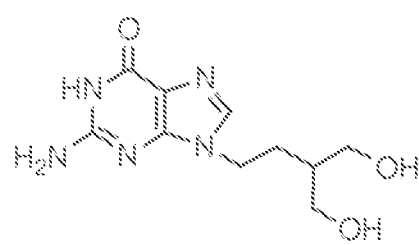
Figure 5C:
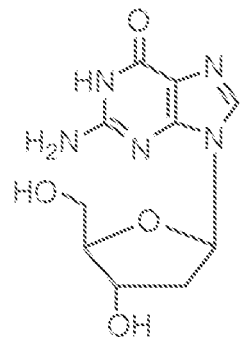

In some embodiments, the aptamer domain can be between 30, 35, 40, 45, 50, 55, 60, 65, and 70 nucleotides in length on the low end of the range and 35, 40, 45, 50, 55, 60, 65, 70, 75, 80, 85, 90, 95, and 100 nucleotides in length on the high end of the range, for example between 45 and 80 nucleotides in length, between 45 and 60 nucleotides in length, or between 45 and 58 nucleotides in length. In illustrative embodiments, the nucleoside analogue antiviral drug can be the pharmaceutical ligand acyclovir (also known as aciclovir and acycloguanosine) or penciclovir (FIG. 5). In some embodiments, the aptamer domain can have a binding affinity to the nucleoside analogue antiviral drug greater than, for example at least 2, 3, 4, 5, 6, 7, 8, 9, 10, 20, 30, 40, 50, 60, 70, 80, 90, or 100-fold greater than the binding affinity to the nucleoside or nucleotide.

The control element, for example a riboswitch, in some embodiments is operably linked to a target gene and can control expression of the target gene in vitro and/or in vivo. promotes expansion of transduced T cells in vivo. In some embodiments, expansion is dependent on the presence of the control element. However, in other embodiments, expansion of the transduced T cells can be at least partially driven by other factors such as the presence of interleukins within the subject and binding of the ASTR of a CAR on the recombinant T cell to its ligand.

In some embodiments, a nucleoside analogue antiviral drug, for example acyclovir or penciclovir, is administered to a subject before, during, and/or after PBLs are isolated from the blood and before T cells and/or NK cells are contacted with a replication incompetent recombinant retroviral particle that includes a control element, which in illustrative non-limiting examples is a riboswitch, that binds to the nucleoside analogue antiviral drug and regulates expression of one or more target polynucleotides. The one or more target polynucleotides can encode one or more polypeptides that in non-limiting illustrative examples are one or more engineered signaling polypeptides, at least one of which encodes at least one lymphoproliferative element. In some embodiments, the nucleoside analogue antiviral drug, for example acyclovir or penciclovir, is administered to the subject for between 5, 10, 15, 30, and 60 minutes on the low end of the range, and 1.5, 2, 3, 4, 5, 6, 8, 12, 24, 48, or 72 hours on the high end of the range, before PBLs are isolated from the blood or before T cells and/or NK cells are contacted with replication incompetent recombinant retroviral particles. In some embodiments, the nucleoside analogue antiviral drug, for example acyclovir or penciclovir, is administered to the subject for between 1.5, 2, 3, 4, 5, 6, 8, 12, or 24 hours on the low end of the range, ½, 1, 2, 3, 4, 5, 6, 7, 10, 14, 21, or 28 days on the high end of the range, after PBLs are isolated from the blood or after T cells and/or NK cells are contacted with replication incompetent recombinant retroviral particles in methods provided herein. In some embodiments, the nucleoside analogue antiviral drug, for example acyclovir or penciclovir, is administered to the subject for at least 1.5, 2, 3, 4, 5, 6, 8, 12, or 24 hours, or at least 2, 3, 4, 5, 6, 7, 10, 14, 21, or 28 days after PBLs are isolated from the blood or after T cells and/or NK cells are contacted with replication incompetent recombinant retroviral particles in methods provided herein. In some embodiments, the nucleoside analogue antiviral drug, for example acyclovir or penciclovir, is administered to the subject for at least 1, 2, 3, 4, 5, 7, 10, 14, 21, 28, 30, 60, 90, or 120 days or 5, 6, 9, 12, 24, 36, 48, 60, 72, 84, 96, 120 months or indefinitely after the PBLs have been reinfused into the subject. In any of the embodiments disclosed herein, the nucleoside analogue antiviral drug can be administered before and/or during the reinfusion of the PBLs and/or after the PBLs have been reinfused. In some embodiments, the nucleoside analogue antiviral drug is administered until a subject no longer experiences symptoms of, or is afflicted by, a disease for which the target polynucleotide is related.

In some embodiments, the aptamer domain can preferentially bind penciclovir over acyclovir or alternatively another antiviral agent, such that concomitant antiviral therapy may be utilized without affecting the riboswitch. In some embodiments, the aptamer domain can bind penciclovir with a binding affinity greater than, for example at least 2, 3, 4, 5, 6, 7, 8, 9, 10, 20, 30, 40, 50, 60, 70, 80, 90, or 100-fold greater than the aptamer domain binds acyclovir or another antiviral agent. In some embodiments, the aptamer domain can preferentially bind acyclovir over penciclovir or alternatively another antiviral agent, such that concomitant antiviral therapy may be utilized without affecting the riboswitch. In some embodiments, the aptamer domain can bind acyclovir with a binding affinity greater than, for example at least 2, 3, 4, 5, 6, 7, 8, 9, 10, 20, 30, 40, 50, 60, 70, 80, 90, or 100-fold greater than the aptamer domain binds penciclovir or another antiviral agent. In some embodiments, the oral prodrugs of penciclovir (famciclovir) and acyclovir (valaciclovir) can be given to a subject.

In some embodiments, the aptamer domain of an isolated polynucleotide can share at least 80%, 85%, 90%, 91%, 92%, 93%, 94%, 95%, 96%, 97%, 98%, or 99% sequence identity or be identical to any one of the sequences of SEQ ID NOs:87-93 and retain the ability to bind acyclovir and a reduced ability to bind to guanine or 2'-deoxyguanosine relative to the nucleoside analogue antiviral drug, and wherein the aptamer domain retains the ability to induce or suppress the expression regulating activity of the function switching domain when bound by acyclovir. In some embodiments, the aptamer domain of an isolated polynucleotide can share at least 80%, 85%, 90%, 91%, 92%, 93%, 94%, 95%, 96%, 97%, 98%, or 99% sequence identity or be identical to the aptamer domain of SEQ ID NOs:94-100 and retain the ability to bind penciclovir and a reduced ability to bind to guanine or 2'-deoxyguanosine relative to the nucleoside analogue antiviral drug, and wherein the aptamer domain retains the ability to induce or suppress the expression regulating activity of the function switching domain when bound by penciclovir. In some embodiments, a region of an isolated polynucleotide or a region of a riboswitch can share at least 80%, 85%, 90%, 91%, 92%, 93%, 94%, 95%, 96%, 97%, 98%, or 99% sequence identity or be identical to any one of the sequences of SEQ ID NOs:87-100.

In some embodiments, a DNA sequence containing a region of an aptamer domain of an isolated polynucleotide can share at least 80%, 85%, 90%, 91%, 92%, 93%, 94%, 95%, 96%, 97%, 98%, or 99% sequence identity or be identical to any one of the sequences of SEQ ID NOs:108-221. In some embodiments, a region of an isolated polynucleotide can share at least 80%, 85%, 90%, 91%, 92%, 93%, 94%, 95%, 96%, 97%, 98%, or 99% sequence identity or be identical to any one of the sequences of SEQ ID NOs:108-221.

In some embodiments, a DNA sequence containing a region of an aptamer domain of an isolated polynucleotide can share at least 80%, 85%, 90%, 91%, 91.84%, 92%, 93%, 94%, 95%, 96%, 97%, 98%, or 99% sequence identity or be identical to SEQ ID NO:108. In some embodiments, a DNA sequence containing a region of an aptamer domain of an isolated polynucleotide can share at least 80%, 85%, 90%, 91%, 92%, 93%, 94%, 95%, 95.83%, 96%, 97%, 98%, or 99% sequence identity or be identical to SEQ ID NO:147. In some embodiments, a DNA sequence containing a region of an aptamer domain of an isolated polynucleotide can share at least 80%, 85%, 90%, 91%, 92%, 93%, 93.88%, 94%, 95%, 96%, 97%, 98%, or 99% sequence identity or be identical to SEQ ID NO:164. In some embodiments, a DNA sequence containing a region of an aptamer domain of an isolated polynucleotide can share at least 80%, 85%, 90%, 91%, 92%, 93%, 94%, 95%, 95.83%96%, 97%, 98%, or 99% sequence identity or be identical to SEQ ID NO:183. In some embodiments, a DNA sequence containing a region of an aptamer domain of an isolated polynucleotide can share at least 80%, 85%, 90%, 91%, 91.84%, 92%, 93%, 94%, 95%, 95.83%96%, 97%, 98%, or 99% sequence identity or be identical to SEQ ID NO:198.

In some embodiments, a region of an isolated polynucleotide can include any one of the consensus sequences of SEQ ID NOs:222-226. In some embodiments, a region of an isolated polynucleotide can share at least 80%, 85%, 90%, 91%, 92%, 93%, 94%, 95%, 95.83%, 96%, 97%, 98%, or 99% sequence identity or be identical to any one of the sequences of SEQ ID NOs:222-226.

In any of the embodiments disclosed herein, the isolated polynucleotide can retain the ability to bind acyclovir and/or penciclovir. In any of the embodiments disclosed herein, an isolated polynucleotide can be the reverse complement of any one of the sequences of SEQ ID NOs: 87-100 or SEQ ID NOs:108-221. In any of the embodiments disclosed herein, an isolated polynucleotide can be a transcription or RNA version of either the DNA sequences of SEQ ID NOs:108-221 or the DNA sequences complementary to SEQ ID NOs:108-221. In any of the embodiments disclosed herein, an isolated polynucleotide can be a reverse transcription or DNA version of any one of the RNA sequences of SEQ ID NOs:87-100 or the DNA strand complementary to a reverse transcription of any one of the RNA sequences of SEQ ID NOs:87-100.

In some embodiments provided herein, riboswitch scaffolds can be used for mutational analysis or molecular evolution. The riboswitches selected for mutational analysis or molecular evolution can be from any known organism, for example, bacteria. In some embodiments, the type I-A deoxyguanosine riboswitch from *Mesoplasma florum* can be used for molecular evolution. In some embodiments, the derived aptamer domain can be at least 50%, 60%, 70%, 75%, 80%, 85%, 90%, or 95% identical to the aptamer domain from the type I-A deoxyguanosine riboswitch from *Mesoplasma florum* (SEQ ID NO:237). In other embodiments, the xpt riboswitch from *Bacillus subtilis* can be used. In some embodiments, the derived aptamer domain can be at least 50%, 60%, 70%, 75%, 80%, 85%, 90%, or 95% identical to the aptamer domain from the xpt riboswitch from *Bacillus subtilis* (SEQ ID NO:243).

The aptamer domains can be used as modular components and combined with any of the function switching domains to affect the RNA transcript. In any of the embodiments disclosed herein, the riboswitch can affect the RNA transcript by regulating any of the following activities: internal ribosomal entry site (IRES), pre-mRNA splice donor accessibility, translation, termination of transcription, transcript degradation, miRNA expression, or shRNA expression. In some embodiments, the function switching domain can control binding of an anti-IRES to an IRES (see, e.g. Ogawa, *RNA* (2011), 17:478-488, the disclosure of which is incorporated by reference herein in its entirety). In any of the embodiments disclosed herein, the presence or absence of the small molecule ligand can cause the riboswitch to affect the RNA transcript. In some embodiments, the riboswitch can include a ribozyme. Riboswitches with ribozymes can inhibit or enhance transcript degradation of target polynucleotides in the presence of the small molecule ligand. In some embodiments, the ribozyme can be a pistol class of ribozyme, a hammerhead class of ribozyme, a twisted class of ribozyme, a hatchet class of ribozyme, or the HDV (hepatitis delta virus) ribozyme.

In any of the embodiments disclosed herein, the riboswitch can be located in various positions relative to the target polynucleotide, as is known generally for riboswitches. In some embodiments, the riboswitch can regulate pre-mRNA splice donor accessibility and be located before the target polynucleotide. In some embodiments, the riboswitch can regulate the inclusion of a poly(A) tail and be located after the target polynucleotide. In some embodiments, the riboswitch can regulate an anti-IRES and be located upstream of an IRES. In non-limiting illustrative embodiments, a riboswitch provided herein can be located in any of these positions relative to a nucleic acid encoding one or more engineered signaling polypeptides provided herein.

In some embodiments, the riboswitch can be destabilized at temperatures above 37.5° C., 38° C., 38.5° C., 39° C., 39.5° C., or 40° C. such that the riboswitch is no longer responsive to the ligand. In some embodiments, molecular evolution can be used to select riboswitches that are destabilized at temperatures above 37.5° C., 38° C., 38.5° C., 39° C., 39.5° C., or 40° C.

In some embodiments, the target polynucleotide can encode a miRNA, shRNA, and/or a polypeptide, wherein the target polynucleotide is operably linked to a promoter. In some embodiments, the target polynucleotide can encode a lymphoproliferative element. In some embodiments, the target polynucleotide can be an miRNA or shRNA. In some embodiments, the miRNA or shRNA can potentiate the STAT5 pathway or inhibit the SOCS pathway. In some embodiments, the miRNA or shRNA can target transcripts from SOCS1, SMAD2, TGFb, or PD-1. In some embodiments, the miRNA is miR-155. In some embodiments, the target polynucleotide encodes a polypeptide and the polypeptide can include a CAR including an antigen-specific targeting region, a transmembrane domain, and an intracellular activating domain.

In another aspect, provided herein is an isolated polynucleotide for regulating expression of a target polynucleotide, including: a polynucleotide encoding the target polynucleotide operably linked to a promoter and a riboswitch, wherein the riboswitch includes: a.) an aptamer domain capable of binding a nucleoside analogue antiviral drug with a binding affinity at least two-fold greater affinity than the aptamer domain binds guanine or 2'-deoxyguanosine; and b.) a function switching domain capable of regulating expression of the target polynucleotide, wherein binding of the nucleoside analogue by the aptamer domain induces or suppresses the expression regulating activity of the function switching domain. In some embodiments, the aptamer domain can bind the nucleoside analogue antiviral drug with a binding affinity at least 3, 4, 5, 6, 7, 8, 9, 10, 20, 30, 40, 50, 60, 70, 80, 90, or 100-fold greater affinity than the aptamer domain binds guanine or 2'-deoxyguanosine. In some embodiments, the aptamer domain can be between 30, 35, 40, 45, 50, 55, 60, 65, and 70 nucleotides in length on the low end of the range and 35, 40, 45, 50, 55, 60, 65, 70, 75, 80, 85, 90, 95, and 100 nucleotides in length on the high end of the range, for example between 45 and 80 nucleotides in length or between 45 and 58 nucleotides in length. In illustrative embodiments, the nucleoside analogue antiviral drug can be the pharmaceutical ligand acyclovir (also known as aciclovir and acycloguanosine) or penciclovir. In some embodiments, the aptamer domain can have a binding affinity to the nucleoside analogue antiviral drug that is greater than, for example at least 2, 3, 4, 5, 6, 7, 8, 9, 10, 20, 30, 40, 50, 60, 70, 80, 90, or 100-fold greater than the binding affinity to the nucleoside or nucleotide. In some embodiments, binding of the nucleoside analogue by the aptamer domain can induce an activity in the riboswitch.

In some embodiments, the aptamer domain can be specific for penciclovir and lack reactivity to acyclovir or alternatively another antiviral agent, such that concomitant antiviral therapy may be utilized without affecting the riboswitch. In some embodiments, the aptamer domain can bind penciclovir with a binding affinity at least 2, 3, 4, 5, 6, 7, 8, 9, 10, 20, 30, 40, 50, 60, 70, 80, 90, or 100-fold greater than the aptamer domain binds acyclovir or another antiviral agent. In some embodiments, the aptamer domain can be specific for acyclovir and lack reactivity to penciclovir or alternatively another antiviral agent, such that concomitant antiviral therapy may be utilized without affecting the riboswitch. In some embodiments, the aptamer domain can bind acyclovir with a binding affinity at least 2, 3, 4, 5, 6, 7, 8, 9, 10, 20, 30, 40, 50, 60, 70, 80, 90, or 100-fold greater than the aptamer domain binds penciclovir or another antiviral agent. In some embodiments, the oral prodrugs of penciclovir (famciclovir) and acyclovir (valaciclovir) can be given to a subject. In some embodiments, the derived aptamer domain can be at least 50%, 60%, 70%, 75%, 80%, 85%, 90%, or 95% identical to the aptamer domain from the type I-A deoxyguanosine riboswitch from *Mesoplasma florum*. In some embodiments, the derived aptamer domain can be at least 50%, 60%, 70%, 75%, 80%, 85%, 90%, or 95% identical to the aptamer domain from the xpt riboswitch from *Bacillus subtilis*. In any of the embodiments disclosed herein, the riboswitch can affect the RNA transcript by regulating any of the following activities: internal ribosomal entry site, pre-mRNA splice donor accessibility in the retroviral gene construct, translation, termination of transcription, transcript degradation, miRNA expression, or shRNA expression. In some embodiments, the function switching domain can control binding of an anti-IRES to an IRES. In any of the embodiments disclosed herein, the presence or absence of the small molecule ligand can cause the riboswitch to affect the RNA transcript. In some embodiments, the riboswitch can include a ribozyme. Riboswitches with ribozymes can inhibit or enhance transcript degradation of genes of interest in the presence of the small molecule ligand. In some embodiments, the ribozyme can be a pistol class of ribozyme, a hammerhead class of ribozyme, a twisted class of ribozyme, a hatchet class of ribozyme, or the HDV (hepatitis delta virus) ribozyme. In some embodiments, the riboswitch can be destabilized at temperatures above 37.5° C., 38° C., 38.5° C., 39° C., 39.5° C., or 40° C. such that the riboswitch is no longer responsive to the ligand. In some embodiments, molecular evolution can be used to select riboswitches that are destabilized at temperatures above 37.5° C., 38° C., 38.5° C., 39° C., 39.5° C., or 40° C. In some embodiments, the target polynucleotide can encode a miRNA, shRNA, and/or a polypeptide, wherein the target polynucleotide is operably linked to a promoter. In some embodiments, the target polynucleotide can encode a lymphoproliferative element. In some embodiments, the target polynucleotide can be an miRNA and, optionally, the miRNA can stimulate the STAT5 pathway or inhibit the SOCS pathway. In some embodiments, the miRNA can target transcripts from SOCS1, SHP, SMAD2, TGFb, or PD-1. In these embodiments, the miRNA can be miR-155. In some embodiments, the target polynucleotide encodes a polypeptide and the polypeptide can include a CAR including an antigen-specific targeting region, a transmembrane domain, and an intracellular activating domain. Further embodiments of CARs are disclosed elsewhere herein.

In some embodiments, the evolution of aptamers can be performed via aptamer selection from randomized native purine or guanine aptamer libraries using SELEX (Systematic Evolution of Ligands by EXponential enrichment) methods including, but not limited to, those methods that employ graphene oxide in the selection process and screening. In other embodiments, random mutagenesis methodology such as error prone PCR can be used to evolve aptamer constructs or riboswitch constructs where the aptamer is incorporated in the context of any of the riboswitch activities described herein by screening in vitro or in mammalian cells. In other embodiments, random libraries of nucleotides can be used in the evolution of the riboswitch. In any of the embodiments disclosed herein, riboswitches can be identified from screening such libraries in vitro or in mammalian cells.

In some embodiments, the evolved or derived aptamer domain can have increased binding to analogues of the native ligand and decreased binding to the native ligand. In some embodiments, the aptamer domain can be configured to have increased binding to analogues of the native ligand and decreased binding to the native ligand. In some embodiments, the aptamer domain can be derived from the purine riboswitch family. In some embodiments, the native ligand can be a nucleoside or nucleotide and the analogue can be a nucleoside analogue or nucleotide analogue. In some embodiments, the nucleoside analogue is an antiviral drug. In illustrative embodiments, the aptamer domains can be derived from 2'-deoxyguanosine and guanine riboswitch scaffolds and the derived aptamer domains can show reduced binding to 2'-deoxyguanosine and guanine relative to the wild-type riboswitch.

In some embodiments, the riboswitch can regulate pre-mRNA splice donor accessibility in the retroviral gene construct, wherein the retroviral construct drives the CAR genes or other genes of interest from the reverse strand under a general promoter or a T cell specific promoter. In other embodiments, the riboswitch can regulate an IRES in the retroviral gene construct, wherein the retroviral construct drives the translation of CAR genes or other genes of interest. In other embodiments, the riboswitch can control transcription termination of the RNA, miRNA, or gene transcripts or can control translation of the transcript. In other embodiments, the nucleoside analogue riboswitch can be integrated with a ribozyme to inhibit or enhance transcript degradation of the CAR genes or other genes of interest in the presence of the nucleoside analogue.

In some embodiments, the isolated polynucleotide for regulating expression of a target polynucleotide that includes a polynucleotide encoding the target polynucleotide operably linked to a promoter and a riboswitch that binds a nucleoside analogue antiviral drug, is a molecular cloning vector. The molecular cloning vector can be any type of molecular cloning vector known in the art. As non-limiting examples, the vector can be a plasmid, a virus, or a replication incompetent recombinant retroviral particle, any of which can be an expression vector. Such an expression vector can encode any of the target polynucleotides provided hereinabove. One or more restriction and/or multiple cloning sites can be included on a molecular cloning vector 5' or 3' to a riboswitch provided herein such that the riboswitch is operably linked to a target polynucleotide inserted into the restriction and/or multiple cloning site.

Molecular Chaperones

In one aspect, provided herein is a method for genetically modifying and expanding lymphocytes of a subject, comprising:

A. contacting resting T cells and/or NK cells of the subject ex vivo, typically without requiring prior ex vivo stimulation, with replication incompetent recombinant retroviral particles comprising:
  i. a pseudotyping element on its surface that is capable of binding to a T cell and/or NK cell and facilitating membrane fusion of the replication incompetent recombinant retroviral particles thereto; and
  ii. a polynucleotide comprising one or more transcriptional units operatively linked to a promoter active in T cells and/or NK cells, wherein the one or more transcriptional units encode a first engineered signaling polypeptide regulated by a control element, wherein said first engineered signaling polypeptide comprises at least one lymphoproliferative element and/or a chimeric antigen receptor,
    wherein said contacting facilitates transduction of at least some of the resting T cells and/or NK cells by the replication incompetent recombinant retroviral particles, thereby producing genetically modified T cells and/or NK cells;

B. introducing the genetically modified T cells and/or NK cells into the subject; and C. exposing the genetically modified T cells and/or NK cells in vivo to a compound that acts as the control element to affect expression of the first engineered signaling polypeptide and promote expansion of the lymphocytes in vivo, thereby genetically modifying and expanding lymphocytes of the subject.

In illustrative embodiments, the transduction is carried out without ex vivo stimulation. In illustrative embodiments, the compound is a molecular chaperone, such as a small molecule molecular chaperone. In illustrative embodiments, binding of the molecular chaperone to the lymphoproliferative element and/or CAR component increases the proliferative activity of the lymphoproliferative element and/or the CAR. The molecular chaperone can be administered to the subject before the blood is collected, during the contacting, and/or after the T cells and/or NK cells are introduced into the subject. Some embodiments of this aspect include collecting blood from the subject. In these embodiments, the introducing is a reintroducing of the cells that were collected and genetically modified before reintroduction. The entire process, in illustrative embodiments, is a shorter process than prior art methods, as for other aspects herein. For example, the entire process can be completed in less than 48 hours, less than 24 hours, or less than 12 hours. The entire process in other embodiments, can be completed in 2, 4, 6, or 8 hours on the low end of the range, and 12, 24, 36, or 48 hours on the high end of the range.

Accordingly, in some embodiments of the methods and compositions provided herein, the control element is a molecular chaperone. As compared to other embodiments herein with other in vivo control elements, such as riboswitches that typically bind a compound to affect expression of a lymphoproliferative element or other component of a first or second engineered signaling polypeptide herein, the molecular chaperones are compounds that are the control elements and as such, directly affect activity of, typically by binding to, a lymphoproliferative element or other component of a first or second engineered signaling polypeptide herein. In illustrative examples of such embodiments of methods herein that include the administration of molecular chaperones, a lymphoproliferative element, membrane-bound cytokine, and/or CAR component, can be a less active or inactive lymphoproliferative element, membrane-bound cytokine, and/or CAR component, that is bound by the molecular chaperone to increase its activity. Thus, the target bound by a molecular chaperone is typically a target polypeptide. In some embodiments, as indicated the polypeptide can be a first and/or a second engineered signaling polypeptide, or a polypeptide component thereof, whose activity is affected by binding to the molecular chaperone, which in illustrative embodiments is a small molecule molecular chaperone. In some embodiments, the polypeptide can include a lymphoproliferative element whose activity is regulated, in illustrative embodiments, up-regulated by a molecular chaperone, preferably a small molecule molecular chaperone. The molecular chaperone in the methods provided herein can be a compound that binds to the mutant lymphoproliferative element and/or inactive CAR component, thus rendering them active.

In other embodiments, a lymphoproliferative element or other signaling domain has been mutated to permit transit to the plasma membrane only in the presence of a small molecular synthetic chaperone. In other embodiments, the chaperone promotes stability of the lymphoproliferative element or other signaling domain or protein and half-life as a potentiator.

It will be understood that aspects and embodiments of the present invention include many of the same steps and compositions provided in detail herein. Accordingly, it will be understood that the teachings throughout this specification that relate to these common elements apply to aspects and embodiments that utilize a molecular chaperone as the control element, which typically binds a lymphoproliferative element or other target molecule directly, in addition to, or instead of other in vivo control elements provided herein, such as riboswitches, which typically utilize a molecule, such as a drug, that binds the riboswitch.

In some embodiments, the molecular chaperone is a compound that can regulate sub-cellular localization of a target, for example, the proper folding and transit of a target protein, such as a lymphoproliferative element and/or a component of a CAR, from the endoplasmic reticulum to the plasma membrane or its half-life on the surface. In other embodiments, the molecular chaperone can promote the functional conformation of a dysfunctional target, thus acting as a potentiator. Examples of molecules that act as chaperones or potentiators to naturally mutated proteins include lumacaftor and ivacaftor. These proteins act upon the mutant CFTR chloride channel variants such as G551D or F508del. Ivacaftor potentiates the activity of the G551D or F508del mutated ion channel, whereas lumacaftor promotes stabilization of mutant chloride channels and subsequent potentiation by ivacaftor. Such chaperone dependent proteins can be generated from naturally functional proteins and screening for functional activity only in the presence of the molecular chaperones. Thus, such proteins are only active when the chaperone is present. Examples of such molecules which can be screened for specific chaperone activity include small molecule antivirals or anti-infectives that show no activity to normal human proteins. Accordingly, in one embodiment, the molecular chaperone used in methods herein is a small molecule antiviral or anti-infective compound that shows no activity to normal human proteins.

In some embodiments, genetically modified lymphocytes can be exposed and/or a subject can be administered the molecular chaperone. In some embodiments, the compound is administered to the subject before, during, and/or after PBLs are isolated from the blood and before T cells and/or NK cells are contacted with a replication incompetent recombinant retroviral particle. The replication incompetent recombinant retroviral particle in such embodiments includes a less active or inactive lymphoproliferative element and/or CAR component that binds to, and is regulated by, the molecular chaperone compound.

For any of the embodiments provided herein for modifying and expanding lymphocytes, which can be part of methods of adoptive cell therapy, the compound can be administered to the subject for between 5, 10, 15, 30, and 60 minutes on the low end of the range, and 1.5, 2, 3, 4, 5, 6, 8, 12, or 24 hours on the high end of the range, before PBLs are isolated from the blood or before T cells and/or NK cells are contacted with a replication incompetent recombinant retroviral particle. In some embodiments, the compound is administered to the subject for between 1.5, 2, 3, 4, 5, 6, 8, 12, or 24 hours on the low end of the range, ½, 1, 2, 3, 4, 5, 6, 7, 10, 14, 21, or 28 days on the high end of the range, after PBLs are isolated from the blood or after T cells and/or NK cells are contacted with a replication incompetent recombinant retroviral particle in methods provided herein. In some embodiments, the compound is administered to the subject for at least 1.5, 2, 3, 4, 5, 6, 8, 12, or 24 hours, or at least 2, 3, 4, 5, 6, 7, 10, 14, 21, or 28 days after PBLs are isolated from the blood or after T cells and/or NK cells are contacted with a replication incompetent recombinant retroviral particle in methods provided herein. In some embodiments, the compound is administered to the subject for at least 1, 2, 3, 4, 5, 7, 10, 14, 21, 28, 30, 60, 90, or 120 days or 5, 6, 9, 12, 24, 36, 48, 60, 72, 84, 96, 120 months or indefinitely after the PBLs have been reinfused into the subject. In any of the embodiments disclosed herein, the compound can be administered before and/or during the reinfusion of the PBLs and/or after the PBLs have been reinfused.

For any of the embodiments herein, molecular chaperones are not in the control elements that are bound by compounds that regulate and/or activate them. Molecular chaperones are compounds, preferably small molecule compounds, that are the control elements and regulate the activity of lymphoproliferative elements and/or functional components of CARs.

Packaging Cell Lines/Methods of Making Recombinant Retroviral Particles

In one aspect, provided herein is a retroviral packaging system including: a mammalian cell including: a) a first transactivator expressed from a constitutive promoter and capable of binding a first ligand and a first inducible promoter for affecting expression of a nucleic acid sequence operably linked thereto in the presence versus absence of the first ligand; b) a second transactivator capable of binding a second ligand and a second inducible promoter, and affecting expression of a nucleic acid sequence operably linked thereto in the presence versus absence of a second ligand; and c) a packageable RNA genome for a retroviral particle, wherein the first transactivator regulates expression of the second transactivator, and wherein the second transactivator regulates expression of retroviral polypeptides involved in viral packaging, such as, for example, a gag polypeptide, a pol polypeptide, and/or a pseudotyping element, and optionally other polypeptides that will become incorporated in or on the replication incompetent recombinant retroviral particle and are believed to be toxic to packaging cell lines, such as, for example, HEK-293. In certain aspects, the second transactivator itself is cytotoxic to packaging cell lines. Pseudotyping elements are typically capable of binding to a cell membrane of a target cell and facilitating fusion thereto, as discussed in detail herein. Thus, not to be limited by theory, the system provides the ability to accumulate certain polypeptides/proteins that do not inhibit, or do not substantially inhibit, or are not believed to inhibit proliferation or survival of the mammalian cells, for example, non-toxic proteins, while culturing a population of the mammalian cells for days or indefinitely, and controlling induction of polypeptides that are desired for retroviral product but that are inhibitory or can be inhibitory or have been reported to be inhibitory to the survival and/or proliferation of the mammalian cell, for example toxic polypeptides, until a later time closer to the time of when replication incompetent recombinant retroviral particles will be produced and harvested. The packageable RNA genome is typically encoded by a polynucleotide operably linked to a promoter, sometimes referred to herein as a third promoter for convenience, wherein said third promoter is typically inducible by either the first transactivator or the second transactivator. In illustrative embodiments, the packageable RNA genome is encoded by a polynucleotide operably linked to a third promoter, wherein said third promoter is inducible by the second transactivator. As such, the packageable RNA genome can be produced at the later time point, closer to when the replication incompetent recombinant retroviral particles will be harvested.

A skilled artisan will appreciate many different transactivators, ligands, and inducible promoters can be used in the retroviral packaging system. Such inducible promoters can be isolated and derived from many organisms, e.g., eukaryotes and prokaryotes. Modification of inducible promoters derived from a first organism for use in a second organism, e.g., a first prokaryote and a second a eukaryote, a first eukaryote and a second a prokaryote, etc., is well known in the art. Such inducible promoters, and systems based on such inducible promoters but also including additional control proteins, include, but are not limited to, alcohol regulated promoters (e.g., alcohol dehydrogenase I (alcA) gene promoter, promoters responsive to alcohol transactivator proteins (AlcR), etc.), tetracycline regulated promoters, (e.g., promoter systems including TetActivators, TetON, TetOFF, etc.), steroid regulated promoters (e.g., rat glucocorticoid receptor promoter systems, human estrogen receptor promoter systems, retinoid promoter systems, thyroid promoter systems, ecdysone promoter systems, mifepristone promoter systems, etc.), metal regulated promoters (e.g., metallothionein promoter systems, etc.), pathogenesis-related regulated promoters (e.g., salicylic acid regulated promoters, ethylene regulated promoters, benzothiadiazole regulated promoters, etc.), temperature regulated promoters (e.g., heat shock inducible promoters (e.g., HSP-70, HSP-90, soybean heat shock promoter, etc.), light regulated promoters, synthetic inducible promoters, and the like. In some embodiments, a mifepristone-regulated system can be used. In some embodiments, a mifepristone-inducible system with an autoregulatory feedback loop can be used. In some embodiments, a GAL4 regulatory fusion protein is expressed from one construct that also contains the transposon terminal repeats and lox and FRT sites. In some embodiments, the GAL4 regulatory fusion protein controls expression of a reverse tet transactivator (rtTA) and BiTRE. In some embodiments, another construct with lox and FRT sites contains a GAL4 upstream activating sequences (UAS) and an E1b TATA box promoter driving a reporter like mCherry. In some embodiments, a GAL4 regulatory fusion protein binds to GAL4 upstream activating sequences (UAS) in both the promoter controlling expression of the GAL4 regulatory fusion protein and the promoter controlling expression of a target polynucleotide. In some embodiments, mifepristone, doxycycline, and puromycin will be used for induction and selection of packaging cell line.

In some embodiments, either or both transactivators can be split into two or more polypeptides. In some embodiments, the two or more polypeptides can include a DNA binding domain and an activation domain capable of stimulating transcription on separate polypeptides. This "activation domain" is not to be confused with an "activation element," such as a polypeptide that binds CD3, which is capable of activating a T cell and/or NK cell, and typically does activate such T cell and/or NK cell when contacted with it, as discussed in detail herein. The separate polypeptides can further include fusions with polypeptides capable of dimerization through the addition of a ligand. In some embodiments, the activation domain can be the p65 activation domain or a functional fragment thereof. In illustrative embodiments of the packaging systems herein, the DNA binding domain can be the DNA binding domain from ZFHD1 or a functional fragment thereof. In some embodiments, one polypeptide can be a fusion with FKBP, or functional mutants and/or fragments thereof, or multiple FKBPs and another polypeptide can be a fusion with the FRB domain of mTOR, or functional mutants and/or fragments thereof, and the ligand can be rapamycin or a functional rapalog. In some embodiments, the FRB contains the mutations K2095P, T2098L, and/or W2101F. In some embodiments, the separate polypeptides can be FKBP, or functional fragments thereof, and CalcineurinA, or functional fragments thereof, and the dimerizing agent can be FK506. In some embodiments, the separate polypeptides can be FKBP, or functional fragments thereof, and CyP-Fas, or functional fragments thereof, and the dimerizing agent can be FKCsA. In some embodiments, the separate polypeptides can be GAI, or functional fragments thereof, and GID1, or functional fragments thereof, and the dimerizing agent can be gibberellin. In some embodiments, the separate polypeptides can be Snap-tag and HaloTag, or functional fragments thereof, and the dimerizing agent can be HaXS. In some embodiments, the separate polypeptides can include the same polypeptide. For example, the DNA binding domain and activation domain can be expressed as fusion proteins with FKBP or GyrB and the dimerizing agent can be FK1012 or coumermycin, respectively. In some embodiments, the inducible promoter can be the DNA sequence where the DNA binding domain typically binds. In some embodiments, the inducible promoter can vary from the DNA sequence where the DNA binding domain typically binds. In some embodiments, either transactivator can be an rtTA, the ligand can be tetracycline or doxycycline, and the inducible promoter can be a TRE. In illustrative embodiments, the first transactivator is the p65 activation domain fused to FRB and the ZFHD1 DNA binding domain fused to three FKBP polypeptides and the first ligand is rapamycin. In further illustrative embodiments, the second transactivator can be an rtTA, the second ligand can be tetracycline or doxycycline, and the inducible promoter can be a TRE.

In some embodiments, the first transactivator can regulate expression of an element to control the nuclear export of transcripts containing a consensus sequence, such as an HIV Rev and the consensus sequence can be the Rev response element. In illustrative embodiments, the target cell is a T cell.

In some embodiments, the pseudotyping element is a retroviral envelope polypeptide. The pseudotyping element typically includes a binding polypeptide and a fusogenic polypeptide for binding to and facilitating membrane fusion of the target cell and viral membranes, as discussed in more detail herein. In some embodiments, the pseudotyping element is the feline endogenous virus (RD114) envelope protein, the oncoretroviral amphotropic envelope protein, the oncoretroviral ecotropic envelope protein, and/or vesicular stomatitis virus envelope protein (VSV-G). In illustrative embodiments, the pseudotyping element includes a binding polypeptide and a fusogenic polypeptide derived from different proteins, as discussed in further detail herein. For example, in an illustrative embodiment, especially where the target cell is a T cell and/or NK cell, the binding polypeptide is a hemagglutinin (H) polypeptide of a Measles Virus (such as the Edmonston strain of the Measles Virus), or a cytoplasmic domain deletion variant thereof, and the fusogenic polypeptide other is a fusion (F) polypeptide of a Measles Virus (such as the Edmonston strain of the Measles Virus), or a cytoplasmic domain deletion variant thereof. In some embodiments, the fusogenic polypeptide can include multiple elements expressed as one polypeptide. In some embodiments, the binding polypeptide and the fusogenic polypeptide can be translated from the same transcript but from separate ribosome binding sites, or the polypeptide is cleaved after translation using a peptide cleavage signal or a ribosomal skip sequence, as disclosed elsewhere herein, to generate the binding polypeptide and the fusogenic polypeptide. In some embodiments, where the binding polypeptide is a Measles Virus H polypeptide, or a cytoplasmic domain deletion thereof, and the fusogenic polypeptide is a Measles Virus F polypeptide, or a cytoplasmic domain deletion thereof, translation of the F and H polypeptides from separate ribosome binding sites results in a higher amount of the F polypeptide as compared to the H polypeptide. In some embodiments, the ratio of the F polypeptides (or cytoplasmic domain deletions thereof) to H polypeptides (or cytoplasmic domain deletions thereof) is at least 2:1, at least 3:1, at least 4:1, at least 5:1, at least 6:1, at least 7:1, or at least 8:1.

In some embodiments, the first transactivator can regulate the expression of an activation element capable of binding to and activating a target cell, such as a T cell. Any of the activation elements disclosed herein can be expressed. For example, in these embodiments, the activation element can include: a.) a membrane-bound polypeptide capable of binding to and activating CD3: and/or b.) a membrane-bound polypeptide capable of binding to and activating CD28. In some embodiments, the membrane-bound polypeptide capable of binding to and activating CD28 is CD80, CD86, or functional fragments thereof, such as an extracellular domain of CD80.

In some embodiments, the second transactivator can regulate the expression of a packageable RNA genome that can include an RNA that encodes one or more target polypeptides, including as a non-limiting example, any of the engineered signaling polypeptides disclosed herein and/or one or more (e.g. two or more) inhibitory RNA molecules. It should be noted that it is envisioned that the retroviral packaging system aspect, and the method of making a replication incompetent recombinant retroviral particle aspect, are not limited to making replication incompetent recombinant retroviral particles for transduction of T cell and/or NK cells, but rather for any cell type that can be transduced by replication incompetent recombinant retroviral particles. The packageable RNA genome, in certain illustrative embodiments, includes is designed to express one or more target polypeptides, including as a non-limiting example, any of the engineered signaling polypeptides disclosed herein and/or one or more (e.g. two or more) inhibitory RNA molecules in opposite orientation (e.g., encoding on the opposite strand and in the opposite orientation), from retroviral components such as gag and pol. For example, the packageable RNA genome can include from 5' to 3': a 5' long terminal repeat, or active truncated fragment thereof; a nucleic acid sequence encoding a retroviral cis-acting RNA packaging element; a nucleic acid sequence encoding a first and optionally second target polypeptide, such as, but not limited to, an engineered signaling polypeptide(s) in opposite orientation, which can be driven off a promoter in this opposite orientation with respect to the 5' long terminal repeat and the cis-acting RNA packaging element, which in some embodiments is called a "fourth" promoter for convenience only (and sometimes referred to herein as the promoter active in T cells and/or NK cells). which is active in a target cell such as a T cell and/or an NK cell but in illustrative examples is not active in the packaging cell or is only inducibly or minimally active in the packaging cell; and a 3' long terminal repeat, or active truncated fragment thereof. In some embodiments, the packageable RNA genome can include a central polypurine tract (cPPT)/central termination sequence (CTS) element. In some embodiments, the retroviral cis-acting RNA packaging element can be HIV Psi. In some embodiments, the retroviral cis-acting RNA packaging element can be the Rev Response Element. The engineered signaling polypeptide driven by the promoter in the opposite orientation from the 5' long terminal repeat, in illustrative embodiments, is one or more of the engineered signaling polypeptides disclosed herein and can optionally express one or more inhibitory RNA molecules as disclosed in more detail herein.

It will be understood that promoter number, such as a first, second, third, fourth, etc. promoter is for convenience only. A promoter that is called a "fourth" promoter should not be taken to imply that there are any additional promoters, such as first, second or third promoters, unless such other promoters are explicitly recited. It should be noted that each of the promoters are capable of driving expression of a transcript in an appropriate cell type and such transcript forms a transcription unit.

In some embodiments, the engineered signaling polypeptide can include a first lymphoproliferative element. Suitable lymphoproliferative elements are disclosed in other sections herein. As a non-limiting example, the lymphoproliferative element can be expressed as a fusion with a recognition domain, such as an eTag, as disclosed herein. In some embodiments, the packageable RNA genome can further include a nucleic acid sequence encoding a second engineered polypeptide including a chimeric antigen receptor, encoding any CAR embodiment provided herein. For example, the second engineered polypeptide can include a first antigen-specific targeting region, a first transmembrane domain, and a first intracellular activating domain. Examples of antigen-specific targeting regions, transmembrane domains, and intracellular activating domains are disclosed elsewhere herein. In some embodiments where the target cell is a T cell, the promoter that is active in a target cell is active in a T cell, as disclosed elsewhere herein.

In some embodiments, the packageable RNA genome can further include a riboswitch, as discussed in other sections herein. In some embodiments, the nucleic acid sequence encoding the engineered signaling polypeptide can be in reverse orientation. In further embodiments, the packageable RNA genome can further include a riboswitch and, optionally, the riboswitch can be in reverse orientation. In any of the embodiments disclosed herein, a polynucleotide including any of the elements can include a primer binding site. In illustrative embodiments, transcription blockers or polyA sequences can be placed near genes to prevent or reduce unregulated transcription. In any of the embodiments disclosed herein, a nucleic acid sequence encoding Vpx can be on the second or an optional third transcriptional unit, or on an additional transcriptional unit that is operably linked to the first inducible promoter.

Provided in another aspect herein is a mammalian packaging cell line comprising a packageable RNA genome for a replication incompetent retroviral particle, wherein said packageable RNA genome comprises:
a. a 5' long terminal repeat, or active fragment thereof;
b. a nucleic acid sequence encoding a retroviral cis-acting RNA packaging element;
c. a polynucleotide comprising one or more nucleic acid sequences operatively linked to a promoter active in T cells and/or NK cells, wherein a first nucleic acid sequence of the one or more nucleic acids encodes one or more (e.g. two or more) inhibitory RNA molecules directed against one or more RNA targets and a second nucleic acid sequence of the one or more nucleic acid sequences encodes a chimeric antigen receptor (CAR) comprising an antigen-specific targeting region (ASTR), a transmembrane domain, and an intracellular activating domain; and
d. a 3' long terminal repeat, or active fragment thereof.

The inhibitory RNA molecules in the above aspect can include any of the inhibitory RNA molecules, as non-limiting examples, shRNA or miRNA, provided herein in other sections of this disclosure.

In some embodiments of the mammalian packaging cell line aspect, the polynucleotide of (c) can be in reverse orientation to the nucleic acid sequence encoding the retroviral cis-acting RNA packaging element (b), the 5' long terminal repeat (a), and/or the 3' long terminal repeat (d).

In some embodiments of the mammalian packaging cell line aspect, expression of the packageable RNA genome is driven by an inducible promoter active in the mammalian packaging cell line.

The promoter active in T cells and/or NK cells that drives expression of the inducible RNA and the CAR in these aspects provided immediately above, in illustrative embodiments is not active or is only minimally or inducibly active in the packaging cell line. This promoter active in T cells and/or NK cells in illustrative embodiments is located on the packageable RNA genome between the nucleic acids encoding the one (e.g. two) or more inducible RNAs and the CAR and the 3' LTR.

In any of the aspects directed to packageable cells or cell lines herein, that encode one or more inhibitory RNA molecules directed against one or more RNA targets, at least one and in some embodiments all inhibitory RNA molecules can include a 5' strand and a 3' strand that are partially or fully complementary to one another, wherein said 5' strand and said 3' strand are capable of forming an 18-25 nucleotide RNA duplex. In some embodiments, the 5' strand can be 18, 19, 20, 21, 22, 23, 24, or 25 nucleotides in length, and the 3' strand can be 18, 19, 20, 21, 22, 23, 24, or 25 nucleotides in length. In some embodiments, the 5' strand and the 3' strand can be the same or different lengths. In some embodiments, the RNA duplex can include one or more mismatches. In alternate embodiments, the RNA duplex has no mismatches.

In any of the aspects provided immediately above directed to packageable cells or cell lines herein, that encode inhibitory RNA molecules directed against one or more RNA targets, the inhibitory RNA molecule can be a miRNA or an shRNA. In some embodiments, the inhibitory molecule can be a precursor of a miRNA, such as for example, a Pri-miRNA or a Pre-miRNA, or a precursor of an shRNA. In some embodiments, the one or more inhibitory RNA molecules can be an artificially derived miRNA or shRNA. In other embodiments, the inhibitory RNA molecule can be a dsRNA (either transcribed or artificially introduced) that is processed into an siRNA or the siRNA itself. In some embodiments, the inhibitory RNA molecule can be a miRNA or shRNA that has a sequence that is not found in nature, or has at least one functional segment that is not found in nature, or has a combination of functional segments that are not found in nature. In illustrative embodiments, at least one or all of the inhibitory RNA molecules are miR-155.

In any of the aspects provided immediately above directed to packageable cells or cell lines herein, that encode inhibitory RNA molecules directed against one or more RNA targets, the one or more inhibitory RNA molecule(s), in some embodiments, can comprises from 5' to 3' orientation: a 5' arm, a 5' stem, a loop, a 3' stem that is partially or fully complementary to said 5' stem, and a 3' arm. In some embodiments, at least one of the two or more inhibitory RNA molecules has this arrangement. In other embodiments, all of the two or more inhibitory RNA molecules have this arrangement. In some embodiments, the 5' stem can be 18, 19, 20, 21, 22, 23, 24 or 25 nucleotides in length. In some embodiments, the 3' stem can be 18, 19, 20, 21, 22, 23, 24, or 25 nucleotides in length. In some embodiments, the loop can be 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides in length. In some embodiments, the 5' arm, 3' arm, or both, are derived from a naturally occurring miRNA. In some embodiments, the 5' arm, 3' arm, or both, are derived from a naturally occurring miRNA is selected from the group consisting of: miR-155, miR-30, miR-17-92, miR-122, and miR-21. In illustrative embodiments, the 5' arm, 3' arm, or both are derived from miR-155. In some embodiments, the 5' arm, 3' arm, or both are derived from *Mus musculus* miR-155 or *Homo sapiens* miR-155. In some embodiments, the 5' arm has the sequence set forth in SEQ ID NO:256 or is a functional variant thereof, such as, for example, a sequence that is the same length as SEQ ID NO:256, or 95%, 90%, 85%, 80%, 75%, or 50% as long as SEQ ID NO: 256 or is 100 nucleotides or less, 95 nucleotides or less, 90 nucleotides or less, 85 nucleotides or less, 80 nucleotides or less, 75 nucleotides or less, 70 nucleotides or less, 65 nucleotides or less, 60 nucleotides or less, 55 nucleotides or less, 50 nucleotides or less, 45 nucleotides or less, 40 nucleotides or less, 35 nucleotides or less, 30 nucleotides or less, or 25 nucleotides or less; and is at least 50%, 55%, 60%, 65%, 70%, 75%, 80%, 85%, 90%, or 95% identical to SEQ ID NO:256. In some embodiments, the 3' arm has the sequence set forth in SEQ ID NO:260 or is a functional variant thereof, such as, for example, the same length as SEQ ID NO:260, or 95%, 90%, 85%, 80%, 75%, or 50% as long as SEQ ID NO: 260 or is a sequence that is 100 nucleotides or less, 95 nucleotides or less, 90 nucleotides or less, 85 nucleotides or less, 80 nucleotides or less, 75 nucleotides or less, 70 nucleotides or less, 65 nucleotides or less, 60 nucleotides or less, 55 nucleotides or less, 50 nucleotides or less, 45 nucleotides or less, 40 nucleotides or less, 35 nucleotides or less, 30 nucleotides or less, or 25 nucleotides or less; and is at least 50%, 55%, 60%, 65%, 70%, 75%, 80%, 85%, 90%, or 95% identical to SEQ ID NO:260. In some embodiments, the 3' arm comprises nucleotides 221-283 of the *Mus musculus* BIC.

In another aspect, provided herein is a method for making replication incompetent recombinant retroviral particles, including: culturing a population of packaging cells to accumulate a first transactivator, wherein the packaging cells include the first transactivator expressed from a constitutive promoter, wherein the first transactivator is capable of binding a first ligand and a first inducible promoter for affecting expression of a nucleic acid sequence operably linked thereto in the presence versus absence of the first ligand, and wherein expression of a second transactivator is regulated by the first transactivator; incubating the population of packaging cells including accumulated first transactivator in the presence of the first ligand to accumulate the second transactivator, wherein the second transactivator is capable of binding a second ligand and a second inducible promoter for affecting expression of a nucleic acid sequence operably linked thereto in the presence versus absence of the second ligand; and incubating the population of packaging cells including accumulated second transactivator in the presence of the second ligand thereby inducing expression of retroviral polypeptides involved in viral packaging, such as, for example, a gag polypeptide, a pol polypeptide, and/or a pseudotyping element, and optionally other polypeptides that are believed to inhibit mammalian cell proliferation or survival that will become incorporated in or on the replication incompetent recombinant retroviral particle, thereby making the replication incompetent recombinant retroviral particle. In illustrative embodiments, a packageable RNA genome is encoded by a polynucleotide operably linked to a promoter, sometimes referred to for convenience as a "third" promoter wherein said third promoter is either constitutively active or inducible by either the first transactivator or, in illustrative embodiments, the second transactivator, thereby making the replication incompetent recombinant retroviral particle. The pseudotyping elements are typically capable of binding to a cell membrane of a target cell and facilitating fusion of the target cell membrane to the replication incompetent recombinant retroviral particle membrane. The pseudotyping elements can be any envelope proteins known in the art. In some embodiments, the envelope protein can be vesicular stomatitis virus envelope protein (VSV-G), feline endogenous virus (RD114) envelope protein, oncoretroviral amphotropic envelope protein, and/or oncoretroviral ecotropic envelope protein. A skilled artisan will appreciate many different transactivators, ligands, and inducible promoters can be used in the method for making a replication incompetent recombinant retroviral particle. Suitable transactivators, ligands, and inducible promoters are disclosed elsewhere herein, including above. A skilled artisan will further appreciate that the teachings hereinabove related to a retroviral packaging system aspect provided herein, apply to method of making replication incompetent recombinant retroviral particles aspects as well, and the reverse.

In some embodiments, the first transactivator can regulate expression of an element to control the nuclear export of transcripts containing a consensus sequence, such as an HIV Rev and the consensus sequence can be the Rev Response Element (RRE). In illustrative embodiments, the target cell is typically a T cell. In some embodiments, the HIV RREs and the polynucleotide region encoding HIV Rev can be replaced with HIV-2 RREs and a polynucleotide region encoding the HIV-2 Rev, respectively. In some embodiments, the HIV RREs and the polynucleotide region encoding HIV Rev can be replaced with SIV RREs and a polynucleotide region encoding the SIV Rev, respectively. In some embodiments, the HIV RREs and the polynucleotide region encoding HIV Rev can be replaced with RemRREs and a polynucleotide region encoding a betaretrovirus Rem, respectively. In some embodiments, the HIV RREs and the polynucleotide region encoding HIV Rev can be replaced with a deltaretrovirus RexRRE and a polynucleotide region encoding a deltaretrovirus Rex, respectively. In some embodiments, a Rev-like protein is not required and the RREs can be replaced with cis-acting RNA elements, such as the constitutive transport element (CTE).

In some embodiments, the pseudotyping element is a viral envelope protein. The pseudotyping element typically includes a binding polypeptide and a fusogenic polypeptide for binding to and facilitating membrane fusion of viral and target cell membranes. In some embodiments, the pseudotyping element can be the feline endogenous virus (RD114) envelope protein, the oncoretroviral amphotropic envelope protein, the oncoretroviral ecotropic envelope protein, and/or vesicular stomatitis virus envelope protein (VSV-G). In illustrative embodiments, the pseudotyping element includes a binding polypeptide and a fusogenic polypeptide derived from different proteins, as discussed in further detail herein. For example, in an illustrative embodiment, especially where the target cell is a T cell and/or NK cell, the binding polypeptide can be a cytoplasmic domain deletion variant of a Measles Virus H polypeptide and the fusogenic polypeptide can be the cytoplasmic domain deletion variant of a Measles Virus F polypeptide. In some embodiments, the fusogenic polypeptide can include multiple elements expressed as one polypeptide. In some embodiments, the binding polypeptide and fusogenic polypeptide can be translated from the same transcript and translated from separate ribosome binding sites, or the polypeptide can be cleaved after translation using a peptide cleavage signal or a ribosomal skip sequence, as disclosed elsewhere herein, to generate the binding polypeptide and the fusogenic polypeptide. In some embodiments, the translation of the binding polypeptide and fusogenic polypeptide from separate ribosome binding sites results in a higher amount of the fusogenic polypeptide as compared to the binding polypeptide. In some embodiments, the ratio of the fusogenic polypeptide to the binding polypeptide is at least 2:1, at least 3:1, at least 4:1, at least 5:1, at least 6:1, at least 7:1, or at least 8:1.

In some embodiments, the first transactivator can regulate the expression of an activation element capable of binding to and activating a target cell, such as a T cell. In these embodiments, the activation element can include: a.) aa membrane-bound polypeptide capable of binding to and activating CD3: and/or b.) a membrane-bound polypeptide capable of binding to and activating CD28. In some embodiments, the membrane-bound polypeptide capable of binding to and activating CD28 is CD80, CD86, or functional fragments thereof. In some embodiments, the replication incompetent recombinant retroviral particle can include the activation element on a retroviral membrane and the retroviral RNA within a nucleocapsid, thereby making a replication incompetent recombinant retroviral particles.

In some embodiments, the second transactivator can regulate the expression of an RNA including from 5' to 3': a 5' long terminal repeat, or active truncated fragment thereof; a nucleic acid sequence encoding a retroviral cis-acting RNA packaging element; a nucleic acid sequence encoding a first target polypeptide and optional second target polypeptide, as non-limiting example, one or two engineered signaling polypeptides; a promoter that is active in a target cell; and a 3' long terminal repeat, or active truncated fragment thereof. In some embodiments, the RNA can include a cPPT/CTS element. In some embodiments, the RNA can include a primer binding site. In some embodiments, the retroviral cis-acting RNA packaging element can be HIV Psi. In some embodiments, the retroviral cis-acting RNA packaging element can be the Rev Response Element. In any of the embodiments disclosed herein, retroviral components on the RNA, including RRE and Psi, can be located in any position, as a skilled artisan will understand. The engineered signaling polypeptide in illustrative embodiments, is one or more of the engineered signaling polypeptides disclosed herein.

In some embodiments, the engineered signaling polypeptide can include a first lymphoproliferative element. Suitable lymphoproliferative elements are disclosed in other sections herein. In some illustrative embodiments, the lymphoproliferative element is an IL-7 receptor mutant fused to a recognition domain, such as an eTag. In some embodiments, the packageable RNA genome can further include a nucleic acid sequence encoding a second engineered polypeptide including a chimeric antigen receptor, encoding any CAR embodiment provided herein. For example, the second engineered polypeptide can include a first antigen-specific targeting region, a first transmembrane domain, and a first intracellular activating domain. Examples of antigen-specific targeting regions, transmembrane domains, and intracellular activating domains are disclosed elsewhere herein. In some embodiments where the target cell is a T cell, the promoter that is active in a target cell is active in a T cell, as disclosed elsewhere herein.

In some embodiments, the packageable RNA genome can further include a riboswitch, as discussed in other sections herein. In some embodiments, the nucleic acid sequence encoding the engineered signaling polypeptide can be in reverse orientation. In further embodiments, the packageable RNA genome can further include a riboswitch and, optionally, the riboswitch can be in reverse orientation. In any of the embodiments disclosed herein, a polynucleotide including any of the elements can include a primer binding site. In illustrative embodiments, transcription blockers or polyA sequences can be placed near genes to prevent or reduce unregulated transcription. In any of the embodiments disclosed herein, a nucleic acid sequence encoding Vpx can be on the second or an optional third transcriptional unit, or on an additional transcriptional unit that is operably linked to the first inducible promoter.

In some embodiments of the packaging system or methods for making replication incompetent recombinant retroviral particles aspects, the encoded RNA can include an intron, which can be transcribed, for example, from the same promoter for expressing the target polypeptide(s). Such intron can encode 1, 2, 3, or 4 miRNAs, in certain illustrative embodiments. In these and other embodiments of the packaging system or methods for making replication incompetent recombinant retroviral particles aspects, the packageable RNA genome is 11,000 KB or less and in some instances 10,000 KB or less in size.

In some embodiments, the first transactivator can affect the expression of one or more polypeptides that are non-toxic. In some embodiments, the second transactivator can affect the expression of one or more polypeptides that are toxic. For example, the first transactivator can induce expression of the retroviral proteins Rev and Vpx in addition to polypeptides that will be transported to the cell membrane of the packaging cell and the second transactivator can induce expression of the retroviral proteins GAG, POL, MV(Ed)-FΔ30, and either MV(Ed)-HΔ18 or MV(Ed)-HΔ24 and expression of the lentiviral genome. In some embodiments, the first transactivator can affect the expression of one or more polypeptides that are toxic and/or the second transactivator can affect the expression of one or more polypeptides that are non-toxic.

In another aspect, provided herein is a mammalian packaging cell, including: a.) a first transcriptional unit in the genome of the mammalian packaging cell, including a nucleic acid sequence encoding a first transactivator, wherein said first transcriptional unit is operably linked to a constitutive promoter and wherein said transactivator is capable of binding a first inducible promoter and affecting expression of a nucleic acid sequence operably linked thereto in the presence versus absence of a first ligand, and wherein said first transactivator is capable of binding said first ligand; b.) a second and optional third transcriptional unit in the genome of the mammalian packaging cell, including a nucleic acid sequence encoding a retroviral REV protein and a nucleic acid sequence encoding a second transactivator capable of binding a second inducible promoter and affecting expression of a nucleic acid sequence operably linked thereto in the presence versus absence of a second ligand, wherein the second transactivator is capable of binding the second ligand, and wherein the second and optional third transcriptional units are operably linked to the first inducible promoter; c.) a fourth and optional fifth transcriptional unit in the genome of the mammalian packaging cell, including a nucleic acid sequence encoding a retroviral gag polypeptide and a retroviral pol polypeptide, and a binding polypeptide and a fusogenic polypeptide that are capable of binding to and facilitating fusion of a target cell membrane and the retroviral membrane, wherein the fourth and optional fifth transcriptional unit are operably linked to the second inducible promoter; and d) a sixth transcriptional unit in the genome of the mammalian packaging cell, including, from 5' to 3', a 5' LTR, or active truncated fragment thereof, a nucleic acid sequence encoding a retroviral cis-acting RNA packaging element, a cPPT/CTS element, a reverse complement of a nucleic acid sequence encoding an engineered signaling polypeptide, an intron, a promoter that is active in a target cell, and a 3' LTR, or active truncated fragment thereof, wherein the sixth transcriptional unit is operably linked to the second inducible promoter.

In another aspect, provided herein is a method for making a replication incompetent recombinant retroviral particle, including: 1.) culturing a population of packaging cells to accumulate a first transactivator, wherein the packaging cells include: a.) a first transcriptional unit in the genome of the mammalian packaging cell, including a nucleic acid sequence encoding a first transactivator, wherein said first transcriptional unit is operably linked to a constitutive promoter and wherein said transactivator is capable of binding a first inducible promoter and affecting expression of a nucleic acid sequence operably linked thereto in the presence versus absence of a first ligand, and wherein said first transactivator is capable of binding said first ligand; b.) a second and optional third transcriptional unit in the genome of the mammalian packaging cell, including a nucleic acid sequence encoding a retroviral REV protein and a nucleic acid sequence encoding a second transactivator capable of binding a second inducible promoter and affecting expression of a nucleic acid sequence operably linked thereto in the presence versus absence of a second ligand, wherein the second transactivator is capable of binding the second ligand, and wherein the second and optional third transcriptional units are operably linked to the first inducible promoter; c.) a fourth and optional fifth transcriptional unit in the genome of the mammalian packaging cell, including a nucleic acid sequence encoding a retroviral gag polypeptide and a retroviral pol polypeptide, and a binding polypeptide and a fusogenic polypeptide that are capable of binding to and facilitating fusion of the retroviral membrane with a target cell membrane, wherein the fourth and optional fifth transcriptional unit are operably linked to the second inducible promoter; and d.) a sixth transcriptional unit in the genome of the mammalian packaging cell, including from 5' to 3', a 5' LTR, or active truncated fragment thereof, a primer binding site (PBS), a nucleic acid sequence encoding a retroviral cis-acting RNA packaging element, a cPPT/CTS element, a reverse complement of a nucleic acid sequence encoding an engineered signaling polypeptide, an intron, a target cell promoter that is active in a target cell, a 3' LTR, or active truncated fragment thereof, wherein the fifth transcriptional unit is operably linked to the second inducible promoter; and 2.) incubating the population of packaging cells including the first transactivator in the presence of the first ligand to accumulate the second transactivator and the retroviral REV protein; and 3.) incubating the population of packaging cells including the second transactivator and the retroviral REV protein in the presence of the second ligand thereby inducing expression of the retroviral gag polypeptide, the retroviral pol polypeptide, the binding polypeptide, the fusogenic polypeptide, and a retroviral RNA including from 5' to 3', a 5' LTR, or active fragment thereof, the PBS, the retroviral cis-acting RNA packaging element, the reverse complement of the nucleic acid sequence encoding the engineered signaling polypeptide, the target cell promoter, and a 3' LTR, or active truncated fragment thereof, wherein replication incompetent recombinant retroviral particles are formed and release from the packaging cells, and wherein the replication incompetent recombinant retroviral particles include the binding polypeptide and/or the fusogenic polypeptide on a retroviral membrane and the retroviral RNA within a nucleocapsid, thereby making replication incompetent recombinant retroviral particles.

In one aspect provided herein, the retroviral packaging system can include a mammalian cell including: 1.) a first transactivator expressed from a constitutive promoter and capable of binding a first ligand and a first inducible promoter for affecting expression of a nucleic acid sequence operably linked thereto in the presence versus absence of the first ligand; 2.) a second transactivator capable of binding a second ligand and a second inducible promoter and affecting expression of a nucleic acid sequence operably linked thereto in the presence versus absence of a second ligand; and 3.) a packageable RNA genome for a retroviral particle, wherein the first transactivator regulates expression of the second transactivator, HIV REV, an IL7 GPI DAF, and an activation element, and wherein the second transactivator regulates expression of a gag polypeptide, a pol polypeptide, a retroviral cis-acting RNA packaging element, and one or more envelope polypeptides. In illustrative embodiments, the first transactivator can be an FRB domain fused to a p65 activation domain and one or more FKBP domains fused to a ZFHD1 DNA binding domain, the first ligand can be rapamycin, and the first inducible promoter can be one or more ZFHD1 binding sites. In illustrative embodiments, the second transactivator can be an rtTA protein, the second ligand can be tetracycline or doxycycline, and the second inducible promoter can be a TRE promoter or a bi-directional TRE promoter. In illustrative embodiments, the retroviral cis-acting RNA packaging element can be HIV Psi. In illustrative embodiments, the one or more envelope proteins include the cytoplasmic domain deletion variants of F and H polypeptides of a Measles Virus. In illustrative embodiments, transcription blockers or polyA sequences can be placed near genes to prevent or reduce unregulated transcription. In some embodiments, a rapamycin-doxycycline inducible lentiviral genome with riboswitch can be used (SEQ ID NO:83). In some embodiments, a rapamycin-doxycycline inducible GAG POL ENV can be used (SEQ ID NO:84). In some embodiments, a rapamycin-inducible TET activator can be used (SEQ ID NO:85). In some embodiments, a rapamycin inducer inducible REV srcVpx can be used (SEQ ID NO:86).

Some aspects of the present disclosure include or are cells, in illustrative examples, mammalian cells, that are used as packaging cells to make replication incompetent recombinant retroviral particles, such as lentiviruses, for transduction of T cells and/or NK cells. Any of a wide variety of cells can be selected for in vitro production of a virus or virus particle, such as a redirected recombinant retroviral particle, according to the invention. Eukaryotic cells are typically used, particularly mammalian cells including human, simian, canine, feline, equine and rodent cells. In illustrative examples, the cells are human cells. In further illustrative embodiments, the cells reproduce indefinitely, and are therefore immortal. Examples of cells that can be advantageously used in the present invention include NIH 3T3 cells, COS cells, Madin-Darby canine kidney cells, human embryonic 293T cells and any cells derived from such cells, such as gpnlslacZ φNX cells, which are derived from 293T cells. Highly transfectable cells, such as human embryonic kidney 293T cells, can be used. By "highly transfectable" it is meant that at least about 50%, more preferably at least about 70% and most preferably at least about 80% of the cells can express the genes of the introduced DNA.

Suitable mammalian cells include primary cells and immortalized cell lines. Suitable mammalian cell lines include human cell lines, non-human primate cell lines, rodent (e.g., mouse, rat) cell lines, and the like. Suitable mammalian cell lines include, but are not limited to, HeLa cells (e.g., American Type Culture Collection (ATCC) No. CCL-2), CHO cells (e.g., ATCC Nos. CRL9618, CCL61, CRL9096), 293 cells (e.g., ATCC No. CRL-1573), Vero cells, NIH 3T3 cells (e.g., ATCC No. CRL-1658), Huh-7 cells, BHK cells (e.g., ATCC No. CCL1O), PC12 cells (ATCC No. CRL1721), COS cells, COS-7 cells (ATCC No. CRL1651), RAT1 cells, mouse L cells (ATCC No. CCLI.3), human embryonic kidney (HEK) cells (ATCC No. CRL1573), HLHepG2 cells, Hut-78, Jurkat, HL-60, NK cell lines (e.g., NKL, NK92, and YTS), and the like.

In any of the embodiments disclosed herein, the methods of making a replication incompetent recombinant retroviral particle can include growing a mammalian packaging cells to 50%, 60%, 70%, 80%, 90% or 95% confluence or confluence or to 25%, 30%, 40%, 50%, 60%, 70%, 80%, 90% or 95% peak cell density or peak cell density and then splitting or diluting the cells. In some embodiments, a stirred tank reactor can be used to grow the cells. In some embodiments, the cells can be split at least about 1:2, 1:3, 1:4, 1:5, 1:6, 1:7, 1:8, 1:9, 1:10, 1:12, 1:15, or 1:20 using methods a skilled artisan will understand. In some embodiments, the cells can be diluted to 25%, 30%, 40%, 50%, 60%, 70%, 80%, 90% or 95% peak cell density. In some embodiments, after splitting or diluting the cells the cells can be grown for 1, 2, 3, 4, 5, 6, 7, 8, 10, or 16 hours or 1, 2, 3, 4, 5, 6, or 7 days before adding the first ligand. In some embodiments, the cells are grown in the presence of the first ligand for 1, 2, 3, 4, 5, 6, 7, 8, 9, 10, 11, 12, 13, 14, 21, or 28 days in the presence of the first ligand, which in illustrative embodiments can be rapamycin or a rapalog. In some embodiments, the second ligand can be added and the cells can be grown for at least 1, 2, 3, 4, 5, 6, 7, 8, 9, 10, 11, 12, 13, 14, 21, or 28 days which in illustrative embodiments can be tetracycline or doxycyline. Conditions for culturing will depend on the cells and ligands used and the methods are known in the art. A specific example of conditions for culturing and inducing HEK293S cells is shown in Example 8.

As disclosed herein, replication incompetent recombinant retroviral particles are a common tool for gene delivery (Miller, Nature (1992) 357:455-460). The ability of replication incompetent recombinant retroviral particles to deliver an unrearranged nucleic acid sequence into a broad range of rodent, primate and human somatic cells makes replication incompetent recombinant retroviral particles well suited for transferring genes to a cell. In some embodiments, the replication incompetent recombinant retroviral particles can be derived from the Alpharetrovirus genus, the Betaretrovirus genus, the Gammaretrovirus genus, the Deltaretrovirus genus, the Epsilonretrovirus genus, the Lentivirus genus, or the Spumavirus genus. There are many retroviruses suitable for use in the methods disclosed herein. For example, murine leukemia virus (MLV), human immunodeficiency virus (HIV), equine infectious anaemia virus (EIAV), mouse mammary tumor virus (MMTV), Rous sarcoma virus (RSV), Fujinami sarcoma virus (FuSV), Moloney murine leukemia virus (Mo-MLV), FBR murine osteosarcoma virus (FBR MSV), Moloney murine sarcoma virus (Mo-MSV), Abelson murine leukemia virus (A-MLV), Avian myelocytomatosis virus-29 (MC29), and Avian erythroblastosis virus (AEV) can be used. A detailed list of retroviruses may be found in Coffin et al ("Retroviruses" 1997 Cold Spring Harbor Laboratory Press Eds: J M Coffin, S M Hughes, H E Varmus pp 758-763). Details on the genomic structure of some retroviruses may be found in the art. By way of example, details on HIV may be found from the NCBI Genbank (i.e. Genome Accession No. AF033819).

In illustrative embodiments, the replication incompetent recombinant retroviral particles can be derived from the Lentivirus genus. In some embodiments, the replication incompetent recombinant retroviral particles can be derived from HIV, SIV, or FIV. In further illustrative embodiments, the replication incompetent recombinant retroviral particles can be derived from the human immunodeficiency virus (HIV) in the Lentivirus genus. Lentiviruses are complex retroviruses which, in addition to the common retroviral genes gag, pol and env, contain other genes with regulatory or structural function. The higher complexity enables the lentivirus to modulate the life cycle thereof, as in the course of latent infection. A typical lentivirus is the human immunodeficiency virus (HIV), the etiologic agent of AIDS. In vivo, HIV can infect terminally differentiated cells that rarely divide, such as lymphocytes and macrophages.

In illustrative embodiments, replication incompetent recombinant retroviral particles provided herein contain Vpx polypeptide. Vpx polypeptide can be expressed in a packaging cell line, after integration of a Vpx coding nucleic acid in its genome, for example as a cell membrane bound protein that gets incorporated into a retrovirus membrane (Durand et al., *J Virol.* (2013) 87: 234-242). A retroviral membrane bound. Vpx can be constructed with a processing sequence for a viral protease such that free Vpx is released once incorporated in a viral particle, Such an example of a Vpx fusion with this functionality is Src-Flag-Vpx, which includes a membrane-targeting domain (MGSSKSKPKDP) (SEQ ID NO:227) of the first 11 amino acids of c-Src followed by a viral protease cleavage domain KARVLAEA (SEQ ID NO:228) followed by Hag-tagged Vpx.

Not to be limited by theory, Vpx polypeptide aids in transduction of resting cells by stimulating the efficiency of the process of reverse transcription by degrading the restriction factor SAMHD1. Accordingly, it is believed that in the methods provided herein where Vpx is present in a replication incompetent recombinant retroviral particles used to transduce T cells and/or NK cells, Vpx is released into the cytoplasm of a resting T cell or a resting NK cell upon transduction of the cell by a replication incompetent recombinant retroviral particle that contains Vpx. Vpx then degrades SAMHD1, which causes an increase in free dNTPs, which in turn, stimulates reverse transcription of the retroviral genome.

Retroviral Genome Size

In the methods and compositions provided herein, the recombinant retroviral genomes, in non-limiting illustrative examples, lentiviral genomes, have a limitation to the number of polynucleotides that can be packaged into the viral particle. In some embodiments provided herein, the polypeptides encoded by the polynucleotide encoding region can be truncations or other deletions that retain a functional activity such that the polynucleotide encoding region is encoded by less nucleotides than the polynucleotide encoding region for the wild-type polypeptide. In some embodiments, the polypeptides encoded by the polynucleotide encoding region can be fusion polypeptides that can be expressed from one promoter. In some embodiments, the fusion polypeptide can have a cleavage signal to generate two or more functional polypeptides from one fusion polypeptide and one promoter. Furthermore, some functions that are not required after initial ex vivo transduction are not included in the retroviral genome, but rather are present on the surface of the replication incompetent recombinant retroviral particles via the packaging cell membrane. These various strategies are used herein to maximize the functional elements that are packaged within the replication incompetent recombinant retroviral particles.

In some embodiments, the recombinant retroviral genome to be packaged can be between 1,000, 2,000, 3,000, 4,000, 5,000, 6,000, 7,000, and 8,000 nucleotides on the low end of the range and 2,000, 3,000, 4,000, 5,000, 6,000, 7,000, 8,000, 9,000, 10,000, and 11,000 nucleotides on the high end of the range. The retroviral genome to be packaged includes one or more polynucleotide regions encoding a first and second engineering signaling polypeptide as disclosed in detail herein. In some embodiments, the recombinant retroviral genome to be packaged can be less than 5,000, 6,000, 7,000, 8,000, 9,000, 10,000, or 11,000 nucleotides. Functions discussed elsewhere herein that can be packaged include required retroviral sequences for retroviral assembly and packaging, such as a retroviral rev, gag, and pol coding regions, as well as a 5' LTR and a 3' LTR, or an active truncated fragment thereof, a nucleic acid sequence encoding a retroviral cis-acting RNA packaging element, and a cPPT/CTS element. Furthermore, in illustrative embodiments a replication incompetent recombinant retroviral particle herein can include any one or more or all of the following, in some embodiments in reverse orientation of these retroviral functional regions: one or more polynucleotide regions encoding a first and second engineering signaling polypeptide, at least one of which includes at least one lymphoproliferative element and can further include an ASTR; a second engineered signaling polypeptide that can include a chimeric antigen receptor; a control element, such as a riboswitch, which typically regulates expression of the first and/or the second engineering signaling polypeptide; a recognition domain, an intron, a promoter that is active in a target cell, such as a T cell, a 2A cleavage signal and/or an IRES.

Recombinant Retroviral Particles

Recombinant retroviral particles are disclosed in methods and compositions provided herein, for example, to transduce T cells and/or NK cells to make genetically modified T cells and/or NK cells. The recombinant retroviral particles are themselves aspects of the present invention. Typically, the recombinant retroviral particles included in aspects provided herein, are replication incompetent, meaning that a recombinant retroviral particle cannot replicate once it leaves the packaging cell. In illustrative embodiments, the recombinant retroviral particles are lentiviral particles.

Provided herein in some aspects, is a recombinant retroviral particle that includes (i) a pseudotyping element capable of binding to a T cell and/or NK cell and facilitating membrane fusion of the recombinant retroviral particle thereto; (ii) a polynucleotide having one or more transcriptional units operatively linked to a promoter active in T cells and/or NK cells, wherein the one or more transcriptional units encode a first engineered signaling polypeptide having a chimeric antigen receptor that includes an antigen-specific targeting region, a transmembrane domain, and an intracellular activating domain, and a second engineered signaling polypeptide that includes at least one lymphoproliferative element; wherein expression of the first engineered signaling polypeptide and/or the second engineered signaling polypeptide are regulated by an in vivo control element; and (iii) an activation element on its surface, wherein the activation element is capable of binding to a T cell and/or NK cell and is not encoded by a polynucleotide in the recombinant retroviral particle. In some embodiments, the promoter active in T cells and/or NK cells is not active in the packaging cell line or is only active in the packaging cell line in an inducible manner. In any of the embodiments disclosed herein, either of the first and second engineered signaling polypeptides can have a chimeric antigen receptor and the other engineered signaling polypeptide can have at least one lymphoproliferative element.

Various elements and combinations of elements that are included in replication incompetent, recombinant retroviral particles are provided throughout this disclosure, such as, for example, pseudotyping elements, activation elements, and membrane bound cytokines, as well as nucleic acid sequences that are included in a genome of a replication incompetent, recombinant retroviral particle such as, but not limited to, a nucleic acid encoding a CAR; a nucleic acid encoding a lymphoproliferative element; a nucleic acid encoding a control element, such as a riboswitch; a promoter, especially a promoter that is constitutively active or inducible in a T cell; and a nucleic acid encoding an inhibitory RNA molecule. Furthermore, various aspects provided herein, such as methods of making recombinant retroviral particles, methods for performing adoptive cell therapy, and methods for transducing T cells, produce and/or include replication incompetent, recombinant retroviral particles. Replication incompetent recombinant retroviruses that are produced and/or included in such methods themselves form separate aspects of the present invention as replication incompetent, recombinant retroviral particle compositions, which can be in an isolated form. Such compositions can be in dried down (e.g. lyophilized) form or can be in a suitable solution or medium known in the art for storage and use of retroviral particles.

Accordingly, as a non-limiting example, provided herein in another aspect, is a replication incompetent recombinant retroviral particle having in its genome a polynucleotide having one or more nucleic acid sequences operatively linked to a promoter active in T cells and/or NK cells that in some instances, includes a first nucleic acid sequence that encodes one or more (e.g. two or more) inhibitory RNA molecules directed against one or more RNA targets and a second nucleic acid sequence that encodes a chimeric antigen receptor, or CAR, as described herein. In other embodiments, a third nucleic acid sequence is present that encodes at least one lymphoproliferative element described previously herein that is not an inhibitory RNA molecule. In certain embodiments, the polynucleotide includes one or more riboswitches as presented herein, operably linked to the first nucleic acid sequence, the second nucleic acid sequence, and/or the third nucleic acid sequence, if present. In such a construct, expression of one or more inhibitory RNAs, the CAR, and/or one or more lymphoproliferative elements that are not inhibitory RNAs is controlled by the riboswitch. In some embodiments, two to 10 inhibitory RNA molecules are encoded by the first nucleic acid sequence. In further embodiments, two to six inhibitory RNA molecules are encoded by the first nucleic acid sequence. In illustrative embodiments, 4 inhibitory RNA molecules are encoded by the first nucleic acid sequence. In some embodiments, the first nucleic acid sequence encodes one or more inhibitory RNA molecules and is located within an intron. In certain embodiments, the intron includes all or a portion of a promoter. The promoter can be a Pol I, Pol II, or Pol III promoter. In some illustrative embodiments, the promoter is a Pol II promoter. In some embodiments, the intron is adjacent to and downstream of the promoter active in a T cell and/or NK cell. In some embodiments, the intron is EF1-α intron A.

Recombinant retroviral particle embodiments herein include those wherein the retroviral particle comprises a genome that includes one or more nucleic acids encoding one or more inhibitory RNA molecules. Various alternative embodiments of such nucleic acids that encode inhibitory RNA molecules that can be included in a genome of a retroviral particle, including combinations of such nucleic acids with other nucleic acids that encode a CAR or a lymphoproliferative element other than an inhibitory RNA molecule, are included for example, in the inhibitory RNA section provided herein, as well as in various other paragraphs that combine these embodiments. Furthermore, various alternatives of such replication incompetent recombinant retroviruses can be identified by exemplary nucleic acids that are disclosed within packaging cell line aspects disclosed herein. A skilled artisan will recognize that disclosure in this section of a recombinant retroviral particle that includes a genome that encodes one or more (e.g. two or more) inhibitory RNA molecules, can be combined with various alternatives for such nucleic acids encoding inhibitory RNA molecules provided in other sections herein. Furthermore, a skilled artisan will recognize that such nucleic acids encoding one or more inhibitory RNA molecules can be combined with various other functional nucleic acid elements provided herein, as for example, disclosed in the section herein that focuses on inhibitory RNA molecules and nucleic acid encoding these molecules. In addition, the various embodiments of specific inhibitory RNA molecules provided herein in other sections can be used in recombinant retroviral particle aspects of the present disclosure.

Necessary elements of recombinant retroviral vectors, such as lentiviral vectors, are known in the art. These elements are included in the packaging cell line section and in details for making replication incompetent, recombinant retroviral particles provided in the Examples section. For example, lentiviral particles typically include packaging elements REV, GAG and POL, which can be delivered to packaging cell lines via one or more packaging plasmids, a pseudotyping element, various examples which are provided herein, which can be delivered to a packaging cell line via a pseudotyping plasmid, and a genome, which is produced by a polynucleotide that is delivered to a host cell via a transfer plasmid. This polynucleotide typically includes the viral LTRs and a psi packaging signal. The 5' LTR can be a chimeric 5' LTR fused to a heterologous promoter, which includes 5' LTRs that are not dependent on Tat transactivation. The transfer plasmid can be self-inactivating, for example, by removing a U3 region of the 3' LTR. In some non-limiting embodiments, Vpx, such as Src-FLAG-Vpx, is packaged within the retroviral particle. Not to be limited by theory, upon transduction of a T cells, Vpx enters the cytosol of the cells and promotes the degradation of SAMHD1, resulting in an increased pool of cytoplasmic dNTPs available for reverse transcription.

Retroviral particles (e.g. lentiviral particles) included in various aspects of the present invention are in illustrative embodiments, replication incompetent, especially for safety reasons for embodiments that include introducing cells transduced with such retroviral particles into a subject. When replication incompetent retroviral particles are used to transduce a cell, retroviral particles are not produced from the transduced cell. Modifications to the retroviral genome are known in the art to assure that retroviral particles that include the genome are replication incompetent. However, it will be understood that in some embodiments for any of the aspects provided herein, replication competent recombinant retroviral particles can be used.

A skilled artisan will recognize that the functional elements discussed herein can be delivered to packaging cells and/or to T cells using different types of vectors, such as expression vectors. Illustrative aspects of the invention utilize retroviral vectors, and in some particularly illustrative embodiments lentiviral vectors. Other suitable expression vectors can be used to achieve certain embodiments herein. Such expression vectors include, but are not limited to, viral vectors (e.g. viral vectors based on vaccinia virus; poliovirus; adenovirus (see, e.g., Li et al., *Invest Opthalmol Vis Sci*

35:2543 2549, 1994; Borras et al., *Gene Ther* 6:515 524, 1999; Li and Davidson, *PNAS* 92:7700 7704, 1995; Sakamoto et al., H *Gene Ther* 5:1088 1097, 1999; WO 94/12649, WO 93/03769; WO 93/19191; WO 94/28938; WO 95/11984 and WO 95/00655); adeno-associated virus (see, e.g., Ali et al., *Hum Gene Ther* 9:81 86, 1998, Flannery et al., *PNAS* 94:6916 6921, 1997; Bennett et al., *Invest Opthalmol Vis Sci* 38:2857 2863, 1997; Jomary et al., *Gene Ther* 4:683 690, 1997, Rolling et al., *Hum Gene Ther* 10:641 648, 1999; Ali et al., *Hum Mol Genet* 5:591 594, 1996; Srivastava in WO 93/09239, Samulski et al., *J. Vir.* (1989) 63:3822-3828; Mendelson et al., *Virol.* (1988) 166:154-165; and Flotte et al., *PNAS* (1993) 90: 10613-10617); SV40; herpes simplex virus; or a retroviral vector (e.g., Murine Leukemia Virus, spleen necrosis virus, and vectors derived from retroviruses such as Rous Sarcoma Virus, Harvey Sarcoma Virus, avian leukosis virus, human immunodeficiency virus, myeloproliferative sarcoma virus, and mammary tumor virus), for example a gamma retrovirus; or human immunodeficiency virus (see, e.g., Miyoshi et al., *PNAS* 94:10319 23, 1997; Takahashi et al., *J Virol* 73:7812 7816, 1999); and the like.

In illustrative embodiments, a retroviral particle is a lentiviral particle. Such retroviral particle typically includes a retroviral genome within a capsid which is located within a viral envelope.

In some embodiments, DNA-containing viral particles are utilized instead of recombinant retroviral particles. Such viral particles can be adenoviruses, adeno-associated viruses, herpesviruses, cytomegaloviruses, poxviruses, avipox viruses, influenza viruses, vesicular stomatitis virus (VSV), or Sindbis virus. A skilled artisan will appreciate how to modify the methods disclosed herein for use with different viruses and retroviruses, or retroviral particles. Where viral particles are used that include a DNA genome, a skilled artisan will appreciate that functional units can be included in such genomes to induce integration of all or a portion of the DNA genome of the viral particle into the genome of a T cell transduced with such virus.

In some embodiments, the HIV RREs and the polynucleotide region encoding HIV Rev can be replaced with N-terminal RGG box RNA binding motifs and a polynucleotide region encoding ICP27. In some embodiments, the polynucleotide region encoding HIV Rev can be replaced with one or more polynucleotide regions encoding adenovirus E1B 55-kDa and E4 Orf6.

Provided herein in one aspect is a commercial container containing a replication incompetent recombinant retroviral particle and instructions for the use thereof to treat tumor growth in a subject, wherein the replication incompetent recombinant retroviral particle comprises in its genome a polynucleotide comprising one or more nucleic acid sequences operatively linked to a promoter active in T cells and/or NK cells, wherein a first nucleic acid sequence of the one or more nucleic acid sequences encodes two or more inhibitory RNA molecules directed against one or more RNA targets and a second nucleic acid sequence of the one or more nucleic acid sequences encodes a chimeric antigen receptor (CAR) comprising an antigen-specific targeting region (ASTR), a transmembrane domain, and an intracellular activating domain.

The container that contains the recombinant retroviral particles can be a tube, vial, well of a plate, or other vessel for storage of a recombinant retroviral particle. The kit can include two or more containers wherein a second or other container can include, for example, a solution or media for transduction of T cells and/or NK cells, and/or a the second or other container can include a pH-modulating pharmacologic agent. Any of these containers can be of industrial strength and grade. The replication incompetent recombinant retroviral particle in such aspects that include a kit and a nucleic acid encoding an inhibitory RNA molecule, can be any of the embodiments for such replication incompetent recombinant retroviral particles provided herein, which include any of the embodiments for inhibitory RNA provided herein.

Genetically Modified T Cells and NK Cells

In embodiments of the methods and compositions herein, genetically modified lymphocytes are produced, which themselves are a separate aspect of the invention. Such genetically modified lymphocytes can be transduced lymphocytes. In some embodiments, genetically modified lymphocytes are lymphocytes such as T cells or NK cells that have been genetically modified to express a first engineered signaling polypeptide comprising at least one lymphoproliferative element and/or a second engineered signaling polypeptide comprising a chimeric antigen receptor, which includes an antigen-specific targeting region (ASTR), a transmembrane domain, and an intracellular activating domain.

Genetically modified lymphocytes of the present disclosure possess a heterologous nucleic acid sequence that has been introduced into the lymphocyte by a recombinant DNA method. For example, the heterologous sequence in illustrative embodiments is inserted into the lymphocyte during a method for transducing the lymphocyte provided herein. The heterologous nucleic acid is found within the lymphocyte and in some embodiments is or is not integrated into the genome of the genetically modified lymphocyte.

In illustrative embodiments, the heterologous nucleic acid is integrated into the genome of the genetically modified lymphocyte. Such lymphocytes are produced, in illustrative embodiments, using a method for transducing lymphocytes provided herein, that utilizes a recombinant retroviral particle. Such recombinant retroviral particle can include a polynucleotide that encodes a chimeric antigen receptor that typically includes at least an antigen-specific targeting region (ASTR), a transmembrane domain, and an intracellular activating domain. Provided herein in other sections of this disclosure are various embodiments of replication incompetent recombinant retroviral particles and polynucleotides encoded in a genome of the replication incompetent retroviral particle, that can be used to produce genetically modified lymphocytes that themselves form another aspect of the present disclosure.

Genetically modified lymphocytes of the present disclosure can be isolated outside the body. For example, such lymphocytes can be found in media and other solutions that are used for ex vivo transduction as provided herein. The lymphocytes can be present in a genetically unmodified form in blood that is collected from a subject in methods provided herein, and then genetically modified during method of transduction. The genetically modified lymphocytes can be found inside a subject after they are introduced or reintroduced into the subject after they have been genetically modified. The genetically modified lymphocytes can be a resting T cell or a resting NK cell, or the genetically modified T cell or NK cell can be actively dividing, especially after it expresses some of the functional elements provided in nucleic acids that are inserted into the T cell or NK cell after transduction as disclosed herein.

Provided herein in one aspect is a transduced and/or genetically modified T cell or NK cell, comprising a recombinant polynucleotide comprising one or more transcriptional units operatively linked to a promoter active in T cells and/or NK cells, in its genome, that expresses one or more of the functional elements provided in any of the aspects and embodiments of the present disclosure. For example, the one or more transcriptional units can express a CAR, which can include any of the CAR elements provided herein such as an ASTR, as a non-limiting example a MBR-ASTR, a transmembrane domain, and an intracellular signaling domain, and can further include as non-limiting example, a modulatory domain. Furthermore, the functional element(s) expressed within the transduced and/or genetically modified T cell or NK cell, one or more of the lymphoproliferative elements provided herein, for example a constitutively active IL-7 receptor mutant or other lymphoproliferative element that is not an inhibitory RNA molecule (e.g. an miRNA or an shRNA), a recognition and/or elimination domain.

In one aspect, provided herein is a genetically modified T cell or NK cell comprising:
a. one or more (e.g. two or more) inhibitory RNA molecules directed against one or more RNA targets; and
b. a chimeric antigen receptor (CAR) comprising an antigen-specific targeting region (ASTR), a transmembrane domain, and an intracellular activating domain,
and/or nucleic acids encoding the inhibitory RNA molecules directed against one or more RNA targets and the CAR, wherein said one (e.g. two) or more inhibitory RNA molecules and the CAR, or the nucleic acids encoding the same are encoded by or are nucleic acid sequences that are genetic modifications of the T cell and/or NK cell.

The genetically modified T cell or NK cell can be a population of genetically modified T cells and/or NK cells that include the one (e.g. two) or more inhibitory RNA molecules directed against one or more RNA targets; and the CAR.

In some embodiments of the aspect immediately above where the T cell or NK cell comprises one or more (e.g. two or more) inhibitory RNA molecules and the CAR, or nucleic acids encoding the same, any of the specific embodiments provided herein for elements that can be included as part of the CAR or that can be expressed along with a lymphoproliferative element or used to control a lymphoproliferative element can be included.

In some embodiments of the aspect immediately above where the T cell or NK cell comprises one or more (e.g. two or more) inhibitory RNA molecules and the CAR, or nucleic acids encoding the same, the CAR is a microenvironment restricted biologic (MRB)-CAR and/or the genetically modified T cell or NK cell can further include at least one lymphoproliferative element that is not an inhibitory RNA molecule, and/or a nucleic acid encoding the lymphoproliferative element. In such embodiments, the lymphoproliferative element is encoded by nucleic acid sequences that are genetic modifications of the T cell and/or NK cell. Any of the lymphoproliferative elements disclosed herein can be used and/or encoded for, in such embodiments. For example, the at least one lymphoproliferative element can be a constitutively active IL-7 receptor.

In some embodiments of the aspect immediately above where the T cell or NK cell comprises one or more (e.g. two or more) inhibitory RNA molecules and the CAR, or nucleic acids encoding the same, the inhibitory RNA molecule is a precursor of a miRNA or an shRNA. In some embodiments of this aspect the one (e.g. two) or more inhibitory RNA molecules are polycistronic. In some embodiments of this aspect the one (e.g. two) or more inhibitory RNA molecules are directed against the same or in illustrative embodiments, different RNA targets. In some embodiments of this aspect, one, most or all of the one (e.g. two) or more inhibitory RNA molecules decreases expression of an endogenous TCR.

In some embodiments of the aspect immediately above where the T cell or NK cell comprises one or more (e.g. two or more) inhibitory RNA molecules and the CAR, or nucleic acids encoding the same, the RNA target is mRNA transcribed from a gene selected from the group consisting of: PD-1, CTLA4, TCR alpha, TCR beta, CD3 zeta, SOCS, SMAD2, a miR-155 target, IFN gamma, cCBL, TRAIL2, PP2A, and ABCG1. In 144. The genetically modified T cell and/or NK cell of any one of claims 135-140, wherein said RNA target is mRNA transcribed from the TCR alpha gene. In some embodiments of this aspect at least one of the one (e.g. two) or more inhibitory RNA molecules is miR-155.

In some embodiments of the aspect immediately above where the T cell or NK cell comprises one or more (e.g. two or more) inhibitory RNA molecules and the CAR, or nucleic acids encoding the same, the ASTR of the CAR is an MRB ASTR and/or the ASTR of the CAR binds to a tumor associated antigen. Furthermore, in some embodiments of the above aspect, the first nucleic acid sequence is operably linked to a riboswitch, which for example is capable of binding a nucleoside analog, and in illustrative embodiments is an antiviral drug such as acyclovir.

In the methods and compositions disclosed herein, expression of engineered signaling polypeptides is regulated by a control element, and in some embodiments, the control element is a polynucleotide comprising a riboswitch. In certain embodiments, the riboswitch is capable of binding a nucleoside analog and when the nucleoside analog is present, one or both of the engineered signaling polypeptides are expressed.

The genetically modified lymphocytes disclosed herein can also have polypeptides on their surface that are remnants of fusion of a replication incompetent recombinant retroviral particle during a transduction method provided herein. Such polypeptides can include, an activation element, a pseudotyping element, and/or one or more fusion polypeptides that include a cytokine.

Provided herein in one aspect, is a genetically modified T cell and/or NK cell that expresses one or more (e.g. two or more) inhibitory RNA molecules directed against one or more RNA targets and a chimeric antigen receptor, or CAR, as disclosed herein. In some embodiments, the genetically modified T cell and/or NK cell further expresses at least one lymphoproliferative element as disclosed herein that is not an inhibitory RNA molecule. In certain embodiments, the genetically modified T cell and/or NK cell also expresses one or more riboswitches that control expression of the one or more inhibitory RNA molecules, the CAR, and/or the at least one lymphoproliferative element that is not an inhibitory RNA molecule. In some embodiments, the genetically modified T cell and/or NK cell expresses two to 10 inhibitory RNA molecules. In further embodiments, the genetically modified T cell and/or NK cell expresses two to six inhibitory RNA molecules. In illustrative embodiments, the genetically modified T cell and/or NK cell expresses four inhibitory RNA molecules.

Nucleic Acids

The present disclosure provides nucleic acid encoding polypeptides of the present disclosure. A nucleic acid will in some embodiments be DNA, including, e.g., a recombinant expression vector. A nucleic acid will in some embodiments be RNA, e.g., in vitro synthesized RNA.

In some cases, a nucleic acid provides for production of a polypeptide of the present disclosure, e.g., in a mammalian cell. In other cases, a subject nucleic acid provides for amplification of the nucleic acid encoding a polypeptide of the present disclosure.

A nucleotide sequence encoding a polypeptide of the present disclosure can be operably linked to a transcriptional control element, e.g., a promoter, and enhancer, etc.

Suitable promoter and enhancer elements are known in the art. For expression in a bacterial cell, suitable promoters include, but are not limited to, lacI, lacZ, T3, T7, gpt, lambda P and trc. For expression in a eukaryotic cell, suitable promoters include, but are not limited to, light and/or heavy chain immunoglobulin gene promoter and enhancer elements; cytomegalovirus immediate early promoter; herpes simplex virus thymidine kinase promoter; early and late SV40 promoters; promoter present in long terminal repeats from a retrovirus; mouse metallothionein-I promoter; and various art-known tissue specific promoters.

Suitable reversible promoters, including reversible inducible promoters are known in the art. Such reversible promoters may be isolated and derived from many organisms, e.g., eukaryotes and prokaryotes. Modification of reversible promoters derived from a first organism for use in a second organism, e.g., a first prokaryote and a second a eukaryote, a first eukaryote and a second a prokaryote, etc., is well known in the art. Such reversible promoters, and systems based on such reversible promoters but also comprising additional control proteins, include, but are not limited to, alcohol regulated promoters (e.g., alcohol dehydrogenase I (alcA) gene promoter, promoters responsive to alcohol transactivator proteins (AlcR), etc.), tetracycline regulated promoters, (e.g., promoter systems including TetActivators, TetON, TetOFF, etc.), steroid regulated promoters (e.g., rat glucocorticoid receptor promoter systems, human estrogen receptor promoter systems, retinoid promoter systems, thyroid promoter systems, ecdysone promoter systems, mifepristone promoter systems, etc.), metal regulated promoters (e.g., metallothionein promoter systems, etc.), pathogenesis-related regulated promoters (e.g., salicylic acid regulated promoters, ethylene regulated promoters, benzothiadiazole regulated promoters, etc.), temperature regulated promoters (e.g., heat shock inducible promoters (e.g., HSP-70, HSP-90, soybean heat shock promoter, etc.), light regulated promoters, synthetic inducible promoters, and the like.

In some instances, the locus or construct or trans gene containing the suitable promoter is irreversibly switched through the induction of an inducible system. Suitable systems for induction of an irreversible switch are well known in the art, e.g., induction of an irreversible switch may make use of a Cre-lox-mediated recombination (see, e.g., Fuhrmann-Benzakein, et al., *PNAS* (2000) 28:e99, the disclosure of which is incorporated herein by reference). Any suitable combination of recombinase, endonuclease, ligase, recombination sites, etc. known to the art may be used in generating an irreversibly switchable promoter. Methods, mechanisms, and requirements for performing site-specific recombination, described elsewhere herein, find use in generating irreversibly switched promoters and are well known in the art, see, e.g., Grindley et al. (2006) *Annual Review of Biochemistry*, 567-605 and Tropp (2012) Molecular Biology (Jones & Bartlett Publishers, Sudbury, Mass.), the disclosures of which are incorporated herein by reference.

In some cases, the promoter is a CD8 cell-specific promoter, a CD4 cell-specific promoter, a neutrophil-specific promoter, or an NK-specific promoter. For example, a CD4 gene promoter can be used; see, e.g., Salmon et al. (1993) *Proc. Natl. Acad. Sci. USA* 90:7739; and Marodon et al. (2003) *Blood* 101:3416. As another example, a CD8 gene promoter can be used. NK cell-specific expression can be achieved by use of an Ncr1 (p46) promoter; see, e.g., Eckelhart et al. (2011) *Blood* 117:1565.

In some embodiments, e.g., for expression in a yeast cell, a suitable promoter is a constitutive promoter such as an ADH1 promoter, a PGK1 promoter, an ENO promoter, a PYK1 promoter and the like; or a regulatable promoter such as a GAL1 promoter, a GAL10 promoter, an ADH2 promoter, a PHO5 promoter, a CUP1 promoter, a GAL7 promoter, a MET25 promoter, a MET3 promoter, a CYC1 promoter, a HIS3 promoter, an ADH1 promoter, a PGK promoter, a GAPDH promoter, an ADC1 promoter, a TRP1 promoter, a URA3 promoter, a LEU2 promoter, an ENO promoter, a TP1 promoter, and AOX1 (e.g., for use in *Pichia*). Selection of the appropriate vector and promoter is well within the level of ordinary skill in the art.

Suitable promoters for use in prokaryotic host cells include, but are not limited to, a bacteriophage T7 RNA polymerase promoter; a trp promoter; a lac operon promoter; a hybrid promoter, e.g., a lac/tac hybrid promoter, a tac/trc hybrid promoter, a trp/lac promoter, a T7/lac promoter; a trc promoter; a tac promoter, and the like; an araBAD promoter; in vivo regulated promoters, such as an ssaG promoter or a related promoter (see, e.g., U.S. Patent Publication No. 20040131637), a pagC promoter (Pulkkinen and Miller, *J. Bacterial.*, 1991: 173(1): 86-93; Alpuche-Aranda et al., PNAS, 1992; 89(21): 10079-83), a nirB promoter (Harborne et al. (1992) *Mal. Micro.* 6:2805-2813), and the like (see, e.g., Dunstan et al. (1999) *Infect. Immun.* 67:5133-5141; McKelvie et al. (2004) *Vaccine* 22:3243-3255; and Chatfield et al. (1992) *Biotechnol.* 10:888-892); a sigma70 promoter, e.g., a consensus sigma70 promoter (see, e.g., GenBank Accession Nos. AX798980, AX798961, and AX798183); a stationary phase promoter, e.g., a dps promoter, an spy promoter, and the like; a promoter derived from the pathogenicity island SPI-2 (see, e.g., WO96/17951); an actA promoter (see, e.g., Shetron-Rama et al. (2002) *Infect. Immun.* 70:1087-1096); an rpsM promoter (see, e.g., Valdivia and Falkow (1996). *Mal. Microbial.* 22:367); a tet promoter (see, e.g., Hillen, W. and Wissmann, A. (1989) In Saenger, W. and Heinemann, U. (eds), *Topics in Molecular and Structural Biology, Protein-Nucleic Acid Interaction*. Macmillan, London, UK, Vol. 10, pp. 143-162); an SP6 promoter (see, e.g., Melton et al. (1984) *Nucl. Acids Res.* 12:7035); and the like. Suitable strong promoters for use in prokaryotes such as *Escherichia coli* include, but are not limited to Trc, Tac, T5, T7, and PLambda. Non-limiting examples of operators for use in bacterial host cells include a lactose promoter operator (LacI repressor protein changes conformation when contacted with lactose, thereby preventing the LacI repressor protein from binding to the operator), a tryptophan promoter operator (when complexed with tryptophan, TrpR repressor protein has a conformation that binds the operator; in the absence of tryptophan, the TrpR repressor protein has a conformation that does not bind to the operator), and a tac promoter operator (see, for example, deBoer et al. (1983) Proc. Natl. Acad. Sci. U.S.A. 80:21-25).

A nucleotide sequence encoding a polypeptide of the disclosure can be present in an expression vector and/or a cloning vector. Nucleotide sequences encoding two separate polypeptides can be cloned in the same or separate vectors. An expression vector can include a selectable marker, an origin of replication, and other features that provide for replication and/or maintenance of the vector. Suitable expression vectors include, e.g., plasmids, viral vectors, and the like.

Large numbers of suitable vectors and promoters are known to those of skill in the art; many are commercially available for generating a subject recombinant constructs. The following bacterial vectors are provided by way of example: pBs, phagescript, PsiX174, pBluescript SK, pBs KS, pNH8a, pNH16a, pNH18a, pNH46a (Stratagene, La Jolla, Calif., USA); pTrc99A, pKK223-3, pKK233-3, pDR540, and pRIT5 (Pharmacia, Uppsala, Sweden). The following eukaryotic vectors are provided by way of example: pWLneo, pSV2cat, pOG44, PXR1, pSG (Stratagene) pSVK3, pBPV, pMSG, and pSVL (Pharmacia).

Expression vectors generally have convenient restriction sites located near the promoter sequence to provide for the insertion of nucleic acid sequences encoding heterologous proteins. A selectable marker operative in the expression host may be present.

As noted above, in some embodiments, a nucleic acid encoding a polypeptide of the present disclosure will in some embodiments be RNA, e.g., in vitro synthesized RNA. Methods for in vitro synthesis of RNA are known in the art; any known method can be used to synthesize RNA including a nucleotide sequence encoding a polypeptide of the present disclosure. Methods for introducing RNA into a host cell are known in the art. See, e.g., Zhao et al. (2010) Cancer Res. 15:9053. Introducing RNA including a nucleotide sequence encoding a polypeptide of the present disclosure into a host cell can be carried out in vitro or ex vivo or in vivo. For example, a host cell (e.g., an NK cell, a cytotoxic T lymphocyte, etc.) can be electroporated in vitro or ex vivo with RNA comprising a nucleotide sequence encoding a polypeptide of the present disclosure.

Cells

The present disclosure provides mammalian cell lines that produce replication incompetent recombinant retroviral particles that genetically modify target mammalian cells and the target mammalian cells themselves.

Suitable mammalian cells include primary cells and immortalized cell lines. Suitable mammalian cell lines include human cell lines, non-human primate cell lines, rodent (e.g., mouse, rat) cell lines, and the like. Suitable mammalian cell lines include, but are not limited to, HeLa cells (e.g., American Type Culture Collection (ATCC) No. CCL-2), CHO cells (e.g., ATCC Nos. CRL9618, CCL61, CRL9096), 293 cells (e.g., ATCC No. CRL-1573), Vero cells, NIH 3T3 cells (e.g., ATCC No. CRL-1658), Huh-7 cells, BHK cells (e.g., ATCC No. CCL10), PC12 cells (ATCC No. CRL1721), COS cells, COS-7 cells (ATCC No. CRL1651), RAT1 cells, mouse L cells (ATCC No. CCLI.3), human embryonic kidney (HEK) cells (ATCC No. CRL1573), HLHepG2 cells, Hut-78, Jurkat, HL-60, NK cell lines (e.g., NKL, NK92, and YTS), and the like.

In some instances, the cell is not an immortalized cell line, but is instead a cell (e.g., a primary cell) obtained from an individual or an ex vivo cell. For example, in some cases, the cell is an immune cell obtained from an individual. As another example, the cell is a stem cell or progenitor cell obtained from an individual.

Methods of Activating an Immune Cell

The present disclosure provides methods of activating an immune cell in vitro, in vivo, or ex vivo. The methods generally involve contacting an immune cell (in vitro, in vivo, or ex vivo) with one or more target antigens, where the immune cell has been genetically modified to produce a microenvironment restricted CAR of the present disclosure. In the presence of the one or more target antigens, the microenvironment restricted CAR activates the immune cell, thereby producing an activated immune cell. Immune cells include, e.g., a cytotoxic T lymphocyte, an NK cell, a $CD4^+$ T cell, a T regulatory (Treg) cell, a γδ T cell, an NK-T cell, neutrophils, etc.

Contacting the genetically modified immune cell (e.g., a T lymphocyte, an NK cell) with one or more target antigens can increase production of a cytokine by the immune cell by at least about 10%, at least about 15%, at least about 20%, at least about 25%, at least about 30%, at least about 40%, at least about 50%, at least about 75%, at least about 2-fold, at least about 2.5-fold, at least about 5-fold, at least about 10-fold, or more than 10-fold, compared with the amount of cytokine produced by the immune cell in the absence of the one or more target antigens. Cytokines whose production can be increased include, but are not limited to, IL-2 and IFN-γ.

Contacting a genetically modified cytotoxic cell (e.g., cytotoxic T lymphocyte) with AAR can increase cytotoxic activity of the cytotoxic cell by at least about 10%, at least about 15%, at least about 20%, at least about 25%, at least about 30%, at least about 40%, at least about 50%, at least about 75%, at least about 2-fold, at least about 2.5-fold, at least about 5-fold, at least about 10-fold, or more than 10-fold, compared to the cytotoxic activity of the cytotoxic cell in the absence of the one or more target antigens.

Contacting a genetically modified cytotoxic cell (e.g., cytotoxic T lymphocyte) with one or more target antigens can increase cytotoxic activity of the cytotoxic cell by at least about 10%, at least about 15%, at least about 20%, at least about 25%, at least about 30%, at least about 40%, at least about 50%, at least about 75%, at least about 2-fold, at least about 2.5-fold, at least about 5-fold, at least about 10-fold, or more than 10-fold, compared to the cytotoxic activity of the cytotoxic cell in the absence of the one or more target antigens.

In other embodiments, e.g., depending on the host immune cell, contacting a genetically modified host cell with an antigen can increase or decrease cell proliferation, cell survival, cell death, and the like.

Methods for Making a Microenvironment Restricted Antigen-Specific Targeting Region In some embodiments, antigen binding domains (also referred to herein as "antigen-specific target regions" or "ASTRs") of CARs constitutively bind their cognate antigens. In other embodiments, the ASTRs can be microenvironment restricted, preferentially or only binding their cognate antigen under certain aberrant conditions, such as those that exist in the tumor microenvironment, as disclosed in more detail herein. Microenvironment restricted ASTRs that bind preferentially or exclusively under aberrant conditions of a tumor microenvironment, can provide a reduction in on-target off-tumor effects as binding to the antigen in normal physiological conditions is reduced, in some situations to levels below detection by immunoassays. In certain aspects, CARs provided herein include a microenvironment restricted ASTR that specifically binds to a target protein, wherein the ASTR is an scFv fragment that includes a heavy chain variable region and a light chain variable region.

Certain illustrative embodiments of the aspects disclosed herein, for example the methods, cells, cells lines, replication incompetent recombinant retroviral particles, polynucleotides, or vectors disclosed herein, include CARs that include microenvironment restricted antigen-specific targeting regions.

Accordingly, in one aspect, provided herein is a chimeric antigen receptor for binding a target antigen, that includes:
 a) a microenvironment restricted antigen-specific targeting region that exhibits an increase in binding to the target antigen in an aberrant condition compared to a normal physiological environment, wherein the antigen-specific targeting region binds to the target;
b) a transmembrane domain; and
c) an intracellular activating domain In another aspect, provided herein is a chimeric antigen receptor for binding a target antigen, that includes:
a) at least one microenvironment restricted antigen specific targeting region selected by panning a polypeptide library and having an increase in activity in a target antigen binding assay at an aberrant condition compared to a normal physiological condition;
b) a transmembrane domain; and
c). an intracellular activating domain.

In some embodiments of any aspect disclosed herein, any of the chimeric antigen receptors can be microenvironment restricted such that they exhibit an increase in binding activity at an aberrant condition compared to a normal physiological condition. In some illustrative embodiments of any aspect disclosed herein, the microenvironment restricted ASTR is identified from an initial polypeptide library without mutating/evolving members of the library before screening/evolving and/or without mutating during or between optional repeated rounds of screening. Exemplary transmembrane domains and intracellular activating domains can be any of those disclosed herein for CARs.

In one aspect, provided herein is a method for selecting a microenvironment restricted ASTR, comprising panning a polypeptide display library by:
a. subjecting polypeptides of the polypeptide display library to a target antigen binding assay under a normal physiological condition and a target antigen binding assay under an aberrant condition; and
b. selecting a polypeptide which exhibits an increase in target antigen binding activity at the aberrant condition compared to the physiological condition, thereby selecting the microenvironment restricted antigen specific targeting region.

In another aspect, provided herein is a method for isolating a microenvironment restricted ASTR, that includes panning a polypeptide library by:
contacting the polypeptide library under aberrant conditions with a target antigen bound to a solid support, wherein clones expressing polypeptides that bind the target antigen remain bound to the solid support through the target antigen;
incubating the solid supports with bound polypeptides under physiological conditions; and collecting clones that elute from the solid support under the physiological conditions, thereby isolating the microenvironment restricted antigen-specific targeting region.

In some illustrative embodiments of any aspect disclosed herein, the microenvironment restricted antigen-specific targeting region is identified from an initial polypeptide library screen without mutating/evolving members of the library before screening and/or without mutating/evolving during or between optional repeated rounds of screening or panning.

Normal physiological conditions can include those of temperature, pH, osmotic pressure, osmolality, oxidative stress, and electrolyte concentration that would be considered within a normal range at the site of administration, or at the tissue or organ at the site of action, to a subject. An aberrant condition is that which deviates from the normally acceptable range for that condition. In one aspect, a microenvironment restricted antigen-specific targeting region (i.e. polypeptide) is virtually inactive at normal conditions but is active at other than normal conditions at a level that is equal or better than at normal conditions. For example, in one aspect, the microenvironment restricted antigen-specific targeting region is virtually inactive at body temperature, but is active at lower temperatures. In another aspect, the microenvironment restricted antigen-specific targeting region is reversibly or irreversibly inactivated at the normal conditions. In a further aspect, the microenvironment restricted antigen-specific targeting region is a therapeutic protein. In another aspect, the microenvironment restricted antigen-specific targeting region is used as a drug, or therapeutic agent. In yet another aspect, the microenvironment restricted antigen-specific targeting region is more or less active in highly oxygenated blood, such as, for example, after passage through the lung or in the lower pH environments found in the kidney.

In some embodiments, a single round of selection is performed to obtain the microenvironment restricted antigen-specific targeting region. In certain embodiments, the screening or panning method is repeated after identifying free polypeptides that bound antigen under aberrant conditions and did not bind under physiological conditions, or cells expressing a test polypeptide that had these properties, or phage coated with a test polypeptide that has such properties in an initial or previous round. In some methods, phage that are collected are used to infect cells, which can be infected with helper phage as well, in order to amplify the collected phage. In other methods where polypeptides on the surface of cells are tested, collected cells can be grown to "amplify" the polypeptides expressed by the cells by amplifying polynucleotides in the cells that encode the polypeptides. In some embodiments, the amplifying is done by growing cells that express the identified polypeptides without performing a process to mutate the polynucleotides encoding the identified polypeptides between rounds. Thus, polypeptides that were collected in a previous round are enriched by amplifying cells that contain polynucleotides encoding these collected polypeptides.

The panning or screening method can be performed a single time, or repeated for 1 to 1000 times. In illustrative embodiments, the panning is repeated 1 to 20 times or 2 to 10 times or 2 to 5 times.

In other methods, microenvironment restricted ASTRs against an antigen of interest (i.e. target antigen) are performed using one or more rounds of mutation/evolution between rounds of panning. In one method, a wild-type protein is identified for example by generating a polypeptide or protein library and screening the polypeptide or protein library for a polypeptide or protein with a desired binding affinity to a target antigen. In some embodiments where the wild-type proteins are antibodies, the wild-type antibodies can be discovered by generating and screening polyclonal or monoclonal antibody libraries, including phage display antibody libraries, for example phage display humanized antibody libraries.

Evolved ASTRs can be generated by subjecting the wild-type protein, or a nucleic acid sequence encoding the wild-type protein, to a process of mutagenesis to produce a population of mutant polypeptides that can be screened to identify a mutant ASTR with an increased activity (e.g. enhanced binding affinity to the target antigen) in a tumor environment and/or in an in vitro tumor surrogate assay condition, compared to a normal physiological environment. Examples of such methods are provided in WO2016033331 ("CONDITIONALLY ACTIVE CHIMERIC ANTIGEN RECEPTORS FOR MODIFIED T CELLS") or U.S. Pat. No. 8,709,755, both herein incorporated by reference in their entirety. This method of generating a microenvironment restricted antibody is hereby incorporated by reference in its entirety herein.

In other embodiments, microenvironment restricted antigen-specific polypeptides (i.e. targeting regions, e.g. antibodies) can be identified by screening an initial polypeptide library under aberrant versus physiological conditions and identifying a test polypeptide from the initial polypeptide library, that binds preferentially or exclusively under aberrant vs. physiological conditions. In some examples, the identified and isolated microenvironment restricted antigen-specific polypeptides (i.e. targeting regions, e.g. antibodies) identified from an initial polypeptide library in an initial polypeptide library screen, bind their cognate antigen preferentially or exclusively under aberrant vs. physiological conditions. In such instances, no rounds of mutating/evolving are performed. Accordingly, the method in illustrative embodiments is performed without mutating polynucleotides encoding the isolated microenvironment restricted antigen-specific targeting region between rounds of screening (e.g. rounds of panning), or performed for only a single binding assay under aberrant versus physiological conditions to isolate and identify the microenvironment restricted antigen-specific polypeptide (i.e. targeting region, e.g. antibody). The method can be performed by culturing, high fidelity amplifying, and/or diluting polynucleotides encoding antigen-specific targeting regions, or host organisms including the same, between rounds of screening and/or panning, without any mutating/evolving. Furthermore, the method can be performed without repeating the screening and/or panning and can be performed without mutating/evolving a polynucleotide encoding the isolated microenvironment restricted antigen-specific targeting region, after the microenvironment restricted antigen-specific polypeptide (i.e. target region, e.g. antibody) is isolated.

Assays for use in the methods provided herein to detect binding of a polypeptide to a cognate binding partner include cell based assays, and in particular assays performed using cell surface display systems, such as mammalian cell surface display systems. In an exemplary method, nucleic acids encoding a polypeptide or a library of variant polypeptides, including a library of modified polypeptides, can be introduced into a vector suitable for expression in cells, such as mammalian cells. Cells are then transfected with the vector, and the polypeptide(s) is/are expressed by the cells. The library of cells containing surface-expressed polypeptides can be contacted with a solution containing a soluble or surface-bound cognate binding partner. Binding activity can be detected using any assay that can detect the binding to the surface of the cells. Activity also can be assessed by assessing a functional activity of the polypeptide or polypeptide. Any cell based assay known to the skilled artisan is contemplated for use in the methods provided herein, including cell proliferation assays, cell death assays, flow cytometry, cell separation techniques, fluorescence activated cell sorting (FACS), phase microscopy, fluorescence microscopy, receptor binding assays, cell signaling assays, immunocytochemistry and reporter gene assays. In some examples, the assays are fluorescence activated cell sorting (FACS) assays.

Polypeptides or proteins can be expressed by mammalian cells as secreted, soluble molecules, cell surface molecules, or intracellular antibodies. In an exemplary method, cells can be transfected with a library of proteins under conditions whereby most or all of the cells display a member of the protein library anchored on the cell surface. Optionally, an expression system can be used in which most of mammalian cell transfectants have only one plasmid integrated in their genome. Therefore, most (i.e., at least about 70% or about 80% or about 90%) of the transfectants express one or more molecules of one polypeptide. This can be verified, for example, by isolating and culturing individual transfectants; and amplifying and sequencing the expressed sequences to determine whether they have a single sequence.

In some examples of the methods provided herein, the polypeptides are antibodies displayed on the surface of mammalian cells. Any antibody described herein can be expressed on the surface of mammalian cells, including full length, bivalent, functional antibodies, such as IgG antibodies. The antibody can be a fragment, for example, Fab fragments or scFv fragments. Antibodies can include an Fc region, such as an scFv-Fc or a full length antibody, which comprises two heavy and two light chains. The skilled artisan can select a suitable antibody fragment. For example, an ScFv-Fcs and full length antibodies made in mammalian cells can have several advantages over scFv's or Fab fragments.

Solid supports that can be used in the binding assays provided herein include any carrier that is capable of being affixed with a binding partner of a polypeptide such as a ligand, receptor or antigen. Typically, to facilitate high throughput screening a cognate binding partner is affixed to the solid support. Examples of carriers for use as solid supports in the methods provided herein include, but are not limited to, glass, polystyrene, polypropylene, polyethylene, dextran, nylon, amyloses, natural and modified celluloses, polyacrylamides, agaroses and magnetic solid supports, such as solid supports that include magnetite. The solid support can be one or more beads or particles, microspheres, a surface of a tube or plate, a filter membrane, and other solid supports known in the art. Exemplary solid support systems include, but are not limited to, a flat surface constructed, for example, of glass, silicon, metal, nylon, cellulose, plastic or a composite, including multiwell plates or membranes; or can be in the form of a bead such as a silica gel, a controlled pore glass, a magnetic or cellulose bead. Further, such methods can be adapted for use in suspension or in the form of a column. In some embodiments, the microenvironment restricted antigen-specific polypeptide (i.e. target region, e.g. antibody) is identified and isolated by biopanning a phage display or yeast surface display (Colby et al., "Engineering Antibody Affinity by Yeast Surface Display," *Meth. Enzym.* 388, 26 (2004)) antibody (e.g. humanized antibody) library with an immobilized target antigen. For example, either a naïve humanized antibody library or a synthetic humanized antibody library can be panned using the phage display or yeast surface display methods herein. In some embodiments, an initial phage display process, phage clones can be transferred to a mammalian vector and used to a mammalian cell surface screening method (See e.g., Yoon et al., *BMC Biotechnology* 12:62; 1472-6750 (2012)). An exemplary method for performing phage display to isolate a microenvironment restricted antigen-specific target region is provided in Example 2.

A microenvironment restricted ASTR identified using methods provided herein, can be an antibody, an antigen, a ligand, a receptor binding domain of a ligand, a receptor, a ligand binding domain of a receptor, or an affibody. In embodiments where the microenvironment restricted ASTR is an antibody, it can be a full-length antibody, a single-chain antibody, an Fab fragment, an Fab' fragment, an (Fab')2 fragment, an Fv fragment, and a divalent single-chain antibody or a diabody. wherein the antigen-specific targeting region comprises a heavy chain and a light chain from an antibody. In some embodiments, the microenvironment restricted ASTR is a single-chain variable fragment. Such single-chain variable fragment can have heavy and light chains separated by a linker, wherein the linker is between 6 and 100 amino acids in length. In some embodiments the heavy chain is positioned N-terminal to the light chain on the chimeric antigen receptor. In other embodiments, the light chain is positioned N-terminal to the heavy chain. The microenvironment restricted ASTR can be a bispecific ASTR.

Microenvironment restricted ASTRs identified using methods provided herein are typically polypeptides and more specifically polypeptide antibodies, and in illustrative embodiments, single chain antibodies. These polypeptides can bind to their cognate antigens with higher or lower affinity under aberrant conditions vs. normal conditions, but in illustrative embodiments, bind with higher affinity under aberrant conditions than normal conditions. In some embodiments, these polypeptides can bind to their cognate antigen with a 10%, 20%, 25%, 50%, 75%, 90%, 95% or 99% greater affinity under aberrant conditions than physiological (i.e. normal) conditions. In some embodiments, the ASTRs identifying using methods provided herein do not bind to their cognate antigens under normal physiological conditions to any detectable level above background levels obtained using negative controls, such as negative control antibodies.

The nucleotide sequence encoding a microenvironment restricted ASTR isolated by the method provided herein, can be determined by sequencing nucleotides of the collected cell expressing the microenvironment restricted antigen-specific targeting. This nucleotide sequence information can then be used to make a microenvironment restricted biologic chimeric antigen receptor (MRB-CAR) by generating a polynucleotide that encodes a polypeptide comprising the microenvironment restricted antigen-specific targeting region, a transmembrane domain, and an intracellular activating domain. Microenvironment restricted antigen-specific targeting regions can be cloned into a CAR construct expression system, which can be used to generate recombinant lentiviruses that include the CAR in their genome, and then the recombinant lentiviruses can be used to transduce T cells for testing for CAR-mediated tumor antigen expressing target cell killing in a tumor-selective environment compared to physiologic conditions.

Conditions for Conditional Activity

In the methods provided herein, the activity of one or more polypeptides, such as, for example, single chain antibodies, is screened or tested under two different sets of conditions that simulate a condition or conditions in two different physiologic environments such as, for example, a diseased microenvironment and the normal physiologic condition of a non-diseased microenvironment. Typically, the conditions are conditions that can be simulated or replicated in vitro. A set of conditions can include one or more conditions to simulate a microenvironment associated with a disease. Disease can alter intracellular and extracellular homeostasis. For example, the diseased microenvironment can simulate one or more conditions in a tumor microenvironment or a cancer microenvironment. Typically, the difference or differences in activity under the two sets of conditions can result in the conditional activity of the molecule. Thus, a molecule that exhibits greater activity under the first set of conditions (e.g. simulating conditions in a tumor microenvironment) compared to the second set of conditions (e.g. simulating conditions in a normal or non-diseased environment) is identified as a candidate molecule that is microenvironment restricted.

The two sets of conditions can be selected to vary by one or more parameters that differ in two physiologic environments, such as described herein or known to one of skill in the art, including but not limited to chemical conditions, biological conditions, or physical conditions. Parameters that can be varied between the two sets of conditions can include one or more conditions selected from among pressure, temperature, pH, ionic strength, osmotic pressure, osmolality, oxidative stress, turbidity, exposure to light (including UV, infrared or visible light), concentration of one or more solutes, such as electrolytes, concentration of glucose, concentration of hyaluronan, concentration of lactic acid or lactate, concentration of albumin, levels of adenosine, levels of R-2-hydroxyglutarate, concentration of pyruvate, concentration of oxygen, and/or presence of oxidants, reductants, or co-factors. By varying the electrolyte and buffer systems in the calibration solutions, physiological conditions such as pH, buffer capacity, ionic environment, temperature, glucose concentration, and ionic strength can be adjusted to those of the biological environment to be simulated. The set of conditions that simulate a normal physiologic environment can be selected to be different from the set of conditions that simulate a diseased microenvironment, such as a tumor microenvironment, by one or more conditions described herein.

For example, as discussed below, various parameters of the tumor microenvironment differ compared to a non-tumor microenvironment, including, but not limited to, oxygen concentration, pressure, presence of co-factors, pH, hyaluronan concentration, lactate concentration, albumin concentration, levels of adenosine, levels of R-2-hydroxyglutarate, and pyruvate concentration. Any of these parameters can be replicated in vitro to simulate one or more conditions that exist in a tumor or cancer environment compared to conditions that exist in a non-tumor or a normal environment. The normal physiologic conditions that can be simulated include environments found in healthy or nondiseased tissue at any location of the body such as the GI tract, the skin, the vasculature, the blood, and extracellular matrix. Typically, in the assays herein, physiologic conditions can be simulated in vitro by the choice of buffer that is used to assess the activity of the protein. For example, any one or more conditions of a diseased microenvironment (such as a tumor microenvironment) and a non-diseased environment can be simulated by differences in the assay buffer used to assess activity in the assay. Hence, in the methods herein to identify a microenvironment restricted polypeptide, a component or components or characteristic or characteristics of an assay buffer are altered or made to be different in a first assay to test activity under a first condition and in a second assay to test activity under a second condition. For example, as discussed herein, various parameters of the tumor microenvironment are different compared to a non-tumor environment including, but not limited to, oxygen, pressure, presence of co-factors, pH, hyaluronan concentration (such as increased or decreased hyaluronan concentration), lactate concentration (such as increased or decreased lactate concentration), albumin concentration (such as increased or decreased albumin concentration), levels of adenosine (such as increased or decreased adenosine levels), levels of R-2-hydroxyglutarate (such as increased or decreased R-2-hydroxyglutarate levels) and pyruvate concentration (including increased or decreased pyruvate concentration). More specifically, conditions in a tumor microenvironment can include lower pH, higher concentrations of hyaluronan, higher concentrations of lactate and pyruvate, higher concentrations of albumin, increased levels of adenosine, increased levels of R-2-hydroxyglutarate, hypoxia, lower concentration of glucose, and slightly higher temperature in comparison with non-tumor microenvironment. For example, a microenvironment restricted ASTR is virtually inactive at normal body temperature, but is active at a higher temperature in a tumor microenvironment. In yet another aspect, the microenvironment restricted antibody is less active in normal oxygenated blood, but more active under a less oxygenated environment that exists in a tumor. In yet another aspect, the microenvironment restricted antibody is less active in normal physiological pH 7.2-7.8, but more active under an acidic pH 5.8-7.0, or 6.0-6.8 that exists in a tumor microenvironment. For example, the microenvironment restricted antibody is more active at a pH of 6.7 than at pH 7.4. There are other conditions in the tumor microenvironment known to a person skilled in the field that may also be used as the condition in the present invention under which the conditionally active ASTRs have different binding affinities. In vitro assay conditions that mimic these in vivo tumor conditions are referred to herein as in vitro tumor surrogate assay conditions.

Any one or more of these conditions can be simulated in vitro by choice of the particular assay buffer. The composition of the assay buffer that simulates a diseased microenvironment can be selected to be identical to the composition of the assay buffer that simulate a normal environment, with the exception of one or more conditions known or described herein that is altered in the diseased microenvironment. Further, in screening or identifying the activity of one or more polypeptides under two different sets of conditions, generally the only conditions that are varied in the assay relate to the buffer conditions simulating the in vivo microenvironment. The other conditions of the assay, such as time, temperature and incubation conditions, can be the same for both sets of conditions. Typically, the same base buffer is used in the set of conditions that simulate a diseased microenvironment and conditions that simulate a normal microenvironment, but the design of the buffer composition can be made to differ in one or more parameters such as pH, oxygen, pressure, presence of co-factors, pH, hyaluronan concentration (such as increased or decreased hyaluronan concentration), lactate concentration (such as increased or decreased lactate concentration), albumin concentration (such as increased or decreased hyaluronan concentration) and/or pyruvate concentration (including increased or decreased pyruvate concentration). In the conditions that simulate a diseased microenvironment and the conditions that simulate a normal microenvironment, any base buffer known to one of skill in the art that can be used Methods of Generating a Microenvironment Restricted Cell The present disclosure provides a method of generating a microenvironment restricted cell. The method generally involves genetically modifying a mammalian cell with an expression vector (e.g. a plasmid or a retroviral vector), or an RNA (e.g., in vitro transcribed RNA), including nucleotide sequences encoding microenvironment restricted CARs of the present disclosure. The genetically modified cell is microenvironment restricted in the presence of one or more target antigens. The genetic modification can be carried out in vivo, in vitro, or ex vivo. The cell can be an immune cell (e.g., a T lymphocyte, a T-helper cell, or an NK cell), a stem cell, a progenitor cell, etc.

In some cases, the genetic modification is carried out ex vivo. For example, a T lymphocyte, a stem cell, a T-helper cell, or an NK cell is obtained from an individual; and the cell obtained from the individual is genetically modified to express a CAR of the present disclosure. The genetically modified cell is microenvironment restrictable in the presence of one or more target antigens. In some cases, the genetically modified cell is activated ex vivo. In other cases, the genetically modified cell is introduced into an individual (e.g., the individual from whom the cell was obtained); and the genetically modified cell is activated in vivo. For example, where the one or more target antigens are present on the surface of a cell in the individual, there is no need to administer the antigen. The genetically modified cell comes into contact with the antigen present on the surface of a cell in the individual and the genetically modified cell is activated. For example, where the genetically modified cell is a T lymphocyte, the genetically modified cell can exhibit cytotoxicity toward a cell that expresses the one or more target antigens on its surface to which the CAR binds.

Methods for Modulating MRB Car-Expressing T Cell and/or NK Cell Activity by Changing pH Provided herein in certain aspects, are methods for modulating binding and resulting lysis/killing of a target cell by an MRB CAR-expressing T cell and/or NK cell by causing a change or shift in pH within a microenvironment that includes a target cell either within a target tissue or within one or more non-target (e.g. healthy/normal) tissues, by modulating binding of the MRB-CAR to its cognate antigen on a target cell(s). Such methods typically include contacting a target cell, such as a mammalian cell (e.g. a human cell) with an MRB CAR-expressing T cell and/or NK cell in a microenvironment and then changing the pH of the microenvironment, either by decreasing or more typically increasing the pH. The microenvironment can be a target microenvironment, for example a tumor, or an off-target microenvironment, where off-target binding can cause side-effects. In some embodiments, such methods can provide a transient reduction of tumor microenvironment sensitive CAR-T target binding.

Accordingly, in one aspect, provided herein is a method for modulating binding of a microenvironment restricted biologic chimeric antigen receptor (MRB-CAR)-expressing T cell or NK cell to a cell expressing a cognate antigen of the MRB-CAR in a subject, that includes the following:

a. introducing a T cell and/or NK cell comprising a nucleic acid encoding the MRB-CAR into the subject, wherein after (and optionally and/or during) the introducing, the T cell and/or the NK cell comprising the nucleic acid encoding the MRB-CAR expresses the MRB-CAR and binds to the cell expressing the cognate antigen in the subject; and b. administering a pharmacologic agent to the subject in sufficient amount to increase blood pH and/or pH of a tissue and/or pH of a microenvironment, wherein the administering is performed before, during, or after the introducing, and wherein the increased pH of the blood, the tissue, and/or the microenvironment modulates binding of the MRB-CAR expressing T cell and/or NK cell to the cell expressing the cognate antigen in the blood, the tissue, or the microenvironment with the increased pH.

The change/shift in pH in aspects that include a step of administering a pH-modulating pharmacologic agent of the present disclosure can be accomplished by exposing target or non-target cells/tissue to a pH-modulating pharmacologic agent, such as by administering the pH modulating pharmacologic agent to a subject. Non-limiting examples of pH-modulating pharmacologic agents are provided herein. In certain aspects, provided herein is a pharmacologic agent for use in a method for modulating binding of an MRB-CAR to its cognate antigen or for modulating binding of an MRB CAR-expressing T cell and/or NK cell to a cell that expresses its cognate antigen or for reducing or alleviating on target off tumor toxicity in a subject. Such aspects in certain embodiments, relate to treating tumor growth, cancer, hyperplasia, or cell proliferative disorders.

In other aspects, provided herein is use of a pH-modulating pharmacologic agent for use in the manufacture of a medicament or a kit for controlling binding of a genetically engineered T cell and/or NK cell to a target mammalian cell in a subject in vivo. In other aspects, provided herein is a kit that includes a container containing a replication incompetent recombinant retroviral particle, and instructions for use thereof for performing a method for treating tumor growth, wherein the instructions instruct a method for controlling binding of a T cell and/or NK cell to a target mammalian cell by modulating pH. Such method can be any of the methods provided herein this section for modulating MRB CAR-expressing T cell and/or NK cell binding and/or activity by changing pH. The container that contains the recombinant retroviral particles can be a tube, vial, well of a plate, or other vessel for storage of a recombinant retroviral particle and/or a pH-modulating pharmacologic agent. Any of these can be of industrial strength and grade. The kit can include two or more containers in certain embodiments. One container/vessel can include the recombinant retroviral particles and another container/vessel can include a pH-modulating pharmacologic agent. In such methods the pharmacologic agent is delivered/administered in sufficient amount to increase blood pH and/or a tissue pH and/or a microenvironment pH to modulate binding of the MRB-CAR of a modified/recombinant T cell and/or NK cell expressing the MRB CAR, to its cognate antigen in the blood and/or the tissue with the increased pH. Non-limiting exemplary details are provided herein for administering a pH modulating pharmacologic agent in sufficient amount and for a sufficient time.

Target cells, whether on target or off target with respect to a tissue, can be contacted with a pH modulating agent, such as a pH modulating pharmacologic agent, after introducing the MRB-CAR into a subject. Accordingly, exemplary aspects provided herein for modulating binding and/or cytotoxic activity of an MRB CAR-expressing T cell, for example for alleviating on target off tumor activity and/or for inhibiting target cell proliferation, such as tumor cell proliferation, can include the following steps:

a. introducing a T cell and/or NK cell comprising a nucleic acid encoding an MRB-CAR into a subject wherein after the introducing, the T cell and/or the NK cell comprising the nucleic acid encoding the MRB-CAR expresses the MRB-CAR, and optionally binds to the cell expressing the cognate antigen in the subject; and b. administering a pharmacologic agent to the subject in sufficient amount to increase blood pH and/or a tissue pH and/or a microenvironment pH to modulate binding of the MRB CAR-expressing T cell and/or NK cell to cells expressing the cognate antigen of the MRB CAR, in the blood, the tissue, or the microenvironment with the increased pH. It will be understood that depending on the specific method used to introduce the nucleic acid encoding the MRB-CAR into the T cell and/or NK cell, the T cell and/or NK cell may or may not express the MRB-CAR before it is introduced into the subject. However, at some timepoint after introduction into the subject, e.g. 2 hours, 4 hours, 8 hours, 12 hours, 1 day, 2 days, 4 days and/or 7 days, or longer, the T cell and/or NK cell that include the nucleic acid encoding the MRB-CAR, express the MRB-CAR. Then such cells typically bind to a target cell expressing the cognate antigen for the MRB-CAR.

Methods provided herein for genetically modifying and optionally expanding lymphocytes of a subject can be used to introduce a nucleic acid sequence that encodes an MRB-CAR into the genome of a T cell and/or NK cell of the subject to produce an T cell and/or NK cell capable of expressing the MRB CAR, and then to introduce the T cell and/or NK cell capable of expressing the MRB CAR into the subject, wherein after introducing the T cell and/or NK cell expresses the MRB CAR in order to contact the MRB-CAR with a target cells/tissue. The present disclosure provides details of how to perform such methods, along with various alternatives for modifying and expanding lymphocytes, any of which can be used in aspects of the disclosure that include changing pH to modulate binding of an MRB CAR-expressing T cell and/or NK cell to a target cell expressing a cognate antigen for the MRB-CAR.

Such methods for genetically modifying and expanding lymphocytes typically involve contacting T cells and/or NK cells, which can be resting cells in illustrative embodiments, with a replication incompetent recombinant retroviral particle to transduce the T cells and/or NK cells. Such contacting typically occurs ex vivo after removing the lymphocytes from the subject. The T cells and/or NK cells are then introduced/reintroduced into the subject, typically from whom they were removed. The replication incompetent recombinant retroviral particle includes a genome with a polynucleotide that encodes the MRB-CAR. Many alternative embodiments and further details regarding such a replication incompetent recombinant retroviral particle are provided in other sections herein and can be used in methods provided herein for regulating binding and resulting lysis/killing of MRB-CARs by modulating pH in a microenvironment of a cell expressing a cognate target polypeptide recognized by the MRB-CAR in a pH-dependent manner.

Particularly illustrative aspects that include such combinations can include other elements for regulating binding, cell killing activity, and/or survival of MRB CAR-expressing T cells that are provided herein in other sections. Such control elements that can be combined with MRB CAR-expression in methods that include a change in pH as well as other embodiments provided herein, include riboswitches and elimination domains, Thus, the combination of such methods and compositions provided herein, form a powerful multi-faceted approach to assuring safety of a subject after administration of CAR-expressing T cells, including MRB CAR-expressing T cells, to a subject.

Such methods for modulating binding of a target cell by an MRB CAR-expressing T cell and/or NK cell can be used, for example, to reduce on target, off-tumor toxicity by increasing the pH of blood and/or a non-tumor tissue(s) within the subject. For example, in a situation where a "normal" tissue pH within a subject becomes transiently lower, a pH modulating agent can be delivered in a manner where pH of the normal tissue is increased while pH of the tumor remains lower and still at a pH where the MRB-CAR-expressing T cell and/or NK cell binds a target tumor cell. In these embodiments, the pH modulating agent can be delivered at a lower concentration or in a targeted manner to the normal tissue.

In some embodiments, this can be accomplished while allowing the pH within the tumor microenvironment to remain low enough for an MRB-CAR T cell and/or NK cell to bind to its cognate target-expressing cells within the tumor. In illustrative aspects of methods provided herein, the pH of a tissue remains at a pH under which an MRB CAR-expressing T cell and/or NK cell binds its target for a period of time sufficient for a MRB CAR-expressing T cell and/or NK cell to contact and bind to a cell expressing its cognate antigen (e.g. 2, 4, 8, 12, or 24 hours, or 2, 4, 7, 14, 28, or 30 days, or 1, 2, 3, 4, 5, 6, 12, 24 months, or longer), and then the pH is shifted/changed, for example by increasing the pH of the tissue to such a magnitude as to affect binding of the MRB CAR-expressing T cell and/or NK cell to a target cell.

Accordingly, provided herein, in one aspect, is a method for transient reduction of tumor microenvironment sensitive CAR-T cell target binding through pharmacologic modification of vascular and tissue pH. The target binding portions of the tumor microenvironment sensitive CAR-T cell with different binding in different conditions are also referred to as microenvironment restricted biologic, microenvironment restricted, microenvironmentally controlled, or conditionally active and can refer to the entire CAR or any target binding domain thereof, for example, an ASTR, scFv, or scFvFc. These microenvironmentally controlled ASTRs in CAR-T cells provide an additional level of protection against on-target off tumor toxicity, requiring tumor local environmental conditions to enable T cell engagement. While attractive for some monoclonal antibody therapies, adoptive cellular therapy may create local environments that are transiently permissive for their CAR-T targets. For example, CAR-T cells activated in tissues with a low pH may further reduce the pH of the microenvironment, depending on cytoplasmic domains present in the CAR construct. In other instances, cytokine release syndrome and other morbidity associated with adoptive cellular therapy may result in loss of the bicarbonate buffering capacity of blood, leading to lactic acidosis. It has been established that adoptive cellular therapies administered by intravenous infusion result in temporary pulmonary entrapment. For some cellular therapies, infusion rate requires constant monitoring of dissolved oxygen (Fischer et al. *Stem Cells Dev.* 2009 June; 18(5): 683-691). The extent of pulmonary entrapment is dependent upon cell size, activation state, cell dose, and infusion rate. Cruz et al (*Cytotherapy.* 2010 October; 12(6): 743-749) report the adverse findings from over 300 T cell infusions, that low doses and slow infusion may reduce pulmonary entrapment. However, with certain high potency CAR-T cells, targets present even in low levels on lung endothelium, such as Her2 (Morgan et al. *Mol Ther.* 2010 April; 18(4): 843-851), can result in immediate toxicity that cannot be controlled, and results in rapid patient deterioration due to the initial high CAR-T cellular concentration in the lung following infusion and the presence of the T cell target in these tissues. In other cases, the presence of T cell targets in other off target tissues such as bile duct may create on target off tumor toxicities that cannot be controlled (Lamers *Mol Ther.* 2013 April; 21(4):904-12) and result in severe organ toxicity before other agents such as steroids or cell elimination epitopes can be utilized. While venous and arterial plasma have strong buffering capacity against acidosis, conditions of respiratory acidosis, shock, metabolic acidosis and ischemic acidosis can occur in patients with cancer treated with adoptive cellular therapy.

In some aspects provided herein, the binding of an MRB-CAR in a subject can be modulated by administering a pharmacologic agent to the subject to increase or decrease the pH of the blood, a tissue and/or a microenvironment. In some aspects, on-target off tumor toxicity can be alleviated in a subject by administering a pharmacologic agent to the subject to increase or decrease the blood pH and/or the pH of a tissue and/or the pH of a microenvironment. In some aspects, the binding of a T cell and/or NK cell to a target mammalian cell can be controlled by introducing a pharmacologic agent to increase or decrease the blood pH and/or the pH of a tissue and/or the pH of a microenvironment. In some aspects, the binding of a genetically engineered T cell and/or NK cell to a target mammalian cell in a subject in vivo can be controlled by administering a pH-modulating pharmacologic agent to the subject. In illustrative embodiments, the pharmacologic agent can increase the blood pH and/or the pH of a tissue and/or the pH of a microenvironment. In some embodiments, the microenvironment can be an in vivo microenvironment. In illustrative embodiments, the microenvironment can be a tumor microenvironment. In some embodiments, the microenvironment can include a target mammalian cell, wherein the target mammalian cell expressed the target antigen on its surface. In some embodiments, administering a pharmacologic agent to a subject can increase the pH of blood, a tissue, and/or a microenvironment from a pH of less than 5.8, 5.9, 6.0, 6.1, 6.2, 6.3, 6.4, 6.5, 6.6, 6.7, 6.8, or 6.9 to a pH of at least 6.6, 6.7, 6.8, 6.9, 7.0, 7.1, 7.2, 7.3, 7.4, 7.5, or 7.6, wherein the pH of the blood, tissue, and/or microenvironment is lower before administering the pharmacologic agent than after administering the pharmacologic agent. In some embodiments, administering a pharmacologic agent to a subject can decrease the pH of blood, a tissue, or a microenvironment from a pH of more than 6.6, 6.7, 6.8, 6.9, 7.0, 7.1, 7.2, 7.3, 7.4, 7.5, or 7.6 to a pH of less than 5.8, 5.9, 6.0, 6.1, 6.2, 6.3, 6.4, 6.5, 6.6, 6.7, 6.8, 6.9, or 7.0, wherein the pH of the blood, tissue, and/or microenvironment is higher before administering the pharmacologic agent than after administering the pharmacologic agent. In some embodiments, administering a pharmacologic agent to a subject can cause a pH shift in the subject in the blood, a tissue, and/or a microenvironment. In some embodiments, the pH shift can be at least 0.1, 0.2, 0.3, 0.4, 0.5, 0.6, 0.7, 0.8, 0.9, 1.0, 1.1, 1.2, 1.3, 1.4, 1.5, 1.6, 1.7, or 1.8 pH units in either direction, i.e. an increase or decrease in pH after administering the pharmacologic agent relative to the pH before administering the pharmacologic agent. In illustrative embodiments, the pH shift is an increase in pH.

The MRB-CARS of the present disclosure can have reduced binding to its cognate antigen at one pH than at a different pH. In illustrative embodiments where illustrative pH values for differential binding of an MRB-CAR are not already provided in the broadest aspect and alternatively for other embodiments in place of those values for such aspects, the MRB-CAR can have reduced binding at a higher pH than at a lower pH. For example, the MRB-CAR can have reduced binding to its cognate antigen at a pH above 7.0, 7.1, 7.2, 7.3, 7.4, or 7.5 than at a pH below 6.4, 6.5, 6.6, 6.7, 6.8, 6.9, or 7.0. In other embodiments, the MRB-CAR can have reduced binding at a higher pH than at a lower pH. For example, the MRB-CAR can have reduced binding to its cognate antigen at a pH below 6.4, 6.5, 6.6, 6.7, 6.8, 6.9, or 7.0 than at a pH above 7.0, 7.1, 7.2, 7.3, 7.4, or 7.5. In some illustrative embodiments, the MRB-CAR exhibits increased binding at a pH of 6.5 to 6.7 compared to pH 7.4 to 7.6. In other illustrative embodiments, the MRB-CAR exhibits increased binding at a pH of 6.7 compared to a pH of 7.4. In other embodiments, the MRB-CAR exhibits increased binding in the pH of a tumor compared to the pH of blood. In some embodiments, the MRB-CAR can include an antigen-specific targeting region, a stalk, and an intracellular activating domain. In some embodiments, the MRB-CAR can also include a co-stimulatory domain. In some embodiments, the MRB-CAR can bind to a tumor associated antigen.

In methods that include modulating the pH of the blood, a tissue, or a microenvironment, the pH of the microenvironment can be increased from a pH below 7.0 to a pH above 7.0. For example, the pH can be increased from a pH below 6.4, 6.5, 6.6, 6.7, 6.8, 6.9, or 7.0 to a pH above 7.0, 7.1, 7.2, 7.3, or 7.4. In some embodiments, the MRB-CAR can bind to the cognate antigen at the increased pH but not a pH of the microenvironment before introducing the pharmacologic agent. In certain embodiments, the pH can be increased from below 7.0 to a pH of 7.1 to 8.0 or to a pH of 7.1 to 7.8 or to a pH of 7.2 to 7.8 or a pH of 7.2 to 7.6 or a pH of 7.3 to 7.6 or to a pH of 7.4 to 7.8 or to a pH of 7.4 to 7.6. Such an increase in pH can occur for less than 1, 2, 4, 6, 8, 12, or 24 hours or for more than 1, 2, 4, 6, 8, 12 or 24 hours depending on the type and dose of pharmacologic agent administered. In certain embodiments, the pharmacologic agent is administered such that the pH remains above 7.0, 7.1, 7.2, 7.3, 7.4, or 7.5; or between 7.0, 7.1, 7.2, 7.3 on the low end of the range and 7.4, 7.5, 7.6, 7.7, or 7.8 on the high end of the range, in the target tissue, such as a tumor, and for example in at least a surface of a target tissue (e.g. tumor) microenvironment, in at least a portion of a target tissue (e.g. tumor) microenvironment, and in illustrative embodiments throughout a target tissue (e.g. tumor) microenvironment. The microenvironment can be an in vivo microenvironment, such as a tumor, a tissue, a non-tumor tissue, a normal tissue, or a tissue that has undergone a transient shift in pH. For example, tissues that typically undergo transient shifts in pH include a muscle tissue in anaerobic conditions or muscle tissue undergoing exercise or an inflamed tissue or a tissue experiencing inflammation. In some embodiments that include a target mammalian cell, the target mammalian cell can be a tumor cell or a non-tumor or normal cell.

In some aspects, methods for transiently increasing vascular pH to reduce affinity of microenvironmentally controlled MRB-CARs for their antigens are provided. A 0.4 U shift in blood pH can reduce the affinity of certain scFvs that form a portion of an MRB-CAR, for their cognate antigen by greater than 10-fold. In some embodiments, therapeutic pH control can be achieved via IV or oral administration routes of various pharmacologic agents. For example, in some embodiments, inactivation of binding affinity can be achieved with bicarbonate or sodium bicarbonate. In other embodiments, Tris-hydroxymethyl aminomethane (also known as tromethamine, trometamol, and THAM) and/or Carbicarb™ (an equimolar hypertonic solution of sodium bicarbonate and sodium carbonate) can be utilized to increase the pH of the blood in a sufficient amount to alleviate on-target off tumor toxicities. In still other embodiments, small molecule proton pump inhibitors can be utilized to increase blood pH and/or tissue pH in a sufficient amount to alleviate on-target off tumor toxicities. Proton pump inhibitors that can be used in methods that include modulating pH include, but are not limited to, esomeprazole (Nexium), esomeprazole and naproxen (Vimovo), lansoprazole (Prevacid), omeprazole (Prilosec and Zegerid), and rabeprazole (Aciphex). Administration of proton pump inhibitors can be used effectively over longer time periods to modulate the binding affinity of the antigen biding domain to its cognate antigen for days, weeks, months, or years. In other embodiments, the affinity of the antigen binding domain for its cognate antigen can be modulated by altering the blood pH and/or tissue pH by controlling the transcription, translation, membrane expression, and stability of transporters and pumps. Examples of such transporters and pumps whose altered expression can be to modulate pH include, but are not limited to, proton pumps, members of the sodium proton exchange family (NHE), bicarbonate transporter family (BCT), and monocarboxylate transporter family.

In certain embodiments, a pH-modulating pharmacologic agent, such as, for example, bicarbonate, THAM, or Caricarb™ are administered prior to or concurrent with infusion of a patient's CAR-T cells expressing microenvironment restricted biologic ASTRs (e.g. scFvs or scFvFcs). Such treatment will alleviate the immediate cytotoxicity that is otherwise associated with the temporary pulmonary entrapment of CAR-T cell infusions. Accordingly, in certain aspects provided herein is a method for reducing cytotoxicity caused to normal, healthy tissue of a subject by administering a pharmacologic agent to the subject in sufficient amount to increase blood pH and/or a tissue pH and/or a microenvironment pH; and either concomitantly or subsequently (e.g. 1, 2, 4, 6, 8, 12, or 24 hours, or 1, 2, 3, 4, or 7 days later) introducing an MRB CAR-expressing T cell or NK cell into the subject. In certain embodiments, at a target time after such introducing (e.g. 1, 2, 4, 6, 8, 12, or 24 hours, or 1, 2, 3, 4, or 7 days later), administration of the pharmacologic agent is terminated for a period of time or indefinitely, in order to change the pH of the blood, a tissue, or a microenvironment of the subject and modulate binding/activity of the MRB CAR-expressing T cell.

Various effective dosing regimens for administering the pharmacologic agents capable of modulating pH (e.g. increasing blood pH and/or a tissue pH and/or the pH of a microenvironment in a subject) can be used, as will be understood by a skilled artisan. Herein, administering can refer to giving a pharmacologic agent to a subject including injecting a pharmacologic agent through an IV into a subject or providing an oral dose of a pharmacologic agent to a subject or a subject taking a pharmacologic agent. The pharmacologic agents can be administered to the subject or patient for various lengths of time, for example, at least 1, 2, 3, 4, 5, or 6 days; 1, 2, 3, 4, 5, 6, 7, 8, 9, 10, or 11 weeks; 3, 4, 5, 6, 7, 8, 9, 10, 12, 15, or 18 months; or 2, 2.5, 3, 3.5, 4, 4.5, or 5 years or indefinitely. In some embodiments, the pharmacologic agent can be bicarbonate, sodium bicarbonate (NaHCO$_3$), or a solution of sodium bicarbonate and sodium carbonate and a parenteral or IV dosage can be: 0.2×weight of subject (kg)×base deficit of the subject; HCO$_3$ (mEq) required=0.5×weight (kg)×[24− serum HCO$_3$ (mEq/L)]; or 2 to 5 mEq/kg IV infusion over 4 to 8 hours. In some embodiments, standard dosing regimens of bicarbonate, sodium bicarbonate, or a solution of sodium bicarbonate can be used depending on the severity of the acidosis. For example, 50 to 150 mEq bicarbonate diluted in 1 L of 5% dextrose in water can be administered via IV at a rate of 1 to 1.5 L/hour. In another non-limiting example, 90 to 180 mEq bicarbonate diluted in 1 L of 5% dextrose in water can be administered via IV at a rate of 1 to 1.5 L/hour. In some embodiments where the pharmacologic agent is bicarbonate or sodium bicarbonate (NaHCO$_3$), an enteral or oral dosage can be, for example, 325 to 2000 mg sodium bicarbonate given to a subject 1 to 4 times/day.

In some embodiments, the pharmacologic agent can be tris-hydroxymethyl aminomethane (also known as tromethamine, trometamol, and THAM) and a parenteral or IV dosage can be estimated as: Tromethamine solution (mL of 0.3 M) required=Body Weight (kg)×Base Deficit (mEq/liter)×1.1. In some embodiments, the IV dosage of tris-hydroxymethyl aminomethane can be estimated from the buffer base deficit of the extracellular fluid in mEq/L as determined by means of the Siggaard-Andersen nomogram. In some embodiments, the initial dose can be 500 ml (150 mEq) of tris-hydroxymethyl aminomethane injected by slow IV infusion with up to 1000 mL, wherein the maximum dose is 500 mg/kg (227 mg/lb) over a period of not less than one hour.

In some embodiments, the pharmacologic agent can be a small molecule proton pump inhibitor and can be administered for extended treatment lengths. For example, the small molecule proton pump inhibitor can be administered for at least 1, 2, 3, 4, 5, or 6 days; 1, 2, 3, 4, 5, 6, 7, 8, 9, 10, or 11 weeks; 3, 4, 5, 6, 7, 8, 9, 10, 12, 15, or 18 months; or 2, 2.5, 3, 3.5, 4, 4.5, or 5 years or indefinitely. In some embodiments, the proton pump inhibitor can be esomeprazole (Nexium) and 20 mg or 40 mg esomeprazole can be administered orally once or twice daily. In some embodiments, the proton pump inhibitor can be a combination of esomeprazole and naproxen (Vimovo) and 20 mg esomeprazole with 375 or 500 mg naproxen can be administered orally twice daily. In some embodiments, the proton pump inhibitor can be lansoprazole (Prevacid) and 15, 30, or 60 mg lansoprazole can be administered orally once or twice daily. In some embodiments, lansoprazole can be administered by IV with 30 mg lansoprazole injected over 30 minutes once daily for up to 7 days. The subject can then switch to oral lansoprazole and continue treatment. In some embodiments, the proton pump inhibitor can be omeprazole (Prilosec and Zegerid) and 10, 20, or 40 mg omeprazole can be administered orally once or twice daily. In some embodiments, the proton pump inhibitor can be rabeprazole (Aciphex) and 20 or 60 mg rabeprazole can be administered orally once or twice daily or 100 mg rabeprazole can be administered orally once daily. In any of the embodiments disclosed herein, the pharmacologic agents can be used in combination with each other.

In any of the embodiments disclosed herein, the pH of the blood, a tissue, and/or a microenvironment of a subject can be measured before, during, or after the administration of a pharmacologic agent. In some embodiments, the decision to administer or to continue to administer, to a subject the pharmacologic agent to increase or decrease the pH can be based on the pH measurement of the blood, a tissue, and/or a microenvironment of the subject. Methods to measure the blood pH and/or bicarbonate levels of the blood of a subject are well-known in the art. In some embodiments, positron emission tomography (PET), magnetic resonance spectroscopy (MRS), magnetic resonance imaging (MRI), and optical imaging can be used to measure in vivo pH in microenvironments, for example, in tumors (for details of measuring tumor pH, see: Zhang X, Lin Y, Gillies R J. Tumor pH and its measurement. J Nucl Med. 2010 August; 51(8):1167-70).

In another aspect, provided herein is a method for alleviating on target off tumor toxicity in a subject, that includes the following:
 a. introducing a polynucleotide encoding an microenvironment restricted biologic chimeric antigen receptor (MRB-CAR) into a T cell or NK cell of the subject to produce a T cell and/or NK cell capable of expressing the MRB-CAR;
 b. introducing the T cell and/or NK cell capable of expressing the MRB-CAR into the subject, wherein the T cell and/or NK cell express the MRB-CAR in the subject; and
 c. administering a pharmacologic agent to the subject in sufficient amount to increase blood pH and/or pH of a tissue and/or pH of a microenvironment to modulate binding of the MRB-CAR to its cognate antigen in the blood, the tissue, and/or the microenvironment with the increased pH, thereby alleviating on target off tumor toxicity in the subject.

In the introducing step, the T cell or NK cell is capable of expressing the MRB-CAR because it is genetically modified to contain the nucleic acid that encodes the MRB-CAR. This genetic modification can be the presence of the MRB-CAR coding sequence on a vector that has been introduced inside the T cell or NK cell by transfection or transduction. In illustrative embodiments the nucleic acid encoding the MRB-CAR is integrated into the genome of the T cell or NK cell.

It is envisioned that various methods known in the art for introducing a polynucleotide into a T cell and/or NK cell could be used with methods provided herein for aspects that include changing pH to affect binding of an MRB-CAR T cell or NK cell to its cognate antigen on a cell using an agent such as a pH-modulating pharmacologic agent (sometimes referred to herein as "pH Switch aspects"). Typically, a vector, in illustrative examples an expression vector, is used to deliver the polynucleotide. Such vectors can include various vectors known in the art for delivery nucleic acids to T cells and/or NK cells. Illustrative aspects of the invention utilize retroviral vectors and retroviral particles, and in some particularly illustrative embodiments lentiviral vectors and in illustrative embodiments, recombinant lentiviral particles.

Other suitable expression vectors can be used in pH switch aspects provided herein. Such expression vectors include, but are not limited to, viral vectors (e.g. viral vectors based on vaccinia virus; poliovirus; adenovirus (see, e.g., Li et al., Invest Opthalmol Vis Sci 35:2543 2549, 1994; Borras et al., Gene Ther 6:515 524, 1999; Li and Davidson, PNAS 92:7700 7704, 1995; Sakamoto et al., H Gene Ther 5:1088 1097, 1999; WO 94/12649, WO 93/03769; WO 93/19191; WO 94/28938; WO 95/11984 and WO 95/00655); adeno-associated virus (see, e.g., Ali et al., Hum Gene Ther 9:81 86, 1998, Flannery et al., PNAS 94:6916 6921, 1997; Bennett et al., Invest Opthalmol Vis Sci 38:2857 2863, 1997; Jomary et al., Gene Ther 4:683 690, 1997, Rolling et al., Hum Gene Ther 10:641 648, 1999; Ali et al., Hum Mol Genet 5:591 594, 1996; Srivastava in WO 93/09239, Samulski et al., J. Vir. (1989) 63:3822-3828; Mendelson et al., Virol. (1988) 166:154-165; and Flotte et al., PNAS (1993) 90: 10613-10617); SV40; herpes simplex virus; or a retroviral vector (e.g., Murine Leukemia Virus, spleen necrosis virus, and vectors derived from retroviruses such as Rous Sarcoma Virus, Harvey Sarcoma Virus, avian leukosis virus, human immunodeficiency virus, myeloproliferative sarcoma virus, and mammary tumor virus), for example a gamma retrovirus; or human immunodeficiency virus (see, e.g., Miyoshi et al., PNAS 94:10319 23, 1997; Takahashi et al., J Virol 73:7812 7816, 1999); and the like.

In some embodiments, DNA-containing viral particles are utilized instead of recombinant retroviral particles. Such viral particles can be adenoviruses, adeno-associated viruses, herpesviruses, cytomegaloviruses, poxviruses, avipox viruses, influenza viruses, vesicular stomatitis virus (VSV), or Sindbis virus. A skilled artisan will appreciate how to modify the methods disclosed herein for use with different viruses and retroviruses, or retroviral particles. Where viral particles are used that include a DNA genome, a skilled artisan will appreciate that functional units can be included in such genomes to induce integration of all or a portion of the DNA genome of the viral particle into the genome of a T cell and/or NK cell transduced with such virus. Alternatively, functional DNA can be delivered to a T cell and/or NK cell that is expressed in the cell but is not integrated into the genome of the T cell and/or NK cell.

In illustrative embodiments, the vector used in a pH switch aspect of the present disclosure is a recombinant retroviral particle and in certain embodiments, a recombinant lentiviral particle. Such retroviral particle typically includes a retroviral genome within a capsid which is located within a viral envelope. The present disclosure in various sections herein, provide various embodiments of recombinant retroviral particles that disclose elements that can be included on the surface or within, and/or in the genome of a recombinant retroviral particle. Any of these recombinant retroviral particle embodiments can be used in the pH switch aspects provided herein.

Inhibitory RNA Molecules

In certain embodiments, methods provided herein for the present disclosure include inhibiting expression of one or more endogenous genes expressed in T cells and/or NK cells. Methods provided herein illustrate the ability to make recombinant retroviral particles that express one or more, and in illustrative embodiments two or more, inhibitory RNA molecules, such as for example, a miRNA or shRNA, that can be used for such methods. In fact, the methods provided herein illustrate that such inhibitory RNA molecules can be encoded within introns, including for example, an Ef1 a intron. This takes advantage of the present teachings of methods to maximize the functional elements that can be included in a packageable retroviral genome to overcome shortcomings of prior teachings and maximize the effectiveness of such recombinant retroviral particles in adoptive T cell therapy.

In some embodiments, the inhibitory RNA molecule includes a 5' strand and a 3' strand (in some examples, sense strand and antisense strand) that are partially or fully complementary to one another such that the two strands are capable of forming a 18-25 nucleotide RNA duplex within a cellular environment. The 5' strand can be 18, 19, 20, 21, 22, 23, 24, or 25 nucleotides in length, and the 3' strand can be 18, 19, 20, 21, 22, 23, 24, or 25 nucleotides in length. The 5' strand and the 3' strand can be the same or different lengths, and the RNA duplex can include one or more mismatches. Alternatively, the RNA duplex has no mismatches.

The inhibitory RNA molecules included in compositions and methods provided herein, in certain illustrative examples, do not exist and/or are not expressed naturally in T cells into whose genome they are inserted. In some embodiments, the inhibitory RNA molecule is a miRNA or an shRNA. In some embodiments, where reference is made herein or in priority filings, to a nucleic acid encoding an siRNA, especially in a context where the nucleic acid is part of a genome, it will be understood that such nucleic acid is capable of forming an siRNA precursor such as miRNA or shRNA in a cell that is processed by DICER to form a double stranded RNA that typically interacts with, or becomes part of a RISK complex. In some embodiments, an inhibitory molecule of an embodiment of the present disclosure is a precursor of a miRNA, such as for example, a Pri-miRNA or a Pre-miRNA, or a precursor of an shRNA. In some embodiments, the miRNA or shRNA are artificially derived (i.e. artificial miRNAs or siRNAs). In other embodiments, the inhibitory RNA molecule is a dsRNA (either transcribed or artificially introduced) that is processed into an siRNA or the siRNA itself. In some embodiments, the miRNA or shRNA has a sequence that is not found in nature, or has at least one functional segment that is not found in nature, or has a combination of functional segments that are not found in nature.

In some embodiments, inhibitory RNA molecules are positioned in the first nucleic acid molecule in a series or multiplex arrangement such that multiple miRNA sequences are simultaneously expressed from a single polycistronic miRNA transcript. In some embodiments, the inhibitory miRNA molecules can be adjoined to one another either directly or indirectly by non-functional linker sequence(s). The linker sequence in some embodiments, is between 5 and 120 nucleotides in length, and in some embodiments can be between 10 and 40 nucleotides in length, as non-limiting examples. In illustrative embodiments the first nucleic acid sequence encoding one or more (e.g. two or more) inhibitory RNAs and the second nucleic acid sequence encoding a CAR (e.g. an MRB-CAR) are operably linked to a promoter that is active constitutively or that can be induced in a T cell or NK cell. As such, the inhibitory RNA molecule(s) (e.g. miRNAs) as well as the CAR are expressed in a polycistronic manner Additionally, functional sequences can be expressed from the same transcript. For example, any of the lymphoproliferative elements provided herein that are not inhibitory RNA molecules, can be expressed from the same transcript as the CAR and the one or more (e.g. two or more) inhibitory RNA molecules.

In some embodiments, the inhibitory RNA molecule is a naturally occurring miRNA such as but not limited to miR-155. Alternatively, artificial miRNAs can be produced in which sequences capable of forming a hybridizing/complementary stem structure and directed against a target RNA, are placed in a miRNA framework that includes microRNA flanking sequences for microRNA processing and a loop, which can optionally be derived from the same naturally occurring miRNA as the flanking sequences, between the stem sequences. Thus, in some embodiments, an inhibitory RNA molecule includes from 5' to 3' orientation: a 5' microRNA flanking sequence, a 5' stem, a loop, a 3' stem that is partially or fully complementary to said 5' stem, and a 3' microRNA flanking sequence. In some embodiments, the 5' stem (also called a 5' arm herein) is 18, 19, 20, 21, 22, 23, 24 or 25 nucleotides in length. In some embodiments, the 3' stem (also called a 3' arm herein) is 18, 19, 20, 21, 22, 23, 24, or 25 nucleotides in length. In some embodiments, the loop is 3 to 40, 10 to 40, 20 to 40, or 20 to 30 nucleotides in length, and in illustrative embodiments the loop can be 18, 19, 20, 21, or 22 nucleotides in length. In some embodiments, one stem is two nucleotides longer than the other stem. The longer stem can be the 5' or the 3' stem.

In some embodiments, the 5' microRNA flanking sequence, 3' microRNA flanking sequence, or both, are derived from a naturally occurring miRNA, such as but not limited to miR-155, miR-30, miR-17-92, miR-122, and miR-21. In certain embodiments, the 5' microRNA flanking sequence, 3' microRNA flanking sequence, or both, are derived from a miR-155, such as, e.g, the miR-155 from *Mus musculus* or *Homo sapiens*. Inserting a synthetic miRNA stem-loop into a miR-155 framework (i.e. the 5' microRNA flanking sequence, the 3' microRNA flanking sequence, and the loop between the miRNA 5' and 3' stems) is known to one of ordinary skill in the art (Chung, K. et al. 2006. *Nucleic Acids Research.* 34(7):e53; U.S. Pat. No. 7,387, 896). The SIBR (synthetic inhibitory BIC-derived RNA) sequence (Chung et al. 2006 supra), for example, has a 5' microRNA flanking sequence consisting of nucleotides 134-161 (SEQ ID NO:256) of the *Mus musculus* BIC noncoding mRNA (Genbank ID AY096003.1) and a 3' microRNA flanking sequence consisting of nucleotides 223-283 of the *Mus musculus* BIC noncoding mRNA (Genbank ID AY096003.1). In one study, the SIBR sequence was modified (eSIBR) to enhance expression of miRNAs (Fowler, D. K. et al. 2015. Nucleic acids Research 44(5):e48). In some embodiments of the present disclosure, miRNAs can be placed in the SIBR or eSIBR miR-155 framework. In illustrative embodiments herein, miRNAs are placed in a miR-155 framework that includes the 5' microRNA flanking sequence of miR-155 represented by SEQ ID NO:256, the 3' microRNA flanking sequence represented by SEQ ID NO:260 (nucleotides 221-265 of the *Mus musculus* BIC noncoding mRNA); and a modified miR-155 loop (SEQ ID NO:258). Thus, in some embodiments, the 5' microRNA flanking sequence of miR-155 is SEQ ID NO:256 or a functional variant thereof, such as, for example, a sequence that is the same length as SEQ ID NO:256, or 95%, 90%, 85%, 80%, 75%, or 50% as long as SEQ ID NO: 256 or is 100 nucleotides or less, 95 nucleotides or less, 90 nucleotides or less, 85 nucleotides or less, 80 nucleotides or less, 75 nucleotides or less, 70 nucleotides or less, 65 nucleotides or less, 60 nucleotides or less, 55 nucleotides or less, 50 nucleotides or less, 45 nucleotides or less, 40 nucleotides or less, 35 nucleotides or less, 30 nucleotides or less, or 25 nucleotides or less; and is at least 50%, 55%, 60%, 65%, 70%, 75%, 80%, 85%, 90%, or 95% identical to SEQ ID NO:256. In some embodiments, the 3' microRNA flanking sequence of miR-155 is SEQ ID NO:260 or a functional variant thereof, such as, for example, the same length as SEQ ID NO:260, or 95%, 90%, 85%, 80%, 75%, or 50% as long as SEQ ID NO: 260 or is a sequence that is 100 nucleotides or less, 95 nucleotides or less, 90 nucleotides or less, 85 nucleotides or less, 80 nucleotides or less, 75 nucleotides or less, 70 nucleotides or less, 65 nucleotides or less, 60 nucleotides or less, 55 nucleotides or less, 50 nucleotides or less, 45 nucleotides or less, 40 nucleotides or less, 35 nucleotides or less, 30 nucleotides or less, or 25 nucleotides or less; and is at least 50%, 55%, 60%, 65%, 70%, 75%, 80%, 85%, 90%, or 95% identical to SEQ ID NO:260. However, any known microRNA framework that is functional to provide proper processing within a cell of miRNAs inserted therein to form mature miRNA capable of inhibiting expression of a target mRNA to which they bind, is contemplated within the present disclosure.

In some embodiments, at least one, at least two, at least three, or at least four of the inhibitory RNA molecules encoded by a nucleic acid sequence in a polynucleotide of a replication incompetent recombinant retroviral particle has the following arrangement in the 5' to 3' orientation: a 5' microRNA flanking sequence, a 5' stem, a loop, a 3' stem that is partially or fully complementary to said 5' stem, and a 3' microRNA flanking sequence. In some embodiments, all of the inhibitory RNA molecules have the following arrangement in the 5' to 3' orientation: a 5' microRNA flanking sequence, a 5' stem, a loop, a 3' stem that is partially or fully complementary to said 5' stem, and a 3' microRNA flanking sequence. As disclosed herein, the inhibitory RNA molecules can be separated by one or more linker sequences, which in some embodiments have no function except to act as spacers between inhibitory RNA molecules.

In some embodiments, where two or more inhibitory RNA molecules (in some examples, 1, 2, 3, 4, 5, 6, 7, 8, 9, or 10 inhibitory RNA molecules) are included, these inhibitory RNA molecules are directed against the same or different RNA targets (such as e.g. mRNAs transcribed from genes of interest). In illustrative embodiments, between 2 and 10, 2 and 8, 2 and 6, 2 and 5, 3 and 5, or 3 and 6 inhibitory RNA molecules are included in the first nucleic acid sequence. In an illustrative embodiment, four inhibitory RNA molecules are included in the first nucleic acid sequence.

In some embodiments, the RNA targets are mRNAs transcribed from genes that are expressed by T cells such as but not limited to PD-1 (prevent inactivation); CTLA4 (prevent inactivation); TCRa (safety—prevent autoimmunity); TCRb (safety—prevent autoimmunity); CD3Z (safety—prevent autoimmunity); SOCS1 (prevent inactivation); SMAD2 (prevent inactivation); a miR-155 target (promote activation); IFN gamma (reduce CRS); cCBL (prolong signaling); TRAIL2 (prevent death); PP2A (prolong signaling); ABCG1 (increase cholesterol microdomain content by limiting clearance of cholesterol). In illustrative examples, miRNAs inserted into the genome of T cells in methods provided herein, are directed at targets such that proliferation of the T cells is induced and/or enhanced and/or apoptosis is suppressed.

In some embodiments, the RNA targets include mRNAs that encode components of the T cell receptor (TCR) complex. Such components can include components for generation and/or formation of a T cell receptor complex and/or components for proper functioning of a T cell receptor complex. Accordingly, in one embodiment at least one of the two or more of inhibitory RNA molecules causes a decrease in the formation and/or function of a TCR complex, in illustrative embodiments one or more endogenous TCR complexes of a T cell. The T cell receptor complex includes TCRa, TCRb, CD3d, CD3e, CD3 g, and CD3z. It is known that there is a complex interdependency of these components such that a decrease in the expression of any one subunit will result in a decrease in the expression and function of the complex. Accordingly, in one embodiment the RNA target is an mRNA expressing one or more of TCRa, TCRb, CD3d, CD3e, CD3 g, and CD3z endogenous to a transduced T cell. In certain embodiments, the RNA target is mRNA transcribed from the endogenous TCRα or TCRβ gene of the T cell whose genome comprises the first nucleic acid sequence encoding the one or more miRNAs. In illustrative embodiments, the RNA target is mRNA transcribed from the TCRα gene. In certain embodiments, inhibitory RNA molecules directed against mRNAs transcribed from target genes with similar expected utilities can be combined. In other embodiments, inhibitory RNA molecules directed against target mRNAs transcribed from target genes with complementary utilities can be combined. In some embodiments, the two or more inhibitory RNA molecules are directed against the mRNAs transcribed from the target genes CD3Z, PD1, SOCS1, and/or IFN gamma In some embodiments provided herein, the two or more inhibitory RNA molecules can be delivered in a single intron, such as but not limited to EF1-aa intron A. Intron sequences that can be used to harbor miRNAs for the present disclosure include any intron that is processed within a T cell. As indicated herein, one advantage of such an arrangement is that this helps to maximize the ability to include miRNA sequences within the size constraints of a retroviral genome used to deliver such sequences to a T cell in methods provided herein. This is especially true where an intron of the first nucleic acid sequence includes all or a portion of a promoter sequence used to express that intron, a CAR sequence, and other functional sequences provided herein, such as lymphoproliferative element(s) that are not inhibitory RNA molecules, in a polycistronic manner Sequence requirements for introns are known in the art. In some embodiments, such intron processing is operably linked to a riboswitch, such as any riboswitch disclosed herein. Thus, the riboswitch can provide a regulatory element for control of expression of the one or more miRNA sequences on the first nucleic acid sequence. Accordingly, in illustrative embodiments provided herein is a combination of an miRNA directed against an endogenous T cell receptor subunit, wherein the expression of the miRNA is regulated by a riboswitch, which can be any of the riboswitches discussed herein.

In some embodiments, inhibitory RNA molecules can be provided on multiple nucleic acid sequences that can be included on the same or a different transcriptional unit. For example, a first nucleic acid sequence can encode one or more inhibitory RNA molecules and be expressed from a first promoter and a second nucleic acid sequence can encode one or more inhibitory RNA molecules and be expressed from a second promoter. In illustrative embodiments, two or more inhibitory RNA molecules are located on a first nucleic acid sequence that is expressed from a single promoter. The promoter used to express such miRNAs, are typically promoters that are inactive in a packaging cell used to express a retroviral particle that will deliver the miRNAs in its genome to a target T cell, but such promoter is active, either constitutively or in an inducible manner, within a T cell. The promoter can be a Pol I, Pol II, or Pol III promoter. In some illustrative embodiments, the promoter is a Pol II promoter.

Treatment Methods

The present disclosure provides various treatment methods using a CAR. A CAR of the present disclosure, when present in a T lymphocyte or an NK cell, can mediate cytotoxicity toward a target cell. A CAR of the present disclosure binds to an antigen present on a target cell, thereby mediating killing of a target cell by a T lymphocyte or an NK cell genetically modified to produce the CAR. The ASTR of the CAR binds to an antigen present on the surface of a target cell.

The present disclosure provides methods of killing, or inhibiting the growth of, a target cell, the method involving contacting a cytotoxic immune effector cell (e.g., a cytotoxic T cell, or an NK cell) that is genetically modified to produce a subject CAR, such that the T lymphocyte or NK cell recognizes an antigen present on the surface of a target cell, and mediates killing of the target cell.

The present disclosure provides a method of treating a disease or disorder in an individual having the disease or disorder, the method including: a. introducing an expression vector including a polynucleotide sequence encoding a CAR into peripheral blood cells obtained from the subject to produce a genetically engineered cytotoxic cell; and b. administering the genetically engineered cytotoxic cell to the subject.

Subjects Suitable for Treatment

A variety of subjects are suitable for treatment with the methods and compositions presented herein. Suitable subjects include any individual, e.g., a human or non-human animal who has a disease or disorder, who has been diagnosed with a disease or disorder, who is at risk for developing a disease or disorder, who has had a disease or disorder and is at risk for recurrence of the disease or disorder, who has been treated with an agent for the disease or disorder and failed to respond to such treatment, or who has been treated with an agent for the disease or disorder but relapsed after initial response to such treatment.

Subjects suitable for treatment with an immunomodulatory method include individuals who have an autoimmune disorder; individuals who are organ or tissue transplant recipients; and the like; individuals who are immunocompromised; and individuals who are infected with a pathogen.

EXEMPLARY EMBODIMENTS

In one aspect, provided herein is a method for genetically modifying and expanding lymphocytes of a subject, comprising:
  A. contacting resting T cells and/or NK cells of the subject ex vivo without requiring prior ex vivo stimulation, with replication incompetent recombinant retroviral particles comprising:
    iii. a pseudotyping element on its surface that is capable of binding to a T cell and/or NK cell and facilitating membrane fusion of the replication incompetent recombinant retroviral particles thereto; and
    iv. a polynucleotide comprising one or more transcriptional units operatively linked to a promoter active in T cells and/or NK cells, wherein the one or more transcriptional units encode a first engineered signaling polypeptide regulated by a control element, wherein said first engineered signaling polypeptide comprises at least one lymphoproliferative element, wherein said contacting facilitates transduction of at least some of the resting T cells and/or NK cells by the replication incompetent recombinant retroviral particles, thereby producing genetically modified T cells and/or NK cells;
  B. introducing the genetically modified T cells and/or NK cells into the subject; and
  C. exposing the genetically modified T cells and/or NK cells in vivo to a compound that binds the control element to affect expression of the first engineered signaling polypeptide and promote and/or potentiate expansion, engraftment, and/or persistence of the lymphocytes in vivo, thereby genetically modifying and expanding lymphocytes of the subject. In illustrative embodiments, the transduction is carried out without ex vivo stimulation.

In the above aspect and any of the method aspects for genetically modifying and expanding lymphocytes or for performing cellular therapy herein, if not recited in the broadest aspect, in certain embodiments the polynucleotide further comprises a transcriptional unit that encodes a second engineered signaling polypeptide comprising a first chimeric antigen receptor comprising an antigen-specific targeting region (ASTR), a transmembrane domain, and an intracellular activating domain.

In another aspect, provided herein is a method for performing adoptive cell therapy on a subject, comprising:
  A. collecting blood from the subject;
  B. contacting resting T cells and/or NK cells from the blood of the subject ex vivo with replication incompetent recombinant retroviral particles, wherein the replication incompetent recombinant retroviral particles comprise
    i. a pseudotyping element on their surface that is capable of binding to a T cell and/or NK cell and facilitating membrane fusion of the replication incompetent recombinant retroviral particles thereto; and
    ii. a polynucleotide comprising one or more transcriptional units operatively linked to a promoter active in T cells and/or NK cells, wherein the one or more transcriptional units encode a first engineered signaling polypeptide comprising at least one lymphoproliferative element whose expression is regulated by a control element, and a second engineered signaling polypeptide comprising a chimeric antigen receptor comprising an antigen-specific targeting region (ASTR), a transmembrane domain, and an intracellular activating domain,
wherein said contacting results in at least some of the resting T cells and/or NK cells becoming genetically modified; and C. reintroducing the genetically modified T cells and/or NK cells into the subject, wherein expansion, engraftment, and/or persistence of the genetically modified T cells and/or NK cells occurs in vivo within the subject, and wherein the method between the collecting blood and the reintroducing the genetically modified T cells and/or NK cells is performed in no more than 24 hours, thereby performing adoptive cell therapy on the subject.

Provided in another aspect herein is a method for performing adoptive cell therapy on a subject, comprising:
A. collecting blood from a subject;
B. isolating peripheral blood mononuclear cells (PBMCs) comprising resting T cells and/or resting NK cells;
C. contacting the resting T cells and/or resting NK cells of the subject ex vivo, with replication incompetent recombinant retroviral particles, wherein the replication incompetent recombinant retroviral particles comprise a pseudotyping element on their surface that is capable of binding a resting T cell and/or NK cell and facilitating membrane fusion of the replication incompetent recombinant retroviral particles thereto, wherein said contacting facilitates transduction of the resting T cells and/or NK cells by the replication incompetent recombinant retroviral particles, thereby producing genetically modified T cells and/or NK cells; and
D. reintroducing the genetically modified cells into the subject within 24 hours of collecting blood from the subject, thereby performing adoptive cell therapy in the subject.

Provided in another aspect herein, is a method of transducing resting lymphocytes of a subject, comprising contacting resting T cells and/or resting NK cells of a subject ex vivo, with replication incompetent recombinant retroviral particles, wherein the replication incompetent recombinant retroviral particles comprise a pseudotyping element on their surface that is capable of binding a resting T cell and/or resting NK cell and facilitating membrane fusion of the replication incompetent recombinant retroviral particles thereto, wherein said contacting facilitates transduction of the resting T cells and/or NK cells by the replication incompetent recombinant retroviral particles, thereby producing genetically modified T cells and/or NK cells. In illustrative embodiments of this aspect, at least 10, 20, or 25% of the resting T cells and/or NK cells, or between 10% and 70%, or 20% and 50% of T cells and/or NK cells are transduced as a result of the process are transduced as a result of the process.

Provided in another aspect herein is a method for transducing resting T cells and/or resting NK cells from isolated blood, comprising:
D. collecting blood from a subject;
E. isolating peripheral blood mononuclear cells (PBMCs) comprising resting T cells and/or resting NK cells;
F. contacting the resting T cells and/or resting NK cells of the subject ex vivo, with replication incompetent recombinant retroviral particles, wherein the replication incompetent recombinant retroviral particles comprise a pseudotyping element on their surface that is capable of binding a resting T cell and/or resting NK cell and facilitating membrane fusion of the replication incompetent recombinant retroviral particles thereto, wherein said contacting facilitates transduction of at least 5% of the resting T cells and/or resting NK cells by the replication incompetent recombinant retroviral particles, thereby producing genetically modified T cells and/or NK cells, thereby transducing resting T cells and/or NK cells.

In one aspect, provided herein are replication incompetent recombinant retroviral particles, comprising:
A. one or more pseudotyping elements capable of binding to a T cell and/or an NK cell and facilitating membrane fusion of the replication incompetent recombinant retroviral particles thereto;
B. a polynucleotide comprising one or more transcriptional units operatively linked to a promoter active in T cells and/or NK cells, wherein the one or more transcriptional units encode a first engineered signaling polypeptide comprising a chimeric antigen receptor comprising an antigen-specific targeting region, a transmembrane domain, and an intracellular activating domain, and a second engineered signaling polypeptide comprising at least one lymphoproliferative element; wherein expression of the first engineered signaling polypeptide and/or the second engineered signaling polypeptide are regulated by a control element; and
C. an activation element on its surface, wherein the activation element is capable of binding to a T cell and/or NK cell and is not encoded by a polynucleotide in the replication incompetent recombinant retroviral particles.

In another aspect, provided herein are replication incompetent recombinant retroviral particles, each comprising:
A. a pseudotyping element on its surface that is capable of binding to a T cell and/or NK cell and facilitating membrane fusion of the replication incompetent recombinant retroviral particle thereto, wherein said pseudotyping element comprises cytoplasmic domain deletion variants of a measles virus F polypeptide and/or a measles virus H polypeptide;
B. a polynucleotide comprising one or more transcriptional units operatively linked to a promoter active in T cells and/or NK cells, wherein the one or more transcriptional units encode a first engineered signaling polypeptide comprising a chimeric antigen receptor comprising an antigen-specific targeting region, a transmembrane domain, and an intracellular activating domain, and a second engineered signaling polypeptide comprising a constitutively active IL-7 receptor mutant; wherein expression of the IL-7 receptor mutant is regulated by a riboswitch that binds a nucleoside analog antiviral drug; and
C. a polypeptide capable of binding to CD3 and a polypeptide capable of binding to CD28, wherein said polypeptides are expressed on the surface of a replication incompetent recombinant retroviral particle; are capable of binding to a T cell and/or NK cell; and are not encoded by a polynucleotide in the replication incompetent recombinant retroviral particle. In illustrative embodiments of this aspect, binding of the nucleoside analog antiviral drug to the riboswitch increases expression of the IL-7 receptor mutant.

In any of the method or composition aspects provided herein, if not already recited in the broadest aspect, the replication incompetent recombinant retroviral particle(s) comprises or further comprises an activation element on their surface that is capable of activating a resting T cell and/or a resting NK cell.

In any of the methods or compositions herein that recite a T cell and/or a NK cell, or a resting T cell or a resting NK cell, in certain illustrative embodiments, the cell is a T cell.

Typically, the recombinant retroviral particle in any of the methods and compositions provided herein, is replication incompetent, i.e. cannot replicate. In illustrative embodiments, the retrovirus is a lentivirus, such as a replication defective HIV lentivirus. In illustrative embodiments, the retroviral particle is a lentiviral particle, such as a replication defective HIV lentiviral particle.

In illustrative embodiments of any of the methods aspects for genetically modifying and expanding lymphocytes or for performing adoptive cellular therapy herein, or similar methods, between 10% and 75%, or 10% and 70%, or 10% and 60%, or 10% and 50%, or 10% and 25%, or 20% and 75%, or 20% and 50%, or at least 10%, 20%, or 25% of resting T cells are transduced and between 0% and 75% of NK cells are transduced. In other embodiments, between 5% and 80%, or 10% and 80%, or 10% and 70%, or 10% and 60%, or 10% and 50%, or 10% and 25%, or 10% and 20%, or 20% and 50% of resting NK cells are transduced.

In illustrative embodiments of any of the methods aspects for genetically modifying and expanding lymphocytes or for performing adoptive cellular therapy herein, or similar methods or any compositions provided herein, if not explicitly recited in the broadest aspect, expression of said second engineered signaling polypeptide is regulated by the control element.

In illustrative embodiments of any of the methods aspects for genetically modifying and expanding lymphocytes or for performing cellular therapy herein, or similar methods, if not explicitly recited in the broadest aspect the method, the contacting can be carried out for between 15, 30 or 45 minutes or 1, 2, 3, 4, 5, 6, 7, or 8 hours on the low end of the range, and between 6, 8, 10, 12, 18, 24, 36, 48, and 72 hours on the high end of the range. For example, in illustrative embodiments, the contacting is carried out for between 2 and 24 hours, or between 4 and 12 hours, or between 4 and 8 hours.

In illustrative embodiments of any of the methods aspects for genetically modifying and expanding lymphocytes or for performing adoptive cellular therapy herein, or similar methods, if not explicitly recited in the broadest aspect the method can further comprise exposing the genetically modified T cells and/or NK cells in vivo to a compound that binds the control element to affect expression of the first engineered signaling polypeptide and optionally the second engineered signaling polypeptide, and to promote expansion, engraftment, and/or persistence of the lymphocytes in vivo.

In illustrative embodiments of any of the methods aspects for genetically modifying and expanding lymphocytes or for performing adoptive cellular therapy herein, or similar methods, if not explicitly recited in the broadest aspect, the genetically modified T cells and/or NK cells undergo 8, 7, 6, 5, 4, 3 or fewer cell divisions ex vivo prior to being introduced or reintroduced into the subject.

In illustrative embodiments of any of the methods aspects for genetically modifying and expanding lymphocytes or for performing cellular therapy herein, or similar methods, if not explicitly recited in the broadest aspect, expansion, engraftment, and/or persistence of genetically modified T cells and/or NK cells in vivo is dependent on either the presence or absence of the compound that binds the control element, and in illustrative embodiments, is dependent on the presence of the compound that binds the control element.

In illustrative embodiments of any of the methods aspects for genetically modifying and expanding lymphocytes or for performing adoptive cellular therapy herein, or similar methods, if not explicitly recited in the broadest aspect, the subject is not exposed to a lymphodepleting agent within 7, 14, or 21 days of performing the contacting, during the contacting, and/or within 7, 14, or 21 days after the modified T cells and/or NK cells are introduced into the subject. In other embodiments, the subject is not exposed to a lymphodepleting agent during the contacting.

In illustrative embodiments of any of the methods aspects for genetically modifying and expanding lymphocytes or for performing cellular therapy herein, or similar methods, if not explicitly recited in the broadest aspect, the resting T cells and/or resting NK cells are in contact with the replication incompetent recombinant retroviral particles for between 15 minutes and 12 hours.

In illustrative embodiments of any of the methods aspects for genetically modifying and expanding lymphocytes or for performing adoptive cellular therapy herein, or similar methods, if not explicitly recited in the broadest aspect, the method further includes the step of separating the replication incompetent recombinant retroviral particles from the T cells and/or NK cells after the contacting but before the introducing. In illustrative embodiments of any of the methods aspects for genetically modifying and expanding lymphocytes or for performing cellular therapy herein, or similar methods, if not explicitly recited in the broadest aspect, said exposing step comprises administering a dose of the compound to the subject prior to or during the contacting, and/or after the genetically modified T cells and/or NK cells have been introduced into the subject.

In illustrative embodiments of any of the methods aspects for genetically modifying and expanding lymphocytes or for performing adoptive cellular therapy herein, or similar methods, if not explicitly recited in the broadest aspect, the method comprises collecting blood comprising the T cells and/or the NK cells from the subject prior to contacting the T cells and/or NK cells ex vivo with the replication incompetent recombinant retroviral particles, and wherein the introducing is reintroducing. For example, between 20 and 250 ml of blood are withdrawn from the subject.

In illustrative embodiments of any of the methods aspects for genetically modifying and expanding lymphocytes or for performing cellular therapy herein, or similar methods, if not explicitly recited in the broadest aspect, no more than 8, 12, 24, or 48 hours pass between the time blood is collected from the subject and the time the modified T cells and/or NK cells are reintroduced into the subject.

In illustrative embodiments of any of the methods aspects for genetically modifying and expanding lymphocytes or for performing cellular therapy herein, or similar methods, if not explicitly recited in the broadest aspect, between 4 or 8 hours on the low end and 12. 24, 36, or 48 hours on the high end of the range pass between the time blood is collected from the subject and the time the modified T cells and/or NK cells are reintroduced into the subject.

In illustrative embodiments of any of the methods aspects for genetically modifying and expanding lymphocytes or for performing adoptive cellular therapy herein, or similar methods, if not explicitly recited in the broadest aspect, all steps after the blood is collected and before the blood is reintroduced, are performed in a closed system in which a person monitors the closed system throughout the processing. In another embodiment, after the blood is collected and before the blood is reintroduced, are performed in a closed system that remains in the same room with the subject.

In illustrative embodiments of any of the methods and compositions provided herein that include one or more engineered signaling polypeptides, if not recited in the broadest aspect, one of the engineered signaling polypeptide comprises or further comprises an antigen-specific targeting region (ASTR) and a transmembrane domain connecting the ASTR to the lymphoproliferative element. The ASTR of this engineered signaling polypeptide is capable of binding to a first tumor antigen and where present, the ASTR of the second engineered signaling polypeptide is capable of binding to a second tumor antigen. in illustrative embodiments, the first engineered signaling polypeptide and/or the second engineered signaling polypeptide further comprise a co-stimulatory domain. Furthermore, the first engineered signaling polypeptide and/or the second engineered signaling polypeptide further comprise a stalk. Furthermore, the first engineered signaling polypeptide further comprises an intracellular activating domain. The intracellular activating domain on the first engineered signaling polypeptide and/or the second engineered signaling polypeptide can be derived from CD3 zeta.

In illustrative embodiments of any of the methods and compositions provided herein that include a lymphoproliferative element, the lymphoproliferative element can comprise a T cell survival motif. The T cell survival motif can comprise all or a functional fragment of IL-7 receptor, IL-15 receptor, or CD28. In other embodiments, the lymphoproliferative element can include a cytokine or cytokine receptor polypeptide, or a fragment thereof comprising a signaling domain. For example, the lymphoproliferative element can comprise an interleukin polypeptide covalently attached to its cognate interleukin receptor polypeptide via a linker. Alternatively, the lymphoproliferative element can be an intracellular signaling domain of an IL-7 receptor, an intracellular signaling domain of an IL-12 receptor, an intracellular signaling domain of IL-23, an intracellular signaling domain of IL-27, an intracellular signaling domain of IL-15 receptor, an intracellular signaling domain of an IL-21 receptor, or an intracellular signaling domain of a transforming growth factor β (TGFβ) decoy receptor. In other illustrative embodiments, the lymphoproliferative element is constitutively active. Furthermore, the lymphoproliferative element can include a mutated IL-7 receptor or a fragment thereof, which can further include a constitutively active mutated IL-7 receptor or a constitutively active fragment thereof.

In illustrative embodiments of any of the methods and compositions provided herein that include a replication incompetent recombinant retroviral particle(s), if not explicitly recited in the broadest aspect, the replication incompetent recombinant retroviral particles can comprise on their surface an activation element comprising:

A. a membrane-bound polypeptide capable of binding to CD3; and/or

B. a membrane-bound polypeptide capable of binding to CD28.

Furthermore, the membrane-bound polypeptide capable of binding to CD3 is a polypeptide capable of binding to CD3 that can be fused to a heterologous GPI anchor attachment sequence and the membrane-bound polypeptide capable of binding to CD28 can be a polypeptide capable of binding to CD28 that 8 is fused to a heterologous GPI anchor attachment sequence. In some embodiments, the membrane-bound polypeptide capable of binding to CD28 is CD80, CD86, or a functional fragment thereof that is capable of inducing CD28-mediated activation of Akt, such as the extracellular domain of CD80.

In illustrative embodiments of any of the methods and compositions provided herein that include a replication incompetent recombinant retroviral particle, the membrane-bound polypeptide capable of binding CD3 can be an anti-CD3 scFv bound to a CD14 GPI anchor attachment sequence, and the membrane-bound polypeptide capable of binding to CD28 can be CD80, or the extracellular domain thereof, bound to a CD16B GPI anchor attachment sequence. In illustrative embodiments of any of the methods and compositions provided herein that include a replication incompetent recombinant retroviral particle, the replication incompetent recombinant retroviral particles can comprise on their surface, an anti-CD3 scFv bound to a CD14 GPI anchor attachment sequence, CD80, or the extracellular domain thereof, bound to a CD16B GPI anchor attachment sequence, and a fusion polypeptide of IL-7, or an active fragment thereof, and DAF comprising a GPI anchor attachment sequence. In illustrative embodiments of any of the methods and compositions provided herein that include a replication incompetent recombinant retroviral particle, the IL-7, or an active fragment thereof, and DAF fusion, the anti-CD3 scFV, and the CD80, or extracellular domain thereof each comprises a DAF signal sequence.

In illustrative embodiments of any of the methods and compositions provided herein that include a replication incompetent recombinant retroviral particle(s), if not explicitly recited in the broadest aspect, the replication incompetent recombinant retroviral particles can comprise on their surface a membrane-bound cytokine. The membrane-bound cytokine can be IL-7, IL-15, or an active fragment thereof. In other embodiments, the membrane-bound cytokine is a fusion polypeptide of IL-7, or an active fragment thereof, and DAF. For example, the fusion polypeptide can comprise the DAF signal sequence (nucleotides 1-34 of SEQ ID NO:286), IL-7 without its signal sequence (nucleotides 35-186 of SEQ ID NO:286), and a fragment of DAF that includes its GPI anchor attachment sequence (nucleotides 187-532 of SEQ ID NO:286).

Illustrative embodiments of any of the method and composition aspects provided herein the pseudotyping element can comprise one or more heterologous envelope proteins. In other examples, the pseudotyping element can include one or more viral polypeptides recognized by T cells. The one or more pseudotyping elements can comprise a Measles Virus F polypeptide, a Measles Virus H polypeptide, and/or a fragment thereof. The one or more pseudotyping elements can be cytoplasmic domain deletion variants of a measles virus F polypeptide and/or a measles virus H polypeptide.

In illustrative embodiments of any of the methods and compositions provided herein that include the control element is the control element can regulate the lymphoproliferative element, wherein the lymphoproliferative element is inactive or less active at promoting proliferation of the T cells and/or NK cells in the absence of the compound, and wherein the compound is a molecular chaperone that binds the lymphoproliferative element and induces the activity of the lymphoproliferative element.

In illustrative embodiments of any of the methods and compositions provided herein that include the control element, the control element can be a polynucleotide comprising a riboswitch. The riboswitch can be capable of binding a nucleoside analog and the compound that binds the control element is the nucleoside analog. The nucleoside analog can be an antiviral agent. The antiviral agent can be acyclovir or penciclovir.

In illustrative embodiments of any of the methods and compositions provided herein that include an engineered signaling polypeptide, that includes an ASTR, the ASTR of either or both of the engineered signaling polypeptides can bind to a tumor associated antigen. In some illustrative embodiments, the antigen-specific targeting region of the second engineered polypeptide is a microenvironment restricted antigen-specific targeting region.

In illustrative embodiments of any of the methods and compositions provided herein that include a replication incompetent recombinant retroviral particle(s), if not explicitly recited in the broadest aspect, the replication incompetent recombinant retroviral particles can encode a recognition domain for a monoclonal antibody approved biologic. In some embodiments, the recognition domain is expressed on the same transcript as the chimeric antigen receptor and wherein the recognition domain is separated from the chimeric antigen receptor by a ribosome skipping and/or cleavage signal. The ribosome skipping and/or cleavage signal can be 2A-1. The recognition domain can include a polypeptide that is recognized by an antibody that recognizes EGFR, or an epitope thereof. The recognition domain can be an EGFR mutant that is recognized by an EGFR antibody and expressed on the surface of transduced T cells and/or NK cells as another control mechanism provided herein. In related embodiments, the recognition domain can include a polypeptide that is recognized by an antibody that recognizes EGFR, or an epitope thereof.

In any of the methods or compositions provided herein that include a lymphoproliferative element, the lymphoproliferative element can include an inhibitory RNA molecule, such as, e.g., a miRNA or shRNA, that stimulates the STAT5 pathway or inhibits the SOCS pathway. For example, an inhibitory RNA molecule can bind to a nucleic acid encoding a protein selected from the group consisting of: ABCG1, SOCS, TGFbR2, SMAD2, cCBL, and PD1. In illustrative embodiments for any of the replication incompetent recombinant retroviral particles or transduced cells provided herein, or methods including the same, such replication incompetent recombinant retroviral particles or transduced cells can encode two or more inhibitory RNA molecules, such as, e.g., a miRNA or shRNA, within an intron, in some embodiments, 1, 2, 3, or 4 inhibitory RNA molecules that bind nucleic acids encoding one or more of the following target endogenous T cell expressed genes: PD-1; CTLA4; TCR alpha; TCR beta; CD3 zeta; SOCS; SMAD2; miR-155; IFN gamma; cCBL; TRAIL2; PP2A; or ABCG1. For example, in one embodiment, a combination of miRNAs targeting any of the following can be included in a genome of a replication incompetent recombinant retroviral particle or transduced cell: TCR alpha, CD3 zeta, IFN gamma, and PD-1; and in another embodiment SOCS 1, IFN gamma, TCR alpha, and CD3 zeta.

In illustrative embodiments of any of the methods and compositions provided herein, the replication incompetent recombinant retroviral particles, mammalian cells, and/or packaging cells, can comprise a Vpx polypeptide. The Vpx polypeptide can be, for example, a fusion polypeptide, and in some examples, especially in packaging cells, a membrane bound Vpx polypeptide.

In any of the methods or compositions provided herein, the one or more pseudotyping elements can include a vesicular stomatitis virus envelope protein (VSV-G), a feline endogenous virus (RD114) envelope protein, an oncoretroviral amphotropic envelope protein, or an oncoretroviral ecotropic envelope protein, or functional fragments thereof.

Provided herein in another aspect is a genetically modified T cell and/or NK cell comprising:

a. a first engineered signaling polypeptide comprising at least one lymphoproliferative element; and
b. a second engineered signaling polypeptide comprising a chimeric antigen receptor comprising an antigen-specific targeting region (ASTR), a transmembrane domain, and an intracellular activating domain.

In any of the methods provided herein that include a mammalian packaging cell, including a replication incompetent recombinant retroviral particle packaging system aspect, or a method for making a replication incompetent recombinant retroviral particle, for example, the packageable RNA genome is encoded by a polynucleotide operably linked to a promoter, wherein said promoter is either constitutively active or inducible by either the first transactivator or the second transactivator. The packageable RNA genome can be encoded by a polynucleotide operably linked to a promoter, wherein said promoter is inducible by the second transactivator. A promoter used herein to drive expression of the first and/or second engineered signaling polypeptide, is typically active in target cells, for example lymphocytes, PBLs, T-cells and/or NK cells, but in illustrative embodiments, is not active in the packaging cell line. The second transactivator can regulate the expression of an activation element capable of binding to and activating the target cell. In any of the methods provided herein that include a mammalian packaging cell, including a replication incompetent recombinant retroviral particle packaging system aspect, or a method for making a replication incompetent recombinant retroviral particle, for example, the packageable RNA genome in some embodiments, expression of the packageable RNA genome can be regulated by the second trans activator.

Furthermore, the packageable RNA genome can comprise, from 5' to 3':

1.) a 5' long terminal repeat, or active fragment thereof;
2.) a nucleic acid sequence encoding a retroviral cis-acting RNA packaging element;
3.) a nucleic acid sequence encoding a first target polypeptide and/or a nucleic acid sequence encoding one or more (e.g. two or more) inhibitory RNA molecules;
4.) a promoter that is active in the target cell; and
5.) a 3' long terminal repeat, or active fragment thereof.

In some embodiments, the nucleic acid sequence encoding the first target polypeptide is in reverse orientation to an RNA encoding retroviral components for packaging and assembly and the 5' LTR.

In any of the methods provided herein that include a mammalian packaging cell, including a replication incompetent recombinant retroviral particle packaging system aspect, or a method for making a replication incompetent recombinant retroviral particle, for example, the first target polypeptide comprises a first engineered signaling polypeptide and wherein said first engineered signaling polypeptide comprises at least one lymphoproliferative element. The packageable RNA genome can further comprises a nucleic acid sequence encoding a second target polypeptide. The second target polypeptide can comprise a second engineered signaling polypeptide including a chimeric antigen receptor comprising:

1.) a first antigen-specific targeting region;
2.) a first transmembrane domain; and
3.) a first intracellular activating domain.

In any of the methods provided herein that include a mammalian packaging cell, including a replication incompetent recombinant retroviral particle packaging system aspect, or a method for making a replication incompetent recombinant retroviral particle, for example, the mammalian cell, for example the packaging cell can include a nucleic acid sequence encoding Vpx, for example on the second or an optional third transcriptional unit, or on an additional transcriptional unit that is operably linked to the first inducible promoter. The mammalian cell, which can be a packaging cell, can be a 293 cell.

In any of the methods provided herein that include a mammalian packaging cell, including a replication incompetent recombinant retroviral particle packaging system aspect, or a method for making a replication incompetent recombinant retroviral particle, a first ligand can be rapamycin and a second ligand can be tetracycline or doxorubicin or the first ligand can be tetracycline or doxorubicin and the second ligand can be rapamycin.

In some aspects, provided herein is a cell that has been transduced with any of the replication incompetent recombinant retroviral particles provided herein. The cell can be, for example, a lymphocyte, such as a T cell or NK cell. The cell in illustrative embodiments, is a human cell.

In one aspect provided herein, is a method of expanding modified T cells and/or NK cells in a subject, said method comprising:
  a.) contacting isolated resting T cells and/or resting NK cells obtained m said subject with the replication incompetent recombinant retroviral particle of any of the embodiments disclosed herein;
  b.) introducing the genetically modified T cells and/or NK cells into the subject; and
  c.) providing an effective amount of acyclovir, an acyclovir prodrug, penciclovir, or a penciclovir prodrug to said subject, wherein said modified T cells and/or NK cells proliferate in said subject upon administration of acyclovir, an acyclovir prodrug, penciclovir, or a penciclovir prodrug, thereby expanding the modified T cells and/or NK cells in the subject.

In another aspect, provided herein is a method of stopping the expansion, engraftment, and/or persistence of modified. T cells and/or NK cells in a subject, said method comprising:
  a.) contacting isolated quiescent T cell and/or NK cells obtained from said subject with the replication incompetent recombinant retroviral particles of any of the embodiments disclosed herein;
  b.) introducing the modified T cell and/or NK cells into the subject;
  c.) administering an effective amount of acyclovir, an acyclovir prodrug, penciclovir, or a penciclovir prodrug to said subject to expand the modified T cell and/or NK cells in the subject, wherein said modified T cell and/or NK cells proliferate in said subject upon administration of acyclovir, an acyclovir prodrug, penciclovir, or a penciclovir prodrug, thereby expanding the modified PBLs in the subject; and
  d.) stopping administration of acyclovir, an acyclovir prodrug, penciclovir, or a penciclovir prodrug, wherein said modified T cell and/or NK cells stop proliferating in said subject upon stopping administration of acyclovir, an acyclovir prodrug, penciclovir, or a penciclovir prodrug, thereby controlling the expansion, expansion, and/or persistence of the modified T cell and/or NK cells in the subject.

In another aspect, provided herein is a method of treating cancer in a subject, comprising:
  a. contacting isolated quiescent T cells and/or NK cells obtained from said subject the replication incompetent recombinant retroviral particles according to any of the embodiments disclosed herein;
  b. introducing the genetically modified T cells and/or NK cells into the subject; and
  c. administering an effective amount of acyclovir, an acyclovir prodrug, penciclovir, or a penciclovir prodrug to said subject to expand the modified. T cell and/or NK cells in the subject, wherein said modified T cell and/or NK cells proliferate in said subject upon administration of acyclovir, an acyclovir prodrug, penciclovir, or a penciclovir prodrug, and wherein the chimeric antigen receptor in said modified T cell and/or NK cells binds cancer cells in said subject, thereby treating cancer in the subject.

In another aspect, provided herein is a transduced T cell and/or NK cell, comprising a recombinant polynucleotide comprising one or more transcriptional units operatively linked to a promoter active in T cells and/or NK cells, wherein the one or more transcriptional units encode a first engineered signaling polypeptide regulated by a control element, wherein said first engineered signaling polypeptide comprises a constitutively active IL-7 receptor mutant, and wherein the control element is capable of binding, and/or designed and/or configured to bind, to a compound in vivo.

In another aspect, provided herein is a retroviral packaging system, comprising:
  a mammalian cell comprising:
    A. a first transactivator expressed from a constitutive promoter and capable of binding a first ligand and a first inducible promoter for affecting expression of a nucleic acid sequence operably linked thereto in the presence versus absence of the first ligand;
    B. a second transactivator capable of binding a second ligand and a second inducible promoter, and affecting expression of a nucleic acid sequence operably linked thereto in the presence versus absence of the second ligand; and
    C. a packageable RNA genome for a retroviral particle, wherein the first transactivator regulates expression of the second transactivator and a retroviral REV protein, wherein the second transactivator regulates expression of a gag polypeptide, a pol polypeptide, and one or more pseudotyping elements capable of binding to a target cell and facilitating membrane fusion thereto, and wherein the retroviral proteins are derived from a retrovirus. Embodiments of this aspect, can include any of the embodiments provided herein for the recited elements in other aspects.

In another aspect, provided herein is a method for making a replication incompetent recombinant retroviral particle, comprising:
  A. culturing a population of packaging cells to accumulate a first transactivator, wherein the packaging cells comprise the first transactivator expressed from a first constitutive promoter, wherein the first transactivator is capable of binding a first ligand and a first inducible promoter for affecting expression of a nucleic acid sequence operably linked thereto in the presence versus absence of the first ligand, and wherein expression of a second transactivator and a retroviral REV protein is regulated by the first transactivator;
  B. incubating the population of packaging cells comprising accumulated first transactivator in the presence of the first ligand to accumulate the second transactivator and the retroviral REV protein, wherein the second transactivator is capable of binding a second ligand and a second inducible promoter for affecting expression of a nucleic acid sequence operably linked thereto in the presence versus absence of the second ligand; and C. incubating the population of packaging cells comprising accumulated second transactivator and retroviral REV protein in the presence of the second ligand thereby inducing expression of a gag polypeptide, a pol polypeptide, and one or more pseudotyping elements, thereby making the replication incompetent recombinant retroviral particle, wherein a packageable RNA genome is encoded by a polynucleotide operably linked to a third promoter, wherein said third promoter is either constitutively active or inducible by either the first transactivator or the second transactivator, and wherein the one or more pseudotyping elements are capable of binding to a target cell and/or facilitating membrane fusion of the replication incompetent recombinant retroviral particle thereto.

In some embodiments of the retroviral packaging system and method for making a replication incompetent recombinant retroviral particles provided herein, the mammalian cell further comprises an activation element capable of binding to and activating a target cell, and the first transactivator regulates the expression of the activation element. The activation element is on the surface of the replication incompetent recombinant retroviral particle and wherein the activation element can include: a membrane-bound polypeptide capable of binding to CD3; and/or a membrane-bound polypeptide capable of binding to CD28. The membrane-bound polypeptide capable of binding to CD3 is a polypeptide capable of binding to CD3 that is fused to a heterologous GPI anchor attachment sequence and the membrane-bound polypeptide capable of binding to CD28 is a polypeptide capable of binding to CD28 that is fused to a heterologous GPI anchor attachment sequence. The membrane-bound polypeptide capable of binding to CD28 in some embodiments comprises CD80, CD86, or a functional fragment thereof that is capable of inducing CD28-mediated activation of Akt, such as the extracellular domain of CD80. In other embodiments, membrane-bound polypeptide capable of binding CD3 is an anti-CD3 scFv or an anti-CD3 scFvFc bound to a CD14 GPI anchor attachment sequence, and wherein the membrane-bound polypeptide capable of binding to CD28 is CD80, or an extracellular fragment thereof, bound to a CD16B GPI anchor attachment sequence.

In some embodiments of the retroviral packaging system and method for making a replication incompetent recombinant retroviral particle aspects provided herein, the mammalian cell further comprises a membrane-bound cytokine, and the first transactivator regulates the expression of the membrane-bound cytokine. The membrane-bound cytokine can be, for example, IL-7, IL-15, or an active fragment thereof. The membrane-bound cytokine in embodiments can be a fusion polypeptide of IL-7, or an active fragment thereof, and DAF. For example, the fusion polypeptide can comprise the DAF signal sequence and IL-7 without its signal sequence, followed by residues 36-525 of DAF.

In some embodiments of the retroviral packaging system and method for making a replication incompetent recombinant retroviral particle aspects provided herein, the mammalian cell comprises associated with its membrane, an activation element comprising an anti-CD3 scFV or an anti-CD3 scFvFc bound to a CD14 GPI anchor attachment sequence and a CD80 bound, or an extracellular fragment thereof to a CD16B GPI anchor attachment sequence; and membrane-bound cytokine comprising a fusion polypeptide of IL-7, or an active fragment thereof, and DAF comprising a GPI anchor attachment sequence, and wherein the first transactivator regulates the expression of each of the activation element and membrane-bound cytokine. In some embodiments, the IL-7, or an active fragment thereof, and DAF fusion, the anti-CD3 scFV or an anti-CD3 scFvFc, and the CD80, or extracellular fragment thereof, each comprises a DAF signal sequence.

In some embodiments of the retroviral packaging system and method for making a replication incompetent recombinant retroviral particle aspects provided herein, the mammalian cell further comprises a Vpx polypeptide. In these or other embodiments, the one or more pseudotyping elements comprise one or more viral polypeptides recognized by T cells. The one or more pseudotyping elements can comprise a Measles Virus F polypeptide, a Measles Virus H polypeptide, and/or a fragment thereof. In certain illustrative embodiments, the one or more pseudotyping elements are cytoplasmic domain deletion variants of a measles virus F polypeptide and/or a measles virus H polypeptide.

In some embodiments of the retroviral packaging system and method for making a replication incompetent recombinant retroviral particle aspects provided herein, the packageable RNA genome is encoded by a polynucleotide operably linked to a third promoter, wherein said third promoter is either constitutively active or inducible by either the first transactivator or the second transactivator. In illustrative embodiments, the packageable RNA genome is encoded by a polynucleotide operably linked to a third promoter, wherein said third promoter is inducible by the second transactivator.

In some embodiments of the retroviral packaging system and method for making a replication incompetent recombinant retroviral particle aspects provided herein, the packageable RNA genome further comprises, from 5' to 3':
a) a 5' long terminal repeat, or active fragment thereof;
b) a nucleic acid sequence encoding a retroviral cis-acting RNA packaging element;
c) a nucleic acid sequence encoding a first target polypeptide and an optional second target polypeptide;
d) a fourth promoter operably linked to the first target polypeptide and the optional second polypeptide, wherein said fourth promoter is active in the target cell but not active in the packaging cell line; and
e) a 3' long terminal repeat, or active fragment thereof.

In some embodiments of the retroviral packaging system and method for making a replication incompetent recombinant retroviral particle aspects provided herein including the construct immediately above, the third promoter promotes transcription or expression in the opposite direction from transcription or expression promoted from the fourth promoter.

In some embodiments of the retroviral packaging system and method for making a replication incompetent recombinant retroviral particle aspects provided herein, the packageable RNA genome encodes the replication incompetent recombinant retroviral particle of any embodiment disclosed in this disclosure, wherein the first target polypeptide and the second target polypeptide are the first engineered signaling polypeptide and the second engineered signaling polypeptide, respectively. In some embodiments, for example, the packageable RNA genome further comprises a control element operably linked to the nucleic acid encoding the first engineered signaling polypeptide or the second engineered signaling polypeptide. The control element in illustrative embodiments is a riboswitch. The riboswitch in illustrative embodiments is capable of binding a compound and the compound that binds the control element is a nucleoside analog, and the nucleoside analog can be an antiviral drug, for example acyclovir or penciclivir.

In some embodiments of the retroviral packaging system and method for making a replication incompetent recombinant retroviral particle aspects provided herein, the packageable RNA genome further comprises an intron comprising a polynucleotide encoding an inhibitory RNA molecules, such as, e.g., a miRNA or shRNA. The intron can be adjacent to and downstream of the fourth promoter.

In some embodiments of the retroviral packaging system and method for making a replication incompetent recombinant retroviral particle aspects provided herein, the target cell can be a T cell and/or an NK cell.

In some embodiments of the retroviral packaging system and method for making a replication incompetent recombinant retroviral particle aspects provided herein, the one or more pseudotyping elements comprise a vesicular stomatitis virus envelope protein (VSV-G), a feline endogenous virus (RD114) envelope protein, an oncoretroviral amphotropic envelope protein, or an oncoretroviral ecotropic envelope protein, or functional fragments thereof.

In some embodiments of the retroviral packaging system and method for making a replication incompetent recombinant retroviral particle aspects provided herein, the packageable RNA genome is 11,000 KB or less or 10,000 KB or less in size. In some embodiments of the retroviral packaging system and method for making a replication incompetent recombinant retroviral particle aspects provided herein, the first target polypeptide comprises a first engineered signaling polypeptide and wherein said first engineered signaling polypeptide comprises at least one lymphoproliferative element, and the second target polypeptide comprises a second engineered signaling polypeptide including a CAR.

In one aspect, provided herein is an isolated polynucleotide for regulating expression of a target polynucleotide, comprising:
a polynucleotide encoding a target polynucleotide operably linked to a promoter and a riboswitch, wherein the riboswitch comprises:
a.) an aptamer domain capable of binding a nucleoside analogue antiviral drug and having reduced binding to guanine or 2'-deoxyguanosine relative to the nucleoside analogue antiviral drug; and
b.) a function switching domain capable of regulating expression of the target polynucleotide, wherein binding of the nucleoside analogue by the aptamer domain induces or suppresses the expression regulating activity of the function switching domain, thereby regulating expression of the target polynucleotide.

In illustrative embodiments of any of the methods and compositions provided herein that include the control element can be a polynucleotide comprising a riboswitch. The riboswitch can be capable of binding a nucleoside analog and the compound that binds the control element is the nucleoside analog. The nucleoside analog can be an antiviral agent. The antiviral agent can be acyclovir or penciclovir. The riboswitch can preferentially bind acyclovir over penciclovir or preferentially bind penciclovir over acyclovir. The riboswitch can have reduced binding to the nucleoside analogue antiviral drug at temperatures above 37° C., 37.5° C., 38° C., 38.5° C., or 39° C., for example, above 39° C. The riboswitch can be between 35, 40, 45, and 50 nucleotides in length on the low end of the range and 60, 65, 70, 75, 80, 85, 90, 95, and 100 nucleotides in length on the high end of the range, for example, between 45 and 80 nucleotides in length. In illustrative embodiments of any of the methods and compositions provided herein that include the riboswitch, the target polynucleotide that is regulated by the riboswitch can include a region encoding a miRNA, an shRNA, and/or a polypeptide. The target polynucleotide can encode a lymphoproliferative element. The target polynucleotide can be operably linked to a promoter. The target polynucleotide can include a region encoding a polypeptide and the polypeptide can include a chimeric antigen receptor comprising an antigen-specific targeting region, a transmembrane domain, and an intracellular activating domain. In illustrative embodiments of any of the methods and compositions provided herein that include the riboswitch, the function switching domain can regulate an internal ribosome entry site, pre-mRNA splice donor accessibility in the viral gene construct, translation, termination of transcription, transcript degradation, miRNA expression, or shRNA expression, thereby regulating expression of the target polynucleotide. The riboswitch can include a ribozyme. In illustrative embodiments of any of the methods and compositions provided herein that include the riboswitch, the isolated polynucleotide can be a molecular cloning vector or an expression vector. In illustrative embodiments of any of the methods and compositions provided herein that include the riboswitch, the isolated polynucleotide can be integrated into a retroviral genome or into a mammalian chromosome, or fragment thereof.

Another aspect provided herein, is a method for genetically modifying and expanding lymphocytes of a subject, comprising:
A. collecting blood from the subject;
B. contacting T cells and/or NK cells from the blood of the subject ex vivo with replication incompetent recombinant retroviral particles comprising:
i. a pseudotyping element on its surface that is capable of binding to a T cell and/or NK cell and facilitating membrane fusion of the replication incompetent recombinant retroviral particle thereto, wherein said pseudotyping element comprises cytoplasmic domain deletion variants of a measles virus F polypeptide and/or a measles virus H polypeptide;
ii. a polypeptide capable of binding to CD3 and a polypeptide capable of binding to CD28, wherein said polypeptides are expressed on the surface of a replication incompetent recombinant retroviral particle and are capable of binding to a T cell and/or a NK cell and further wherein said polypeptides are not encoded by a polynucleotide in the replication incompetent recombinant retroviral particle; and
iii. a polynucleotide comprising one or more transcriptional units operatively linked to a promoter active in T cells and/or NK cells,
wherein the one or more transcriptional units encode a first engineered signaling polypeptide comprising a constitutively active IL-7 receptor mutant and a second engineered signaling polypeptide comprising a chimeric antigen receptor comprising an antigen-specific targeting region (ASTR), a transmembrane domain, and an intracellular activating domain,
wherein expression of the IL-7 receptor mutant is regulated by a riboswitch that binds a nucleoside analog antiviral drug, wherein binding of the nucleoside analog antiviral drug to the riboswitch increases expression of the IL-7 receptor mutant, and wherein said contacting results in at least some of the resting T cells and/or NK cells becoming genetically modified;

C. reintroducing the genetically modified T cells and/or NK cells into the subject; and D. exposing the genetically modified T cells and/or NK cells in vivo to the nucleoside analog antiviral drug to promote expansion of the T cells and/or NK cells, wherein the method between the collecting blood and the reintroducing the genetically modified T cells and/or NK cells is performed in no more than 24 hours and/or without requiring prior ex vivo stimulation, thereby genetically modifying and expanding lymphocytes of the subject.

In illustrative embodiments of this method aspect, the retroviral particle is a lentiviral particle. In another illustrative embodiment, the replication incompetent recombinant retroviral particle genetically modifies a T cell. In another illustrative embodiment, the polypeptide capable of binding to CD3 and the polypeptide capable of binding to CD28 are each fused to a heterologous GPI anchor attachment sequence. In some instances, the polypeptide capable of binding to CD3 can be anti-CD3 scFvFc or anti-CD3 scFv, and the polypeptide capable of binding to CD28 can be CD80. The anti-CD3 scFvFc or anti-CD3 scFv and CD80 can each be further fused to a DAF signal sequence. In another illustrative embodiment, the replication incompetent recombinant retroviral particles further comprise on their surface a fusion polypeptide comprising a cytokine covalently attached to DAF. In some instances, the cytokine can be IL-7 or IL-15, and the fusion polypeptide can comprise the DAF signal sequence, IL-7 without its signal sequence, and a fragment of DAF comprising a GPI anchor attachment sequence.

In another illustrative embodiment of this method aspect immediately above, the riboswitch further controls expression of the chimeric antigen receptor in a manner regulated by binding of the riboswitch to the nucleoside analog antiviral drug, which in some instances is acyclovir and/or penciclovir. In another embodiment, the constitutively active IL-7 can be replaced with a miRNA or shRNA or nucleic acids encoding an miRNA or shRNA and IL-7 can be present. In some instances, the miRNA or shRNA can be encoded by nucleic acids within an intron.

Another aspect provided herein is a replication incompetent recombinant retroviral particle, comprising:

A. a pseudotyping element on its surface that is capable of binding to a T cell and/or NK cell and facilitating membrane fusion of the replication incompetent recombinant retroviral particle thereto, wherein said pseudotyping element comprises cytoplasmic domain deletion variants of a measles virus F polypeptide and/or a measles virus H polypeptide;

B. a polynucleotide comprising one or more transcriptional units operatively linked to a promoter active in T cells and/or NK cells, wherein the one or more transcriptional units encode a first engineered signaling polypeptide comprising a chimeric antigen receptor comprising an antigen-specific targeting region, a transmembrane domain, and an intracellular activating domain, and a second engineered signaling polypeptide comprising a constitutively active IL-7 receptor mutant; wherein expression of the IL-7 receptor mutant is regulated by a riboswitch that binds a nucleoside analog antiviral drug, wherein binding of the nucleoside analog antiviral drug to the riboswitch increases expression of the IL-7 receptor mutant; and C. a polypeptide capable of binding to CD3 and a polypeptide capable of binding to CD28, wherein said polypeptides are expressed on the surface of a replication incompetent recombinant retroviral particle; are capable of binding to a T cell and/or NK cell; and are not encoded by a polynucleotide in the replication incompetent recombinant retroviral particle.

In illustrative embodiments of the replication incompetent recombinant retroviral particle aspect immediately above, the retroviral particle is a lentiviral particle. In other illustrative embodiments of the method, the polypeptide capable of binding to CD3 and the polypeptide capable of binding to CD28 are each fused to a heterologous GPI anchor attachment sequence. In some instances, the polypeptide capable of binding to CD3 can be anti-CD3 scFvFc or anti-CD3 scFv, and the polypeptide capable of binding to CD28 can be CD80. The anti-CD3 scFvFc or anti-CD3 scFv and CD80 can each be further fused to a DAF signal sequence. In another illustrative embodiment, the replication incompetent recombinant retroviral particles further comprise on their surface a fusion polypeptide comprising a cytokine covalently attached to DAF. In some instances, the cytokine can be IL-7 or IL-15, and the fusion polypeptide can comprise the DAF signal sequence, IL-7 without its signal sequence, and a fragment of DAF comprising a GPI anchor attachment sequence.

In another illustrative embodiment of the replication incompetent recombinant retroviral particle aspect immediately above, the riboswitch further controls expression of the chimeric antigen receptor in a manner regulated by binding of the riboswitch to the nucleoside analog antiviral drug, which in some instances is acyclovir and/or penciclovir. In another embodiment, the constitutively active IL-7 can be replaced with a miRNA or shRNA or nucleic acids encoding an miRNA or shRNA and IL-7 can be present. The miRNA or shRNA can be encoded by nucleic acids within an intron.

Another aspect provided herein is a method for making a replication incompetent recombinant retroviral particle, comprising:

A. culturing a population of packaging cells to accumulate a first transactivator, wherein the packaging cells comprise the first transactivator expressed from a constitutive promoter, wherein the first transactivator is capable of binding a first ligand and a first inducible promoter for affecting expression of a nucleic acid sequence operably linked thereto in the presence versus absence of the first ligand, and wherein expression of a second transactivator and a retroviral REV protein is regulated by the first transactivator;

B. incubating the population of packaging cells comprising accumulated first transactivator in the presence of the first ligand to accumulate the second transactivator and the retroviral REV protein and an activation element typically on their surface, comprising a polypeptide capable of binding to CD3 and a polypeptide capable of binding to CD28, wherein the second transactivator is capable of binding a second ligand and a second inducible promoter for affecting expression of a nucleic acid sequence operably linked thereto in the presence versus absence of the second ligand; and C. incubating the population of packaging cells comprising accumulated second transactivator and retroviral REV protein in the presence of the second ligand thereby inducing expression of a gag polypeptide, a pol polypeptide and a pseudotyping element capable of binding to a T cell and/or an NK cell and facilitating membrane fusion of the replication incompetent recombinant retroviral particle thereto, wherein said pseudotyping element comprises cytoplasmic domain deletion variants of a measles virus F polypeptide and/or a measles virus H polypeptide, wherein a packageable RNA genome is encoded by a polynucleotide operably linked to a third promoter and wherein said promoter is inducible by the second transactivator, wherein the packageable RNA genome comprises, from 5' to 3':

i. a 5' long terminal repeat, or active fragment thereof;
ii. a nucleic acid sequence encoding a retroviral cis-acting RNA packaging element;
iii. a nucleic acid sequence encoding a first engineered signaling polypeptide comprising a chimeric antigen receptor and a second engineered signaling polypeptide comprising a constitutively active IL-7 receptor mutant separated by a cleavage signal;
iv. a fourth promoter that is active in the T cell and/or the NK cell; and
v. a 3' long terminal repeat, or active fragment thereof, and wherein the packageable RNA genome further comprises a riboswitch that binds a nucleoside analog antiviral drug, wherein binding of the riboswitch to the nucleoside analog antiviral drug to the riboswitch increases expression of the IL-7 receptor mutant, thereby making the replication incompetent recombinant retroviral particle.

In an illustrative embodiment of the method, the riboswitch further controls expression of the chimeric antigen receptor in a manner regulated by binding of the riboswitch to the nucleoside analog antiviral drug. In another illustrative embodiment, the nucleoside analog antiviral drug is acyclovir and/or penciclovir. In another illustrative embodiment, the packageable RNA genome further comprises a recognition domain, wherein the recognition domain comprises a polypeptide that is recognized by an antibody that recognizes EGFR or an epitope thereof. In another illustrative embodiment, the first ligand is rapamycin and the second ligand is tetracycline or doxorubicin or the first ligand is tetracycline or doxorubicin and the second ligand is rapamycin. In another illustrative embodiment, the packaging cell further comprises a nucleic acid sequence encoding Vpx on the second or an optional third transcriptional unit, or on an additional transcriptional unit that is operably linked to the first inducible promoter. In another illustrative embodiment, the polypeptide capable of binding to CD3 and the polypeptide capable of binding to CD28 are each fused to a heterologous GPI anchor attachment sequence. In some instances, the polypeptide capable of binding to CD3 can be anti-CD3 scFvFc or anti-CD3 scFv, or anti-CD3 scFv, and the polypeptide capable of binding to CD28 can be CD80. The anti-CD3 scFvFc or anti-CD3 scFv and CD80 can each be further fused to a DAF signal sequence. In another illustrative embodiment, expression of a fusion polypeptide comprising a cytokine covalently attached to DAF is also induced. In some instances, the cytokine can be IL-7 or IL-15, and the fusion polypeptide can comprise the DAF signal sequence, IL-7 without its signal sequence, and a fragment of DAF comprising a GPI anchor attachment sequence. In another illustrative embodiment, the riboswitch further controls expression of the chimeric antigen receptor in a manner regulated by binding of the riboswitch to the nucleoside analog antiviral drug, which in some instances is acyclovir and/or penciclovir. In another embodiment, the constitutively active IL-7 can be replaced with a miRNA or shRNA or nucleic acids encoding an miRNA or shRNA and IL-7 can be present. The miRNA or shRNA can be encoded by nucleic acids within an intron. In an illustrative embodiment, the retroviral particle is a lentiviral particle.

Provided in another aspect herein is a genetically modified lymphocyte comprising:
A. a first engineered signaling polypeptide comprising a constitutively active IL-7 receptor mutant; and
B. a second engineered signaling polypeptide comprising a chimeric antigen receptor comprising an antigen-specific targeting region (ASTR), a transmembrane domain, and an intracellular activating domain.

In illustrative embodiments of the genetically modified lymphocyte aspect above, the genetically modified lymphocyte is a T cell and/or an NK cell. In certain embodiments, the lymphocyte is a T cell. In another illustrative embodiment, expression of said first engineered signaling polypeptide and/or said second engineered signaling polypeptide is regulated by a riboswitch that binds a nucleoside analog antiviral drug, wherein binding of the nucleoside analog antiviral drug to the riboswitch increases expression of the IL-7 receptor mutant. In another embodiment, the genetically modified lymphocytes express at least one (e.g. two) inhibitory RNA molecules, such as, e.g. a miRNA or an shRNA. The inhibitory RNA molecules can further be encoded by nucleic acids within an intron.

Provided in another aspect herein is a genetically modified T cell and/or NK cell comprising:
a. a first engineered signaling polypeptide comprising at least one lymphoproliferative element; and
b. a second engineered signaling polypeptide comprising a chimeric antigen receptor comprising an antigen-specific targeting region (ASTR), a transmembrane domain, and an intracellular activating domain.

In illustrative embodiments of the genetically modified T cell and/or NK cell aspect, the lymphoproliferative element is constitutively active, and in some instances, is a constitutively active mutated IL-7 receptor or a fragment thereof. In another illustrative embodiment, expression of the first engineered signaling polypeptide and/or the second engineered signaling polypeptide is regulated by a control element. In some instances, the control element is a polynucleotide comprising a riboswitch. In some instances, the riboswitch is capable of binding a nucleoside analog and when the nucleoside analog is present, the first engineered signaling polypeptide and/or the second engineered polypeptide are expressed. In other illustrative embodiments, the genetically modified T cell and/or NK cell has on its surface an activation element, a pseudotyping element, and/or a membrane-bound cytokine. In some instances, the activation element comprises a membrane-bound polypeptide capable of binding to CD3; and/or a membrane-bound polypeptide capable of binding to CD28. In a certain embodiment, the activation element comprises anti-CD3 scFV or an anti-CD3 scFvFc fused to a heterologous GPI anchor attachment sequence and/or CD80 fused to a heterologous GPI anchor attachment sequence. In an illustrative embodiment, the pseudotyping element comprises a Measles Virus F polypeptide, a Measles Virus H polypeptide, and/or cytoplasmic domain deletion variants of a measles virus F polypeptide and/or a measles virus H polypeptide. In other embodiments, the membrane-bound cytokine is a fusion polypeptide comprising IL-7, or a fragment thereof, fused to DAF, or a fragment thereof comprising a GPI anchor attachment sequence.

In one aspect, provided herein is a method for genetically modifying and expanding lymphocytes of a subject, comprising:

A. contacting resting T cells and/or NK cells of the subject ex vivo, typically without requiring prior ex vivo stimulation, with replication incompetent recombinant retroviral particles comprising:
   i. a pseudotyping element on its surface that is capable of binding to a T cell and/or NK cell and facilitating membrane fusion of the replication incompetent recombinant retroviral particle thereto; and
   ii. a polynucleotide comprising one or more transcriptional units operatively linked to a promoter active in T cells and/or NK cells, wherein the one or more transcriptional units encode a first engineered signaling polypeptide regulated by a control element, wherein said first engineered signaling polypeptide comprises at least one lymphoproliferative element and optionally encode a second engineered signaling polypeptide optionally regulated by a control element, wherein the second engineered signaling polypeptide comprises an intracellular activating domain and optionally other components of a CAR, wherein said contacting facilitates transduction of at least some of the resting T cells and/or NK cells by the replication incompetent recombinant retroviral particles, thereby producing genetically modified T cells and/or NK cells;
B. introducing the genetically modified T cells and/or NK cells into the subject; and
exposing the genetically modified T cells and/or NK cells in vivo to a compound that acts as the control element to affect expression of the first engineered signaling polypeptide and promote expansion, engraftment, and/or persistence of the lymphocytes in vivo, thereby genetically modifying and expanding lymphocytes of the subject.

In illustrative embodiments, the transduction is carried out without ex vivo stimulation. In illustrative embodiments, the compound is a molecular chaperone, such as a small molecular chaperone. In illustrative embodiments, binding of the molecular chaperone to the lymphoproliferative element increases the proliferative activity of the lymphoproliferative element. The molecular chaperone can be administered to the subject before the blood is collected, during the contacting, and/or after the T cells and/or NK cells are introduced into the subject. It will be understood with this aspect where the compound is the control element, that such compound typically is capable of binding to a lymphoproliferative element and/or a component of a CAR, and does bind to such lymphoproliferative element or car component during performance of the method. Other embodiments and teaches related to methods provided herein that include transfecting a T cell and/or an NK cell with a replication incompetent recombinant retroviral particle, apply to this aspect, including a molecular chaperone embodiment, as well.

In another aspect, provided herein is a method for selecting a microenvironment restricted antigen-specific targeting region, comprising panning a polypeptide display library by:
   a. subjecting polypeptides of the polypeptide display library to a binding assay under a normal physiological condition and a binding assay under an aberrant condition; and
   b. selecting a polypeptide which exhibits an increase in binding activity at the aberrant condition compared to the physiological condition, thereby selecting the microenvironment restricted antigen specific targeting region.

In another aspect, provided herein is a method for isolating a microenvironment restricted antigen-specific targeting region, comprising:
panning a polypeptide library by:
   a) contacting the polypeptide library under aberrant conditions with a target antigen bound to a solid support, wherein clones expressing polypeptides that bind the target antigen remain bound to the solid support through the target antigen;
   b) incubating the solid supports with bound polypeptides under physiological conditions; and
   c) collecting clones that elute from the solid support under the physiological conditions, thereby isolating the microenvironment restricted antigen-specific targeting region.

In another aspect, provided herein is a chimeric antigen receptor for binding a target antigen, comprising:
   a) at least one microenvironment restricted antigen specific targeting region selected by panning a polypeptide library and having an increase in activity in a binding assay at an aberrant condition compared to a normal physiological condition;
   b) a transmembrane domain; and
   c). an intracellular activating domain.

In another aspect, provided herein is a chimeric antigen receptor for binding a target antigen, comprising:
   a) a microenvironment restricted antigen-specific targeting region that exhibits an increase in binding to the target antigen in an aberrant condition compared to a normal physiological environment, wherein the antigen-specific targeting region binds to the target;
   b) a transmembrane domain; and
   c) an intracellular activating domain.

In illustrative embodiments of any of the methods and compositions provided herein that include a microenvironment restricted antigen specific targeting region (ASTR), the ASTR can have at least a 5%, 10%, 15%, 20%, 25%, 30%, 40%, 50%, 60%, 70%, 80%, 90%, or 100% increase in binding affinity to the target antigen in the assay at the aberrant condition compared to the normal condition. The aberrant conditions can be hypoxia, an acidic pH, a higher concentration of lactic acid, a higher concentration of hyaluronan, a higher concentration of albumin, a higher concentration of adenosine, a higher concentration of R-2-hydroxyglutarate, a higher concentration of PAD enzymes, a higher pressure, a higher oxidation, and a lower nutrient availability. The microenvironment restricted ASTR can exhibit an increase in antigen binding at a pH of 6.7 as compared to a pH of 7.4. The microenvironment restricted ASTR can exhibit an increase in antigen binding in a tumor environment and/or in an in vitro tumor surrogate assay condition, relative to a corresponding physiological condition. The target can be 4-1BB, ST4, adenocarcinoma antigen, alpha-fetoprotein, AXL, BAFF, B-lymphoma cell, C242 antigen, CA-125, carbonic anhydrase 9 (CA-IX), C-MET, CCR4, CD 152, CD 19, CD20, CD200, CD22, CD221, CD23 (IgE receptor), CD28, CD30 (TNFRSF8), CD33, CD4, CD40, CD44 v6, CD51, CD52, CD56, CD74, CD80, CEA, CNT0888, CTLA-4, DR5, EGFR, EpCAM, CD3, FAP, fibronectin extra domain-B, folate receptor 1, GD2, GD3 ganglioside, glycoprotein 75, GPNMB, HER2/neu, HGF, human scatter factor receptor kinase, IGF-1 receptor, IGF-I, IgG1, L1-CAM, IL-13, IL-6, insulin-like growth factor I receptor, integrin nSP1, integrin nvP3, MORAb-009, MS4A1, MUC1, mucin CanAg, Nglycolyl-neuraminic acid, NPC-1C, PDGF-R a, PDL192, phosphatidylserine, prostatic carcinoma cells, RANKL, RON, ROR1, ROR2 SCH 900105, SDC1, SLAMF7, TAG-72, tenascin C, TGF beta 2, TGF-P, TRAIL-R1, TRAIL-R2, tumor antigen CTAA16. 88, VEGF-A, VEGFR-1, VEGFR2, and vimentin. The ASTR can be an antibody, an antigen, a ligand, a receptor binding domain of a ligand, a receptor, a ligand binding domain of a receptor, or an affibody. The ASTR can be a full-length antibody, a single-chain antibody, an Fab fragment, an Fab' fragment, an (Fab')$_2$ fragment, an Fv fragment, and a divalent single-chain antibody or a diabody. The ASTR can include a heavy chain and a light chain from an antibody. The antibody can be a single-chain variable fragment. In some embodiments, the heavy and light chains can be separated by a linker, wherein the linker is between 6 and 100 amino acids in length. In some embodiments, the heavy chain can be positioned N-terminal to the light chain on the chimeric antigen receptor and in some embodiments the light chain can be positioned N-terminal to the heavy chain on the chimeric antigen receptor.

In illustrative embodiments of any of the methods that include a polypeptide display library, the polypeptide display library can be a phage display library or a yeast display library. The polypeptide display library can be an antibody display library. The antibody display library can be a human or humanized antibody display library. The antibody display library can be a naïve library. The methods can include infecting bacterial cells with the collected phage to generate a refined phage display library, and repeating the contacting, incubating, and collecting for 1 to 1000 cycles, using the refined phage display library generated from a previous cycle.

In illustrative embodiments of any of the methods provided herein that include isolating or selecting a microenvironment restricted ASTR, the method can include determining the nucleotide sequence of a polynucleotide encoding the microenvironment restricted antigen-specific targeting region, thereby determining the polypeptide sequence of the microenvironment restricted ASTR. The methods can include making a microenvironment restricted biologic chimeric antigen receptor by generating a polynucleotide that encodes a polypeptide comprising the microenvironment restricted ASTR, a transmembrane domain, and an intracellular activating domain. The library can be a single chain antibody library.

The methods for isolating a microenvironment restricted ASTR can include the panning is repeated for between 1 and 1000 times. The methods for isolating a microenvironment restricted ASTR can be performed without mutating polynucleotides encoding the isolated microenvironment restricted antigen-specific targeting region between rounds of panning. The methods for isolating a microenvironment restricted ASTR can be performed by culturing, high fidelity amplifying, and/or diluting polynucleotides encoding antigen-specific targeting regions, or host organisms including the same, between rounds of panning. The methods can include, prior to repeating, mutagenizing the selected and/or isolated microenvironment restricted antigen-specific targeting region. The methods can include determining the sequence of the selected and/or isolated microenvironment restricted antigen-specific targeting region, and/or a polynucleotide encoding the same after one or more round of panning via long read DNA sequencing. The methods can include determining the sequence before and after expansion of the isolated microenvironment restricted ASTR. The methods for isolating a microenvironment restricted ASTR can be performed without repeating the panning. The methods for isolating a microenvironment restricted ASTR can be performed without mutating a polynucleotide encoding the isolated microenvironment restricted ASTR after the microenvironment restricted ASTR is isolated.

In illustrative embodiments of any of the compositions provided herein that include a chimeric antigen receptor with a microenvironment restricted ASTR, the microenvironment restricted ASTR can be identified by panning an antibody library. In some embodiments, the microenvironment restricted ASTR is identified by panning a phage display or a yeast display library. In some embodiments, the chimeric antigen receptor comprises a bispecific ASTR.

Provided herein in another aspect is a transduced T cell and/or NK cell, comprising a recombinant polynucleotide comprising one or more transcriptional units operatively linked to a promoter active in T cells and/or NK cells, wherein the one or more transcriptional units encode a first engineered signaling polypeptide regulated by a control element, wherein said first engineered signaling polypeptide comprises a constitutively active IL-7 receptor mutant, and wherein the control element is capable of binding to a compound in vitro or in vivo or is configured to bind a compound in vivo.

Provided herein in another aspect is a replication incompetent recombinant retroviral particle, comprising a recombinant polynucleotide comprising one or more transcriptional units operatively linked to a promoter active in T cells and/or NK cells, wherein the one or more transcriptional units encode a first engineered signaling polypeptide regulated by a control element, which can be an in vivo control element, wherein said first engineered signaling polypeptide comprises a constitutively active IL-7 receptor mutant, and wherein the control element is capable of binding to a compound in vivo or is configured to bind a compound in vivo.

Provided herein in another aspect is a method of transducing a T cell and/or NK cell, comprising contacting a T cell and/or NK cell, with a replication incompetent recombinant retroviral particle comprising a recombinant polynucleotide comprising one or more transcriptional units operatively linked to a promoter active in T cells and/or NK cells, wherein the one or more transcriptional units encode a first engineered signaling polypeptide regulated by a control element, wherein said first engineered signaling polypeptide comprises a constitutively active IL-7 receptor mutant, and wherein the in vivo control element is capable of binding to a compound in vivo or in vitro, under transduction conditions, thereby transducing the T cell and/or NK cell.

In illustrative embodiments of the transduced T cell and/or NK cell aspects, the replication incompetent recombinant retroviral particle aspects, and the method aspects, provided in the preceding paragraphs, the recombinant polynucleotide further comprises a transcriptional unit that encodes a second engineered signaling polypeptide comprising a first chimeric antigen receptor comprising an antigen-specific targeting region (ASTR), a transmembrane domain, and an intracellular activating domain. In other illustrative embodiments, the lymphoproliferative element comprises a mutated IL-7 receptor or a fragment thereof. In other illustrative embodiments, the control element is a polynucleotide comprising a riboswitch. In some instances, the riboswitch is capable of binding a nucleoside analog and the compound that binds the control element is the nucleoside analog. In some instances, the nucleoside analog is an antiviral agent such as for example acyclovir or penciclovir. In certain embodiments, the antiviral agent is acyclovir. In other illustrative embodiments, the constitutively active IL-7 receptor mutant is fused to EGFR or an epitope thereof. In other illustrative embodiments, the constitutively active IL-7 receptor mutant comprises an eTag. In other illustrative embodiments, the constitutively active IL-7 receptor mutant comprises a PPCL insertion. In other illustrative embodiments, the constitutively active IL-7 receptor mutant comprises a PPCL insertion at a position equivalent to position 243 in a wild-type human IL-8 receptor. In other illustrative embodiments, the transduced T cell or NK cell is a transduced T cell.

In another aspect, provided herein is a method for modulating binding of a microenvironment restricted biologic chimeric antigen receptor (MRB-CAR)-expressing T cell or NK cell to a cell expressing a cognate antigen of the MRB-CAR in a subject, including:
  a. introducing a T cell and/or NK cell including a nucleic acid encoding the MRB-CAR into the subject, wherein after the introducing, the T cell and/or the NK cell including the nucleic acid encoding the MRB-CAR expresses the MRB-CAR and binds to the cell expressing the cognate antigen in the subject; and
  b. administering a pharmacologic agent to the subject in sufficient amount to increase blood pH and/or pH of a tissue and/or pH of a microenvironment, wherein the administering is performed before, during, or after the introducing, and wherein the increased pH of the blood, the tissue, and/or the microenvironment modulates binding of the MRB-CAR expressing T cell and/or NK cell to the cell expressing the cognate antigen in the blood, the tissue, or the microenvironment with the increased pH.

In another aspect, provided herein is a method for alleviating on target off tumor toxicity in a subject, including:
  a. introducing a nucleic acid encoding an microenvironment restricted biologic chimeric antigen receptor (MRB-CAR) into a T cell or NK cell of the subject to produce a T cell and/or NK cell including a nucleic acid encoding the MRB-CAR;
  b. introducing the T cell and/or NK cell including the nucleic acid encoding the MRB-CAR into the subject, wherein after the introducing, the T cell and/or the NK cell including the nucleic acid encoding the MRB-CAR expresses the MRB-CAR and binds to the cell expressing the cognate antigen in the subject; and
  c. administering a pharmacologic agent to the subject in sufficient amount to increase blood pH and/or pH of a tissue and/or pH of a microenvironment to modulate binding of the MRB-CAR to its cognate antigen in the blood, the tissue, and/or the microenvironment with the increased pH, thereby alleviating on target off tumor toxicity in the subject.

In some embodiments, the nucleic acid can be a vector. In illustrative embodiments, the vector is a retroviral particle.

In another aspect, provided herein is a method for controlling binding of a T cell and/or NK cell to a target mammalian cell, including:
  a. contacting the target mammalian cell with the T cell and/or NK cell in a microenvironment, wherein the target mammalian cell expresses a cognate antigen, and the T cell and/or NK cell expresses a microenvironment restricted biologic chimeric antigen receptor (MRB-CAR) that binds to the cognate antigen differentially at pH 6.7 as compared to pH 7.4; and
  b. increasing the pH of the microenvironment by introducing a pharmacologic agent to the microenvironment in sufficient amount, thereby controlling the binding of the T cell and/or NK cell to the target mammalian cell.

In another aspect, provided herein is a method for controlling the binding of a T cell and/or NK cell expressing a microenvironment restricted biologic chimeric antigen receptor (MRB-CAR) to a target mammalian cell in a subject in vivo, including administering a pH-modulating pharmacologic agent to the subject through an effective dosing regimen that increases the pH of a microenvironment within the subject, wherein the subject includes the T cell and/or the NK cell expressing the MRB-CAR, wherein the MRB-CAR binds to its cognate antigen differentially at pH 6.7 as compared to pH 7.4, wherein the microenvironment include the target mammalian cell, wherein the target mammalian cell expresses the cognate antigen on its surface, and wherein the T cell and/or NK cell binds to the target mammalian cell differentially before versus after the pH of the microenvironment is increased, thereby controlling the binding of the T cell and/or NK cell to the target mammalian cell in a subject in vivo.

In any of the aspects provided immediately above that include a pharmacologic agent and an MRB-CAR, the MRB-CAR can have reduced binding to its cognate antigen at one pH than at a different pH. In illustrative embodiments where illustrative pH values for differential binding of an MRB-CAR are not already provided in the broadest aspect and alternatively for other embodiments in place of those values for such aspects, the MRB-CAR can have reduced binding at a higher pH than at a lower pH. For example, the MRB-CAR can have reduced binding to its cognate antigen at a pH above 7.0, 7.1, 7.2, 7.3, 7.4, or 7.5 than at a pH below 6.4, 6.5, 6.6, 6.7, 6.8, 6.9, or 7.0. In other embodiments, the MRB-CAR can have reduced binding at a higher pH than at a lower pH. For example, the MRB-CAR can have reduced binding to its cognate antigen at a pH below 6.4, 6.5, 6.6, 6.7, 6.8, 6.9, or 7.0 than at a pH above 7.0, 7.1, 7.2, 7.3, 7.4, or 7.5. In some illustrative embodiments, the MRB-CAR exhibits increased binding at a pH of 6.5 to 6.7 compared to pH 7.4 to 7.6. In other illustrative embodiments, the MRB-CAR exhibits increased binding at a pH of 6.7 compared to a pH of 7.4. In other embodiments, the MRB-CAR exhibits increased binding in the pH of a tumor compared to the pH of blood. In some embodiments, the MRB-CAR can include an antigen-specific targeting region, a stalk, and an intracellular activating domain. In some embodiments, the MRB-CAR can also include a co-stimulatory domain. In some embodiments, the MRB-CAR can bind to a tumor associated antigen.

In any of the aspects provided immediately above that include a pharmacologic agent and an MRB-CAR, the pH of the microenvironment can be increased from a pH below 7.0 to a pH above 7.0. For example, the pH can be increased from a pH below 6.4, 6.5, 6.6, 6.7, 6.8, 6.9, or 7.0 to a pH above 7.0, 7.1, 7.2, 7.3, or 7.4. In some embodiments, the MRB-CAR can bind to the cognate antigen at the increased pH but not a pH of the microenvironment before introducing the pharmacologic agent. In certain embodiments, the pH can be increased from below 7.0 to a pH of 7.1 to 8.0 or to a pH of 7.1 to 7.8 or to a pH of 7.2 to 7.8 or a pH of 7.2 to 7.6 or a pH of 7.3 to 7.6 or to a pH of 7.4 to 7.8 or to a pH of 7.4 to 7.6. Such an increase in pH can occur for less than 1, 2, 4, 6, 8, 12, or 24 hours or for more than 1, 2, 4, 6, 8, 12 or 24 hours depending on the type and dose of pharmacologic agent administered. In certain embodiments, the pharmacologic agent is administered such that the pH remains above 7.0, 7.1, 7.2, 7.3, 7.4, or 7.5; or between 7.0, 7.1, 7.2, 7.3 on the low end of the range and 7.4, 7.5, 7.6, 7.7, or 7.8 on the high end of the range, in the target tissue, such as a tumor, and for example in at least a surface of a target tissue (e.g. tumor) microenvironment, in at least a portion of a target tissue (e.g. tumor) microenvironment, and in illustrative embodiments throughout a target tissue (e.g. tumor) microenvironment.

In any of the aspects provided immediately above that include a pharmacologic agent and an MRB-CAR, the microenvironment can be an in vivo microenvironment, such as a tumor, a tissue, a non-tumor tissue, a normal tissue, or a tissue that has undergone a transient shift in pH. For example, tissues that typically undergo transient shifts in pH include a muscle tissue in anaerobic conditions or muscle tissue undergoing exercise or an inflamed tissue or a tissue experiencing inflammation. In some embodiments that include a target mammalian cell, the target mammalian cell can be a tumor cell or a non-tumor or normal cell.

In any of the aspects provided immediately above that include a pharmacologic agent and an MRB-CAR, the pharmacologic agent can be sodium bicarbonate, tris-hydroxylmethyl aminomethane, an equimolar hypertonic solution of sodium bicarbonate and sodium carbonate, or proton pump inhibitors such esomeprazole, esomeprazole and naproxen, lansoprazole, omeprazole, and rabeprazole.

Nucleic acids encoding MRB-CARs of the present disclosure can be introduced through various means into T cells and/or NK cells. In any of the aspects provided immediately above that include a pharmacologic agent and an MRB-CAR, the introducing step or steps can be performed by
a. contacting resting T cells and/or NK cells of the subject ex vivo without requiring prior ex vivo stimulation, with a replication incompetent recombinant retroviral particle including:
  i. one or more pseudotyping elements on its surface that is capable of binding to a T cell and/or NK cell and facilitating membrane fusion of the replication incompetent recombinant retroviral particle thereto; and
  ii. a polynucleotide including a transcriptional unit operatively linked to a promoter active in T cells and/or NK cells, that encodes the MRB-CAR, wherein said contacting facilitates transduction of at least some of the resting T cells and/or NK cells by the replication incompetent recombinant retroviral particle, thereby producing T cells and/or NK cells capable of expressing the MRB-CAR, typically because they now include the polynucleotide that includes a transcriptional unit operatively linked to a promoter active in T cells and/or NK cells, that encodes the MRB-CAR; and
b. introducing the T cells and/or NK cells capable of expressing the MRB-CAR into the subject.

In some embodiments, the T cells and/or NK cells can undergo 2, 3, 4, 5, 6, 7, 8, 9, or 10 or fewer cells divisions ex vivo prior to being introduced. In some embodiments, the resting T cells and/or resting NK cells can be in contact with the replication incompetent recombinant retroviral particle for between 1, 2, 3, 4, 5, 6, 7, 8, 9, 10, 11, or 12 hours on the low end of the range and 6, 7, 8, 9, 10, 11, 12, 13, 14, 15, 16, 17, 18, 19, 20, 21, 22, 23 or 24 hours on the high end of the range, where for a given range a low value is below a high value. In some embodiments, the resting T cells and/or resting NK cells can be from blood which has been collected from the subject. In illustrative embodiments, no more than 12, 15. 16, 18, 21, 24, 30, 36, 42, or 48 hours can pass between the time the blood is collected from the subject and the time the T cells and/or resting NK cells capable of expressing the MRB-CAR are introduced into the subject. In some embodiments, all the steps after collecting the blood and before introducing the T cells and/or resting NK cells capable of expressing the MRB-CAR can be performed in a closed system.

In any embodiment provided immediately above that includes a replication incompetent recombinant retroviral particle in a method that includes an MRB-CAR and a pharmacologic agent, the polynucleotide that includes a transcriptional unit operatively linked to a promoter active in T cells and/or NK cells that encodes the MRB-CAR is taken up by the T cell(s) and/or NK cell(s) such that such the cell(s) is capable of expressing the MRB-CAR. In illustrative embodiments, the T cell(s) and/or NK cell(s) integrate the polynucleotide into their genome.

In any embodiment provided immediately above that includes a replication incompetent recombinant retroviral particle in a method that includes an MRB-CAR and a pharmacologic agent, the replication incompetent recombinant retroviral particle can further include an activation element on its surface, such as an activation element that is capable of activating a resting T cell and/or resting NK cell. In some embodiments, the activation element can include any activation element provided in this disclosure. In illustrative embodiments, the activation element can include a membrane-bound polypeptide capable of binding to CD3 and/or a membrane-bound polypeptide capable of binding to CD28. In any of the embodiments that includes an activation element on the surface of replication incompetent recombinant retroviral particle in a method that includes an MRB-CAR and a pharmacologic agent, one or more of the membrane-bound polypeptides can be fused to a heterologous GPI anchor attachment sequence. In some embodiments, the membrane-bound polypeptide capable of binding CD3 and/or the membrane-bound polypeptide capable of binding CD28 can be an scFv or scFvFc that binds CD3 or CD28, respectively. In illustrative embodiments, the membrane-bound polypeptide capable of binding CD3 can be an scFv or scFvFc that binds CD3. In some embodiments, the membrane-bound polypeptide capable of binding CD28 can be the extracellular domains of CD80, CD86, or a functional fragment thereof that is capable of inducing CD28-mediated activation of Akt.

In any embodiment provided immediately above that includes a replication incompetent recombinant retroviral particle in a method that includes an MRB-CAR and a pharmacologic agent, the polynucleotide encoding the MRB-CAR can be operably linked to a riboswitch. In some embodiments, the riboswitch can be capable of binding a nucleoside analog. In some embodiments, the nucleoside analog can be an antiviral drug, such as acyclovir or penciclovir.

In any embodiment provided immediately above that includes a replication incompetent recombinant retroviral particle in a method that includes an MRB-CAR and a pharmacologic agent, the replication incompetent recombinant retroviral particle can include on its surface a recognition domain of a monoclonal antibody approved biologic. For example, the recognition domain can include a polypeptide that is recognized by an antibody that recognizes EGFR, or an epitope thereof.

In any embodiment provided immediately above that includes a replication incompetent recombinant retroviral particle in a method that includes an MRB-CAR and a pharmacologic agent, the one or more pseudotyping elements can include a Measles Virus F polypeptide, a Measles Virus H polypeptide, and/or a fragment thereof that retains the ability to bind to resting T cells and/or resting NK cells. In some embodiments, the one or more pseudotyping elements can include a VSV-G polypeptide. In some embodiments, the replication incompetent recombinant retroviral particle can include on its surface a fusion polypeptide of IL-7, or an active fragment thereof, and DAF including a GPI anchor attachment sequence.

In any embodiment provided immediately above that includes a replication incompetent recombinant retroviral particle in a method that includes an MRB-CAR and a pharmacologic agent, the genome of the replication incompetent recombinant retroviral particle can encode one or more inhibitory RNA molecules, for example two or more, three or more, four or more, five or more, or six or more inhibitory RNA molecules. In some embodiments, the inhibitory RNA molecules can be directed against different RNA targets. In some embodiments, the inhibitory RNA molecules can be located within an intron. In some embodiments, the inhibitory RNA molecules are capable of forming a 5' stem and a 3' stem that form a 18-25 nucleotide RNA duplex. In some embodiments, at least one of the inhibitory RNA molecules can include from 5' to 3' orientation: a 5' microRNA flanking sequence, a 5' stem, a loop, a 3' stem, and a 3' microRNA flanking sequence, wherein the 5' stem or the 3' stem is capable of binding to an RNA target. In further embodiments, the 5' stem can 18 to 25 nucleotides in length, wherein said 3' stem is 18 to 25 nucleotides in length, wherein said loop is 3 to 40 nucleotides in length. In some embodiments, one or more of the 5' microRNA flanking sequence and the 3' microRNA flanking sequence can be derived from a naturally occurring miRNA, such as mIR-155.

In another aspect, provided herein is a pH-modulating pharmacologic agent for use in a method for controlling the binding of a T cell and/or NK cell to a target mammalian cell in a subject in vivo, including administering the pH-modulating pharmacologic agent to the subject through an effective dosing regimen that increases the pH of a microenvironment within the subject, wherein the subject includes the T cell and/or the NK cell, wherein the T cell and/or NK cell expresses a microenvironment restricted biologic chimeric antigen receptor (MRB-CAR) that binds to its cognate antigen differentially at pH 6.7 as compared to pH 7.4, wherein the T cell and/or NK cell expresses the MRB-CAR, wherein the microenvironment includes the target mammalian cell, wherein the target mammalian cell expresses the cognate antigen on their surface, and wherein the T cell and/or NK cell binds to the target mammalian cell differentially before versus after the pH of the microenvironment is increased by administering the pH-modulating pharmacologic agent thereby controlling the binding of the T cell and/or NK cell to the target mammalian cell in a subject in vivo.

In another aspect, provided herein is a pharmacologic agent for use in a method for modulating the binding of a microenvironment restricted biologic chimeric antigen receptor (MRB-CAR) expressing T cell or NK cell to a cell expressing a cognate antigen of the MRB-CAR in a subject, for treating tumor growth, wherein the method includes:
  a. introducing a T cell and/or NK cell capable of expressing the MRB-CAR into the subject, wherein the MRB-CAR binds to the cell expressing the cognate antigen in the subject, wherein after the introducing, the T cell and/or the NK cell including the nucleic acid encoding the MRB-CAR expresses the MRB-CAR and binds to the cell expressing the cognate antigen in the subject; and
  b. administering the pharmacologic agent to the subject in sufficient amount to increase blood pH and/or a tissue pH and/or a microenvironment pH to modulate binding of the MRB-CAR expressing T cell and/or NK cell to the cell expressing the cognate antigen in the blood, the tissue, or the microenvironment with the increased pH.

In another aspect, provided herein is a pharmacologic agent for use in a method for alleviating on target off tumor toxicity in a subject, wherein the method includes:
  a. introducing a nucleic acid encoding a microenvironment restricted biologic chimeric antigen receptor (MRB-CAR) into a T cell or NK cell of the subject, to produce a T cell and/or NK cell capable of expressing the MRB-CAR;
  b. introducing the T cell and/or NK cell capable of expressing the MRB-CAR into the subject, wherein after the introducing, the T cell and/or the NK cell including the nucleic acid encoding the MRB-CAR expresses the MRB-CAR and binds to the cell expressing the cognate antigen in the subject; and
  c. administering the pharmacologic agent to the subject in sufficient amount to increase blood pH and/or a tissue pH and/or a microenvironment pH to modulate binding of the MRB-CAR to its cognate antigen in the blood, the tissue, and/or the microenvironment with the increased pH, thereby alleviating on target off tumor toxicity in the subject.

In another aspect, provided herein is a pharmacologic agent for use in a method for controlling the binding of a T cell and/or NK cell expressing a microenvironment restricted biologic chimeric antigen receptor (MRB-CAR) to a target mammalian cell, for treating tumor growth, wherein the method includes:
  a. contacting the target mammalian cell with the T cell and/or NK cell expressing the MRB-CAR in a microenvironment, wherein the target mammalian cell expresses a cognate antigen, and the T cell and/or NK cell expresses the MRB-CAR that binds to the cognate antigen differentially at pH 6.7 as compared to pH 7.4; and
  b. increasing the pH of the microenvironment by introducing the pharmacologic agent to the microenvironment in sufficient amount, thereby controlling the binding of the T cell and/or NK cell expressing the MRB-CAR to the target mammalian cell.

In another aspect, provided herein is a pharmacologic agent for use in a method for controlling the binding of a T cell and/or NK cell expressing a microenvironment restricted biologic chimeric antigen receptor (MRB-CAR) to a target mammalian cell in a subject in vivo, for treating tumor growth, wherein the pharmacologic agent is a pH-modulating pharmacologic agent, and wherein the method includes administering the pH-modulating pharmacologic agent to the subject through an effective dosing regimen that increases the pH of a microenvironment within the subject, wherein the subject includes the T cell and/or NK cell expressing the MRB-CAR, wherein the MRB-CAR binds to its cognate antigen differentially at pH 6.7 as compared to pH 7.4, wherein the microenvironment includes the target mammalian cell, wherein the target mammalian cell expresses the cognate antigen on its surface, and wherein the T cell and/or NK cell binds to the target mammalian cell differentially before versus after the pH of the microenvironment is increased.

In another aspect, provided herein is a pH-modulating pharmacologic agent for use in a method for controlling the binding of a T cell and/or NK cell expressing a microenvironment restricted biologic chimeric antigen receptor (MRB-CAR) to a target mammalian cell in a subject in vivo, for treating tumor growth, wherein the method includes administering the pH-modulating pharmacologic agent to the subject through an effective dosing regimen that increases the pH of a microenvironment within the subject, wherein the subject includes the T cell and/or NK cell expressing the MRB-CAR, wherein the MRB-CAR binds to its cognate antigen differentially at pH 6.7 as compared to pH 7.4, wherein the microenvironment includes the target mammalian cell, wherein the target mammalian cell expresses the cognate antigen on its surface, and wherein the T cell and/or NK cell binds to the target mammalian cell differentially before versus after the pH of the microenvironment is increased by administering the pH-modulating pharmacologic agent.

In another aspect, provided herein is a use of a pH-modulating pharmacologic agent for use in the manufacture of a medicament for controlling the binding of a T cell and/or NK cell expressing a microenvironment restricted biologic chimeric antigen receptor (MRB-CAR) to a target mammalian cell in a subject in vivo, wherein the pH-modulating pharmacologic agent is to be administered to the subject through an effective dosing regimen that increases the pH of a microenvironment within the subject, wherein the subject includes the T cell and/or NK cell expressing the MRB-CAR, wherein the MRB-CAR binds to its cognate antigen differentially at pH 6.7 as compared to pH 7.4, wherein the microenvironment includes the target mammalian cell, wherein the target mammalian cell expresses the cognate antigen on their surface, and wherein the T cell binds to the target mammalian cell differentially before versus after the pH of the microenvironment is increased by administering the pH-modulating pharmacologic agent.

In any of the aspects provided immediately above that include a pH-modulating pharmacologic agent or a pharmacologic agent for use in a method and an MRB-CAR or include the use of a pH-modulating pharmacologic agent and an MRB-CAR, the MRB-CAR can have reduced binding to its cognate antigen at one pH than at a different pH. In illustrative embodiments where illustrative pH values for differential binding of an MRB-CAR are not already provided in the broadest aspect and alternatively for other embodiments in place of those values for such aspects, the MRB-CAR can have reduced binding at a higher pH than at a lower pH. For example, the MRB-CAR can have reduced binding to its cognate antigen at a pH above 7.0, 7.1, 7.2, 7.3, 7.4, or 7.5 than at a pH below 6.4, 6.5, 6.6, 6.7, 6.8, 6.9, or 7.0. In other embodiments, the MRB-CAR can have reduced binding at a higher pH than at a lower pH. For example, the MRB-CAR can have reduced binding to its cognate antigen at a pH below 6.4, 6.5, 6.6, 6.7, 6.8, 6.9, or 7.0 than at a pH above 7.0, 7.1, 7.2, 7.3, 7.4, or 7.5. In some illustrative embodiments, the MRB-CAR exhibits increased binding at a pH of 6.5 to 6.7 compared to pH 7.4 to 7.6. In other illustrative embodiments, the MRB-CAR exhibits increased binding at a pH of 6.7 compared to a pH of 7.4. In other embodiments, the MRB-CAR exhibits increased binding in the pH of a tumor compared to the pH of blood. In some embodiments, the MRB-CAR can include an antigen-specific targeting region, a stalk, and an intracellular activating domain. In some embodiments, the MRB-CAR can also include a co-stimulatory domain. In some embodiments, the MRB-CAR can bind to a tumor associated antigen.

In any of the aspects provided immediately above that include a pH-modulating pharmacologic agent or a pharmacologic agent for use in a method and an MRB-CAR or include the use of a pH-modulating pharmacologic agent and an MRB-CAR, the pH of the microenvironment can be increased from a pH below 7.0 to a pH above 7.0. For example, the pH can be increased from a pH below 6.4, 6.5, 6.6, 6.7, 6.8, 6.9, or 7.0 to a pH above 7.0, 7.1, 7.2, 7.3, or 7.4. In some embodiments, the MRB-CAR can bind to the cognate antigen at the increased pH but not a pH of the microenvironment before introducing the pharmacologic agent. In certain embodiments, the pH can be increased from below 7.0 to a pH of 7.1 to 8.0 or to a pH of 7.1 to 7.8 or to a pH of 7.2 to 7.8 or a pH of 7.2 to 7.6 or a pH of 7.3 to 7.6 or to a pH of 7.4 to 7.8 or to a pH of 7.4 to 7.6. Such an increase in pH can occur for less than 1, 2, 4, 6, 8, 12, or 24 hours or for more than 1, 2, 4, 6, 8, 12 or 24 hours depending on the type and dose of pharmacologic agent administered. In certain embodiments, the pharmacologic agent is administered such that the pH remains above 7.0, 7.1, 7.2, 7.3, 7.4, or 7.5; or between 7.0, 7.1, 7.2, 7.3 on the low end of the range and 7.4, 7.5, 7.6, 7.7, or 7.8 on the high end of the range, in the target tissue, such as a tumor, and for example in at least a surface of a target tissue (e.g. tumor) microenvironment, in at least a portion of a target tissue (e.g. tumor) microenvironment, and in illustrative embodiments throughout a target tissue (e.g. tumor) microenvironment.

In any of the aspects provided immediately above that include a pH-modulating pharmacologic agent or a pharmacologic agent for use in a method and an MRB-CAR or include the use of a pH-modulating pharmacologic agent and an MRB-CAR, the microenvironment can be an in vivo microenvironment, such as a tumor, a tissue, a non-tumor tissue, a normal tissue, or a tissue that has undergone a transient shift in pH. For example, tissues that typically undergo transient shifts in pH include a muscle tissue in anaerobic conditions or muscle tissue undergoing exercise or an inflamed tissue or a tissue experiencing inflammation. In some embodiments that include a target mammalian cell, the target mammalian cell can be a tumor cell or a non-tumor or normal cell.

In any of the aspects provided immediately above that include a pH-modulating pharmacologic agent or a pharmacologic agent for use in a method and an MRB-CAR or include the use of a pH-modulating pharmacologic agent and an MRB-CAR, the pharmacologic agent can be sodium bicarbonate, tris-hydroxylmethyl aminomethane, an equimolar hypertonic solution of sodium bicarbonate and sodium carbonate, or proton pump inhibitors such esomeprazole, esomeprazole and naproxen, lansoprazole, omeprazole, and rabeprazole.

In any of the aspects provided immediately above that include a pH-modulating pharmacologic agent or a pharmacologic agent for use in a method and an MRB-CAR or include the use of a pH-modulating pharmacologic agent and an MRB-CAR, the pharmacologic agent can be used in a method for the treatment of cancer, tumors, tumor growth, or a cell proliferative disorder.

In another aspect, provided herein is a kit containing a container containing a replication incompetent recombinant retroviral particle, and instructions for use thereof for treating tumor growth, wherein the instructions instruct a method for controlling the binding of a T cell and/or NK cell to a target mammalian cell, in a method including:
 a. transducing the T cell and/or NK cell with the replication incompetent recombinant retroviral particle including in its genome a microenvironment restricted biologic chimeric antigen receptor (MRB-CAR) that binds to the cognate antigen differentially at pH 6.7 as compared to pH 7.4 to produce a T cell and/or NK cell capable of expressing the MRB-CAR;

b. introducing the T cell and/or NK cell capable of expressing the MRB-CAR into the subject, wherein after the introducing, the T cell and/or the NK cell including the nucleic acid encoding the MRB-CAR expresses the MRB-CAR and binds to the cell expressing the cognate antigen in the subject;

c. contacting the target mammalian cell with the MRB-CAR expressing T cell and/or NK cell in a microenvironment, wherein the target mammalian cell expresses a cognate antigen of the MRB-CAR, and the T cell and/or NK cell expresses the MRB-CAR; and d. increasing the pH of the microenvironment by introducing a pH-modulating pharmacologic agent to the microenvironment in sufficient amount, thereby affecting the binding of the target mammalian cell with the T cell and/or NK cell.

In some embodiments, the kit can further include a pH-modulating pharmacologic agent.

In some embodiments of the kit, the MRB-CAR can have reduced binding to its cognate antigen at one pH than at a different pH. In illustrative embodiments where illustrative pH values for differential binding of an MRB-CAR are not already provided in the broadest aspect and alternatively for other embodiments in place of those values for such aspects, the MRB-CAR can have reduced binding at a higher pH than at a lower pH. For example, the MRB-CAR can have reduced binding to its cognate antigen at a pH above 7.0, 7.1, 7.2, 7.3, 7.4, or 7.5 than at a pH below 6.4, 6.5, 6.6, 6.7, 6.8, 6.9, or 7.0. In other embodiments, the MRB-CAR can have reduced binding at a higher pH than at a lower pH. For example, the MRB-CAR can have reduced binding to its cognate antigen at a pH below 6.4, 6.5, 6.6, 6.7, 6.8, 6.9, or 7.0 than at a pH above 7.0, 7.1, 7.2, 7.3, 7.4, or 7.5. In some illustrative embodiments, the MRB-CAR exhibits increased binding at a pH of 6.5 to 6.7 compared to pH 7.4 to 7.6. In other illustrative embodiments, the MRB-CAR exhibits increased binding at a pH of 6.7 compared to a pH of 7.4. In other embodiments, the MRB-CAR exhibits increased binding in the pH of a tumor compared to the pH of blood. In some embodiments, the MRB-CAR can include an antigen-specific targeting region, a stalk, and an intracellular activating domain. In some embodiments, the MRB-CAR can also include a co-stimulatory domain. In some embodiments, the MRB-CAR can bind to a tumor associated antigen.

In some embodiments of the kit, the pH of the microenvironment can be increased from a pH below 7.0 to a pH above 7.0. For example, the pH can be increased from a pH below 6.4, 6.5, 6.6, 6.7, 6.8, 6.9, or 7.0 to a pH above 7.0, 7.1, 7.2, 7.3, or 7.4. In some embodiments, the MRB-CAR can bind to the cognate antigen at the increased pH but not a pH of the microenvironment before introducing the pharmacologic agent. In certain embodiments, the pH can be increased from below 7.0 to a pH of 7.1 to 8.0 or to a pH of 7.1 to 7.8 or to a pH of 7.2 to 7.8 or a pH of 7.2 to 7.6 or a pH of 7.3 to 7.6 or to a pH of 7.4 to 7.8 or to a pH of 7.4 to 7.6. Such an increase in pH can occur for less than 1, 2, 4, 6, 8, 12, or 24 hours or for more than 1, 2, 4, 6, 8, 12 or 24 hours depending on the type and dose of pharmacologic agent administered. In certain embodiments, the pharmacologic agent is administered such that the pH remains above 7.0, 7.1, 7.2, 7.3, 7.4, or 7.5; or between 7.0, 7.1, 7.2, 7.3 on the low end of the range and 7.4, 7.5, 7.6, 7.7, or 7.8 on the high end of the range, in the target tissue, such as a tumor, and for example in at least a surface of a target tissue (e.g. tumor) microenvironment, in at least a portion of a target tissue (e.g. tumor) microenvironment, and in illustrative embodiments throughout a target tissue (e.g. tumor) microenvironment. In some embodiments, the microenvironment can be an in vivo microenvironment, such as a tumor, a tissue, a non-tumor tissue, a normal tissue, or a tissue that has undergone a transient shift in pH. For example, tissues that typically undergo transient shifts in pH include a muscle tissue in anaerobic conditions or muscle tissue undergoing exercise or an inflamed tissue or a tissue experiencing inflammation. In some embodiments that include a target mammalian cell, the target mammalian cell can be a tumor cell or a non-tumor or normal cell.

In some embodiments of the kit, the pharmacologic agent can be sodium bicarbonate, tris-hydroxylmethyl aminomethane, an equimolar hypertonic solution of sodium bicarbonate and sodium carbonate, or proton pump inhibitors such esomeprazole, esomeprazole and naproxen, lansoprazole, omeprazole, and rabeprazole.

In one aspect, provided herein is a replication incompetent recombinant retroviral particle comprising in its genome a polynucleotide comprising one or more nucleic acid sequences operatively linked to a promoter active in T cells and/or NK cells, wherein:

a. a first nucleic acid sequence of the one or more nucleic acid sequences encodes one or more (e.g. two or more) inhibitory RNA molecules directed against one or more RNA targets, and b. a second nucleic acid sequence of the one or more nucleic acid sequences encodes a chimeric antigen receptor (CAR) comprising an antigen-specific targeting region (ASTR), a transmembrane domain, and an intracellular activating domain.

Provided in another aspect herein is a mammalian packaging cell line comprising a packageable RNA genome for a replication incompetent retroviral particle, wherein said packageable RNA genome comprises:

a. a 5' long terminal repeat, or active fragment thereof;

b. a nucleic acid sequence encoding a retroviral cis-acting RNA packaging element;

c. a polynucleotide comprising one or more nucleic acid sequences operatively linked to a promoter active in T cells and/or NK cells, wherein a first nucleic acid sequence of the one or more nucleic acids encodes one or more (e.g. two or more) inhibitory RNA molecules directed against one or more RNA targets and a second nucleic acid sequence of the one or more nucleic acid sequences encodes a chimeric antigen receptor (CAR) comprising an antigen-specific targeting region (ASTR), a transmembrane domain, and an intracellular activating domain; and d. a 3' long terminal repeat, or active fragment thereof.

In some embodiments of the mammalian packaging cell line aspect, the polynucleotide of (c) can be in reverse orientation to the nucleic acid sequence encoding the retroviral cis-acting RNA packaging element (b), the 5' long terminal repeat (a), and/or the 3' long terminal repeat (d).

In some embodiments of the mammalian packaging cell line aspect, expression of the packageable RNA genome is driven by an inducible promoter active in the mammalian packaging cell line.

In some embodiments of the mammalian packaging cell line aspect, the retroviral cis-acting RNA packaging element can comprise a central polypurine tract (cPPT)/central termination sequence, an HIV Psi, or a combination thereof.

Provided in another aspect herein is a retroviral vector comprising a packageable RNA genome for a replication incompetent retroviral particle, wherein said packageable RNA genome comprises:

a. a 5' long terminal repeat, or active fragment thereof;
b. a nucleic acid sequence encoding a retroviral cis-acting RNA packaging element;
c. a polynucleotide comprising one or more nucleic acid sequences operatively linked to a promoter active in T cells and/or NK cells, wherein a first nucleic acid sequence of the one or more nucleic acids encodes one or more (e.g. two or more) inhibitory RNA molecules directed against one or more RNA targets and a second nucleic acid sequence of the one or more nucleic acid sequences encodes a chimeric antigen receptor (CAR) comprising an antigen-specific targeting region (ASTR), a transmembrane domain, and an intracellular activating domain; and
d. a 3' long terminal repeat, or active fragment thereof.

In some embodiments of the retroviral vector aspect, the polynucleotide of (c) can be in reverse orientation to the nucleic acid sequence encoding the retroviral cis-acting RNA packaging element (b), the 5' long terminal repeat (a), and/or the 3' long terminal repeat (d).

In some embodiments of the retroviral vector aspect, expression of the packageable RNA genome is driven by an inducible promoter active in the mammalian packaging cell line.

In some embodiments of the retroviral vector aspect, the retroviral cis-acting RNA packaging element can comprise a central polypurine tract (cPPT)/central termination sequence, an HIV Psi, or a combination thereof. The retroviral vector can optionally include an antibiotic resistance gene and/or a detectable marker.

Provided herein in another aspect is a method for genetically modifying or transducing a lymphocyte (e.g. a T cell or an NK cell) or a population thereof, of a subject, comprising contacting the lymphocyte (e.g. the T cell or NK cell) or a population thereof, of the subject ex vivo, with a replication incompetent recombinant retroviral particle comprising in its genome a polynucleotide comprising one or more nucleic acid sequences operatively linked to a promoter active in lymphocytes (e.g. T cells and/or NK cells), wherein a first nucleic acid sequence of the one or more nucleic acid sequences encodes one or more (e.g. two or more) inhibitory RNA molecules directed against one or more RNA targets and a second nucleic acid sequence of the one or more nucleic acid sequences encodes a chimeric antigen receptor (CAR) comprising an antigen-specific targeting region (ASTR), a transmembrane domain, and an intracellular activating domain, wherein said contacting facilitates genetic modification and/or transduction of the lymphocyte (e.g. T cell or NK cell), or at least some of the lymphocytes (e.g. T cells and/or NK cells) by the replication incompetent recombinant retroviral particle, thereby producing a genetically modified and/or transduced lymphocyte (e.g. T cell and/or NK cell).

In some embodiments of the method provided immediately above, the genetically modified and/or transduced lymphocyte (e.g. T cell and/or NK cell) or population thereof, is introduced into the subject. In some embodiments, the genetically modified and/or transduced lymphocyte (e.g. T cell and/or NK cell) or population thereof, undergoes 4 or fewer cell divisions ex vivo prior to being introduced or reintroduced into the subject. In some embodiments, the lymphocyte(s) are resting T cells and/or resting NK cells that are in contact with the replication incompetent recombinant retroviral particles for between 1 hour and 12 hours. In some embodiments, no more than 8 hours pass between the time blood is collected from the subject and the time the genetically modified T cells and/or NK cells are reintroduced into the subject. In some embodiments, all steps after the blood is collected and before the blood is reintroduced, are performed in a closed system in which a person monitors the closed system throughout the processing.

Provided herein in another aspect is a genetically modified T cell and/or NK cell comprising:
a. one or more (e.g. two or more) inhibitory RNA molecules directed against one or more RNA targets; and
b. a chimeric antigen receptor (CAR) comprising an antigen-specific targeting region (ASTR), a transmembrane domain, and an intracellular activating domain, wherein said one or more (e.g. two or more) inhibitory RNA molecules and the CAR are encoded by nucleic acid sequences that are genetic modifications of the T cell and/or NK cell.

In some embodiments of the genetically modified T cell and/or NK cell aspect, the genetically modified T cell and/or NK cell also comprises at least one lymphoproliferative element that is not an inhibitory RNA molecule, wherein said lymphoproliferative element is encoded by a nucleic acid that is a genetic modification of the T cell and/or NK cell. In some embodiments, the inhibitory RNA molecules, the CAR, and/or the at least one lymphoproliferative element are expressed in a polycistronic matter. In illustrative embodiments, the inhibitory RNA molecules are expressed from a single polycistronic transcript.

Provided herein in another aspect is a replication incompetent recombinant retroviral particle for use in a method for genetically modifying a lymphocyte of a subject, for treating tumor growth, wherein the replication incompetent recombinant retroviral particle comprises in its genome a polynucleotide comprising one or more nucleic acid sequences operatively linked to a promoter active in T cells and/or NK cells, wherein a first nucleic acid sequence of the one or more nucleic acid sequences encodes one or more (e.g. two or more) inhibitory RNA molecules directed against one or more RNA targets and a second nucleic acid sequence of the one or more nucleic acid sequences encodes a chimeric antigen receptor (CAR) comprising an antigen-specific targeting region (ASTR), a transmembrane domain, and an intracellular activating domain, wherein the method comprises contacting a T cell and/or NK cell of the subject ex vivo, and said contacting facilitates transduction of at least some of the resting T cells and/or NK cells by the replication incompetent recombinant retroviral particles, thereby producing a genetically modified T cell and/or NK cell.

In the method for genetically modifying a lymphocyte of a subject aspect provided immediately above, in some embodiments, a pharmacologic agent is used in the method, which further includes introducing the genetically engineered T cell and/or an NK cell into the subject.

Provided herein in another aspect is a replication incompetent recombinant retroviral particle for use in a method for genetically modifying a T cell and/or NK cell of a subject, for treating tumor growth, wherein the method comprises:
a. contacting the T cell and/or NK cell of the subject ex vivo, with a replication incompetent recombinant retroviral particle comprising in its genome a polynucleotide comprising one or more nucleic acid sequences operatively linked to a promoter active in T cells and/or NK cells, wherein a first nucleic acid sequence of the one or more nucleic acid sequences encodes one or more (e.g. two or more) inhibitory RNA molecules directed against one or more RNA targets and a second nucleic acid sequence of the one or more nucleic acid sequences encodes a chimeric antigen receptor (CAR) comprising an antigen-specific targeting region (ASTR), a transmembrane domain, and an intracellular activating domain, wherein said contacting facilitates transduction of at least some of the resting T cells and/or NK cells by the replication incompetent recombinant retroviral particles, thereby producing a genetically modified T cell and/or NK cell; and b. introducing the genetically modified T cell and/or NK cell into the subject, thereby genetically modifying the T cell and/or NK cell of the subject.

In the aspect provided immediately above, in some embodiments, a population of T cells and/or NK cells are contacted in the contacting step, and introduced into the subject in the introducing step.

Provided herein in another aspect is the use of a replication incompetent recombinant retroviral particle in the manufacture of a kit for genetically modifying a T cell and/or NK cell of a subject, wherein the use of the kit comprises:

1. contacting the T cell and/or NK cell of the subject ex vivo, with a replication incompetent recombinant retroviral particle comprising in its genome a polynucleotide comprising one or more nucleic acid sequences operatively linked to a promoter active in T cells and/or NK cells, wherein a first nucleic acid sequence of the one or more nucleic acid sequences encodes one or more (e.g. two or more) inhibitory RNA molecules directed against one or more target and a second nucleic acid sequence of the one or more nucleic acid sequences encodes a chimeric antigen receptor (CAR) comprising an antigen-specific targeting region (ASTR), a transmembrane domain, and an intracellular activating domain, wherein said contacting facilitates transduction of at least some of the resting T cells and/or NK cells by the replication incompetent recombinant retroviral particles, thereby producing a genetically modified T cell and/or NK cell; and 2. introducing the genetically modified T cell and/or NK cell into the subject, thereby genetically modifying the T cell and/or NK cell of the subject.

Provided herein in another aspect is the use of a replication incompetent recombinant retroviral particle in the manufacture of a medicament for genetically modifying a T cell and/or NK cell of a subject, wherein the use of the medicament comprises:

A) contacting the T cell and/or NK cell of the subject ex vivo, with a replication incompetent recombinant retroviral particle comprising in its genome a polynucleotide comprising one or more nucleic acid sequences operatively linked to a promoter active in T cells and/or NK cells, wherein a first nucleic acid sequence of the one or more nucleic acid sequences encodes one or more (e.g. two or more) inhibitory RNA molecules directed against one or more target and a second nucleic acid sequence of the one or more nucleic acid sequences encodes a chimeric antigen receptor (CAR) comprising an antigen-specific targeting region (ASTR), a transmembrane domain, and an intracellular activating domain, wherein said contacting facilitates transduction of at least some of the resting T cells and/or NK cells by the replication incompetent recombinant retroviral particles, thereby producing a genetically modified T cell and/or NK cell; and B) introducing the genetically modified T cell and/or NK cell into the subject, thereby genetically modifying the T cell and/or NK cell of the subject.

Provided herein in another aspect is a commercial container containing a replication incompetent recombinant retroviral particle and instructions for the use thereof to treat tumor growth in a subject, wherein the replication incompetent recombinant retroviral particle comprises in its genome a polynucleotide comprising one or more nucleic acid sequences operatively linked to a promoter active in T cells and/or NK cells, wherein a first nucleic acid sequence of the one or more nucleic acid sequences encodes one or more (e.g. two or more) inhibitory RNA molecules directed against one or more RNA targets and a second nucleic acid sequence of the one or more nucleic acid sequences encodes a chimeric antigen receptor (CAR) comprising an antigen-specific targeting region (ASTR), a transmembrane domain, and an intracellular activating domain.

In some embodiments, in the aspects of the commercial container, the instructions instruct a user to contact a T cell and/or NK cell of the subject ex vivo, to facilitate transduction of at least one resting T cell and/or NK cell of the subject by the replication incompetent recombinant retroviral particles, thereby producing a genetically modified T cell and/or NK cell.

In any of the aspects provided immediately above that include a polynucleotide comprising one or more nucleic acid sequences operatively linked to a promoter active in T cells and/or NK cells, wherein a first nucleic acid sequence of the one or more nucleic acid sequences encodes one or more (e.g. two or more) inhibitory RNA molecules directed against one or more RNA targets, and a second nucleic acid sequence of the one or more nucleic acid sequences encodes a chimeric antigen receptor (CAR) comprising an antigen-specific targeting region (ASTR), a transmembrane domain, and an intracellular activating domain, the polynucleotide may further include a third nucleic acid sequence that encodes at least one lymphoproliferative element that is not an inhibitory RNA molecule. In some embodiments, the lymphoproliferative element can be a cytokine or cytokine receptor polypeptide, or a fragment thereof comprising a signaling domain. In some embodiments, the lymphoproliferative element is constitutively active. In certain embodiments, the lymphoproliferative element can be an IL-7 receptor or a fragment thereof. In illustrative embodiments, the lymphoproliferative element can be a constitutively active IL-7 receptor or a constitutively active fragment thereof.

In any of the aspects provided immediately above that include a polynucleotide comprising one or more nucleic acid sequences operatively linked to a promoter active in T cells and/or NK cells, wherein a first nucleic acid sequence of the one or more nucleic acid sequences encodes one or more (e.g. two or more) inhibitory RNA molecules directed against one or more RNA targets, an inhibitory RNA molecule can in some embodiments include a 5' strand and a 3' strand that are partially or fully complementary to one another, wherein said 5' strand and said 3' strand are capable of forming an 18-25 nucleotide RNA duplex. In some embodiments, the 5' strand can be 18, 19, 20, 21, 22, 23, 24, or 25 nucleotides in length, and the 3' strand can be 18, 19, 20, 21, 22, 23, 24, or 25 nucleotides in length. In some embodiments, the 5' strand and the 3' strand can be the same or different lengths. In some embodiments, the RNA duplex can include one or more mismatches. In alternate embodiments, the RNA duplex has no mismatches.

In any of the aspects provided immediately above that include a polynucleotide comprising one or more nucleic acid sequences operatively linked to a promoter active in T cells and/or NK cells, wherein a first nucleic acid sequence of the one or more nucleic acid sequences encodes one or more (e.g. two or more) inhibitory RNA molecules directed against one or more RNA targets, an inhibitory RNA molecule can be a miRNA or an shRNA. In some embodiments, the inhibitory molecule can be a precursor of a miRNA, such as for example, a Pri-miRNA or a Pre-miRNA, or a precursor of an shRNA. In some embodiments, the inhibitory molecule can be an artificially derived miRNA or shRNA. In other embodiments, the inhibitory RNA molecule can be a dsRNA (either transcribed or artificially introduced) that is processed into an siRNA or the siRNA itself. In some embodiments, the inhibitory RNA molecule can be a miRNA or shRNA that has a sequence that is not found in nature, or has at least one functional segment that is not found in nature, or has a combination of functional segments that are not found in nature. In illustrative embodiments, at least one or all of the inhibitory RNA molecules are miR-155.

In any of the aspects provided immediately above that include a polynucleotide comprising one or more nucleic acid sequences operatively linked to a promoter active in T cells and/or NK cells, wherein a first nucleic acid sequence of the one or more nucleic acid sequences encodes one or more (e.g. two or more) inhibitory RNA molecules directed against one or more RNA targets, an inhibitory RNA molecule, in some embodiments, can comprises from 5' to 3' orientation: a 5' arm, a 5' stem, a loop, a 3' stem that is partially or fully complementary to said 5' stem, and a 3' arm. In some embodiments, at least one of the two or more inhibitory RNA molecules has this arrangement. In other embodiments, all of the two or more inhibitory RNA molecules have this arrangement. In some embodiments, the 5' stem can be 18, 19, 20, 21, 22, 23, 24 or 25 nucleotides in length. In some embodiments, the 3' stem can be 18, 19, 20, 21, 22, 23, 24, or 25 nucleotides in length. In some embodiments, the loop can be 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides in length. In some embodiments, the 5' arm, 3' arm, or both, are derived from a naturally occurring miRNA. In some embodiments, the 5' arm, 3' arm, or both, are derived from a naturally occurring miRNA is selected from the group consisting of: miR-155, miR-30, miR-17-92, miR-122, and miR-21. In illustrative embodiments, the 5' arm, 3' arm, or both are derived from miR-155. In some embodiments, the 5' arm, 3' arm, or both are derived from *Mus musculus* miR-155 or *Homo sapiens* miR-155. In some embodiments, the 5' arm has the sequence set forth in SEQ ID NO:256 or is a functional variant thereof, such as, for example, a sequence that is the same length as SEQ ID NO:256, or 95%, 90%, 85%, 80%, 75%, or 50% as long as SEQ ID NO: 256 or is 100 nucleotides or less, 95 nucleotides or less, 90 nucleotides or less, 85 nucleotides or less, 80 nucleotides or less, 75 nucleotides or less, 70 nucleotides or less, 65 nucleotides or less, 60 nucleotides or less, 55 nucleotides or less, 50 nucleotides or less, 45 nucleotides or less, 40 nucleotides or less, 35 nucleotides or less, 30 nucleotides or less, or 25 nucleotides or less; and is at least 50%, 55%, 60%, 65%, 70%, 75%, 80%, 85%, 90%, or 95% identical to SEQ ID NO:256. In some embodiments, the 3' arm has the sequence set forth in SEQ ID NO:260 or is a functional variant thereof, such as, for example, the same length as SEQ ID NO:260, or 95%, 90%, 85%, 80%, 75%, or 50% as long as SEQ ID NO: 260 or is a sequence that is 100 nucleotides or less, 95 nucleotides or less, 90 nucleotides or less, 85 nucleotides or less, 80 nucleotides or less, 75 nucleotides or less, 70 nucleotides or less, 65 nucleotides or less, 60 nucleotides or less, 55 nucleotides or less, 50 nucleotides or less, 45 nucleotides or less, 40 nucleotides or less, 35 nucleotides or less, 30 nucleotides or less, 25 nucleotides or less; and is at least 50%, 55%, 60%, 65%, 70%, 75%, 80%, 85%, 90%, or 95% identical to SEQ ID NO:260. In some embodiments, the 3' arm comprises nucleotides 221-283 of the *Mus musculus* BIC.

In any of the aspects provided immediately above that include a polynucleotide comprising one or more nucleic acid sequences operatively linked to a promoter active in T cells and/or NK cells, wherein a first nucleic acid sequence of the one or more nucleic acid sequences encodes two or more inhibitory RNA molecules directed against one or more RNA targets, the two or more inhibitory RNA molecules, in some embodiments, can be positioned in the first nucleic acid sequence in series. In some embodiments, the inhibitory RNA molecules can be adjoined to one another either directly or indirectly by non-functional linker sequence(s). In some embodiments, the linker sequences can be between 5 and 120 nucleotides in length, or between 10 and 40 nucleotides in length.

In any of the aspects provided immediately above that include a polynucleotide comprising one or more nucleic acid sequences operatively linked to a promoter active in T cells and/or NK cells, wherein a first nucleic acid sequence of the one or more nucleic acid sequences encodes two or more inhibitory RNA molecules directed against one or more RNA targets, in some embodiments, the first nucleic acid sequence encodes two to four inhibitory RNA molecules. In illustrative embodiments, between 2 and 10, 2 and 8, 2 and 6, 2 and 5, 2 and 4, 3 and 5, or 3 and 6 inhibitory RNA molecules are included in the first nucleic acid sequence. In an illustrative embodiment, four inhibitory RNA molecules are included in the first nucleic acid sequence.

In any of the aspects provided immediately above that include a polynucleotide comprising one or more nucleic acid sequences operatively linked to a promoter active in T cells and/or NK cells, wherein a first nucleic acid sequence of the one or more nucleic acid sequences encodes one or more (e.g. two or more) inhibitory RNA molecules directed against one or more RNA targets, the one or more (e.g. two or more) inhibitory RNA molecules can be in an intron. In some embodiments, the intron is in a promoter. In illustrative embodiments, the intron is EF-1alpha intron A. In some embodiments, the intron is adjacent to and downstream of a promoter, which in illustrative embodiments, is inactive in a packaging cell used to produce the replication incompetent recombinant retroviral particle.

In any of the aspects provided immediately above that include a polynucleotide comprising one or more nucleic acid sequences operatively linked to a promoter active in T cells and/or NK cells, wherein a first nucleic acid sequence of the one or more nucleic acid sequences encodes two or more inhibitory RNA molecules directed against one or more RNA targets, the two or more inhibitory RNA molecules, in some embodiments, can be directed against different targets. In an alternate embodiment, the two or more inhibitory RNA molecules are directed against the same target. In some embodiments, the RNA targets are mRNAs transcribed from genes that are expressed by T cells such as but not limited to PD-1 (prevent inactivation); CTLA4 (prevent inactivation); TCRα (safety—prevent autoimmunity); TCRb (safety—prevent autoimmunity); CD3Z (safety—prevent autoimmunity); SOCS1 (prevent inactivation); SMAD2 (prevent inactivation); a miR-155 target (promote activation); IFN gamma (reduce CRS); cCBL (prolong signaling); TRAIL2 (prevent death); PP2A (prolong signaling); ABCG1 (increase cholesterol microdomain content by limiting clearance of cholesterol). In some embodiments, the RNA targets are mRNAs transcribed from genes that encode components of the T cell receptor (TCR) complex. In some embodiments, at least one of the two or more of inhibitory RNA molecules can decrease expression of T cell receptors, in illustrative embodiments, one or more endogenous T cell receptor(s) of a T cell. In certain embodiments, the RNA target can be mRNA transcribed from the endogenous TCRα or TCRβ gene of the T cell whose genome comprises the first nucleic acid sequence encoding the one or more miRNAs. In illustrative embodiments, the RNA target is mRNA transcribed from the TCRα gene.

In any of the aspects provided immediately above that include a polynucleotide comprising one or more nucleic acid sequences operatively linked to a promoter active in T cells and/or NK cells, wherein a first nucleic acid sequence of the one or more nucleic acid sequences encodes one or more (e.g. two or more) inhibitory RNA molecules directed against one or more RNA targets, and a second nucleic acid sequence of the one or more nucleic acid sequences encodes a chimeric antigen receptor (CAR) comprising an antigen-specific targeting region (ASTR), a transmembrane domain, and an intracellular activating domain, in some embodiments, the CAR is a microenvironment restricted biologic (MRB)-CAR. In other embodiments, the ASTR of the CAR binds to a tumor associated antigen. In other embodiments, the ASTR of the CAR is a microenvironment-restricted biologic (MRB)-ASTR.

In any of the aspects provided immediately above that include a polynucleotide comprising one or more nucleic acid sequences operatively linked to a promoter active in T cells and/or NK cells, wherein a first nucleic acid sequence of the one or more nucleic acid sequences encodes one or more (e.g. two or more) inhibitory RNA molecules directed against one or more RNA targets, and a second nucleic acid sequence of the one or more nucleic acid sequences encodes a chimeric antigen receptor (CAR) comprising an antigen-specific targeting region (ASTR), a transmembrane domain, and an intracellular activating domain, and in some instances a third nucleic acid sequence of the one or more nucleic acid sequences that encodes at least one lymphoproliferative element that is not an inhibitory RNA molecule, in some embodiments, any or all of the first nucleic acid sequence, second nucleic acid sequence, and third nucleic acid sequence is operably linked to a riboswitch. In some embodiments, the riboswitch is capable of binding a nucleoside analog. In some embodiments, the nucleoside analog is an antiviral drug.

In any of the aspects provided immediately above that include a replication incompetent recombinant retroviral particle, in some embodiments, the replication incompetent recombinant retroviral particle comprises a pseudotyping element on its surface that is capable of binding to a T cell and/or NK cell and facilitating membrane fusion of the replication incompetent recombinant retroviral particle thereto. In some embodiments, the pseudotyping element can be a Measles Virus F polypeptide, a Measles Virus H polypeptide, a VSV-G polypeptide, or a fragment of any thereof that retains the ability to bind to resting T cells and/or resting NK cells. In illustrative embodiments, the pseudotyping element is VSV-G.

In any of the aspects provided immediately above that include a replication incompetent recombinant retroviral particle, in some embodiments, the replication incompetent recombinant retroviral particle comprises an activation element on its surface that comprises a membrane-bound polypeptide capable of binding to CD3; and/or a membrane-bound polypeptide capable of binding to CD28. In some embodiments, the membrane-bound polypeptide capable of binding to CD3 is fused to a heterologous GPI anchor attachment sequence and/or the membrane-bound polypeptide capable of binding to CD28 is fused to a heterologous GPI anchor attachment sequence. In some embodiments, the membrane-bound polypeptide capable of binding CD3 is an anti-CD3 scFV or anti-CD3 scFvFc. In illustrative embodiments, the membrane-bound polypeptide capable of binding to CD3 is anti-CD3 scFvFc. In illustrative embodiments, the membrane-bound polypeptide capable of binding to CD28 is CD80, or an extra-cellular domain thereof, bound to a CD16B GPI anchor attachment sequence.

In any of the aspects provided immediately above that include a replication incompetent recombinant retroviral particle, in some embodiments, the replication incompetent recombinant retroviral particle comprises on its surface a nucleic acid encoding a domain recognized by a monoclonal antibody approved biologic.

Provided herein in one aspect, is a method of transducing and/or genetically modifying lymphocytes (e.g. T cell and/or NK cells), in illustrative embodiments resting lymphocytes (resting T cells and/or NK cells), of a subject, comprising contacting resting T cells and/or resting NK cells of a subject ex vivo, with replication incompetent recombinant retroviral particles, wherein the replication incompetent recombinant retroviral particles comprise a pseudotyping element on their surface and a membrane-bound anti-CD3 scFvFc antibody on their surface, that is capable of binding a resting T cell and/or resting NK cell and facilitating membrane fusion of the replication incompetent recombinant retroviral particle thereto, wherein said contacting facilitates transduction of the resting T cells and/or NK cells by the replication incompetent recombinant retroviral particles, thereby producing genetically modified T cells and/or NK cells.

Provided herein in one aspect, is a method for transducing and/or genetically modifying resting T cells and/or resting NK cells from isolated blood, comprising: collecting blood from a subject; isolating peripheral blood mononuclear cells (PBMCs) comprising resting T cells and/or resting NK cells; and contacting the resting T cells and/or resting NK cells of the subject ex vivo for an effective time, with replication incompetent recombinant retroviral particles, wherein the replication incompetent recombinant retroviral particle comprise a pseudotyping element on their surface and a membrane-bound anti-CD3 scFvFc antibody on their surface, thereby producing genetically modified T cells and/or NK cells, thereby transducing resting T cells and/or NK cells.

In these aspects in the immediately above paragraphs for transducing and/or genetically modifying T lymphocytes (e.g. T cell and/or NK cells) that include a membrane-bound anti-CD3 scFvFc antibody, the pseudotyping element in certain embodiments is the vesicular stomatitis virus envelope protein (VSV-G). In some embodiments, the replication incompetent retroviral particles further comprise a membrane-bound polypeptide capable of binding to CD28, which can include, for example, an extracellular domain of CD80, CD86, or functional fragments thereof that retains the ability to bind CD28. In some embodiments, the anti-CD3 scFvFc antibody is fused to a heterologous GPI anchor attachment sequence. In some embodiments, the anti-CD3 scFvFc antibody is not encoded by a polynucleotide in the replication incompetent recombinant retroviral particle.

In these aspects in the immediately above paragraphs for transducing and/or genetically modifying T lymphocytes (e.g. T cell and/or NK cells) that include a membrane-bound anti-CD3 scFvFc antibody, the recombinant retroviral particle can further include a polynucleotide comprising one or more transcriptional units operatively linked to a promoter active in T cells and/or NK cells, wherein the one or more transcriptional units encode a chimeric antigen receptor. In some embodiments, the membrane-bound polypeptide capable of binding to CD3 is not encoded by a polynucleotide in the replication incompetent recombinant retroviral particle. In some embodiments, the anti-CD3 scFvFc antibody is not encoded by a polynucleotide in the replication incompetent recombinant retroviral particle.

In another aspect provided herein is a method of transducing and/or genetically modifying resting lymphocytes of a subject, comprising contacting resting T cells and/or resting NK cells of a subject ex vivo, with replication incompetent recombinant retroviral particles, wherein the replication incompetent recombinant retroviral particles comprise a pseudotyping element on their surface and a membrane-bound polypeptide capable of binding to CD3 on their surface, but not a membrane-bound polypeptide capable of binding to and activating CD28 on their surface, wherein said contacting facilitates transduction of the resting T cells and/or NK cells by the replication incompetent recombinant retroviral particles, thereby producing genetically modified T cells and/or NK cells.

In another aspect, provided herein is a method for transducing and/or genetically modifying resting T cells and/or resting NK cells from isolated blood, comprising: collecting blood from a subject; isolating peripheral blood mononuclear cells (PBMCs) comprising resting T cells and/or resting NK cells; and contacting the resting T cells and/or resting NK cells of the subject ex vivo for an effective time, with replication incompetent recombinant retroviral particles, wherein the replication incompetent recombinant retroviral particles comprise a pseudotyping element on their surface and a membrane-bound polypeptide capable of binding to CD3 on their surface, but not a membrane-bound polypeptide capable of binding to and activating CD28 on their surface, thereby producing genetically modified T cells and/or NK cells, thereby transducing resting T cells and/or NK cells.

In these aspects in the immediately above paragraphs for transducing and/or genetically modifying resting T lymphocytes that include a membrane-bound polypeptide capable of binding to CD3 on their surface, but not a membrane-bound polypeptide capable of binding to and activating CD28 on their surface, the pseudotyping element can be, for example, the vesicular stomatitis virus envelope protein (VSV-G). In illustrative embodiments, the membrane-bound polypeptide capable of binding to CD3 is an anti-CD3 scFvFc antibody, which in some embodiments is fused to a heterologous GPI anchor attachment sequence. In some embodiments of this aspect, the contacting is performed for at least 2 hours, or between 2 hours and 24 hours, or between 2 hours and 6 hours. In some embodiments, a detectable marker is encoded by the genome of the replication incompetent recombinant retroviral particle, and detected in the T cells and/or NK cells after the transduction. In some embodiments, the membrane-bound polypeptide capable of binding to CD3 is not encoded by a polynucleotide in the replication incompetent recombinant retroviral particle. In some embodiments, a detectable marker is encoded by the genome of the replication incompetent recombinant retroviral particles, and detected in the T cells and/or NK cells after the transduction.

In another aspect, provided herein is a replication incompetent recombinant retroviral particle, comprising: one or more pseudotyping elements; a polynucleotide comprising one or more transcriptional units operatively linked to a promoter active in T cells and/or NK cells, wherein the one or more transcriptional units encode a chimeric antigen receptor; and a pseudotyping element on its surface and an activation element on its surface, wherein the activation element is capable of binding to a T cell and/or NK cell and is not encoded by a polynucleotide in the replication incompetent recombinant retroviral particle, and wherein the activation element is an anti-CD3 scFvFc antibody.

In another aspect, provided herein is a replication incompetent recombinant retroviral particle, comprising: one or more pseudotyping elements capable of binding to a T cell and/or an NK cell and facilitating membrane fusion of the replication incompetent recombinant retroviral particle thereto;

a polynucleotide comprising one or more transcriptional units operatively linked to a promoter active in T cells and/or NK cells, wherein the one or more transcriptional units encode a chimeric antigen receptor; and a pseudotyping element on its surface and an activation element on its surface, wherein the activation element is capable of binding to a T cell and/or NK cell and is not encoded by a polynucleotide in the replication incompetent recombinant retroviral particle, and wherein the activation elements is a membrane-bound polypeptide capable of binding to CD3 on their surface, but not a membrane-bound polypeptide capable of binding to and activating CD28 on their surface.

In the replication incompetent recombinant retroviral particle aspects in the paragraphs immediately above, the recombinant retroviral particle further comprises a polynucleotide comprising one or more transcriptional units operatively linked to a promoter active in T cells and/or NK cells, wherein the one or more transcriptional units encode a chimeric antigen receptor. In some embodiments in these aspects, the membrane-bound polypeptide capable of binding to CD3 is not encoded by a polynucleotide in the replication incompetent recombinant retroviral particle. In some embodiments of these aspects, the anti-CD3 scFvFc antibody is not encoded by a polynucleotide in the replication incompetent recombinant retroviral particle.

The following non-limiting examples are provided purely by way of illustration of exemplary embodiments, and in no way limit the scope and spirit of the present disclosure. Furthermore, it is to be understood that any inventions disclosed or claimed herein encompass all variations, combinations, and permutations of any one or more features described herein. Any one or more features may be explicitly excluded from the claims even if the specific exclusion is not set forth explicitly herein. It should also be understood that disclosure of a reagent for use in a method is intended to be synonymous with (and provide support for) that method involving the use of that reagent, according either to the specific methods disclosed herein, or other methods known in the art unless one of ordinary skill in the art would understand otherwise. In addition, where the specification and/or claims disclose a method, any one or more of the reagents disclosed herein may be used in the method, unless one of ordinary skill in the art would understand otherwise.

EXAMPLES

Example 1. Generation of Riboswitches that Respond Specifically to Nucleoside Analogue Antiviral Drugs This example provides a method to screen libraries based on natural structural riboswitches that bind guanosine and deoxyguanosine. These riboswitches were used as scaffolds to develop biased libraries for the selection of aptamers that bind specifically to a ligand nucleoside analogue. Previously, isothermal titration calorimetry has been used to show these natural riboswitches bind to their native ligands. Additional tests showed a deoxyguanosine switch also interacted weakly with the nucleoside analogues acyclovir and penciclovir, leading to the re-design of this sequence into a new library. The single-stranded regions of the riboswitch were targeted for mutation and variant sequences that specifically respond to acyclovir or penciclovir were selected for.

Materials

Selection components guanine, guanosine, deoxyguanosine, acyclovir, and penciclovir were ordered from Sigma-Aldrich (St. Louis, Mo.). Acyclovir was the initial target while penciclovir was a special interest analyte used in latter rounds and guanine, guanosine, and deoxyguanosine were used as counter-targets. Graphene oxide (GrO), to be used as the partitioning medium, was purchased from Angstron Materials (Dayton, Ohio). HEPES (pH 7.3) and $MgCl_2$ were purchased from Amersco LLC. (Solon, Ohio). KCl was purchased from Teknova (Hollister, Calif.). Selection buffer was prepared at 5× (1× as 50 mM HEPES, 100 mM KCl, 20 mM $MgCl_2$, pH 7.3). Targets, counter-targets, and oligos were reconstituted in nuclease-free water for preliminary analysis and aptamer screening. Aliquots were prepared for all targets and stored at −20° C. to maximize shelf life.

Generation of the Aptamer Library

The initial aptamer library template was synthesized by IBA GmbH (Gottingen, Germany) as the reverse complement of the sequences in FIG. 14. In FIG. 14, the nucleotides in boxes are single-stranded in the known sequences, with "mutations" introduced during synthesis to allow for better binding to analogues of the original targets. For nucleotides within the boxes outlined with solid lines, substitution mutations were allowed; for nucleotides within the boxes outlined with dashed lines, substitution mutations as well as insertions or deletions were allowed. Primers were synthesized by IDT (Coralville, Iowa) as single-stranded DNA. T7 primer (SEQ ID NO:240) was combined with library template sequences for primer extension with Titanium Taq DNA polymerase (Clontech; Mountain View, Calif.). Primer-extended material was transcribed using the Ampliscribe T7 High Yield Transcription Kit (Epicentre; Madison, Wis.) and then purified on 10% denaturing polyacrylamide gel electrophoresis (PAGE) with 8 M urea before use in selection. During selection, the library was reverse-transcribed using SuperScript IV Reverse Transcriptase (Invitrogen; Carlsbad, Calif.) using reverse primer (SEQ ID NO:241) and amplified using Titanium Taq DNA polymerase (Clontech; Mountain View, Calif.). The aptamer with SEQ ID NO:248 had a J2-3 loop variation of −3 to −1 and a diversity of ~$2.25\times10^{10}$. The aptamer with SEQ ID NO:250 had a J2-3 loop variation of 0 (native) to +5 and a diversity of ~$9.38\times10^{14}$. The two oligonucleotides (SEQ ID NOs:249 and 250) were mixed at a ratio of 1:4160 to produce equimolar diversity in the combined library pool, with a total diversity of ~$9.38\times10^{13}$.

Library Screening

Library screening was conducted using a graphene oxide-Systematic Evolution of Ligands by EXponential enrichment (GO-SELEX) approach (FIG. 15) (Park et al., 2012), taking advantage of the π-π interaction that grants graphene oxide a high affinity for single-stranded nucleic acids (Zeng et al., 2015). The goal was to select sequences that did not interact with the 1× selection buffer or with the counter-targets (guanine, guanosine, and deoxyguanosine) but did bind to the positive target acyclovir.

For each round, a given amount of library was first refolded in 1× selection buffer (5-minute denaturing at 90° C., 5 minutes at 4° C., then room temperature). The counter-targets were then added to refolded libraries and incubated for 30 minutes at 37° C. The exceptions to this were rounds 1 and 2, where the counter-targets were only briefly (<1 minute) included to help load the library onto the GrO. After allowing the library to interact with the counter-targets and buffer components, unbound library was loaded onto GrO (mass equal to 100 times the mass of the library at the start of the round) over the course of a 10-minute incubation at 37° C. The solution was then centrifuged at 7,000×g to sediment the GrO. The supernatant, which contained sequences bound to the counter-targets and/or to the buffer, was removed. The sediment was then washed twice with 200 μL 1× selection buffer, centrifuging at 7,000×g and removing the supernatant after each wash. A positive target-containing solution was then added and allowed to elute library from the GrO under the conditions indicated in Table 1 for up to 60 minutes at 37° C., essentially allowing the target to compete with graphene oxide for library binding. Sequences that bound more strongly to the target would desorb from graphene oxide and remain bound to the target at the end of the incubation. A final centrifugation step separated the released material, located in the supernatant, from the non-responsive library that remained bound to the graphene oxide.

After positive selection, the recovered RNA purified using 10% denaturing PAGE with 8 M Urea, was then quantified using a spectrophotometer reading (Table 1), reverse-transcribed with SuperScript IV, and amplified using PCR with Titanium Taq DNA polymerase. Amplification products were transcribed into RNA for the next round of selection.

Three tiers of stringency were implemented over the course of selection (Table 1). The first two rounds of selection did not include screening against counter-targets to maximize library loading onto GrO. Additionally, a large excess of acyclovir was used in positive incubations to maximize library recovery, thus the low-stringency designation. Counter-target incubations were introduced after library recovery was achieved, as middle-stringency conditions. The ratio of acyclovir to library was also reduced during these three rounds to increase library competition for binding to target. Once greater than 10% recovery was achieved, the final rounds of high-stringency selection were implemented. Counter-targets/library ratio remained high and positive target/library ratio was brought to 1:1 while positive incubation time was reduced, to select for faster binding sequences. Once library recovery was shown to remain over 10% after more than two rounds of the high-stringency conditions, parallel assessments were conducted.

TABLE 1

Selection and Assessment Conditions. Conditions used for each round of selection or incubation, with recovery as the ratio between recovered sample and input library for each round. Library enrichment was monitored over the course of selection.

| Generation (Stringency) | Library:X-Targets (30-min inc.) | Library:(+) Target | (+) Incubation Time (min) | Recovery (%) |
|---|---|---|---|---|
| G0/R1 (low) | 1:1000* | 1:1000 | 60 | 0.43 |
| G1/R2 (low) | 1:1000* | 1:1000 | 60 | 2.00 |
| G2/R3 (middle) | 1:1000 | 1:500 | 60 | 3.60 |
| G3/R4 (middle) | 1:1000 | 1:100 | 60 | 8.73 |
| G4/R5 (middle) | 1:1000 | 1:10 | 60 | 10.20 |
| G5/R6 (high) | 1:1000 | 1:1 | 60 | 12.00 |
| G6/R7 (high) | 1:1000 | 1:1 | 60 | 8.60 |
| G7/R8 (high) | 1:1000 | 1:1 | 60 | 9.72 |
| G8/R9 (high) | 1:1000 | 1:1 | 30 | 20.08 |
| G9/R10 (high) | 1:1000 | 1:1 | 30 | 10.62 |

TABLE 1-continued Selection and Assessment Conditions. Conditions used for each round of selection or incubation, with recovery as the ratio between recovered sample and input library for each round. Library enrichment was monitored over the course of selection.

| Generation (Stringency) | Library:X-Targets (30-min inc.) | Library:(+) Target | (+) Incubation Time (min) | Recovery (%) |
|---|---|---|---|---|
| G10(−)† (parallel 1) | — | — | 30 | 3.74 |
| G10(X)† (parallel 1) | 1:40 | — | 30 | 3.60 |
| G10(+)† (parallel 1) | — | 1:4 | 30 | 14.14 |
| G10(P)† (parallel 1) | — | 1:4 | 30 | 5.46 |
| G11(−)‡ (parallel 2) | — | — | 30 | 4.60 |
| G11(X)‡ (parallel 2) | 1:40 | — | 30 | 5.26 |
| G11(+)† (parallel 2) | — | 1:2 | 30 | 9.34 |
| G11(P)‡ (parallel 2) | — | 1:4 | 30 | 6.32 |

*Counter-targets used for loading, not extended incubation.
†Pre-loading incubation conducted with pooled counter-targets.
‡Pre-loading incubation conducted with positive target acyclovir. This was done to minimize the recovery of cross-reactive species.
The following abbreviations are used in this table:
"X-Targets" are counter-targets;
"(+) Target" is acyclovir or penciclovir;
"(+) Incubation Time (min)" is the time the "Library:(+) Target" solution was incubated on the GrO.
G0 is Generation 0 and so on;
R1 is Round 1 and so on.
For the parallel assessment (parallel 1 and parallel 2) the incubations were performed with: (−) 1X selection buffer only, (X) counter-targets in 1X selection buffer, (+) acyclovir in 1X selection buffer, and (P) penciclovir in 1X selection buffer.

Figure 16:
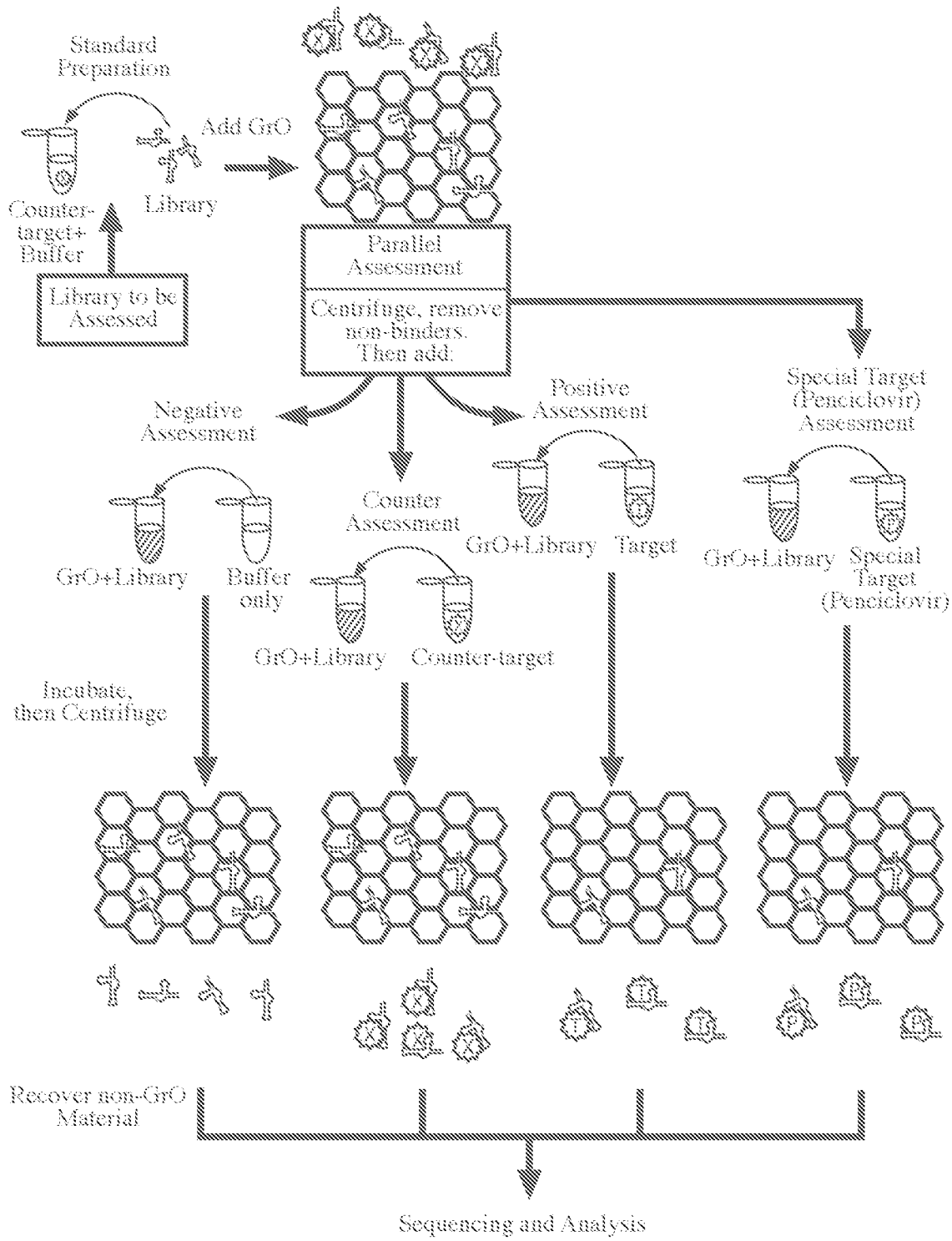
FIG. 16 shows an illustration of graphene oxide parallel assessment. Enriched libraries undergoing parallel assessment were divided into four equal portions. Library samples were then added to graphene oxide and allowed to incubate to load the library on the graphene oxide. Two 5-minute washes were used to remove non-binding material. For the positive (acyclovir) and special target (penciclovir) sample, each target was prepared separately in 1× selection buffer to 1 μM; the counter target replaced the positive target with 10 μM of each counter-target in solution; the negative sample replaced the positive target with an equal volume of nuclease-free water. Samples were then combined with their respective graphene oxide preparations and incubated. Post-incubation, samples were centrifuged to recover their supernatants, and library recovery was determined by NanoDrop-1000 spectrophotometer reading (Thermo Fisher Scientific; Wilmington, Del.). Remaining library sample was analyzed on denaturing PAGE. Images of the gels were taken after staining/destaining with Gel-Star. Bands corresponding to expected library size were recovered for a follow-up round of parallel assessment, with positive target acyclovir replacing counter-targets for the negative, counter, and special target samples' pre-loading incubation. Material recovered from the second parallel assessment was used for sequencing and analysis.

For the two parallel assessments, library to be assessed was divided into four equal amounts for preparation and refolding as above (FIG. 16). For each condition, 50 pmoles of library were combined with 1× selection buffer, refolded (90° C. for 5 minutes, 4° C. for 5 minutes), and then incubated with 200 µL of 10 µM combined counter-targets in 1× selection buffer for 30 minutes at 37° C. These samples were then loaded onto an amount of graphene oxide equal to 100 times the mass of library in the sample and incubated for 10 minutes at 37° C. and then washed twice with 200 µL of 1× selection buffer as before. The loaded graphene oxide samples were then incubated in parallel with 200 µL of the appropriate assessment condition (1× selection buffer only, 10 µM pooled counter-targets, 1 µM penciclovir, 1 µM acyclovir for the first parallel assessment, or 0.5 µM acyclovir for the second parallel assessment; in Table 1 these conditions are shown as: (−); (X); (P); (+); and (+), respectively) in 1× selection buffer for 30 minutes at 37° C. A final centrifugation step separated desorbed responsive library from non-responsive graphene oxide-bound library. The responsive libraries were quantified using spectrophotometric reading (Table 1), verified using 10% denaturing PAGE with 8 M urea, and prepared for a second parallel assessment. This follow-up assessment continued to use counter-targets for the positive sample's pre-loading incubation, but utilized positive target acyclovir for each other samples' pre-incubation. This was done to minimize representation of cross-reactive sequences in a given sample (i.e. responsive to counter-targets in the positive sample, responsive to acyclovir in the negative, counter-targets, or penciclovir samples). Material recovered from the second parallel assessment was quantified using spectrophotometric reading (Table 1), verified using 10% denaturing PAGE with 8 M urea, and prepared for sequencing by reverse transcription and PCR to generate double-stranded DNA.

Sequencing

The initial library was subjected to over 10 rounds of GrO-based selection and parallel assessment (Table 1). The GO-SELEX process is designed to enrich for sequences over multiple rounds of selection that bind to the given targets of interest and remove sequences that bind to the non-target compounds or buffer components. As a result, the populations to be sequenced are expected to contain multiple copies of potential aptamer candidates.

The Illumina MiSeq system (San Diego, Calif.) was implemented to sequence the aptamer libraries after parallel assessment using a single-end read technique. Deep sequencing and subsequent data analysis reduces the large number of screening rounds traditional SELEX requires, which may introduce error and bias due to the screening process (Schütze et al., 2011). Five samples were sequenced: the final generation library that responded to acyclovir, the final generation library that responded to the counter-targets, the final generation library that responded to 1× selection buffer (negative condition), the penultimate generation library that responded to acyclovir, and the final generation library that responded to the additional target of interest, penciclovir. From these sets of data, sequence families were constructed at 95% homology (sequence similarity considering mutations, deletions, and insertion) for aptamer candidate identification. There were 1,711,535 raw sequences (124,600 unique sequences) from the library that responded to acyclovir and 2,074,832 raw sequences (110,149 unique sequences) from the library that responded to penciclovir.

Aptamer Candidate Selection

Sequence family construction focused primarily on sequence similarity. This means that a sequence's frequency in the positive target population was factored in, but greater emphasis was placed on the degree of variation between similar sequences, with 95% homology being the minimum requirement (100% match over the entire sequence is not necessary to join a family, up to 2 bases can be mismatched, inserted, or deleted). One would therefore expect families with the greatest number of members to rank highly as aptamer candidates. After families are constructed, consideration can be given to the relative presence of a family in a given population—families that occur frequently in the negative and counter-target populations are considered weaker candidates, as they demonstrate a degree on non-specific interaction in binding to buffer or counter-target components. Additionally, families that demonstrate a high rate of enrichment (i.e. large ratio between the final positive population and penultimate positive population) improve their candidacy, as enrichment rate has been linked to the binding affinity of a candidate relative to the rest of the population (Levay et al., 2015; Wang et al., 2014). Under these conditions, several candidate families appeared to be strong candidates for binding acyclovir (Table 2) and penciclovir.

TABLE 2

Candidates for acyclovir and penciclovir. DNA sequences corresponding to the non-stem regions of the acyclovir binding RNA riboswitches. Seven families were identified in the screen: 582, 769, 795, 935, 946, 961, and 996 with between 1 and 39 sequences in each family. The percent identity for each sequence in the family was compared to the most prevalent sequence within

TABLE 2-continued

Candidates for acyclovir and penciclovir. DNA sequences corresponding to the non-stem regions of the acyclovir binding RNA riboswitches. Seven families were identified in TABLE 2-continued Candidates for acyclovir and penciclovir. DNA sequences corresponding to the non-stem regions of the acyclovir binding RNA riboswitches. Seven families were identified in the screen: 582, 769, 795, 935, 946, 961, and 996 with between 1 and 39 sequences in each family. The percent identity for each sequence in the family was compared to the most prevalent sequence within each family (582-1, 769-1, 795-1, 935-1, 946-1, 961-1, and 996-1). The percent identity for each sequence in the family was also compared to the wild type sequence.

| Candidate Family-Sequence Number | SEQ ID NO: | Sequence | Length | % Identity Consensus | Wildtype |
|---|---|---|---|---|---|
| 769-4 | 150 | ACAGGTCAGCATAATGTGCTAGTGCG CATTCAAACCTATTTAGAGACT | 48 | 97.92 | 80.77 |
| 769-5 | 151 | ACAGGTTAGCATAATGTGCTAGTGCG CCTTCAAACCTATTTTGAGACT | 48 | 95.83 | 84.62 |
| 769-6 | 152 | ACAGGTTATCATAATGTGCTAGTGCG CCTTCAAACCTATTTAGAGACT | 48 | 95.83 | 82.69 |
| 769-7 | 153 | ACAGGTTAGCATGATGTGCTAGTGCG CCTTCAAACCTATTTAGAGACT | 48 | 95.83 | 82.69 |
| 769-8 | 154 | ACAGGTTAGCATAATGGGCTAGTGC GCCTTCAAACCTATTTAGAGACT | 48 | 95.83 | 86.54 |
| 769-9 | 155 | ACAGGTCAGCAAAATGTGCAAGTGC GCCTTCAAACCTATTTAGAGACT | 48 | 95.83 | 78.85 |
| 769-10 | 156 | ACAGGTCAGCATAATGTGCTAGTGCG CCTTCAAACCTATCTGGAGACT | 48 | 95.83 | 82.69 |
| 769-11 | 157 | ACAGCTTAGCATAATGTGCTAGTGCG CCTTCAAACCTATTTAGAGACT | 48 | 95.83 | 82.69 |
| 769-12 | 158 | ACAGGTCAGCATAATGTGCTAGTGCG CCTTCAAACCTATTTACAGACT | 48 | 97.92 | 80.77 |
| 769-13 | 159 | ACAGGTCAGCATAATGTGCTAGTGCG CCTTCAAACATATTTAGAGACT | 48 | 97.92 | 80.77 |
| 769-14 | 160 | ACAGGGTAGCATAATGTGCTAGTGC GCCTTCAAACCTATTTAGAGACT | 48 | 95.83 | 86.54 |
| 769-15 | 161 | ACAGGTTAGCATAATGTGCTAGTGCG CCCTCAAACCTATTTAGAGACT | 48 | 95.83 | 82.69 |
| 769-16 | 162 | ACAGGTTAGCATAATGTGCCAGTGCG CCTTCAAACCTATTTAGAGACT | 48 | 95.83 | 82.69 |
| 769-17 | 163 | ACAGGTCAGCATAATGGGCTAGTGC GCCTTCAAACCTATTTAGAGACT | 48 | 97.92 | 84.62 |
| 769 Consensus Sequence | 223 | ACAGSKYAKCAWRATGKGCHAKTGC GCMYTCAAACMTATYTDSAGACT | 48 | — | — |
| 795-1 | 164 | ACAGCGAAGCATAATGGCTACTGAC GCCCTCAAACCCTATTTGCAGACT | 49 | 100 | 83.02 |
| 795-2 | 165 | ACAGCGAAGCATAATGGCTACTGAC GCCCTCAAACCCTATTTACAGACT | 49 | 97.96 | 81.13 |
| 795-3 | 166 | ACAGCGAAGCATAATGGCTTCTGAC GCCCTCAAACCCTATTTGCAGACT | 49 | 97.96 | 81.13 |
| 795-4 | 167 | ACAGCCAAGCATACTGGCTACTGAC GCCCTCAAACCCTATTTGCAGACT | 49 | 95.92 | 79.25 |
| 795-5 | 168 | ACAGCGAAGCATAATGGCTACTGAC GCCCGCAAACCCTATTTGCAGACT | 49 | 97.96 | 81.13 |
| 795-6 | 169 | ACAGCGAAGCATAATGGCTACTGAC GGCCTCAAACCCTATTTGCAGACT | 49 | 97.96 | 80.77 |
| 795-7 | 170 | ACAGCGAGGCATAATGGCTACTGAC GCCCTCAAACCCTATTTGCAGACT | 49 | 97.96 | 81.13 |

TABLE 2-continued

Candidates for acyclovir and penciclovir. DNA sequences corresponding to the non-stem regions of the acyclovir binding RNA riboswitches. Seven families were identified in the screen: 582, 769, 795, 935, 946, 961, and 996 with between 1 and 39 sequences in each family. The percent identity for each sequence in the family was compared to the most prevalent sequence within each family (582-1, 769-1, 795-1, 935-1, 946-1, 961-1, and 996-1). The percent identity for each sequence in the family was also compared to the wild type sequence.

| Candidate Family-Sequence Number | SEQ ID NO: | Sequence | Length | % Identity Consensus | % Identity Wildtype |
|---|---|---|---|---|---|
| 795-8 | 171 | ACAGCGAAGCATAATGGCTACTGAC GCCTTCAAACCCTATTTGCAGACT | 49 | 97.96 | 84.91 |
| 795-9 | 172 | ACAGCGAAGCATAATGGCTACAGAC GCCCTCAAAACCTATTTGCAGACT | 49 | 95.92 | 80.77 |
| 795-10 | 173 | ACAGCGAAGCATAATGGCTACTGAC GCCCTCAAACCCTATTTGAGACT | 48 | 97.96 | 83.02 |
| 795-11 | 174 | ACAGCGAAGCATAATGGCTACTGAC GCCCTCAAACCCTATTGTCGACT | 48 | 93.88 | 76.92 |
| 795-12 | 175 | ACAGCCAAGCATAATGGCTACTGAC GCCCTCAAACCCTATTTGCAGACT | 49 | 97.96 | 81.13 |
| 795-13 | 176 | ACAGCGAAGCATAATGGCTACTGAC GCCCTCAAACCCTATTTGGCGACT | 49 | 95.92 | 83.02 |
| 795-14 | 177 | ACAGCGAAGCATAATGTCTACTGAC GCCCTCAAACCCTATTTGCAGACT | 49 | 97.96 | 81.13 |
| 795-15 | 178 | ACAGCGAAGCATAATGGCTACTGAC GCCGTCAAACCCTATTTGTAGACT | 49 | 95.92 | 83.02 |
| 795-16 | 179 | ACAGCGAAGCATAATGGCTACTGAC GCCCTCAAACCTTATTTGCAGACT | 49 | 97.96 | 83.02 |
| 795-17 | 180 | ACAGGTAGCATAATGGCTACTGACG CCCTCAAACCCTATTTGCAGACT | 48 | 95.92 | 84.91 |
| 795-18 | 181 | ACAGCGAAGCATAATGGCTACTGAC GCCCTCAAACCCTATTTCTAGACT | 49 | 95.92 | 81.13 |
| 795-19 | 182 | ACAGCGAAGCATAATGGCTACTGAC GCCCTCAAACCCTATTTGTAGACT | 49 | 97.96 | 83.02 |
| 795 Consensus Sequence | 224 | ACAGNSWRGCATAMTGKCTWCWGA CGSCBKCAAAMCYTANTTVNMGACT Where the N at position 5 can be C or no nucleotide, the N at position 40 can be T or no nucleotide, and the N at position 44 can be C, G, T, or no nucleotide | 49 | — | — |
| 935-1 | 183 | ACAGGGTAGCATAATGGGCTACTTG ACGCCTTCACCTATTTGTAGACT | 48 | 100 | 86.79 |
| 935-2 | 184 | ACAGGGTAGCATAATGGGCTACTTG ACGCCTTCACCTATTTGAGACT | 47 | 97.92 | 86.79 |
| 935-3 | 185 | ACAGGGTAGCATAATGGGCTACTTTA CGCCTTCACCTATTTGTAGACT | 48 | 97.92 | 84.62 |
| 935-4 | 186 | ACAGGGTAGCATAATGGGCTACTTG ACGCCTTCACCTATTTCTAGACT | 48 | 97.92 | 84.91 |
| 935-5 | 187 | ACAGGGTAGCATAATGGGCTACTTG ACGCCTTCACCTATTTGGAGACT | 48 | 97.92 | 88.68 |
| 935-6 | 188 | ACAGGGTAGCATAGTGGGCTACTTG ACGCCTTCACCTATTTGTAGACT | 48 | 97.92 | 84.91 |
| 935-7 | 189 | ACAGGGTAGCATGATGGGCTACTTG ACGCCTTCACCTATTTGTAGACT | 48 | 97.92 | 84.91 |
| 935-8 | 190 | ACAGGGTAGCATAATGGGCTACTTG ACGCCTTCACCTATTAGTAGACT | 48 | 97.92 | 84.91 |

TABLE 2-continued

Candidates for acyclovir and penciclovir. DNA sequences corresponding to the non-stem regions of the acyclovir binding RNA riboswitches. Se TABLE 2-continued Candidates for acyclovir and penciclovir. DNA sequences corresponding to the non-stem regions of the acyclovir binding RNA riboswitches. Seven families were identified in the screen: 582, 769, 795, 935, 946, 961, and 996 with between 1 and 39 sequences in each family. The percent identity for each sequence in the family was compared to the most prevalent sequence within each family (582-1, 769-1, 795-1, 935-1, 946-1, 961-1, and 996-1). The percent identity for each sequence in the family was also compared to the wild type sequence.

| Candidate Family-Sequence Number | SEQ ID NO: | Sequence | Length | % Identity Consensus | Wildtype |
|---|---|---|---|---|---|
| 946-14 | 211 | ACAGTGTAGCATAATGGGCTGCAGA CGCCGTCAAACCTATTTGAGACT | 48 | 95.92 | 84.62 |
| 946-15 | 212 | ACAGCGTAGCATAATGGGCTGCTGA CGCCGTCAAACCTATTTGGAGACT | 49 | 95.92 | 88.46 |
| 946-16 | 213 | ACAGCGTAGCATAATGGGCTGCAGA CGCCGTCAAACCTATTTACAGACT | 49 | 97.96 | 82.69 |
| 946-17 | 214 | ACAGCGTAGCATAATGGGCTGCTGA CGCCGTCAAACCTATTTGCAGACT | 49 | 97.96 | 86.54 |
| 946-18 | 215 | ACAGGGTAGCATAATGGGCTGCAGA CGCCGTCAAACCTATTTGGAGACT | 49 | 95.92 | 88.46 |
| 946-19 | 216 | ACAGCGTAGCATAATGGGCTACAGA CGCCGTCAAACCTATTTGCAGACT | 49 | 97.96 | 86.54 |
| 946-20 | 217 | ACAGCGTCGCATAATGGGCTGCAGA CGCCGTCAAATCTATTTGCAGACT | 49 | 95.92 | 80.77 |
| 946-21 | 218 | ACAGCGTAGCATAATGGGCTTCAGA CGCCGTCAAACCTATTTGCAGACT | 49 | 97.96 | 84.62 |
| 946-22 | 219 | ACATGTAGCATAATGGGCTGCAGAC GCCGTCAAACCTATTTGGAGACT | 48 | 93.88 | 84.62 |
| 946 Consensus Sequence | 226 | ACANNGTMGCATADTGGGCTDCWGR CGCMKTCAAAYCTATTTRNAGACT Where the N at position 4 can be G or no nucleotide, the N at position 5 can be C, G, T, or no nucleotide, and the N at position 44 can be A, C, G, or no nucleotide. | 49 | — | — |
| 961-1 | 220 | ACACCGTAGCATAATGGGCTACTGCC GCCGTCGACCTTTTGGAGACT | 47 | 100% | 82.69 |
| 996-1 | 221 | ACAGGGTAGCATAATGGCTTAGGAC GCCTTCAAACCTATCAAGACT | 46 | 100% | 76.92 |

Positive target acyclovir produced seven strong candidates (SEQ ID NOs:87-93; RNA sequences including stem regions) corresponding to 582-1 (SEQ ID NO:108), 769-1 (SEQ ID NO:147), 795-1 (SEQ ID NO:164), 935-1 (SEQ ID NO:183), 946-1 (SEQ ID NO:198), 961-1 (SEQ ID NO:220), and 996-1 (SEQ ID NO:221), each designated F1A (FIG. 17). These sequences were the most prevalent sequences in each family (the DNA sequences of all the members of each family are: 582 (SEQ ID NOs:108-146); 769 (SEQ ID NOs:147-163); 795 (SEQ ID NOs:164-182); 935 (SEQ ID NOs:183-197); 946 (SEQ ID NOs:198-219); 961 (SEQ ID NO:220); and 996 (SEQ ID NO:221)). The consensus sequences show all possible substitutions or gaps at each nucleotide position for each family (SEQ ID NOs: 222-226). As the goal was to identify aptamers from a library based on RNA that is known to bind to deoxyguanosine, strong candidates needed to have minimal presence in the counter-targets population. Candidates F1A-795, F1A-935, and F1A-946 met this criterion very well, as they were not detected in the counter-target population. F1A-996 and F1A-961 are considered the next best candidates in this regard, although they do show up to a small degree in the counter-targets population. In addition, candidates should appear minimally in the negative population, as those sequences desorbed from GrO without the influence of acyclovir and could represent false positives. F1A-935 and F1A-946 performed ideally under this criterion as well, as they were not found in the negative population. Candidate F1A-769 was minimally detected in the negative population, with candidates F1A-961, F1A-795 and F1A-996 performing less well. Enrichment rate was the final condition to be considered, with F1A-935, F1A-946, and F1A-769 performing adequately. Candidate F1A-582 was included because it exhibited the greatest enrichment rate, although it did not perform well under the other criteria. The remaining candidates did not perform well relative to these four, but exhibited acceptable characteristics.

Additional target penciclovir produced seven strong candidates (SEQ ID NOs:94-100), each designated F1P (FIG. 18). As before, the goal was to identify aptamers from a library based on RNA that is known to bind to deoxyguanosine, diverging from libraries enriched for binding to acyclovir (acyclovir) after Round 10. Strong candidates needed to have minimal presence in both the acyclovir and the counter-targets populations to minimize cross-reactivity. Candidate F1P-923 met the first criterion, candidate F1P-710 met the second criterion, and candidate F1P-584 met both criteria to a degree. Candidate F1P-584 also demonstrated moderate favorability for penciclovir over the negative condition, as well as moderate enrichment relative to the previous generation's response to acyclovir. The remaining candidates demonstrated either minimal favoring of penciclovir over acyclovir or minimal favoring of penciclovir over counter-targets (F1P-837 and F1P-932; F1P-991 and F1P-718; respectively). These four candidates demonstrated some favorability for penciclovir over the negative condition which minimizes the chance of a false positive, although this criterion is not as significant if a candidate does not demonstrate selectivity for penciclovir over its analogues. Enrichment rate was the final condition to be considered, with F1P-923, F1P-932, and F1P-584 performing adequately.

Qualitative PAGE assessment of selected aptamers was performed. Individually synthesized and transcribed aptamers were subjected to selection on Graphene Oxide (GrO) under physiological Mg++(0.5 mM) and elution with either acyclovir (+) or counter-targets (x). The specifically eluted aptamer fractions for each sample were subjected to PAGE for analysis.

100 pmoles of each aptamer candidate (per trial/lane) was resuspended in 1× modified selection buffer (50 mM HEPES, 100 mM KCl, 0.5 mM $MgCl_2$, pH 7.3) and refolded (90° C. for 5 min, then 4° C. for 5 min), then incubated at 37° C. for 30 minutes with 200 pmoles (each) of pooled counter-targets or target. Final library concentration was 0.5 µM, target/counter-targets concentration was 1 µM (incubation volume was 200 µl).

After target/counter-target incubation, 250 µg of GrO (Angstron Materials (Dayton, Ohio) was added to adsorb unbound candidate (10-minute incubation at 37° C.).

Samples were centrifuged for 5 minutes at 7,000×g. Supernatant was recovered, denatured using 2× Formamide with 40 mM EDTA, and run on 10% denaturing PAGE with 8 M urea (supplier: American Bioanalytical; catalog #'s AB13021-01000. AB13022-01000). Running buffer was 1×TBE (supplier: Amresco/VWR; catalog #0658-20L, diluted using DI water). DNA ladder was 20/100 DNA ladder (IDT). Gels stained with Gel Star (Lonza, 50535) and imaged on a blue light transilluminator.

Candidates F1A-769, F1A-795, F1A-946, and F1A-996 appear to exhibit selective positive response in this qualitative PAGE assessment (good elution of the Aptamer from GrO with Acyclovir target and relatively lower or minimal elution with counter-targets).

Conclusion

Strong candidates for acyclovir were identified after twelve rounds of iterative screening and parallel assessment; reasonable candidates for penciclovir were identified after two rounds of screening and parallel assessment.

Example 2. Isolation of Conditional scFv's

Potential splice site liabilities are removed and tumor antigen specific scFv's are synthesized by overlapping oligo synthesis and cloned into the CAR shuttle construct containing the acyclovir responsive element and the primate CD3 promoter. As an initial prototype, anti-ECD of EPCAM or ERBB2scFv with a CD8-alpha signal peptide, stalk, and transmembrane domain is utilized. Solid tumor microenvironment restricted CAR products are generated either using methods as described in U.S. Pat. No. 8,709,755 and PCT Publication No. WO/2016/033331A1 or by direct selection from human phage libraries under permissive and non-permissive conditions. Briefly, a human $V_H \times V_L$ library from Creative Biolabs (Shirley, N.Y.) is panned in the following tumor permissive conditions: 100 µg/ml hyaluronan, 100 kDa fraction (Lifecore Biomedical, Chaska, Minn.), 20 mg/ml recombinant HSA (Cyagen, Santa Clara, Calif.), 200 ng/ml recombinant human VEGF in 25 mM sodium bicarbonate buffer, 2 µM adenosine, 10 mM sodium lactate pH 6.7, following clearance with streptavidin magnetic beads (ThermoFisher, Carlsbad, Calif.) bound to biotinylated human IgG. Binding to biotinylated-target receptor ECD of EPCAM and ERBB2 conjugated beads at 37° C. is performed under permissive conditions followed by serial washes in permissive conditions. Phage are released with physiologic conditions (1 µg/ml hyaluronan, 20 mg/ml HSA, 25 mM bicarbonate, 1 mM sodium lactate pH 7.2) followed by elution of tight variants with acid elution and rapid neutralization with 1 M Tris. Phage are expanded and genomic DNA is split for deep sequence analysis of $V_H \times V_L$ chains using long read sequencing (PacBio, Menlo Park, Calif.) Panning can be repeated for enrichment. $V_H \times V_L$ sequences showing preferential amplification of reads during the phage culturing process over enrichment to target are excluded for further analysis. Phage with selective binding to the target that are enriched under tumor permissive conditions but released under physiologic conditions are chosen for further characterization by cloning into the CAR construct expression system, generation of lentivirus, and transduction into T cells for testing CAR-mediated tumor antigen expressing target cell killing in a tumor-selective environment compared to physiologic conditions.

Example 3. Generation of MRB-CARs Using Microenvironment Restricted scFv's

Microenvironment restricted ASTRs were obtained that were made by subjecting $V_H$ and $V_L$ sequences with low selectivity for the low pH microenvironment by evolution as described in application WO/2016/033331A1, Chimeric antigen receptors (CARs) for binding either of two cognate tumor antigens, Target 1 or Target 2, with increased activity at the reduced pH of a tumor microenvironment compared to the microenvironment of normal tissue MRB-CARs were made by incorporating the heavy chains and light chains of the microenvironment restricted single-chain antibodies into lentiviral expression vectors along with other CAR domains to generate a series of candidate MRB-CARs. These MRB-CARs included various combinations of modules. The MRB-CARs included, from amino to carboxy terminus, in positions 1 through 9, a CD8 signal peptide (sp) (P1) (SEQ ID NO:74); a microenvironment restricted anti-Target 1 ASTR or anti-Target 2 ASTR (P2-P4); a stalk and transmembrane (TM) domain from CD8 (SEQ ID NO:75) (P5) and a co-stimulatory domain from CD137 (P6) (SEQ ID NO:1) in the cases of T2A and T2B or a stalk and transmembrane (TM) domain from CD28 (SEQ ID NO:76) (P5) and a co-stimulatory domain from ICΔ (SEQ ID NO:3) (P6) in the case of T1A; an activation domain from CD3Z (SEQ ID NO:13) (P7); a 2A-1 ribosomal skip sequence (SEQ ID NO:77) (P8); and an exemplary eTAG (SEQ ID NO:78) (P9).

Pan T cells (AllCells, Alameda, Calif.) were transduced with the recombinant lentiviral particles to express the series of candidate MRB-CARs and the percent transduced cells was calculated by determining the percent of cells expressing the eTag using FACS. Pan T cells were successfully transduced with the recombinant lentiviral particles encoding the candidate MRB-CARs.

The cytotoxic activity of the candidate MRB-CARs against target cells expressing either Target 1 or Target 2 (CHO-Target 1 and CHO-Target 2, respectively) was analyzed at a pH of 7.4 (normal tissue) or a pH of 6.7 (reduced pH of a tumor microenvironment) by xCELLigence System (ACEA). Briefly, target cells expressing Target 1 or Target 2 were seeded to a 96-well E-plate at 20,000 cells/well with tumor conditional or normal medium one day before the experiment. Effector cells were rested for two days in human T cell medium containing 100 IU/mL of IL-2 and added into experimental wells containing Target cells at effector cell/target cell ratios (E/T) of 3:1, 1:1, and 0.3:1.

Impedance readings were taken every 5 minutes for approximately 40 hours after effector cell addition and impedance was reported as the Cell Index (CI). Percentage of specific cytolysis was calculated as follows ((CI Target+Control virus transduced effector T cells)−(CI Target+effector T cells transduced with CARs directed to Target 1 or Target 2))/(CI Target+Control virus transduced effector T cells)×100.

Results

Many of the candidate MRB-CARs had higher cytotoxic activity on the target cells at a pH of 6.7 than at a pH of 7.4. Exemplary MRB-CARs that were more effective at lysing target cells at a pH of 6.7 than at a pH of 7.4 included MRB-CAR T1A, MRB-CAR T2A, and MRB-CAR T2B. The ASTR of MRB-CAR T1A comprised, from 5' to 3', Target 1 MRB VH (SEQ ID NO:281) and Target 1 MRB VL (SEQ ID NO:282) separated by Linker 1 (SEQ ID NO:283). The ASTR of MRB-CAR T2A comprised, from 5' to 3', Target 2 MRB VH (SEQ ID NO:289) and Target 2 MRB VL (SEQ ID NO:290) separated by Linker 2 (SEQ ID NO:291). The ASTR of MRB-CAR T2B was the same as that for MRB-CAR T2A except that the positions of VH and VL were swapped.

Example 4. Construction of Ligand-Inducible Riboswitches

Figure 7:
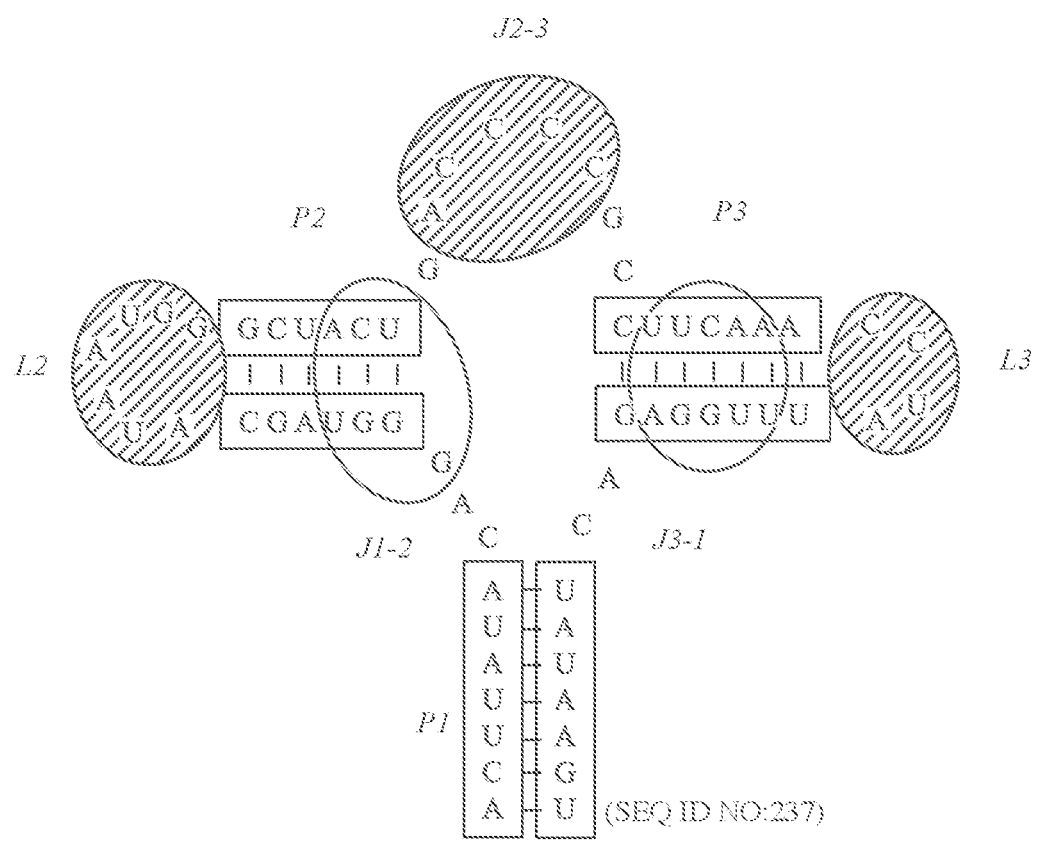
FIG. 7 represents the *M. florum* type I-A deoxyguanosine riboswitch aptamer regions targeted for directed evolution strategy. Nucleotides within empty ovals were targeted for randomization. Nucleotides within striped ovals were targeted for insertion/deletion and randomization.
Figure 8A:
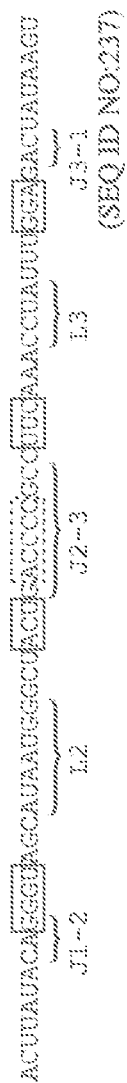
FIGS. 8A and 8B represent the *M. florum* type I-A deoxyguanosine riboswitch aptamer screening library.
Figure 8B:
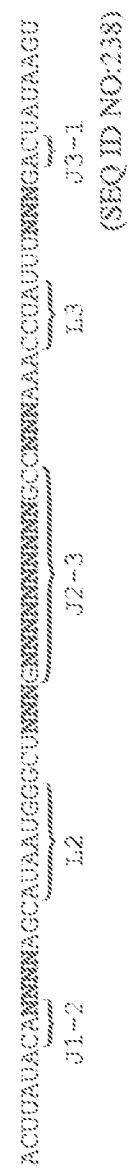
Figure 11:
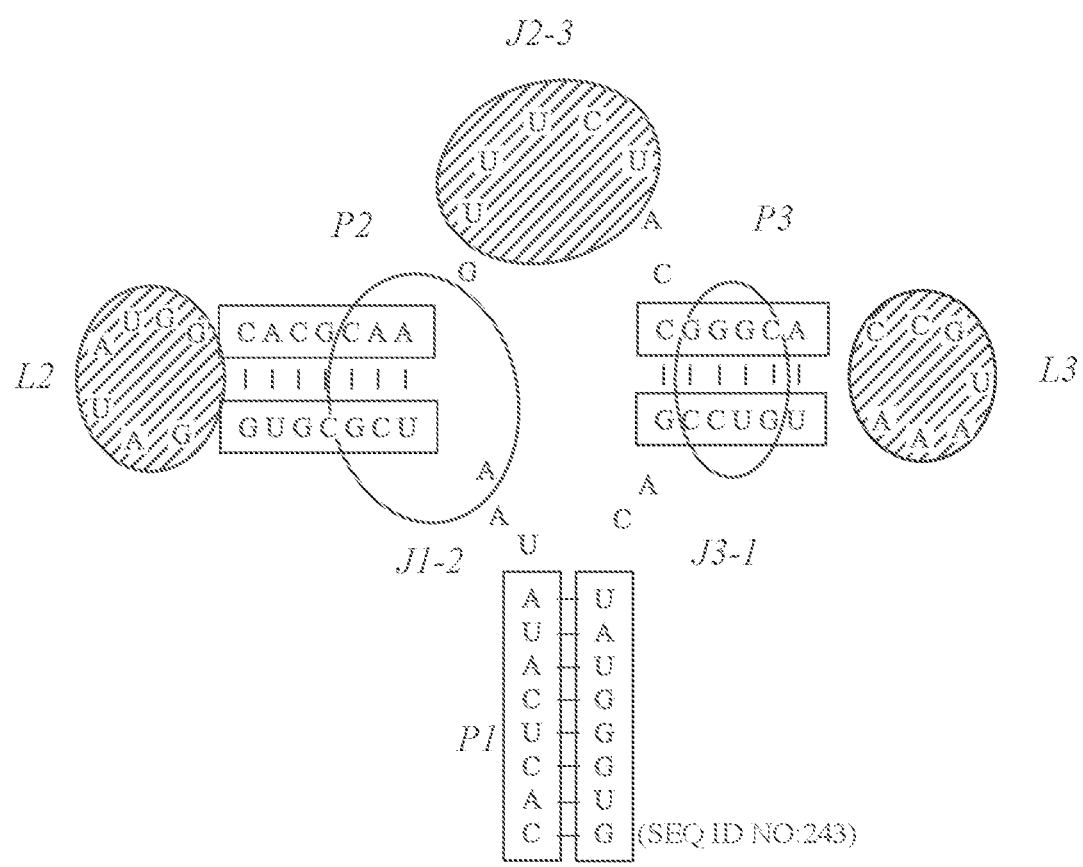
FIG. 11 represents the *B. subtilis* guanosine xpt riboswitch aptamer regions targeted for directed evolution strategy. Nucleotides within empty ovals were targeted for randomization. Nucleotides within striped ovals were targeted for insertion/deletion and randomization
Figure 14:
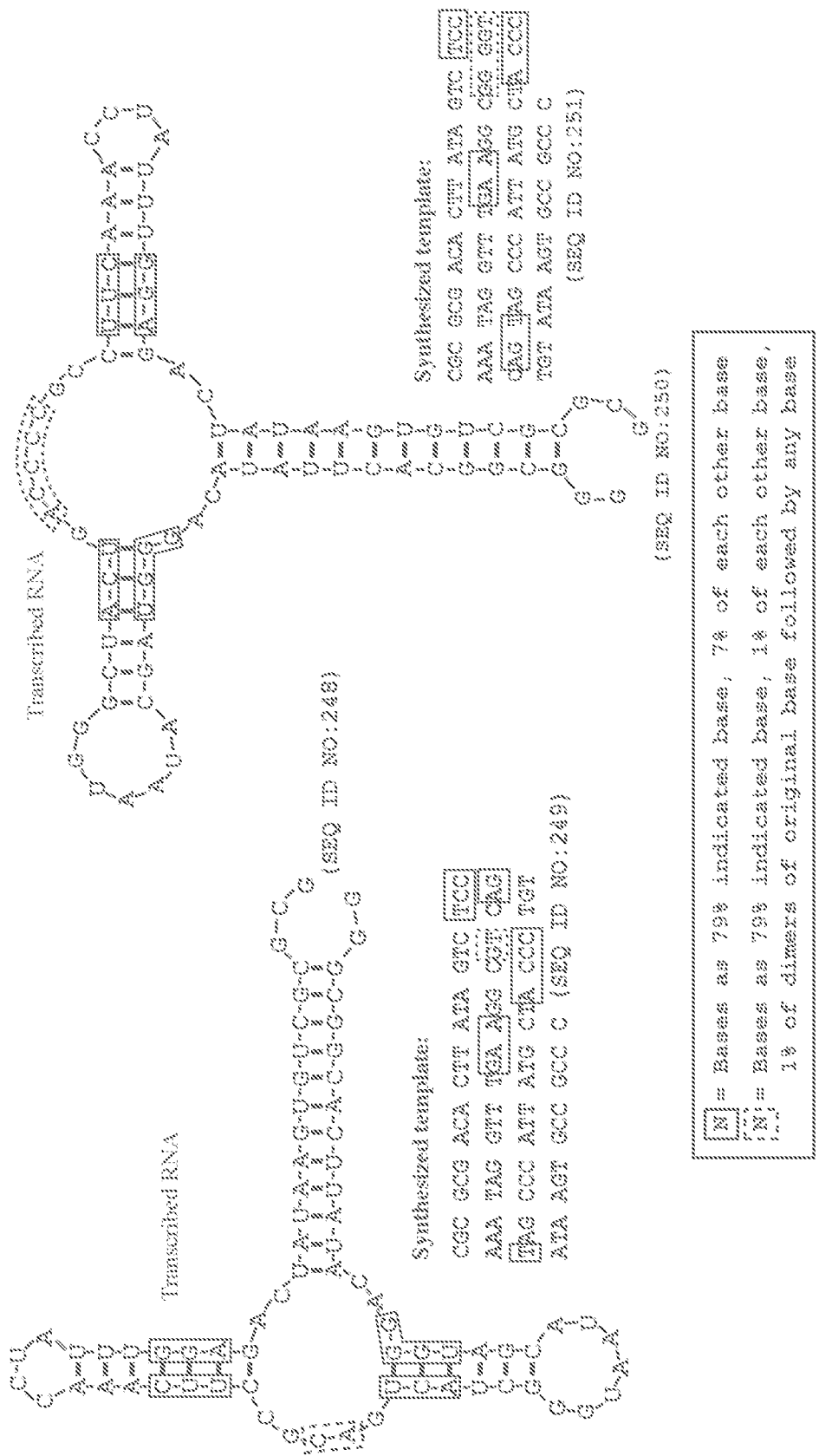
FIG. 14 shows the selection library construction. The library was constructed on the basis of known guanosine- and deoxyguanosine-binding RNA (Pikovskaya, 2013).
Figure 15:
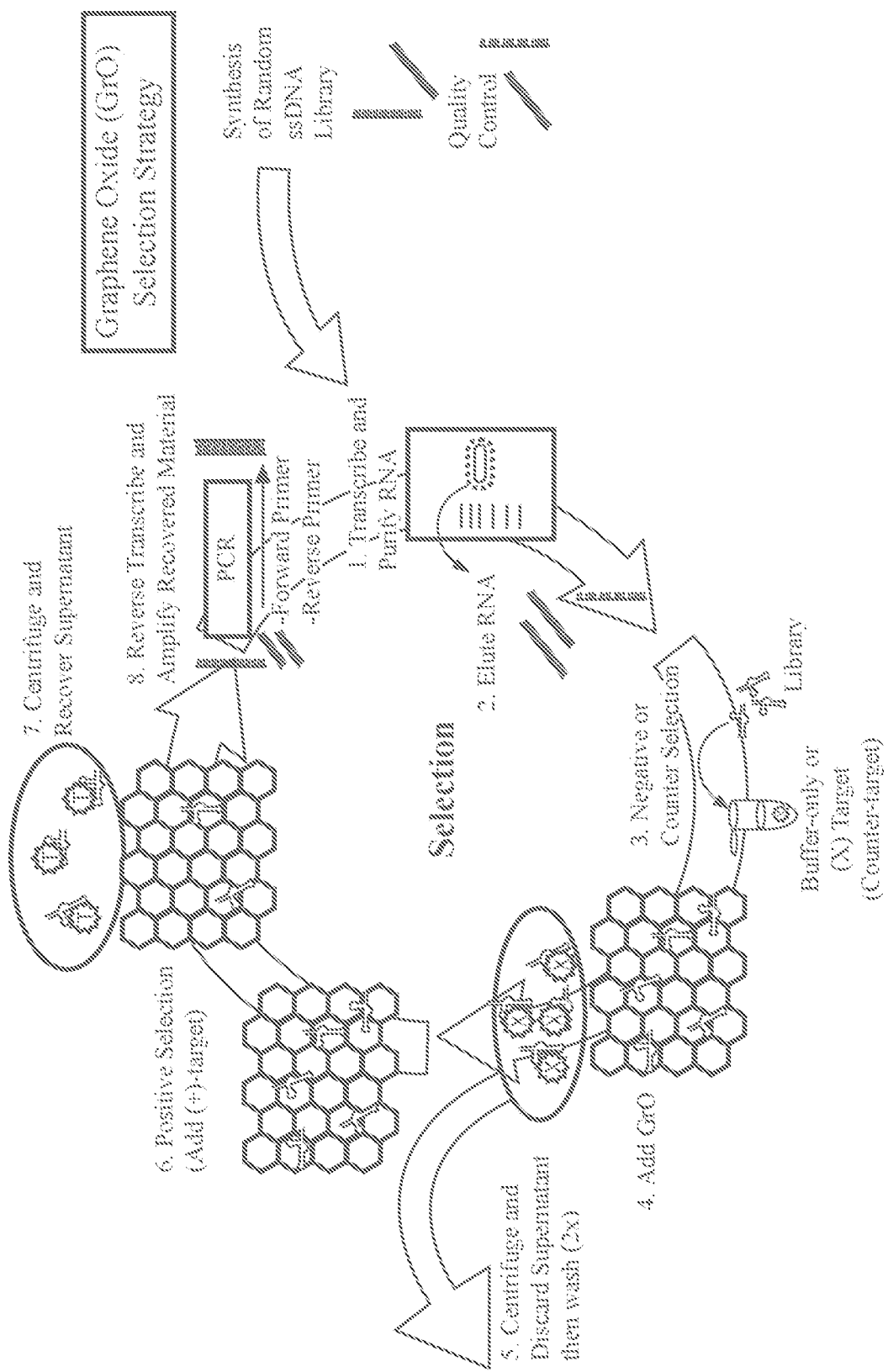
FIG. 15 shows an illustration of graphene oxide (GrO) aptamer selection. In step (1), RNA was transcribed and purified. In step (2), purified RNA was eluted. In step (3), aptamers were incubated with counter-targets and buffer. In step (4), sequences bound to counter-targets or buffer components were removed with graphene oxide. In step (5), centrifugation partitioned the non-specifically-responsive species within the supernatant, which is then discarded. Two additional 5-minute washes removed most of the residual counter-target-binding and buffer-binding sequences. In step (6), a solution of acyclovir in 1× selection buffer was added to the GrO-bound library for positive selection so potential aptamer sequences desorb from the GrO through interaction with the positive target. In step (7), a final centrifugation step separates the target-binding sequences in the supernatant from the non-responsive sequences still adsorbed to the GrO. In step (8) selected sequences were reverse-transcribed, then the library was amplified through PCR, then transcribed to generate library for the next selection round.

Deoxyguanosine riboswitch aptamer and guanine riboswitch aptamers (Pikovskaya, 2014; Kim, 2007) or other purine riboswitch aptamers are synthesized as oligonucleotides. In one example, the deoxyguanosine IA riboswitch from *Mesoplasma florum* (underlined and in bold in FIG. 6; FIG. 7) is selected for evolution to generate an acyclovir-responsive riboswitch. In another example, the guanine xpt riboswitch from *Bacillus subtilis* (underlined and in bold in FIG. 10; FIG. 11) is selected for evolution to generate an acyclovir-responsive riboswitch. For each of these two examples, a random RNA library is generated with alternate nucleotides at targeted sequence positions in the P2, P3, J1-2, and J2-3 segments (FIGS. 7 and 11). Each segment allows for 3 alternate nucleic acids at each targeted sequence position, or alternatively base deletion and insertion of 4 nucleotides in the +1 site at each targeted sequence position for saturation mutagenesis as indicated in FIGS. 8A-8B and 9 (*M. florum* IA) and FIGS. 12A-12B and 13 (*B. subtilis* xpt). Primer extension and reagent preparation is followed by RNA transcription. The resultant RNA library is negatively selected on graphene oxide in the presence of guanine, guanosine, and deoxyguanosine followed by positive selection with acyclovir or penciclovir. During the negative and positive selection processes, human cell physiologic magnesium levels (0.5 mM to 1.2 mM) are used and the temperature is kept at 37° C. Recovered aptamers are reverse transcribed and PCR amplified followed by transcription and subsequent screening for at least 8 successive rounds of selection. In a parallel approach, aptamers are screened with an additional negative screen at 40° C. Resultant positive pools are examined by NextGen sequencing and analysis. Individual aptamers are synthesized and examined for affinity by isothermal calorimetry at 35-40° C. in human cell physiologic magnesium levels. Following selection for positive acyclovir and penciclovir specific aptamers, aptamers are integrated with ribozyme hammerhead and pistol ribozymes. Positive acyclovir selective aptamers are combined with pistol ribozymes to identify acyclovir regulated ribozymes. (Harris K A RNA. 2015 November; 21(11): 1852-8. doi: 10.1261/rna). Variants are subjected to gel shift based PAGE purification in the presence of acyclovir and absence of penciclovir. Additionally, the acycloguanosine selective riboswitch is placed immediately 3' in a loop to a splice acceptor upstream of the CAR/IL-7 construct. In the absence of acyclovir, the splice site position is bound in the riboswitch complex but in the presence of acyclovir becomes accessible, generating a functional CAR transcript.

Example 5. Construction of In Vivo Propagation Domains

A series of constitutively active IL7 receptor (IL7R) transmembrane mutants from T cell lymphoblastic leukemias (243 InsPPCL (SEQ ID NO:82); 246 InsKCH (SEQ ID NO:101); 241 InsFSCGP (SEQ ID NO:102); 244 InsCHL (SEQ ID NO:103); and 244 InsPPVCSVT (SEQ ID NO:104); all from Shochat et al 2011, J. Exp. Med. Vol. 208 No. 5 901-908) are synthesized by overlapping oligo nucleotide synthesis (DNA2.0, Newark, Calif.). The synthesized constitutively active IL7R transmembrane mutants are inserted into a constitutively expressing lentiviral vector backbone immediately behind a 2A ribosomal skip sequence followed by an anti-CD19 CD3ξ expression cassette, which includes a CD8A stalk (SEQ ID NO:79) and a leader peptide (SEQ ID NO:74). HEK293 packaging cells are transfected with the IL7R transmembrane mutant lentiviral vectors and lentiviral packaging constructs, grown, and viral supernatants are harvested using methods known in the art. CD3/CD28-stimulated T cells are transduced with the viral supernatants and grown in IL2 deficient AIM V, CTS OpTmizer T Cell Expansion SFM, or X-VIVO 15 media for 4 weeks, supplemented weekly with frozen PBMCs from the same donor. The resulting expanded transduced T cells expressing IL7R variants are cloned by FACS sorting and the sequences of the IL7R constructs are identified by sequencing RT-PCR products. The 243 InsPPCL variant (PPCL) (SEQ ID NO:82) is selected for further evolution to generate a conditionally active CAR.

Example 6. Screening of Accessory Components for CAR-T Activation and Propagation A series of protein-encoding domains (ABCG1, SOCS1, SMAD2, TGFBR2, cCBL, and PD1) and miRNA sequences are constructed for incorporation into a synthetic intron on the reverse strand of a CD3-promoter driven CAR cassette. Each construct containing the CD3-promoter driven CAR cassette and a protein-encoding domain or miRNA sequence includes a unique bar code for deep sequencing and is assembled using Gibson assembly followed by transformation and library expansion in *E. coli*. Viral stocks are produced and used to transduce CD3/CD28-stimulated T cells in AIM V, CTS OpTmizer T Cell Expansion SFM, or X-VIVO 15 media without IL2 and allowed to grow for 4 weeks in culture with serial sampling of DNA for amplification and deep sequencing for code identification. The library is also subject to PACBio full length sequencing to determine library diversity and to decode the bar code components. The miRNA sequences and protein-encoding domains are tested for synergistic activation of CAR CD3ξ domains.

Example 7. Engineering a Retroviral Packaging and Transducing System to Target Resting T Cells for Selective T Cell Integration and Expression from PBMCs Although producing high-titer lentiviral vectors by transient transfection is possible, this method carries the risk of generating replication competent retroviruses (RCRs) and is not scalable for clinical applications. Herein, a stable retroviral packaging cell line is generated by the simultaneous introduction of multiple constructs encoding inducible promoters and their regulators into HEK293 suspension-adapted cells (HEK293S) to stably produce the viral components, CAR genes, and their regulatory components. Two distinct inducible systems can be used to temporally control the expression of genes. One system is based on rapamycin- or rapalog-induced dimerization of two transcription factors. One transcription factor consists of three copies of the FKPB protein fused to a ZFHD1 DNA binding domain and the other transcription factor consists of a FRB protein fused to a p65 activation domain. Rapamycin or a rapalog dimerizes the transcription factors to form ZFHD1/p65 AD and can activate gene transcription at 12×ZFHD1 binding sites.

A series of vectors as shown in FIGS. 3A-3E are generated with flanking transposon sequences for integration into the HEK293S genome. Once integrated into the genome of a cell, these sequences function as regulatory components and lox and/or FRT sites for subsequent integration using Cre and/or flp recombinases, herein referred to as landing pads. The initial 5 constructs contain polynucleotide sequences encoding puromycin resistance, GFP, RFP, and an extracellular MYC tag that is targeted to the cell membrane through an N-terminal PLss (bovine prolactin signal peptide) and anchored to the cell membrane through a platelet-derived growth factor receptor (PDGFR) C-terminal transmembrane anchoring domain. The initial 5 constructs can also include constitutive minimal CMV and minimal IL-2 promoters, a rapamycin-regulated ZFHD1-based promoter, a tetracycline-responsive element (TRE) promoter, or a bidirectional TRE (BiTRE) promoter. The construct in FIG. 3A contains a polynucleotide sequence encoding FRB domain fused to the NFκB p65 activator domain (p65 AD) and ZFHD1 DNA binding domain fused to three FKBP repeats that is constitutively expressed. The construct in FIG. 3A also includes HIV1 REV and HSV VP65 domain SrcFlagVpx under the rapamycin-inducible ZFHD1/p65 AD promoter. The construct in FIG. 3B includes a polynucleotide encoding an rtTA sequence under the control of the ZFHD1/p65 AD promoter. The construct in FIG. 3C includes a polynucleotide encoding a puromycin resistance gene flanked by loxP sites and the extracellular MYC tag flanked by lox2272 sites. Both of these selectable markers are under the control of a BiTRE promoter, which is flanked by FRT sites. The construct in FIG. 3D includes a polynucleotide encoding GFP flanked by loxP sites that is under the control of a TRE promoter. The construct in FIG. 3D also includes a single FRT site between the TRE promoter and the 5' loxP site of GFP. The construct in FIG. 3E includes a polynucleotide encoding RFP flanked by loxP sites that is under the control of the ZFHD1/p65 AD promoter. The construct in FIG. 3E also includes a single FRT site between the ZFHD1/p65 AD promoter and the 5' loxP site of RFP The constructs in FIGS. 3C-3E function as landing pads for other polynucleotide sequences to insert into the genome of the packaging cell line. The polynucleotide sequences to be inserted can be flanked by lox sites and inserted into the genome using Cre recombinase and the loxP sites. This results in insertion and simultaneous removal of the genomic regions encoding puromycin resistance, the extracellular MYC tag, GFP, and RFP. Alternatively, the polynucleotide sequences can be flanked by FRT sites and inserted into the genome using flp recombinase and the FRT sites followed by removal of the polynucleotide sequences encoding puromycin resistance, the extracellular MYC tag, GFP, and RFP using Cre recombinase.

To generate the packaging cell line with landing pads integrated into the genome, HEK293S cells are co-transfected with equimolar concentrations of the 5 plasmids (FIGS. 3A-3E) plus 5 µg of in vitro-transcribed piggybac transposase mRNA or 5 µg of a plasmid with a promoter for expressing piggybac transposase in the presence of PEI at a ratio of 2:1 or 3:1 PEI to DNA (w/w) or 2-5 µg piggybac transposase protein using a cationic peptide mixture. The transfected cells are selected with puromycin in the presence of 100 nm rapamycin and 1 ug/mL doxycycline for 2-5 days followed by fluorescence-activated cell sorting to collect cells expressing GFP and RFP. The sorted cells are grown 5 days in the absence of puromycin, rapamycin, and doxycycline and cells expressing GFP and RFP are removed also myc positive cells are removed with myc beads. Individual clones from negatively sorted cells are then screened for induction of GFP and RFP by rapamycin and doxycycline and single cell cloned. The DNA from clones is harvested and sequenced for integration analysis. Clones positive for strong inducible expression of GFP and RFP in the presence of rapamycin and doxycycline with limited background expression in the absence of rapamycin and doxycycline are expanded and banked.

Figure 4C:
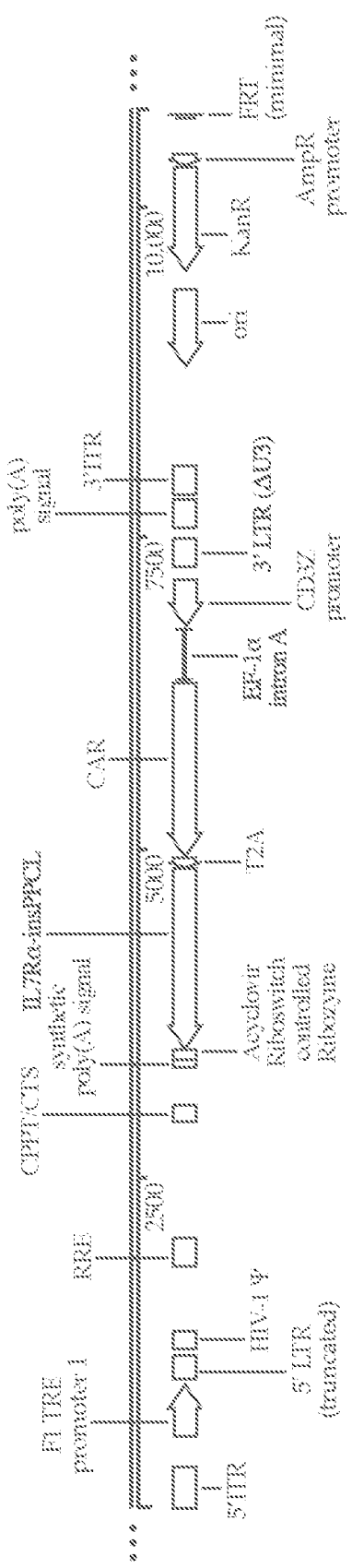

The HEK293S cells with the constructs from FIGS. 3A-3E integrated into the genome are then transfected with a construct containing a tricistronic polynucleotide encoding a DAF signal sequence/anti-CD3 scFvFc (UCHT1)/CD14 GPI anchor attachment site (SEQ ID NO:287), a DAF signal sequence/CD80 extra-cellular domain capable of binding CD28/CD16B GPI anchor attachment site (SEQ ID NO:286), and a DAF signal sequence/IL-7/DAF (SEQ ID NO:286) and transposon sequences flanking the polynucleotide region for integration into the HEK293S genome (FIG. 4A). After transfection, cells are expanded for 2 days in the absence of rapamycin and doxycycline and colonies that are constitutively red are selected. Positive colonies are then transiently transfected with a construct for expressing Cre recombinase to remove remaining genomic DNA, and the RFP encoding region. Another construct (FIG. 4B) containing a polynucleotide with a BiTRE promoter and a polynucleotide region encoding the gag and pol polypeptides in one direction and a polynucleotide region encoding the measles virus F and H proteins in the other direction is transfected at the same time. The Cre recombinase integrates the construct into the genome to generate the integrated sequence shown in FIG. 4B. Resultant colonies are evaluated for protein expression in the presence of doxycycline and rapamycin and analyzed by deep sequencing for genomic integration. The remaining TRE responsive GFP site is retained for the lentiviral genome insertion.

Example 8. Generation of Lentivirus Vector and Retroviral Packaging

The retroviral packaging stable cell line generated in Example 7 is transfected with a construct (FIG. 4C) for expressing Flp recombinase and a construct containing a polynucleotide sequence encoding a CAR and the lymphoproliferative element IL7Rα-insPPCL under the control of a CD3Z promoter that is not active in HEK293S cells, wherein the CAR and IL7Rα-insPPCL are separated by a polynucleotide sequence encoding a T2A ribosomal skip sequence and the IL7Rα-insPPCL has an acyclovir riboswitch controlled ribozyme. The CAR-containing construct further includes cPPT/CTS and RRE sequences and a polynucleotide sequence encoding HIV-1 Psi. The entire polynucleotide sequence on the CAR-containing construct to be integrated into the genome is flanked by FRT sites. Successful integration of the CAR-containing construct causes constitutive expression of GFP that is consequently removed by transient transfection with a construct for expressing Cre recombinase. The HEK293S line is grown in serum free media. Following growth to peak cell density in a stirred tank reactor, the cells are diluted to 70% peak cell density and treated with 100 nM rapamycin for 2 days to induce expression of early genes REV, Vpx, and aCD3 scFv CD16B GPI, aCD28 scFv CD16B GPI, and IL-7 SD GPI DAF followed by the addition of 1 ug/mL doxycycline in the media to induce expression of structural elements like Gag Pol, MV(Ed)-FΔ30, MV(Ed)-HΔ18, and lentiviral genome including the therapeutic target. Levels of virus production are examined by qPCR of the packaging sequence and p24 ELISA. Virus is harvested by depth filtration of cells, and concentration/diafiltration using a TFF cartridge followed by flash freezing for vialing.

Example 9. Peripheral Blood Mononuclear Cell (PBMC) Isolation, Transduction, and Expansion The following example illustrates the use of a closed system for ex vivo processing of PBMCs before in vivo expansion. As an example, 30 to 200 ml of human blood is drawn from a subject with Acid Citrate Dextrose Solution (ACD) as an anticoagulant into a blood collection bag. Alternatively, blood is drawn into Vacutainer tubes, a syringe, or an equivalent and is transferred to an empty blood collection or IV bag. The whole blood is processed using a Neat Cell kit (Cat # CS-900.2, Omniamed) on a Sepax 2 cell processing system (BioSafe) according to the manufacturers' instructions. The peripheral blood mononuclear cells (PBMCs) are collected either into a culture bag, or alternatively a syringe. An aliquot is taken aseptically for cell counting to determine the number of viable cells. The PBMCs are transferred to a G-Rex100MCS Gas Permeable Cell Culture System device (Wilson Wolf) at a final concentration of $0.1$-$1.0 \times 10^6$ viable cells/ml in X-VIVO 15 (Cat #08-879H, Lonza) or CTS OpTmizer Cell Expansion SFM (Cat # A1048501, Thermo Fisher Scientific) media with 10-300 IU/ml IL-2 (Cat #202-IL-010, R&D Systems) in up to 200 ml final volume. In addition to IL-2, CTS Immune Cell SR (Cat # A2596101, Thermo Fisher Scientific) can be added to the media. The closed G-Rex Gas Permeable Cell Culture System device can be pre-coated with Retronectin (Cat # CH-296, Takara), or a similar fibronectin-derived equivalent, according to the manufacturer's instructions.

The PBMCs isolated from peripheral blood are loaded onto a PALL PBMC filter, washed once through the filter with 10 ml of AIM V (Thermo Fisher Scientific) or X-VIVO 15 media followed by perfusion with 10-60 ml of lentivirus stock (as prepared in Example 8) at 37° C. at 5 ml/hr. The PBMCs are then washed again with AIM V, CTS OpTmizer T Cell Expansion SFM, or X-VIVO 15 media containing recombinant human DNase (Pulmozyme, Genentech) followed by a wash with DNase-free Lactated Ringers (Cat # L7500, Braun). The PBMCs are then reverse perfused through the filter into a syringe. The cells (target levels of cells are $5 \times 10^5$ to $1 \times 10^6$ cells/kg) are then reinfused into the subject through intravenous infusion.

Depending upon the riboswitch contained within the retroviral genome, the subject is given the respective nucleoside analogue antiviral drug or nucleoside analogue antiviral prodrug (acyclovir, valaciclovir, penciclovir, or famciclovir). Subjects can be given any therapeutically effective dose, such as 500 mg of the nucleoside analogue antiviral drug or prodrug orally three times/day. Treatment with the nucleoside analogue antiviral drug or prodrug preferably begins before reinfusion, such as 2 hours before, and can also begin at the time of reinfusion or at some time after reinfusion. The treatment can continue for at least 1, 2, 3, 4, 5, 7, 10, 14, 21, 28, 30, 60, 90, 120 days or 5, 6, 9, 12, 24, 36, or 48 months or longer. The treatment can include administration of the nucleoside analogue antiviral drug or prodrug once, twice, three, or four times daily. After reinfusion and treatment is begun, the number of infected cells is determined through blood counts on days 2, 5, 7, 11, 13, 18, 28, and 56 post-reinfusion using qPCR to quantitate the amount of viral genome. A subject experiencing fever or cytokine release syndrome may have the dose or frequency of the nucleoside analogue antiviral drug or prodrug reduced or halted. If the infected T cells fail to amplify 10,000-100,000 fold by day 18, the dose or frequency of the nucleoside analogue antiviral drug or prodrug may be increased. The clinical response of the subject can be measured through FDG PET imaging and serial CT scan. Oral dosing of the nucleoside analogue antiviral drug or prodrug can be reduced or halted following prolonged remission or in the event of excessive T cell propagation beyond 30% of total peripheral T cell counts.

Example 10. Therapeutic Intervention to Raise Vascular or Tissue pH

To reduce the binding of an antigen binding domain to its cognate antigen, $NaHCO_3$ is administered as an IV bolus or by IV infusion. The standard dosage is 1 mg/kg of body weight as the initial dose followed by 0.5 mg/kg every 10 minutes. A 50-milliliter bolus of $NaHCO_3$ will raise the serum pH approximately 0.1 of a pH unit. If the pH is 7.0, it requires four 50 mEq ampules of $HCO_3$ to correct the pH to 7.40

Example 11. Testing Activity of IL-7 Receptor Lymphoproliferative/Survival Elements in PBMCs To test IL-7Rα variants for their ability to mediate antigen-independent survival of T cells, thirty milliliters of human blood were drawn with acid citrate dextrose (ACD) as an anticoagulant into Vacutainer tubes. The whole blood was processed using density gradient centrifugation with Ficoll-Pacque™ (General Electric) following manufacturer's instruction, to obtain peripheral blood mononuclear cells (PBMCs). Aliquots of the PBMCs were transferred aseptically to wells of a 12 well tissue culture plate, along with X-Vivo™ 15 media (Lonza) to a final concentration of 0.5 million viable cells/mL in a final volume of 1 mL. Recombinant human interleukin-2 (IL-2) (Novoprotein) was also added to a concentration of 100 IU/ml in some samples. Activating anti-CD3 Ab (OKT3, Novoprotein) was added at a concentration of 50 ng/ml, to activate the PBMC for viral transduction. The plates were incubated overnight in a standard humidified tissue culture incubator at 37 degrees C. and 5% Carbon Dioxide. After overnight incubation, lentivirus particle preparations containing the desired test constructs (FIG. 19A) were added to individual wells at a multiplicity of infection (MOI) of 5. The plate was incubated overnight in a standard humidified tissue culture incubator at 37 degrees C. and 5% Carbon Dioxide. Following the overnight incubation, the contents of each of the wells of the 12 well plate were collected and centrifuged to obtain a pellet. The samples were washed once with D-PBS+2% Human Serum Albumin (HSA), resuspended in X-Vivo15™ media, and transferred to wells of G-Rex® 6-well gas permeable cell culture devices (Wilson Wolf). Additional X-Vivo™ 15 media was added to bring the final volume of each well to 30 ml. Matching control samples for each of the constructs were transferred to wells of G-Rex® 6-well gas permeable cell culture devices (Wilson Wolf) and additional media was added to bring the final volume to 30 ml with 100 IU/ml IL-2 for some control samples. The G-Rex® device was incubated in a standard humidified tissue culture incubator at 37 degrees C. and 5% Carbon Dioxide for 7 days. Fresh IL-2 was added to the control samples containing IL-2 during the culture every 2-3 days. Matched test samples without IL-2 were not supplemented. Samples were removed for tracking cell numbers and viability during expansion (Countess, Thermo Fisher) at day 7.

Figure 19A:
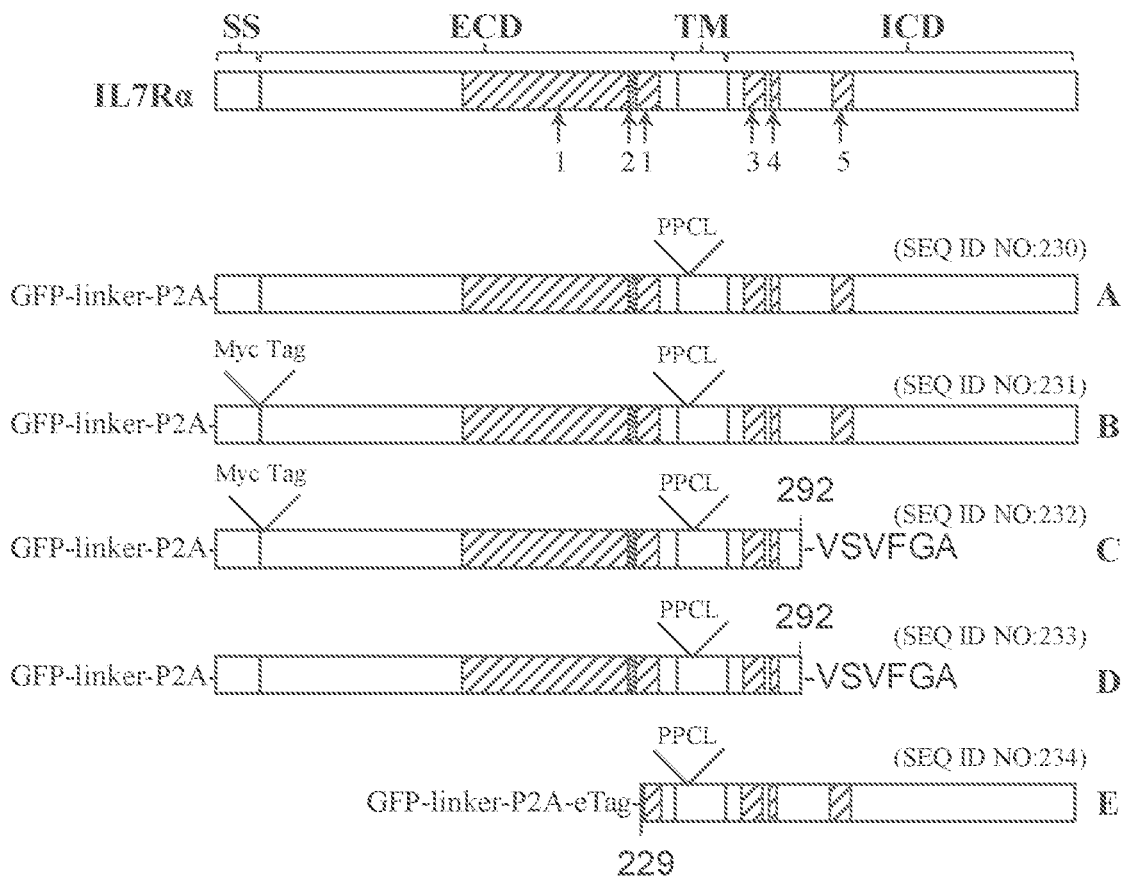
FIG. 19A provides a schematic of IL7Rα variants tested for lymphoproliferative/survival activity when expressed in PBMCs.

FIG. 19A provides a schematic of the IL7Rα constructs that were tested. These constructs were inserted into a recombinant lentiviral genome. The replication incompetent recombinant retroviral particles were used to transduce PBMCs. FIG. 19A shows a schematic of wild-type IL7Rα (SEQ ID NO:229), which consists of a signal sequence (SS), an extracellular domain (ECD), a transmembrane (TM), and an intracellular domain (ICD). "1" indicates the site of a fibronectin type III domain; "2" indicates the site of a WSXWS motif; "3" indicates a Box 1 site, "4" indicates the site of a protein kinase C (PKC) phosphorylation site, and "5" indicates a Box 2 site.

Variant "A" is the IL-7Rα with an InsPPCL at position 243 (Shochat et al 2011, *J. Exp. Med.* Vol. 208 No. 5 901-908) but without the S185C mutation, expressed on a transcript with a GFP polypeptide, a GSG linker, and a P2A ribosomal skip sequence fused to its N-terminus. Variant "B" is the IL-7Rα InsPPCL with a GFP polypeptide, a GSG linker, and a P2A ribosomal skip sequence fused to its N-terminus as well as a Myc Tag between the signal sequence and the extracellular domain. Variant "C" is similar to variant "B" except its intracellular domain is truncated at position 292. Variant "D" is similar to variant "A" except its intracellular domain is truncated at position 292. Variant "E" is the IL-7Rα InsPPCL variant truncated at its N terminus such that the signal sequence and most of the extracellular domain (residues 1-228) are not present; variant "E" also has a GFP polypeptide, a GSG linker, a P2A ribosomal skip sequence, and an eTag fused to the N terminus, in that order from the amino terminus. Numbering of the amino acid residues is based on IL7Rα (NCBI GI No. 002176.2). T cells containing each of the variants were tested for viability in the presence or absence of IL-2 using Trypan Blue exclusion.

Figure 19B:
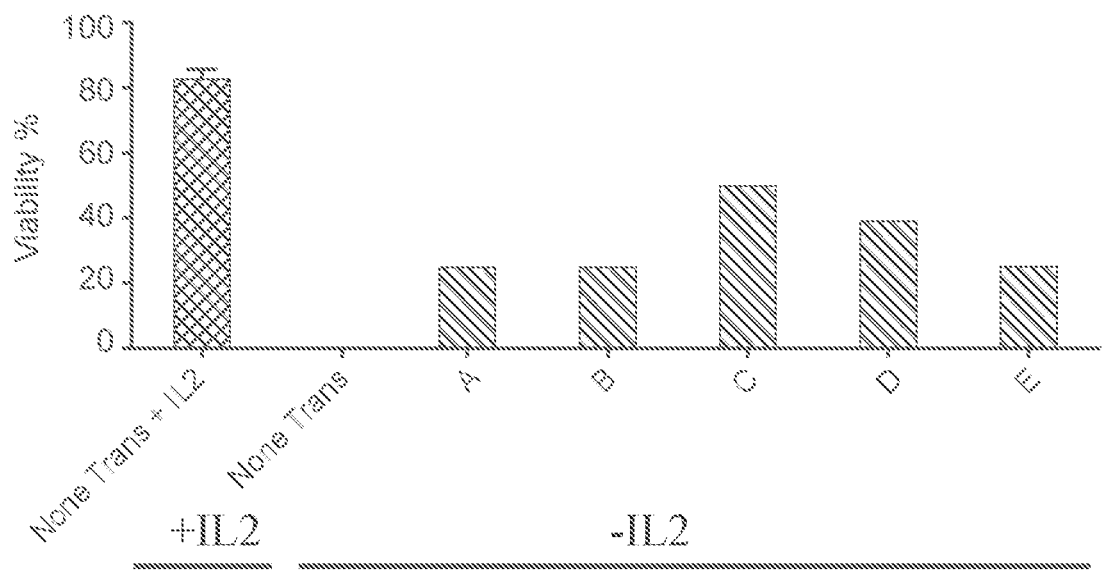
FIG. 19B provides a bar graph showing percent viability of PBMCs in the presence and absence of IL-2.

As shown in FIG. 19B, PBMCs require IL-2 for survival in vitro. As illustrated in FIG. 19B, untransfected PBMCs have about 80% viability in the presence of IL-2 and 0% viability in the absence of IL-2. PBMCs having the full-length versions of IL-7Rα InsPPCL (IL-7Rα variants A and B in FIG. 19A) had over 20% viability in the absence of IL-2, indicating that expression of the constitutively active IL-7Rα InsPPCL receptor has survival activity in these cells. Furthermore, T cells expressing the IL-7Rα InsPPCL variants with a truncated intracellular domain (ICD) (IL-7Rα variants C and D in FIG. 19A) had increased viability compared to the wild-type IL-7 receptor. Finally, the N-terminal IL-7 receptor mutant (IL-7Rα variant E in FIG. 19A) as shown in FIG. 19B had survival activity in these cells. Accordingly, this example illustrates that IL-7 receptor has survival activity when expressed in PBMCs.

Figure 20:
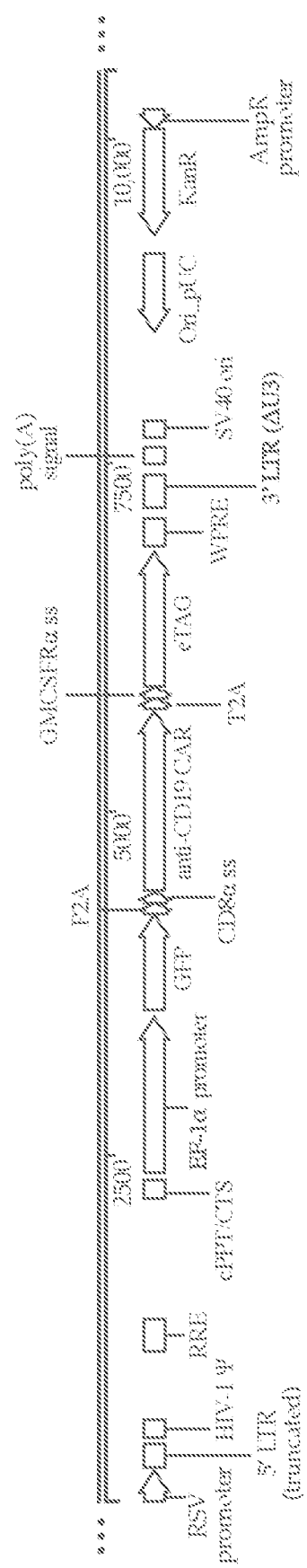
FIG. 20 shows a schematic of the lentiviral expression vector encoding GFP, an anti-CD19 chimeric antigen receptor, and an eTAG referred to herein as F1-0-03.

Example 12. Transduction Efficiency of Freshly Isolated and Unstimulated Human T Cells by Retroviral Particles Pseudotyped with VSV-G and Expressing Anti-CD3 scFvFc on their Surfaces Recombinant lentiviral particles were produced by transient transfection of 293T cells (Lenti-X™ 293T, Clontech) with separate lentiviral packaging plasmids encoding gag/pol and rev, and a pseudotyping plasmid encoding VSV-G. A third generation lentiviral expression vector encoding GFP, an anti-CD19 chimeric antigen receptor, and an eTAG referred to herein as F1-0-03 (FIG. 20) was co-transfected with the packaging plasmids. The cells were adapted to suspension culture by serial growth in Freestyle™ 293 Expression Medium (ThermoFisher Scientific). The cells in suspension were seeded at $1\times10^6$ cells/mL (30 mL) in a 125 mL Erlenmeyer flask, and immediately transfected using polyethylenimine (PEI) (Polysciences) dissolved in weak acid.

Plasmid DNA was diluted in 1.5 ml Gibco™ Opti-MEM™ media for 30 mL of cells. To obtain lentiviral particles pseudotyped with VSV-G, the total DNA (1 μg/mL of culture volume) used was a mixture of 4 plasmids with the following molar ratios: 2× genomic plasmid (F1-0-03), 1× Rev-containing plasmid, 1×VSV-G-containing plasmid, and 1×gag/pol-containing plasmid. To obtain lentiviral particles pseudotyped with VSV-G and expressing an antiCD3-scFvFc on their surfaces, the total DNA (1 μg/mL of culture volume) used was a mixture of 5 plasmids with the following molar ratios: 2× genomic plasmid (F1-0-03), 1×Rev-containing plasmid, 1×VSV-G-containing plasmid, 1× anti-CD3-scFvFc-GPI-containing plasmid, and 1×gag/pol-containing plasmid. To obtain lentiviral particles pseudotyped with VSV-G and expressing anti-CD3-scFvFc and CD80 on their surfaces, the total DNA (1 μg/mL of culture volume) used was a mixture of 6 plasmids with the following molar ratios: 2× genomic plasmid (F1-0-03), 1×Rev-containing plasmid, 1×VSV-G-containing plasmid, 1× anti-CD3-scFvFc containing plasmid, 1×CD80-containing plasmid, and 1×gag/pol-containing plasmid. Separately, the PEI was diluted in 1.5 ml Gibco™ Opti-MEM™ to 2 μg/mL (culture volume, 2:1 ratio to DNA). After a 5-minute room temperature incubation, the two solutions were mixed together thoroughly, and incubated at room temperature for 20 more minutes. The final volume (3 ml) was added to the cells. The cells were then incubated at 37° C. for 72 hours with rotation at 125 rpm and with 8% $CO_2$. The antiCD3-scFvFc containing plasmids included scFvs derived from either OKT3 or UCHT1, and a GPI anchor attachment sequence. The UCHT1scFvFc-GPI vector encodes a peptide (SEQ ID NO:278) that includes human Ig Kappa signal peptide (amino acids 1-22 of NCBI GI No. CAA45494.1) fused to the UCHT1 scFv (amino acids 21-264 of NCBI GI No. CAH69219.1), fused to human IgG1 Fc (amino acids 1-231 of NCBI GI No. AEV43323.1) with an A to T substitution at position 115, fused to the human DAF GPI anchor attachment sequence (amino acids 345-381 of NCBI GI No. NP_000565). The OKT3scFvFc-GPI vector encodes a peptide (SEQ ID NO:279) that includes a human Ig Kappa signal peptide (amino acids 1-22 of NCBI GI No. CAA45494.1) fused to the OKT3 scFv (SEQ ID NO:285) fused to human IgG1 Fc (amino acids 1-231 of NCBI GI No. AEV43323.1) fused to the human DAF GPI anchor attachment sequence (amino acids 345-381 of NCBI GI No. NP_000565). The CD80-containing plasmid encodes a peptide (SEQ ID NO:280) that includes the human CD80 signal peptide and extracellular domain (amino acids 1-242 of NCBI GI No. NP_005182) fused to the human CD16b GPI anchor attachment sequence (amino acids 196-233 of NCBI GI No. NP_000561).

After 72 hours, the supernatants were harvested and clarified by centrifugation at 1,200 g for 10 minutes. The clarified supernatants were decanted to a new tube. The lentiviral particles were precipitated by overnight centrifugation at 3,300 g, at 4° C. The supernatant was discarded, and the lentiviral particle pellets were resuspended in 1:100 of initial volume of X-Vivo™ 15 medium (Lonza). Lentiviral particles were titered by serial dilution and analysis of GFP expression, in 293T and Jurkat cells, 72 hours post-transduction, by flow cytometry.

Peripheral blood mononuclear cells (PBMCs) were first isolated from either fresh blood in ACD (acid citrate dextrose) tubes, for Donors 12F and 12M, or from a buffy coat for Donor 13F, collected and distributed by the San Diego Blood Bank, Calif. SepMate™ 50 (Stemcell™)-based gradient density separation of PBMCs on Ficoll-Paque PLUS® (GE Healthcare Life Sciences) was performed per manufacturers' instructions. 30 mL of blood or buffy-coat diluted in PBS-2% HIFCS (heat inactivated fetal calf serum) were layered per each SepMate™ tube. After centrifugation at room temperature, at 1,200 g, for 20 min, the PBMC layers were collected, pooled and washed three times with 45 mL of PBS-2% HIFCS and centrifugation at 400 g for 10 min at room temperature. The pellets were then incubated at room temperature for 10 min in 10 mL of RBC lysis buffer (Alfa Aesar) and washed an additional two times with 45 mL of PBS-2% HIFCS, and centrifugation at 400 g for 10 min at room temperature. A final wash was performed in the transduction and culture media: X-Vivo™ 15 for Donor 13F, or RPMI-1640+10% HIFCS for Donors 12F and 12M. No additional steps were taken to remove monocytes. After isolation, fresh and unstimulated PBMCs were resuspended to a final concentration of 1E6/mL in their respective medium, and were transduced, in duplicates or triplicates, with the lentiviral particles disclosed previously. The transductions were conducted for 14 h, at 37° C., 5% $CO_2$, in X-Vivo™ 15 medium for Donor 13F, or in RPMI-1640+ 10% HIFCS for Donors 12F and 12M. Transductions were usually conducted at MOI 1 in a 12 wells plate format, 1 mL/well. For the kinetic experiment, 0.5E6 PBMCs/mL were transduced in 7 mL final, at MOI 1, in a 125 mL shake flask incubated at 37° C. for 2-20 h hours with rotation at 125 rpm and with 8% $CO_2$. After incubation with the retroviral particles for the selected time, the cells were washed three times with X-Vivo™ 15 medium for Donor 13F, or PBS+2% HIFCS for Donors 12F and 12M, and finally incubated at a cell density of 1E6/mL in X-Vivo™ 15 medium for Donor 13F, or RPMI-1640+10% HIFCS for Donors 12F and 12M, at 37° C., 5% $CO_2$. Samples were collected at various days post-transduction (Day 3-17) to evaluate, by GFP expression levels, the transduction efficiencies of each type of lentivirus that was generated.

At various days post-transduction, for lentiviral particles pseudotyped with VSV-G, with or without OKT3 antibody (Biolegend) at 1 µg/m; lentiviral particles pseudotyped with VSV-G and expressing anti-CD3 scFvFc on their surface; or lentiviral particles pseudotyped with VSV-G and expressing anti-CD3 scFvFc and CD80 on their surface; 100 µL of cells were collected and analyzed by flow cytometry for expression of GFP in the CD3+ cell population.

Figure 21B:
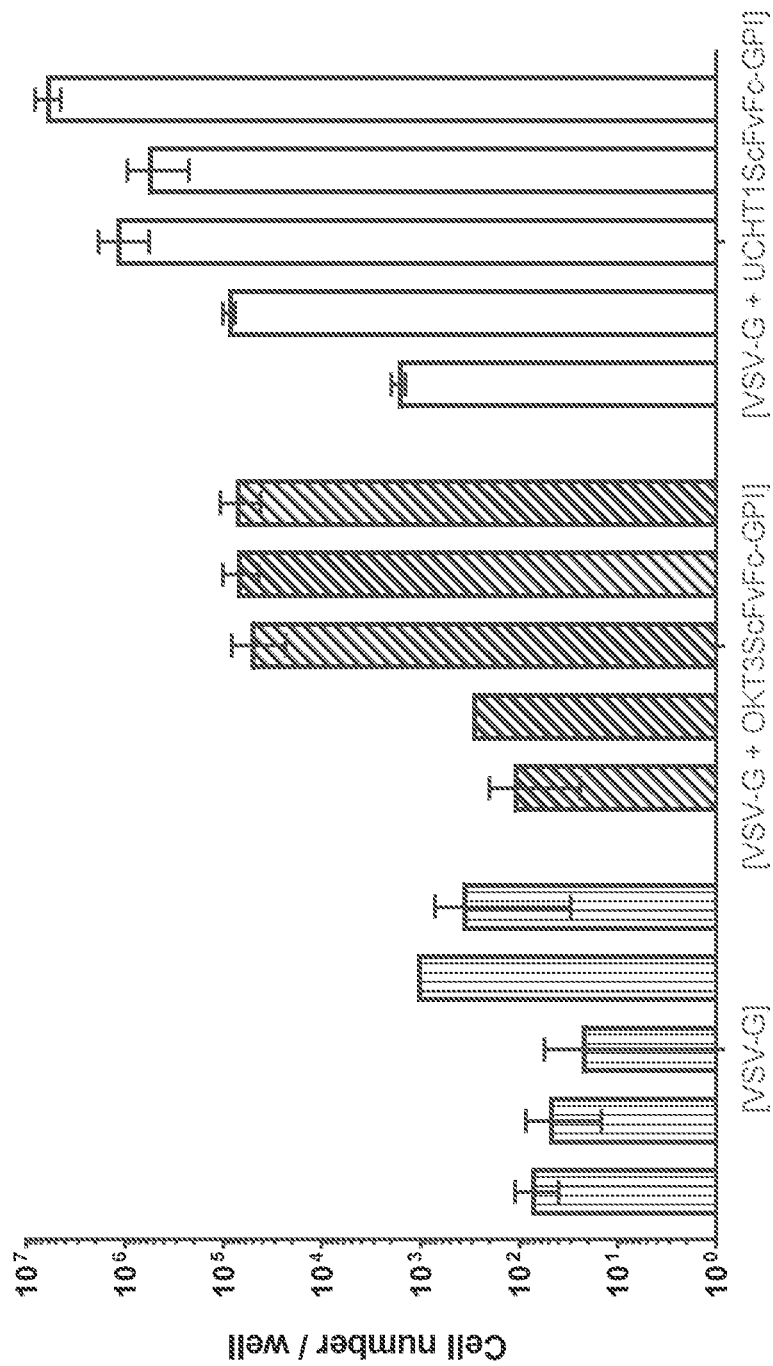

FIG. 21A and FIG. 21B show a histogram of the percentage (%) CD3+GFP+ cells in the total CD3+ population and a histogram of the absolute cell count per well of the CD3+GFP+ population, respectively, at 3, 6, 9, 13 and 17 days after transduction of freshly isolated and unstimulated PBMCs from Donor 12M, for 14 h with the indicated lentiviral particles. Each bar represents the mean+/−SD of duplicates. FIGS. 21A and 21B show that pseudotyping lentiviral particles with VSV-G and expressing antiCD3-scFvFc on the surface of the lentiviral particles effectively transduces freshly isolated and unstimulated PBMCs. Anti-CD3 scFv's derived from either OKT3 or UCHT1, when in the form of an scFvFc, were effective.

Figure 22A:
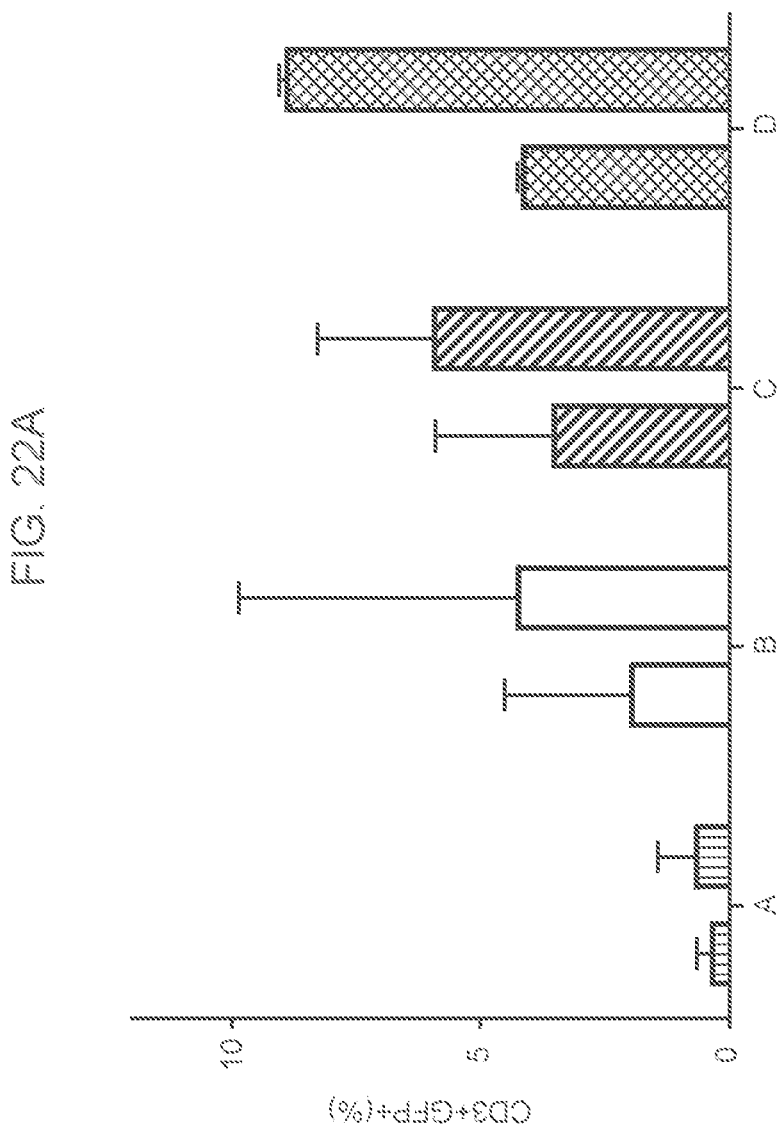

FIG. 22A and FIG. 22B show a histogram of (%) CD3+GFP+ cells in the total CD3+ population and a histogram of the absolute cell count per well of the CD3+GFP+ population, respectively, at 3 and 6 days after transduction of freshly isolated and unstimulated PBMCs from Donor 13F, for 14 h, with the indicated lentiviral particles. Please note that "A" are results using VSV-G pseudotyped lentiviral particles (triplicate experiments); "B" are results using VSV-G pseudotyped lentiviral particles with OKT3 antibody (1 ug/mL) added to the transduction medium (duplicate experiments); "C" are results using VSV-G pseudotyped lentiviral particles expressing GPI-anchored UCHT1scFvFc on their surface (triplicate experiments); and "D" are results using VSV-G pseudotyped lentiviral particles expressing GPI anchored UCHT1scFvFc and GPI-anchored CD80 on their surface (duplicate experiments). Each bar represents the mean+/−SD of duplicates or triplicates, as indicated in FIG. 22A. FIGS. 22A and 22B show that pseudotyping lentiviral particles with VSV-G and expressing antiCD3-scFvFc and CD80 on their surfaces also effectively transduces freshly isolated and unstimulated PBMCs when the transduction is performed for 14 hours.

Figure 23B:
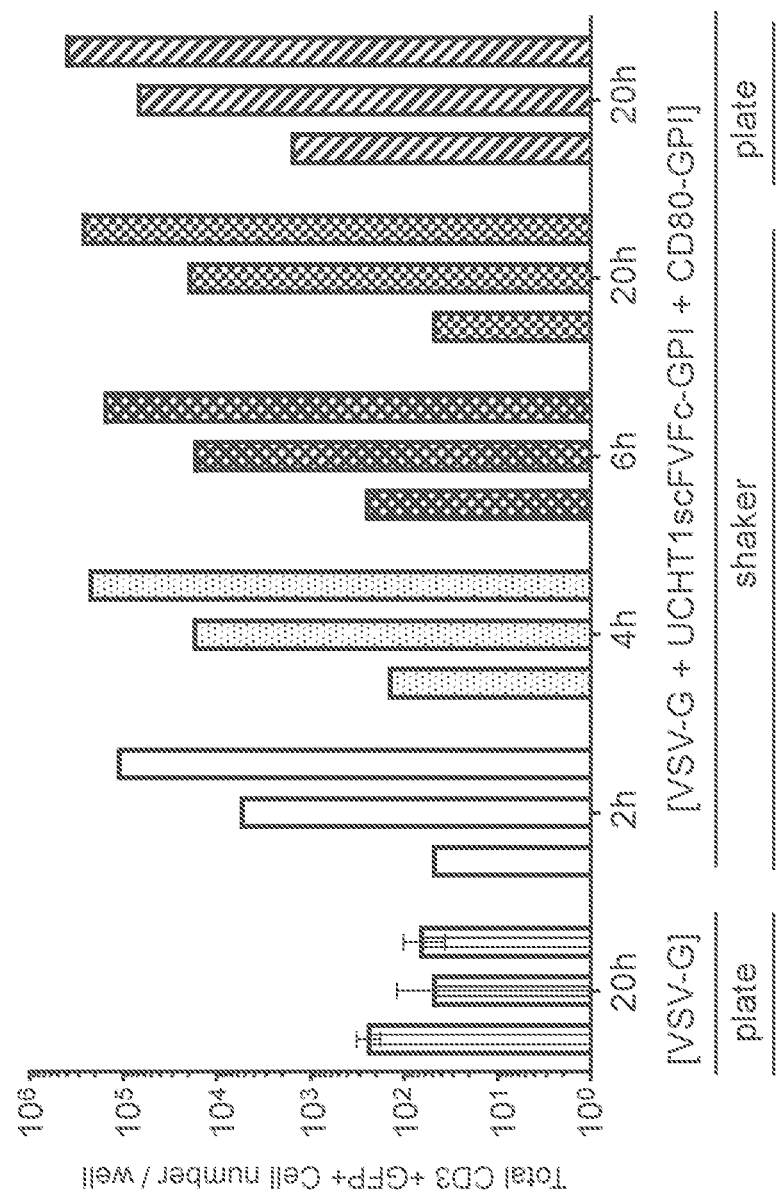

FIGS. 23A and 23B show a histogram of percentage (%) CD3+GFP+ cells in the total CD3+ population and a histogram of the absolute cell count per well of the CD3+GFP+ population, respectively, at 3, 6 and 9 days after transduction of freshly isolated and unstimulated PBMCs from Donor 12M for the indicated time of exposure (2-20 h), with the indicated lentiviral particles. Transduction was performed in a plate or a shaker flask as indicated. Each bar represents the mean+/−SD of duplicates for lentiviral particles pseudotyped with VSV-G ("[VSV-G]"); the other experiments did not have replicates. FIGS. 23A and 23B show that freshly isolated and unstimulated PMBCs can be effectively transduced in as few as 2 hours with lentivirus particles pseudotyped with VSV-G and expressing anti-CD3 scFvFc and CD80 on their surfaces.

Example 13. Functionality of miRNAs Inserted into the EF-1Alpha Promoter Intron Four separate gBlocks® Gene Fragments were designed, each containing a miR-155 framework, including a miR-155 5' flanking sequence or "5' arm" (SEQ ID NO:256) and a miR-155 3' flanking sequence or "3' arm" (SEQ ID NO:260). For each gBlock®, a unique miRNA fragment targeting the CD3zeta mRNA transcript was used to replace the miR-155 stem-loop precursor. Each gBlock® contained a 40 bp overlap sequence designed to facilitate assembly of all four gBlocks® as a single chain into the EF-1alpha promoter intron. The gBlocks® were assembled using a commercial kit for performing Gibson® assembly ultra (NEBuilder, New England Biolabs, Inc.).

The synthetic EF-1alpha promoter and intron A containing the miRNAs (in SEQ ID NO:255) was part of a transgene expression cassette driving expression of GFP and eTag contained in a lentivirus vector backbone (the lentivirus vector backbone with the GFP and exemplary eTag recognized by cetuximab is referred to herein as F1-0-02; FIGS. 24A and 24B). The nucleotide positions of each gBlock® and its respective components in SEQ ID NO:255 are denoted in Table 3 as are the positions of each "Feature" in FIG. 24B. Proper assembly of four miRNA into the lentivirus vector backbone was confirmed by comprehensive sequencing of the modified EF-1alpha promoter and intron region.

TABLE 3

Nucleotide positions of features in SEQ ID NO: 255

| Feature | Nucleotide positions in SEQ ID NO: 255 | SEQ ID NO: | Feature in FIG. 24B |
|---|---|---|---|
| gBlock® 1 | 927-1138 | | |
| EF1alpha overlap | 927-966 | | 1 |
| miR155- 5' arm | 967-994 | SEQ ID NO: 256 CTGGAGGCTTGCTGAAGGCTGTATGCTG | 2 |
| miRNA1- 5' Stem | 995-1015 | SEQ ID NO: 257 ACATGGTACAGTTCAATGGTG | 3 |
| miR loop | 1016-1034 | SEQ ID NO: 258 GTTTTGGCCACTGACTGAC | 4 |
| miRNA1- 3' Stem | 1035-1053 | SEQ ID NO: 259 CACCATTGCTGTACCATGT | 5 |
| miR155- 3' arm | 1054-1098 | SEQ ID NO: 260 CAGGACACAAGGCCTGTTACTAGCACTCACATGGAACAAATGGCC | 6 |
| gBlock® 2 | 1099-1310 | | |
| 40 bp 50% GC Linker 1 | 1099-1138 | | 7 |
| miR155- 5' arm | 1139-1166 | SEQ ID NO: 256 | 2 |
| miRNA2- 5' Stem | 1167-1187 | SEQ ID NO: 261 TCAGTCTGTTCATCTTCTGGC | 8 |
| miR loop | 1188-1206 | SEQ ID NO: 258 | 4 |
| miRNA2- 3' Stem | 1207-1225 | SEQ ID NO: 262 GCCAGAAGGAACAGACTGA | 9 |
| miR155- 3' arm | 1226-1270 | SEQ ID NO: 260 | 6 |
| gBlock® 3 | 1271-1482 | | |
| 40 bp 50% GC Linker 2 | 1271-1310 | | 7 |

TABLE 3-continued

Nucleotide positions of features in SEQ ID NO: 255

| Feature | Nucleotide positions in SEQ ID NO: 255 | SEQ ID NO: | Feature in FIG. 24B |
|---|---|---|---|
| miR155-5' arm | 1311-1338 | SEQ ID NO: 256 | 2 |
| miRNA3-5' Stem | 1339-1359 | SEQ ID NO: 263 AAGCGTGAAGTGAATCAACGG | 10 |
| miR loop | 1360-1378 | SEQ ID NO: 258 | 4 |
| miRNA3-3' Stem | 1379-1397 | SEQ ID NO: 264 CCGTTGATACTTCACGCTT | 11 |
| miR155-3' arm | 1398-1442 | SEQ ID NO: 260 | 6 |
| gBlock® 4 | 1443-1654 | | |
| 40 bp 50% GC Linker 4 | 1443-1482 | | 7 |
| miR155-5' arm | 1483-1510 | SEQ ID NO: 256 | 2 |
| miRNA4-5' Stem | 1511-1531 | SEQ ID NO: 265 GCAGTATCCTAGTACATTGAC | 12 |
| miR loop | 1532-1550 | SEQ ID NO: 258 | 4 |
| miRNA4-3' Stem | 1551-1569 | SEQ ID NO: 266 GTCAATGTTAGGATACTGC | 13 |
| miR155-3' arm | 1570-1614 | SEQ ID NO: 260 | 6 |
| EF-1alpha overlap | 1615-1654 | | |

Replication incompetent lentiviral particles containing a nucleic acid encoding the four miRNAs directed against CD3zeta in their genome were produced by transient co-transfection of four plasmids into suspension HEK293 cells: a plasmid containing the nucleic acid encoding F1-0-02 modified to include the four miRNAs targeting the CD3zeta mRNA transcript, a plasmid encoding VSV-G, a plasmid encoding REV, and a plasmid encoding GAG-POL. Lentiviral particle supernatant was harvested after 48 hours and PEG-precipitated for 24 hours. Supernatants were centrifuged, and pelleted lentivirus particles were resuspended in complete PBMC growth media without IL-2. Lentivirus particle titers were calculated by 48 hour transduction of Jurkat cells.

For transduction, PBMCs were thawed on Day 0 and incubated for 24 hours with 100 U/mL of hrIL-2. On Day 1, PBMCs were activated via CD3/CD28 conjugated beads. On Day 2, activated PBMCs were transduced with the lentiviral particles containing a genome with a nucleic acid sequence encoding the miRNAs at an MOI of 10. Cells were expanded until Day 11, with fresh hrIL-2 added every two days. On days 7, 9, and 11, 1 million cells were harvested for FACS analysis.

Cells were stained for CD3 Epsilon surface expression, using PE conjugated OKT-3 antibody (Biolegend). Expression levels were determined by the mean fluorescence intensity (MF) of PE in the GFP positive population (transduced cells). Expression levels of transduced cells were compared between retroviral particles derived from F1-0-02 and retroviral particles derived from F1-0-02 in which the nucleic acid sequence encoding the CD3z miRNAs positioned in series were inserted into the EF-1alpha promoter and intron A.

Figure 25:
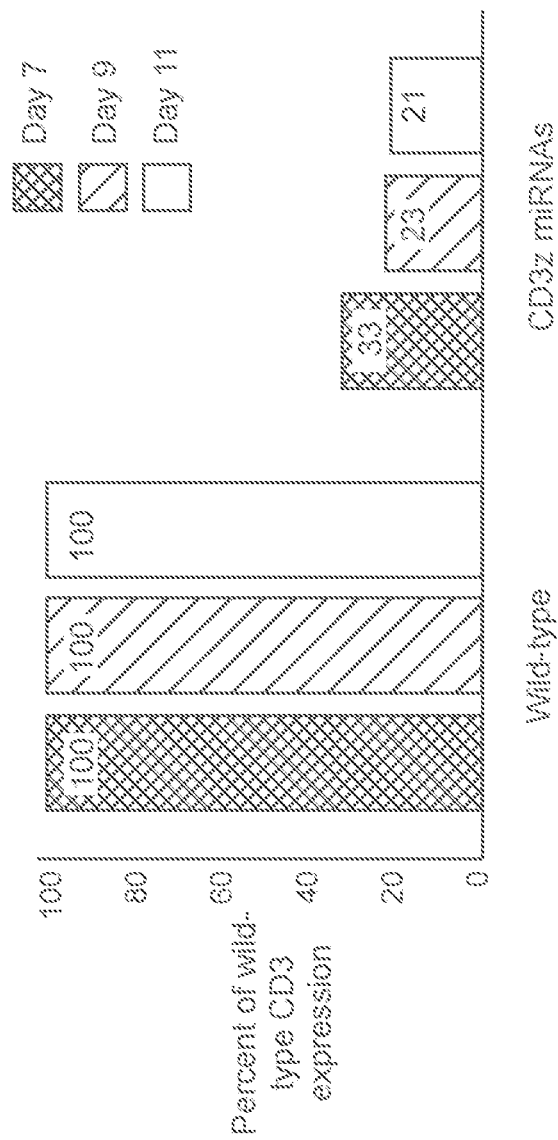
FIG. 25 is a graph showing that the miRNAs targeting CD3zeta that are in the EF-1alpha promoter intron are able to knockdown expression of the CD3 complex.

Results are shown in FIG. 25. This data shows that serial miRNAs targeting CD3zeta encoded by a nucleic acid sequence within the EF-1alpha promoter intron A, are effective at knocking down expression of the CD3 complex.

Example 14. Positional Independence of Serial Inhibitory RNAs Inserted into the EF-1Alpha Promoter Intron Cloning Four miRNA-expressing lentiviral vector constructs were designed to test the processing of individual miRNA precursors in a structure comprising 4 miRNA precursors in series. Table 4 shows the names of the individual constructs and the position of the miR-TCRα in each construct.

TABLE 4

Constructs containing polycistronic miRNAs

| Construct | Position 1 | Position 2 | Position 3 | Position 4 |
|---|---|---|---|---|
| TCRa-P1 | miR-TCRa | miR-155 | miR-PD-1 | miR-CTLA-4 |
| TCRa-P2 | miR-155 | miR-TCRa | miR-PD-1 | miR-CTLA-4 |
| TCRa-P3 | miR-155 | miR-PD-1 | miR-TCRa | miR-CTLA-4 |
| TCRa-P4 | miR-155 | miR-CTLA-4 | miR-PD-1 | miR-TCRa |

Each miRNA contained the miR-155 framework used in Example 13, i.e. a miR-155 5' arm (SEQ ID NO:256), a miR-155 3' arm (SEQ ID NO:260), a loop (SEQ ID NO:258), and a specific order of stem sequences as shown in Table 5. The type IIs assembly method was used to achieve assembly of the four miRNA fragments into their appropriate positions within the EF-1 alpha intron of the lentivirus vector construct (F1-0-02; provided in Example 13 and shown in FIG. 24A).

TABLE 5

Sequences in miRNA constructs

|  | TCRa-P1 (SEQ ID NO: 278) | TCRa-P2 (SEQ ID NO: 279) | TCRa-P3 (SEQ ID NO: 280) | TCRa-P4 (SEQ ID NO: 281) |
|---|---|---|---|---|
| 5' arm | SEQ ID NO: 256 | SEQ ID NO: 256 | SEQ ID NO: 256 | SEQ ID NO: 256 |
| miRNA1 - 5' Stem | SEQ ID NO: 267 | SEQ ID NO: 270 | SEQ ID NO: 270 | SEQ ID NO: 270 |
| miR loop | SEQ ID NO: 258 | SEQ ID NO: 258 | SEQ ID NO: 258 | SEQ ID NO: 258 |
| miRNA1 - 3' Stem | SEQ ID NO: 268 | SEQ ID NO: 271 | SEQ ID NO: 271 | SEQ ID NO: 271 |
| 3' arm | SEQ ID NO: 260 | SEQ ID NO: 260 | SEQ ID NO: 260 | SEQ ID NO: 260 |
| Linker 1 | SEQ ID NO: 269 | SEQ ID NO: 269 | SEQ ID NO: 269 | SEQ ID NO: 269 |
| 5' arm | SEQ ID NO: 256 | SEQ ID NO: 256 | SEQ ID NO: 256 | SEQ ID NO: 256 |
| miRNA2 - 5' Stem | SEQ ID NO: 270 | SEQ ID NO: 267 | SEQ ID NO: 273 | SEQ ID NO: 276 |
| miR loop | SEQ ID NO: 258 | SEQ ID NO: 258 | SEQ ID NO: 258 | SEQ ID NO: 258 |
| miRNA2 - 3' Stem | SEQ ID NO: 271 | SEQ ID NO: 268 | SEQ ID NO: 274 | SEQ ID NO: 277 |
| 3' arm | SEQ ID NO: 260 | SEQ ID NO: 260 | SEQ ID NO: 260 | SEQ ID NO: 260 |
| Linker 2 | SEQ ID NO: 272 | SEQ ID NO: 272 | SEQ ID NO: 272 | SEQ ID NO: 272 |
| 5' arm | SEQ ID NO: 256 | SEQ ID NO: 256 | SEQ ID NO: 256 | SEQ ID NO: 256 |
| miRNA3 - 5' Stem | SEQ ID NO: 273 | SEQ ID NO: 273 | SEQ ID NO: 267 | SEQ ID NO: 273 |
| miR loop | SEQ ID NO: 258 | SEQ ID NO: 258 | SEQ ID NO: 258 | SEQ ID NO: 258 |
| miRNA3 - 3' Stem | SEQ ID NO: 274 | SEQ ID NO: 274 | SEQ ID NO: 268 | SEQ ID NO: 274 |
| 3' arm | SEQ ID NO: 260 | SEQ ID NO: 260 | SEQ ID NO: 260 | SEQ ID NO: 260 |
| Linker 3 | SEQ ID NO: 275 | SEQ ID NO: 275 | SEQ ID NO: 275 | SEQ ID NO: 275 |
| 5' arm | SEQ ID NO: 256 | SEQ ID NO: 256 | SEQ ID NO: 256 | SEQ ID NO: 256 |
| miRNA4 - 5' Stem | SEQ ID NO: 276 | SEQ ID NO: 276 | SEQ ID NO: 276 | SEQ ID NO: 267 |
| miR loop | SEQ ID NO: 258 | SEQ ID NO: 258 | SEQ ID NO: 258 | SEQ ID NO: 258 |
| miRNA4 - 3' Stem | SEQ ID NO: 277 | SEQ ID NO: 277 | SEQ ID NO: 277 | SEQ ID NO: 268 |
| 3' arm | SEQ ID NO: 260 | SEQ ID NO: 260 | SEQ ID NO: 260 | SEQ ID NO: 260 | where:
SEQ ID NO: 267 = TCRalpha miRNA Stem 1; ATATGTACTTGGCTGGACAGC
SEQ ID NO: 268 = TCRalpha miRNA Stem 2; GCTGTCCACAAGTACATAT
SEQ ID NO: 269 = Linker 1; CACATTGGTGCCGGATGAAGCTCT-TATGTTGCCGGTCAT
SEQ ID NO: 270 = mir-155 Stem 1; CTGTTAATGCTAATCGTGATA
SEQ ID NO: 271 = mir-155 Stem 2; TATCACGATTATTAACAG
SEQ ID NO: 272 = Linker2; GTTGCCGGAGTCTTGGCAGCGAGAGATCACTAT-CAACTAA
SEQ ID NO: 273 = PD-1 miRNA Stem 1; TACCAGTTTAGCACGAAGCTC
SEQ ID NO: 274 = PD-1 miRNA Stem 2; GAGCTTCGCTAAACTGGTA
SEQ ID NO: 275 = Linker3; GTGTTAATTGTCCATGTAGCGAGGCATCCT-TATGGCGTGG
SEQ ID NO: 276 = CTLA-4 miRNA Stem 1; TGCCGCTGAAATCCAAGGCAA
SEQ ID NO: 277 = CTLA-4 miRNA Stem 2; TTGCCTTGTTTCAGCGGCA Lentiviral Particle Production The four constructs and the control F1-0-02, which includes no nucleic acid sequence encoding a miRNA, were used to produce lentiviral particles in 30 mL suspension cultures of 293T cells. The lentiviral particles were harvested and concentrated by PEG precipitation. Functional lentiviral particle titers were obtained by transducing Jurkat cells at multiple dilutions (1:1000, 1:10000, 1:100000), incubating the lentiviral particles and cells for 2 days at 37° C., washing the cells 2× with FACS buffer, and analyzing for GFP by flow cytometry. Other details regarding lentiviral particle production are provided in Example 13 herein.

Transduction

For transduction, PBMCs were thawed and recovered overnight in complete media containing 100 U/mL hrIL-2. 1e5 PBMCs were activated via exposure to CD3/CD28 conjugated beads for 24 hours. Cells were transduced in duplicate wells with each of the four miRNA constructs or with control retroviral particle F1-0-02 at MOI 10. The cells were supplied with 100 U/mL hrIL-2 every 3 days and expanded until day 10.

FACS

Cells were harvested for FACS analysis which confirmed that the cells were transduced with the replication incompetent lentiviral vectors. The results showed that approximately equivalent amounts of miRNA containing virus were delivered to each well in the experiment.

Cells-to-Ct miRNA RT-qPCR and Analysis

An RT-qPCR assay was designed to detect expression and processing of the miRNA precursors into mature processed miRs. Analysis was done by first normalizing all miR-TCRa ct values to the RNU48 internal control to produce ΔCt values. Next, the ΔCt values of each transduced sample were subtracted from the ΔCt of the non-transduced control to produce ΔΔCt. This value is representative of the amount of processed miR-TCRa miRNA in each transduced sample, relative to the non-transduced control.

Figure 26:
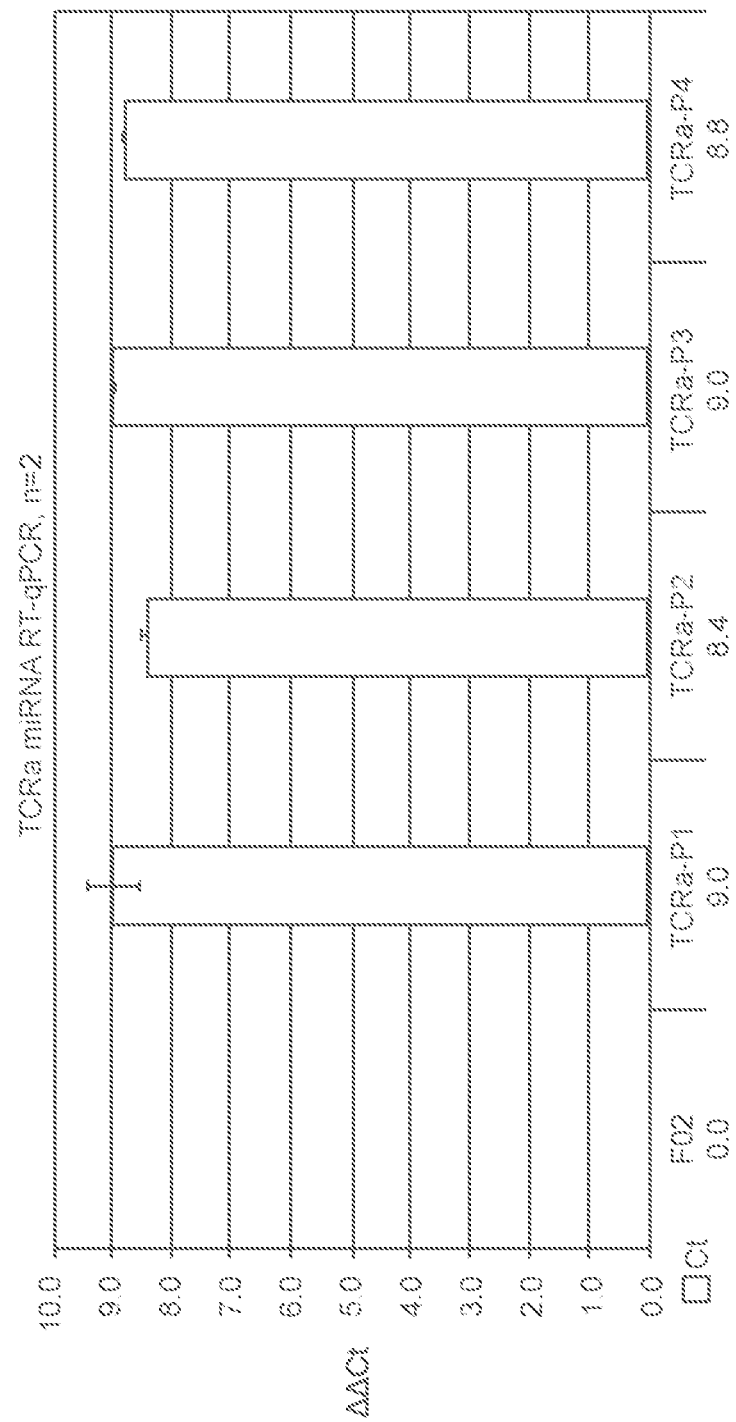
FIG. 26 is a histogram showing the ΔΔCt of samples transduced with miR-TCRα containing replication incompetent lentiviral particles. The ΔΔCt values are representative of the amount of processed miR-TCRa miRNA in each transduced sample relative to the non-transduced control.

As shown in FIG. 26, the RT-qPCR assay successfully detected processed miR-TCRα in samples transduced with miR-TCRα containing replication incompetent lentiviral particles. Furthermore, the results clearly indicate that there is no remarkable difference in miRNA TCRα processing at any of the four positions tested.

Example 15. Cytotoxic Activity of Microenvironment Restricted Biologic CAR-Expressing T Cells can be Controlled by Changing pH The following example illustrates how the cytotoxic activity of transduced T cells (also referred to as effector cells) expressing MRB-CARs can be modulated by changes in the pH of the microenvironment. In this example, nucleic acids encoding an MRB-CAR capable of binding the cognate antigen Target 1 (anti-Target 1) were used to generate replication incompetent recombinant lentiviral particles. Pan T cells were transduced with the lentiviral particles and the cytotoxic activity of the effector cells were compared using Real-Time Cell Analysis (RTCA) before and after changing the pH of the media.

Production of Replication Incompetent Recombinant Lentiviral Particles

A nucleic acid that encoded T1B, an anti-Target 1 MRB-CAR from the series of candidate MRB-CARs in Example 3, was tested. Replication incompetent recombinant lentiviral particles were produced by transient transfection of Lenti-X 293T cells (Clontech, Mountain View, Calif.) with lentiviral expression vectors and nucleic acids that included segments encoding either the MRB-CAR or a control, C1, that contained a GMCFsp and an eTAG (SEQ ID NO:284), but did not include an anti-Target 1 MRB-CAR. The cells were adapted to suspension culture by serial growth in Freestyle 293 Expression Medium (ThermoFisher Scientific, Waltham, Mass.). The cells in suspension were transfected using PEI (Polysciences, Warminster, Pa.) dissolved in weak acid. Cells (30 mL) were grown to 1×10$^6$ cells/mL in a 125 mL Erlenmeyer flask.

Total DNA was diluted in 1.5 ml Optimem media for 30 mL of cells. Total DNA (1 μg/mL of culture volume) was a mixture of 4 plasmids with the following molar ratios: 2× genomic plasmid that included lentiviral packaging elements, LTRs and the nucleic acid encoding T1B, 1× Rev-encoding plasmid, 1×VSVg-encoding plasmid, and 1× Gagpol-encoding plasmid. Separately, the PEI was diluted in 1.5 ml Optimem to 2 μg/mL (culture volume, 2:1 ratio to DNA). After a 5 minute room temperature incubation, the two solutions were mixed together well and incubated at room temperature for 20 minutes. The final volume (3 ml) was added to the cells. The cells were then incubated at 37° C. for 72 hours with rotation at 120 rpm and with 5-8% CO2.

After 72 hours, the supernatant was harvested by centrifugation at 1,000 g for 10 minutes. The supernatant was decanted to a fresh tube and ¼ of the supernatant volume in PEG solution (PEG-IT, System Biosciences) was added. The replication incompetent recombinant lentiviral particles were precipitated by incubation overnight at 4° C. followed by centrifugation at 1,500 g for 20 minutes at 4° C. The supernatant was removed, and the virus was resuspended in 1:100 volume of X-VIVO 15 media. Viruses were titered by eTAG expression in Jurkat cells.

T Cell Transduction/Expansion

Pan T cells were obtained from AllCells. Anti-Target 1 MRB-CAR replication incompetent recombinant lentiviral particles were made as discussed above. Two days prior to lentiviral transduction, cells were thawed and cultured in X-VIVO 15 media (Lonza, Basel, Switzerland) with 5% human AB serum (Valley Biomedical Inc., Winchester, Va.) and 10 mM N-acetyl L-Cysteine (Sigma-Aldrich, St. Louis, Mo.). Recombinant human IL-2 (R&D Systems, Minneapolis, Minn.) was added to a final concentration of 100 IU/mL. Twenty-four hours prior to viral transduction, primary human T cells were seeded into a 12-well plate at 0.5×10$^6$ cells/well and activated using Dynabeads Human T-Activator CD3/CD28 (ThermoFisher Scientific) at a 1:3 cell:bead ratio. On the day of transduction, the lentiviral particle solution was added to the wells at an MOI of 5. Transduced Pan T cells were maintained at ~10$^6$/mL in X-VIVO 15 media for 3 days, then transferred into a 6-well G-Rex plate with 30 mL/well of X-VIVO 15 media with 100 IU/mL IL-2. Cells were cultured for at least 10 days before experiments were conducted and IL-2 was added every other day.

pH Shift Cytotoxicity Assay

The cytotoxic activity of transduced T cells before and after pH change by addition of NaHCO$_3$ or NaOH was measured using the xCELLigence System. Briefly, one day before the experiment, target cells (CHO cells stably transfected with a construct to express Target 1 on the cell surface (CHO-Target 1 cells)), were seeded into a 96-well E-plate (ACEA; San Diego, Calif.) at 10,000 cells/well with X-VIVO 15 media containing 40 mM HEPES and 40 mM PIPES, pH 6.7. Cryopreserved effector cells previously transduced with either lentiviral particles containing the nucleic acid encoding T1B or C1 (T1BVP and C1VP, respectively) produced as discussed above, were thawed and cultured for two days in X-VIVO 15 media containing 100 IU/mL of IL-2 (R&D Systems, Minneapolis, Minn.). On the day of the experiment, cells transduced with T1BVP or C1VP were washed and resuspended in X-VIVO 15 media containing 40 mM HEPES and 40 mM PIPES, pH 6.7 and then added into the experimental wells at effector cell/target cell ratios (E/T) of 1:1.

Impedance readings measured on the xCELLigence System (ACEA) were taken every 5 minutes and reported as the Cell Index (CI) to quantitate cell confluency as a measure of cell proliferation/cell lysis. Approximately 3 hours after effector cell addition, 8 μl of 7.5% NaHCO$_3$ or 14 μl of 0.5 M NaOH was added into the wells with X-VIVO 15 media containing 40 mM HEPES and 40 mM PIPES, pH 6.7 to increase the pH from 6.7 to 7.4. Impedance readings were continued for approximately 20 hours after effector cell addition. Percentage of specific cytolysis was calculated as follows ((CI Target+C1VP transduced effector T cells)−(CI Target+T1BVP transduced effector T cells))/(CI Target+C1VP transduced effector T cells)×100.

HCl Switch on RTCA Killing Assay

The cytotoxic activity of transduced T cells before and after pH change by addition of HCl was measured using the xCELLigence System. Briefly, one day before the experiment, CHO-Target 1 cells were seeded into a 96 well E-plate at 10,000 cells/well with X-VIVO 15 media containing 40 mM HEPES and 40 mM PIPES, pH 7.4. Cryopreserved effector cells previously transduced with either C1VP or T1BVP, were thawed and cultured for two days in X-VIVO 15 media containing 100 IU/mL of IL-2. On the day of the experiment, cells transduced with T1BVP or C1VP were washed and resuspended in X-VIVO 15 media containing 40 mM HEPES and 40 mM PIPES, pH 7.4 and then added into experimental wells at effector cell/target cell ratios (E/T) of 1:1.

Impedance readings were taken every 5 minutes and reported as the Cell Index (CI). Approximately 3 hours after effector cell addition, 8 µl of 1 M HCl was added into the wells with X-VIVO 15 media containing 40 mM HEPES and 40 mM PIPES, pH 7.4 to switch the pH from 7.4 to 6.7. Impedance readings were continued for approximately 20 hours after effector cell addition. Percentage of specific cytolysis was calculated as follows ((CI Target+C1VP transduced effector T cells)−(CI Target+T1BVP transduced effector T cells))/(CI Target C1VP)×100.

Results

Figure 27A:
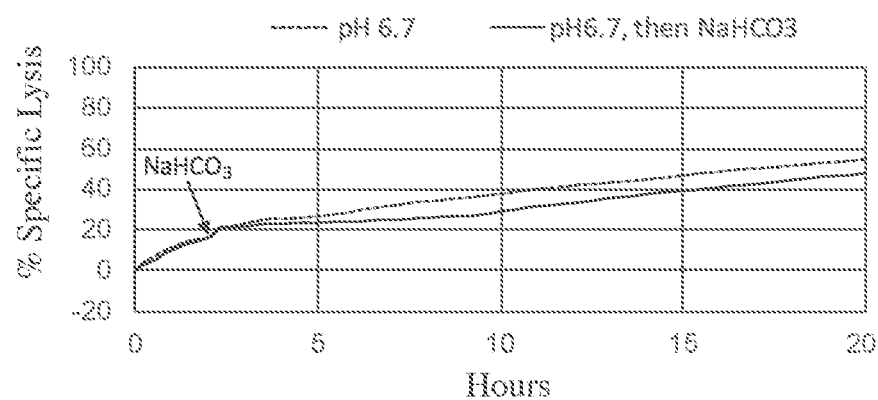
FIGS. 27A-C are graphs showing the percent specific lysis of CHO-Target 1 cells with and without treatment with a pH-modulating pharmacologic agent.
Figure 27B:
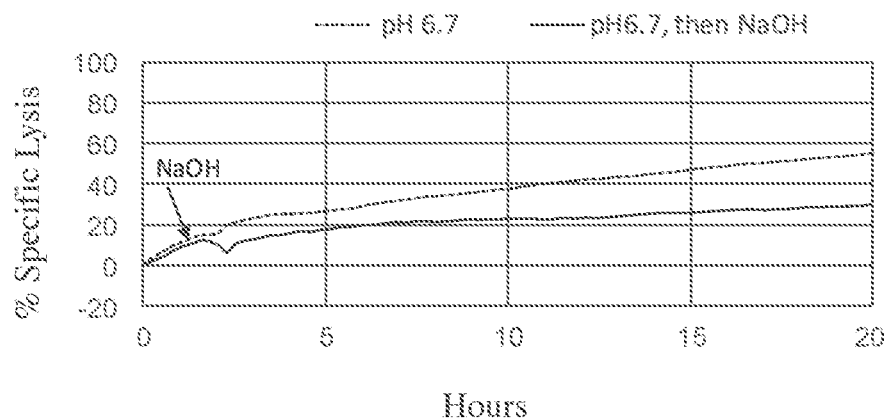

The cytotoxic activity of an MRB-CAR capable of binding cognate antigen Target 1 with increased activity at a reduced pH was compared in pH 6.7 and pH 7.4. T cells that were transduced with lentiviral particles encoding an anti-Target 1 MRB-CAR were used to kill CHO cells expressing Target 1, and then the pH was increased to determine whether the cytotoxic activity could be inhibited by a pH shift. As shown in FIGS. 27A and 27B, the addition of either $NaHCO_3$ or NaOH to the microenvironment of active CAR-T cells to increase the pH of the media inhibited the cytotoxic activity of the T cells expressing the MRB-CAR. These results show that active MRB-CAR expressing T cells can kill target-expressing cells and then this killing activity can be inhibited by increasing the pH of the microenvironment.

Figure 27C:
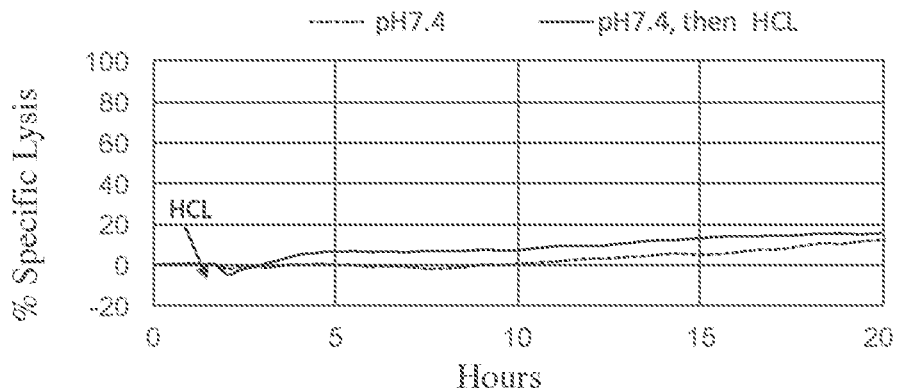

The ability of the cytotoxic activity of T cells expressing the MRB-CAR to be activated by a pH change was also determined. As shown in FIG. 27C, the cytotoxic activity of anti-Target 1 MRB-CAR expressing T cells on CHO-Target 1 cells was low at a pH of 7.4 and was increased by the addition of HCl to reduce the pH of the microenvironment. Cumulatively, these results demonstrate the cytotoxic activity of T cells expressing MRB-CARs can be modulated by a shift in pH within the microenvironment, both by reducing cytotoxic activity after an increase in pH and increasing cytotoxic activity after a decrease in pH. In this non-limiting example, pH was increased from pH 6.7 and decreased from 7.4.

Example 16. Bicarbonate Administration can Increase pH of the Tumor Microenvironment in Mice The following example demonstrates the pH of an in vivo tumor microenvironment can be modulated by administering a pharmacologic agent. In this example, the pharmacologic agent is sodium bicarbonate and the tumor microenvironment is a CHO xenograft tumor in mice. The example includes two methods of measuring the pH of a tumor microenvironment, both in vivo and ex vivo.

The extracellular microenvironment of most solid tumors is acidic, with a pH typically between 6.5 and 6.9. On the contrary, normal tissue pH is basic, with a pH typically between 7.2 and 7.5. However, directly measuring the in vivo pH of a tumor microenvironment can be difficult. Fortunately, the relative protease activity of cathepsin is higher at lower pH and lower at higher pH. Therefore, the measurement of intratumoral cathepsin activity can serve as a surrogate measure of the pH of the tumor microenviroment. To measure in vivo activities of cathepsin B, L, S, K, V, and D, the near-infrared ProSense 750 FAST probe (PerkinElmer) was used. To further confirm modulation of the pH in the tumor microenvironment by administration of sodium bicarbonate, excised tumors were treated with phenol red and the color was noted. Phenol red is a pH indicator which undergoes a pH-dependent color transition. The sodium salt of phenol red is widely used in cell culture media to identify pH values. A solution of phenol red has a yellow color at a pH of 6.4 or below, an orange color around pH 7.0, a red color around pH 7.4, and a purple color above pH 7.8.

Mice were handled in accordance with Institutional Animal Care and Use Committee approved protocols. Subcutaneous (sc) Chinese Hamster Ovary (CHO) tumor xenografts were established in the hind flank of 12-14 week old female B-NSG mice (NOD-Prkdcscidl12rgtml/Bcgen (Beijing Biocytogen Co. Ltd.). Briefly, cultured CHO cells (ATCC, Manassas, Va.) were washed in DPBS (ThermoFisher), counted, resuspended in cold DPBS and mixed with an appropriate volume of Matrigel ECM (Corning; final concentration 5 mg/mL) at a concentration of $1.5 \times 10^6$ cells/200 µl on ice.

Animals were prepared for injection using standard approved anesthesia with hair removal (Nair) prior to injection. 200 µl of the cell suspension in ECM was injected sc into the rear flanks of the mice. Once tumors were palpable, the tumors were measured using calipers 2 times/week. Tumor volume was calculated using the following equation: (longest diameter*shortest $diameter^2$)/2. When average tumor volume reached 200 $mm^3$, mice were randomly assigned to the respective treatment groups.

Two days before the administration of bicarbonate, the drinking water for the B-NSG mice was changed from acidic to regular pH autoclaved purified water. The following day, the 750 ProSense FAST probe was administered to 6 CHO-xenograft tumor bearing mice via 100 µl tail vein injections (4 nmol ProSense 750 FAST probe/100 µl PBS). A separate group of CHO-xenograft tumor bearing mice was left untreated. The following day, sodium bicarbonate was administered and imaging of the mice treated with the ProSense 750 FAST probe was performed using a Caliper IVIS Lumina XR. Briefly, mice were anesthetized using 3% $O_2$ 2 L/min isoflurane in $O_2$ carrier gas at 2 L/min and then placed with nose cones supplying 1.5% isoflurane to anesthetized mice during imaging. Image acquisitions consisted of a 5 sec exposure for near-infrared probes (745/810 nm excitation/emission wavelength). Fluorescence images were overlaid on normal light images of the mice. Time 0 (pre-treatment) images were acquired before administration of either PBS (control) or sodium bicarbonate. The mice were then administered either 1 ml/mouse PBS (control, ThermoFisher) or 1 ml/mouse 1 M sodium bicarbonate (Shanghai Experiment Reagent Co., LTD) via intraperitoneal injection (ip). Mice were then imaged at 30 min post administration of PBS or bicarbonate. The collected fluorescence images were adjusted to have identical minimums, maximums, and threshold values. The photon counts were defined in this study as relative fluorescence units (RFU). RFU was calculated by normalizing the photon counts from the 30 min time point to the pretreatment time point (time 0; 100%) in each mouse. Due to variability between fluorescence values in each mouse at the time 0 pretreatment value, the observed fluorescence intensity values at different time points were normalized only to the individual mouse and not to a mean pretreatment value.

In a separate arm of the experiment, the 6 mice that did not receive the NIR cathepsin probe were euthanized by cervical dislocation at 1.5 hours post ip administration of PBS or sodium bicarbonate. The CHO xenograft tumor was excised from each mouse. The xenograft tumors were split into two halves with a scalpel and placed on a petri dish. The tumor tissue halves were then cut/sliced repeatedly using the scalpel. Water or 0.05% phenol red solution (50 mg phenol red/100 ml water) was added dropwise to each tumor half, respectively. The color was noted and images were taken of the treated tumor xenografts and of the phenol red solution remaining on the petri plate once the tumor xenograft samples were removed.

Results

Figure 29:
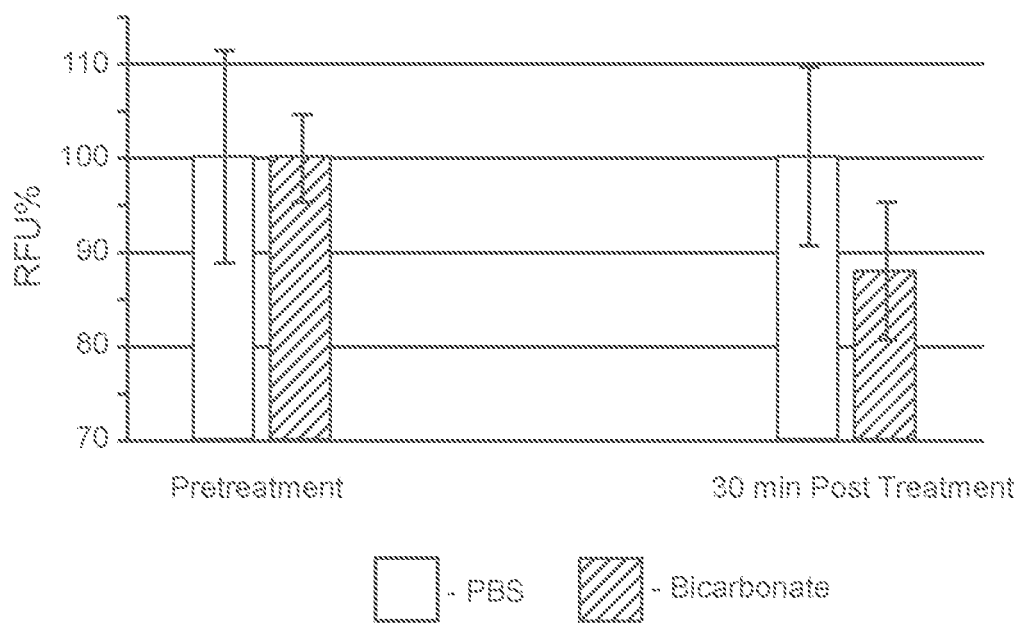
FIG. 29 is a graph showing the RFU percentage from ProSense FAST probe in CHO-xenograft tumor bearing mice before and after administration of PBS or bicarbonate.

FIG. 29 shows the RFU results (mean with SEM) from imaging intratumoral cathepsin activity in CHO-xenograft tumor bearing mice before and after administration of PBS (control; n=3) or bicarbonate (n=3). These results suggest that sodium bicarbonate administration can increase the pH of the tumor microenvironment in vivo as evidenced by the decreased cathepsin activity observed following ip sodium bicarbonate administration.

A color change of the phenol red indicator from yellow/orange to red was observed using the tumor tissue excised from sodium bicarbonate-treated mice (n=3) relative to the PBS-treated mice (n=3). These results suggest that sodium bicarbonate administration increased the pH of the tumor microenvironment in vivo following ip administration as evidenced by the color change of the phenol red indicator from yellow/orange to red.

Example 17. Thermal Denaturation of F1A-795 in the Absence and Presence of Acyclovir by Differential Scanning Calorimetry (DSC)

In this example, the binding of a nucleoside analogue antiviral drug to an aptamer domain of a riboswitch (SEQ ID NO:87) was demonstrated by comparing the thermal denaturation of the aptamer domain in the absence versus presence of the nucleoside analogue antiviral drug acyclovir.

Aptamer Preparation

The T7 primer (SEQ ID NO:246) as well as the template (reverse complement) of the identified candidate sequence was synthesized by IDT (Coralville, Iowa) as single-stranded DNA. Candidates were primer-extended by combining components to 1 µM template, 2 µM T7 primer, 200 µM dNTPs, 1× Titanium Taq DNA Polymerase, and 1× Titanium Taq buffer (Clontech Laboratories; Mountain View, Calif.), then heating for 3 minutes at 95° C., 1 minute at 55° C., and 2 minutes at 68° C. (no cycling). 42 pmoles of double-stranded DNA were used for twelve 20-µl reactions with the Ampliscribe T7 High Yield Transcription Kit (Lucigen; Middleton, Wis.) according to standard kit directions (1× reaction buffer, 7.5 mM each NTP, 10 mM DTT, 1× RiboGuard RNase inhibitor, 1× Ampliscribe T7 enzyme solution). Reactions were incubated at 42° C. overnight, then stopped by adding 1 µl of DNase I and incubating for 15 minutes at 37° C. Transcription products were purified on 10% denaturing PAGE with 8 M urea. At least 10 nmole of each candidate was lyophilized, and resuspended in 1× Binding Buffer (50 mM HEPES, 100 mM KCl, 0.5 mM $MgCl_2$, pH 7.3) on the day of binding assessment.

Briefly, DSC was used to analyze F1A-795 (7.2 µM) in the absence of acyclovir or F1A-795 (2.77 µM) in the presence of acyclovir (29.4 µM). All analyses were conducted in 1× Binding Buffer and all water used was DEPC-treated. All analytes were resuspended first in DEPC-treated water then diluted to their final listed concentration in 1× Binding Buffer. Prior to loading of the DSC (GE Healthcare MicroCal VP-DSC), the samples were degassed at 25° C. for 10 minutes. The sample without acyclovir was scanned from 10° C. to 115° C. at a rate of 1° C. per minute. The sample with acyclovir was scanned from 10° C. to 105° C. at a rate of 1° C. per minute.

Results

Figure 28:
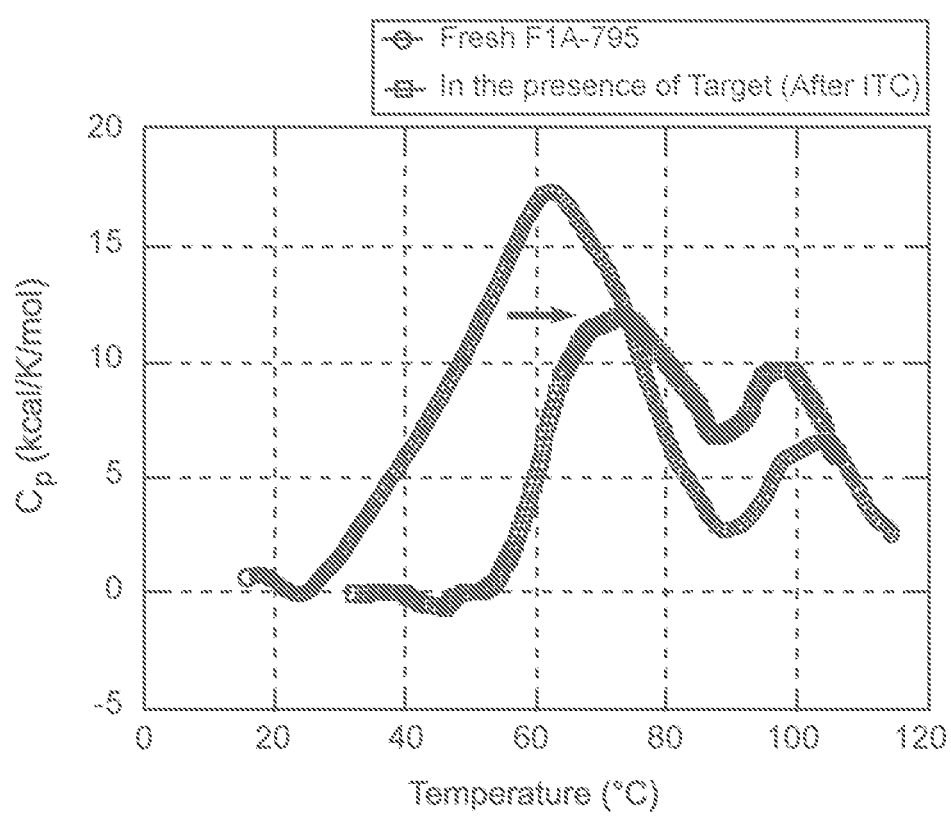
FIG. 28 is a graph showing the heat flux versus time for F1A-795 in the absence (circles) or presence (squares) of acyclovir as measured by DSC.

The thermal denaturation of F1A-795 in the absence of acyclovir as measured by DSC has a transition centered at about 60° C. (FIG. 28). This transition suggests the aptamer domain is structured in the absence of acyclovir. In the presence of acyclovir, F1A-795 has a transition centered at about 75° C. (FIG. 28). This stabilizing effect indicates the nucleoside analogue antiviral drug acyclovir binds to the aptamer domain F1A-795. Thus, this experiment confirmed that F1A-795 is bound by acyclovir.

The disclosed embodiments, examples and experiments are not intended to limit the scope of the disclosure or to represent that the experiments below are all or the only experiments performed. Efforts have been made to ensure accuracy with respect to numbers used (e.g., amounts, temperature, etc.) but some experimental errors and deviations should be accounted for. It should be understood that variations in the methods as described may be made without changing the fundamental aspects that the experiments are meant to illustrate.

Those skilled in the art can devise many modifications and other embodiments within the scope and spirit of the present disclosure. Indeed, variations in the materials, methods, drawings, experiments, examples, and embodiments described may be made by skilled artisans without changing the fundamental aspects of the present disclosure. Any of the disclosed embodiments can be used in combination with any other disclosed embodiment.

In some instances, some concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

What is claimed is:

1. A replication incompetent recombinant retroviral particle, comprising:
   A. one or more pseudotyping elements on the surface of the replication incompetent recombinant retroviral particle, wherein the one or more pseudotyping elements comprises a vesicular stomatitis virus (VSV-G) envelope protein, a feline endogenous virus (RD114) envelope protein, or a Paramyxoviridae envelope protein;
   B. a polynucleotide comprising one or more transcriptional units, wherein each of the one or more transcriptional units is operatively linked to a promoter active in T cells, and wherein the one or more transcriptional units encode
      i. a first engineered signaling polypeptide comprising a lymphoproliferative element wherein the lymphoproliferative element comprises a cytokine receptor polypeptide comprising a signaling domain that is capable of activating a Stat pathway, and promoting proliferation and/or survival of T cells; and
      ii. a second engineered signaling polypeptide comprising a chimeric antigen receptor comprising an antigen-specific targeting region, a transmembrane domain, and an intracellular activating domain; and
   C. an activation element on the surface of the replication incompetent recombinant retroviral particle, wherein the activation element is fused to a heterologous membrane attachment sequence, wherein the activation element is a polypeptide capable of binding to CD3 on the surface of a resting T cell and activating the resting T cell and is not encoded by a polynucleotide in the recombinant retroviral particle and wherein the activation element comprises an anti-CD3 antibody.

2. The replication incompetent recombinant retroviral particle of claim 1, wherein the first engineered signaling polypeptide is encoded in a reverse orientation with respect to a cis-acting RNA packaging element in the genome of the recombinant retroviral particle.

3. The replication incompetent recombinant retroviral particle of claim 1, wherein the promoter of at least one of the one or more transcriptional units is a T cell specific promoter.

4. The replication incompetent recombinant retroviral particle of claim 1, wherein the promoter of at least one of the one or more transcriptional units is the EF1a promoter, the MSCV promoter, or the CD3z promoter.

5. The replication incompetent recombinant retroviral particle of claim 1, wherein the polynucleotide further comprises an intron, and wherein the intron encodes an shRNA or one or more miRNAs.

6. The replication incompetent recombinant retroviral particle of claim 5, wherein the intron is an EF1a intron.

7. The replication incompetent recombinant retroviral particle of claim 1, wherein the first engineered signaling polypeptide coding sequence is operably linked to an intron in a first transcription unit of the one or more transcriptional units, and wherein the first transcriptional unit is in reverse orientation with respect to a cis-acting RNA packaging element in the genome of the recombinant retroviral particle.

8. The replication incompetent recombinant retroviral particle of claim 1, wherein the Stat pathway is a Stat1 pathway, a Stat3 pathway, a Stat4 pathway, or a Stat5 pathway.

9. The replication incompetent recombinant retroviral particle of claim 1, wherein the signaling domain is an intracellular signaling domain of an IL-7 receptor, an intracellular signaling domain of an IL-12 receptor, an intracellular signaling domain of an IL-15 receptor, or an intracellular signaling domain of an IL-21 receptor.

10. The replication incompetent recombinant retroviral particle of claim 1, wherein the lymphoproliferative element is constitutively active.

11. The replication incompetent recombinant retroviral particle of claim 10, wherein the constitutively active lymphoproliferative element is an IL-7Rα mutant, or a functional fragment thereof.

12. The replication incompetent recombinant retroviral particle of claim 11, wherein the IL-7Rα mutant comprises amino acids 229 to 292 of SEQ ID NO:229 with an insertion of PPCL at amino acid 243 of SEQ ID NO:229.

13. The replication incompetent recombinant retroviral particle of claim 1, wherein the lymphoproliferative element is a fusion polypeptide comprising a recognition domain that is recognized by a monoclonal antibody approved biologic.

14. The replication incompetent recombinant retroviral particle of claim 1, wherein the transcriptional unit encoding the first engineered signaling polypeptide further comprises a riboswitch.

15. The replication incompetent recombinant retroviral particle of claim 1, wherein the activation element further comprises a second polypeptide, wherein the second polypeptide is capable of binding CD28.

16. The replication incompetent recombinant retroviral particle of claim 1, wherein the polypeptide capable of binding to CD3 is fused to a heterologous GPI anchor attachment sequence.

17. The replication incompetent recombinant retroviral particle of claim 1, wherein the anti-CD3 antibody is a GPI-anchored anti-CD3scFvFc.

18. The replication incompetent recombinant retroviral particle of claim 1, wherein the Paramyxoviridae envelope protein is a Measles Virus F polypeptide, or a Measles Virus H polypeptide.

19. The replication incompetent recombinant retroviral particle of claim 1, wherein the replication incompetent recombinant retroviral particle is a lentivirus or a gammaretroviral particle.

20. The replication incompetent recombinant retroviral particle of claim 1, wherein the genome of the recombinant retroviral particle is less than 10,000 kb, wherein the replication incompetent recombinant retroviral particle is a lentiviral particle, wherein the lymphoproliferative element is a constitutively active cytokine receptor that is not tethered to a cytokine, and wherein the replication incompetent recombinant retroviral particle further encodes a polypeptide that is recognized by a monoclonal antibody approved biologic.

21. The replication incompetent recombinant retroviral particle of claim 1, wherein the recombinant retroviral particle further comprises a membrane-bound cytokine on the surface of the recombinant retroviral particle, wherein the membrane-bound cytokine comprises a fusion polypeptide of IL-7 and DAF, and wherein the fusion polypeptide comprises the amino acid sequence of SEQ ID NO:286.

* * * * *

SEQUENCE LISTING

<160> NUMBER OF SEQ ID NOS: 291

<210> SEQ ID NO 1
<211> LENGTH: 42
<212> TYPE: PRT
<213> ORGANISM: Homo sapiens

```
<400> SEQUENCE: 1

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Gly Gly Cys Glu Leu
            35                  40

<210> SEQ ID NO 2
<211> LENGTH: 41
<212> TYPE: PRT
<213> ORGANISM: Homo sapiens

<400> SEQUENCE: 2

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
            35                  40

<210> SEQ ID NO 3
<211> LENGTH: 41
<212> TYPE: PRT
<213> ORGANISM: Homo sapiens

<400> SEQUENCE: 3

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Ala Tyr Ala Ala
            20                  25                  30

Ala Arg Asp Phe Ala Ala Tyr Arg Ser
            35                  40

<210> SEQ ID NO 4
<211> LENGTH: 35
<212> TYPE: PRT
<213> ORGANISM: Homo sapiens

<400> SEQUENCE: 4

Thr Lys Lys Lys Tyr Ser Ser Val His Asp Pro Asn Gly Glu Tyr
1               5                   10                  15

Met Phe Met Arg Ala Val Asn Thr Ala Lys Lys Ser Arg Leu Thr Asp
            20                  25                  30

Val Thr Leu
    35

<210> SEQ ID NO 5
<211> LENGTH: 37
<212> TYPE: PRT
<213> ORGANISM: Homo sapiens

<400> SEQUENCE: 5

Arg Arg Asp Gln Arg Leu Pro Pro Asp Ala His Lys Pro Pro Gly Gly
1               5                   10                  15

Gly Ser Phe Arg Thr Pro Ile Gln Glu Glu Gln Ala Asp Ala His Ser
            20                  25                  30

Thr Leu Ala Lys Ile
            35
```

<210> SEQ ID NO 6
<211> LENGTH: 49
<212> TYPE: PRT
<213> ORGANISM: Homo sapiens

<400> SEQUENCE: 6

```
His Gln Arg Arg Lys Tyr Arg Ser Asn Lys Gly Glu Ser Pro Val Glu
1               5                   10                  15

Pro Ala Glu Pro Cys Arg Tyr Ser Cys Pro Arg Glu Glu Glu Gly Ser
            20                  25                  30

Thr Ile Pro Ile Gln Glu Asp Tyr Arg Lys Pro Glu Pro Ala Cys Ser
        35                  40                  45

Pro
```

<210> SEQ ID NO 7
<211> LENGTH: 114
<212> TYPE: PRT
<213> ORGANISM: Homo sapiens

<400> SEQUENCE: 7

```
Cys Cys Leu Arg Arg His Gln Gly Lys Gln Asn Glu Leu Ser Asp Thr
1               5                   10                  15

Ala Gly Arg Glu Ile Asn Leu Val Asp Ala His Leu Lys Ser Glu Gln
            20                  25                  30

Thr Glu Ala Ser Thr Arg Gln Asn Ser Gln Val Leu Leu Ser Glu Thr
        35                  40                  45

Gly Ile Tyr Asp Asn Asp Pro Asp Leu Cys Phe Arg Met Gln Glu Gly
    50                  55                  60

Ser Glu Val Tyr Ser Asn Pro Cys Leu Glu Glu Asn Lys Pro Gly Ile
65                  70                  75                  80

Val Tyr Ala Ser Leu Asn His Ser Val Ile Gly Pro Asn Ser Arg Leu
                85                  90                  95

Ala Arg Asn Val Lys Glu Ala Pro Thr Glu Tyr Ala Ser Ile Cys Val
            100                 105                 110

Arg Ser
```

<210> SEQ ID NO 8
<211> LENGTH: 187
<212> TYPE: PRT
<213> ORGANISM: Homo sapiens

<400> SEQUENCE: 8

```
Arg Arg Ala Cys Arg Lys Arg Ile Arg Gln Lys Leu His Leu Cys Tyr
1               5                   10                  15

Pro Val Gln Thr Ser Gln Pro Lys Leu Glu Leu Val Asp Ser Arg Pro
            20                  25                  30

Arg Arg Ser Ser Thr Gln Leu Arg Ser Gly Ala Ser Val Thr Glu Pro
        35                  40                  45

Val Ala Glu Glu Arg Gly Leu Met Ser Gln Pro Leu Met Glu Thr Cys
    50                  55                  60

His Ser Val Gly Ala Ala Tyr Leu Glu Ser Leu Pro Leu Gln Asp Ala
65                  70                  75                  80

Ser Pro Ala Gly Gly Pro Ser Ser Pro Arg Asp Leu Pro Glu Pro Arg
                85                  90                  95

Val Ser Thr Glu His Thr Asn Asn Lys Ile Glu Lys Ile Tyr Ile Met
            100                 105                 110
```

```
Lys Ala Asp Thr Val Ile Val Gly Thr Val Lys Ala Glu Leu Pro Glu
            115                 120                 125

Gly Arg Gly Leu Ala Gly Pro Ala Glu Pro Glu Leu Glu Gly Glu Leu
        130                 135                 140

Glu Ala Asp His Thr Pro His Tyr Pro Glu Gln Glu Thr Glu Pro Pro
145                 150                 155                 160

Leu Gly Ser Cys Ser Asp Val Met Leu Ser Val Glu Glu Gly Lys
                165                 170                 175

Glu Asp Pro Leu Pro Thr Ala Ala Ser Gly Lys
            180                 185
```

<210> SEQ ID NO 9
<211> LENGTH: 54
<212> TYPE: PRT
<213> ORGANISM: Homo sapiens

<400> SEQUENCE: 9

```
His Ile Trp Gln Leu Arg Ser Gln Cys Met Trp Pro Arg Glu Thr Gln
1               5                   10                  15

Leu Leu Leu Glu Val Pro Pro Ser Thr Glu Asp Ala Arg Ser Cys Gln
            20                  25                  30

Phe Pro Glu Glu Glu Arg Gly Glu Arg Ser Ala Glu Lys Gly Arg
        35                  40                  45

Leu Gly Asp Leu Trp Val
    50
```

<210> SEQ ID NO 10
<211> LENGTH: 60
<212> TYPE: PRT
<213> ORGANISM: Homo sapiens

<400> SEQUENCE: 10

```
Cys Val Lys Arg Arg Lys Pro Arg Gly Asp Val Val Lys Val Ile Val
1               5                   10                  15

Ser Val Gln Arg Lys Arg Gln Glu Ala Glu Gly Glu Ala Thr Val Ile
            20                  25                  30

Glu Ala Leu Gln Ala Pro Pro Asp Val Thr Thr Val Ala Val Glu Glu
        35                  40                  45

Thr Ile Pro Ser Phe Thr Gly Arg Ser Pro Asn His
    50                  55                  60
```

<210> SEQ ID NO 11
<211> LENGTH: 163
<212> TYPE: PRT
<213> ORGANISM: Homo sapiens

<400> SEQUENCE: 11

```
Met Lys Trp Lys Ala Leu Phe Thr Ala Ala Ile Leu Gln Ala Gln Leu
1               5                   10                  15

Pro Ile Thr Glu Ala Gln Ser Phe Gly Leu Leu Asp Pro Lys Leu Cys
            20                  25                  30

Tyr Leu Leu Asp Gly Ile Leu Phe Ile Tyr Gly Val Ile Leu Thr Ala
        35                  40                  45

Leu Phe Leu Arg Val Lys Phe Ser Arg Ser Ala Asp Ala Pro Ala Tyr
    50                  55                  60

Gln Gln Gly Gln Asn Gln Leu Tyr Asn Glu Leu Asn Leu Gly Arg Arg
65                  70                  75                  80

Glu Glu Tyr Asp Val Leu Asp Lys Arg Arg Gly Arg Asp Pro Glu Met
```

```
                    85                  90                  95

Gly Gly Lys Pro Arg Arg Lys Asn Pro Gln Glu Gly Leu Tyr Asn Glu
            100                 105                 110

Leu Gln Lys Asp Lys Met Ala Glu Ala Tyr Ser Glu Ile Gly Met Lys
            115                 120                 125

Gly Glu Arg Arg Arg Gly Lys Gly His Asp Gly Leu Tyr Gln Gly Leu
        130                 135                 140

Ser Thr Ala Thr Lys Asp Thr Tyr Asp Ala Leu His Met Gln Ala Leu
145                 150                 155                 160

Pro Pro Arg

<210> SEQ ID NO 12
<211> LENGTH: 164
<212> TYPE: PRT
<213> ORGANISM: Homo sapiens

<400> SEQUENCE: 12

Met Lys Trp Lys Ala Leu Phe Thr Ala Ala Ile Leu Gln Ala Gln Leu
1               5                   10                  15

Pro Ile Thr Glu Ala Gln Ser Phe Gly Leu Leu Asp Pro Lys Leu Cys
            20                  25                  30

Tyr Leu Leu Asp Gly Ile Leu Phe Ile Tyr Gly Val Ile Leu Thr Ala
        35                  40                  45

Leu Phe Leu Arg Val Lys Phe Ser Arg Ser Ala Asp Ala Pro Ala Tyr
    50                  55                  60

Gln Gln Gly Gln Asn Gln Leu Tyr Asn Glu Leu Asn Leu Gly Arg Arg
65                  70                  75                  80

Glu Glu Tyr Asp Val Leu Asp Lys Arg Arg Gly Arg Asp Pro Glu Met
                85                  90                  95

Gly Gly Lys Pro Gln Arg Arg Lys Asn Pro Gln Glu Gly Leu Tyr Asn
            100                 105                 110

Glu Leu Gln Lys Asp Lys Met Ala Glu Ala Tyr Ser Glu Ile Gly Met
            115                 120                 125

Lys Gly Glu Arg Arg Arg Gly Lys Gly His Asp Gly Leu Tyr Gln Gly
        130                 135                 140

Leu Ser Thr Ala Thr Lys Asp Thr Tyr Asp Ala Leu His Met Gln Ala
145                 150                 155                 160

Leu Pro Pro Arg

<210> SEQ ID NO 13
<211> LENGTH: 112
<212> TYPE: PRT
<213> ORGANISM: Homo sapiens

<400> SEQUENCE: 13

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80
```

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 14
<211> LENGTH: 21
<212> TYPE: PRT
<213> ORGANISM: Homo sapiens

<400> SEQUENCE: 14

Asn Gln Leu Tyr Asn Glu Leu Asn Leu Gly Arg Arg Glu Glu Tyr Asp
1               5                   10                  15

Val Leu Asp Lys Arg
            20

<210> SEQ ID NO 15
<211> LENGTH: 22
<212> TYPE: PRT
<213> ORGANISM: Homo sapiens

<400> SEQUENCE: 15

Glu Gly Leu Tyr Asn Glu Leu Gln Lys Asp Lys Met Ala Glu Ala Tyr
1               5                   10                  15

Ser Glu Ile Gly Met Lys
            20

<210> SEQ ID NO 16
<211> LENGTH: 21
<212> TYPE: PRT
<213> ORGANISM: Homo sapiens

<400> SEQUENCE: 16

Asp Gly Leu Tyr Gln Gly Leu Ser Thr Ala Thr Lys Asp Thr Tyr Asp
1               5                   10                  15

Ala Leu His Met Gln
            20

<210> SEQ ID NO 17
<211> LENGTH: 171
<212> TYPE: PRT
<213> ORGANISM: Homo sapiens

<400> SEQUENCE: 17

Met Glu His Ser Thr Phe Leu Ser Gly Leu Val Leu Ala Thr Leu Leu
1               5                   10                  15

Ser Gln Val Ser Pro Phe Lys Ile Pro Ile Glu Glu Leu Glu Asp Arg
            20                  25                  30

Val Phe Val Asn Cys Asn Thr Ser Ile Thr Trp Val Glu Gly Thr Val
                35                  40                  45

Gly Thr Leu Leu Ser Asp Ile Thr Arg Leu Asp Leu Gly Lys Arg Ile
        50                  55                  60

Leu Asp Pro Arg Gly Ile Tyr Arg Cys Asn Gly Thr Asp Ile Tyr Lys
65                  70                  75                  80

Asp Lys Glu Ser Thr Val Gln Val His Tyr Arg Met Cys Gln Ser Cys
            85                  90                  95

Val Glu Leu Asp Pro Ala Thr Val Ala Gly Ile Ile Val Thr Asp Val
            100                 105                 110

Ile Ala Thr Leu Leu Leu Ala Leu Gly Val Phe Cys Phe Ala Gly His
        115                 120                 125

Glu Thr Gly Arg Leu Ser Gly Ala Ala Asp Thr Gln Ala Leu Leu Arg
        130                 135                 140

Asn Asp Gln Val Tyr Gln Pro Leu Arg Asp Arg Asp Asp Ala Gln Tyr
145                 150                 155                 160

Ser His Leu Gly Gly Asn Trp Ala Arg Asn Lys
                165                 170

<210> SEQ ID NO 18
<211> LENGTH: 127
<212> TYPE: PRT
<213> ORGANISM: Homo sapiens

<400> SEQUENCE: 18

Met Glu His Ser Thr Phe Leu Ser Gly Leu Val Leu Ala Thr Leu Leu
1               5                   10                  15

Ser Gln Val Ser Pro Phe Lys Ile Pro Ile Glu Leu Glu Asp Arg
                20                  25                  30

Val Phe Val Asn Cys Asn Thr Ser Ile Thr Trp Val Glu Gly Thr Val
                35                  40                  45

Gly Thr Leu Leu Ser Asp Ile Thr Arg Leu Asp Leu Gly Lys Arg Ile
        50                  55                  60

Leu Asp Pro Arg Gly Ile Tyr Arg Cys Asn Gly Thr Asp Ile Tyr Lys
65                  70                  75                  80

Asp Lys Glu Ser Thr Val Gln Val His Tyr Arg Thr Ala Asp Thr Gln
                85                  90                  95

Ala Leu Leu Arg Asn Asp Gln Val Tyr Gln Pro Leu Arg Asp Arg Asp
            100                 105                 110

Asp Ala Gln Tyr Ser His Leu Gly Gly Asn Trp Ala Arg Asn Lys
        115                 120                 125

<210> SEQ ID NO 19
<211> LENGTH: 21
<212> TYPE: PRT
<213> ORGANISM: Homo sapiens

<400> SEQUENCE: 19

Asp Gln Val Tyr Gln Pro Leu Arg Asp Arg Asp Asp Ala Gln Tyr Ser
1               5                   10                  15

His Leu Gly Gly Asn
            20

<210> SEQ ID NO 20
<211> LENGTH: 206
<212> TYPE: PRT
<213> ORGANISM: Homo sapiens

<400> SEQUENCE: 20

Met Gln Ser Gly Thr His Trp Arg Val Leu Gly Leu Cys Leu Leu Ser
1               5                   10                  15

Val Gly Val Trp Gly Gln Asp Gly Asn Glu Glu Met Gly Gly Ile Thr
                20                  25                  30

Gln Thr Pro Tyr Lys Val Ser Ile Ser Gly Thr Thr Val Ile Leu Thr
            35                  40                  45

Cys Pro Gln Tyr Pro Gly Ser Glu Ile Leu Trp Gln His Asn Asp Lys
        50                  55                  60

Asn Ile Gly Gly Asp Glu Asp Asp Lys Asn Ile Gly Ser Asp Glu Asp
65                  70                  75                  80

His Leu Ser Leu Lys Glu Phe Ser Glu Leu Glu Gln Ser Gly Tyr Tyr
            85                  90                  95

Val Cys Tyr Pro Arg Gly Ser Lys Pro Glu Asp Ala Asn Phe Tyr Leu
            100                 105                 110

Tyr Leu Arg Ala Arg Val Cys Glu Asn Cys Met Glu Met Asp Met Ser
            115                 120                 125

Val Ala Thr Ile Val Ile Val Asp Ile Cys Ile Thr Gly Gly Leu Leu
            130                 135                 140

Leu Leu Val Tyr Tyr Trp Ser Lys Asn Arg Lys Ala Lys Ala Lys Pro
145                 150                 155                 160

Val Thr Arg Gly Ala Gly Ala Gly Gly Arg Gln Arg Gly Gln Asn Lys
            165                 170                 175

Glu Arg Pro Pro Pro Val Pro Asn Pro Asp Tyr Glu Pro Ile Arg Lys
            180                 185                 190

Gly Gln Arg Asp Leu Tyr Ser Gly Leu Asn Gln Arg Arg Ile
            195                 200                 205

<210> SEQ ID NO 21
<211> LENGTH: 21
<212> TYPE: PRT
<213> ORGANISM: Homo sapiens

<400> SEQUENCE: 21

Asn Pro Asp Tyr Glu Pro Ile Arg Lys Gly Gln Arg Asp Leu Tyr Ser
1               5                   10                  15

Gly Leu Asn Gln Arg
            20

<210> SEQ ID NO 22
<211> LENGTH: 182
<212> TYPE: PRT
<213> ORGANISM: Homo sapiens

<400> SEQUENCE: 22

Met Glu Gln Gly Lys Gly Leu Ala Val Leu Ile Leu Ala Ile Ile Leu
1               5                   10                  15

Leu Gln Gly Thr Leu Ala Gln Ser Ile Lys Gly Asn His Leu Val Lys
            20                  25                  30

Val Tyr Asp Tyr Gln Glu Asp Gly Ser Val Leu Leu Thr Cys Asp Ala
            35                  40                  45

Glu Ala Lys Asn Ile Thr Trp Phe Lys Asp Gly Lys Met Ile Gly Phe
50                  55                  60

Leu Thr Glu Asp Lys Lys Lys Trp Asn Leu Gly Ser Asn Ala Lys Asp
65                  70                  75                  80

Pro Arg Gly Met Tyr Gln Cys Lys Gly Ser Gln Asn Lys Ser Lys Pro
            85                  90                  95

Leu Gln Val Tyr Tyr Arg Met Cys Gln Asn Cys Ile Glu Leu Asn Ala
            100                 105                 110

Ala Thr Ile Ser Gly Phe Leu Phe Ala Glu Ile Val Ser Ile Phe Val
            115                 120                 125

Leu Ala Val Gly Val Tyr Phe Ile Ala Gly Gln Asp Gly Val Arg Gln
            130                 135                 140

Ser Arg Ala Ser Asp Lys Gln Thr Leu Leu Pro Asn Asp Gln Leu Tyr
145                 150                 155                 160

Gln Pro Leu Lys Asp Arg Glu Asp Asp Gln Tyr Ser His Leu Gln Gly
            165                 170                 175

Asn Gln Leu Arg Arg Asn
            180

<210> SEQ ID NO 23
<211> LENGTH: 21
<212> TYPE: PRT
<213> ORGANISM: Homo sapiens

<400> SEQUENCE: 23

Asp Gln Leu Tyr Gln Pro Leu Lys Asp Arg Glu Asp Gln Tyr Ser
1               5                   10                  15

His Leu Gln Gly Asn
            20

<210> SEQ ID NO 24
<211> LENGTH: 226
<212> TYPE: PRT
<213> ORGANISM: Homo sapiens

<400> SEQUENCE: 24

Met Pro Gly Gly Pro Gly Val Leu Gln Ala Leu Pro Ala Thr Ile Phe
1               5                   10                  15

Leu Leu Phe Leu Leu Ser Ala Val Tyr Leu Gly Pro Gly Cys Gln Ala
            20                  25                  30

Leu Trp Met His Lys Val Pro Ala Ser Leu Met Val Ser Leu Gly Glu
        35                  40                  45

Asp Ala His Phe Gln Cys Pro His Asn Ser Asn Asn Ala Asn Val
    50                  55                  60

Thr Trp Trp Arg Val Leu His Gly Asn Tyr Thr Trp Pro Pro Glu Phe
65                  70                  75                  80

Leu Gly Pro Gly Glu Asp Pro Asn Gly Thr Leu Ile Ile Gln Asn Val
                85                  90                  95

Asn Lys Ser His Gly Gly Ile Tyr Val Cys Arg Val Gln Glu Gly Asn
            100                 105                 110

Glu Ser Tyr Gln Gln Ser Cys Gly Thr Tyr Leu Arg Val Arg Gln Pro
        115                 120                 125

Pro Pro Arg Pro Phe Leu Asp Met Gly Glu Gly Thr Lys Asn Arg Ile
    130                 135                 140

Ile Thr Ala Glu Gly Ile Ile Leu Leu Phe Cys Ala Val Val Pro Gly
145                 150                 155                 160

Thr Leu Leu Leu Phe Arg Lys Arg Trp Gln Asn Glu Lys Leu Gly Leu
                165                 170                 175

Asp Ala Gly Asp Glu Tyr Glu Asp Glu Asn Leu Tyr Glu Gly Leu Asn
            180                 185                 190

Leu Asp Asp Cys Ser Met Tyr Glu Asp Ile Ser Arg Gly Leu Gln Gly
        195                 200                 205

Thr Tyr Gln Asp Val Gly Ser Leu Asn Ile Gly Asp Val Gln Leu Glu
    210                 215                 220

Lys Pro
225

<210> SEQ ID NO 25
<211> LENGTH: 188
<212> TYPE: PRT
<213> ORGANISM: Homo sapiens

<400> SEQUENCE: 25

Met Pro Gly Gly Pro Gly Val Leu Gln Ala Leu Pro Ala Thr Ile Phe

```
            1               5                  10                 15
            Leu Leu Phe Leu Leu Ser Ala Val Tyr Leu Gly Pro Gly Cys Gln Ala
                            20                 25                 30

Leu Trp Met His Lys Val Pro Ala Ser Leu Met Val Ser Leu Gly Glu
                            35                 40                 45

Asp Ala His Phe Gln Cys Pro His Asn Ser Ser Asn Ala Asn Val
                50                  55                 60

Thr Trp Trp Arg Val Leu His Gly Asn Tyr Thr Trp Pro Glu Phe
            65                  70                 75                 80

Leu Gly Pro Gly Glu Asp Pro Asn Glu Pro Pro Arg Pro Phe Leu
                            85                 90                 95

Asp Met Gly Glu Gly Thr Lys Asn Arg Ile Ile Thr Ala Glu Gly Ile
                            100                105                110

Ile Leu Leu Phe Cys Ala Val Val Pro Gly Thr Leu Leu Leu Phe Arg
                            115                120                125

Lys Arg Trp Gln Asn Glu Lys Leu Gly Leu Asp Ala Gly Asp Glu Tyr
                            130                135                140

Glu Asp Glu Asn Leu Tyr Glu Gly Leu Asn Leu Asp Asp Cys Ser Met
            145                 150                155                160

Tyr Glu Asp Ile Ser Arg Gly Leu Gln Gly Thr Tyr Gln Asp Val Gly
                            165                170                175

Ser Leu Asn Ile Gly Asp Val Gln Leu Glu Lys Pro
                            180                185

<210> SEQ ID NO 26
<211> LENGTH: 21
<212> TYPE: PRT
<213> ORGANISM: Homo sapiens

<400> SEQUENCE: 26

Glu Asn Leu Tyr Glu Gly Leu Asn Leu Asp Asp Cys Ser Met Tyr Glu
1               5                   10                  15

Asp Ile Ser Arg Gly
            20

<210> SEQ ID NO 27
<211> LENGTH: 113
<212> TYPE: PRT
<213> ORGANISM: Homo sapiens

<400> SEQUENCE: 27

Met Gly Gly Leu Glu Pro Cys Ser Arg Leu Leu Leu Leu Pro Leu Leu
1               5                   10                  15

Leu Ala Val Ser Gly Leu Arg Pro Val Gln Ala Gln Ala Gln Ser Asp
                20                  25                  30

Cys Ser Cys Ser Thr Val Ser Pro Gly Val Leu Ala Gly Ile Val Met
                35                  40                  45

Gly Asp Leu Val Leu Thr Val Leu Ile Ala Leu Ala Val Tyr Phe Leu
                50                  55                  60

Gly Arg Leu Val Pro Arg Gly Arg Gly Ala Ala Glu Ala Ala Thr Arg
65              70                  75                  80

Lys Gln Arg Ile Thr Glu Thr Glu Ser Pro Tyr Gln Glu Leu Gln Gly
                85                  90                  95

Gln Arg Ser Asp Val Tyr Ser Asp Leu Asn Thr Gln Arg Pro Tyr Tyr
                100                 105                 110

Lys
```

<210> SEQ ID NO 28
<211> LENGTH: 107
<212> TYPE: PRT
<213> ORGANISM: Homo sapiens

<400> SEQUENCE: 28

Met Gly Gly Leu Glu Pro Cys Ser Arg Leu Leu Leu Leu Pro Leu Leu
1               5                   10                  15

Leu Ala Val Ser Gly Leu Arg Pro Val Gln Ala Gln Ala Gln Ser Asp
            20                  25                  30

Cys Ser Cys Ser Thr Val Ser Pro Gly Val Leu Ala Gly Ile Val Met
        35                  40                  45

Gly Asp Leu Val Leu Thr Val Leu Ile Ala Leu Ala Val Tyr Phe Leu
    50                  55                  60

Gly Arg Leu Val Pro Arg Gly Arg Gly Ala Ala Glu Ala Thr Arg Lys
65                  70                  75                  80

Gln Arg Ile Thr Glu Thr Glu Ser Pro Tyr Gln Glu Leu Gln Gly Gln
                85                  90                  95

Arg Ser Asp Val Tyr Ser Asp Leu Asn Thr Gln
            100                 105

<210> SEQ ID NO 29
<211> LENGTH: 102
<212> TYPE: PRT
<213> ORGANISM: Homo sapiens

<400> SEQUENCE: 29

Met Gly Gly Leu Glu Pro Cys Ser Arg Leu Leu Leu Leu Pro Leu Leu
1               5                   10                  15

Leu Ala Val Ser Asp Cys Ser Cys Ser Thr Val Ser Pro Gly Val Leu
            20                  25                  30

Ala Gly Ile Val Met Gly Asp Leu Val Leu Thr Val Leu Ile Ala Leu
        35                  40                  45

Ala Val Tyr Phe Leu Gly Arg Leu Val Pro Arg Gly Arg Gly Ala Ala
    50                  55                  60

Glu Ala Thr Arg Lys Gln Arg Ile Thr Glu Thr Glu Ser Pro Tyr
65                  70                  75                  80

Gln Glu Leu Gln Gly Gln Arg Ser Asp Val Tyr Ser Asp Leu Asn Thr
                85                  90                  95

Gln Arg Pro Tyr Tyr Lys
            100

<210> SEQ ID NO 30
<211> LENGTH: 101
<212> TYPE: PRT
<213> ORGANISM: Homo sapiens

<400> SEQUENCE: 30

Met Gly Gly Leu Glu Pro Cys Ser Arg Leu Leu Leu Leu Pro Leu Leu
1               5                   10                  15

Leu Ala Val Ser Asp Cys Ser Cys Ser Thr Val Ser Pro Gly Val Leu
            20                  25                  30

Ala Gly Ile Val Met Gly Asp Leu Val Leu Thr Val Leu Ile Ala Leu
        35                  40                  45

Ala Val Tyr Phe Leu Gly Arg Leu Val Pro Arg Gly Arg Gly Ala Ala
    50                  55                  60

```
Glu Ala Thr Arg Lys Gln Arg Ile Thr Glu Thr Glu Ser Pro Tyr Gln
 65                  70                  75                  80

Glu Leu Gln Gly Gln Arg Ser Asp Val Tyr Ser Asp Leu Asn Thr Gln
                 85                  90                  95

Arg Pro Tyr Tyr Lys
            100

<210> SEQ ID NO 31
<211> LENGTH: 21
<212> TYPE: PRT
<213> ORGANISM: Homo sapiens

<400> SEQUENCE: 31

Glu Ser Pro Tyr Gln Glu Leu Gln Gly Gln Arg Ser Asp Val Tyr Ser
 1               5                  10                  15

Asp Leu Asn Thr Gln
            20

<210> SEQ ID NO 32
<211> LENGTH: 86
<212> TYPE: PRT
<213> ORGANISM: Homo sapiens

<400> SEQUENCE: 32

Met Ile Pro Ala Val Val Leu Leu Leu Leu Leu Val Glu Gln Ala
 1               5                  10                  15

Ala Ala Leu Gly Glu Pro Gln Leu Cys Tyr Ile Leu Asp Ala Ile Leu
                 20                  25                  30

Phe Leu Tyr Gly Ile Val Leu Thr Leu Leu Tyr Cys Arg Leu Lys Ile
             35                  40                  45

Gln Val Arg Lys Ala Ala Ile Thr Ser Tyr Glu Lys Ser Asp Gly Val
         50                  55                  60

Tyr Thr Gly Leu Ser Thr Arg Asn Gln Glu Thr Tyr Glu Thr Leu Lys
 65                  70                  75                  80

His Glu Lys Pro Pro Gln
                 85

<210> SEQ ID NO 33
<211> LENGTH: 21
<212> TYPE: PRT
<213> ORGANISM: Homo sapiens

<400> SEQUENCE: 33

Asp Gly Val Tyr Thr Gly Leu Ser Thr Arg Asn Gln Glu Thr Tyr Glu
 1               5                  10                  15

Thr Leu Lys His Glu
            20

<210> SEQ ID NO 34
<211> LENGTH: 20
<212> TYPE: PRT
<213> ORGANISM: Homo sapiens

<400> SEQUENCE: 34

Arg Pro Arg Arg Ser Pro Ala Gln Asp Gly Lys Val Tyr Ile Asn Met
 1               5                  10                  15

Pro Gly Arg Gly
            20

<210> SEQ ID NO 35
```

```
<211> LENGTH: 68
<212> TYPE: PRT
<213> ORGANISM: Homo sapiens

<400> SEQUENCE: 35

Phe Trp Val Leu Val Val Gly Gly Val Leu Ala Cys Tyr Ser Leu
1               5                   10                  15

Leu Val Thr Val Ala Phe Ile Ile Phe Trp Val Arg Ser Lys Arg Ser
            20                  25                  30

Arg Leu Leu His Ser Asp Tyr Met Asn Met Thr Pro Arg Pro Gly
        35                  40                  45

Pro Thr Arg Lys His Tyr Gln Pro Tyr Ala Pro Arg Asp Phe Ala
    50                  55                  60

Ala Tyr Arg Ser
65

<210> SEQ ID NO 36
<211> LENGTH: 619
<212> TYPE: PRT
<213> ORGANISM: Homo sapiens

<400> SEQUENCE: 36

Met Pro Asp Pro Ala Ala His Leu Pro Phe Phe Tyr Gly Ser Ile Ser
1               5                   10                  15

Arg Ala Glu Ala Glu His Leu Lys Leu Ala Gly Met Ala Asp Gly
            20                  25                  30

Leu Phe Leu Leu Arg Gln Cys Leu Arg Ser Leu Gly Gly Tyr Val Leu
        35                  40                  45

Ser Leu Val His Asp Val Arg Phe His His Phe Pro Ile Glu Arg Gln
50                  55                  60

Leu Asn Gly Thr Tyr Ala Ile Ala Gly Gly Lys Ala His Cys Gly Pro
65                  70                  75                  80

Ala Glu Leu Cys Glu Phe Tyr Ser Arg Asp Pro Asp Gly Leu Pro Cys
            85                  90                  95

Asn Leu Arg Lys Pro Cys Asn Arg Pro Ser Gly Leu Glu Pro Gln Pro
        100                 105                 110

Gly Val Phe Asp Cys Leu Arg Asp Ala Met Val Arg Asp Tyr Val Arg
    115                 120                 125

Gln Thr Trp Lys Leu Glu Gly Glu Ala Leu Glu Gln Ala Ile Ile Ser
    130                 135                 140

Gln Ala Pro Gln Val Glu Lys Leu Ile Ala Thr Thr Ala His Glu Arg
145                 150                 155                 160

Met Pro Trp Tyr His Ser Ser Leu Thr Arg Glu Glu Ala Glu Arg Lys
                165                 170                 175

Leu Tyr Ser Gly Ala Gln Thr Asp Gly Lys Phe Leu Leu Arg Pro Arg
            180                 185                 190

Lys Glu Gln Gly Thr Tyr Ala Leu Ser Leu Ile Tyr Gly Lys Thr Val
        195                 200                 205

Tyr His Tyr Leu Ile Ser Gln Asp Lys Ala Gly Lys Tyr Cys Ile Pro
    210                 215                 220

Glu Gly Thr Lys Phe Asp Thr Leu Trp Gln Leu Val Glu Tyr Leu Lys
225                 230                 235                 240

Leu Lys Ala Asp Gly Leu Ile Tyr Cys Leu Lys Glu Ala Cys Pro Asn
                245                 250                 255

Ser Ser Ala Ser Asn Ala Ser Gly Ala Ala Ala Pro Thr Leu Pro Ala
            260                 265                 270
```

-continued

```
His Pro Ser Thr Leu Thr His Pro Gln Arg Arg Ile Asp Thr Leu Asn
        275                 280                 285

Ser Asp Gly Tyr Thr Pro Glu Pro Ala Arg Ile Thr Ser Pro Asp Lys
290                 295                 300

Pro Arg Pro Met Pro Met Asp Thr Ser Val Tyr Glu Ser Pro Tyr Ser
305                 310                 315                 320

Asp Pro Glu Glu Leu Lys Asp Lys Lys Leu Phe Leu Lys Arg Asp Asn
                325                 330                 335

Leu Leu Ile Ala Asp Ile Glu Leu Gly Cys Gly Asn Phe Gly Ser Val
                340                 345                 350

Arg Gln Gly Val Tyr Arg Met Arg Lys Lys Gln Ile Asp Val Ala Ile
        355                 360                 365

Lys Val Leu Lys Gln Gly Thr Glu Lys Ala Asp Thr Glu Glu Met Met
        370                 375                 380

Arg Glu Ala Gln Ile Met His Gln Leu Asp Asn Pro Tyr Ile Val Arg
385                 390                 395                 400

Leu Ile Gly Val Cys Gln Ala Glu Ala Leu Met Leu Val Met Glu Met
                405                 410                 415

Ala Gly Gly Gly Pro Leu His Lys Phe Leu Val Gly Lys Arg Glu Glu
                420                 425                 430

Ile Pro Val Ser Asn Val Ala Glu Leu Leu His Gln Val Ser Met Gly
        435                 440                 445

Met Lys Tyr Leu Glu Glu Lys Asn Phe Val His Arg Asp Leu Ala Ala
        450                 455                 460

Arg Asn Val Leu Leu Val Asn Arg His Tyr Ala Lys Ile Ser Asp Phe
465                 470                 475                 480

Gly Leu Ser Lys Ala Leu Gly Ala Asp Asp Ser Tyr Tyr Thr Ala Arg
                485                 490                 495

Ser Ala Gly Lys Trp Pro Leu Lys Trp Tyr Ala Pro Glu Cys Ile Asn
                500                 505                 510

Phe Arg Lys Phe Ser Ser Arg Ser Asp Val Trp Ser Tyr Gly Val Thr
        515                 520                 525

Met Trp Glu Ala Leu Ser Tyr Gly Gln Lys Pro Tyr Lys Lys Met Lys
        530                 535                 540

Gly Pro Glu Val Met Ala Phe Ile Glu Gln Gly Lys Arg Met Glu Cys
545                 550                 555                 560

Pro Pro Glu Cys Pro Pro Glu Leu Tyr Ala Leu Met Ser Asp Cys Trp
                565                 570                 575

Ile Tyr Lys Trp Glu Asp Arg Pro Asp Phe Leu Thr Val Glu Gln Arg
                580                 585                 590

Met Arg Ala Cys Tyr Tyr Ser Leu Ala Ser Lys Val Glu Gly Pro Pro
        595                 600                 605

Gly Ser Thr Gln Lys Ala Glu Ala Ala Cys Ala
    610                 615

<210> SEQ ID NO 37
<211> LENGTH: 9
<212> TYPE: PRT
<213> ORGANISM: Artificial sequence
<220> FEATURE:
<223> OTHER INFORMATION: synthetic HA Epitope

<400> SEQUENCE: 37

Tyr Pro Tyr Asp Val Pro Asp Tyr Ala
1               5
```

```
<210> SEQ ID NO 38
<211> LENGTH: 8
<212> TYPE: PRT
<213> ORGANISM: Artificial sequence
<220> FEATURE:
<223> OTHER INFORMATION: synthetic FLAG Epitope

<400> SEQUENCE: 38

Asp Tyr Lys Asp Asp Asp Asp Lys
1               5

<210> SEQ ID NO 39
<211> LENGTH: 10
<212> TYPE: PRT
<213> ORGANISM: Artificial sequence
<220> FEATURE:
<223> OTHER INFORMATION: synthetic c-myc Epitope

<400> SEQUENCE: 39

Glu Gln Lys Leu Ile Ser Glu Glu Asp Leu
1               5                   10

<210> SEQ ID NO 40
<211> LENGTH: 5
<212> TYPE: PRT
<213> ORGANISM: Artificial sequence
<220> FEATURE:
<223> OTHER INFORMATION: synthetic His5 Affinity

<400> SEQUENCE: 40

His His His His His
1               5

<210> SEQ ID NO 41
<211> LENGTH: 6
<212> TYPE: PRT
<213> ORGANISM: Artificial sequence
<220> FEATURE:
<223> OTHER INFORMATION: synthetic HisX6 Affinity

<400> SEQUENCE: 41

His His His His His His
1               5

<210> SEQ ID NO 42
<211> LENGTH: 8
<212> TYPE: PRT
<213> ORGANISM: Artificial sequence
<220> FEATURE:
<223> OTHER INFORMATION: synthetic Strep Tag Affinity

<400> SEQUENCE: 42

Trp Ser His Pro Gln Phe Glu Lys
1               5

<210> SEQ ID NO 43
<211> LENGTH: 5
<212> TYPE: PRT
<213> ORGANISM: Artificial sequence
<220> FEATURE:
<223> OTHER INFORMATION: synthetic HisX6 Affinity

<400> SEQUENCE: 43

Arg Tyr Ile Arg Ser
1               5
```

-continued

<210> SEQ ID NO 44
<211> LENGTH: 4
<212> TYPE: PRT
<213> ORGANISM: Artificial sequence
<220> FEATURE:
<223> OTHER INFORMATION: synthetic Affinity

<400> SEQUENCE: 44

Phe His His Thr
1

<210> SEQ ID NO 45
<211> LENGTH: 17
<212> TYPE: PRT
<213> ORGANISM: Artificial sequence
<220> FEATURE:
<223> OTHER INFORMATION: synthetic Affinity

<400> SEQUENCE: 45

Trp Glu Ala Ala Ala Arg Glu Ala Cys Cys Arg Glu Cys Cys Ala Arg
1               5                   10                  15

Ala

<210> SEQ ID NO 46
<211> LENGTH: 24
<212> TYPE: PRT
<213> ORGANISM: Homo sapiens

<400> SEQUENCE: 46

Ile Tyr Ile Trp Ala Pro Leu Ala Gly Thr Cys Gly Val Leu Leu Leu
1               5                   10                  15

Ser Leu Val Ile Thr Leu Tyr Cys
            20

<210> SEQ ID NO 47
<211> LENGTH: 23
<212> TYPE: PRT
<213> ORGANISM: Homo sapiens

<400> SEQUENCE: 47

Leu Gly Leu Leu Val Ala Gly Val Leu Val Leu Leu Val Ser Leu Gly
1               5                   10                  15

Val Ala Ile His Leu Cys Cys
            20

<210> SEQ ID NO 48
<211> LENGTH: 25
<212> TYPE: PRT
<213> ORGANISM: Homo sapiens

<400> SEQUENCE: 48

Ala Leu Ile Val Leu Gly Gly Val Ala Gly Leu Leu Leu Phe Ile Gly
1               5                   10                  15

Leu Gly Ile Phe Phe Cys Val Arg Cys
            20                  25

<210> SEQ ID NO 49
<211> LENGTH: 23
<212> TYPE: PRT
<213> ORGANISM: Homo sapiens

<400> SEQUENCE: 49

Leu Cys Tyr Leu Leu Asp Gly Ile Leu Phe Ile Tyr Gly Val Ile Leu

```
                     1               5                   10                  15

Thr Ala Leu Phe Leu Arg Val
                 20

<210> SEQ ID NO 50
<211> LENGTH: 27
<212> TYPE: PRT
<213> ORGANISM: Homo sapiens

<400> SEQUENCE: 50

Phe Trp Val Leu Val Val Val Gly Gly Val Leu Ala Cys Tyr Ser Leu
1               5                   10                  15

Leu Val Thr Val Ala Phe Ile Ile Phe Trp Val
                 20                  25

<210> SEQ ID NO 51
<211> LENGTH: 26
<212> TYPE: PRT
<213> ORGANISM: Homo sapiens

<400> SEQUENCE: 51

Val Ala Ala Ile Leu Gly Leu Gly Leu Val Leu Gly Leu Leu Gly Pro
1               5                   10                  15

Leu Ala Ile Leu Leu Ala Leu Tyr Leu Leu
                 20                  25

<210> SEQ ID NO 52
<211> LENGTH: 24
<212> TYPE: PRT
<213> ORGANISM: Homo sapiens

<400> SEQUENCE: 52

Ala Leu Pro Ala Ala Leu Ala Val Ile Ser Phe Leu Leu Gly Leu Gly
1               5                   10                  15

Leu Gly Val Ala Cys Val Leu Ala
                 20

<210> SEQ ID NO 53
<211> LENGTH: 15
<212> TYPE: PRT
<213> ORGANISM: Artificial sequence
<220> FEATURE:
<223> OTHER INFORMATION: synthetic Linker 1

<400> SEQUENCE: 53

Gly Gly Gly Gly Ser Gly Gly Gly Gly Ser Gly Gly Gly Gly Ser
1               5                   10                  15

<210> SEQ ID NO 54
<211> LENGTH: 30
<212> TYPE: PRT
<213> ORGANISM: Artificial sequence
<220> FEATURE:
<223> OTHER INFORMATION: synthetic Linker 2

<400> SEQUENCE: 54

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
                 20                  25                  30

<210> SEQ ID NO 55
<211> LENGTH: 14
```

```
<212> TYPE: PRT
<213> ORGANISM: Artificial sequence
<220> FEATURE:
<223> OTHER INFORMATION: synthetic Linker 3

<400> SEQUENCE: 55

Gly Gly Gly Gly Ser Gly Gly Gly Ser Gly Gly Gly Ser
1               5                   10

<210> SEQ ID NO 56
<211> LENGTH: 4
<212> TYPE: PRT
<213> ORGANISM: Artificial sequence
<220> FEATURE:
<223> OTHER INFORMATION: synthetic Linker 4

<400> SEQUENCE: 56

Gly Gly Ser Gly
1

<210> SEQ ID NO 57
<211> LENGTH: 5
<212> TYPE: PRT
<213> ORGANISM: Artificial sequence
<220> FEATURE:
<223> OTHER INFORMATION: synthetic Linker 5

<400> SEQUENCE: 57

Gly Gly Ser Gly Gly
1               5

<210> SEQ ID NO 58
<211> LENGTH: 5
<212> TYPE: PRT
<213> ORGANISM: Artificial sequence
<220> FEATURE:
<223> OTHER INFORMATION: synthetic Linker 6

<400> SEQUENCE: 58

Gly Ser Gly Ser Gly
1               5

<210> SEQ ID NO 59
<211> LENGTH: 5
<212> TYPE: PRT
<213> ORGANISM: Artificial sequence
<220> FEATURE:
<223> OTHER INFORMATION: synthetic Linker 7

<400> SEQUENCE: 59

Gly Ser Gly Gly Gly
1               5

<210> SEQ ID NO 60
<211> LENGTH: 5
<212> TYPE: PRT
<213> ORGANISM: Artificial sequence
<220> FEATURE:
<223> OTHER INFORMATION: synthetic Linker 8

<400> SEQUENCE: 60

Gly Gly Gly Ser Gly
1               5

<210> SEQ ID NO 61
<211> LENGTH: 5
<212> TYPE: PRT
```

```
<213> ORGANISM: Artificial sequence
<220> FEATURE:
<223> OTHER INFORMATION: synthetic Linker 9

<400> SEQUENCE: 61

Gly Ser Ser Ser Gly
1               5

<210> SEQ ID NO 62
<211> LENGTH: 4
<212> TYPE: PRT
<213> ORGANISM: Artificial sequence
<220> FEATURE:
<223> OTHER INFORMATION: synthetic Hinge 1

<400> SEQUENCE: 62

Cys Pro Pro Cys
1

<210> SEQ ID NO 63
<211> LENGTH: 5
<212> TYPE: PRT
<213> ORGANISM: Artificial sequence
<220> FEATURE:
<223> OTHER INFORMATION: synthetic Hinge 2

<400> SEQUENCE: 63

Asp Lys Thr His Thr
1               5

<210> SEQ ID NO 64
<211> LENGTH: 15
<212> TYPE: PRT
<213> ORGANISM: Artificial sequence
<220> FEATURE:
<223> OTHER INFORMATION: synthetic Hinge 3

<400> SEQUENCE: 64

Cys Pro Glu Pro Lys Ser Cys Asp Thr Pro Pro Pro Cys Pro Arg
1               5                   10                  15

<210> SEQ ID NO 65
<211> LENGTH: 12
<212> TYPE: PRT
<213> ORGANISM: Artificial sequence
<220> FEATURE:
<223> OTHER INFORMATION: synthetic Hinge 4

<400> SEQUENCE: 65

Glu Leu Lys Thr Pro Leu Gly Asp Thr Thr His Thr
1               5                   10

<210> SEQ ID NO 66
<211> LENGTH: 10
<212> TYPE: PRT
<213> ORGANISM: Artificial sequence
<220> FEATURE:
<223> OTHER INFORMATION: synthetic Hinge 5

<400> SEQUENCE: 66

Lys Ser Cys Asp Lys Thr His Thr Cys Pro
1               5                   10

<210> SEQ ID NO 67
<211> LENGTH: 7
<212> TYPE: PRT
<213> ORGANISM: Artificial sequence
```

```
<220> FEATURE:
<223> OTHER INFORMATION: synthetic Hinge 6

<400> SEQUENCE: 67

Lys Cys Cys Val Asp Cys Pro
1               5

<210> SEQ ID NO 68
<211> LENGTH: 7
<212> TYPE: PRT
<213> ORGANISM: Artificial sequence
<220> FEATURE:
<223> OTHER INFORMATION: synthetic Hinge 7

<400> SEQUENCE: 68

Lys Tyr Gly Pro Pro Cys Pro
1               5

<210> SEQ ID NO 69
<211> LENGTH: 15
<212> TYPE: PRT
<213> ORGANISM: Artificial sequence
<220> FEATURE:
<223> OTHER INFORMATION: synthetic Hinge 8

<400> SEQUENCE: 69

Glu Pro Lys Ser Cys Asp Lys Thr His Thr Cys Pro Pro Cys Pro
1               5                   10                  15

<210> SEQ ID NO 70
<211> LENGTH: 12
<212> TYPE: PRT
<213> ORGANISM: Artificial sequence
<220> FEATURE:
<223> OTHER INFORMATION: synthetic Hinge 9

<400> SEQUENCE: 70

Glu Arg Lys Cys Cys Val Glu Cys Pro Pro Cys Pro
1               5                   10

<210> SEQ ID NO 71
<211> LENGTH: 17
<212> TYPE: PRT
<213> ORGANISM: Artificial sequence
<220> FEATURE:
<223> OTHER INFORMATION: synthetic Hinge 10

<400> SEQUENCE: 71

Glu Leu Lys Thr Pro Leu Gly Asp Thr Thr His Thr Cys Pro Arg Cys
1               5                   10                  15

Pro

<210> SEQ ID NO 72
<211> LENGTH: 12
<212> TYPE: PRT
<213> ORGANISM: Artificial sequence
<220> FEATURE:
<223> OTHER INFORMATION: synthetic Hinge 11

<400> SEQUENCE: 72

Ser Pro Asn Met Val Pro His Ala His His Ala Gln
1               5                   10

<210> SEQ ID NO 73
<211> LENGTH: 45
<212> TYPE: PRT
```

<213> ORGANISM: Artificial sequence
<220> FEATURE:
<223> OTHER INFORMATION: synthetic Hinge 12

<400> SEQUENCE: 73

```
Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
        35                  40                  45
```

<210> SEQ ID NO 74
<211> LENGTH: 21
<212> TYPE: PRT
<213> ORGANISM: Homo sapiens

<400> SEQUENCE: 74

```
Met Ala Leu Pro Val Thr Ala Leu Leu Leu Pro Leu Ala Leu Leu Leu
1               5                   10                  15

His Ala Ala Arg Pro
            20
```

<210> SEQ ID NO 75
<211> LENGTH: 24
<212> TYPE: PRT
<213> ORGANISM: Homo sapiens

<400> SEQUENCE: 75

```
Ile Tyr Ile Trp Ala Pro Leu Ala Gly Thr Cys Gly Val Leu Leu Leu
1               5                   10                  15

Ser Leu Val Ile Thr Leu Tyr Cys
            20
```

<210> SEQ ID NO 76
<211> LENGTH: 27
<212> TYPE: PRT
<213> ORGANISM: Homo sapiens

<400> SEQUENCE: 76

```
Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25
```

<210> SEQ ID NO 77
<211> LENGTH: 21
<212> TYPE: PRT
<213> ORGANISM: Artificial sequence
<220> FEATURE:
<223> OTHER INFORMATION: synthetic 2A-1 Cleavage signal

<400> SEQUENCE: 77

```
Gly Ser Gly Glu Gly Arg Gly Ser Leu Leu Thr Cys Gly Asp Val Glu
1               5                   10                  15

Glu Asn Pro Gly Pro
            20
```

<210> SEQ ID NO 78
<211> LENGTH: 357
<212> TYPE: PRT
<213> ORGANISM: Homo sapiens

<400> SEQUENCE: 78

```
Met Leu Leu Leu Val Thr Ser Leu Leu Cys Glu Leu Pro His Pro
 1               5                  10                 15

Ala Phe Leu Leu Ile Pro Arg Lys Val Cys Asn Gly Ile Gly Ile Gly
            20                  25                  30

Glu Phe Lys Asp Ser Leu Ser Ile Asn Ala Thr Asn Ile Lys His Phe
            35                  40                  45

Lys Asn Cys Thr Ser Ile Ser Gly Asp Leu His Ile Leu Pro Val Ala
     50                  55                  60

Phe Arg Gly Asp Ser Phe Thr His Thr Pro Pro Leu Asp Pro Gln Glu
 65                  70                  75                  80

Leu Asp Ile Leu Lys Thr Val Lys Glu Ile Thr Gly Phe Leu Leu Ile
                 85                  90                  95

Gln Ala Trp Pro Glu Asn Arg Thr Asp Leu His Ala Phe Glu Asn Leu
                100                 105                 110

Glu Ile Ile Arg Gly Arg Thr Lys Gln His Gly Gln Phe Ser Leu Ala
            115                 120                 125

Val Val Ser Leu Asn Ile Thr Ser Leu Gly Leu Arg Ser Leu Lys Glu
130                 135                 140

Ile Ser Asp Gly Asp Val Ile Ile Ser Gly Asn Lys Asn Leu Cys Tyr
145                 150                 155                 160

Ala Asn Thr Ile Asn Trp Lys Lys Leu Phe Gly Thr Ser Gly Gln Lys
                165                 170                 175

Thr Lys Ile Ile Ser Asn Arg Gly Glu Asn Ser Cys Lys Ala Thr Gly
            180                 185                 190

Gln Val Cys His Ala Leu Cys Ser Pro Glu Gly Cys Trp Gly Pro Glu
        195                 200                 205

Pro Arg Asp Cys Val Ser Cys Arg Asn Val Ser Arg Gly Arg Glu Cys
210                 215                 220

Val Asp Lys Cys Asn Leu Leu Glu Gly Glu Pro Arg Glu Phe Val Glu
225                 230                 235                 240

Asn Ser Glu Cys Ile Gln Cys His Pro Glu Cys Leu Pro Gln Ala Met
                245                 250                 255

Asn Ile Thr Cys Thr Gly Arg Gly Pro Asp Asn Cys Ile Gln Cys Ala
            260                 265                 270

His Tyr Ile Asp Gly Pro His Cys Val Lys Thr Cys Pro Ala Gly Val
        275                 280                 285

Met Gly Glu Asn Asn Thr Leu Val Trp Lys Tyr Ala Asp Ala Gly His
290                 295                 300

Val Cys His Leu Cys His Pro Asn Cys Thr Tyr Gly Cys Thr Gly Pro
305                 310                 315                 320

Gly Leu Glu Gly Cys Pro Thr Asn Gly Pro Lys Ile Pro Ser Ile Ala
                325                 330                 335

Thr Gly Met Val Gly Ala Leu Leu Leu Leu Val Val Ala Leu Gly
            340                 345                 350

Ile Gly Leu Phe Met
        355
```

<210> SEQ ID NO 79
<211> LENGTH: 45
<212> TYPE: PRT
<213> ORGANISM: Homo sapiens

<400> SEQUENCE: 79

-continued

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
                20                  25                  30

Gly Ala Val His Thr Arg Gly Leu Asp Phe Ala Cys Asp
            35                  40                  45

<210> SEQ ID NO 80
<211> LENGTH: 39
<212> TYPE: PRT
<213> ORGANISM: Homo sapiens

<400> SEQUENCE: 80

Ile Glu Val Met Tyr Pro Pro Tyr Leu Asp Asn Glu Lys Ser Asn
1               5                   10                  15

Gly Thr Ile Ile His Val Lys Gly Lys His Leu Cys Pro Ser Pro Leu
                20                  25                  30

Phe Pro Gly Pro Ser Lys Pro
            35

<210> SEQ ID NO 81
<211> LENGTH: 113
<212> TYPE: PRT
<213> ORGANISM: Homo sapiens

<400> SEQUENCE: 81

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
                20                  25                  30

Asp Val Leu Asp Lys Arg Arg Gly Arg Asp Pro Glu Met Gly Gly Lys
            35                  40                  45

Pro Gln Arg Arg Lys Asn Pro Gln Glu Gly Leu Tyr Asn Glu Leu Gln
        50                  55                  60

Lys Asp Lys Met Ala Glu Ala Tyr Ser Glu Ile Gly Met Lys Gly Glu
65                  70                  75                  80

Arg Arg Arg Gly Lys Gly His Asp Gly Leu Tyr Gln Gly Leu Ser Thr
                85                  90                  95

Ala Thr Lys Asp Thr Tyr Asp Ala Leu His Met Gln Ala Leu Pro Pro
            100                 105                 110

Arg

<210> SEQ ID NO 82
<211> LENGTH: 463
<212> TYPE: PRT
<213> ORGANISM: Homo sapiens

<400> SEQUENCE: 82

Met Thr Ile Leu Gly Thr Thr Phe Gly Met Val Phe Ser Leu Leu Gln
1               5                   10                  15

Val Val Ser Gly Glu Ser Gly Tyr Ala Gln Asn Gly Asp Leu Glu Asp
                20                  25                  30

Ala Glu Leu Asp Asp Tyr Ser Phe Ser Cys Tyr Ser Gln Leu Glu Val
            35                  40                  45

Asn Gly Ser Gln His Ser Leu Thr Cys Ala Phe Glu Asp Pro Asp Val
        50                  55                  60

Asn Thr Thr Asn Leu Glu Phe Glu Ile Cys Gly Ala Leu Val Glu Val
65                  70                  75                  80

```
Lys Cys Leu Asn Phe Arg Lys Leu Gln Glu Ile Tyr Phe Ile Glu Thr
                 85                  90                  95

Lys Lys Phe Leu Leu Ile Gly Lys Ser Asn Ile Cys Val Lys Val Gly
            100                 105                 110

Glu Lys Ser Leu Thr Cys Lys Lys Ile Asp Leu Thr Thr Ile Val Lys
        115                 120                 125

Pro Glu Ala Pro Phe Asp Leu Ser Val Ile Tyr Arg Glu Gly Ala Asn
    130                 135                 140

Asp Phe Val Val Thr Phe Asn Thr Ser His Leu Gln Lys Lys Tyr Val
145                 150                 155                 160

Lys Val Leu Met His Asp Val Ala Tyr Arg Gln Glu Lys Asp Glu Asn
                165                 170                 175

Lys Trp Thr His Val Asn Leu Ser Ser Thr Lys Leu Thr Leu Leu Gln
                180                 185                 190

Arg Lys Leu Gln Pro Ala Ala Met Tyr Glu Ile Lys Val Arg Ser Ile
        195                 200                 205

Pro Asp His Tyr Phe Lys Gly Phe Trp Ser Glu Trp Ser Pro Ser Tyr
    210                 215                 220

Tyr Phe Arg Thr Pro Glu Ile Asn Asn Ser Ser Gly Glu Met Asp Pro
225                 230                 235                 240

Ile Leu Leu Pro Pro Cys Leu Thr Ile Ser Ile Leu Ser Phe Phe Ser
                245                 250                 255

Val Ala Leu Leu Val Ile Leu Ala Cys Val Leu Trp Lys Lys Arg Ile
                260                 265                 270

Lys Pro Ile Val Trp Pro Ser Leu Pro Asp His Lys Lys Thr Leu Glu
            275                 280                 285

His Leu Cys Lys Lys Pro Arg Lys Asn Leu Asn Val Ser Phe Asn Pro
        290                 295                 300

Glu Ser Phe Leu Asp Cys Gln Ile His Arg Val Asp Asp Ile Gln Ala
305                 310                 315                 320

Arg Asp Glu Val Glu Gly Phe Leu Gln Asp Thr Phe Pro Gln Gln Leu
                325                 330                 335

Glu Glu Ser Glu Lys Gln Arg Leu Gly Gly Asp Val Gln Ser Pro Asn
            340                 345                 350

Cys Pro Ser Glu Asp Val Val Val Thr Pro Glu Ser Phe Gly Arg Asp
        355                 360                 365

Ser Ser Leu Thr Cys Leu Ala Gly Asn Val Ser Ala Cys Asp Ala Pro
    370                 375                 380

Ile Leu Ser Ser Ser Arg Ser Leu Asp Cys Arg Glu Ser Gly Lys Asn
385                 390                 395                 400

Gly Pro His Val Tyr Gln Asp Leu Leu Leu Ser Leu Gly Thr Thr Asn
                405                 410                 415

Ser Thr Leu Pro Pro Pro Phe Ser Leu Gln Ser Gly Ile Leu Thr Leu
            420                 425                 430

Asn Pro Val Ala Gln Gly Gln Pro Ile Leu Thr Ser Leu Gly Ser Asn
        435                 440                 445

Gln Glu Glu Ala Tyr Val Thr Met Ser Ser Phe Tyr Gln Asn Gln
    450                 455                 460

<210> SEQ ID NO 83
<211> LENGTH: 13673
<212> TYPE: DNA
<213> ORGANISM: Artificial sequence
<220> FEATURE:
```

<223> OTHER INFORMATION: synthetic Dox-rapamycin inducible lentiviral
genome with riboswitch

<400> SEQUENCE: 83

```
gatatctata acaagaaaat atatatataa taagttatca cgtaagtaga acatgaaata      60
acaatataat tatcgtatga gttaaatctt aaaagtcacg taaaagataa tcatgcgtca     120
ttttgactca cgcggtcgtt atagttcaaa atcagtgaca cttaccgcat tgacaagcac     180
gcctcacggg agctccaagc ggcgactgag atgtcctaaa tgcacagcga cggattcgcg     240
ctatttagaa agagagagca atatttcaag aatgcatgcg tcaattttac gcagactatc     300
tttctagggt taagacggat cgggagatct cccgatcccc tatggtgcac tctcagtaca     360
atctgctctg atgccgcata gttaagccag tatctgctcc ctgcttgtgt gttggaggtc     420
gctgagtagt gcgcgagcaa aatttaagct acaacaaggc aaggcttgac cgacaattgc     480
atgaagaatc tgcttagggt taggcgtttt gcgctgcttc gcgatgtacg gccagatat     540
acgcgttgac attgattatt gactagttat taatagtaat caattacggg gtcattagtt     600
catagcccat atatggagtt ccgcgttaca taacttacgg taaatggccc gcctggctga     660
ccgcccaacg acccccgccc attgacgtca ataatgacga atgttcccat agtaacgcca     720
atagggactt tccattgacg tcaatgggtg gagtatttac ggtaaactgc ccacttggca     780
gtacatcaag tgtatcatat gccaagtacg cccctattg acgtcaatga cggtaaatgg     840
cccgcctggc attatgccca gtacatgacc ttatgggact ttcctacttg gcagtacatc     900
tacgtattag tcatcgctat taccatggtg atgcggtttt ggcagtacat caatgggcgt     960
ggatagcggt ttgactcacg gggatttcca agtctccacc ccattgacgt caatgggagt    1020
ttgttttgga accaaaatca acgggacttt ccaaaatgtc gtaacaactc cgccccattg    1080
acgcaaatgg gcggtaggcg tgtacggtgg gaggtctata taagcagagc tctccctatc    1140
agtgatagag atctccctat cagtgataga gatcgtcgac gagctcgttt agtgaaccgt    1200
cagatcgcct ggagacgccc tcgaagccgc ggtgcgggtg ccagggcgtg ccctgggtct    1260
ctctggttag accagatctg agcctgggag ctctctggct aactagggaa cccactgctt    1320
aagcctcaat aaagcttgcc ttgagtgctt caagtagtgt gtgcccgtct gttgtgtgac    1380
tctggtaact agagatccct cagacccttt tagtcagtgt ggaaaatctc tagcagtggc    1440
gcccgaacag ggacttgaaa gcgaaaggga accagagga gctctctcga cgcaggactc    1500
ggcttgctga agcgcgcacg gcaagaggcg aggggcggcg actggtgagt acgccaaaaa    1560
ttttgactag cggaggctag aaggagagag atgggtgcga gagcgtcagt attaagcggg    1620
ggagaattag atcgcgatgg gaaaaaattc ggttaaggcc agggggaaag aaaaaatata    1680
aattaaaaca tatagtatgg gcaagcaggg agctagaacg attcgcagtt aatcctggcc    1740
tgttagaaac atcagaaggc tgtagacaaa tactgggaca gctacaacca tcccttcaga    1800
caggatcaga gaacttagat cattatata atacagtagc aaccctctat tgtgtgcatc    1860
aaaggataga gataaaagac accaaggaag ctttagacaa gatagaggaa gagcaaaaca    1920
aaagtaagac caccgcacag caagcggccg ctgatcttca gacctggagg aggagatatg    1980
agggacaatt ggagaagtga attatataaa tataaagtag taaaaattga accattagga    2040
gtagcaccca ccaaggcaaa gagaagagtg gtgcagagag aaaaaagagc agtgggaata    2100
ggagctttgt tccttgggtt cttgggagca gcaggaagca ctatgggcgc agcgtcaatg    2160
acgctgacgg tacaggccag acaattattg tctggtatag tgcagcagca gaacaatttg    2220
```

```
ctgagggcta ttgaggcgca acagcatctg ttgcaactca cagtctgggg catcaagcag    2280
ctccaggcaa gaatcctggc tgtggaaaga tacctaaagg atcaacagct cctgggatt    2340
tggggttgct ctggaaaact catttgcacc actgctgtgc cttggaatgc tagttggagt    2400
aataaatctc tggaacagat ttggaatcac acgacctgga tggagtggga cagagaaatt    2460
aacaattaca caagcttaat acactcctta attgaagaat cgcaaaacca gcaagaaaag    2520
aatgaacaag aattattgga attagataaa tgggcaagtt tgtggaattg gtttaacata    2580
acaaattggc tgtggtatat aaaattattc ataatgatag taggaggctt ggtaggttta    2640
agaatagttt ttgctgtact ttctatagtg aatagagtta ggcagggata ttcaccatta    2700
tcgtttcaga cccacctccc aaccccgagg ggacccgaca ggcccgaagg aatagaagaa    2760
gaaggtggag agagagacag agacagatcc attcgattag tgaacggatc tcgacggtat    2820
cgattagact gtagcccagg aatatggcag ctagattgta cacatttaga aggaaaagtt    2880
atcttggtag cagttcatgt agccagtgga tatatagaag cagaagtaat tccagcagag    2940
acagggcaag aaacagcata cttcctctta aaattagcag gaagatggcc agtaaaaaca    3000
gtacatacag acaatggcag caatttcacc agtactacag ttaaggccgc ctgttggtgg    3060
gcggggatca agcaggaatt tggcattccc tacaatcccc aaagtcaagg agtaatagaa    3120
tctatgaata aagaattaaa gaaaattata ggacaggtaa gagatcaggc tgaacatctt    3180
aagacagcag tacaaatggc agtattcatc cacaatttta aaagaaaagg ggggattggg    3240
gggtacagtg caggggaaag aatagtagac ataatagcaa cagacataca aactaaagaa    3300
ttacaaaaac aaattacaaa aattcaaaat tttcgggttt attacaggga cagcagagat    3360
ccagtttggc tgcattgatc acgtgagggg ctctagactc tagcacaca aaaaaccaac    3420
acacagatct aatgaaaata aagatctttt attgagaaac ttatacaggg tagcataatg    3480
ggctactgac cccgccttca aacctatttg agactataa gtgaaaatta tcactggttt    3540
tggtagaagc tggacatggt gacatatgct tcttcttgat ttgatcccag ggaagtaaga    3600
atgggctgac cctgagcaac tgggttcaat gtcaggattc cagattggag agaaaatgga    3660
ggggcagcg tgctgtttgt agtcccaagg ctaagcagga ggtcctggta cacatgaggc    3720
ccattcttgc cactctccct gcagtctagg gacctggaag aggagagaat aggggcgtca    3780
catgcactga cattcccagc caggcatgtg agggatgaat ctcttccaaa gctttctgga    3840
gtgacgacta catcctcaga tgggcagttg gggctctgca catcccctcc aagcctctgc    3900
ttctcagatt cttctagttg ctgaggaaac gtatcttgca gaaaaccttc cacttcatct    3960
ctagcttgaa tgtcatccac cctatgaatc tggcagtcca ggaaactttc aggattgaaa    4020
ctcacattta aattttttct tggtttctta caaagatgtt ccagagtctt cttatgatcg    4080
gggagactgg gccatacgat aggcttaatc cttttttttcc ataacacaca ggccaagatg    4140
accaacagag cgacagagaa aaaactcaaa atgctgatgg tcaggcatgg tggtagtaag    4200
ataggatcca tctcccctga gctattattg atctctggag ttctgaagta ataacttgga    4260
ctccattcac tccagaagcc tttaaaatag tgatcaggga tggatcgaac tttaatctca    4320
tacattgctg ccggttggag ctttctctgc aggagtgtca gctttgtgct ggataaattc    4380
acatgcgtcc atttgttttc atccttttcc tggcggtaag ctacatcatg cattaaaact    4440
tttacatact tcttttgcaa gtgtgatgta ttaaatgtca ccacaaagtc attggctcct    4500
tcccgataga tgacactcag gtcaaaagga gcctcaggtt taactatagt ggttaggtct    4560
attttttttgc aggttagact cttttctcca accttcacac atatattgct ctttccaatc    4620
```

-continued

```
agtaagaatt tctttgtctc gatgaaatat atctcttgta gtttcctgaa attcaggcac    4680
tttacctcca cgagggcccc acatatttca aattccagat tggtggtgtt gacatctggg    4740
tcctcaaaag cacatgtcag tgaatgctgc gatccattca cttccaactg gctatagcat    4800
gagaatgagt agtcatccag ttctgcatct tccaagtctc cattttgagc atagccactt    4860
tctccagaaa cgacttgaag taaagaaaaa accatgccaa aagttgtacc tagaattgtc    4920
attgggccgg gattttcctc cacgtccccg catgttagta gacttcccct gccctcgccg    4980
gagcgagggg gcagggcctg catgtgaagg gcgtcgtagg tgtccttggt ggctgtactg    5040
agaccctggt aaaggccatc gtgccccttg ccctccggc gctcgccttt catcccaatc    5100
tcactgtagg cctccgccat cttatctttc tgcagttcat tgtacaggcc ttcctgaggg    5160
ttcttccttc tcggctttcc ccccatctca gggtcccggc cacgtctctt gtccaaaaca    5220
tcgtactcct ctcttcgtcc tagattgagc tcgttataga gctggttctg gccctgcttg    5280
tacgcggggg cgtctgcgct cctgctgaac ttcactctca gttcacatcc tccttcttct    5340
tcttctggaa atcggcagct acagccatct tcctcttgag tagtttgtac tggtctcata    5400
aatggttgtt tgaatatata caggagtttc tttctgcccc gtttgcagta aagggtgata    5460
accagtgaca ggagaaggac cccacaagtc ccggccaagg gcgcccagat gtagatatca    5520
caggcgaagt ccagcccct cgtgtgcact gcgccccccg ccgctggccg gcacgcctct    5580
gggcgcaggg acagggctg cgacgcgatg gtgggcgccg gtgttggtgg tcgcggcgct    5640
ggcgtcgtgg ttgaggagac ggtgactgag gttccttggc cccagtagtc catagcatag    5700
ctaccaccgt agtaataatg tttggcacag tagtaaatgg ctgtgtcatc agtttgcaga    5760 ctgttcatt ttaagaaaac ttggctcttg gagttgtcct tgatgatggt cagtctggat    5820
ttgagagctg aattatagta tgtggtttca ctaccccata ttactcccag ccactccaga    5880
ccctttcgtg gaggctggcg aatccagctt acaccatagt cgggtaatga ccccctgag    5940 acagtgcatg tgacggacag gctctgtgag ggcgccacca ggccaggtcc tgactcctgc    6000
agtttcacct cagatccgcc gccacccgac ccaccaccgc ccgagccacc gccacctgtg    6060
atctccagct tggtccccc tccgaacgtg tacggaagcg tattaccctg ttggcgaagt    6120
aggtggcaat atcttcttgc tccaggttgc taattgtcag agaataatct gttccagacc    6180
cactgccact gaaccttgat gggactcctg agtgtaatct tgatgtatgg tagatcagga    6240
gtttaacagt tccatctggt ttctgctgat accaatttaa atatttacta atgtcctgac    6300
ttgccctgca actgatggtg actctgtctc ccagagaggc agacagggag gatgtagtct    6360
gtgtcatctg gatgtccggc ctggcggcgt ggagcagcaa ggccagcggc aggagcaagg    6420
cggtcactgg taaggccatg gatcctctag atcacgacac ctgaaatgga agaaaaaaac    6480
tttgaaccac tgtctgaggc ttgagaatga accaagatcc aaactcaaaa agggcaaatt    6540
ccaaggagaa ttcatcaag tgccaagctg gcctaacttc agtctccacc cactcagtgt    6600
ggggaaactc catcgcataa aacccctccc cccaacctaa agacgacgta ctccaaaagc    6660
tcgagaacta atcgaggtgc ctggacggcg cccggtactc agtggagtca catgaagcga    6720
cggctgagga cggaaaggcc ctttcctttt gtgtgggaga aacttataca gggtagcata    6780
atgggctact gaccccgcct tcaaacctat ttggagacta taagtgaaaa tgactcaccc    6840
gcccgctctc ccggcacctt catcttgtcc tttccctcag aaagaggctg ggaggcagag    6900
gctgaggcag cggtggccgg gacggttagg agaaaaggag tctctgctgg ttttattctg    6960
```

```
cagctacctc cccaggaagt ggaggactgt ggggcctttg agaagcacct gccgacaggg      7020
ccaagaaatt cgcactcccc ctttcggttc acaggcagga agccctggag gtttgagggt      7080
ttggggtgtg tgtatgtatc tgtctgtctg aattttgctt tttctctcat ttgaccattg      7140
ttttaatgct ccttttttta aaaaaaataa ttcttatcta attcctatct tgattggtaa      7200
agtccatctc taggcaaata caagttctcg atggaaaaca ataagtaatg taaaatacag      7260
catagcaaaa ctttaacctc caaatcaagc ctctacttga atccttttct gagggatgaa      7320
taaggcatag gcatcagggg ctgttgccaa tgtgcattag ctgtttgcag cctcaccttc      7380
tttcatggag tttaagatat agtgtatttt cccaaggttt gaactagctc ttcatttctt      7440
tatgttttaa atgcactgac ctcccacatt ccctttttag taaaatattc agaaataatt      7500
taaatacatc attgcaatga aaataaatgt ttttattag gcagaatcca gatgctcaag      7560
gcccttcata atatccccca gtttagtagt tggacttagg gaacaaagga acctttaata      7620
gaaattggac agcaagaaag cgagcttagt gatacttgtg atcctctaga tcacgacacc      7680
tgaaatggaa gaaaaaaact gcaccttcat cttgtccttt ccctcagaaa gaggctggga      7740
ggcagaggct gaggcagcgg tggccgggac ggttaggaga aaaggagtct ctgctggttt      7800
tattctgcag ctacctcccc aggaagtgga ggactgtggg gcctttgaga agcacctgcc      7860
gacagggcca agaaattcgc actccccctt tcggttcaca ggcaggaagc cctggaggtt      7920
tgagggtttg gggtgtgtgt atgtatctgt ctgtctgaat tttgcttttt ctctcatttg      7980
accattgttt taatgctcct ttttttaaaa aaaataattc ttatctaatt cctatcttga      8040
ttggtaaagt ccatctctag gcaaatacaa gttctcgatg gaaaacaata gtaatgtaa      8100 aatacagcat agcaaaactt taacctccaa atcaagcctc tacttgaatc cttttctgag      8160
ggatgaataa ggcataggca tcaggggctg ttgccaatgt gcattagctg tttgcagcct      8220
caccttcttt catggagttt aagatatagt gtattttccc aaggtttgaa ctagctcttc      8280
atttctttat gttttaaatg cactgacctc ccacattccc tttttagtaa atattcaga      8340 aataatttaa atacatcatt gcaatgaaaa taaatgtttt ttattaggca gaatccagat      8400
gctcaaggcc cttcataata tcccccagtt tagtagttgg acttagggaa caaaggaacc      8460
tttaatagaa attggacagc aagaaagcga gcttagtgat acttgtaaaa agagacgcgt      8520
ctctaaaagt cctttccatg gctgctcgcc tgtgttgcca cctggattct gcgcgggacg      8580
tccttctgct acgtcccttc ggccctcaat ccagcggacc ttccttcccg cggcctgctg      8640
ccggctctgc ggcctcttcc gcgtcttcgc cttcgccctc agacgagtcg gatctccctt      8700
tgggccgcct ccccgcctgg aattcgagct cggtacctt aagaccaatg acttacaagg      8760
cagctgtaga tcttagccac ttttaaaag aaaggggg actggaaggg ctaattcact      8820
cccaacgaag acaagatctg cttttgctt gtactgggtc tctctggtta gaccagatct      8880
gagcctggga gctctctggc taactagggg acccactgct taagcctcaa taaagcttgc      8940
cttgagtgct tcaagtagtg tgtgcccgtc tgttgtgtga ctctggtaac tagagatccc      9000
tcagaccctt ttagtcagtg tggaaaatct ctagcagtag tagttcatgt catcttatta      9060
ttcagtattt ataacttgca aagaaatgaa tatcagagag tgagaggaac ttgtttattg      9120
cagcttataa tggttacaaa taaagcaata gcatcacaaa tttcacaaat aaagcatttt      9180
tttcactgca ttctagttgt ggtttgtcca aactcatcaa tgtatcttat catgtctggc      9240
tctagctatc ccgcccctaa ctccgcccat cccgccccta actccgccca gttccgccca      9300
ttctccgccc catggctgac taatttttt tatttatgca gaggccgagg ccgcctcggc      9360
```

```
ctctgagcta ttccagaagt agtgaggagg ctttttttgga ggcctaggga cgtatggcca   9420
caacctgggc tccccgggcg cgtactccac ctcacccatc atccacgctg ttttatgagt   9480
aaaggagaag aacttttcac tggagttgtc ccaattcttg ttgaattaga tggtgatgtt   9540
aatgggcaca aattttctgt cagtggagag ggtgaaggtg atgcaacata cggaaaactt   9600
acccttaaat ttatttgcac tactggaaaa ctacctgttc catggccaac acttgtcact   9660
actttctctt atggtgttca atgctttca agatacccag atcatatgaa acggcatgac   9720
ttttcaaga gtgccatgcc cgaaggttat gtacaggaaa gaactatatt tttcaaagat   9780
gacgggaact acaagacacg tgctgaagtc aagtttgaag gtgatacccc tgttaataga   9840
atcgagttaa aagtattga ttttaaagaa gatggaaaca ttcttggaca caaattggaa   9900
tacaactata actcacacaa tgtatacatc atggcagaca acaaaagaa tggaatcaaa   9960
gttaacttca aaattagaca caacattgaa gatggaagcg ttcaactagc agaccattat  10020
caacaaaata ctccaattgg cgatggccct gtccttttac cagacaacca ttacctgtcc  10080
acacaatctg ccctttcgaa agatcccaac gaaaagagag accacatggt ccttcttgag  10140
tttgtaacag ctgctgggat tacacatggc atggatgaac tatacaaata ggacctccat  10200
agaagacacc gggaccgatc caataacttc gtatagcata cattatacga agttatgcct  10260
ccggactcta gcgtttaaac ttaagcttgg gaagttccta ttccgaagtt cctattctct  10320
agaaagtata ggaacttcta ccgagctcgg atccactagt ccagtgtggt ggaattctgc  10380
agatatccag cacagtggcg gccgctcgag tctagagggc ccgtttaaac ccgctgatca  10440
gcctcgactg tgccttctag ttgccagcca tctgttgttt gcccctcccc cgtgccttcc  10500
ttgaccctgg aaggtgccac tcccactgtc ctttcctaat aaaatgagga aattgcatcg  10560
cattgtctga gtaggtgtca ttctattctg ggggtgggg tggggcagga cagcaagggg  10620
gaggattggg aagacaatag caggcatgct ggggatgcgg tgggctctat ggcttctgag  10680
gcggaaagtt aaccctagaa agataatcat attgtgacgt acgttaaaga taatcatgcg  10740
taaaattgac gcatgtgttt tatcggtctg tatatcgagg tttatttatt aatttgaata  10800
gatattaagt tttattatat ttacacttac atactaataa taaattcaac aaacaattta  10860
tttatgttta tttatttatt aaaaaaaaac aaaaactcaa aatttcttct ataaagtaac  10920
aaaaccagc tggggctcga agttcctata ctttctagag aataggaact tctatagtga  10980
gtcgaataag ggcgacacaa aatttattct aaatgcataa taaatactga taacatctta  11040
tagtttgtat tatattttgt attatcgttg acatgtataa ttttgatatc aaaaactgat  11100
tttcccttta ttattttcga gatttatttt cttaattctc tttaacaaac tagaaatatt  11160
gtatatacaa aaaatcataa ataatagatg aatagtttaa ttataggtgt tcatcaatcg  11220
aaaaagcaac gtatcttatt taaagtgcgt tgcttttttc tcatttataa ggttaaataa  11280
ttctcatata tcaagcaaag tgacaggcgc ccttaaatat tctgacaaat gctctttccc  11340
taaactcccc ccataaaaaa acccgccgaa gcgggttttt acgttatttg cggattaacg  11400
attactcgtt atcagaaccg cccagggggc ccgagcttaa gactggccgt cgttttacaa  11460
cacagaaaga gtttgtagaa acgcaaaaag gccatccgtc aggggccttc tgcttagttt  11520
gatgcctggc agttccctac tctcgccttc cgcttcctcg ctcactgact cgctgcgctc  11580
ggtcgttcgg ctgcggcgag cggtatcagc tcactcaaag gcggtaatac ggttatccac  11640
agaatcaggg gataacgcag gaaagaacat gtgagcaaaa ggccagcaaa aggccaggaa  11700
```

```
ccgtaaaaag gccgcgttgc tgcgtttttt ccataggctc cgccccctg  acgagcatca    11760 caaaaatcga cgctcaagtc agaggtggcg aaacccgaca ggactataaa gataccaggc    11820
gtttccccct ggaagctccc tcgtgcgctc tcctgttccg accctgccgc ttaccggata    11880
cctgtccgcc tttctccctt cgggaagcgt ggcgctttct catagctcac gctgtaggta    11940
tctcagttcg gtgtaggtcg ttcgctccaa gctgggctgt gtgcacgaac cccccgttca    12000
gcccgaccgc tgcgccttat ccggtaacta tcgtcttgag tccaacccgg taagacacga    12060
cttatcgcca ctggcagcag ccactggtaa caggattagc agagcgaggt atgtaggcgg    12120
tgctacagag ttcttgaagt ggtgggctaa ctacggctac actagaagaa cagtatttgg    12180
tatctgcgct ctgctgaagc cagttacctt cggaaaaaga gttggtagct cttgatccgg    12240
caaacaaacc accgctggta gcggtggttt ttttgtttgc aagcagcaga ttacgcgcag    12300
aaaaaaagga tctcaagaag atcctttgat cttttctacg gggtctgacg ctcagtggaa    12360
cgacgcgcgc gtaactcacg ttaagggatt ttggtcatga gcttgcgccg tcccgtcaag    12420
tcagcgtaat gctctgcttt tagaaaaact catcgagcat caaatgaaac tgcaatttat    12480
tcatatcagg attatcaata ccatattttt gaaaaagccg tttctgtaat gaaggagaaa    12540
actcaccgag gcagttccat aggatggcaa gatcctggta tcggtctgcg attccgactc    12600
gtccaacatc aatacaacct attaatttcc cctcgtcaaa ataaggttat caagtgaga    12660 aatcaccatg agtgacgact gaatccggtg agaatggcaa aagtttatgc atttctttcc    12720
agacttgttc aacaggccag ccattacgct cgtcatcaaa atcactcgca tcaaccaaac    12780
cgttattcat tcgtgattgc gcctgagcga ggcgaaatac gcgatcgctg ttaaaaggac    12840
aattacaaac aggaatcgag tgcaaccggc gcaggaacac tgccagcgca tcaacaatat    12900
tttcacctga tcaggatat  tcttctaata cctggaacgc tgttttccg gggatcgcag    12960 tggtgagtaa ccatgcatca tcaggagtac ggataaaatg cttgatggtc ggaagtggca    13020
taaattccgt cagccagttt agtctgacca tctcatctgt aacatcattg gcaacgctac    13080
ctttgccatg tttcagaaac aactctggcg catcgggctt cccatacaag cgatagattg    13140
tcgcacctga ttgcccgaca ttatcgcgag cccatttata cccatataaa tcagcatcca    13200
tgttggaatt taatcgcggc ctcgacgttt cccgttgaat atggctcata ttcttccttt    13260
ttcaatatta ttgaagcatt tatcagggtt attgtctcat gagcggatac atatttgaat    13320
gtatttagaa aaataaacaa ataggggtca gtgttacaac caattaacca attctgaaca    13380
ttatcgcgag cccatttata cctgaatatg gctcataaca ccccttgttt gcctggcggc    13440
agtagcgcgg tggtcccacc tgaccccatg ccgaactcag aagtgaaacg ccgtagcgcc    13500
gatggtagtg tggggactcc ccatgcgaga gtagggaact gccaggcatc aaataaaacg    13560
aaaggctcag tcgaaagact gggcctttcg cccgggctaa ttaggggggtg tcgcccttat    13620 tcgactctat agtgaagttc ctattctcta gaaagtatag gaacttctga agt           13673
```

<210> SEQ ID NO 84
<211> LENGTH: 15025
<212> TYPE: DNA
<213> ORGANISM: Artificial sequence
<220> FEATURE:
<223> OTHER INFORMATION: synthetic Dox-rapamycin inducible GAG POL ENV

<400> SEQUENCE: 84

```
gatatctata acaagaaaat atatatataa taagttatca cgtaagtaga acatgaaata     60
acaatataat tatcgtatga gttaaatctt aaaagtcacg taaaagataa tcatgcgtca    120
```

```
ttttgactca cgcggtcgtt atagttcaaa atcagtgaca cttaccgcat tgacaagcac    180
gcctcacggg agctccaagc ggcgactgag atgtcctaaa tgcacagcga cggattcgcg    240
ctatttagaa agagagagca atatttcaag aatgcatgcg tcaattttac gcagactatc    300
tttctagggt taagacggat cgggagatct cccgatcccc tatggtgcac tctcagtaca    360
atctgctctg atgccgcata gttaagccag tatctgctcc ctgcttgtgt gttggaggtc    420
gctgagtagt gcgcgagcaa aatttaagct acaacaaggc aaggcttgac cgacaattgc    480
atgaagaatc tgcttagggt taggcgtttt gaagttccta tactttctag agaataggaa    540
cttcggaata ggaacttcgg atgcaatttc ctcatttat taggaaagga cagtgggagt     600
ggcaccttcc agggtcaagg aaggcacggg ggaggggcaa acaacagatg gctggcaact    660
agaaggcaca gcgttagtga tacttgtggg ccagggcatt agccacacca gccaccactt    720
tctgataggc agcctgcact ggtggggtga attccgcgga agcttgtgta attgttaatt    780
tctctgtccc actccatcca ggtcgtgtga ttccaaatct gttccagaga tttattactc    840
caactagcat tccaaggcac agcagtggtg caaatgagtt ttccagagca ccccaaatc    900 cccaggagct gttgatcctt taggtatctt tccacagcca ggattcttgc ctggagctgc    960
ttgatgcccc agactgtgag ttgcaacaga tgctgttgcg cctcaatagc cctcagcaaa   1020
ttgttctgct gctgcactat accagacaat aattgtctgg cctgtaccgt cagcgtcatt   1080
gacgctgcgc ccatagtgct tcctgctgct cccaagaacc caaggaacaa agctcctgcg   1140
gccgctccgg aattccatgt gttaatcctc atcctgtcta cttgccacac aatcatcacc   1200
tgccatctgt tttccataat ccctgatgat ctttgctttt cttcttggca ctactttat   1260 gtcactatta tcttgtatta ctactgcccc ttcaccttc cagaggagct ttgctggtcc    1320
tttccaaact ggatctctgc tgtccctgta ataaacccga aaattttgaa tttttgtaat   1380
ttgtttttgt aattctttag tttgtatgtc tgttgctatt atgtctacta ttctttcccc    1440
tgcactgtac cccccaatcc cccttttct tttaaaattg tggatgaata ctgccatttg    1500
tactgctgtc ttaagatgtt cagcctgatc tcttacctgt cctataattt tctttaattc   1560
tttattcata gattctatta ctccttgact ttggggattg tagggaatgc caaattcctg    1620
cttgatcccc gcccaccaac aggcggcctt aactgtagta ctggtgaaat tgctgccatt   1680
gtctgtatgt actgtttta ctggccatct tcctgctaat tttaagagga agtatgctgt    1740
ttcttgccct gtctctgctg gaattacttc tgcttctata tatccactgg ctacatgaac    1800
tgctaccaag ataactttc cttctaaatg tgtacaatct agctgccata ttcctgggct    1860
acagtctact tgtccatgca tggcttcccc ttttagctga catttatcac agctggctac   1920
tatttctttt gctactacag gtggtaggtt aaaatcacta gccattgctc tccaattact   1980
gtgatatttc tcatgttctt cttgggcctt atctattcca tctaaaaata gtactttcct   2040
gattccagca ctgaccaatt tatctacttg ttcatttcct ccaattcctt tgtgtgctgg   2100
tacccatgcc aggtagactt tttccttttt tattaactgc tctattattt gactgactaa   2160
ctctgattca ctcttatctg gttgtgcttg aatgattccc aatgcatatt gtgagtctgt   2220
cactatgttt acttctaatc ccgaatcctg caaagctaga tgaattgctt gtaactcagt    2280
cttctgattt gttgtgtccg ttaggggac aacttttgt cttcctctgt cagttacata    2340
tcctgctttt cctaatttag tttccctatt ggctgcccca tctacataga aagtttctgc   2400
tcctattatg ggttctttct ctaactggta ccataacttc actaagggag gggtattgac   2460
```

```
aaactcccac tcaggaatcc aggtggcttg ccaatactct gtccaccatg cttcccatgt    2520
ttccttttgt atgggtaatt taaatttagg agtctttccc catattacta tgctttctgt    2580
ggctattttt tgtactgcct ctgttaattg tttcacatca ttagtgtggg cacccttcat    2640
tcttgcatac tttcctgttt tcagattttt aaatggctct tgataaattt gatatgtcca    2700
ttggccttgc ccctgcttct gtatttctgc tattaagtct tttgatgggt cataatacac    2760
tccatgtacc ggttctttta gaatctccct gttttctgcc agttctagct ctgcttcttc    2820
tgttagtggt actacttctg ttagtgcttt ggttccccta agaagtttac ataattgcct    2880
tactttaatc cctgcataaa tctgacttgc ccaattcaat tttcccacta atttctgtat    2940
gtcattgaca gtccagctgt cctttctggg cagcactata ggctgtactg tccatttatc    3000 aggatgagt tcataaccca tccaaaggaa tggaggttct ttctgatgtt ttttgtctgg    3060
tgtggtaaat ccccacctca acagatgttg tctcagttcc tctattttg ttctatgctg     3120 ccctatttct aagtcagatc ctacatacaa atcatccatg tattgataga tgactatgtc    3180
tggattttgt tttctaaaag gctctaagat ttttgtcatg ctacactgga atattgctgg    3240
tgatcctttc catccctgtg aagcacatt gtactgatat ctaatccctg gtgtctcatt     3300
gtttatacta ggtatggtaa atgcagtata cttcctgaag tctttatcta agggaactga    3360
aaaatatgca tcgcccacat ccagtactgt tactgatttt ttctgtttta accctgcagg    3420
atgtggtatt cctaattgaa cttcccagaa atcttgagtt ctcttattaa gttctctgaa    3480
atctactaat tttctccatt tagtactgtc ttttttcttt atggcaaata ctggagtatt    3540
gtatggattt tcaggcccaa tttttgaaat ttttccttcc ttttccattt ctgtacaaat    3600
ttctactaat gcttttattt tttcttctgt caatggccat tgtttaactt ttgggccatc    3660
cattcctggc tttaatttta ctggtacagt ctcaatagga ctaatgggaa aatttaaagt    3720
gcagccaatc tgagtcaaca gatttcttcc aattatgttg acaggtgtag gtcctactaa    3780
tactgtacct atagctttat gtccgcagat ttctatgagt atctgatcat actgtcttac    3840
tttgataaaa cctccaattc ccctatcat ttttggtttc catcttcctg gcaaattcat     3900
ttcttctaat actgtatcat ctgctcctgt atctaataga gcttccttta attgcccccc    3960
tatctttatt gtgacgaggg gtcgctgcca aagagtgatc tgagggaagc taaaggatac    4020
agttccttgt ctatcggctc ctgcttctga gagggagttg ttgtctcttc cccaaacctg    4080
aagctctctt ctggtggggc tgttggctct ggtctgctct gaagaaaatt ccctggcctt    4140
cccttgtggg aaggccagat cttccctaaa aaattagcct gtctctcagt acaatctttc    4200
atttggtgtc cttcctttcc acatttccaa cagccctttt tcctaggggc cctgcaattt    4260
ttggctatgt gcccttcttt gccacaattg aaacacttaa cagtctttct ttggttccta    4320
aaattgcctt tctgtatcat tatggtagct ggatttgtta cttggctcat tgcttcagcc    4380
aaaactcttg cttatggcc gggtccccc actccctgac atgctgtcat catttcttct     4440
agtgtcgctc ctggtcccaa tgcttttaaa atagtcttac aatctgggtt cgcattttgg    4500
accaacaagg tttctgtcat ccaatttttt acctcttgtg aagcttgctc ggctcttaga    4560
gttttataga atcggtctac atagtctcta aagggttcct ttggtccttg tcttatgtcc    4620
agaatgctgg tagggctata cattcttact attttattta atcccaggat tatccatctt    4680
ttatagattt ctcctactgg gataggtgga ttatgtgtca tccatcctat ttgttcctga    4740
agggtactag tagttcctgc tatgtcactt cccttggtt ctctcatctg gcctggtgca     4800
ataggccctg catgcactgg atgcactcta tcccattctg cagcttcctc attgatggtc    4860
```

```
tcttttaaca tttgcatggc tgcttgatgt ccccccactg tgtttagcat ggtgtttaaa    4920
tcttgtgggg tggctccttc tgataatgct gaaaacatgg gtatcacttc tgggctgaaa    4980
gccttctctt ctactacttt tacccatgca tttaaagttc taggtgatat ggcctgatgt    5040
accatttgcc cctggatgtt ctgcactata gggtaatttt ggctgacctg attgctgtgt    5100
cctgtgtcag ctgctgcttg ctgtgctttt ttcttacttt tgttttgctc ttcctctatc    5160
ttgtctaaag cttccttggt gtcttttatc tctatccttt gatgcacaca atagagggtt    5220
gctactgtat tatataatga tctaagttct tctgatcctg tctgaaggga tggttgtagc    5280
tgtcccagta tttgtctaca gccttctgat gtttctaaca ggccaggatt aactgcgaat    5340
cgttctagct ccctgcttgc ccatactata tgttttaatt tatatttttt ctttcccct    5400 ggccttaacc gaattttttc ccatcgatct aattctcccc cgcttaatac tgacgctctc    5460
gcacccatgg cggcggcaga tctcgaattc agatctcacg tgctttgcca aagtgatggg    5520
ccagcacaca gaccagcacg ttgcccagga gctgtgggag gaagataaga ggtatgaaca    5580
tgattagcaa aagggcctag cttggactca gaataatcca gccttatccc aaccataaaa    5640
taaaagcaga atggtagctg gattgtagct gctattagca atatgaaacc tcttacatca    5700
gttacaattt atatgcagaa atatttatat gcagaaatat tgctattgcc ttaacccaga    5760
aattatcact gttattcttt agaatggtgc aaagaggcat gatacattgt atcattattg    5820
ccctgaaaga aagagattag ggaaagtatt agaaataaga taaacaaaaa agtatattaa    5880
aagaagaaag catttttaa aattacaaat gcaaaattac cctgatttgg tcaatatgtg    5940
taccctgtta cttctcccct tcctatgaca tgaacttaac catagaaaag aaggggaaag    6000
aaaacatcaa gggtcccata gactcaccct gaagttctca ggatccgagc tcggtaccac    6060
atgtaagctt cgaggggagg ctggatcggt cccggtgtct tctatggagg tcaaaacagc    6120
gtggatggcg tctccaggcg atctgacggt tcactaaacg ctgcttcgcg atgtacgggc    6180
cagatatacg cgttgcgatc tgacggttca ctaaacgagc tctgcttata taggcctccc    6240
accgtacacg ccacctcgac atactcgagt ttactcccta tcagtgatag agaacgtatg    6300
aagagtttac tccctatcag tgatagagaa cgtatgcaga ctttactccc tatcagtgat    6360
agagaacgta taaggagttt actccctatc agtgatagag aacgtatgac cagtttactc    6420
cctatcagtg atagagaacg tatctacagt ttactcccta tcagtgatag agaacgtata    6480
tccagtttac tccctatcag tgatagagaa cgtataagct ttaggcgtgt acggtgggcg    6540
cctataaaag cagagctcgt ttagtgaacc gtcagatcgc ctggagcaat tccacaacac    6600
ttttgtctta taccaacttt ccgtaccact tcctaccctc gtaaatcgtc gacgagctcg    6660
tttagtgaac cgtcagatcg cctggagacg ccctcgaagc cgcggtgcgg gtgccagggc    6720
gtgcccttgg gctccatgtc catcatgggt ctcaaggtga acgtctctgc catattcatg    6780
gcagtactgt taactctcca acacccacc ggtcaaatcc attggggcaa tctctctaag    6840
ataggggtgg taggaatagg aagtgcaagc tacaaagtta tgactcgttc cagccatcaa    6900
tcattagtca taaaattaat gcccaatata actctcctca ataactgcac gagggtagag    6960
attgcagaat acaggagact actgagaaca gttttggaac caattagaga tgcacttaat    7020
gcaatgaccc agaatataag accggttcag agtgtagctt caagtaggag acacaagaga    7080
tttgcgggag tagtcctggc aggtgcggcc ctaggcgttg ccacagctgc tcagataaca    7140
gccggcattg cacttcacca gtccatgctg aactctcaag ccatcgacaa tctgagagcg    7200
```

| | |
|---|---|
| agcctggaaa ctactaatca ggcaattgag gcaatcagac aagcagggca ggagatgata | 7260 |
| ttggctgttc agggtgtcca agactacatc aataatgagc tgataccgtc tatgaaccaa | 7320 |
| ctatcttgtg atttaatcgg ccagaagctc gggctcaaat tgctcagata ctatacagaa | 7380 |
| atcctgtcat tatttggccc cagcttacgg gacccatat ctgcggagat atctatccag | 7440 |
| gctttgagct atgcgcttgg aggagacatc aataaggtgt tagaaaagct cggatacagt | 7500 |
| ggaggtgatt tactgggcat cttagagagc agaggaataa aggcccggat aactcacgtc | 7560 |
| gacacagagt cctacttcat tgtcctcagt atagcctatc cgacgctgtc cgagattaag | 7620 |
| ggggtgattg tccaccggct agaggggtc tcgtacaaca taggctctca agagtggtat | 7680 |
| accactgtgc ccaagtatgt tgcaacccaa gggtacctta tctcgaattt tgatgagtca | 7740 |
| tcgtgtactt tcatgccaga ggggactgtg tgcagccaaa atgccttgta cccgatgagt | 7800 |
| cctctgctcc aagaatgcct ccgggggtcc accaagtcct gtgctcgtac actcgtatcc | 7860 |
| gggtcttttg gaaccggtt cattttatca caagggaacc taatagccaa ttgtgcatca | 7920 |
| atcctttgca agtgttacac aacaggaacg atcattaatc aagaccctga caagatccta | 7980 |
| acatacattg ctgccgatca ctgcccggta gtcgaggtga acggcgtgac catccaagtc | 8040 |
| gggagcagga ggtatccaga cgctgtgtac ttgcacagaa ttgacctcgg tcctcccata | 8100 |
| tcattggaga ggttggacgt agggacaaat ctggggaatg caattgctaa gttggaggat | 8160 |
| gccaaggaat tgttggagtc atcggaccag atattgagga gtatgaaagg tttatcgagc | 8220 |
| actagcatag tctacatcct gattgcagtg tgtcttggag ggttgatagg gatccccgct | 8280 |
| ttaatatgtt gctgcagggg gcgttgaccc ctctccctcc ccccccccta acgttactgg | 8340 |
| ccgaagccgc ttggaataag gccggtgtgc gtttgtctat atgttatttt ccaccatatt | 8400 |
| gccgtctttt ggcaatgtga gggcccggaa acctggccct gtcttcttga cgagcattcc | 8460 |
| tagggtctt tccctctcg ccaaaggaat gcaaggtctg ttgaatgtcg tgaaggaagc | 8520 |
| agttcctctg gaagcttctt gaagacaaac aacgtctgta cgacccttt gcaggcagcg | 8580 |
| gaacccccca cctggcgaca ggtgcctctg cggccaaaag ccacgtgtat aagatacacc | 8640 |
| tgcaaaggcg gcacaacccc agtgccacgt tgtgagttgg atagttgtgg aaagagtcaa | 8700 |
| atggctctcc tcaagcgtat tcaacaaggg gctgaaggat gcccagaagg taccccattg | 8760 |
| tatgggatct gatctggggc ctcggtacac atgctttaca tgtgtttagt cgaggttaaa | 8820 |
| aaaacgtcta ggccccccga accacgggga cgtggttttc ctttgaaaaa cacgatgata | 8880 |
| atatggccac aaccatggga agtaggatag tcattaacag agaacatctt atgattgata | 8940 |
| gaccttatgt tttgctggct gttctgtttg tcatgtttct gagcttgatc gggttgctag | 9000 |
| ccattgcagg cattagactt catcgggcag ccatctacac cgcagagatc cataaaagcc | 9060 |
| tcagcaccaa tctagatgta actaactcaa tcgagcatca ggtcaaggac gtgctgacac | 9120 |
| cactcttcaa aatcatcggt gatgaagtgg gcctgaggac acctcagaga ttcactgacc | 9180 |
| tagtgaaatt catctctgac aagattaaat tccttaatcc ggatagggag tacgacttca | 9240 |
| gagatctcac ttggtgtatc aacccgccag agagaatcaa attggattat gatcaatact | 9300 |
| gtgcagatgt ggctgctgaa gagctcatga atgcattggt gaactcaact ctactggaga | 9360 |
| ccagaacaac caatcagttc ctagctgtct caaagggaaa ctgctcaggg cccactacaa | 9420 |
| tcagaggtca attctcaaac atgtcgctgt ccctgttaga cttgtattta ggtcgaggtt | 9480 |
| acaatgtgtc atctatagtc actatgacat cccaggaat gtatggggga acttacctag | 9540 |
| tggaaaagcc taatctgagc agcaaaaggt cagagttgtc acaactgagc atgtaccgag | 9600 |

```
tgtttgaagt aggtgttatc agaaatccgg gtttggggc tccggtgttc catatgacaa    9660
actatcttga gcaaccagtc agtaatgatc tcagcaactg tatggtggct ttggggagc    9720
tcaaactcgc agcccttgt cacggggaag attctatcac aattccctat cagggatcag    9780
ggaaaggtgt cagcttccag ctcgtcaagc taggtgtctg gaaatcccca accgacatgc    9840
aatcctgggt cccttatca acggatgatc cagtgataga caggctttac ctctcatctc    9900
acagaggtgt tatcgctgac aaycaagcaa aatgggctgt cccgacaaca cgaacagatg    9960
acaagttgcg aatggagaca tgcttccaac aggcgtgtaa gggtaaaatc caagcactct   10020
gcgagaatcc cgagtgggca ccattgaagg ataacaggat tccttcatac ggggtcttgt   10080
ctgttgatct gagtctgaca gttgagctta aaatcaaaat tgcttcggga ttcgggccat   10140
tgatcacaca cggttcaggg atggacctat acaaatccaa ccacaacaat gtgtattggc   10200
tgactatccc rccaatgaag aacctagcct taggtgtaat caacacattg gagtggatac   10260
cgagattcaa ggttagtccc tacctcttca mtgtcccaat taaggaagca ggcgaagact   10320
gccatgcccc aacataccta cctgcggagg tggatggtga tgtcaaactc agttccaatc   10380
tggtgattct acctggtcaa gatctccaat atgttttggc aacctacgat acttccaggg   10440
ttgaacatgc tgtggtttat tacgtttaca gcccaagccg ctcatttct tactttatc    10500
cttttaggtt gcctataaag gggtcccca tcgaattaca agtggaatgc ttcacatggg    10560
accaaaaact ctggtgccgt cacttctgtg tgcttgcgga ctcagaatct ggtggacata   10620
tcactcactc tgggatggtg ggcatgggag tcagctgcac agtcacccgg gaagatggaa   10680
ccaatcgcag atagggctgc tagtgaacya atcwcatgat gtcacccaga catcaggcat   10740
acccactagt gtgaaataga catcagaatt aagaaaaatg ggctccccgg gcgcgtactc   10800
cacctcaccc atcatccacg ctcggcaata aaaagacaga ataaaacgca cgggtgttgg   10860
gtcgtttgtt cgccgggcgc gtactccacc tcacccatca tccacgctgt tttatggata   10920
gcactgagaa cgtcatcaag cccttcatgc gcttcaaggt gcacatggag ggctccgtga   10980
acggccacga gttcgagatc gagggcgagg gcgagggcaa gccctacgag ggcacccaga   11040
ccgccaagct gcaggtgacc aagggcggcc ccctgccctt cgcctgggac atcctgtccc   11100
cccagttcca gtacggctcc aaggtgtacg tgaagcaccc cgccgacatc cccgactaca   11160
agaagctgtc cttccccgag ggcttcaagt gggagcgcgt gatgaacttc gaggacggcg   11220
gcgtggtgac cgtgacccag gactcctccc tgcaggacgg caccttcatc taccacgtga   11280
agttcatcgg cgtgaacttc ccctccgacg gccccgtaat gcagaagaag actctgggct   11340
gggagccctc caccgagcgc ctgtacccc gcgacggcgt gctgaagggc gagatccaca   11400
aggcgctgaa gctgaaggc gcggccact acctggtgga gttcaagtca atctacatgg   11460
ccaagaagcc cgtgaagctg cccggctact actacgtgga ctccaagctg gacatcacct   11520
cccacaacga ggactacacc gtggtggagc agtacgagcg cgccgaggcc gccaccacc    11580
tgttccagta ggacctccat agaagacacc gggaccgatc caataacttc gtatagcata   11640
cattatacga agttatgcct ccggactcta gcgtttaaac ttaagcttgg taccgagctc   11700
ggatccacta gtccagtgtg gtggaattct gcagatatcc agcacagtgg cggccgctcg   11760
agtctagagg gcccgtttaa acccgctgat cagcctcgac tgtgccttct agttgccagc   11820
catctgttgt ttgcccctcc cccgtgcctt ccttgaccct ggaaggtgcc actcccactg   11880
tcctttccta ataaaatgag gaaattgcat cgcattgtct gagtaggtgt cattctattc   11940
```

```
tgggggtgg ggtggggcag gacagcaagg gggaggattg ggaagacaat agcaggcatg    12000
ctggggatgc ggtgggctct atggcttctg aggcggaaag ttaaccctag aaagataatc    12060
atattgtgac gtacgttaaa gataatcatg cgtaaaattg acgcatgtgt tttatcggtc    12120
tgtatatcga ggtttattta ttaatttgaa tagatattaa gttttattat atttacactt    12180
acatactaat aataaattca acaaacaatt tatttatgtt tatttattta ttaaaaaaaa    12240
acaaaaactc aaaatttctt ctataaagta acaaaaacca gctggggctc gaagttccta    12300
tactttctag agaataggaa cttctatagt gagtcgaata agggcgacac aaaatttatt    12360
ctaaatgcat aataaatact gataacatct tatagtttgt attatatttt gtattatcgt    12420
tgacatgtat aattttgata tcaaaaactg attttcccct tattattttc gagatttatt    12480
ttcttaattc tctttaacaa actagaaata ttgtatatac aaaaaatcat aaataataga    12540
tgaatagttt aattataggt gttcatcaat cgaaaaagca acgtatctta tttaaagtgc    12600
gttgcttttt tctcatttat aaggttaaat aattctcata tatcaagcaa agtgacaggc    12660
gcccttaaat attctgacaa atgctctttc cctaaactcc ccccataaaa aaacccgccg    12720
aagcgggttt ttacgttatt tgcggattaa cgattactcg ttatcagaac cgcccagggg    12780
gcccgagctt aagactggcc gtcgttttac aacacagaaa gagtttgtag aaacgcaaaa    12840
aggccatccg tcaggggcct tctgcttagt ttgatgcctg gcagttccct actctcgcct    12900
tccgcttcct cgctcactga ctcgctgcgc tcggtcgttc ggctgcggcg agcggtatca    12960
gctcactcaa aggcggtaat acggttatcc acagaatcag gggataacgc aggaaagaac    13020
atgtgagcaa aaggccagca aaaggccagg aaccgtaaaa aggccgcgtt gctggcgttt    13080
ttccataggc tccgcccccc tgacgagcat cacaaaaatc gacgctcaag tcagaggtgg    13140
cgaaacccga caggactata aagataccag gcgtttcccc ctggaagctc cctcgtgcgc    13200
tctcctgttc cgaccctgcc gcttaccgga tacctgtccg cctttctccc ttcgggaagc    13260
gtggcgcttt ctcatagctc acgctgtagg tatctcagtt cggtgtaggt cgttcgctcc    13320
aagctgggct gtgtgcacga accccccgtt cagcccgacc gctgcgcctt atccggtaac    13380
tatcgtcttg agtccaaccc ggtaagacac gacttatcgc cactggcagc agccactggt    13440
aacaggatta gcagagcgag gtatgtaggc ggtgctacag agttcttgaa gtggtgggct    13500
aactacggct acactagaag aacagtattt ggtatctgcg ctctgctgaa gccagttacc    13560
ttcggaaaaa gagttggtag ctcttgatcc ggcaaacaaa ccaccgctgg tagcggtggt    13620
ttttttgttt gcaagcagca gattacgcgc agaaaaaaag gatctcaaga agatcctttg    13680
atcttttcta cggggtctga cgctcagtgg aacgacgcgc gcgtaactca cgttaaggga    13740
ttttggtcat gagcttgcgc cgtcccgtca agtcagcgta atgctctgct tttagaaaaa    13800
ctcatcgagc atcaaatgaa actgcaattt attcatatca ggattatcaa taccatattt    13860
ttgaaaaagc cgtttctgta atgaaggaga aaactcaccg aggcagttcc ataggatggc    13920
aagatcctgg tatcggtctg cgattccgac tcgtccaaca tcaatacaac ctattaattt    13980
cccctcgtca aaaataaggt tatcaagtga gaaatcacca tgagtgacga ctgaatccgg    14040
tgagaatggc aaaagtttat gcatttcttt ccagacttgt tcaacaggcc agccattacg    14100
ctcgtcatca aaatcactcg catcaaccaa accgttattc attcgtgatt gcgcctgagc    14160
gaggcgaaat acgcgatcgc tgttaaaagg acaattacaa acaggaatcg agtgcaaccg    14220
gcgcaggaac actgccagcg catcaacaat attttcacct gaatcaggat attcttctaa    14280
tacctggaac gctgttttc cggggatcgc agtggtgagt aaccatgcat catcaggagt    14340
```

```
acggataaaa tgcttgatgg tcggaagtgg cataaattcc gtcagccagt ttagtctgac   14400
catctcatct gtaacatcat tggcaacgct acctttgcca tgtttcagaa acaactctgg   14460
cgcatcgggc ttcccataca agcgatagat tgtcgcacct gattgcccga cattatcgcg   14520
agcccattta tacccatata aatcagcatc catgttggaa tttaatcgcg gcctcgacgt   14580
ttcccgttga atatggctca tattcttcct ttttcaatat tattgaagca tttatcaggg   14640
ttattgtctc atgagcggat acatatttga atgtatttag aaaaataaac aaataggggt   14700
cagtgttaca accaattaac caattctgaa cattatcgcg agcccattta tacctgaata   14760
tggctcataa caccccttgt ttgcctggcg gcagtagcgc ggtggtccca cctgacccca   14820
tgccgaactc agaagtgaaa cgccgtagcg ccgatggtag tgtggggact ccccatgcga   14880
gagtagggaa ctgccaggca tcaaataaaa cgaaaggctc agtcgaaaga ctgggccttt   14940
cgcccgggct aattagggg tgtcgccctt attcgactct atagtgaagt tcctattctc   15000
tagaaagtat aggaacttct gaagt                                         15025

<210> SEQ ID NO 85
<211> LENGTH: 6584
<212> TYPE: DNA
<213> ORGANISM: Artificial sequence
<220> FEATURE:
<223> OTHER INFORMATION: synthetic Rapamycin-inducible TET activator

<400> SEQUENCE: 85
gatatctata acaagaaaat atatatataa taagttatca cgtaagtaga acatgaaata     60
acaatataat tatcgtatga gttaaatctt aaaagtcacg taaaagataa tcatgcgtca    120
ttttgactca cgcggtcgtt atagttcaaa atcagtgaca cttaccgcat tgacaagcac    180
gcctcacggg agctccaagc ggcgactgag atgtcctaaa tgcacagcga cggattcgcg    240
ctatttagaa agagagagca atatttcaag aatgcatgcg tcaattttac gcagactatc    300
tttctagggt taagacggat cgggagatct cccgatcccc tatggtgcac tctcagtaca    360
atctgctctg atgccgcata gttaagccag tatctgctcc ctgcttgtgt gttggaggtc    420
gctgagtagt gcgcgagcaa aatttaagct acaacaaggc aaggcttgac cgacaattgc    480
atgaagaatc tgcttagggt taggcgtttt gcgctgcttc gcgatgtacg ggccagatat    540
acgcgttctc catagaagac accgaataaa atatctttat tttcattaca tctgtgtgtt    600
ggttttttgt gtgaatcgat agtactaaca tacgctctcc atcaaaacaa aacgaaacaa    660
aacaaactag caaaataggc tgtccccagt gcaagtgcag gtgccagaac atttctctgg    720
accgatccaa taacttcgta tagcatacat tatacgaagt tatgcctccg gactctagcg    780
ttttagttat tactagcgct accggactca gatctcgagc tcaagcttcg aattctgcag    840
tcgacggtac cgcggcttac gcgtgctagc taatgatggg cgctcgagta atgatgggcg    900
gtcgactaat gatgggcgct cgagtaatga tgggcgtcta gctaatgatg gcgctcgag   960 taatgatggg cggtcgacta atgatgggcg ctcgagtaat gatgggcgtc tagctaatga   1020
tgggcgctcg agtaatgatg gcggtcgac taatgatggg cgctcgagta atgatgggcg   1080
tctagaacgc gaattaattc aacatttga caccccata atattttcc agaattaaca   1140 gtataaattg catctcttgt tcaagagttc cctatcactc tctttaatca ctactcacag   1200
taacctcaac tcctgccaca agcttgccct gcagcgggaa ttccaaactt aagcttggta   1260
ccgagctcgg atccactagt ccagtgtggt ggaattctgc agatatccag cacagtggcg   1320
```

```
gccgctcgag tctagagggc ccgtttaaac ccgctgatca atgtctagac tggacaagag    1380
caaagtcata aactctgctc tggaattact caatggagtc ggtatcgaag cctgacgac     1440 aaggaaactc gctcaaaagc tgggagttga gcagcctacc ctgtactggc acgtgaagaa    1500
caagcgggcc ctgctcgatg ccctgccaat cgagatgctg acaggcatc atacccactc     1560 ctgccccctg aaggcgagt catggcaaga ctttctgcgg aacaacgcca agtcataccg     1620
ctgtgctctc ctctcacatc gcgacggggc taaagtgcat ctcggcaccc gcccaacaga    1680
gaaacagtac gaaaccctgg aaaatcagct cgcgttcctg tgtcagcaag cttctccct    1740 ggagaacgca ctgtacgctc tgtccgccgt gggccacttt acactgggct gcgtattgga    1800
ggaacaggag catcaagtag caaaagagga aagagagaca cctaccaccg attctatgcc    1860
cccacttctg aaacaagcaa ttgagctgtt cgaccggcag ggagccgaac ctgccttcct    1920
tttcggcctg gaactaatca tatgtggcct ggagaaacag ctaaagtgcg aaagcggcgg    1980
gccgaccgac gcccttgacg attttgactt agacatgctc ccagccgatg cccttgacga    2040
ctttgacctt gatatgctgc ctgctgacgc tcttgacgat tttgaccttg acatgctccc    2100
cgggtaagtc cctcccccc ccctaacgtt actggccgaa gccgcttgga ataaggccgg     2160
tgtgcgtttg tctatatgtt attttccacc atattgccgt cttttggcaa tgtgagggcc    2220
cggaaacctg gccctgtctt cttgacgagc attcctaggg gtctttcccc tctcgccaaa    2280
ggaatgcaag gtctgttgaa tgtcgtgaag gaagcagttc ctctggaagc ttcttgaaga    2340
caaacaacgt ctgtagcgac cctttgcagg cagcggaacc ccccacctgg cgacaggtgc    2400
ctctgcggcc aaaagccacg tgtataagat acacctgcaa aggcggcaca cccccagtgc    2460
cacgttgtga gttggatagt tgtggaaaga gtcaaatggc tctcctcaag cgtattcaac    2520
aaggggctga aggatgccca gaaggtaccc cattgtatgg gatctgatct ggggcctcgg    2580
tgcacatgct ttacatgtgt ttagtcgagg ttaaaaaacg tctaggcccc ccgaaccacg    2640
gggacgtggt tttcctttga aaaacacgat gataaatgga tagcactgag aacgtcatca    2700
agcccttcat gcgcttcaag gtgcacatgg agggctccgt gaacggccac gagttcgaga    2760
tcgagggcga gggcgagggc aagccctacg agggcaccca gaccgccaag ctgcaggtga    2820
ccaagggcgg cccctgccc ttcgcctggg acatcctgtc cccccagttc cagtacggct     2880
ccaaggtgta cgtgaagcac cccgccgaca tccccgacta caagaagctg tccttccccg    2940
agggcttcaa gtgggagcgc gtgatgaact tcgaggacgg cggcgtggtg accgtgaccc    3000
aggactcctc cctgcaggac ggcaccttca tctaccacgt gaagttcatc ggcgtgaact    3060
tcccctccga cggccccgta atgcagaaga gactctgggg ctgggagccc tccaccgagc    3120
gcctgtaccc ccgcgacggc gtgctgaagg gcgagatcca caaggcgctg aagctgaagg    3180
gcggcggcca ctacctggtg gagttcaagt caatctacat ggccaagaag cccgtgaagc    3240
tgcccggcta ctactacgtg gactccaagc tggacatcac ctcccacaac gaggactaca    3300
ccgtggtgga gcagtacgag cgcgccgagg cccgccacca cctgttccag tagctcgact    3360
gtgccttcta gttgccagcc atctgttgtt tgcccctccc ccgtgccttc cttgaccctg    3420
gaaggtgcca ctcccactgt cctttcctaa taaaatgagg aaattgcatc gcattgtctg    3480
agtaggtgtc attctattct ggggggtggg gtggggcagg acagcaaggg ggaggattgg    3540
gaagacaata gcaggcatgc tggggatgcg gtgggctcta tggcttctga ggcggaaagt    3600
taaccctaga aagataatca tattgtgacg tacgttaaag ataatcatgc gtaaaattga    3660
cgcatgtgtt ttatcggtct gtatatcgag gtttatttat taatttgaat agatattaag    3720
```

```
ttttattata tttacactta catactaata ataaattcaa caaacaattt atttatgttt    3780
atttatttat taaaaaaaaa caaaaactca aatttcttc tataaagtaa caaaaaccag     3840
ctggggctcg aagttcctat actttctaga gaataggaac ttctatagtg agtcgaataa    3900
gggcgacaca aaatttattc taaatgcata ataaatactg ataacatctt atagtttgta    3960
ttatattttg tattatcgtt gacatgtata attttgatat caaaaactga ttttcccttt    4020
attattttcg agatttattt tcttaattct ctttaacaaa ctagaaatat tgtatataca    4080
aaaaatcata ataatagat gaatagttta attataggtg ttcatcaatc gaaaaagcaa     4140
cgtatcttat ttaaagtgcg ttgcttttt ctcatttata aggttaaata attctcatat     4200
atcaagcaaa gtgacaggcg cccttaaata ttctgacaaa tgctctttcc ctaaactccc    4260
cccataaaaa aacccgccga agcgggtttt tacgttattt gcggattaac gattactcgt    4320
tatcagaacc gcccaggggg cccgagctta agactggccg tcgttttaca acacagaaag    4380
agtttgtaga aacgcaaaaa ggccatccgt caggggcctt ctgcttagtt tgatgcctgg    4440
cagttcccta ctctcgcctt ccgcttcctc gctcactgac tcgctgcgct cggtcgttcg    4500
gctgcggcga gcggtatcag ctcactcaaa ggcggtaata cggttatcca cagaatcagg    4560
ggataacgca ggaaagaaca tgtgagcaaa aggccagcaa aaggccagga accgtaaaaa    4620
ggccgcgttg ctggcgtttt tccataggct ccgcccccct gacgagcatc acaaaaatcg    4680
acgctcaagt cagaggtggc gaaacccgac aggactataa agataccagg cgtttccccc    4740
tggaagctcc ctcgtgcgct ctcctgttcc gaccctgccg cttaccggat acctgtccgc    4800
ctttctccct tcgggaagcg tggcgctttc tcatagctca cgctgtaggt atctcagttc    4860
ggtgtaggtc gttcgctcca agctgggctg tgtgcacgaa ccccccgttc agcccgaccg    4920
ctgcgcctta tccggtaact atcgtcttga gtccaacccg gtaagacacg acttatcgcc    4980
actggcagca gccactggta acaggattag cagagcgagg tatgtaggcg gtgctacaga    5040
gttcttgaag tggtgggcta actacggcta cactagaaga acagtatttg gtatctgcgc    5100
tctgctgaag ccagttacct tcggaaaaag agttggtagc tcttgatccg gcaaacaaac    5160
caccgctggt agcggtggtt ttttgtttg caagcagcag attacgcgca gaaaaaaagg     5220
atctcaagaa gatcctttga tcttttctac ggggtctgac gctcagtgga acgacgcgcg    5280
cgtaactcac gttaagggat tttggtcatg agcttgcgcc gtcccgtcaa gtcagcgtaa    5340
tgctctgctt ttagaaaaac tcatcgagca tcaaatgaaa ctgcaattta ttcatatcag    5400
gattatcaat accatatttt tgaaaaagcc gtttctgtaa tgaaggagaa aactcaccga    5460
ggcagttcca taggatggca agatcctggt atcggtctgc gattccgact cgtccaacat    5520
caatacaacc tattaatttc ccctcgtcaa aaataaggtt atcaagtgag aaatcaccat    5580
gagtgacgac tgaatccggt gagaatggca aaagtttatg catttctttc cagacttgtt    5640
caacaggcca gccattacgc tcgtcatcaa atcactcgc atcaaccaaa ccgttattca     5700
ttcgtgattg cgcctgagcg aggcgaaata cgcgatcgct gttaaaagga caattacaaa    5760
caggaatcga gtgcaaccgg cgcaggaaca ctgccagcgc atcaacaata ttttcacctg    5820
aatcaggata ttcttctaat acctggaacg ctgtttttcc ggggatcgca gtggtgagta    5880
accatgcatc atcaggagta cggataaaat gcttgatggt cggaagtggc ataaattccg    5940
tcagccagtt tagtctgacc atctcatctg taacatcatt ggcaacgcta cctttgccat    6000
gtttcagaaa caactctggc gcatcgggct tcccatacaa gcgatagatt gtcgcacctg    6060
```

```
attgcccgac attatcgcga gcccatttat acccatataa atcagcatcc atgttggaat   6120
ttaatcgcgg cctcgacgtt tcccgttgaa tatggctcat attcttcctt tttcaatatt   6180
attgaagcat ttatcagggt tattgtctca tgagcggata catatttgaa tgtatttaga   6240
aaaataaaca aataggggtc agtgttacaa ccaattaacc aattctgaac attatcgcga   6300
gcccatttat acctgaatat ggctcataac accccttgtt tgcctggcgg cagtagcgcg   6360
gtggtcccac ctgaccccat gccgaactca gaagtgaaac gccgtagcgc cgatggtagt   6420
gtggggactc cccatgcgag agtagggaac tgccaggcat caaataaaac gaaaggctca   6480
gtcgaaagac tgggcctttc gcccgggcta attagggggt gtcgccctta ttcgactcta   6540
tagtgaagtt cctattctct agaaagtata ggaacttctg aagt                    6584

<210> SEQ ID NO 86
<211> LENGTH: 11528
<212> TYPE: DNA
<213> ORGANISM: Artificial sequence
<220> FEATURE:
<223> OTHER INFORMATION: synthetic Rapamycin inducer inducible REV
      srcVpx

<400> SEQUENCE: 86
gatatctata acaagaaaat atatatataa taagttatca cgtaagtaga acatgaaata     60
acaatataat tatcgtatga gttaaatctt aaaagtcacg taaaagataa tcatgcgtca    120
ttttgactca cgcggtcgtt atagttcaaa atcagtgaca cttaccgcat tgacaagcac    180
gcctcacggg agctccaagc ggcgactgag atgtcctaaa tgcacagcga cggattcgcg    240
ctatttagaa agagagagca atatttcaag aatgcatgcg tcaattttac gcagactatc    300
tttctagggt taagacggat cgggagatct cccgatcccc tatggtgcac tctcagtaca    360
atctgctctg atgccgcata gttaagccag tatctgctcc ctgcttgtgt gttggaggtc    420
gctgagtagt gcgcgagcaa aatttaagct acaacaaggc aaggcttgac cgacaattgc    480
atgaagaatc tgcttagggt taggcgtttt gcgctgcttc gcgatgtacg ggccagatat    540
acgcgttgac attgattatt gactagttat taatagtaat caattacggg gtcattagtt    600
catagcccat atatggagtt ccgcgttaca taacttacgg taaatggccc gcctggctga    660
ccgcccaacg acccccgccc attgacgtca ataatgacgt atgttcccat agtaacgcca    720
atagggactt tccattgacg tcaatgggtg gagtatttac ggtaaactgc ccacttggca    780
gtacatcaag tgtatcatat gccaagtacg ccccctattg acgtcaatga cggtaaatgg    840
cccgcctggc attatgccca gtacatgacc ttatgggact ttcctacttg gcagtacatc    900
tacgtattag tcatcgctat taccatggtg atgcggtttt ggcagtacat caatgggcgt    960
ggatagcggt ttgactcacg gggatttcca agtctccacc ccattgacgt caatgggagt   1020
ttgttttgga accaaaatca acgggacttt ccaaaatgtc gtaacaactc cgccccattg   1080
acgcaaatgg gcggtaggcg tgtacggtgg gaggtctata taagcagagc tcggcattga   1140
ttattgacta gttattaata gtaatcaatt acggggtcat tagttcatag cccatatatg   1200
gagttccgcg ttacataact tacggtaaat ggcccgcctg gctgaccgcc caacgacccc   1260
cgcccattga cgtcaataat gacgtatgtt cccatagtaa cgccaatagg gactttccat   1320
tgacgtcaat gggtggagta tttacggtaa actgcccact tggcagtaca tcaagtgtat   1380
catatgccaa gtccgccccc tattgacgtc aatgacggta aatggcccgc ctggcattat   1440
gcccagtaca tgaccttacg ggactttcct acttggcagt acatctacgt attagtcatc   1500
```

```
gctattacca tggtgatgcg gttttggcag tacaccaatg ggcgtggata gcggtttgac    1560
tcacggggat ttccaagtct ccaccccatt gacgtcaatg ggagtttgtt ttggcaccaa    1620
aatcaacggg actttccaaa atgtcgtaac aactgcgatc gcccgccccg ttgacgcaaa    1680
tgggcggtag gcgtgtacgg tgggaggtct atataagcag agctcgttta gtgaaccgtc    1740
agatcactag aagctttatt gcggtagttt atcacagtta aattgctaac gcagtcagtg    1800
cttctgacac aacagtctcg aacttaagct gcagtgactc tcttaaggta gccttgcaga    1860
agttggtcgt gaggcactgg gcaggtaagt atcaaggtta caagacaggt ttaaggagac    1920
caatagaaac tgggcttgtc gagacagaga agactcttgc gtttctgata ggcacctatt    1980
ggtcttactg acatccactt tgcctttctc tccacaggtg tccactccca gttcaattac    2040
agctcttaag gctagagtac ttaatacgac tcactatagg ctagcctcga gaattcatgg    2100
cttctagaat cctctggcat gagatgtggc atgaaggcct ggaagaggca tctcgtttgt    2160
actttgggga aaggaacgtg aaaggcatgt ttgaggtgct ggagcccttg catgctatga    2220
tggaacgggg cccccagact ctgaaggaaa catcctttaa tcaggccat ggtcgagatt    2280
taatggaggc caagagtgg tgcaggaagt acatgaaatc agggaatgtc aaggacctcc    2340
tccaagcctg ggacctctat tatcatgtgt tccgacgaat ctcaaagact agagatgagt    2400
ttcccaccat ggtgtttcct tctgggcaga tcagccaggc ctcggccttg gccccggccc    2460
ctccccaagt cctgccccag gctccagccc ctgcccctgc tccagccatg gtatcagctc    2520
tggcccaggc ccagcccct gtcccagtcc tagccccagg ccctcctcag gctgtggccc    2580
cacctgcccc caagcccacc caggctgggg aaggaacgct gtcagaggcc ctgctgcagc    2640
tgcagtttga tgatgaagac ctgggggcct tgcttggcaa cagcacagac ccagctgtgt    2700
tcacagacct ggcatccgtc gacaactccg agtttcagca gctgctgaac cagggcatac    2760
ctgtggcccc ccacacaact gagcccatgc tgatggagta ccctgaggct ataactcgcc    2820
tagtgacagg ggcccagagg ccccccgacc cagctcctgc tccactgggg gccccgggc    2880
tccccaatgg cctcctttca ggagatgaag acttctcctc cattgcggac atggacttct    2940
cagccctgct gagtcagatc agctccacta gttattaaga attcacgcgt cgagcatgca    3000
tctagggcgg ccaattccgc ccctctcccc ccccccctc tcctccccc ccctaacg     3060
ttactggccg aagccgcttg gaataaggcc ggtgtgcgtt tgtctatatg ttatttccca    3120
ccatattgcc gtcttttggc aatgtgaggg cccggaaacc tggccctgtc ttcttgacga    3180
gcattcctag gggtctttcc cctctcgcca aaggaatgca aggtctgttg aatgtcgtga    3240
aggaagcagt tcctctggaa gcttcttgaa gacaaacaac gtctgtagcg accctttgca    3300
ggcagcggaa ccccccacct ggcgacaggt gcctctgcgg ccaaaagcca cgtgtataag    3360
atacacctgc aaaggcggca caaccccagt gccacgttgt gagttggata gttgtggaaa    3420
gagtcaaatg gctctcctca agcgtattca acaaggggct gaaggatgcc cagaaggtac    3480
cccattgtat gggatctgat ctgggcctc ggtgcacatg ctttacatgt gtttagtcga    3540
ggttaaaaaa acgtctaggc ccccgaacc acggggacgt ggttttcctt tgaaaaacac    3600
gatgataagc ttgccacaac ccgggatcct ctagagtcga catggactat cctgctgcca    3660
agagggtcaa gttggactct agagaacgcc catatgcttg ccctgtcgag tcctgcgatc    3720
gccgcttttc tcgctcggat gagcttaccc gccatatccg catccacaca ggccagaagc    3780
ccttccagtg tcgaatctgc atgcgtaact tcagtcgtag tgaccacctt accacccaca    3840
tccgcaccca cacaggcggc ggccgcagga ggaagaaacg caccagcata gagaccaaca    3900
```

```
tccgtgtggc cttagagaag agtttcttgg agaatcaaaa gcctacctcg gaagagatca    3960
ctatgattgc tgatcagctc aatatggaaa aagaggtgat tcgtgtttgg ttctgtaacc    4020
gccgccagaa agaaaaaaga atcaacacta gaggagtgca ggtggaaacc atctccccgg    4080
gagacgggcg caccttcccc aagcgcggcc agacctgcgt ggtgcactac accgggatgc    4140
ttgaagatgg aaagaaattt gattcctccc gggacagaaa caagcccttt aagtttatgc    4200
taggcaagca ggaggtgatc cgaggctggg aagaaggggt tgcccagatg agtgtgggtc    4260
agagagccaa actgactata tctccagatt atgcctatgg tgccactggg cacccaggca    4320
tcatcccacc acatgccact ctcgtcttcg atgtggagct tctaaaactg gaagtcgagg    4380
gcgtgcaggt ggaaaccatc tccccaggag acgggcgcac cttccccaag cgcggccaga    4440
cctgcgtggt gcactacacc gggatgcttg aagatggaaa gaaatttgat tcctcccggg    4500
acagaaacaa gccctttaag tttatgctag gcaagcagga ggtgatccga ggctgggaag    4560
aaggggttgc ccagatgagt gtgggtcaga gagccaaact gactatatct ccagattatg    4620
cctatggtgc cactgggcac ccaggcatca tcccaccaca tgccactctc gtcttcgatg    4680
tggagcttct aaaactggaa actagaggag tgcaggtgga accatctccc caggagacg    4740
ggcgcacctt ccccaagcgc ggccagacct gcgtggtgca ctacaccggg atgcttgaag    4800
atggaaagaa atttgattcc tcccgggaca gaaacaagcc ctttaagttt atgctaggca    4860
agcaggaggt gatccgaggc tgggaagaag gggttgccca gatgagtgtg ggtcagagag    4920
ccaaactgac tatatctcca gattatgcct atggtgccac tgggcaccca ggcatcatcc    4980
caccacatgc cactctcgtc ttcgatgtgg agcttctaaa actggaaact agttattaag    5040
tcgacccggg cggccgcttc cctttagtga gggttaatgc ttcgagcaga catgataaga    5100
tacattgatg agtttggaca aaccacaact agaatgcagt gaaaaaaatg ctttatttgt    5160
gaaatttgtg atgctattgc tttatttgta accattataa gctgcaataa acaagttaac    5220
ctccatagaa gacaccggga ccgatccaat aacttcgtat agcatacatt atacgaagtt    5280
atggctgcta gtgaacyaat cwcatgatgt cacccagaca tcaggcatac ccactagtgt    5340
gaaatagaca tcagaattaa gaaaaatggg ctccccgggc gcgtactcca cctcacccat    5400
catccacgct cggcaataaa agacagaat aaaacgcacg ggtgttgggt cgtttgttcg    5460
ttttatggat agcactgaga acgtcatcaa gcccttcatg cgcttcaagg tgcacatgga    5520
gggctccgtg aacggccacg agttcgagat cgagggcgag gcgagggca gccctacga    5580
gggcacccag accgccaagc tgcaggtgac caagggcggc cccctgccct tcgcctggga    5640
catcctgtcc ccccagttcc agtacggctc caaggtgtac gtgaagcacc ccgccgacat    5700
ccccgactac aagaagctgt ccttcccga gggcttcaag tgggagcgcg tgatgaactt    5760
cgaggacggc ggcgtggtga ccgtgaccca ggactcctcc ctgcaggacg gcaccttcat    5820
ctaccacgtg aagttcatcg gcgtgaactt cccctccgac ggccccgtaa tgcagaagaa    5880
gactctgggc tgggagccct ccaccgagcg cctgtacccc cgcgacggcg tgctgaaggg    5940
cgagatccac aaggcgctga agctgaaggg cggcggccac tacctggtgg agttcaagtc    6000
aatctacatg gccaagaagc ccgtgaagct gcccggctac tactacgtgg actccaagct    6060
ggacatcacc tcccacaacg aggactacac cgtggtggag cagtacgagc gcgccgaggc    6120
ccgccaccac ctgttccagt aggacctcca tagaagacac cgaataaaat atctttattt    6180
tcattacatc tgtgtgttgg tttttgtgt gaatcgatag tactaacata cgctctccat    6240
```

```
caaaacaaaa cgaaacaaaa caaactagca aaataggctg tccccagtgc aagtgcaggt    6300
gccagaacat ttctctggac cgatccaata acttcgtata gcatacatta tacgaagtta    6360
tgcctccgga ctctagcgtt ttagttatta ctagcgctac cggactcaga tctcgagctc    6420
aagcttcgaa ttctgcagtc gacggtaccg cggcttacgc gtgctagcta atgatgggcg    6480
ctcgagtaat gatgggcggt cgactaatga tgggcgctcg agtaatgatg ggcgtctagc    6540
taatgatggg cgctcgagta atgatgggcg gtcgactaat gatgggcgct cgagtaatga    6600
tgggcgtcta gctaatgatg gcgctcgag taatgatggg cggtcgacta atgatgggcg    6660
ctcgagtaat gatgggcgtc tagaacgcga attaattcaa cattttgaca ccccccataat    6720
attttttccag aattaacagt ataaattgca tctcttgttc aagagttccc tatcactctc    6780
tttaatcact actcacagta acctcaactc ctgccacaag cttgccctgc agcgggaatt    6840
ccaaacttaa gcttggtacc gagctcggat ccactagtcc agtgtggtgg aattctgcag    6900
atatccagca cagtgcggc cgctcgagtc tagagggccc gtttaaaccc gctgatcaga    6960
tggcaggaag aagcggagac agcgacgaag acctcctcaa ggcagtcaga ctcatcaagt    7020
ttctctatca aagcaaccca cctcccaacc ccgaggggac ccgacaggcc cgaaggaata    7080
gaagaagaag gtggagagag agacagagac agatccattc gattagtgaa cggatcctta    7140
gcacttattt gggacgatct gcggacgctg tgcctcttca gctaccaccg cttgagagac    7200
ttactcttga ttgtgacgag gattgtgaa cttctgggac gcaggggtg ggaagccctc    7260
aaatattggt ggaatctcct acaatattgg agtcaggagc taaagaatag tccctccccc    7320
ccccctaacg ttactggccg aagccgcttg gaataaggcc ggtgtgcgtt tgtctatatg    7380
ttattttcca ccatattgcc gtcttttggc aatgtgaggg cccggaaacc tggccctgtc    7440
ttcttgacga gcattcctag gggtctttcc cctctcgcca aaggaatgca aggtctgttg    7500
aatgtcgtga aggaagcagt tcctctggaa gcttcttgaa gacaaacaac gtctgtagcg    7560
acccttgcag gcagcggaa cccccaccct ggcgacaggt gcctctgcgg ccaaaagcca    7620
cgtgtataag atacacctgc aaaggcggca caaccccagt gccacgttgt gagttggata    7680
gttgtggaaa gagtcaaatg gctctcctca agcgtattca acaaggggct gaaggatgcc    7740
cagaaggtac cccattgtat gggatctgat ctggggcctc ggtgcacatg ctttacatgt    7800
gtttagtcga ggttaaaaaa cgtctaggcc ccccgaacca cggggacgtg ttttcctttt    7860
gaaaaacacg atgataatgg ggaggaggaa gaggaagccg aaggatccga aggcgagggt    7920
gttggcggag gcggattaca aggacgacga tgacaagatg tcagatccca gggagagaat    7980
cccacctgga aacagtggag aagagacaat aggagaggcc ttcgaatggc taaacagaac    8040
agtagaggag ataaacagag aggcagtaaa ccacctacca agggagctga ttttccaggt    8100
ttggcaaagg tcttgggaat actggcatga tgaacaaggg atgtcacaaa gctatgtaaa    8160
atacagatac ttgtgtttaa tgcaaaaggc tttatttatg cattgcaaga aaggctgtag    8220
atgtctaggg gaaggacacg gggcaggagg atggagacca ggacctcctc ctcctccccc    8280
tccaggacta gcataaccct gactgtgcct tctagttgcc agccatctgt tgtttgcccc    8340
tcccccgtgc cttccttgac cctggaaggt gccactccca ctgtcctttc ctaataaaat    8400
gaggaaattg catcgcattg tctgagtagg tgtcattcta ttctgggggg tggggtgggg    8460
caggacagca agggggagga ttgggaagac aatagcaggc atgctgggga tgcggtgggc    8520
tctatggctt ctgaggcgga aagttaaccc tagaaagata atcatattgt gacgtacgtt    8580
aaagataatc atgcgtaaaa ttgacgcatg tgttttatcg gtctgtatat cgaggtttat    8640
```

```
ttattaattt gaatagatat taagttttat tatatttaca cttacatact aataataaat   8700
tcaacaaaca atttatttat gtttatttat ttattaaaaa aaaacaaaaa ctcaaaattt   8760
cttctataaa gtaacaaaaa ccagctgggg ctcgaagttc ctatactttc tagagaatag   8820
gaacttctat agtgagtcga ataagggcga cacaaaattt attctaaatg cataataaat   8880
actgataaca tcttatagtt tgtattatat tttgtattat cgttgacatg tataattttg   8940
atatcaaaaa ctgattttcc ctttattatt ttcgagattt attttcttaa ttctcttttaa  9000
caaactagaa atattgtata tacaaaaaat cataaataat agatgaatag tttaattata   9060
ggtgttcatc aatcgaaaaa gcaacgtatc ttatttaaag tgcgttgctt ttttctcatt   9120
tataaggtta aataattctc atatatcaag caaagtgaca ggcgccctta aatattctga   9180
caaatgctct ttccctaaac tcccccata aaaaaacccg ccgaagcggg ttttacgtt    9240
atttgcggat taacgattac tcgttatcag aaccgcccag ggggcccgag cttaagactg   9300
gccgtcgttt tacaacacag aaagagtttg tagaaacgca aaaaggccat ccgtcagggg   9360
ccttctgctt agtttgatgc ctggcagttc cctactctcg ccttccgctt cctcgctcac   9420
tgactcgctg cgctcggtcg ttcggctgcg gcgagcggta tcagctcact caaaggcggt   9480
aatacggtta tccacagaat caggggataa cgcaggaaag aacatgtgag caaaaggcca   9540
gcaaaaggcc aggaaccgta aaaaggccgc gttgctggcg ttttccata ggctccgccc    9600
ccctgacgag catcacaaaa atcgacgctc aagtcagagg tggcgaaacc cgacaggact   9660
ataaagatac caggcgtttc ccctggaag ctccctcgtg cgctctcctg ttccgaccct    9720
gccgcttacc ggatacctgt ccgcctttct cccttcggga agcgtggcgc tttctcatag   9780
ctcacgctgt aggtatctca gttcggtgta ggtcgttcgc tccaagctgg gctgtgtgca   9840
cgaacccccc gttcagcccg accgctgcgc cttatccggt aactatcgtc ttgagtccaa   9900
cccggtaaga cacgacttat cgccactggc agcagccact ggtaacagga ttagcagagc   9960
gaggtatgta ggcggtgcta cagagttctt gaagtggtgg ctaactacg gctacactag  10020
aagaacagta tttggtatct gcgctctgct gaagccagtt accttcggaa aaagagttgg  10080
tagctcttga tccggcaaac aaaccaccgc tggtagcggt ggttttttg tttgcaagca   10140
gcagattacg cgcagaaaaa aaggatctca agaagatcct ttgatctttt ctacggggtc  10200
tgacgctcag tggaacgacg cgcgcgtaac tcacgttaag ggattttggt catgagcttg  10260
cgccgtcccg tcaagtcagc gtaatgctct gcttttagaa aaactcatcg agcatcaaat  10320
gaaactgcaa tttattcata tcaggattat caataccata ttttttgaaaa agccgtttct  10380
gtaatgaagg agaaaactca ccgaggcagt tccataggat ggcaagatcc tggtatcggt  10440
ctgcgattcc gactcgtcca acatcaatac aacctattaa tttcccctcg tcaaaaataa  10500
ggttatcaag tgagaaatca ccatgagtga cgactgaatc cggtgagaat ggcaaaagtt  10560
tatgcatttc tttccagact tgttcaacag gccagccatt acgctcgtca tcaaaatcac  10620
tcgcatcaac caaaccgtta ttcattcgtg attgcgcctg agcgaggcga aatacgcgat  10680
cgctgttaaa aggacaatta caaacaggaa tcgagtgcaa ccggcgcagg aacactgcca  10740
gcgcatcaac aatattttca cctgaatcag gatattcttc taatacctgg aacgctgttt  10800
ttccggggat cgcagtggtg agtaaccatg catcatcagg agtacggata aaatgcttga  10860
tggtcggaag tggcataaat tccgtcagcc agtttagtct gaccatctca tctgtaacat  10920
cattggcaac gctacctttg ccatgtttca gaaacaactc tggcgcatcg gcttcccat   10980
```

```
acaagcgata gattgtcgca cctgattgcc cgacattatc gcgagcccat ttatacccat    11040
ataaatcagc atccatgttg gaatttaatc gcggcctcga cgtttcccgt tgaatatggc    11100
tcatattctt ccttttttcaa tattattgaa gcatttatca gggttattgt ctcatgagcg   11160
gatacatatt tgaatgtatt tagaaaaata aacaaatagg ggtcagtgtt acaaccaatt    11220
aaccaattct gaacattatc gcgagcccat ttatacctga atatggctca taacaccccct  11280 tgtttgcctg gcggcagtag cgcggtggtc ccacctgacc ccatgccgaa ctcagaagtg    11340
aaacgccgta gcgccgatgg tagtgtgggg actccccatg cgagagtagg gaactgccag    11400
gcatcaaata aaacgaaagg ctcagtcgaa agactgggcc tttcgcccgg gctaattagg    11460
gggtgtcgcc cttattcgac tctatagtga agttcctatt ctctagaaag tataggaact    11520
tctgaagt                                                             11528

<210> SEQ ID NO 87
<211> LENGTH: 76
<212> TYPE: RNA
<213> ORGANISM: Artificial sequence
<220> FEATURE:
<223> OTHER INFORMATION: synthetic Evolved aptamer

<400> SEQUENCE: 87
gggcggcacu uauacagcga agcauaaugg cuacugacgc ccucaaaccc uauuugcaga    60
cuauaagugu cgcgcg                                                    76

<210> SEQ ID NO 88
<211> LENGTH: 73
<212> TYPE: RNA
<213> ORGANISM: Artificial sequence
<220> FEATURE:
<223> OTHER INFORMATION: synthetic Evolved aptamer

<400> SEQUENCE: 88
gggcggcacu uauacagggu agcauaaugg cuuaggacgc cuucaaaccu aucaagacua    60 uaagucgc gcg                                                         73

<210> SEQ ID NO 89
<211> LENGTH: 75
<212> TYPE: RNA
<213> ORGANISM: Artificial sequence
<220> FEATURE:
<223> OTHER INFORMATION: synthetic Evolved aptamer

<400> SEQUENCE: 89
gggcggcacu uauacagggu agcauaaugg gcuacuugac gccuucaccu auugguagac    60
uauaaguguc gcgcg                                                     75

<210> SEQ ID NO 90
<211> LENGTH: 76
<212> TYPE: RNA
<213> ORGANISM: Artificial sequence
<220> FEATURE:
<223> OTHER INFORMATION: synthetic Evolved aptamer

<400> SEQUENCE: 90
gggcggcacu uauacagcgu agcauaaugg gcugcagacg ccgucaaacc uauuugcaga    60
cuauaagugu cgcgcg                                                    76

<210> SEQ ID NO 91
<211> LENGTH: 74
```

```
<212> TYPE: RNA
<213> ORGANISM: Artificial sequence
<220> FEATURE:
<223> OTHER INFORMATION: synthetic Evolved aptamer

<400> SEQUENCE: 91
gggcggcacu uauacaccgu agcauaaugg gcuacugccg ccgucgaccu uuuggagacu    60
auaagugucg cgcg                                                     74

<210> SEQ ID NO 92
<211> LENGTH: 75
<212> TYPE: RNA
<213> ORGANISM: Artificial sequence
<220> FEATURE:
<223> OTHER INFORMATION: synthetic Evolved aptamer

<400> SEQUENCE: 92
gggcggcacu uauacagguc agcauaaugu gcuagugcgc cuucaaaccu auuuagagac    60
uauaaguguc gcgcg                                                    75

<210> SEQ ID NO 93
<211> LENGTH: 76
<212> TYPE: RNA
<213> ORGANISM: Artificial sequence
<220> FEATURE:
<223> OTHER INFORMATION: synthetic Evolved aptamer

<400> SEQUENCE: 93
gggcggcacu uauacagcuu agcguaaugg cuacugacgc cguccaaacc uauuuacaga    60
cuauaagugu cgcgcg                                                   76

<210> SEQ ID NO 94
<211> LENGTH: 76
<212> TYPE: RNA
<213> ORGANISM: Artificial sequence
<220> FEATURE:
<223> OTHER INFORMATION: synthetic Evolved aptamer

<400> SEQUENCE: 94
gggcggcacu uauacagggg agcauaaugg gcuacugacg ccuuuaaacc uauuugagga    60
cuauaagugu cgcgcg                                                   76

<210> SEQ ID NO 95
<211> LENGTH: 74
<212> TYPE: RNA
<213> ORGANISM: Artificial sequence
<220> FEATURE:
<223> OTHER INFORMATION: synthetic Evolved aptamer

<400> SEQUENCE: 95
gggcggcacu uauacaugga agcauaaugg gcugccgacg gcccuuaacc uuuggagacu    60
auaagugucg cgcg                                                     74

<210> SEQ ID NO 96
<211> LENGTH: 79
<212> TYPE: RNA
<213> ORGANISM: Artificial sequence
<220> FEATURE:
<223> OTHER INFORMATION: synthetic Evolved aptamer

<400> SEQUENCE: 96
gggcggcacu uauacagauu agcauaaugg gcuacugacc ccgccggcaa accuauuuga    60
```

```
agacuauaag ugucgcgcg                                              79
```

<210> SEQ ID NO 97
<211> LENGTH: 75
<212> TYPE: RNA
<213> ORGANISM: Artificial sequence
<220> FEATURE:
<223> OTHER INFORMATION: synthetic Evolved aptamer

<400> SEQUENCE: 97

```
gggcggcacu uauacagugu agcauaaugg gcuacugucg caucaaaccu auuggagac   60 uauaaguguc gcgcg                                                  75
```

<210> SEQ ID NO 98
<211> LENGTH: 76
<212> TYPE: RNA
<213> ORGANISM: Artificial sequence
<220> FEATURE:
<223> OTHER INFORMATION: synthetic Evolved aptamer

<400> SEQUENCE: 98

```
gggcggcacu uauacaguga agcauaaugg gcuacugaca cccuuaaacc uauuugcaga   60
cuauaagugu cgcgcg                                                  76
```

<210> SEQ ID NO 99
<211> LENGTH: 76
<212> TYPE: RNA
<213> ORGANISM: Artificial sequence
<220> FEATURE:
<223> OTHER INFORMATION: synthetic Evolved aptamer

<400> SEQUENCE: 99

```
gggcggcacu uauacagagu agcauaaugg gcuacagacg ccgucaaacc uauuuaccga   60
cuauaagugu cgcgcg                                                  76
```

<210> SEQ ID NO 100
<211> LENGTH: 75
<212> TYPE: RNA
<213> ORGANISM: Artificial sequence
<220> FEATURE:
<223> OTHER INFORMATION: synthetic Evolved aptamer

<400> SEQUENCE: 100

```
gggcggcacu uauacagggu gcauaauggg cuagugacgc cuucaaaccu auuguagac   60 uauaaguguc gcgcg                                                  75
```

<210> SEQ ID NO 101
<211> LENGTH: 461
<212> TYPE: PRT
<213> ORGANISM: Homo sapiens

<400> SEQUENCE: 101

Met Thr Ile Leu Gly Thr Thr Phe Gly Met Val Phe Ser Leu Leu Gln
1               5                   10                  15

Val Val Ser Gly Glu Ser Gly Tyr Ala Gln Asn Gly Asp Leu Glu Asp
            20                  25                  30

Ala Glu Leu Asp Asp Tyr Ser Phe Ser Cys Tyr Ser Gln Leu Glu Val
        35                  40                  45

Asn Gly Ser Gln His Ser Leu Thr Cys Ala Phe Glu Asp Pro Asp Val
    50                  55                  60

Asn Thr Thr Asn Leu Glu Phe Glu Ile Cys Gly Ala Leu Val Glu Val

```
            65                  70                  75                  80
Lys Cys Leu Asn Phe Arg Lys Leu Gln Glu Ile Tyr Phe Ile Glu Thr
                    85                  90                  95

Lys Lys Phe Leu Leu Ile Gly Lys Ser Asn Ile Cys Val Lys Val Gly
            100                 105                 110

Glu Lys Ser Leu Thr Cys Lys Lys Ile Asp Leu Thr Ile Val Lys
            115                 120                 125

Pro Glu Ala Pro Phe Asp Leu Ser Val Ile Tyr Arg Glu Gly Ala Asn
    130                 135                 140

Asp Phe Val Val Thr Phe Asn Thr Ser His Leu Gln Lys Lys Tyr Val
145                 150                 155                 160

Lys Val Leu Met His Asp Val Ala Tyr Arg Gln Glu Lys Asp Glu Asn
                165                 170                 175

Lys Trp Thr His Val Asn Leu Ser Ser Thr Lys Leu Thr Leu Leu Gln
                180                 185                 190

Arg Lys Leu Gln Pro Ala Ala Met Tyr Glu Ile Lys Val Arg Ser Ile
            195                 200                 205

Pro Asp His Tyr Phe Lys Gly Phe Trp Ser Glu Trp Ser Pro Ser Tyr
    210                 215                 220

Tyr Phe Arg Thr Pro Glu Ile Asn Asn Ser Ser Gly Glu Met Asp Pro
225                 230                 235                 240

Ile Leu Leu Thr Ile Ser Lys Cys His Leu Ser Phe Phe Ser Val Ala
                245                 250                 255

Leu Leu Val Ile Leu Ala Cys Val Leu Trp Lys Lys Arg Ile Lys Pro
            260                 265                 270

Ile Val Trp Pro Ser Leu Pro Asp His Lys Lys Thr Leu Glu His Leu
            275                 280                 285

Cys Lys Lys Pro Arg Lys Asn Leu Asn Val Ser Phe Asn Pro Glu Ser
    290                 295                 300

Phe Leu Asp Cys Gln Ile His Arg Val Asp Asp Ile Gln Ala Arg Asp
305                 310                 315                 320

Glu Val Glu Gly Phe Leu Gln Asp Thr Phe Pro Gln Gln Leu Glu Glu
                325                 330                 335

Ser Glu Lys Gln Arg Leu Gly Gly Asp Val Gln Ser Pro Asn Cys Pro
            340                 345                 350

Ser Glu Asp Val Val Thr Pro Glu Ser Phe Gly Arg Asp Ser Ser
    355                 360                 365

Leu Thr Cys Leu Ala Gly Asn Val Ser Ala Cys Asp Ala Pro Ile Leu
    370                 375                 380

Ser Ser Ser Arg Ser Leu Asp Cys Arg Glu Ser Gly Lys Asn Gly Pro
385                 390                 395                 400

His Val Tyr Gln Asp Leu Leu Leu Ser Leu Gly Thr Thr Asn Ser Thr
                405                 410                 415

Leu Pro Pro Pro Phe Ser Leu Gln Ser Gly Ile Leu Thr Leu Asn Pro
            420                 425                 430

Val Ala Gln Gly Gln Pro Ile Leu Thr Ser Leu Gly Ser Asn Gln Glu
            435                 440                 445

Glu Ala Tyr Val Thr Met Ser Ser Phe Tyr Gln Asn Gln
            450                 455                 460

<210> SEQ ID NO 102
<211> LENGTH: 463
<212> TYPE: PRT
<213> ORGANISM: Homo sapiens
```

<400> SEQUENCE: 102

Met Thr Ile Leu Gly Thr Thr Phe Gly Met Val Phe Ser Leu Leu Gln
1               5                   10                  15

Val Val Ser Gly Glu Ser Gly Tyr Ala Gln Asn Gly Asp Leu Glu Asp
                20                  25                  30

Ala Glu Leu Asp Asp Tyr Ser Phe Ser Cys Tyr Ser Gln Leu Glu Val
            35                  40                  45

Asn Gly Ser Gln His Ser Leu Thr Cys Ala Phe Glu Asp Pro Asp Val
50                  55                  60

Asn Thr Thr Asn Leu Glu Phe Glu Ile Cys Gly Ala Leu Val Glu Val
65                  70                  75                  80

Lys Cys Leu Asn Phe Arg Lys Leu Gln Glu Ile Tyr Phe Ile Glu Thr
                85                  90                  95

Lys Lys Phe Leu Leu Ile Gly Lys Ser Asn Ile Cys Val Lys Val Gly
                100                 105                 110

Glu Lys Ser Leu Thr Cys Lys Lys Ile Asp Leu Thr Thr Ile Val Lys
            115                 120                 125

Pro Glu Ala Pro Phe Asp Leu Ser Val Ile Tyr Arg Glu Gly Ala Asn
        130                 135                 140

Asp Phe Val Val Thr Phe Asn Thr Ser His Leu Gln Lys Lys Tyr Val
145                 150                 155                 160

Lys Val Leu Met His Asp Val Ala Tyr Arg Gln Glu Lys Asp Glu Asn
                165                 170                 175

Lys Trp Thr His Val Asn Leu Ser Ser Thr Lys Leu Thr Leu Leu Gln
                180                 185                 190

Arg Lys Leu Gln Pro Ala Ala Met Tyr Glu Ile Lys Val Arg Ser Ile
            195                 200                 205

Pro Asp His Tyr Phe Lys Gly Phe Trp Ser Glu Trp Ser Pro Ser Tyr
        210                 215                 220

Tyr Phe Arg Thr Pro Glu Ile Asn Asn Ser Ser Gly Glu Met Asp Pro
225                 230                 235                 240

Ile Phe Ser Cys Gly Pro Leu Thr Ile Ser Ile Leu Ser Phe Phe Ser
                245                 250                 255

Val Ala Leu Leu Val Ile Leu Ala Cys Val Leu Trp Lys Lys Arg Ile
            260                 265                 270

Lys Pro Ile Val Trp Pro Ser Leu Pro Asp His Lys Lys Thr Leu Glu
        275                 280                 285

His Leu Cys Lys Lys Pro Arg Lys Asn Leu Asn Val Ser Phe Asn Pro
290                 295                 300

Glu Ser Phe Leu Asp Cys Gln Ile His Arg Val Asp Asp Ile Gln Ala
305                 310                 315                 320

Arg Asp Glu Val Glu Gly Phe Leu Gln Asp Thr Phe Pro Gln Gln Leu
                325                 330                 335

Glu Glu Ser Glu Lys Gln Arg Leu Gly Gly Asp Val Gln Ser Pro Asn
            340                 345                 350

Cys Pro Ser Glu Asp Val Val Val Thr Pro Glu Ser Phe Gly Arg Asp
        355                 360                 365

Ser Ser Leu Thr Cys Leu Ala Gly Asn Val Ser Ala Cys Asp Ala Pro
370                 375                 380

Ile Leu Ser Ser Ser Arg Ser Leu Asp Cys Arg Glu Ser Gly Lys Asn
385                 390                 395                 400

Gly Pro His Val Tyr Gln Asp Leu Leu Leu Ser Leu Gly Thr Thr Asn

-continued

```
                405                 410                 415
Ser Thr Leu Pro Pro Phe Ser Leu Gln Ser Gly Ile Leu Thr Leu
            420                 425                 430

Asn Pro Val Ala Gln Gly Gln Pro Ile Leu Thr Ser Leu Gly Ser Asn
            435                 440                 445

Gln Glu Glu Ala Tyr Val Thr Met Ser Ser Phe Tyr Gln Asn Gln
    450                 455                 460
```

<210> SEQ ID NO 103
<211> LENGTH: 462
<212> TYPE: PRT
<213> ORGANISM: Homo sapiens

<400> SEQUENCE: 103

```
Met Thr Ile Leu Gly Thr Thr Phe Gly Met Val Phe Ser Leu Leu Gln
1               5                   10                  15

Val Val Ser Gly Glu Ser Gly Tyr Ala Gln Asn Gly Asp Leu Glu Asp
            20                  25                  30

Ala Glu Leu Asp Asp Tyr Ser Phe Ser Cys Tyr Ser Gln Leu Glu Val
        35                  40                  45

Asn Gly Ser Gln His Ser Leu Thr Cys Ala Phe Glu Asp Pro Asp Val
    50                  55                  60

Asn Thr Thr Asn Leu Glu Phe Glu Ile Cys Gly Ala Leu Val Glu Val
65                  70                  75                  80

Lys Cys Leu Asn Phe Arg Lys Leu Gln Glu Ile Tyr Phe Ile Glu Thr
                85                  90                  95

Lys Lys Phe Leu Leu Ile Gly Lys Ser Asn Ile Cys Val Lys Val Gly
            100                 105                 110

Glu Lys Ser Leu Thr Cys Lys Lys Ile Asp Leu Thr Thr Ile Val Lys
        115                 120                 125

Pro Glu Ala Pro Phe Asp Leu Ser Val Ile Tyr Arg Glu Gly Ala Asn
    130                 135                 140

Asp Phe Val Val Thr Phe Asn Thr Ser His Leu Gln Lys Lys Tyr Val
145                 150                 155                 160

Lys Val Leu Met His Asp Val Ala Tyr Arg Gln Glu Lys Asp Glu Asn
                165                 170                 175

Lys Trp Thr His Val Asn Leu Ser Ser Thr Lys Leu Thr Leu Leu Gln
            180                 185                 190

Arg Lys Leu Gln Pro Ala Ala Met Tyr Glu Ile Lys Val Arg Ser Ile
        195                 200                 205

Pro Asp His Tyr Phe Lys Gly Phe Trp Ser Glu Trp Ser Pro Ser Tyr
    210                 215                 220

Tyr Phe Arg Thr Pro Glu Ile Asn Asn Ser Ser Gly Glu Met Asp Pro
225                 230                 235                 240

Ile Leu Leu Thr Cys His Leu Ile Ser Ile Leu Ser Phe Phe Ser Val
                245                 250                 255

Ala Leu Leu Val Ile Leu Ala Cys Val Leu Trp Lys Lys Arg Ile Lys
            260                 265                 270

Pro Ile Val Trp Pro Ser Leu Pro Asp His Lys Lys Thr Leu Glu His
        275                 280                 285

Leu Cys Lys Lys Pro Arg Lys Asn Leu Asn Val Ser Phe Asn Pro Glu
    290                 295                 300

Ser Phe Leu Asp Cys Gln Ile His Arg Val Asp Asp Ile Gln Ala Arg
305                 310                 315                 320
```

```
Asp Glu Val Glu Gly Phe Leu Gln Asp Thr Phe Pro Gln Gln Leu Glu
                325                 330                 335

Glu Ser Glu Lys Gln Arg Leu Gly Gly Asp Val Gln Ser Pro Asn Cys
            340                 345                 350

Pro Ser Glu Asp Val Val Thr Pro Glu Ser Phe Gly Arg Asp Ser
            355                 360                 365

Ser Leu Thr Cys Leu Ala Gly Asn Val Ser Ala Cys Asp Ala Pro Ile
    370                 375                 380

Leu Ser Ser Ser Arg Ser Leu Asp Cys Arg Glu Ser Gly Lys Asn Gly
385                 390                 395                 400

Pro His Val Tyr Gln Asp Leu Leu Ser Leu Gly Thr Thr Asn Ser
            405                 410                 415

Thr Leu Pro Pro Pro Phe Ser Leu Gln Ser Gly Ile Leu Thr Leu Asn
            420                 425                 430

Pro Val Ala Gln Gly Gln Pro Ile Leu Thr Ser Leu Gly Ser Asn Gln
            435                 440                 445

Glu Glu Ala Tyr Val Thr Met Ser Ser Phe Tyr Gln Asn Gln
            450                 455                 460

<210> SEQ ID NO 104
<211> LENGTH: 466
<212> TYPE: PRT
<213> ORGANISM: Homo sapiens

<400> SEQUENCE: 104

Met Thr Ile Leu Gly Thr Thr Phe Gly Met Val Phe Ser Leu Leu Gln
1               5                   10                  15

Val Val Ser Gly Glu Ser Gly Tyr Ala Gln Asn Gly Asp Leu Glu Asp
            20                  25                  30

Ala Glu Leu Asp Asp Tyr Ser Phe Ser Cys Tyr Ser Gln Leu Glu Val
        35                  40                  45

Asn Gly Ser Gln His Ser Leu Thr Cys Ala Phe Glu Asp Pro Asp Val
    50                  55                  60

Asn Thr Thr Asn Leu Glu Phe Glu Ile Cys Gly Ala Leu Val Glu Val
65                  70                  75                  80

Lys Cys Leu Asn Phe Arg Lys Leu Gln Glu Ile Tyr Phe Ile Glu Thr
                85                  90                  95

Lys Lys Phe Leu Leu Ile Gly Lys Ser Asn Ile Cys Val Lys Val Gly
            100                 105                 110

Glu Lys Ser Leu Thr Cys Lys Lys Ile Asp Leu Thr Thr Ile Val Lys
        115                 120                 125

Pro Glu Ala Pro Phe Asp Leu Ser Val Ile Tyr Arg Glu Gly Ala Asn
    130                 135                 140

Asp Phe Val Val Thr Phe Asn Thr Ser His Leu Gln Lys Lys Tyr Val
145                 150                 155                 160

Lys Val Leu Met His Asp Val Ala Tyr Arg Gln Glu Lys Asp Glu Asn
                165                 170                 175

Lys Trp Thr His Val Asn Leu Ser Ser Thr Lys Leu Thr Leu Leu Gln
            180                 185                 190

Arg Lys Leu Gln Pro Ala Ala Met Tyr Glu Ile Lys Val Arg Ser Ile
        195                 200                 205

Pro Asp His Tyr Phe Lys Gly Phe Trp Ser Glu Trp Ser Pro Ser Tyr
    210                 215                 220

Tyr Phe Arg Thr Pro Glu Ile Asn Asn Ser Ser Gly Glu Met Asp Pro
225                 230                 235                 240
```

-continued

```
Ile Leu Leu Thr Pro Pro Val Cys Ser Val Thr Ile Ser Ile Leu Ser
            245                 250                 255

Phe Phe Ser Val Ala Leu Leu Val Ile Leu Ala Cys Val Leu Trp Lys
            260                 265                 270

Lys Arg Ile Lys Pro Ile Val Trp Pro Ser Leu Pro Asp His Lys Lys
            275                 280                 285

Thr Leu Glu His Leu Cys Lys Lys Pro Arg Lys Asn Leu Asn Val Ser
            290                 295                 300

Phe Asn Pro Glu Ser Phe Leu Asp Cys Gln Ile His Arg Val Asp Asp
305                 310                 315                 320

Ile Gln Ala Arg Asp Glu Val Glu Gly Phe Leu Gln Asp Thr Phe Pro
            325                 330                 335

Gln Gln Leu Glu Glu Ser Glu Lys Gln Arg Leu Gly Gly Asp Val Gln
            340                 345                 350

Ser Pro Asn Cys Pro Ser Glu Asp Val Val Thr Pro Glu Ser Phe
            355                 360                 365

Gly Arg Asp Ser Ser Leu Thr Cys Leu Ala Gly Asn Val Ser Ala Cys
            370                 375                 380

Asp Ala Pro Ile Leu Ser Ser Arg Ser Leu Asp Cys Arg Glu Ser
385                 390                 395                 400

Gly Lys Asn Gly Pro His Val Tyr Gln Asp Leu Leu Leu Ser Leu Gly
            405                 410                 415

Thr Thr Asn Ser Thr Leu Pro Pro Pro Phe Ser Leu Gln Ser Gly Ile
            420                 425                 430

Leu Thr Leu Asn Pro Val Ala Gln Gly Gln Pro Ile Leu Thr Ser Leu
            435                 440                 445

Gly Ser Asn Gln Glu Glu Ala Tyr Val Thr Met Ser Ser Phe Tyr Gln
            450                 455                 460

Asn Gln
465

<210> SEQ ID NO 105
<211> LENGTH: 523
<212> TYPE: PRT
<213> ORGANISM: Artificial sequence
<220> FEATURE:
<223> OTHER INFORMATION: synthetic Fc-delta-30

<400> SEQUENCE: 105

Met Ser Ile Met Gly Leu Lys Val Asn Val Ser Ala Ile Phe Met Ala
1               5                   10                  15

Val Leu Leu Thr Leu Gln Thr Pro Thr Gly Gln Ile His Trp Gly Asn
            20                  25                  30

Leu Ser Lys Ile Gly Val Val Gly Ile Gly Ser Ala Ser Tyr Lys Val
            35                  40                  45

Met Thr Arg Ser Ser His Gln Ser Leu Val Ile Lys Leu Met Pro Asn
            50                  55                  60

Ile Thr Leu Leu Asn Asn Cys Thr Arg Val Glu Ile Ala Glu Tyr Arg
65                  70                  75                  80

Arg Leu Leu Arg Thr Val Leu Glu Pro Ile Arg Asp Ala Leu Asn Ala
            85                  90                  95

Met Thr Gln Asn Ile Arg Pro Val Gln Ser Val Ala Ser Ser Arg Arg
            100                 105                 110

His Lys Arg Phe Ala Gly Val Val Leu Ala Gly Ala Ala Leu Gly Val
            115                 120                 125
```

```
Ala Thr Ala Ala Gln Ile Thr Ala Gly Ile Ala Leu His Gln Ser Met
            130                 135                 140
Leu Asn Ser Gln Ala Ile Asp Asn Leu Arg Ala Ser Leu Glu Thr Thr
145                 150                 155                 160
Asn Gln Ala Ile Glu Ala Ile Arg Gln Ala Gly Gln Glu Met Ile Leu
                165                 170                 175
Ala Val Gln Gly Val Gln Asp Tyr Ile Asn Asn Glu Leu Ile Pro Ser
            180                 185                 190
Met Asn Gln Leu Ser Cys Asp Leu Ile Gly Gln Lys Leu Gly Leu Lys
        195                 200                 205
Leu Leu Arg Tyr Tyr Thr Glu Ile Leu Ser Leu Phe Gly Pro Ser Leu
210                 215                 220
Arg Asp Pro Ile Ser Ala Glu Ile Ser Ile Gln Ala Leu Ser Tyr Ala
225                 230                 235                 240
Leu Gly Gly Asp Ile Asn Lys Val Leu Glu Lys Leu Gly Tyr Ser Gly
                245                 250                 255
Gly Asp Leu Leu Gly Ile Leu Glu Ser Arg Gly Ile Lys Ala Arg Ile
            260                 265                 270
Thr His Val Asp Thr Glu Ser Tyr Phe Ile Val Leu Ser Ile Ala Tyr
        275                 280                 285
Pro Thr Leu Ser Glu Ile Lys Gly Val Ile Val His Arg Leu Glu Gly
        290                 295                 300
Val Ser Tyr Asn Ile Gly Ser Gln Glu Trp Tyr Thr Thr Val Pro Lys
305                 310                 315                 320
Tyr Val Ala Thr Gln Gly Tyr Leu Ile Ser Asn Phe Asp Glu Ser Ser
                325                 330                 335
Cys Thr Phe Met Pro Glu Gly Thr Val Cys Ser Gln Asn Ala Leu Tyr
            340                 345                 350
Pro Met Ser Pro Leu Leu Gln Glu Cys Leu Arg Gly Ser Thr Lys Ser
        355                 360                 365
Cys Ala Arg Thr Leu Val Ser Gly Ser Phe Gly Asn Arg Phe Ile Leu
370                 375                 380
Ser Gln Gly Asn Leu Ile Ala Asn Cys Ala Ser Ile Leu Cys Lys Cys
385                 390                 395                 400
Tyr Thr Thr Gly Thr Ile Ile Asn Gln Asp Pro Asp Lys Ile Leu Thr
                405                 410                 415
Tyr Ile Ala Ala Asp His Cys Pro Val Val Glu Val Asn Gly Val Thr
            420                 425                 430
Ile Gln Val Gly Ser Arg Arg Tyr Pro Asp Ala Val Tyr Leu His Arg
        435                 440                 445
Ile Asp Leu Gly Pro Pro Ile Ser Leu Glu Arg Leu Asp Val Gly Thr
        450                 455                 460
Asn Leu Gly Asn Ala Ile Ala Lys Leu Glu Asp Ala Lys Glu Leu Leu
465                 470                 475                 480
Glu Ser Ser Asp Gln Ile Leu Arg Ser Met Lys Gly Leu Ser Ser Thr
                485                 490                 495
Ser Ile Val Tyr Ile Leu Ile Ala Val Cys Leu Gly Gly Leu Ile Gly
            500                 505                 510
Ile Pro Ala Leu Ile Cys Cys Cys Arg Gly Arg
        515                 520

<210> SEQ ID NO 106
<211> LENGTH: 599
```

```
<212> TYPE: PRT
<213> ORGANISM: Artificial sequence
<220> FEATURE:
<223> OTHER INFORMATION: synthetic Hc-delta-18

<400> SEQUENCE: 106

Met Gly Ser Arg Ile Val Ile Asn Arg Glu His Leu Met Ile Asp Arg
1               5                   10                  15

Pro Tyr Val Leu Leu Ala Val Leu Phe Val Met Ser Leu Ser Leu Ile
            20                  25                  30

Gly Leu Leu Ala Ile Ala Gly Ile Arg Leu His Arg Ala Ala Ile Tyr
        35                  40                  45

Thr Ala Glu Ile His Lys Ser Leu Ser Thr Asn Leu Asp Val Thr Asn
    50                  55                  60

Ser Ile Glu His Gln Val Lys Asp Val Leu Thr Pro Leu Phe Lys Ile
65                  70                  75                  80

Ile Gly Asp Glu Val Gly Leu Arg Thr Pro Gln Arg Phe Thr Asp Leu
                85                  90                  95

Val Lys Phe Ile Ser Asp Lys Ile Lys Phe Leu Asn Pro Asp Arg Glu
            100                 105                 110

Tyr Asp Phe Arg Asp Leu Thr Trp Cys Ile Asn Pro Pro Glu Arg Ile
        115                 120                 125

Lys Leu Asp Tyr Asp Gln Tyr Cys Ala Asp Val Ala Ala Glu Glu Leu
    130                 135                 140

Met Asn Ala Leu Val Asn Ser Thr Leu Leu Glu Thr Arg Thr Thr Asn
145                 150                 155                 160

Gln Phe Leu Ala Val Ser Lys Gly Asn Cys Ser Gly Pro Thr Thr Ile
                165                 170                 175

Arg Gly Gln Phe Ser Asn Met Ser Leu Ser Leu Leu Asp Leu Tyr Leu
            180                 185                 190

Ser Arg Gly Tyr Asn Val Ser Ser Ile Val Thr Met Thr Ser Gln Gly
        195                 200                 205

Met Tyr Gly Gly Thr Tyr Leu Val Glu Lys Pro Asn Leu Ser Ser Lys
    210                 215                 220

Arg Ser Glu Leu Ser Gln Leu Ser Met Tyr Arg Val Phe Glu Val Gly
225                 230                 235                 240

Val Ile Arg Asn Pro Gly Leu Gly Ala Pro Val Phe His Met Thr Asn
                245                 250                 255

Tyr Leu Glu Gln Pro Val Ser Asn Asp Leu Ser Asn Cys Met Val Ala
            260                 265                 270

Leu Gly Glu Leu Lys Leu Ala Ala Leu Cys His Gly Glu Asp Ser Ile
        275                 280                 285

Thr Ile Pro Tyr Gln Gly Ser Gly Lys Gly Val Ser Phe Gln Leu Val
    290                 295                 300

Lys Leu Gly Val Trp Lys Ser Pro Thr Asp Met Gln Ser Trp Val Pro
305                 310                 315                 320

Leu Ser Thr Asp Asp Pro Val Ile Asp Arg Leu Tyr Leu Ser Ser His
                325                 330                 335

Arg Gly Val Ile Ala Asp Asn Gln Ala Lys Trp Ala Val Pro Thr Thr
            340                 345                 350

Arg Thr Asp Asp Lys Leu Arg Met Glu Thr Cys Phe Gln Gln Ala Cys
        355                 360                 365

Lys Gly Lys Ile Gln Ala Leu Cys Glu Asn Pro Glu Trp Ala Pro Leu
    370                 375                 380
```

```
Lys Asp Asn Arg Ile Pro Ser Tyr Gly Val Leu Ser Val Asp Leu Ser
385                 390                 395                 400

Leu Thr Val Glu Leu Lys Ile Lys Ile Ala Ser Gly Phe Gly Pro Leu
                405                 410                 415

Ile Thr His Gly Ser Gly Met Asp Leu Tyr Lys Ser Asn His Asn Asn
            420                 425                 430

Val Tyr Trp Leu Thr Ile Pro Pro Met Lys Asn Leu Ala Leu Gly Val
        435                 440                 445

Ile Asn Thr Leu Glu Trp Ile Pro Arg Phe Lys Val Ser Pro Asn Leu
    450                 455                 460

Phe Thr Val Pro Ile Lys Glu Ala Gly Glu Asp Cys His Ala Pro Thr
465                 470                 475                 480

Tyr Leu Pro Ala Glu Val Asp Gly Asp Val Lys Leu Ser Ser Asn Leu
                485                 490                 495

Val Ile Leu Pro Gly Gln Asp Leu Gln Tyr Val Leu Ala Thr Tyr Asp
            500                 505                 510

Thr Ser Arg Val Glu His Ala Val Val Tyr Tyr Val Tyr Ser Pro Gly
        515                 520                 525

Arg Ser Phe Ser Tyr Phe Tyr Pro Phe Arg Leu Pro Ile Lys Gly Val
530                 535                 540

Pro Ile Glu Leu Gln Val Glu Cys Phe Thr Trp Asp Gln Lys Leu Trp
545                 550                 555                 560

Cys Arg His Phe Cys Val Leu Ala Asp Ser Glu Ser Gly Gly His Ile
                565                 570                 575

Thr His Ser Gly Met Val Gly Met Gly Val Ser Cys Thr Val Thr Arg
            580                 585                 590

Glu Asp Gly Thr Asn Arg Arg
        595

<210> SEQ ID NO 107
<211> LENGTH: 529
<212> TYPE: PRT
<213> ORGANISM: Artificial sequence
<220> FEATURE:
<223> OTHER INFORMATION: synthetic DAFss-IL7-DAF fusion

<400> SEQUENCE: 107

Met Thr Val Ala Arg Pro Ser Val Pro Ala Ala Leu Pro Leu Leu Gly
1               5                   10                  15

Glu Leu Pro Arg Leu Leu Leu Leu Val Leu Leu Cys Leu Pro Ala Asp
                20                  25                  30

Cys Asp Ile Glu Gly Lys Asp Gly Lys Gln Tyr Glu Ser Val Leu Met
            35                  40                  45

Val Ser Ile Asp Gln Leu Leu Asp Ser Met Lys Glu Ile Gly Ser Asn
        50                  55                  60

Cys Leu Asn Asn Glu Phe Asn Phe Phe Lys Arg His Ile Cys Asp Ala
65                  70                  75                  80

Asn Lys Glu Gly Met Phe Leu Phe Arg Ala Ala Arg Lys Leu Arg Gln
                85                  90                  95

Phe Leu Lys Met Asn Ser Thr Gly Asp Phe Asp Leu His Leu Leu Lys
                100                 105                 110

Val Ser Glu Gly Thr Thr Ile Leu Leu Asn Cys Thr Gly Gln Val Lys
            115                 120                 125

Gly Arg Lys Pro Ala Ala Leu Gly Glu Ala Gln Pro Thr Lys Ser Leu
    130                 135                 140
```

-continued

Glu Glu Asn Lys Ser Leu Lys Glu Gln Lys Lys Leu Asn Asp Leu Cys
145                 150                 155                 160

Phe Leu Lys Arg Leu Leu Gln Glu Ile Lys Thr Cys Trp Asn Lys Ile
                165                 170                 175

Leu Met Gly Thr Lys Glu His Cys Gly Leu Pro Pro Asp Val Pro Asn
            180                 185                 190

Ala Gln Pro Ala Leu Glu Gly Arg Thr Ser Phe Pro Glu Asp Thr Val
        195                 200                 205

Ile Thr Tyr Lys Cys Glu Glu Ser Phe Val Lys Ile Pro Gly Glu Lys
    210                 215                 220

Asp Ser Val Ile Cys Leu Lys Gly Ser Gln Trp Ser Asp Ile Glu Glu
225                 230                 235                 240

Phe Cys Asn Arg Ser Cys Glu Val Pro Thr Arg Leu Asn Ser Ala Ser
                245                 250                 255

Leu Lys Gln Pro Tyr Ile Thr Gln Asn Tyr Phe Pro Val Gly Thr Val
            260                 265                 270

Val Glu Tyr Glu Cys Arg Pro Gly Tyr Arg Arg Glu Pro Ser Leu Ser
        275                 280                 285

Pro Lys Leu Thr Cys Leu Gln Asn Leu Lys Trp Ser Thr Ala Val Glu
    290                 295                 300

Phe Cys Lys Lys Lys Ser Cys Pro Asn Pro Gly Glu Ile Arg Asn Gly
305                 310                 315                 320

Gln Ile Asp Val Pro Gly Gly Ile Leu Phe Gly Ala Thr Ile Ser Phe
                325                 330                 335

Ser Cys Asn Thr Gly Tyr Lys Leu Phe Gly Ser Thr Ser Ser Phe Cys
            340                 345                 350

Leu Ile Ser Gly Ser Ser Val Gln Trp Ser Asp Pro Leu Pro Glu Cys
        355                 360                 365

Arg Glu Ile Tyr Cys Pro Ala Pro Pro Gln Ile Asp Asn Gly Ile Ile
    370                 375                 380

Gln Gly Glu Arg Asp His Tyr Gly Tyr Arg Gln Ser Val Thr Tyr Ala
385                 390                 395                 400

Cys Asn Lys Gly Phe Thr Met Ile Gly Glu His Ser Ile Tyr Cys Thr
                405                 410                 415

Val Asn Asn Asp Glu Gly Glu Trp Ser Gly Pro Pro Pro Glu Cys Arg
            420                 425                 430

Gly Lys Ser Leu Thr Ser Lys Val Pro Pro Thr Val Gln Lys Pro Thr
        435                 440                 445

Thr Val Asn Val Pro Thr Thr Glu Val Ser Pro Thr Ser Gln Lys Thr
    450                 455                 460

Thr Thr Lys Thr Thr Thr Pro Asn Ala Gln Ala Thr Arg Ser Thr Pro
465                 470                 475                 480

Val Ser Arg Thr Thr Lys His Phe His Glu Thr Thr Pro Asn Lys Gly
                485                 490                 495

Ser Gly Thr Thr Ser Gly Thr Thr Arg Leu Leu Ser Gly His Thr Cys
            500                 505                 510

Phe Thr Leu Thr Gly Leu Leu Gly Thr Leu Val Thr Met Gly Leu Leu
        515                 520                 525

Thr

<210> SEQ ID NO 108
<211> LENGTH: 49
<212> TYPE: DNA
<213> ORGANISM: Artificial sequence

```
<220> FEATURE:
<223> OTHER INFORMATION: synthetic 582-1

<400> SEQUENCE: 108
acagcttagc gtaatggcta ctgacgccgt ccaaacctat ttacagact         49

<210> SEQ ID NO 109
<211> LENGTH: 49
<212> TYPE: DNA
<213> ORGANISM: Artificial sequence
<220> FEATURE:
<223> OTHER INFORMATION: synthetic 582-2

<400> SEQUENCE: 109
acagcttagg ataatggcta ctgacgccgt ccaaacctat ttacagact         49

<210> SEQ ID NO 110
<211> LENGTH: 49
<212> TYPE: DNA
<213> ORGANISM: Artificial sequence
<220> FEATURE:
<223> OTHER INFORMATION: synthetic 582-3

<400> SEQUENCE: 110
acagcttagc ataatggcta ctgacgccgt ccaaacctat tcacagact         49

<210> SEQ ID NO 111
<211> LENGTH: 49
<212> TYPE: DNA
<213> ORGANISM: Artificial sequence
<220> FEATURE:
<223> OTHER INFORMATION: synthetic 582-4

<400> SEQUENCE: 111
acagcttagc ataatggcta ctgacgccgt ccaaacctat tgacagact         49

<210> SEQ ID NO 112
<211> LENGTH: 49
<212> TYPE: DNA
<213> ORGANISM: Artificial sequence
<220> FEATURE:
<223> OTHER INFORMATION: synthetic 582-5

<400> SEQUENCE: 112
acagcatagc ataatggcta ctgacgccgt ccaaacctat ttacagact         49

<210> SEQ ID NO 113
<211> LENGTH: 49
<212> TYPE: DNA
<213> ORGANISM: Artificial sequence
<220> FEATURE:
<223> OTHER INFORMATION: synthetic 582-6

<400> SEQUENCE: 113
acagcttagc ataatggcta ctgacgccgt ccaaacctat gtacagact         49

<210> SEQ ID NO 114
<211> LENGTH: 48
<212> TYPE: DNA
<213> ORGANISM: Artificial sequence
<220> FEATURE:
<223> OTHER INFORMATION: synthetic 582-7

<400> SEQUENCE: 114
acagctagcg taatggctac tgacgccgtc caaacctatt tacagact          48
```

```
<210> SEQ ID NO 115
<211> LENGTH: 49
<212> TYPE: DNA
<213> ORGANISM: Artificial sequence
<220> FEATURE:
<223> OTHER INFORMATION: synthetic 582-8

<400> SEQUENCE: 115
acagcttagc attatggcta ctgacgccgt ccaaacctat ttacagact          49

<210> SEQ ID NO 116
<211> LENGTH: 48
<212> TYPE: DNA
<213> ORGANISM: Artificial sequence
<220> FEATURE:
<223> OTHER INFORMATION: synthetic 582-9

<400> SEQUENCE: 116
acagttagca taatggctac tgacgccgtc caaacctatt tacagact             48

<210> SEQ ID NO 117
<211> LENGTH: 49
<212> TYPE: DNA
<213> ORGANISM: Artificial sequence
<220> FEATURE:
<223> OTHER INFORMATION: synthetic 582-10

<400> SEQUENCE: 117
acagcttagc ataatggcta ctgacgcggt ccaaacctat ttacagact          49

<210> SEQ ID NO 118
<211> LENGTH: 49
<212> TYPE: DNA
<213> ORGANISM: Artificial sequence
<220> FEATURE:
<223> OTHER INFORMATION: synthetic 582-11

<400> SEQUENCE: 118
acagcttagc ttaatggcta ctgacgccgt ccaaacctat ttacagact          49

<210> SEQ ID NO 119
<211> LENGTH: 49
<212> TYPE: DNA
<213> ORGANISM: Artificial sequence
<220> FEATURE:
<223> OTHER INFORMATION: synthetic 582-12

<400> SEQUENCE: 119
acagcttagc ataatggcta ctgacgccgt ccaaacccat ttacagact          49

<210> SEQ ID NO 120
<211> LENGTH: 49
<212> TYPE: DNA
<213> ORGANISM: Artificial sequence
<220> FEATURE:
<223> OTHER INFORMATION: synthetic 582-13

<400> SEQUENCE: 120
acagcttagc ataatggcta ctgacgccgt ccaaaccaat ttacagact          49

<210> SEQ ID NO 121
<211> LENGTH: 49
<212> TYPE: DNA
<213> ORGANISM: Artificial sequence
<220> FEATURE:
<223> OTHER INFORMATION: synthetic 582-14
```

```
<400> SEQUENCE: 121
acagcttagc ataatggata ctgacgccgt ccaaacctat ttacagact          49

<210> SEQ ID NO 122
<211> LENGTH: 49
<212> TYPE: DNA
<213> ORGANISM: Artificial sequence
<220> FEATURE:
<223> OTHER INFORMATION: synthetic 582-15

<400> SEQUENCE: 122
acagcttagc attgtggcta ctgacgccgt ccaaacctat ttacagact          49

<210> SEQ ID NO 123
<211> LENGTH: 49
<212> TYPE: DNA
<213> ORGANISM: Artificial sequence
<220> FEATURE:
<223> OTHER INFORMATION: synthetic 582-16

<400> SEQUENCE: 123
acaggttagc ataatggcta ccgacgccgt ccaaacctat ttacagact          49

<210> SEQ ID NO 124
<211> LENGTH: 49
<212> TYPE: DNA
<213> ORGANISM: Artificial sequence
<220> FEATURE:
<223> OTHER INFORMATION: synthetic 582-17

<400> SEQUENCE: 124
acagcttagc gtaatggcta ctgacgccgc ccaaacctat ttacagact          49

<210> SEQ ID NO 125
<211> LENGTH: 49
<212> TYPE: DNA
<213> ORGANISM: Artificial sequence
<220> FEATURE:
<223> OTHER INFORMATION: synthetic 582-18

<400> SEQUENCE: 125
acagcttagc ataatggcta ctgacgccgt ccaaaactat ttccagact          49

<210> SEQ ID NO 126
<211> LENGTH: 49
<212> TYPE: DNA
<213> ORGANISM: Artificial sequence
<220> FEATURE:
<223> OTHER INFORMATION: synthetic 582-19

<400> SEQUENCE: 126
acagcctagc ataagggcta ctgacgccgt ccaaacctat ttacagact          49

<210> SEQ ID NO 127
<211> LENGTH: 49
<212> TYPE: DNA
<213> ORGANISM: Artificial sequence
<220> FEATURE:
<223> OTHER INFORMATION: synthetic 582-20

<400> SEQUENCE: 127
acagcttagc ataatggcta ctgaggccgt ccaaacctat ttacagact          49

<210> SEQ ID NO 128
```

```
<211> LENGTH: 49
<212> TYPE: DNA
<213> ORGANISM: Artificial sequence
<220> FEATURE:
<223> OTHER INFORMATION: synthetic 582-21

<400> SEQUENCE: 128
acagcttacc ttaatggcta ctgacgccgt ccaaacctat ttacagact           49

<210> SEQ ID NO 129
<211> LENGTH: 49
<212> TYPE: DNA
<213> ORGANISM: Artificial sequence
<220> FEATURE:
<223> OTHER INFORMATION: synthetic 582-22

<400> SEQUENCE: 129
acagcttagc ataatggcta ccgacgctgt ccaaacctat ttacagact           49

<210> SEQ ID NO 130
<211> LENGTH: 49
<212> TYPE: DNA
<213> ORGANISM: Artificial sequence
<220> FEATURE:
<223> OTHER INFORMATION: synthetic 582-23

<400> SEQUENCE: 130
acagcttagc gtaatggcta ctggcgccgt ccaaacctat ttacagact           49

<210> SEQ ID NO 131
<211> LENGTH: 49
<212> TYPE: DNA
<213> ORGANISM: Artificial sequence
<220> FEATURE:
<223> OTHER INFORMATION: synthetic 582-24

<400> SEQUENCE: 131
acagcttagc atactggcta ctgacgccgc ccaaacctat ttacagact           49

<210> SEQ ID NO 132
<211> LENGTH: 49
<212> TYPE: DNA
<213> ORGANISM: Artificial sequence
<220> FEATURE:
<223> OTHER INFORMATION: synthetic 582-25

<400> SEQUENCE: 132
acagcttagc ataatggcta ctgacgccgt cctaacctat ttacagact           49

<210> SEQ ID NO 133
<211> LENGTH: 49
<212> TYPE: DNA
<213> ORGANISM: Artificial sequence
<220> FEATURE:
<223> OTHER INFORMATION: synthetic 582-26

<400> SEQUENCE: 133
acaggttagc ataatgccta ctgacgccgt ccaaacctat ttacagact           49

<210> SEQ ID NO 134
<211> LENGTH: 49
<212> TYPE: DNA
<213> ORGANISM: Artificial sequence
<220> FEATURE:
<223> OTHER INFORMATION: synthetic 582-27

<400> SEQUENCE: 134
```

```
acagcttagc ataattgcta ctgacgccgt tcaaacctat ttacagact          49

<210> SEQ ID NO 135
<211> LENGTH: 49
<212> TYPE: DNA
<213> ORGANISM: Artificial sequence
<220> FEATURE:
<223> OTHER INFORMATION: synthetic 582-28

<400> SEQUENCE: 135
acagcttagc ataaaggcta ctgacgccgt ccaaacctat ttacagact          49

<210> SEQ ID NO 136
<211> LENGTH: 49
<212> TYPE: DNA
<213> ORGANISM: Artificial sequence
<220> FEATURE:
<223> OTHER INFORMATION: synthetic 582-29

<400> SEQUENCE: 136
acagcttagc gtaatggcta ctgacgccgt ctaaacctat ttccagact          49

<210> SEQ ID NO 137
<211> LENGTH: 49
<212> TYPE: DNA
<213> ORGANISM: Artificial sequence
<220> FEATURE:
<223> OTHER INFORMATION: synthetic 582-30

<400> SEQUENCE: 137
acaggttagc ataatggcta ctgacgccgt ccaaacctat ttagagact          49

<210> SEQ ID NO 138
<211> LENGTH: 49
<212> TYPE: DNA
<213> ORGANISM: Artificial sequence
<220> FEATURE:
<223> OTHER INFORMATION: synthetic 582-31

<400> SEQUENCE: 138
acagggtagc gtaatggcta ctgacgccgt ccaaacctat ttacagact          49

<210> SEQ ID NO 139
<211> LENGTH: 49
<212> TYPE: DNA
<213> ORGANISM: Artificial sequence
<220> FEATURE:
<223> OTHER INFORMATION: synthetic 582-32

<400> SEQUENCE: 139
acagcgtagc ataatggcta ctgacgccgt tcaaacctat ttacagact          49

<210> SEQ ID NO 140
<211> LENGTH: 49
<212> TYPE: DNA
<213> ORGANISM: Artificial sequence
<220> FEATURE:
<223> OTHER INFORMATION: synthetic 582-33

<400> SEQUENCE: 140
acagcttagc ataatggcta ctgacgccgt ccaaactcat ttacagact          49

<210> SEQ ID NO 141
<211> LENGTH: 49
<212> TYPE: DNA
```

```
<213> ORGANISM: Artificial sequence
<220> FEATURE:
<223> OTHER INFORMATION: synthetic 582-34

<400> SEQUENCE: 141
acagcgtagc atagtggcta ctgacgccgt ccaaacctat ttacagact        49

<210> SEQ ID NO 142
<211> LENGTH: 49
<212> TYPE: DNA
<213> ORGANISM: Artificial sequence
<220> FEATURE:
<223> OTHER INFORMATION: synthetic 582-35

<400> SEQUENCE: 142
acagcttagt gtaatggcta ctgacgctgt ccaaacctat ttacagact        49

<210> SEQ ID NO 143
<211> LENGTH: 49
<212> TYPE: DNA
<213> ORGANISM: Artificial sequence
<220> FEATURE:
<223> OTHER INFORMATION: synthetic 582-36

<400> SEQUENCE: 143
acagcttagc ataatggcta ctgacggcgt tcaaacctat ttacagact        49

<210> SEQ ID NO 144
<211> LENGTH: 49
<212> TYPE: DNA
<213> ORGANISM: Artificial sequence
<220> FEATURE:
<223> OTHER INFORMATION: synthetic 582-37

<400> SEQUENCE: 144
acaggttagc ataatggcta ctgacgccgt ccaaacctat ttatagact        49

<210> SEQ ID NO 145
<211> LENGTH: 48
<212> TYPE: DNA
<213> ORGANISM: Artificial sequence
<220> FEATURE:
<223> OTHER INFORMATION: synthetic 582-38

<400> SEQUENCE: 145
acagcttagc ataatggcta ctgacgccgt ccaaacctat tgtcgact         48

<210> SEQ ID NO 146
<211> LENGTH: 48
<212> TYPE: DNA
<213> ORGANISM: Artificial sequence
<220> FEATURE:
<223> OTHER INFORMATION: synthetic 582-39

<400> SEQUENCE: 146
acagcttagc ataatggcta ctgacgccgt ccaaacctat ttacgact         48

<210> SEQ ID NO 147
<211> LENGTH: 48
<212> TYPE: DNA
<213> ORGANISM: Artificial sequence
<220> FEATURE:
<223> OTHER INFORMATION: synthetic 769-1

<400> SEQUENCE: 147
acaggtcagc ataatgtgct agtgcgcctt caaacctatt tagagact         48
```

<210> SEQ ID NO 148
<211> LENGTH: 48
<212> TYPE: DNA
<213> ORGANISM: Artificial sequence
<220> FEATURE:
<223> OTHER INFORMATION: synthetic 769-2

<400> SEQUENCE: 148
acaggtcagc ataatgtgct agtgcgccct caaacctatt tagagact        48

<210> SEQ ID NO 149
<211> LENGTH: 48
<212> TYPE: DNA
<213> ORGANISM: Artificial sequence
<220> FEATURE:
<223> OTHER INFORMATION: synthetic 769-3

<400> SEQUENCE: 149
acaggttagc ataatgtgct attgcgcctt caaacctatt tagagact        48

<210> SEQ ID NO 150
<211> LENGTH: 48
<212> TYPE: DNA
<213> ORGANISM: Artificial sequence
<220> FEATURE:
<223> OTHER INFORMATION: synthetic 769-4

<400> SEQUENCE: 150
acaggtcagc ataatgtgct agtgcgcatt caaacctatt tagagact        48

<210> SEQ ID NO 151
<211> LENGTH: 48
<212> TYPE: DNA
<213> ORGANISM: Artificial sequence
<220> FEATURE:
<223> OTHER INFORMATION: synthetic 769-5

<400> SEQUENCE: 151
acaggttagc ataatgtgct agtgcgcctt caaacctatt ttgagact        48

<210> SEQ ID NO 152
<211> LENGTH: 48
<212> TYPE: DNA
<213> ORGANISM: Artificial sequence
<220> FEATURE:
<223> OTHER INFORMATION: synthetic 769-6

<400> SEQUENCE: 152
acaggttatc ataatgtgct agtgcgcctt caaacctatt tagagact        48

<210> SEQ ID NO 153
<211> LENGTH: 48
<212> TYPE: DNA
<213> ORGANISM: Artificial sequence
<220> FEATURE:
<223> OTHER INFORMATION: synthetic 769-7

<400> SEQUENCE: 153
acaggttagc atgatgtgct agtgcgcctt caaacctatt tagagact        48

<210> SEQ ID NO 154
<211> LENGTH: 48
<212> TYPE: DNA
<213> ORGANISM: Artificial sequence
<220> FEATURE:

<223> OTHER INFORMATION: synthetic 769-8

<400> SEQUENCE: 154
acaggttagc ataatgggct agtgcgcctt caaacctatt tagagact        48

<210> SEQ ID NO 155
<211> LENGTH: 48
<212> TYPE: DNA
<213> ORGANISM: Artificial sequence
<220> FEATURE:
<223> OTHER INFORMATION: synthetic 769-9

<400> SEQUENCE: 155
acaggtcagc aaaatgtgca agtgcgcctt caaacctatt tagagact        48

<210> SEQ ID NO 156
<211> LENGTH: 48
<212> TYPE: DNA
<213> ORGANISM: Artificial sequence
<220> FEATURE:
<223> OTHER INFORMATION: synthetic 769-10

<400> SEQUENCE: 156
acaggtcagc ataatgtgct agtgcgcctt caaacctatc tggagact        48

<210> SEQ ID NO 157
<211> LENGTH: 48
<212> TYPE: DNA
<213> ORGANISM: Artificial sequence
<220> FEATURE:
<223> OTHER INFORMATION: synthetic 769-11

<400> SEQUENCE: 157
acagcttagc ataatgtgct agtgcgcctt caaacctatt tagagact        48

<210> SEQ ID NO 158
<211> LENGTH: 48
<212> TYPE: DNA
<213> ORGANISM: Artificial sequence
<220> FEATURE:
<223> OTHER INFORMATION: synthetic 769-12

<400> SEQUENCE: 158
acaggtcagc ataatgtgct agtgcgcctt caaacctatt tacagact        48

<210> SEQ ID NO 159
<211> LENGTH: 48
<212> TYPE: DNA
<213> ORGANISM: Artificial sequence
<220> FEATURE:
<223> OTHER INFORMATION: synthetic 769-13

<400> SEQUENCE: 159
acaggtcagc ataatgtgct agtgcgcctt caaacatatt tagagact        48

<210> SEQ ID NO 160
<211> LENGTH: 48
<212> TYPE: DNA
<213> ORGANISM: Artificial sequence
<220> FEATURE:
<223> OTHER INFORMATION: synthetic 769-14

<400> SEQUENCE: 160
acagggtagc ataatgtgct agtgcgcctt caaacctatt tagagact        48

```
<210> SEQ ID NO 161
<211> LENGTH: 48
<212> TYPE: DNA
<213> ORGANISM: Artificial sequence
<220> FEATURE:
<223> OTHER INFORMATION: synthetic 769-15

<400> SEQUENCE: 161
acaggttagc ataatgtgct agtgcgccct caaacctatt tagagact         48

<210> SEQ ID NO 162
<211> LENGTH: 48
<212> TYPE: DNA
<213> ORGANISM: Artificial sequence
<220> FEATURE:
<223> OTHER INFORMATION: synthetic 769-16

<400> SEQUENCE: 162
acaggttagc ataatgtgcc agtgcgcctt caaacctatt tagagact         48

<210> SEQ ID NO 163
<211> LENGTH: 48
<212> TYPE: DNA
<213> ORGANISM: Artificial sequence
<220> FEATURE:
<223> OTHER INFORMATION: synthetic 769-17

<400> SEQUENCE: 163
acaggtcagc ataatgggct agtgcgcctt caaacctatt tagagact         48

<210> SEQ ID NO 164
<211> LENGTH: 49
<212> TYPE: DNA
<213> ORGANISM: Artificial sequence
<220> FEATURE:
<223> OTHER INFORMATION: synthetic 795-1

<400> SEQUENCE: 164
acagcgaagc ataatggcta ctgacgccct caaaccctat ttgcagact         49

<210> SEQ ID NO 165
<211> LENGTH: 49
<212> TYPE: DNA
<213> ORGANISM: Artificial sequence
<220> FEATURE:
<223> OTHER INFORMATION: synthetic 795-2

<400> SEQUENCE: 165
acagcgaagc ataatggcta ctgacgccct caaaccctat ttacagact         49

<210> SEQ ID NO 166
<211> LENGTH: 49
<212> TYPE: DNA
<213> ORGANISM: Artificial sequence
<220> FEATURE:
<223> OTHER INFORMATION: synthetic 795-3

<400> SEQUENCE: 166
acagcgaagc ataatggctt ctgacgccct caaaccctat ttgcagact         49

<210> SEQ ID NO 167
<211> LENGTH: 49
<212> TYPE: DNA
<213> ORGANISM: Artificial sequence
<220> FEATURE:
<223> OTHER INFORMATION: synthetic 795-4
```

<400> SEQUENCE: 167
acagccaagc atactggcta ctgacgccct caaaccctat ttgcagact            49

<210> SEQ ID NO 168
<211> LENGTH: 49
<212> TYPE: DNA
<213> ORGANISM: Artificial sequence
<220> FEATURE:
<223> OTHER INFORMATION: synthetic 795-5

<400> SEQUENCE: 168
acagcgaagc ataatggcta ctgacgcccg caaaccctat ttgcagact            49

<210> SEQ ID NO 169
<211> LENGTH: 49
<212> TYPE: DNA
<213> ORGANISM: Artificial sequence
<220> FEATURE:
<223> OTHER INFORMATION: synthetic 795-6

<400> SEQUENCE: 169
acagcgaagc ataatggcta ctgacggcct caaaccctat ttgcagact            49

<210> SEQ ID NO 170
<211> LENGTH: 49
<212> TYPE: DNA
<213> ORGANISM: Artificial sequence
<220> FEATURE:
<223> OTHER INFORMATION: synthetic 795-7

<400> SEQUENCE: 170
acagcgaggc ataatggcta ctgacgccct caaaccctat ttgcagact            49

<210> SEQ ID NO 171
<211> LENGTH: 49
<212> TYPE: DNA
<213> ORGANISM: Artificial sequence
<220> FEATURE:
<223> OTHER INFORMATION: synthetic 795-8

<400> SEQUENCE: 171
acagcgaagc ataatggcta ctgacgcctt caaaccctat ttgcagact            49

<210> SEQ ID NO 172
<211> LENGTH: 49
<212> TYPE: DNA
<213> ORGANISM: Artificial sequence
<220> FEATURE:
<223> OTHER INFORMATION: synthetic 795-9

<400> SEQUENCE: 172
acagcgaagc ataatggcta cagacgccct caaaacctat ttgcagact            49

<210> SEQ ID NO 173
<211> LENGTH: 48
<212> TYPE: DNA
<213> ORGANISM: Artificial sequence
<220> FEATURE:
<223> OTHER INFORMATION: synthetic 795-10

<400> SEQUENCE: 173
acagcgaagc ataatggcta ctgacgccct caaaccctat ttgagact             48

<210> SEQ ID NO 174
<211> LENGTH: 48

```
<212> TYPE: DNA
<213> ORGANISM: Artificial sequence
<220> FEATURE:
<223> OTHER INFORMATION: synthetic 795-11

<400> SEQUENCE: 174
acagcgaagc ataatggcta ctgacgccct caaaccctat tgtcgact                    48

<210> SEQ ID NO 175
<211> LENGTH: 49
<212> TYPE: DNA
<213> ORGANISM: Artificial sequence
<220> FEATURE:
<223> OTHER INFORMATION: synthetic 795-12

<400> SEQUENCE: 175
acagccaagc ataatggcta ctgacgccct caaaccctat ttgcagact                   49

<210> SEQ ID NO 176
<211> LENGTH: 49
<212> TYPE: DNA
<213> ORGANISM: Artificial sequence
<220> FEATURE:
<223> OTHER INFORMATION: synthetic 795-13

<400> SEQUENCE: 176
acagcgaagc ataatggcta ctgacgccct caaaccctat ttggcgact                   49

<210> SEQ ID NO 177
<211> LENGTH: 49
<212> TYPE: DNA
<213> ORGANISM: Artificial sequence
<220> FEATURE:
<223> OTHER INFORMATION: synthetic 795-14

<400> SEQUENCE: 177
acagcgaagc ataatgtcta ctgacgccct caaaccctat ttgcagact                   49

<210> SEQ ID NO 178
<211> LENGTH: 49
<212> TYPE: DNA
<213> ORGANISM: Artificial sequence
<220> FEATURE:
<223> OTHER INFORMATION: synthetic 795-15

<400> SEQUENCE: 178
acagcgaagc ataatggcta ctgacgccgt caaaccctat ttgtagact                   49

<210> SEQ ID NO 179
<211> LENGTH: 49
<212> TYPE: DNA
<213> ORGANISM: Artificial sequence
<220> FEATURE:
<223> OTHER INFORMATION: synthetic 795-16

<400> SEQUENCE: 179
acagcgaagc ataatggcta ctgacgccct caaaccttat ttgcagact                   49

<210> SEQ ID NO 180
<211> LENGTH: 48
<212> TYPE: DNA
<213> ORGANISM: Artificial sequence
<220> FEATURE:
<223> OTHER INFORMATION: synthetic 795-17

<400> SEQUENCE: 180
```
acaggtagca taatggctac tgacgccctc aaaccctatt tgcagact        48

<210> SEQ ID NO 181
<211> LENGTH: 49
<212> TYPE: DNA
<213> ORGANISM: Artificial sequence
<220> FEATURE:
<223> OTHER INFORMATION: synthetic 795-18

<400> SEQUENCE: 181
acagcgaagc ataatggcta ctgacgccct caaaccctat ttctagact        49

<210> SEQ ID NO 182
<211> LENGTH: 49
<212> TYPE: DNA
<213> ORGANISM: Artificial sequence
<220> FEATURE:
<223> OTHER INFORMATION: synthetic 795-19

<400> SEQUENCE: 182
acagcgaagc ataatggcta ctgacgccct caaaccctat ttgtagact        49

<210> SEQ ID NO 183
<211> LENGTH: 48
<212> TYPE: DNA
<213> ORGANISM: Artificial sequence
<220> FEATURE:
<223> OTHER INFORMATION: synthetic 935-1

<400> SEQUENCE: 183
acagggtagc ataatgggct acttgacgcc ttcacctatt tgtagact        48

<210> SEQ ID NO 184
<211> LENGTH: 47
<212> TYPE: DNA
<213> ORGANISM: Artificial sequence
<220> FEATURE:
<223> OTHER INFORMATION: synthetic 935-2

<400> SEQUENCE: 184
acagggtagc ataatgggct acttgacgcc ttcacctatt tgagact        47

<210> SEQ ID NO 185
<211> LENGTH: 48
<212> TYPE: DNA
<213> ORGANISM: Artificial sequence
<220> FEATURE:
<223> OTHER INFORMATION: synthetic 935-3

<400> SEQUENCE: 185
acagggtagc ataatgggct actttacgcc ttcacctatt tgtagact        48

<210> SEQ ID NO 186
<211> LENGTH: 48
<212> TYPE: DNA
<213> ORGANISM: Artificial sequence
<220> FEATURE:
<223> OTHER INFORMATION: synthetic 935-4

<400> SEQUENCE: 186
acagggtagc ataatgggct acttgacgcc ttcacctatt tctagact        48

<210> SEQ ID NO 187
<211> LENGTH: 48
<212> TYPE: DNA
<213> ORGANISM: Artificial sequence
<220> FEATURE:
<223> OTHER INFORMATION: synthetic 935-5

<400> SEQUENCE: 187
acagggtagc ataatgggct acttgacgcc ttcacctatt tggagact        48

<210> SEQ ID NO 188
<211> LENGTH: 48
<212> TYPE: DNA
<213> ORGANISM: Artificial sequence
<220> FEATURE:
<223> OTHER INFORMATION: synthetic 935-6

<400> SEQUENCE: 188
acagggtagc atagtgggct acttgacgcc ttcacctatt tgtagact        48

<210> SEQ ID NO 189
<211> LENGTH: 48
<212> TYPE: DNA
<213> ORGANISM: Artificial sequence
<220> FEATURE:
<223> OTHER INFORMATION: synthetic 935-7

<400> SEQUENCE: 189
acagggtagc atgatgggct acttgacgcc ttcacctatt tgtagact        48

<210> SEQ ID NO 190
<211> LENGTH: 48
<212> TYPE: DNA
<213> ORGANISM: Artificial sequence
<220> FEATURE:
<223> OTHER INFORMATION: synthetic 935-8

<400> SEQUENCE: 190
acagggtagc ataatgggct acttgacgcc ttcacctatt agtagact        48

<210> SEQ ID NO 191
<211> LENGTH: 48
<212> TYPE: DNA
<213> ORGANISM: Artificial sequence
<220> FEATURE:
<223> OTHER INFORMATION: synthetic 935-9

<400> SEQUENCE: 191
acagggtagc ataatgggct atttgacgcc ttcacctatt tgtagact        48

<210> SEQ ID NO 192
<211> LENGTH: 48
<212> TYPE: DNA
<213> ORGANISM: Artificial sequence
<220> FEATURE:
<223> OTHER INFORMATION: synthetic 935-10

<400> SEQUENCE: 192
acagggtagc ataatgggct acttgccgcc ttcacctatt tgtagact        48

<210> SEQ ID NO 193
<211> LENGTH: 48
<212> TYPE: DNA
<213> ORGANISM: Artificial sequence
<220> FEATURE:
<223> OTHER INFORMATION: synthetic 935-11

<400> SEQUENCE: 193
acagtgtagc ataattggct acttgacgcc ttcacctatt tgtagact        48

<210> SEQ ID NO 194
<211> LENGTH: 48
<212> TYPE: DNA
<213> ORGANISM: Artificial sequence
<220> FEATURE:
<223> OTHER INFORMATION: synthetic 935-12

<400> SEQUENCE: 194
acagggtagc ataatgggct acttgacgct ttcaccttt tgtagact          48

<210> SEQ ID NO 195
<211> LENGTH: 48
<212> TYPE: DNA
<213> ORGANISM: Artificial sequence
<220> FEATURE:
<223> OTHER INFORMATION: synthetic 935-13

<400> SEQUENCE: 195
acagggtagc ataagggct acttgacgcc ttcacctatt tgtagact           48

<210> SEQ ID NO 196
<211> LENGTH: 48
<212> TYPE: DNA
<213> ORGANISM: Artificial sequence
<220> FEATURE:
<223> OTHER INFORMATION: synthetic 935-14

<400> SEQUENCE: 196
acagggtagc ataatggact acttgacgcc tccacctatt tgtagact          48

<210> SEQ ID NO 197
<211> LENGTH: 48
<212> TYPE: DNA
<213> ORGANISM: Artificial sequence
<220> FEATURE:
<223> OTHER INFORMATION: synthetic 935-15

<400> SEQUENCE: 197
acagggtagc ataatgggct acttgtcgcc ttcacctatt tgtagact          48

<210> SEQ ID NO 198
<211> LENGTH: 49
<212> TYPE: DNA
<213> ORGANISM: Artificial sequence
<220> FEATURE:
<223> OTHER INFORMATION: synthetic 946-1

<400> SEQUENCE: 198
acagcgtagc ataatgggct gcagacgccg tcaaacctat ttgcagact         49

<210> SEQ ID NO 199
<211> LENGTH: 49
<212> TYPE: DNA
<213> ORGANISM: Artificial sequence
<220> FEATURE:
<223> OTHER INFORMATION: synthetic 946-2

<400> SEQUENCE: 199
acagcgtagc ataatgggct gcagacgcag tcaaacctat ttgcagact         49

<210> SEQ ID NO 200
<211> LENGTH: 48
<212> TYPE: DNA
<213> ORGANISM: Artificial sequence
<220> FEATURE:
<223> OTHER INFORMATION: synthetic 946-3

```
<400> SEQUENCE: 200
acatgtagca taatgggcta ctgacgccgt caaacctatt tgcagact                48

<210> SEQ ID NO 201
<211> LENGTH: 49
<212> TYPE: DNA
<213> ORGANISM: Artificial sequence
<220> FEATURE:
<223> OTHER INFORMATION: synthetic 946-4

<400> SEQUENCE: 201
acagcgtagc atagtgggct gcagacgccg tcaaacctat ttgcagact               49

<210> SEQ ID NO 202
<211> LENGTH: 49
<212> TYPE: DNA
<213> ORGANISM: Artificial sequence
<220> FEATURE:
<223> OTHER INFORMATION: synthetic 946-5

<400> SEQUENCE: 202
acagtgtagc ataatgggct gcagacgcct caaacctat ttggagact                49

<210> SEQ ID NO 203
<211> LENGTH: 49
<212> TYPE: DNA
<213> ORGANISM: Artificial sequence
<220> FEATURE:
<223> OTHER INFORMATION: synthetic 946-6

<400> SEQUENCE: 203
acagtgtagc ataatgggct gctgacgccg tcaaacctat ttgaagact               49

<210> SEQ ID NO 204
<211> LENGTH: 49
<212> TYPE: DNA
<213> ORGANISM: Artificial sequence
<220> FEATURE:
<223> OTHER INFORMATION: synthetic 946-7

<400> SEQUENCE: 204
acagcgtagc ataatgggct acaggcgccg tcaaacctat ttgcagact               49

<210> SEQ ID NO 205
<211> LENGTH: 49
<212> TYPE: DNA
<213> ORGANISM: Artificial sequence
<220> FEATURE:
<223> OTHER INFORMATION: synthetic 946-8

<400> SEQUENCE: 205
acagcgtagc ataatgggct actggcgccg tcaaacctat ttgcagact               49

<210> SEQ ID NO 206
<211> LENGTH: 48
<212> TYPE: DNA
<213> ORGANISM: Artificial sequence
<220> FEATURE:
<223> OTHER INFORMATION: synthetic 946-9

<400> SEQUENCE: 206
acagcgtagc ataatgggct gcagacgccg tcaaacctat ttgagact                48

<210> SEQ ID NO 207
```

```
<211> LENGTH: 48
<212> TYPE: DNA
<213> ORGANISM: Artificial sequence
<220> FEATURE:
<223> OTHER INFORMATION: synthetic 946-10

<400> SEQUENCE: 207
acaggtagca taatgggctg cagacgccgt caaacctatt tgcagact                    48

<210> SEQ ID NO 208
<211> LENGTH: 48
<212> TYPE: DNA
<213> ORGANISM: Artificial sequence
<220> FEATURE:
<223> OTHER INFORMATION: synthetic 946-11

<400> SEQUENCE: 208
acaggtagca taatgggctg ctgacgccgt caaacctatt tacagact                    48

<210> SEQ ID NO 209
<211> LENGTH: 49
<212> TYPE: DNA
<213> ORGANISM: Artificial sequence
<220> FEATURE:
<223> OTHER INFORMATION: synthetic 946-12

<400> SEQUENCE: 209
acagcgtagc atattgggct gcagacgccg tcaaacctat ttgcagact                   49

<210> SEQ ID NO 210
<211> LENGTH: 49
<212> TYPE: DNA
<213> ORGANISM: Artificial sequence
<220> FEATURE:
<223> OTHER INFORMATION: synthetic 946-13

<400> SEQUENCE: 210
acagcgtagc ataatgggct gcagacgcct tcaaacctat ttggagact                   49

<210> SEQ ID NO 211
<211> LENGTH: 48
<212> TYPE: DNA
<213> ORGANISM: Artificial sequence
<220> FEATURE:
<223> OTHER INFORMATION: synthetic 946-14

<400> SEQUENCE: 211
acagtgtagc ataatgggct gcagacgccg tcaaacctat ttgagact                    48

<210> SEQ ID NO 212
<211> LENGTH: 49
<212> TYPE: DNA
<213> ORGANISM: Artificial sequence
<220> FEATURE:
<223> OTHER INFORMATION: synthetic 946-15

<400> SEQUENCE: 212
acagcgtagc ataatgggct gctgacgccg tcaaacctat ttggagact                   49

<210> SEQ ID NO 213
<211> LENGTH: 49
<212> TYPE: DNA
<213> ORGANISM: Artificial sequence
<220> FEATURE:
<223> OTHER INFORMATION: synthetic 946-16

<400> SEQUENCE: 213
```

```
acagcgtagc ataatgggct gcagacgccg tcaaacctat ttacagact        49

<210> SEQ ID NO 214
<211> LENGTH: 49
<212> TYPE: DNA
<213> ORGANISM: Artificial sequence
<220> FEATURE:
<223> OTHER INFORMATION: synthetic 946-17

<400> SEQUENCE: 214
acagcgtagc ataatgggct gctgacgccg tcaaacctat ttgcagact        49

<210> SEQ ID NO 215
<211> LENGTH: 49
<212> TYPE: DNA
<213> ORGANISM: Artificial sequence
<220> FEATURE:
<223> OTHER INFORMATION: synthetic 946-18

<400> SEQUENCE: 215
acagggtagc ataatgggct gcagacgccg tcaaacctat ttggagact        49

<210> SEQ ID NO 216
<211> LENGTH: 49
<212> TYPE: DNA
<213> ORGANISM: Artificial sequence
<220> FEATURE:
<223> OTHER INFORMATION: synthetic 946-19

<400> SEQUENCE: 216
acagcgtagc ataatgggct acagacgccg tcaaacctat ttgcagact        49

<210> SEQ ID NO 217
<211> LENGTH: 49
<212> TYPE: DNA
<213> ORGANISM: Artificial sequence
<220> FEATURE:
<223> OTHER INFORMATION: synthetic 946-20

<400> SEQUENCE: 217
acagcgtcgc ataatgggct gcagacgccg tcaaatctat ttgcagact        49

<210> SEQ ID NO 218
<211> LENGTH: 49
<212> TYPE: DNA
<213> ORGANISM: Artificial sequence
<220> FEATURE:
<223> OTHER INFORMATION: synthetic 946-21

<400> SEQUENCE: 218
acagcgtagc ataatgggct tcagacgccg tcaaacctat ttgcagact        49

<210> SEQ ID NO 219
<211> LENGTH: 48
<212> TYPE: DNA
<213> ORGANISM: Artificial sequence
<220> FEATURE:
<223> OTHER INFORMATION: synthetic 946-22

<400> SEQUENCE: 219
acatgtagca taatgggctg cagacgccgt caaacctatt tggagact        48

<210> SEQ ID NO 220
<211> LENGTH: 47
<212> TYPE: DNA
```

```
<213> ORGANISM: Artificial sequence
<220> FEATURE:
<223> OTHER INFORMATION: synthetic 961-1

<400> SEQUENCE: 220
acaccgtagc ataatgggct actgccgccg tcgacctttt ggagact                        47

<210> SEQ ID NO 221
<211> LENGTH: 46
<212> TYPE: DNA
<213> ORGANISM: Artificial sequence
<220> FEATURE:
<223> OTHER INFORMATION: synthetic 996-1

<400> SEQUENCE: 221
acagggtagc ataatggctt aggacgcctt caaacctatc aagact                         46

<210> SEQ ID NO 222
<211> LENGTH: 49
<212> TYPE: DNA
<213> ORGANISM: Artificial sequence
<220> FEATURE:
<223> OTHER INFORMATION: synthetic Family 582 Consensus
<220> FEATURE:
<221> NAME/KEY: misc_feature
<222> LOCATION: (5)..(5)
<223> OTHER INFORMATION: n at position 5 can be C, G, or no nucleotide
<220> FEATURE:
<221> NAME/KEY: misc_feature
<222> LOCATION: (6)..(6)
<223> OTHER INFORMATION: n at position 6 can be A, C, G, T, or no
      nucleotide
<220> FEATURE:
<221> NAME/KEY: misc_feature
<222> LOCATION: (45)..(45)
<223> OTHER INFORMATION: n at position 45 can be A or no nucleotide

<400> SEQUENCE: 222
acagnntasb dtwvdksmta cygrsgsbgy yywaamyhat kbhbngact                      49

<210> SEQ ID NO 223
<211> LENGTH: 48
<212> TYPE: DNA
<213> ORGANISM: Artificial sequence
<220> FEATURE:
<223> OTHER INFORMATION: synthetic Family 769 Consensus

<400> SEQUENCE: 223
acagskyakc awratgkgch aktgcgcmyt caaacmtaty tdsagact                       48

<210> SEQ ID NO 224
<211> LENGTH: 49
<212> TYPE: DNA
<213> ORGANISM: Artificial sequence
<220> FEATURE:
<223> OTHER INFORMATION: synthetic Family 795 Consensus
<220> FEATURE:
<221> NAME/KEY: misc_feature
<222> LOCATION: (5)..(5)
<223> OTHER INFORMATION: n at position 5 can be C or no nucleotide
<220> FEATURE:
<221> NAME/KEY: misc_feature
<222> LOCATION: (40)..(40)
<223> OTHER INFORMATION: n at position 40 can be T or no nucleotide
<220> FEATURE:
<221> NAME/KEY: misc_feature
<222> LOCATION: (44)..(44)
<223> OTHER INFORMATION: n at position 44 can be C, G, T, or no
      nucleotide

<400> SEQUENCE: 224
```

```
acagnswrgc atamtgkctw cwgacgscbk caaamcytan ttvnmgact          49
```

<210> SEQ ID NO 225
<211> LENGTH: 48
<212> TYPE: DNA
<213> ORGANISM: Artificial sequence
<220> FEATURE:
<223> OTHER INFORMATION: synthetic Family 935 Consensus
<220> FEATURE:
<221> NAME/KEY: misc_feature
<222> LOCATION: (43)..(43)
<223> OTHER INFORMATION: n at position 43 can be G, T, or no nucleotide

<400> SEQUENCE: 225

```
acagkgtcgc atrrkkgrct ayttkhcgcy tycacctwtt wsnagact           48
```

<210> SEQ ID NO 226
<211> LENGTH: 49
<212> TYPE: DNA
<213> ORGANISM: Artificial sequence
<220> FEATURE:
<223> OTHER INFORMATION: synthetic Family 946 Consensus
<220> FEATURE:
<221> NAME/KEY: misc_feature
<222> LOCATION: (4)..(4)
<223> OTHER INFORMATION: n at position 4 can be G or no nucleotide
<220> FEATURE:
<221> NAME/KEY: misc_feature
<222> LOCATION: (5)..(5)
<223> OTHER INFORMATION: n at position 5 can be C, G, T, or no
      nucleotide
<220> FEATURE:
<221> NAME/KEY: misc_feature
<222> LOCATION: (44)..(44)
<223> OTHER INFORMATION: n at position 44 can be A, C, G, or no
      nucleotide

<400> SEQUENCE: 226

```
acanngtmgc atadtgggct dcwgrcgcmk tcaaayctat ttrnagact          49
```

<210> SEQ ID NO 227
<211> LENGTH: 11
<212> TYPE: PRT
<213> ORGANISM: Artificial sequence
<220> FEATURE:
<223> OTHER INFORMATION: synthetic Membrane-targeting domain of
      Src-Flag-Vpx

<400> SEQUENCE: 227

Met Gly Ser Ser Lys Ser Lys Pro Lys Asp Pro
1               5                   10

<210> SEQ ID NO 228
<211> LENGTH: 8
<212> TYPE: PRT
<213> ORGANISM: Artificial sequence
<220> FEATURE:
<223> OTHER INFORMATION: synthetic Viral protease cleavage domain

<400> SEQUENCE: 228

Lys Ala Arg Val Leu Ala Glu Ala
1               5

<210> SEQ ID NO 229
<211> LENGTH: 458
<212> TYPE: PRT
<213> ORGANISM: Homo sapiens

<400> SEQUENCE: 229

-continued

```
Met Thr Ile Leu Gly Thr Thr Phe Gly Met Val Phe Ser Leu Leu Gln
1               5                   10                  15

Val Val Ser Gly Glu Ser Gly Tyr Ala Gln Asn Gly Asp Leu Glu Asp
            20                  25                  30

Ala Glu Leu Asp Asp Tyr Ser Phe Ser Cys Tyr Ser Gln Leu Glu Val
            35                  40                  45

Asn Gly Ser Gln His Ser Leu Thr Cys Ala Phe Glu Asp Pro Asp Val
        50                  55                  60

Asn Ile Thr Asn Leu Glu Phe Glu Ile Cys Gly Ala Leu Val Glu Val
65                  70                  75                  80

Lys Cys Leu Asn Phe Arg Lys Leu Gln Glu Ile Tyr Phe Ile Glu Thr
                85                  90                  95

Lys Lys Phe Leu Leu Ile Gly Lys Ser Asn Ile Cys Val Lys Val Gly
            100                 105                 110

Glu Lys Ser Leu Thr Cys Lys Lys Ile Asp Leu Thr Thr Ile Val Lys
            115                 120                 125

Pro Glu Ala Pro Phe Asp Leu Ser Val Val Tyr Arg Glu Gly Ala Asn
130                 135                 140

Asp Phe Val Val Thr Phe Asn Thr Ser His Leu Gln Lys Lys Tyr Val
145                 150                 155                 160

Lys Val Leu Met His Asp Val Ala Tyr Arg Gln Glu Lys Asp Glu Asn
                165                 170                 175

Lys Trp Thr His Val Asn Leu Ser Ser Thr Lys Leu Thr Leu Leu Gln
                180                 185                 190

Arg Lys Leu Gln Pro Ala Ala Met Tyr Glu Ile Lys Val Arg Ser Ile
            195                 200                 205

Pro Asp His Tyr Phe Lys Gly Phe Trp Ser Glu Trp Ser Pro Ser Tyr
210                 215                 220

Tyr Phe Arg Thr Pro Glu Ile Asn Asn Ser Ser Gly Glu Met Asp Pro
225                 230                 235                 240

Ile Leu Leu Thr Ile Ser Ile Leu Ser Phe Phe Ser Val Ala Leu Leu
                245                 250                 255

Val Ile Leu Ala Cys Val Leu Trp Lys Lys Arg Ile Lys Pro Ile Val
                260                 265                 270

Trp Pro Ser Leu Pro Asp His Lys Lys Thr Leu Glu His Leu Cys Lys
            275                 280                 285

Lys Pro Arg Lys Asn Leu Asn Val Ser Phe Asn Pro Glu Ser Phe Leu
            290                 295                 300

Asp Cys Gln Ile His Arg Val Asp Asp Ile Gln Ala Arg Asp Glu Val
305                 310                 315                 320

Glu Gly Phe Leu Gln Asp Thr Phe Pro Gln Gln Leu Glu Glu Ser Glu
                325                 330                 335

Lys Gln Arg Leu Gly Gly Asp Val Gln Ser Pro Asn Cys Pro Ser Glu
            340                 345                 350

Asp Val Val Ile Thr Pro Glu Ser Phe Gly Arg Asp Ser Ser Leu Thr
            355                 360                 365

Cys Leu Ala Gly Asn Val Ser Ala Cys Asp Ala Pro Ile Leu Ser Ser
            370                 375                 380

Ser Arg Ser Leu Asp Cys Arg Glu Ser Gly Lys Asn Gly Pro His Val
385                 390                 395                 400

Tyr Gln Asp Leu Leu Leu Ser Leu Gly Thr Thr Asn Ser Thr Leu Pro
                405                 410                 415
```

```
Pro Pro Phe Ser Leu Gln Ser Gly Ile Leu Thr Leu Asn Pro Val Ala
            420                 425                 430

Gln Gly Gln Pro Ile Leu Thr Ser Leu Gly Ser Asn Gln Glu Glu Ala
        435                 440                 445

Tyr Val Thr Met Ser Ser Phe Tyr Gln Asn
        450                 455

<210> SEQ ID NO 230
<211> LENGTH: 723
<212> TYPE: PRT
<213> ORGANISM: Artificial sequence
<220> FEATURE:
<223> OTHER INFORMATION: synthetic GFP - linker - P2A -IL7Ra lncPPCL
      codon(exceptP2A) and splice optimized

<400> SEQUENCE: 230

Met Ser Gly Gly Glu Glu Leu Phe Ala Gly Ile Val Pro Val Leu Ile
1               5                   10                  15

Glu Leu Asp Gly Asp Val His Gly His Lys Phe Ser Val Arg Gly Glu
            20                  25                  30

Gly Glu Gly Asp Ala Asp Tyr Gly Lys Leu Glu Ile Lys Phe Ile Cys
        35                  40                  45

Thr Thr Gly Lys Leu Pro Val Pro Trp Pro Thr Leu Val Thr Thr Leu
    50                  55                  60

Cys Tyr Gly Ile Gln Cys Phe Ala Arg Tyr Pro Glu His Met Lys Met
65                  70                  75                  80

Asn Asp Phe Phe Lys Ser Ala Met Pro Glu Gly Tyr Ile Gln Glu Arg
                85                  90                  95

Thr Ile Gln Phe Gln Asp Asp Gly Lys Tyr Lys Thr Arg Gly Glu Val
            100                 105                 110

Lys Phe Glu Gly Asp Thr Leu Val Asn Arg Ile Glu Leu Lys Gly Lys
        115                 120                 125

Asp Phe Lys Glu Asp Gly Asn Ile Leu Gly His Lys Leu Glu Tyr Ser
    130                 135                 140

Phe Asn Ser His Asn Val Tyr Ile Arg Pro Asp Lys Ala Asn Asn Gly
145                 150                 155                 160

Leu Glu Ala Asn Phe Lys Thr Arg His Asn Ile Glu Gly Gly Gly Val
                165                 170                 175

Gln Leu Ala Asp His Tyr Gln Thr Asn Val Pro Leu Gly Asp Gly Pro
            180                 185                 190

Val Leu Ile Pro Ile Asn His Tyr Leu Ser Thr Gln Thr Lys Ile Ser
        195                 200                 205

Lys Asp Arg Asn Glu Ala Arg Asp His Met Val Leu Leu Glu Ser Phe
    210                 215                 220

Ser Ala Cys Cys His Thr His Gly Met Asp Glu Leu Tyr Arg Gly Ser
225                 230                 235                 240

Gly Ala Thr Asn Phe Ser Leu Leu Lys Gln Ala Gly Asp Val Glu Glu
                245                 250                 255

Asn Pro Gly Pro Met Thr Ile Leu Gly Thr Thr Phe Gly Met Val Phe
            260                 265                 270

Ser Leu Leu Gln Val Val Ser Gly Glu Ser Gly Tyr Ala Gln Asn Gly
        275                 280                 285

Asp Leu Glu Asp Ala Glu Leu Asp Asp Tyr Ser Phe Ser Cys Tyr Ser
    290                 295                 300

Gln Leu Glu Val Asn Gly Ser Gln His Ser Leu Thr Cys Ala Phe Glu
305                 310                 315                 320
```

```
Asp Pro Asp Val Asn Ile Thr Asn Leu Glu Phe Glu Ile Cys Gly Ala
            325                 330                 335

Leu Val Glu Val Lys Cys Leu Asn Phe Arg Lys Leu Gln Glu Ile Tyr
            340                 345                 350

Phe Ile Glu Thr Lys Lys Phe Leu Leu Ile Gly Lys Ser Asn Ile Cys
            355                 360                 365

Val Lys Val Gly Glu Lys Ser Leu Thr Cys Lys Lys Ile Asp Leu Thr
            370                 375                 380

Thr Ile Val Lys Pro Glu Ala Pro Phe Asp Leu Ser Val Val Tyr Arg
385                 390                 395                 400

Glu Gly Ala Asn Asp Phe Val Val Thr Phe Asn Thr Ser His Leu Gln
            405                 410                 415

Lys Lys Tyr Val Lys Val Leu Met His Asp Val Ala Tyr Arg Gln Glu
            420                 425                 430

Lys Asp Glu Asn Lys Trp Thr His Val Asn Leu Ser Ser Thr Lys Leu
            435                 440                 445

Thr Leu Leu Gln Arg Lys Leu Gln Pro Ala Ala Met Tyr Glu Ile Lys
            450                 455                 460

Val Arg Ser Ile Pro Asp His Tyr Phe Lys Gly Phe Trp Ser Glu Trp
465                 470                 475                 480

Ser Pro Ser Tyr Tyr Phe Arg Thr Pro Glu Ile Asn Asn Ser Ser Gly
            485                 490                 495

Glu Met Asp Pro Ile Leu Leu Pro Pro Cys Leu Thr Ile Ser Ile Leu
            500                 505                 510

Ser Phe Phe Ser Val Ala Leu Leu Val Ile Leu Ala Cys Val Leu Trp
            515                 520                 525

Lys Lys Arg Ile Lys Pro Ile Val Trp Pro Ser Leu Pro Asp His Lys
            530                 535                 540

Lys Thr Leu Glu His Leu Cys Lys Lys Pro Arg Lys Asn Leu Asn Val
545                 550                 555                 560

Ser Phe Asn Pro Glu Ser Phe Leu Asp Cys Gln Ile His Arg Val Asp
            565                 570                 575

Asp Ile Gln Ala Arg Asp Glu Val Glu Gly Phe Leu Gln Asp Thr Phe
            580                 585                 590

Pro Gln Gln Leu Glu Glu Ser Glu Lys Gln Arg Leu Gly Gly Asp Val
            595                 600                 605

Gln Ser Pro Asn Cys Pro Ser Glu Asp Val Val Ile Thr Pro Glu Ser
            610                 615                 620

Phe Gly Arg Asp Ser Ser Leu Thr Cys Leu Ala Gly Asn Val Ser Ala
625                 630                 635                 640

Cys Asp Ala Pro Ile Leu Ser Ser Ser Arg Ser Leu Asp Cys Arg Glu
            645                 650                 655

Ser Gly Lys Asn Gly Pro His Val Tyr Gln Asp Leu Leu Leu Ser Leu
            660                 665                 670

Gly Thr Thr Asn Ser Thr Leu Pro Pro Phe Ser Leu Gln Ser Gly
            675                 680                 685

Ile Leu Thr Leu Asn Pro Val Ala Gln Gly Gln Pro Ile Leu Thr Ser
            690                 695                 700

Leu Gly Ser Asn Gln Glu Glu Ala Tyr Val Thr Met Ser Ser Phe Tyr
705                 710                 715                 720

Gln Asn Gln
```

```
<210> SEQ ID NO 231
<211> LENGTH: 733
<212> TYPE: PRT
<213> ORGANISM: Artificial sequence
<220> FEATURE:
<223> OTHER INFORMATION: synthetic GFP - linker - P2A - Myc Tag - IL7Ra
      IncPPCL codon(exceptP2A) and splice optimized

<400> SEQUENCE: 231

Met Ser Gly Gly Glu Glu Leu Phe Ala Gly Ile Val Pro Val Leu Ile
1               5                   10                  15

Glu Leu Asp Gly Asp Val His Gly His Lys Phe Ser Val Arg Gly Glu
            20                  25                  30

Gly Glu Gly Asp Ala Asp Tyr Gly Lys Leu Glu Ile Lys Phe Ile Cys
        35                  40                  45

Thr Thr Gly Lys Leu Pro Val Pro Trp Pro Thr Leu Val Thr Thr Leu
    50                  55                  60

Cys Tyr Gly Ile Gln Cys Phe Ala Arg Tyr Pro Glu His Met Lys Met
65                  70                  75                  80

Asn Asp Phe Phe Lys Ser Ala Met Pro Glu Gly Tyr Ile Gln Glu Arg
                85                  90                  95

Thr Ile Gln Phe Gln Asp Asp Gly Lys Tyr Lys Thr Arg Gly Glu Val
            100                 105                 110

Lys Phe Glu Gly Asp Thr Leu Val Asn Arg Ile Glu Leu Lys Gly Lys
        115                 120                 125

Asp Phe Lys Glu Asp Gly Asn Ile Leu Gly His Lys Leu Glu Tyr Ser
    130                 135                 140

Phe Asn Ser His Asn Val Tyr Ile Arg Pro Asp Lys Ala Asn Asn Gly
145                 150                 155                 160

Leu Glu Ala Asn Phe Lys Thr Arg His Asn Ile Glu Gly Gly Gly Val
                165                 170                 175

Gln Leu Ala Asp His Tyr Gln Thr Asn Val Pro Leu Gly Asp Gly Pro
            180                 185                 190

Val Leu Ile Pro Ile Asn His Tyr Leu Ser Thr Gln Thr Lys Ile Ser
        195                 200                 205

Lys Asp Arg Asn Glu Ala Arg Asp His Met Val Leu Leu Glu Ser Phe
    210                 215                 220

Ser Ala Cys Cys His Thr His Gly Met Asp Glu Leu Tyr Arg Gly Ser
225                 230                 235                 240

Gly Ala Thr Asn Phe Ser Leu Leu Lys Gln Ala Gly Asp Val Glu Glu
                245                 250                 255

Asn Pro Gly Pro Met Thr Ile Leu Gly Thr Thr Phe Gly Met Val Phe
            260                 265                 270

Ser Leu Leu Gln Val Val Ser Gly Glu Gln Lys Leu Ile Ser Glu Glu
        275                 280                 285

Asp Leu Glu Ser Gly Tyr Ala Gln Asn Gly Asp Leu Glu Asp Ala Glu
    290                 295                 300

Leu Asp Asp Tyr Ser Phe Ser Cys Tyr Ser Gln Leu Glu Val Asn Gly
305                 310                 315                 320

Ser Gln His Ser Leu Thr Cys Ala Phe Glu Asp Pro Asp Val Asn Ile
                325                 330                 335

Thr Asn Leu Glu Phe Glu Ile Cys Gly Ala Leu Val Glu Val Lys Cys
            340                 345                 350

Leu Asn Phe Arg Lys Leu Gln Glu Ile Tyr Phe Ile Glu Thr Lys Lys
        355                 360                 365
```

```
Phe Leu Leu Ile Gly Lys Ser Asn Ile Cys Val Lys Val Gly Glu Lys
            370                 375                 380
Ser Leu Thr Cys Lys Lys Ile Asp Leu Thr Thr Ile Val Lys Pro Glu
385                 390                 395                 400
Ala Pro Phe Asp Leu Ser Val Val Tyr Arg Glu Gly Ala Asn Asp Phe
                405                 410                 415
Val Val Thr Phe Asn Thr Ser His Leu Gln Lys Lys Tyr Val Lys Val
                420                 425                 430
Leu Met His Asp Val Ala Tyr Arg Gln Glu Lys Asp Glu Asn Lys Trp
            435                 440                 445
Thr His Val Asn Leu Ser Ser Thr Lys Leu Thr Leu Leu Gln Arg Lys
            450                 455                 460
Leu Gln Pro Ala Ala Met Tyr Glu Ile Lys Val Arg Ser Ile Pro Asp
465                 470                 475                 480
His Tyr Phe Lys Gly Phe Trp Ser Glu Trp Ser Pro Ser Tyr Tyr Phe
                485                 490                 495
Arg Thr Pro Glu Ile Asn Asn Ser Ser Gly Glu Met Asp Pro Ile Leu
                500                 505                 510
Leu Pro Pro Cys Leu Thr Ile Ser Ile Leu Ser Phe Phe Ser Val Ala
                515                 520                 525
Leu Leu Val Ile Leu Ala Cys Val Leu Trp Lys Lys Arg Ile Lys Pro
            530                 535                 540
Ile Val Trp Pro Ser Leu Pro Asp His Lys Lys Thr Leu Glu His Leu
545                 550                 555                 560
Cys Lys Lys Pro Arg Lys Asn Leu Asn Val Ser Phe Asn Pro Glu Ser
                565                 570                 575
Phe Leu Asp Cys Gln Ile His Arg Val Asp Asp Ile Gln Ala Arg Asp
                580                 585                 590
Glu Val Glu Gly Phe Leu Gln Asp Thr Phe Pro Gln Gln Leu Glu Glu
            595                 600                 605
Ser Glu Lys Gln Arg Leu Gly Gly Asp Val Gln Ser Pro Asn Cys Pro
            610                 615                 620
Ser Glu Asp Val Val Ile Thr Pro Glu Ser Phe Gly Arg Asp Ser Ser
625                 630                 635                 640
Leu Thr Cys Leu Ala Gly Asn Val Ser Ala Cys Asp Ala Pro Ile Leu
                645                 650                 655
Ser Ser Ser Arg Ser Leu Asp Cys Arg Glu Ser Gly Lys Asn Gly Pro
                660                 665                 670
His Val Tyr Gln Asp Leu Leu Leu Ser Leu Gly Thr Thr Asn Ser Thr
            675                 680                 685
Leu Pro Pro Pro Phe Ser Leu Gln Ser Gly Ile Leu Thr Leu Asn Pro
690                 695                 700
Val Ala Gln Gly Gln Pro Ile Leu Thr Ser Leu Gly Ser Asn Gln Glu
705                 710                 715                 720
Glu Ala Tyr Val Thr Met Ser Ser Phe Tyr Gln Asn Gln
                725                 730

<210> SEQ ID NO 232
<211> LENGTH: 572
<212> TYPE: PRT
<213> ORGANISM: Artificial sequence
<220> FEATURE:
<223> OTHER INFORMATION: synthetic GFP - linker - P2A - IL7RaSP - Myc
      Tag - IL7RaIncPPCL C-terminal truncation codon(exceptP2A) and
      splice
```

```
<400> SEQUENCE: 232

Met Ser Gly Gly Glu Glu Leu Phe Ala Gly Ile Val Pro Val Leu Ile
1               5                   10                  15

Glu Leu Asp Gly Asp Val His Gly His Lys Phe Ser Val Arg Gly Glu
            20                  25                  30

Gly Glu Gly Asp Ala Asp Tyr Gly Lys Leu Glu Ile Lys Phe Ile Cys
        35                  40                  45

Thr Thr Gly Lys Leu Pro Val Pro Trp Pro Thr Leu Val Thr Thr Leu
    50                  55                  60

Cys Tyr Gly Ile Gln Cys Phe Ala Arg Tyr Pro Glu His Met Lys Met
65                  70                  75                  80

Asn Asp Phe Phe Lys Ser Ala Met Pro Glu Gly Tyr Ile Gln Glu Arg
                85                  90                  95

Thr Ile Gln Phe Gln Asp Gly Lys Tyr Lys Thr Arg Gly Glu Val
            100                 105                 110

Lys Phe Glu Gly Asp Thr Leu Val Asn Arg Ile Glu Leu Lys Gly Lys
        115                 120                 125

Asp Phe Lys Glu Asp Gly Asn Ile Leu Gly His Lys Leu Glu Tyr Ser
    130                 135                 140

Phe Asn Ser His Asn Val Tyr Ile Arg Pro Asp Lys Ala Asn Asn Gly
145                 150                 155                 160

Leu Glu Ala Asn Phe Lys Thr Arg His Asn Ile Glu Gly Gly Gly Val
                165                 170                 175

Gln Leu Ala Asp His Tyr Gln Thr Asn Val Pro Leu Gly Asp Gly Pro
            180                 185                 190

Val Leu Ile Pro Ile Asn His Tyr Leu Ser Thr Gln Thr Lys Ile Ser
        195                 200                 205

Lys Asp Arg Asn Glu Ala Arg Asp His Met Val Leu Leu Glu Ser Phe
    210                 215                 220

Ser Ala Cys Cys His Thr His Gly Met Asp Glu Leu Tyr Arg Gly Ser
225                 230                 235                 240

Gly Ala Thr Asn Phe Ser Leu Leu Lys Gln Ala Gly Asp Val Glu Glu
                245                 250                 255

Asn Pro Gly Pro Met Thr Ile Leu Gly Thr Thr Phe Gly Met Val Phe
            260                 265                 270

Ser Leu Leu Gln Val Val Ser Gly Glu Gln Lys Leu Ile Ser Glu Glu
        275                 280                 285

Asp Leu Glu Ser Gly Tyr Ala Gln Asn Gly Asp Leu Glu Asp Ala Glu
    290                 295                 300

Leu Asp Asp Tyr Ser Phe Ser Cys Tyr Ser Gln Leu Glu Val Asn Gly
305                 310                 315                 320

Ser Gln His Ser Leu Thr Cys Ala Phe Glu Asp Pro Asp Val Asn Ile
                325                 330                 335

Thr Asn Leu Glu Phe Glu Ile Cys Gly Ala Leu Val Glu Val Lys Cys
            340                 345                 350

Leu Asn Phe Arg Lys Leu Gln Glu Ile Tyr Phe Ile Glu Thr Lys Lys
        355                 360                 365

Phe Leu Leu Ile Gly Lys Ser Asn Ile Cys Val Lys Val Gly Glu Lys
    370                 375                 380

Ser Leu Thr Cys Lys Lys Ile Asp Leu Thr Thr Ile Val Lys Pro Glu
385                 390                 395                 400

Ala Pro Phe Asp Leu Ser Val Val Tyr Arg Glu Gly Ala Asn Asp Phe
                405                 410                 415
```

```
Val Val Thr Phe Asn Thr Ser His Leu Gln Lys Lys Tyr Val Lys Val
            420                 425                 430

Leu Met His Asp Val Ala Tyr Arg Gln Glu Lys Asp Glu Asn Lys Trp
        435                 440                 445

Thr His Val Asn Leu Ser Ser Thr Lys Leu Thr Leu Leu Gln Arg Lys
450                 455                 460

Leu Gln Pro Ala Ala Met Tyr Glu Ile Lys Val Arg Ser Ile Pro Asp
465                 470                 475                 480

His Tyr Phe Lys Gly Phe Trp Ser Glu Trp Ser Pro Ser Tyr Tyr Phe
                485                 490                 495

Arg Thr Pro Glu Ile Asn Asn Ser Ser Gly Glu Met Asp Pro Ile Leu
            500                 505                 510

Leu Pro Pro Cys Leu Thr Ile Ser Ile Leu Ser Phe Phe Ser Val Ala
        515                 520                 525

Leu Leu Val Ile Leu Ala Cys Val Leu Trp Lys Lys Arg Ile Lys Pro
530                 535                 540

Ile Val Trp Pro Ser Leu Pro Asp His Lys Lys Thr Leu Glu His Leu
545                 550                 555                 560

Cys Lys Lys Pro Arg Lys Val Ser Val Phe Gly Ala
                565                 570

<210> SEQ ID NO 233
<211> LENGTH: 562
<212> TYPE: PRT
<213> ORGANISM: Artificial sequence
<220> FEATURE:
<223> OTHER INFORMATION: synthetic GFP - linker - P2A - IL7RaSP -
      IL7RaIncPPCL C-terminal truncation codon(exceptP2A) and splice
      optimized

<400> SEQUENCE: 233

Met Ser Gly Gly Glu Glu Leu Phe Ala Gly Ile Val Pro Val Leu Ile
1               5                   10                  15

Glu Leu Asp Gly Asp Val His Gly His Lys Phe Ser Val Arg Gly Glu
            20                  25                  30

Gly Glu Gly Asp Ala Asp Tyr Gly Lys Leu Glu Ile Lys Phe Ile Cys
        35                  40                  45

Thr Thr Gly Lys Leu Pro Val Pro Trp Pro Thr Leu Val Thr Thr Leu
50                  55                  60

Cys Tyr Gly Ile Gln Cys Phe Ala Arg Tyr Pro Glu His Met Lys Met
65                  70                  75                  80

Asn Asp Phe Phe Lys Ser Ala Met Pro Glu Gly Tyr Ile Gln Glu Arg
                85                  90                  95

Thr Ile Gln Phe Gln Asp Asp Gly Lys Tyr Lys Thr Arg Gly Glu Val
            100                 105                 110

Lys Phe Glu Gly Asp Thr Leu Val Asn Arg Ile Glu Leu Lys Gly Lys
        115                 120                 125

Asp Phe Lys Glu Asp Gly Asn Ile Leu Gly His Lys Leu Glu Tyr Ser
130                 135                 140

Phe Asn Ser His Asn Val Tyr Ile Arg Pro Asp Lys Ala Asn Asn Gly
145                 150                 155                 160

Leu Glu Ala Asn Phe Lys Thr Arg His Asn Ile Glu Gly Gly Gly Val
                165                 170                 175

Gln Leu Ala Asp His Tyr Gln Thr Asn Val Pro Leu Gly Asp Gly Pro
            180                 185                 190
```

Val Leu Ile Pro Ile Asn His Tyr Leu Ser Thr Gln Thr Lys Ile Ser
            195                 200                 205

Lys Asp Arg Asn Glu Ala Arg Asp His Met Val Leu Leu Glu Ser Phe
210                 215                 220

Ser Ala Cys Cys His Thr His Gly Met Asp Glu Leu Tyr Arg Gly Ser
225                 230                 235                 240

Gly Ala Thr Asn Phe Ser Leu Leu Lys Gln Ala Gly Asp Val Glu Glu
                245                 250                 255

Asn Pro Gly Pro Met Thr Ile Leu Gly Thr Thr Phe Gly Met Val Phe
            260                 265                 270

Ser Leu Leu Gln Val Val Ser Gly Glu Ser Gly Tyr Ala Gln Asn Gly
        275                 280                 285

Asp Leu Glu Asp Ala Glu Leu Asp Asp Tyr Ser Phe Ser Cys Tyr Ser
290                 295                 300

Gln Leu Glu Val Asn Gly Ser Gln His Ser Leu Thr Cys Ala Phe Glu
305                 310                 315                 320

Asp Pro Asp Val Asn Ile Thr Asn Leu Glu Phe Glu Ile Cys Gly Ala
                325                 330                 335

Leu Val Glu Val Lys Cys Leu Asn Phe Arg Lys Leu Gln Glu Ile Tyr
            340                 345                 350

Phe Ile Glu Thr Lys Lys Phe Leu Leu Ile Gly Lys Ser Asn Ile Cys
        355                 360                 365

Val Lys Val Gly Glu Lys Ser Leu Thr Cys Lys Lys Ile Asp Leu Thr
370                 375                 380

Thr Ile Val Lys Pro Glu Ala Pro Phe Asp Leu Ser Val Val Tyr Arg
385                 390                 395                 400

Glu Gly Ala Asn Asp Phe Val Val Thr Phe Asn Thr Ser His Leu Gln
                405                 410                 415

Lys Lys Tyr Val Lys Val Leu Met His Asp Val Ala Tyr Arg Gln Glu
            420                 425                 430

Lys Asp Glu Asn Lys Trp Thr His Val Asn Leu Ser Ser Thr Lys Leu
        435                 440                 445

Thr Leu Leu Gln Arg Lys Leu Gln Pro Ala Ala Met Tyr Glu Ile Lys
450                 455                 460

Val Arg Ser Ile Pro Asp His Tyr Phe Lys Gly Phe Trp Ser Glu Trp
465                 470                 475                 480

Ser Pro Ser Tyr Tyr Phe Arg Thr Pro Glu Ile Asn Asn Ser Ser Gly
                485                 490                 495

Glu Met Asp Pro Ile Leu Leu Pro Pro Cys Leu Thr Ile Ser Ile Leu
            500                 505                 510

Ser Phe Phe Ser Val Ala Leu Leu Val Ile Leu Ala Cys Val Leu Trp
        515                 520                 525

Lys Lys Arg Ile Lys Pro Ile Val Trp Pro Ser Leu Pro Asp His Lys
530                 535                 540

Lys Thr Leu Glu His Leu Cys Lys Lys Pro Arg Lys Val Ser Val Phe
545                 550                 555                 560

Gly Ala

<210> SEQ ID NO 234
<211> LENGTH: 824
<212> TYPE: PRT
<213> ORGANISM: Artificial sequence
<220> FEATURE:
<223> OTHER INFORMATION: synthetic GFP - linker - P2A - eTag -
     IL7RaIncPPCL N-terminal deletion codon(exceptP2A) and splice optimized

<400> SEQUENCE: 234

Met Ser Gly Gly Glu Leu Phe Ala Gly Ile Val Pro Val Leu Ile
1               5                   10                  15

Glu Leu Asp Gly Asp Val His Gly His Lys Phe Ser Val Arg Gly Glu
            20                  25                  30

Gly Glu Gly Asp Ala Asp Tyr Gly Lys Leu Glu Ile Lys Phe Ile Cys
        35                  40                  45

Thr Thr Gly Lys Leu Pro Val Pro Trp Pro Thr Leu Val Thr Thr Leu
    50                  55                  60

Cys Tyr Gly Ile Gln Cys Phe Ala Arg Tyr Pro Glu His Met Lys Met
65                  70                  75                  80

Asn Asp Phe Phe Lys Ser Ala Met Pro Glu Gly Tyr Ile Gln Glu Arg
                85                  90                  95

Thr Ile Gln Phe Gln Asp Asp Gly Lys Tyr Lys Thr Arg Gly Glu Val
            100                 105                 110

Lys Phe Glu Gly Asp Thr Leu Val Asn Arg Ile Glu Leu Lys Gly Lys
        115                 120                 125

Asp Phe Lys Glu Asp Gly Asn Ile Leu Gly His Lys Leu Glu Tyr Ser
130                 135                 140

Phe Asn Ser His Asn Val Tyr Ile Arg Pro Asp Lys Ala Asn Asn Gly
145                 150                 155                 160

Leu Glu Ala Asn Phe Lys Thr Arg His Asn Ile Glu Gly Gly Gly Val
                165                 170                 175

Gln Leu Ala Asp His Tyr Gln Thr Asn Val Pro Leu Gly Asp Gly Pro
            180                 185                 190

Val Leu Ile Pro Ile Asn His Tyr Leu Ser Thr Gln Thr Lys Ile Ser
        195                 200                 205

Lys Asp Arg Asn Glu Ala Arg Asp His Met Val Leu Leu Glu Ser Phe
210                 215                 220

Ser Ala Cys Cys His Thr His Gly Met Asp Glu Leu Tyr Arg Gly Ser
225                 230                 235                 240

Gly Ala Thr Asn Phe Ser Leu Leu Lys Gln Ala Gly Asp Val Glu Glu
                245                 250                 255

Asn Pro Gly Pro Met Leu Leu Leu Val Thr Ser Leu Leu Leu Cys Glu
            260                 265                 270

Leu Pro His Pro Ala Phe Leu Leu Ile Pro Arg Lys Val Cys Asn Gly
        275                 280                 285

Ile Gly Ile Gly Glu Phe Lys Asp Ser Leu Ser Ile Asn Ala Thr Asn
    290                 295                 300

Ile Lys His Phe Lys Asn Cys Thr Ser Ile Ser Gly Asp Leu His Ile
305                 310                 315                 320

Leu Pro Val Ala Phe Arg Gly Asp Ser Phe Thr His Thr Pro Pro Leu
                325                 330                 335

Asp Pro Gln Glu Leu Asp Ile Leu Lys Thr Val Lys Glu Ile Thr Gly
            340                 345                 350

Phe Leu Leu Ile Gln Ala Trp Pro Glu Asn Arg Thr Asp Leu His Ala
        355                 360                 365

Phe Glu Asn Leu Glu Ile Ile Arg Gly Arg Thr Lys Gln His Gly Gln
    370                 375                 380

Phe Ser Leu Ala Val Val Ser Leu Asn Ile Thr Ser Leu Gly Leu Arg
385                 390                 395                 400

```
Ser Leu Lys Glu Ile Ser Asp Gly Asp Val Ile Ile Ser Gly Asn Lys
            405                 410                 415

Asn Leu Cys Tyr Ala Asn Thr Ile Asn Trp Lys Lys Leu Phe Gly Thr
        420                 425                 430

Ser Gly Gln Lys Thr Lys Ile Ile Ser Asn Arg Gly Glu Asn Ser Cys
            435                 440                 445

Lys Ala Thr Gly Gln Val Cys His Ala Leu Cys Ser Pro Glu Gly Cys
        450                 455                 460

Trp Gly Pro Glu Pro Arg Asp Cys Val Ser Cys Arg Asn Val Ser Arg
465                 470                 475                 480

Gly Arg Glu Cys Val Asp Lys Cys Asn Leu Leu Glu Gly Glu Pro Arg
            485                 490                 495

Glu Phe Val Glu Asn Ser Glu Cys Ile Gln Cys His Pro Glu Cys Leu
        500                 505                 510

Pro Gln Ala Met Asn Ile Thr Cys Thr Gly Arg Gly Pro Asp Asn Cys
            515                 520                 525

Ile Gln Cys Ala His Tyr Ile Asp Gly Pro His Cys Val Lys Thr Cys
        530                 535                 540

Pro Ala Gly Val Met Gly Glu Asn Asn Thr Leu Val Trp Lys Tyr Ala
545                 550                 555                 560

Asp Ala Gly His Val Cys His Leu Cys His Pro Asn Cys Thr Tyr Gly
            565                 570                 575

Cys Thr Gly Pro Gly Leu Glu Gly Cys Pro Thr Asn Gly Pro Glu Ile
        580                 585                 590

Asn Asn Ser Ser Gly Glu Met Asp Pro Ile Leu Leu Pro Pro Cys Leu
            595                 600                 605

Thr Ile Ser Ile Leu Ser Phe Phe Ser Val Ala Leu Leu Val Ile Leu
        610                 615                 620

Ala Cys Val Leu Trp Lys Lys Arg Ile Lys Pro Ile Val Trp Pro Ser
625                 630                 635                 640

Leu Pro Asp His Lys Lys Thr Leu Glu His Leu Cys Lys Lys Pro Arg
            645                 650                 655

Lys Asn Leu Asn Val Ser Phe Asn Pro Glu Ser Phe Leu Asp Cys Gln
        660                 665                 670

Ile His Arg Val Asp Asp Ile Gln Ala Arg Asp Glu Val Glu Gly Phe
            675                 680                 685

Leu Gln Asp Thr Phe Pro Gln Gln Leu Glu Glu Ser Glu Lys Gln Arg
        690                 695                 700

Leu Gly Gly Asp Val Gln Ser Pro Asn Cys Pro Ser Glu Asp Val Val
705                 710                 715                 720

Ile Thr Pro Glu Ser Phe Gly Arg Asp Ser Ser Leu Thr Cys Leu Ala
            725                 730                 735

Gly Asn Val Ser Ala Cys Asp Ala Pro Ile Leu Ser Ser Ser Arg Ser
        740                 745                 750

Leu Asp Cys Arg Glu Ser Gly Lys Asn Gly Pro His Val Tyr Gln Asp
            755                 760                 765

Leu Leu Leu Ser Leu Gly Thr Thr Asn Ser Thr Leu Pro Pro Pro Phe
        770                 775                 780

Ser Leu Gln Ser Gly Ile Leu Thr Leu Asn Pro Val Ala Gln Gly Gln
785                 790                 795                 800

Pro Ile Leu Thr Ser Leu Gly Ser Asn Gln Glu Glu Ala Tyr Val Thr
            805                 810                 815

Met Ser Ser Phe Tyr Gln Asn Gln
```

<210> SEQ ID NO 235
<211> LENGTH: 593
<212> TYPE: PRT
<213> ORGANISM: Artificial sequence
<220> FEATURE:
<223> OTHER INFORMATION: synthetic MV(ed)-HD24

<400> SEQUENCE: 235

```
Met Asn Arg Glu His Leu Met Ile Asp Arg Pro Tyr Val Leu Leu Ala
1               5                   10                  15

Val Leu Phe Val Met Ser Leu Ser Leu Ile Gly Leu Leu Ala Ile Ala
            20                  25                  30

Gly Ile Arg Leu His Arg Ala Ala Ile Tyr Thr Ala Glu Ile His Lys
        35                  40                  45

Ser Leu Ser Thr Asn Leu Asp Val Thr Asn Ser Ile Glu His Gln Val
    50                  55                  60

Lys Asp Val Leu Thr Pro Leu Phe Lys Ile Ile Gly Asp Glu Val Gly
65                  70                  75                  80

Leu Arg Thr Pro Gln Arg Phe Thr Asp Leu Val Lys Phe Ile Ser Asp
                85                  90                  95

Lys Ile Lys Phe Leu Asn Pro Asp Arg Glu Tyr Asp Phe Arg Asp Leu
            100                 105                 110

Thr Trp Cys Ile Asn Pro Pro Glu Arg Ile Lys Leu Asp Tyr Asp Gln
        115                 120                 125

Tyr Cys Ala Asp Val Ala Ala Glu Glu Leu Met Asn Ala Leu Val Asn
    130                 135                 140

Ser Thr Leu Leu Glu Thr Arg Thr Thr Asn Gln Phe Leu Ala Val Ser
145                 150                 155                 160

Lys Gly Asn Cys Ser Gly Pro Thr Thr Ile Arg Gly Gln Phe Ser Asn
                165                 170                 175

Met Ser Leu Ser Leu Leu Asp Leu Tyr Leu Ser Arg Gly Tyr Asn Val
            180                 185                 190

Ser Ser Ile Val Thr Met Thr Ser Gln Gly Met Tyr Gly Gly Thr Tyr
        195                 200                 205

Leu Val Glu Lys Pro Asn Leu Ser Ser Lys Arg Ser Glu Leu Ser Gln
    210                 215                 220

Leu Ser Met Tyr Arg Val Phe Glu Val Gly Val Ile Arg Asn Pro Gly
225                 230                 235                 240

Leu Gly Ala Pro Val Phe His Met Thr Asn Tyr Leu Glu Gln Pro Val
                245                 250                 255

Ser Asn Asp Leu Ser Asn Cys Met Val Ala Leu Gly Glu Leu Lys Leu
            260                 265                 270

Ala Ala Leu Cys His Gly Glu Asp Ser Ile Thr Ile Pro Tyr Gln Gly
        275                 280                 285

Ser Gly Lys Gly Val Ser Phe Gln Leu Val Lys Leu Gly Val Trp Lys
    290                 295                 300

Ser Pro Thr Asp Met Gln Ser Trp Val Pro Leu Ser Thr Asp Asp Pro
305                 310                 315                 320

Val Ile Asp Arg Leu Tyr Leu Ser Ser His Arg Gly Val Ile Ala Asp
                325                 330                 335

Asn Gln Ala Lys Trp Ala Val Pro Thr Thr Arg Thr Asp Asp Lys Leu
            340                 345                 350

Arg Met Glu Thr Cys Phe Gln Gln Ala Cys Lys Gly Lys Ile Gln Ala
```

| | 355 | | | | 360 | | | | 365 | | |
|---|---|---|---|---|---|---|---|---|---|---|---|
| Leu | Cys | Glu | Asn | Pro | Glu | Trp | Ala | Pro | Leu | Lys | Asp | Asn | Arg | Ile | Pro |
| | | | 370 | | | | | 375 | | | | | 380 | | |

Ser Tyr Gly Val Leu Ser Val Asp Leu Ser Leu Thr Val Glu Leu Lys
385                 390                 395                 400

Ile Lys Ile Ala Ser Gly Phe Gly Pro Leu Ile Thr His Gly Ser Gly
                405                 410                 415

Met Asp Leu Tyr Lys Ser Asn His Asn Asn Val Tyr Trp Leu Thr Ile
            420                 425                 430

Pro Pro Met Lys Asn Leu Ala Leu Gly Val Ile Asn Thr Leu Glu Trp
        435                 440                 445

Ile Pro Arg Phe Lys Val Ser Pro Asn Leu Phe Thr Val Pro Ile Lys
    450                 455                 460

Glu Ala Gly Glu Asp Cys His Ala Pro Thr Tyr Leu Pro Ala Glu Val
465                 470                 475                 480

Asp Gly Asp Val Lys Leu Ser Ser Asn Leu Val Ile Leu Pro Gly Gln
                485                 490                 495

Asp Leu Gln Tyr Val Leu Ala Thr Tyr Asp Thr Ser Arg Val Glu His
            500                 505                 510

Ala Val Val Tyr Tyr Val Tyr Ser Pro Gly Arg Ser Phe Ser Tyr Phe
        515                 520                 525

Tyr Pro Phe Arg Leu Pro Ile Lys Gly Val Pro Ile Glu Leu Gln Val
    530                 535                 540

Glu Cys Phe Thr Trp Asp Gln Lys Leu Trp Cys Arg His Phe Cys Val
545                 550                 555                 560

Leu Ala Asp Ser Glu Ser Gly Gly His Ile Thr His Ser Gly Met Val
                565                 570                 575

Gly Met Gly Val Ser Cys Thr Val Thr Arg Glu Asp Gly Thr Asn Arg
            580                 585                 590

Arg

<210> SEQ ID NO 236
<211> LENGTH: 1275
<212> TYPE: DNA
<213> ORGANISM: Mesoplasma florum

<400> SEQUENCE: 236

```
aaaaaaaata aaatcaatag caaatattaa gatttttaag aaataaaaaa ttaatattaa      60
tttacaactg aatataaaag aaacttatac agggtagcat aatgggctac tgaccccgcc     120
ttcaaaccta tttggagact ataagtgaaa aaccactctt taattattaa agtttctttt     180
tatgtccaaa agacaagaag aaactttttt atttagttga atttataata agagaaaaag     240
aaaggatatt atatggcaaa aataaaaaac caatattaca acgagtctgt ttcgccaatt     300
gaatatgcgc aacaaggatt taaggaaaaa atgcgttcag taaactgaaa cgtagtaaat     360
gatgaaaaag atttagaggt atgaaataga attacacaaa acttctgatt gcctgaaaaa     420
attccagttt caaatgattt aacttcatga agaactttga caccagaatg acaagaatta     480
attacaagaa cttttacagg attaacattg ttagataaca ttcaagctac tgttggtgat     540
gtggctcaag ttcctaactc attaactgac catgaacaag taatttacac aaactttgca     600
tttatggttg cagttcacgc tagatcatat ggttcaatct tttcaacttt atgttcaagt     660
gaacaaattg aagaggctca tgaatgagtt atcaatacag aaacattaca agaaagagct     720
aaagcattaa ttccttatta tgtgaatgat gacccttta a agtcaaaagt tgcagctgct     780
```

-continued

```
ttaatgccag gcttcttatt atatggaggc ttctatttac cattttacct atcagctaga    840
ggtaaattac caaacacttc agatattatt agattaatat taagagataa agttatacat    900
aactactata gtggttataa atatcaaaag aaagttgcta aactttctcc agaaaaacaa    960
gctgaaatga aagaatttgt ttttaaatta ttatatgaat taatagattt agaaaaagct   1020
tatttgaaag aattgtatga ggattttgga ttagctgatg atgctattag atttagtgtt   1080
tacaacgcag gtaaattttt acaaaattta ggttatgatt caccgtttac agaagaagaa   1140
acaagaattg agccagaaat attcacacaa ttatcagcta gagctgatga aaaccatgat   1200
ttcttttcag ggaatggctc atcatatatt atgggagttt cagaagaaac tgaagatgac   1260
gattgggagt tttaa                                                    1275
```

<210> SEQ ID NO 237
<211> LENGTH: 64
<212> TYPE: RNA
<213> ORGANISM: Mesoplasma florum

<400> SEQUENCE: 237

```
acuuauacag gguagcauaa ugggcuacug accccgccuu caaaccuauu uggagacuau    60
aagu                                                                 64
```

<210> SEQ ID NO 238
<211> LENGTH: 69
<212> TYPE: RNA
<213> ORGANISM: Artificial sequence
<220> FEATURE:
<223> OTHER INFORMATION: synthetic Deoxyguanosine riboswitch aptamer
      mutations
<220> FEATURE:
<221> NAME/KEY: misc_feature
<222> LOCATION: (10)..(13)
<223> OTHER INFORMATION: n at positions 10-13 can be A, C, G, or T
<220> FEATURE:
<221> NAME/KEY: misc_feature
<222> LOCATION: (27)..(29)
<223> OTHER INFORMATION: n at positions 27-29 can be A, C, G, or T
<220> FEATURE:
<221> NAME/KEY: misc_feature
<222> LOCATION: (31)..(32)
<223> OTHER INFORMATION: n at positions 31-32 can be A, C, G, or T
<220> FEATURE:
<221> NAME/KEY: misc_feature
<222> LOCATION: (33)..(40)
<223> OTHER INFORMATION: n at positions 33-40 can be A, C, G, T, or no
      nucleotide
<220> FEATURE:
<221> NAME/KEY: misc_feature
<222> LOCATION: (44)..(46)
<223> OTHER INFORMATION: n at positions 44-46 can be A, C, G, or T
<220> FEATURE:
<221> NAME/KEY: misc_feature
<222> LOCATION: (57)..(59)
<223> OTHER INFORMATION: n at positions 57-59 can be A, C, G, or T

<400> SEQUENCE: 238
acuuauacan nnnagcauaa ugggcunnng nnnnnnnnnn gccnnnaaac cuauuunnng    60
acuauaagu                                                            69
```

<210> SEQ ID NO 239
<211> LENGTH: 84
<212> TYPE: DNA
<213> ORGANISM: Artificial sequence
<220> FEATURE:
<223> OTHER INFORMATION: synthetic Oligo library for screen
<220> FEATURE:

```
<221> NAME/KEY: misc_feature
<222> LOCATION: (19)..(21)
<223> OTHER INFORMATION: n at positions 19-21 can be A, C, G, or T
<220> FEATURE:
<221> NAME/KEY: misc_feature
<222> LOCATION: (32)..(34)
<223> OTHER INFORMATION: n at positions 32-34 can be A, C, G, or T
<220> FEATURE:
<221> NAME/KEY: misc_feature
<222> LOCATION: (38)..(39)
<223> OTHER INFORMATION: n at positions 38-39 can be A, C, G, or T
<220> FEATURE:
<221> NAME/KEY: misc_feature
<222> LOCATION: (40)..(47)
<223> OTHER INFORMATION: n at positions 40-47 can be A, C, G, T, or no
      nucleotide
<220> FEATURE:
<221> NAME/KEY: misc_feature
<222> LOCATION: (49)..(51)
<223> OTHER INFORMATION: n at positions 49-51 can be A, C, G, or T
<220> FEATURE:
<221> NAME/KEY: misc_feature
<222> LOCATION: (65)..(68)
<223> OTHER INFORMATION: n at positions 65-68 can be A, C, G, or T

<400> SEQUENCE: 239
cgcgcgacac ttatagtcnn naaataggtt tnnnggcnnn nnnnnnncnn nagcccatta      60
tgctnnnntg tataagtgcc gccc                                            84

<210> SEQ ID NO 240
<211> LENGTH: 33
<212> TYPE: DNA
<213> ORGANISM: Artificial sequence
<220> FEATURE:
<223> OTHER INFORMATION: synthetic T7 promoter amplification primer

<400> SEQUENCE: 240
taatacgact cactataggg cggcacttat aca                                  33

<210> SEQ ID NO 241
<211> LENGTH: 18
<212> TYPE: DNA
<213> ORGANISM: Artificial sequence
<220> FEATURE:
<223> OTHER INFORMATION: synthetic Reverse amplification primer

<400> SEQUENCE: 241
cgcgcgacac ttatagtc                                                   18

<210> SEQ ID NO 242
<211> LENGTH: 915
<212> TYPE: DNA
<213> ORGANISM: Bacillus subtilis

<400> SEQUENCE: 242
tcaaaagcct ggcggcgcgg tcgtcagact cttttatatc gaatccccctt gaaatacgaa     60 tgatatctaa aaaacaaaa ttaaagttcg ggaattttta ttttcagcct atgcaagaga     120
ttagaatctt gatataattt attacaatat aataggaaca ctcatataat cgcgtggata    180
tggcacgcaa gtttctaccg ggcaccgtaa atgtccgact atgggtgagc aatggaaccg    240
cacgtgtacg gttttttgtg atatcagcat tgcttgctct ttatttgagc gggcaatgct    300 tttttttattc tcataacgga ggtagacagg atggaagcac tgaaacggaa aatagaggaa    360
gaaggcgtcg tattatctga tcaggtattg aaagtggatt cttttttgaa tcaccaaatt    420
gatccgctgc ttatgcagag aattggtgat gaatttgcgt ctaggtttgc aaaagacggt    480
```

```
attaccaaaa ttgtgacaat cgaatcatca ggtatcgctc ccgctgtaat gacgggcttg    540
aagctgggtg tgccagttgt cttcgcgaga aagcataaat cgttaacact caccgacaac    600
ttgctgacag cgtctgttta ttcctttacg aagcaaacag aaagccaaat cgcagtgtct    660
gggacccacc tgtcggatca ggatcatgtg ctgattatcg atgattttt ggcaaatgga    720 caggcagcgc acgggcttgt gtcgattgtg aagcaagcgg gagcttctat tgcgggaatc    780
ggcattgtta ttgaaaagtc atttcagccg ggaagagatg aacttgtaaa actgggctac    840
cgagtggaat ctttggcaag aattcagtct ttagaagaag gaaaagtgtc cttcgtacag    900
gaggttcatt catga                                                     915
```

```
<210> SEQ ID NO 243
<211> LENGTH: 69
<212> TYPE: RNA
<213> ORGANISM: Bacillus subtilis

<400> SEQUENCE: 243
cacucauaua aucgcgugga uauggcacgc aaguuucuac cgggcaccgu aaauguccga    60
cuaugggug                                                            69

<210> SEQ ID NO 244
<211> LENGTH: 74
<212> TYPE: RNA
<213> ORGANISM: Artificial sequence
<220> FEATURE:
<223> OTHER INFORMATION: synthetic Guanosine xpt riboswitch aptamer
      mutations
<220> FEATURE:
<221> NAME/KEY: misc_feature
<222> LOCATION: (11)..(14)
<223> OTHER INFORMATION: n at positions 11-14 can be A, C, G, or T
<220> FEATURE:
<221> NAME/KEY: misc_feature
<222> LOCATION: (30)..(35)
<223> OTHER INFORMATION: n at positions 30-35 can be A, C, G, or T
<220> FEATURE:
<221> NAME/KEY: misc_feature
<222> LOCATION: (36)..(43)
<223> OTHER INFORMATION: n at positions 36-43 can be A, C, G, T, or no
      nucleotide
<220> FEATURE:
<221> NAME/KEY: misc_feature
<222> LOCATION: (47)..(49)
<223> OTHER INFORMATION: n at positions 47-49 can be A, C, G, or T
<220> FEATURE:
<221> NAME/KEY: misc_feature
<222> LOCATION: (61)..(63)
<223> OTHER INFORMATION: n at positions 61-63 can be A, C, G, or T

<400> SEQUENCE: 244
cacucauaua nnnncgugga uauggcacgn nngnnnnnnn nnnaccnnnu accguaaaug    60
nnngacuaug ggug                                                      74

<210> SEQ ID NO 245
<211> LENGTH: 89
<212> TYPE: DNA
<213> ORGANISM: Artificial sequence
<220> FEATURE:
<223> OTHER INFORMATION: synthetic Oligo library for screen
<220> FEATURE:
<221> NAME/KEY: misc_feature
<222> LOCATION: (20)..(22)
<223> OTHER INFORMATION: n at positions 20-22 can be A, C, G, or T
<220> FEATURE:
<221> NAME/KEY: misc_feature
<222> LOCATION: (34)..(36)
<223> OTHER INFORMATION: n at positions 34-36 can be A, C, G, or T
```

```
<220> FEATURE:
<221> NAME/KEY: misc_feature
<222> LOCATION: (40)..(41)
<223> OTHER INFORMATION: n at positions 40-41 can be A, C, G, or T
<220> FEATURE:
<221> NAME/KEY: misc_feature
<222> LOCATION: (42)..(49)
<223> OTHER INFORMATION: n at positions 42-49 can be A, C, G, T, or no
      nucleotide
<220> FEATURE:
<221> NAME/KEY: misc_feature
<222> LOCATION: (51)..(53)
<223> OTHER INFORMATION: n at positions 51-53 can be A, C, G, or T
<220> FEATURE:
<221> NAME/KEY: misc_feature
<222> LOCATION: (69)..(72)
<223> OTHER INFORMATION: n at positions 69-72 can be A, C, G, or T

<400> SEQUENCE: 245
cgcgcgacca cccatagtcn nncatttacg gtgnnnggtn nnnnnnnnnc nnncgtgcca        60
tatccacgnn nntatatgag tggccgccc                                         89

<210> SEQ ID NO 246
<211> LENGTH: 34
<212> TYPE: DNA
<213> ORGANISM: Artificial sequence
<220> FEATURE:
<223> OTHER INFORMATION: synthetic T7 promoter amplification primer

<400> SEQUENCE: 246
taatacgact cactataggg cggccactca tata                                   34

<210> SEQ ID NO 247
<211> LENGTH: 19
<212> TYPE: DNA
<213> ORGANISM: Artificial sequence
<220> FEATURE:
<223> OTHER INFORMATION: synthetic Reverse amplification primer

<400> SEQUENCE: 247
cgcgcgacca cccatagtc                                                    19

<210> SEQ ID NO 248
<211> LENGTH: 152
<212> TYPE: RNA
<213> ORGANISM: Artificial sequence
<220> FEATURE:
<223> OTHER INFORMATION: synthetic Oligo 1 Transcribed RNA

<400> SEQUENCE: 248
gggcggcacu uauacagggu agcauaaugg gcuacugacg ccuucaaacc uauuuggaga        60
cuauaagugu cgcgcggggc ggcacuuaua cagguagca uaaugggcua cugacgccuu       120
caaaccuauu uggagacuau aagugucgcg cg                                    152

<210> SEQ ID NO 249
<211> LENGTH: 76
<212> TYPE: DNA
<213> ORGANISM: Artificial sequence
<220> FEATURE:
<223> OTHER INFORMATION: synthetic Oligo 1 Synthesized template

<400> SEQUENCE: 249
cgcgcgacac ttatagtctc caaataggtt tgaaggcgtc agtagcccat tatgctaccc        60
tgtataagtg ccgccc                                                       76
```

<210> SEQ ID NO 250
<211> LENGTH: 79
<212> TYPE: RNA
<213> ORGANISM: Artificial sequence
<220> FEATURE:
<223> OTHER INFORMATION: synthetic Oligo 2 Transcribed RNA

<400> SEQUENCE: 250
gggcggcacu uauacagggu agcauaaugg gcuacugacc ccgccuucaa accuauuugg    60
agacuauaag ugucgcgcg                                                 79

<210> SEQ ID NO 251
<211> LENGTH: 79
<212> TYPE: DNA
<213> ORGANISM: Artificial sequence
<220> FEATURE:
<223> OTHER INFORMATION: synthetic Oligo 2 Synthesized template

<400> SEQUENCE: 251
cgcgcgacac ttatagtctc caaataggtt tgaaggcggg gtcagtagcc cattatgcta    60
ccctgtataa gtgccgccc                                                 79

<210> SEQ ID NO 252
<211> LENGTH: 560
<212> TYPE: PRT
<213> ORGANISM: Artificial sequence
<220> FEATURE:
<223> OTHER INFORMATION: synthetic DAFss-aCD3scFv(UCHT1)IgG1 Fc-CD14GPI

<400> SEQUENCE: 252

Met Thr Val Ala Arg Pro Ser Val Pro Ala Ala Leu Pro Leu Leu Gly
1               5                   10                  15

Glu Leu Pro Arg Leu Leu Leu Val Leu Leu Cys Leu Pro Asp Ile
            20                  25                  30

Gln Met Thr Gln Ser Pro Ser Ser Leu Ser Ala Ser Val Gly Asp Arg
        35                  40                  45

Val Thr Ile Thr Cys Arg Ala Ser Gln Asp Ile Arg Asn Tyr Leu Asn
    50                  55                  60

Trp Tyr Gln Gln Lys Pro Gly Lys Ala Pro Lys Leu Leu Ile Tyr Tyr
65                  70                  75                  80

Thr Ser Arg Leu Glu Ser Gly Val Pro Ser Arg Phe Ser Gly Ser Gly
                85                  90                  95

Ser Gly Thr Asp Tyr Thr Leu Thr Ile Ser Ser Leu Gln Pro Glu Asp
            100                 105                 110

Phe Ala Thr Tyr Tyr Cys Gln Gln Gly Asn Thr Leu Pro Trp Thr Phe
        115                 120                 125

Gly Gln Gly Thr Lys Val Glu Ile Lys Gly Gly Gly Gly Ser Gly Gly
    130                 135                 140

Gly Gly Ser Gly Gly Gly Gly Ser Glu Val Gln Leu Val Glu Ser Gly
145                 150                 155                 160

Gly Gly Leu Val Gln Pro Gly Gly Ser Leu Arg Leu Ser Cys Ala Ala
                165                 170                 175

Ser Gly Tyr Ser Phe Thr Gly Tyr Thr Met Asn Trp Val Arg Gln Ala
            180                 185                 190

Pro Gly Lys Gly Leu Glu Trp Val Ala Leu Ile Asn Pro Tyr Lys Gly
        195                 200                 205

Val Ser Thr Tyr Asn Gln Lys Phe Lys Asp Arg Phe Thr Ile Ser Val
    210                 215                 220

Asp Lys Ser Lys Asn Thr Ala Tyr Leu Gln Met Asn Ser Leu Arg Ala
225                 230                 235                 240

Glu Asp Thr Ala Val Tyr Tyr Cys Ala Arg Ser Gly Tyr Tyr Gly Asp
            245                 250                 255

Ser Asp Trp Tyr Phe Asp Val Trp Gly Gln Gly Thr Leu Val Thr Val
            260                 265                 270

Ser Ser Glu Pro Lys Ser Cys Asp Lys Thr His Thr Cys Pro Pro Cys
        275                 280                 285

Pro Ala Pro Glu Leu Leu Gly Gly Pro Ser Val Phe Leu Phe Pro Pro
    290                 295                 300

Lys Pro Lys Asp Thr Leu Met Ile Ser Arg Thr Pro Glu Val Thr Cys
305                 310                 315                 320

Val Val Val Asp Val Ser His Glu Asp Pro Glu Val Lys Phe Asn Trp
            325                 330                 335

Tyr Val Asp Gly Val Glu Val His Asn Ala Lys Thr Lys Pro Arg Glu
            340                 345                 350

Glu Gln Tyr Asn Ser Thr Tyr Arg Val Val Ser Val Leu Thr Val Leu
        355                 360                 365

His Gln Asp Trp Leu Asn Gly Lys Glu Tyr Lys Cys Lys Val Ser Asn
    370                 375                 380

Lys Ala Leu Pro Ala Pro Ile Glu Lys Thr Ile Ser Lys Ala Lys Gly
385                 390                 395                 400

Gln Pro Arg Glu Pro Gln Val Tyr Thr Leu Pro Pro Ser Arg Glu Glu
            405                 410                 415

Met Thr Lys Asn Gln Val Ser Leu Thr Cys Leu Val Lys Gly Phe Tyr
            420                 425                 430

Pro Ser Asp Ile Ala Val Glu Trp Glu Ser Asn Gly Gln Pro Glu Asn
        435                 440                 445

Asn Tyr Lys Thr Thr Pro Pro Val Leu Asp Ser Asp Gly Ser Phe Phe
    450                 455                 460

Leu Tyr Ser Lys Leu Thr Val Asp Lys Ser Arg Trp Gln Gln Gly Asn
465                 470                 475                 480

Val Phe Ser Cys Ser Val Met His Glu Ala Leu His Asn His Tyr Thr
            485                 490                 495

Gln Lys Ser Leu Ser Leu Ser Pro Gly Val Asp Asn Leu Thr Leu Asp
            500                 505                 510

Gly Asn Pro Phe Leu Val Pro Gly Thr Ala Leu Pro His Glu Gly Ser
        515                 520                 525

Met Asn Ser Gly Val Val Pro Ala Cys Ala Arg Ser Thr Leu Ser Val
    530                 535                 540

Gly Val Ser Gly Thr Leu Val Leu Leu Gln Gly Ala Arg Gly Phe Ala
545                 550                 555                 560

<210> SEQ ID NO 253
<211> LENGTH: 276
<212> TYPE: PRT
<213> ORGANISM: Artificial sequence
<220> FEATURE:
<223> OTHER INFORMATION: synthetic DAFss-CD80ECD-CD16GPI

<400> SEQUENCE: 253

Met Thr Val Ala Arg Pro Ser Val Pro Ala Ala Leu Pro Leu Leu Gly
1               5                   10                  15

Glu Leu Pro Arg Leu Leu Leu Leu Val Leu Leu Cys Leu Pro Val Ile
            20                  25                  30

His Val Thr Lys Glu Val Lys Glu Val Ala Thr Leu Ser Cys Gly His
         35                  40                  45

Asn Val Ser Val Glu Glu Leu Ala Gln Thr Arg Ile Tyr Trp Gln Lys
 50                  55                  60

Glu Lys Lys Met Val Leu Thr Met Met Ser Gly Asp Met Asn Ile Trp
 65                  70                  75                  80

Pro Glu Tyr Lys Asn Arg Thr Ile Phe Asp Ile Thr Asn Asn Leu Ser
                 85                  90                  95

Ile Val Ile Leu Ala Leu Arg Pro Ser Asp Glu Gly Thr Tyr Glu Cys
             100                 105                 110

Val Val Leu Lys Tyr Glu Lys Asp Ala Phe Lys Arg Glu His Leu Ala
         115                 120                 125

Glu Val Thr Leu Ser Val Lys Ala Asp Phe Pro Thr Pro Ser Ile Ser
130                 135                 140

Asp Phe Glu Ile Pro Thr Ser Asn Ile Arg Arg Ile Ile Cys Ser Thr
145                 150                 155                 160

Ser Gly Gly Phe Pro Glu Pro His Leu Ser Trp Leu Glu Asn Gly Glu
                165                 170                 175

Glu Leu Asn Ala Ile Asn Thr Thr Val Ser Gln Asp Pro Glu Thr Glu
            180                 185                 190

Leu Tyr Ala Val Ser Ser Lys Leu Asp Phe Asn Met Thr Thr Asn His
        195                 200                 205

Ser Phe Met Cys Leu Ile Lys Tyr Gly His Leu Arg Val Asn Gln Thr
    210                 215                 220

Phe Asn Trp Asn Thr Thr Lys Gln Glu His Phe Pro Asp Asn Val Ser
225                 230                 235                 240

Thr Ile Ser Ser Phe Ser Pro Pro Gly Tyr Gln Val Ser Phe Cys Leu
                245                 250                 255

Val Met Val Leu Leu Phe Ala Val Asp Thr Gly Leu Tyr Phe Ser Val
            260                 265                 270

Lys Thr Asn Ile
        275

<210> SEQ ID NO 254
<211> LENGTH: 533
<212> TYPE: PRT
<213> ORGANISM: Artificial sequence
<220> FEATURE:
<223> OTHER INFORMATION: synthetic DAFss-IL7-DAF

<400> SEQUENCE: 254

Met Ala Thr Thr Met Thr Val Ala Arg Pro Ser Val Pro Ala Ala Leu
 1               5                  10                  15

Pro Leu Leu Gly Glu Leu Pro Arg Leu Leu Leu Val Leu Leu Cys
             20                  25                  30

Leu Pro Ala Asp Cys Asp Ile Glu Gly Lys Asp Gly Lys Gln Tyr Glu
         35                  40                  45

Ser Val Leu Met Val Ser Ile Asp Gln Leu Leu Asp Ser Met Lys Glu
 50                  55                  60

Ile Gly Ser Asn Cys Leu Asn Asn Glu Phe Asn Phe Lys Arg His
 65                  70                  75                  80

Ile Cys Asp Ala Asn Lys Glu Gly Met Phe Leu Phe Arg Ala Ala Arg
                 85                  90                  95

Lys Leu Arg Gln Phe Leu Lys Met Asn Ser Thr Gly Asp Phe Asp Leu
            100                 105                 110

```
His Leu Leu Lys Val Ser Glu Gly Thr Thr Ile Leu Leu Asn Cys Thr
            115                 120                 125
Gly Gln Val Lys Gly Arg Lys Pro Ala Ala Leu Gly Glu Ala Gln Pro
        130                 135                 140
Thr Lys Ser Leu Glu Glu Asn Lys Ser Leu Lys Glu Gln Lys Lys Leu
145                 150                 155                 160
Asn Asp Leu Cys Phe Leu Lys Arg Leu Leu Gln Glu Ile Lys Thr Cys
                165                 170                 175
Trp Asn Lys Ile Leu Met Gly Thr Lys Glu His Cys Gly Leu Pro Pro
            180                 185                 190
Asp Val Pro Asn Ala Gln Pro Ala Leu Glu Gly Arg Thr Ser Phe Pro
        195                 200                 205
Glu Asp Thr Val Ile Thr Tyr Lys Cys Glu Glu Ser Phe Val Lys Ile
210                 215                 220
Pro Gly Glu Lys Asp Ser Val Ile Cys Leu Lys Gly Ser Gln Trp Ser
225                 230                 235                 240
Asp Ile Glu Glu Phe Cys Asn Arg Ser Cys Glu Val Pro Thr Arg Leu
                245                 250                 255
Asn Ser Ala Ser Leu Lys Gln Pro Tyr Ile Thr Gln Asn Tyr Phe Pro
            260                 265                 270
Val Gly Thr Val Val Glu Tyr Glu Cys Arg Pro Gly Tyr Arg Arg Glu
        275                 280                 285
Pro Ser Leu Ser Pro Lys Leu Thr Cys Leu Gln Asn Leu Lys Trp Ser
    290                 295                 300
Thr Ala Val Glu Phe Cys Lys Lys Lys Ser Cys Pro Asn Pro Gly Glu
305                 310                 315                 320
Ile Arg Asn Gly Gln Ile Asp Val Pro Gly Gly Ile Leu Phe Gly Ala
                325                 330                 335
Thr Ile Ser Phe Ser Cys Asn Thr Gly Tyr Lys Leu Phe Gly Ser Thr
            340                 345                 350
Ser Ser Phe Cys Leu Ile Ser Gly Ser Ser Val Gln Trp Ser Asp Pro
        355                 360                 365
Leu Pro Glu Cys Arg Glu Ile Tyr Cys Pro Ala Pro Pro Gln Ile Asp
    370                 375                 380
Asn Gly Ile Ile Gln Gly Glu Arg Asp His Tyr Gly Tyr Arg Gln Ser
385                 390                 395                 400
Val Thr Tyr Ala Cys Asn Lys Gly Phe Thr Met Ile Gly Glu His Ser
                405                 410                 415
Ile Tyr Cys Thr Val Asn Asn Asp Glu Gly Glu Trp Ser Gly Pro Pro
            420                 425                 430
Pro Glu Cys Arg Gly Lys Ser Leu Thr Ser Lys Val Pro Pro Thr Val
        435                 440                 445
Gln Lys Pro Thr Thr Val Asn Val Pro Thr Thr Glu Val Ser Pro Thr
    450                 455                 460
Ser Gln Lys Thr Thr Thr Lys Thr Thr Thr Pro Asn Ala Gln Ala Thr
465                 470                 475                 480
Arg Ser Thr Pro Val Ser Arg Thr Thr Lys His Phe His Glu Thr Thr
                485                 490                 495
Pro Asn Lys Gly Ser Gly Thr Thr Ser Gly Thr Thr Arg Leu Leu Ser
            500                 505                 510
Gly His Thr Cys Phe Thr Leu Thr Gly Leu Leu Gly Thr Leu Val Thr
        515                 520                 525
Met Gly Leu Leu Thr
```

<210> SEQ ID NO 255
<211> LENGTH: 1823
<212> TYPE: DNA
<213> ORGANISM: Artificial sequence
<220> FEATURE:
<223> OTHER INFORMATION: synthetic EF-1a promoter with miRs

<400> SEQUENCE: 255

```
ggctccggtg cccgtcagtg ggcagagcgc acatcgccca cagtccccga gaagttgggg      60
ggaggggtcg gcaattgaac cggtgcctag agaaggtggc gcggggtaaa ctgggaaagt     120
gatgtcgtgt actggctccg cctttttccc gagggtgggg gagaaccgta tataagtgca     180
gtagtcgccg tgaacgttct ttttcgcaac gggtttgccg ccagaacaca ggtaagtgcc     240
gtgtgtggtt cccgcgggcc tggcctcttt acgggttatg gcccttgcgt gccttgaatt     300
acttccacct ggctgcagta cgtgattctt gatcccgagc ttcgggttgg aagtgggtgg     360
gagagttcga ggccttgcgc ttaaggagcc ccttcgcctc gtgcttgagt tgaggcctgg     420
cctgggcgct ggggccgccg cgtgcgaatc tggtggcacc ttcgcgcctg tctcgctgct     480
ttcgataagt ctctagccat ttaaaatttt tgatgacctg ctgcgacgct ttttttctgg     540
caagatagtc ttgtaaatgc gggccaagat ctgcacactg gtatttcggt ttttggggcc     600
gcgggcggcg acgggcccg tgcgtcccag cgcacatgtt cggcgaggcg gggcctgcga     660
gcgcggccac cgagaatcgg acggggtag tctcaagctg gccggcctgc tctggtgcct     720
ggcctcgcgc cgccgtgtat cgccccgccc tgggcggcaa ggctgcccg tcggcacca     780
gttgcgtgag cggaaagatg gccgcttccc ggccctgctg cagggagctc aaaatggagg     840
acgcggcgct cgggagagcg ggcgggtgag tcacccacac aaaggaaaag gccttttccg     900
tcctcagccg tcgcttcatg tgactccact gagtaccggg cgccgtccag gcacctcgat     960
tagttcctgg aggcttgctg aaggctgtat gctgacatgg tacagttcaa tggtggtttt    1020
ggccactgac tgaccaccat tgctgtacca tgtcaggaca caaggcctgt tactagcact    1080
cacatggaac aaatgcccca cattggtgcc ggatgaagct cttatgttgc acggtcatct    1140
ggaggcttgc tgaaggctgt atgctgtcag tctgttcatc ttctggcgtt ttggccactg    1200
actgacgcca aaggaacag actgacagga cacaaggcct gttactagca ctcacatgga    1260
acaaatggcc gttgccggag tcttggcagc gagagatcac tatcaactaa ctggaggctt    1320
gctgaaggct gtatgctgaa gcgtgaagtg aatcaacggg ttttggccac tgactgaccc    1380
gttgatactt cacgcttcag gacacaaggc ctgttactag cactcacatg gaacaaatgg    1440
ccgtgttaat tgtccatgta gcgaggcatc cttatggcgt ggctggaggc ttgctgaagg    1500
ctgtatgctg gcagtatcct agtacattga cgttttggcc actgactgac gtcaatgtta    1560
ggatactgcc aggacacaag gcctgttact agcactcaca tggaacaaat ggccgctttt    1620
ggagtacgtc gtctttaggt tgggggggagg ggttttatgc gatggagttt ccccacactg    1680
agtgggtgga gactgaagtt aggccagctt ggcacttgat gtaattctcc ttggaatttg    1740
cccttttga gtttggatct tggttcattc tcaagcctca gacagtggtt caaagttttt    1800
ttcttccatt tcaggtgtcg tga                                           1823
```

<210> SEQ ID NO 256
<211> LENGTH: 28
<212> TYPE: DNA
<213> ORGANISM: Mus musculus

```
<400> SEQUENCE: 256
ctggaggctt gctgaaggct gtatgctg                                          28

<210> SEQ ID NO 257
<211> LENGTH: 21
<212> TYPE: DNA
<213> ORGANISM: Artificial sequence
<220> FEATURE:
<223> OTHER INFORMATION: Synthetic DNA encoding MiRNA stem

<400> SEQUENCE: 257
acatggtaca gttcaatggt g                                                 21

<210> SEQ ID NO 258
<211> LENGTH: 19
<212> TYPE: DNA
<213> ORGANISM: Artificial sequence
<220> FEATURE:
<223> OTHER INFORMATION: synthetic DNA encoding loop

<400> SEQUENCE: 258
gttttggcca ctgactgac                                                    19

<210> SEQ ID NO 259
<211> LENGTH: 19
<212> TYPE: DNA
<213> ORGANISM: Artificial sequence
<220> FEATURE:
<223> OTHER INFORMATION: synthetic DNA encoding stem

<400> SEQUENCE: 259
caccattgct gtaccatgt                                                    19

<210> SEQ ID NO 260
<211> LENGTH: 45
<212> TYPE: DNA
<213> ORGANISM: Mus musculus

<400> SEQUENCE: 260
caggacacaa ggcctgttac tagcactcac atggaacaaa tggcc                       45

<210> SEQ ID NO 261
<211> LENGTH: 21
<212> TYPE: DNA
<213> ORGANISM: Artificial sequence
<220> FEATURE:
<223> OTHER INFORMATION: Synthetic DNA encoding MiRNA stem

<400> SEQUENCE: 261
tcagtctgtt catcttctgg c                                                 21

<210> SEQ ID NO 262
<211> LENGTH: 19
<212> TYPE: DNA
<213> ORGANISM: Artificial sequence
<220> FEATURE:
<223> OTHER INFORMATION: Synthetic DNA encoding MiRNA stem

<400> SEQUENCE: 262
gccagaagga acagactga                                                    19

<210> SEQ ID NO 263
<211> LENGTH: 21
<212> TYPE: DNA
```

```
<213> ORGANISM: Artificial sequence
<220> FEATURE:
<223> OTHER INFORMATION: Synthetic DNA encoding MiRNA stem

<400> SEQUENCE: 263
aagcgtgaag tgaatcaacg g                                              21

<210> SEQ ID NO 264
<211> LENGTH: 19
<212> TYPE: DNA
<213> ORGANISM: Artificial sequence
<220> FEATURE:
<223> OTHER INFORMATION: Synthetic DNA encoding MiRNA stem

<400> SEQUENCE: 264
ccgttgatac ttcacgctt                                                 19

<210> SEQ ID NO 265
<211> LENGTH: 21
<212> TYPE: DNA
<213> ORGANISM: Artificial sequence
<220> FEATURE:
<223> OTHER INFORMATION: Synthetic DNA encoding MiRNA stem

<400> SEQUENCE: 265
gcagtatcct agtacattga c                                              21

<210> SEQ ID NO 266
<211> LENGTH: 19
<212> TYPE: DNA
<213> ORGANISM: Artificial sequence
<220> FEATURE:
<223> OTHER INFORMATION: Synthetic DNA encoding MiRNA stem

<400> SEQUENCE: 266
gtcaatgtta ggatactgc                                                 19

<210> SEQ ID NO 267
<211> LENGTH: 21
<212> TYPE: DNA
<213> ORGANISM: Artificial sequence
<220> FEATURE:
<223> OTHER INFORMATION: Synthetic DNA encoding MiRNA stem

<400> SEQUENCE: 267
atatgtactt ggctggacag c                                              21

<210> SEQ ID NO 268
<211> LENGTH: 19
<212> TYPE: DNA
<213> ORGANISM: Artificial sequence
<220> FEATURE:
<223> OTHER INFORMATION: Synthetic DNA encoding MiRNA stem

<400> SEQUENCE: 268
gctgtccaca agtacatat                                                 19

<210> SEQ ID NO 269
<211> LENGTH: 39
<212> TYPE: DNA
<213> ORGANISM: Artificial sequence
<220> FEATURE:
<223> OTHER INFORMATION: synthetic DNA encoding linker

<400> SEQUENCE: 269
cacattggtg ccggatgaag ctcttatgtt gccggtcat                           39
```

<210> SEQ ID NO 270
<211> LENGTH: 21
<212> TYPE: DNA
<213> ORGANISM: Artificial sequence
<220> FEATURE:
<223> OTHER INFORMATION: Synthetic DNA encoding MiRNA stem

<400> SEQUENCE: 270
ctgttaatgc taatcgtgat a                                          21

<210> SEQ ID NO 271
<211> LENGTH: 18
<212> TYPE: DNA
<213> ORGANISM: Artificial sequence
<220> FEATURE:
<223> OTHER INFORMATION: Synthetic DNA encoding MiRNA stem

<400> SEQUENCE: 271
tatcacgatt attaacag                                              18

<210> SEQ ID NO 272
<211> LENGTH: 40
<212> TYPE: DNA
<213> ORGANISM: Artificial sequence
<220> FEATURE:
<223> OTHER INFORMATION: synthetic DNA encoding linker

<400> SEQUENCE: 272
gttgccggag tcttggcagc gagagatcac tatcaactaa                      40

<210> SEQ ID NO 273
<211> LENGTH: 21
<212> TYPE: DNA
<213> ORGANISM: Artificial sequence
<220> FEATURE:
<223> OTHER INFORMATION: Synthetic DNA encoding MiRNA stem

<400> SEQUENCE: 273
taccagttta gcacgaagct c                                          21

<210> SEQ ID NO 274
<211> LENGTH: 19
<212> TYPE: DNA
<213> ORGANISM: Artificial sequence
<220> FEATURE:
<223> OTHER INFORMATION: Synthetic DNA encoding MiRNA stem

<400> SEQUENCE: 274
gagcttcgct aaactggta                                             19

<210> SEQ ID NO 275
<211> LENGTH: 40
<212> TYPE: DNA
<213> ORGANISM: Artificial sequence
<220> FEATURE:
<223> OTHER INFORMATION: synthetic DNA encoding linker

<400> SEQUENCE: 275
gtgttaattg tccatgtagc gaggcatcct tatggcgtgg                      40

<210> SEQ ID NO 276
<211> LENGTH: 21
<212> TYPE: DNA
<213> ORGANISM: Artificial sequence
<220> FEATURE:

```
<223> OTHER INFORMATION: Synthetic DNA encoding MiRNA stem

<400> SEQUENCE: 276
tgccgctgaa atccaaggca a                                              21

<210> SEQ ID NO 277
<211> LENGTH: 19
<212> TYPE: DNA
<213> ORGANISM: Artificial sequence
<220> FEATURE:
<223> OTHER INFORMATION: Synthetic DNA encoding MiRNA stem

<400> SEQUENCE: 277
ttgccttgtt tcagcggca                                                 19

<210> SEQ ID NO 278
<211> LENGTH: 534
<212> TYPE: PRT
<213> ORGANISM: Artificial sequence
<220> FEATURE:
<223> OTHER INFORMATION: Synthetic UCHT1scFvFc-GPI

<400> SEQUENCE: 278
```

Met Asp Met Arg Val Pro Ala Gln Leu Leu Gly Leu Leu Leu Leu Trp
1               5                   10                  15

Leu Ser Gly Ala Arg Cys Asp Ile Gln Met Thr Gln Ser Pro Ser Ser
            20                  25                  30

Leu Ser Ala Ser Val Gly Asp Arg Val Thr Ile Thr Cys Arg Ala Ser
        35                  40                  45

Gln Asp Ile Arg Asn Tyr Leu Asn Trp Tyr Gln Gln Lys Pro Gly Lys
    50                  55                  60

Ala Pro Lys Leu Leu Ile Tyr Tyr Thr Ser Arg Leu Glu Ser Gly Val
65                  70                  75                  80

Pro Ser Arg Phe Ser Gly Ser Gly Ser Gly Thr Asp Tyr Thr Leu Thr
                85                  90                  95

Ile Ser Ser Leu Gln Pro Glu Asp Phe Ala Thr Tyr Tyr Cys Gln Gln
            100                 105                 110

Gly Asn Thr Leu Pro Trp Thr Phe Gly Gln Gly Thr Lys Val Glu Ile
        115                 120                 125

Lys Gly Gly Gly Gly Ser Gly Gly Gly Gly Ser Gly Gly Gly Gly Ser
    130                 135                 140

Glu Val Gln Leu Val Glu Ser Gly Gly Gly Leu Val Gln Pro Gly Gly
145                 150                 155                 160

Ser Leu Arg Leu Ser Cys Ala Ala Ser Gly Tyr Ser Phe Thr Gly Tyr
                165                 170                 175

Thr Met Asn Trp Val Arg Gln Ala Pro Gly Lys Gly Leu Glu Trp Val
            180                 185                 190

Ala Leu Ile Asn Pro Tyr Lys Gly Val Ser Thr Tyr Asn Gln Lys Phe
        195                 200                 205

Lys Asp Arg Phe Thr Ile Ser Val Asp Lys Ser Lys Asn Thr Ala Tyr
    210                 215                 220

Leu Gln Met Asn Ser Leu Arg Ala Glu Asp Thr Ala Val Tyr Tyr Cys
225                 230                 235                 240

Ala Arg Ser Gly Tyr Tyr Gly Asp Ser Asp Trp Tyr Phe Asp Val Trp
                245                 250                 255

Gly Gln Gly Thr Leu Val Thr Val Ser Ser Glu Pro Lys Ser Cys Asp
            260                 265                 270

```
Lys Thr His Thr Cys Pro Pro Cys Pro Ala Pro Glu Leu Leu Gly Gly
            275                 280                 285

Pro Ser Val Phe Leu Phe Pro Pro Lys Pro Lys Asp Thr Leu Met Ile
    290                 295                 300

Ser Arg Thr Pro Glu Val Thr Cys Val Val Val Asp Val Ser His Glu
305                 310                 315                 320

Asp Pro Glu Val Lys Phe Asn Trp Tyr Val Asp Gly Val Glu Val His
                325                 330                 335

Asn Ala Lys Thr Lys Pro Arg Glu Glu Gln Tyr Asn Ser Thr Tyr Arg
            340                 345                 350

Val Val Ser Val Leu Thr Val Leu His Gln Asp Trp Leu Asn Gly Lys
        355                 360                 365

Glu Tyr Lys Cys Lys Val Ser Asn Lys Ala Leu Pro Thr Pro Ile Glu
    370                 375                 380

Lys Thr Ile Ser Lys Ala Lys Gly Gln Pro Arg Glu Pro Gln Val Tyr
385                 390                 395                 400

Thr Leu Pro Pro Ser Arg Glu Glu Met Thr Lys Asn Gln Val Ser Leu
                405                 410                 415

Thr Cys Leu Val Lys Gly Phe Tyr Pro Ser Asp Ile Ala Val Glu Trp
            420                 425                 430

Glu Ser Asn Gly Gln Pro Glu Asn Asn Tyr Lys Thr Thr Pro Pro Val
        435                 440                 445

Leu Asp Ser Asp Gly Ser Phe Phe Leu Tyr Ser Lys Leu Thr Val Asp
    450                 455                 460

Lys Ser Arg Trp Gln Gln Gly Asn Val Phe Ser Cys Ser Val Met His
465                 470                 475                 480

Glu Ala Leu His Asn His Tyr Thr Gln Lys Ser Leu Ser Leu Ser Pro
                485                 490                 495

Gly Pro Asn Lys Gly Ser Gly Thr Thr Ser Gly Thr Thr Arg Leu Leu
            500                 505                 510

Ser Gly His Thr Cys Phe Thr Leu Thr Gly Leu Leu Thr Leu Val
        515                 520                 525

Thr Met Gly Leu Leu Thr
    530

<210> SEQ ID NO 279
<211> LENGTH: 530
<212> TYPE: PRT
<213> ORGANISM: Artificial sequence
<220> FEATURE:
<223> OTHER INFORMATION: Synthetic OKT3scFvFc-GPI

<400> SEQUENCE: 279

Met Asp Met Arg Val Pro Ala Gln Leu Leu Gly Leu Leu Leu Leu Trp
1               5                   10                  15

Leu Ser Gly Ala Arg Cys Gln Ile Val Leu Thr Gln Ser Pro Ala Ile
            20                  25                  30

Met Ser Ala Ser Pro Gly Glu Lys Val Thr Met Thr Cys Ser Ala Ser
        35                  40                  45

Ser Ser Val Ser Tyr Met Asn Trp Tyr Gln Gln Lys Ser Gly Thr Ser
    50                  55                  60

Pro Lys Arg Trp Ile Tyr Asp Thr Ser Lys Leu Ala Ser Gly Val Pro
65                  70                  75                  80

Ala His Phe Arg Gly Ser Gly Ser Gly Thr Ser Tyr Ser Leu Thr Ile
                85                  90                  95
```

```
Ser Gly Met Glu Ala Glu Asp Ala Ala Thr Tyr Tyr Cys Gln Gln Trp
            100                 105                 110

Ser Ser Asn Pro Phe Thr Phe Gly Ser Gly Thr Lys Leu Glu Ile Asn
            115                 120                 125

Gly Gly Gly Gly Ser Gly Gly Gly Gly Ser Gly Gly Gly Gly Ser Gln
        130                 135                 140

Val Gln Leu Gln Gln Ser Gly Ala Glu Leu Ala Arg Pro Gly Ala Ser
145                 150                 155                 160

Val Lys Met Ser Cys Lys Ala Ser Gly Tyr Thr Phe Thr Arg Tyr Thr
                165                 170                 175

Met His Trp Val Lys Gln Arg Pro Gly Gln Gly Leu Glu Trp Ile Gly
            180                 185                 190

Tyr Ile Asn Pro Ser Arg Gly Tyr Thr Asn Tyr Asn Gln Lys Phe Lys
            195                 200                 205

Asp Lys Ala Thr Leu Thr Thr Asp Lys Ser Ser Ser Thr Ala Tyr Met
            210                 215                 220

Gln Leu Ser Ser Leu Thr Ser Glu Asp Ser Ala Val Tyr Tyr Cys Ala
225                 230                 235                 240

Arg Tyr Tyr Asp Asp His Tyr Cys Leu Asp Tyr Trp Gly Gln Gly Thr
                245                 250                 255

Thr Leu Thr Val Ser Ser Glu Pro Lys Ser Cys Asp Lys Thr His Thr
            260                 265                 270

Cys Pro Pro Cys Pro Ala Pro Glu Leu Leu Gly Gly Pro Ser Val Phe
            275                 280                 285

Leu Phe Pro Pro Lys Pro Lys Asp Thr Leu Met Ile Ser Arg Thr Pro
290                 295                 300

Glu Val Thr Cys Val Val Val Asp Val Ser His Glu Asp Pro Glu Val
305                 310                 315                 320

Lys Phe Asn Trp Tyr Val Asp Gly Val Glu Val His Asn Ala Lys Thr
                325                 330                 335

Lys Pro Arg Glu Glu Gln Tyr Asn Ser Thr Tyr Arg Val Val Ser Val
            340                 345                 350

Leu Thr Val Leu His Gln Asp Trp Leu Asn Gly Lys Glu Tyr Lys Cys
            355                 360                 365

Lys Val Ser Asn Lys Ala Leu Pro Ala Pro Ile Glu Lys Thr Ile Ser
            370                 375                 380

Lys Ala Lys Gly Gln Pro Arg Glu Pro Gln Val Tyr Thr Leu Pro Pro
385                 390                 395                 400

Ser Arg Glu Glu Met Thr Lys Asn Gln Val Ser Leu Thr Cys Leu Val
                405                 410                 415

Lys Gly Phe Tyr Pro Ser Asp Ile Ala Val Glu Trp Glu Ser Asn Gly
            420                 425                 430

Gln Pro Glu Asn Asn Tyr Lys Thr Thr Pro Pro Val Leu Asp Ser Asp
            435                 440                 445

Gly Ser Phe Phe Leu Tyr Ser Lys Leu Thr Val Asp Lys Ser Arg Trp
450                 455                 460

Gln Gln Gly Asn Val Phe Ser Cys Ser Val Met His Glu Ala Leu His
465                 470                 475                 480

Asn His Tyr Thr Gln Lys Ser Leu Ser Leu Ser Pro Gly Pro Asn Lys
                485                 490                 495

Gly Ser Gly Thr Thr Ser Gly Thr Thr Arg Leu Leu Ser Gly His Thr
            500                 505                 510

Cys Phe Thr Leu Thr Gly Leu Leu Gly Thr Leu Val Thr Met Gly Leu
```

-continued

```
            515                 520                 525

Leu Thr
    530

<210> SEQ ID NO 280
<211> LENGTH: 280
<212> TYPE: PRT
<213> ORGANISM: Artificial sequence
<220> FEATURE:
<223> OTHER INFORMATION: Synthetic hCD80-CD16 GPI

<400> SEQUENCE: 280

Met Gly His Thr Arg Arg Gln Gly Thr Ser Pro Ser Lys Cys Pro Tyr
1               5                   10                  15

Leu Asn Phe Phe Gln Leu Leu Val Leu Ala Gly Leu Ser His Phe Cys
            20                  25                  30

Ser Gly Val Ile His Val Thr Lys Glu Val Lys Glu Val Ala Thr Leu
        35                  40                  45

Ser Cys Gly His Asn Val Ser Val Glu Glu Leu Ala Gln Thr Arg Ile
    50                  55                  60

Tyr Trp Gln Lys Glu Lys Lys Met Val Leu Thr Met Met Ser Gly Asp
65                  70                  75                  80

Met Asn Ile Trp Pro Glu Tyr Lys Asn Arg Thr Ile Phe Asp Ile Thr
                85                  90                  95

Asn Asn Leu Ser Ile Val Ile Leu Ala Leu Arg Pro Ser Asp Glu Gly
            100                 105                 110

Thr Tyr Glu Cys Val Val Leu Lys Tyr Glu Lys Asp Ala Phe Lys Arg
        115                 120                 125

Glu His Leu Ala Glu Val Thr Leu Ser Val Lys Ala Asp Phe Pro Thr
    130                 135                 140

Pro Ser Ile Ser Asp Phe Glu Ile Pro Thr Ser Asn Ile Arg Arg Ile
145                 150                 155                 160

Ile Cys Ser Thr Ser Gly Gly Phe Pro Glu Pro His Leu Ser Trp Leu
                165                 170                 175

Glu Asn Gly Glu Glu Leu Asn Ala Ile Asn Thr Thr Val Ser Gln Asp
            180                 185                 190

Pro Glu Thr Glu Leu Tyr Ala Val Ser Ser Lys Leu Asp Phe Asn Met
        195                 200                 205

Thr Thr Asn His Ser Phe Met Cys Leu Ile Lys Tyr Gly His Leu Arg
    210                 215                 220

Val Asn Gln Thr Phe Asn Trp Asn Thr Thr Lys Gln Glu His Phe Pro
225                 230                 235                 240

Asp Asn Val Ser Thr Ile Ser Ser Phe Ser Pro Pro Gly Tyr Gln Val
                245                 250                 255

Ser Phe Cys Leu Val Met Val Leu Leu Phe Ala Val Asp Thr Gly Leu
            260                 265                 270

Tyr Phe Ser Val Lys Thr Asn Ile
        275                 280

<210> SEQ ID NO 281
<211> LENGTH: 120
<212> TYPE: PRT
<213> ORGANISM: Artificial sequence
<220> FEATURE:
<223> OTHER INFORMATION: Synthetic Target 1 MRB VH

<400> SEQUENCE: 281
```

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Ser Phe Trp Gly Ala
                20                  25                  30

Thr Met Asn Trp Ile Arg Gln Pro Pro Gly Lys Gly Leu Glu Trp Ile
            35                  40                  45

Gly Leu Ile Lys Pro Ser Asn Gly Gly Thr Ser Tyr Asn Gln Lys Phe
50                  55                  60

Lys Gly Arg Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala His Gly His Tyr Glu Ser Tyr Glu Ala Met Asp Tyr Trp Gly Gln
            100                 105                 110

Gly Thr Leu Val Thr Val Ser Ser
            115                 120

<210> SEQ ID NO 282
<211> LENGTH: 107
<212> TYPE: PRT
<213> ORGANISM: Artificial sequence
<220> FEATURE:
<223> OTHER INFORMATION: Synthetic Target 1 MRB VL

<400> SEQUENCE: 282

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Val Ser Ala
                20                  25                  30

Val Ala Trp Tyr Gln Gln Lys Pro Gly Gln Ala Pro Arg Leu Leu Ile
            35                  40                  45

Tyr Trp Gln Asp Thr Arg His Thr Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Glu His Phe Ser Pro Pro Leu
                85                  90                  95

Thr Phe Gly Gln Gly Thr Lys Val Glu Ile Lys
            100                 105

<210> SEQ ID NO 283
<211> LENGTH: 15
<212> TYPE: PRT
<213> ORGANISM: Artificial sequence
<220> FEATURE:
<223> OTHER INFORMATION: Synthetic Linker 1

<400> SEQUENCE: 283

Gly Gly Gly Gly Ser Gly Gly Gly Gly Ser Gly Gly Gly Gly Ser
1               5                   10                  15

<210> SEQ ID NO 284
<211> LENGTH: 357
<212> TYPE: PRT
<213> ORGANISM: Artificial sequence
<220> FEATURE:
<223> OTHER INFORMATION: Synthetic C1 control polypeptide containing
      GMCSF alpha chain signal sequence (amino acids 1-22) and eTAG
      (amino acids 23-357)

<400> SEQUENCE: 284

```
Met Leu Leu Leu Val Thr Ser Leu Leu Leu Cys Glu Leu Pro His Pro
1               5                   10                  15

Ala Phe Leu Leu Ile Pro Arg Lys Val Cys Asn Gly Ile Gly Ile Gly
                20                  25                  30

Glu Phe Lys Asp Ser Leu Ser Ile Asn Ala Thr Asn Ile Lys His Phe
            35                  40                  45

Lys Asn Cys Thr Ser Ile Ser Gly Asp Leu His Ile Leu Pro Val Ala
50                  55                      60

Phe Arg Gly Asp Ser Phe Thr His Thr Pro Pro Leu Asp Pro Gln Glu
65                      70                  75                  80

Leu Asp Ile Leu Lys Thr Val Lys Glu Ile Thr Gly Phe Leu Leu Ile
                85                  90                      95

Gln Ala Trp Pro Glu Asn Arg Thr Asp Leu His Ala Phe Glu Asn Leu
                100                 105                 110

Glu Ile Ile Arg Gly Arg Thr Lys Gln His Gly Gln Phe Ser Leu Ala
            115                 120                 125

Val Val Ser Leu Asn Ile Thr Ser Leu Gly Leu Arg Ser Leu Lys Glu
            130                 135                 140

Ile Ser Asp Gly Asp Val Ile Ile Ser Gly Asn Lys Asn Leu Cys Tyr
145                 150                     155                 160

Ala Asn Thr Ile Asn Trp Lys Lys Leu Phe Gly Thr Ser Gly Gln Lys
                165                 170                 175

Thr Lys Ile Ile Ser Asn Arg Gly Glu Asn Ser Cys Lys Ala Thr Gly
            180                 185                 190

Gln Val Cys His Ala Leu Cys Ser Pro Glu Gly Cys Trp Gly Pro Glu
            195                 200                 205

Pro Arg Asp Cys Val Ser Cys Arg Asn Val Ser Arg Gly Arg Glu Cys
210                 215                 220

Val Asp Lys Cys Asn Leu Leu Glu Gly Glu Pro Arg Glu Phe Val Glu
225                 230                 235                 240

Asn Ser Glu Cys Ile Gln Cys His Pro Glu Cys Leu Pro Gln Ala Met
                245                 250                 255

Asn Ile Thr Cys Thr Gly Arg Gly Pro Asp Asn Cys Ile Gln Cys Ala
                260                 265                 270

His Tyr Ile Asp Gly Pro His Cys Val Lys Thr Cys Pro Ala Gly Val
            275                 280                 285

Met Gly Glu Asn Asn Thr Leu Val Trp Lys Tyr Ala Asp Ala Gly His
            290                 295                 300

Val Cys His Leu Cys His Pro Asn Cys Thr Tyr Gly Cys Thr Gly Pro
305                 310                 315                 320

Gly Leu Glu Gly Cys Pro Thr Asn Gly Pro Lys Ile Pro Ser Ile Ala
                325                 330                 335

Thr Gly Met Val Gly Ala Leu Leu Leu Leu Val Val Ala Leu Gly
            340                 345                 350

Ile Gly Leu Phe Met
        355
```

<210> SEQ ID NO 285
<211> LENGTH: 240
<212> TYPE: PRT
<213> ORGANISM: Artificial sequence
<220> FEATURE:
<223> OTHER INFORMATION: Synthetic OKT3 ScFv

<400> SEQUENCE: 285

```
Gln Ile Val Leu Thr Gln Ser Pro Ala Ile Met Ser Ala Ser Pro Gly
  1               5                  10                  15

Glu Lys Val Thr Met Thr Cys Ser Ala Ser Ser Val Ser Tyr Met
             20                  25                  30

Asn Trp Tyr Gln Gln Lys Ser Gly Thr Ser Pro Lys Arg Trp Ile Tyr
             35                  40                  45

Asp Thr Ser Lys Leu Ala Ser Gly Val Pro Ala His Phe Arg Gly Ser
 50                  55                  60

Gly Ser Gly Thr Ser Tyr Ser Leu Thr Ile Ser Gly Met Glu Ala Glu
 65                  70                  75                  80

Asp Ala Ala Thr Tyr Tyr Cys Gln Gln Trp Ser Ser Asn Pro Phe Thr
                 85                  90                  95

Phe Gly Ser Gly Thr Lys Leu Glu Ile Asn Gly Gly Gly Gly Ser Gly
                100                 105                 110

Gly Gly Gly Ser Gly Gly Gly Ser Gln Val Gln Leu Gln Gln Ser
             115                 120                 125

Gly Ala Glu Leu Ala Arg Pro Gly Ala Ser Val Lys Met Ser Cys Lys
         130                 135                 140

Ala Ser Gly Tyr Thr Phe Thr Arg Tyr Thr Met His Trp Val Lys Gln
145                 150                 155                 160

Arg Pro Gly Gln Gly Leu Glu Trp Ile Gly Tyr Ile Asn Pro Ser Arg
                165                 170                 175

Gly Tyr Thr Asn Tyr Asn Gln Lys Phe Lys Asp Lys Ala Thr Leu Thr
            180                 185                 190

Thr Asp Lys Ser Ser Ser Thr Ala Tyr Met Gln Leu Ser Ser Leu Thr
        195                 200                 205

Ser Glu Asp Ser Ala Val Tyr Tyr Cys Ala Arg Tyr Tyr Asp His
    210                 215                 220

Tyr Cys Leu Asp Tyr Trp Gly Gln Gly Thr Leu Thr Val Ser Ser
225                 230                 235                 240

<210> SEQ ID NO 286
<211> LENGTH: 532
<212> TYPE: PRT
<213> ORGANISM: Artificial sequence
<220> FEATURE:
<223> OTHER INFORMATION: Synthetic DAFss-IL7-DAF fusion

<400> SEQUENCE: 286

Met Thr Val Ala Arg Pro Ser Val Pro Ala Ala Leu Pro Leu Leu Gly
  1               5                  10                  15

Glu Leu Pro Arg Leu Leu Leu Val Leu Leu Cys Leu Pro Ala Val
             20                  25                  30

Trp Gly Asp Cys Asp Ile Glu Gly Lys Asp Gly Lys Gln Tyr Glu Ser
             35                  40                  45

Val Leu Met Val Ser Ile Asp Gln Leu Leu Asp Ser Met Lys Glu Ile
 50                  55                  60

Gly Ser Asn Cys Leu Asn Asn Glu Phe Asn Phe Lys Arg His Ile
 65                  70                  75                  80

Cys Asp Ala Asn Lys Glu Gly Met Phe Leu Phe Arg Ala Ala Arg Lys
                 85                  90                  95

Leu Arg Gln Phe Leu Lys Met Asn Ser Thr Gly Asp Phe Asp Leu His
                100                 105                 110

Leu Leu Lys Val Ser Glu Gly Thr Thr Ile Leu Leu Asn Cys Thr Gly
            115                 120                 125
```

```
Gln Val Lys Gly Arg Lys Pro Ala Leu Gly Glu Ala Gln Pro Thr
            130                 135                 140
Lys Ser Leu Glu Glu Asn Lys Ser Leu Lys Glu Gln Lys Lys Leu Asn
145                 150                 155                 160
Asp Leu Cys Phe Leu Lys Arg Leu Leu Gln Glu Ile Lys Thr Cys Trp
                165                 170                 175
Asn Lys Ile Leu Met Gly Thr Lys Glu His Cys Gly Leu Pro Pro Asp
            180                 185                 190
Val Pro Asn Ala Gln Pro Ala Leu Glu Gly Arg Thr Ser Phe Pro Glu
        195                 200                 205
Asp Thr Val Ile Thr Tyr Lys Cys Glu Glu Ser Phe Val Lys Ile Pro
210                 215                 220
Gly Glu Lys Asp Ser Val Ile Cys Leu Lys Gly Ser Gln Trp Ser Asp
225                 230                 235                 240
Ile Glu Glu Phe Cys Asn Arg Ser Cys Glu Val Pro Thr Arg Leu Asn
                245                 250                 255
Ser Ala Ser Leu Lys Gln Pro Tyr Ile Thr Gln Asn Tyr Phe Pro Val
            260                 265                 270
Gly Thr Val Val Glu Tyr Glu Cys Arg Pro Gly Tyr Arg Arg Glu Pro
        275                 280                 285
Ser Leu Ser Pro Lys Leu Thr Cys Leu Gln Asn Leu Lys Trp Ser Thr
290                 295                 300
Ala Val Glu Phe Cys Lys Lys Ser Cys Pro Asn Pro Gly Glu Ile
305                 310                 315                 320
Arg Asn Gly Gln Ile Asp Val Pro Gly Gly Ile Leu Phe Gly Ala Thr
                325                 330                 335
Ile Ser Phe Ser Cys Asn Thr Gly Tyr Lys Leu Phe Gly Ser Thr Ser
            340                 345                 350
Ser Phe Cys Leu Ile Ser Gly Ser Val Gln Trp Ser Asp Pro Leu
        355                 360                 365
Pro Glu Cys Arg Glu Ile Tyr Cys Pro Ala Pro Pro Gln Ile Asp Asn
370                 375                 380
Gly Ile Ile Gln Gly Glu Arg Asp His Tyr Gly Tyr Arg Gln Ser Val
385                 390                 395                 400
Thr Tyr Ala Cys Asn Lys Gly Phe Thr Met Ile Gly Glu His Ser Ile
                405                 410                 415
Tyr Cys Thr Val Asn Asn Asp Glu Gly Glu Trp Ser Gly Pro Pro Pro
            420                 425                 430
Glu Cys Arg Gly Lys Ser Leu Thr Ser Lys Val Pro Pro Thr Val Gln
        435                 440                 445
Lys Pro Thr Thr Val Asn Val Pro Thr Thr Glu Val Ser Pro Thr Ser
450                 455                 460
Gln Lys Thr Thr Thr Lys Thr Thr Pro Asn Ala Gln Ala Thr Arg
465                 470                 475                 480
Ser Thr Pro Val Ser Arg Thr Thr Lys His Phe His Glu Thr Thr Pro
                485                 490                 495
Asn Lys Gly Ser Gly Thr Thr Ser Gly Thr Thr Arg Leu Leu Ser Gly
            500                 505                 510
His Thr Cys Phe Thr Leu Thr Gly Leu Leu Gly Thr Leu Val Thr Met
        515                 520                 525
Gly Leu Leu Thr
        530
```

<210> SEQ ID NO 287
<211> LENGTH: 564
<212> TYPE: PRT
<213> ORGANISM: Artificial sequence
<220> FEATURE:
<223> OTHER INFORMATION: Synthetic DAFss-aCD3scFv(UCHT1)IgG1 Fc-CD14GPI

<400> SEQUENCE: 287

Met Thr Val Ala Arg Pro Ser Val Pro Ala Leu Pro Leu Leu Gly
1               5                   10                  15

Glu Leu Pro Arg Leu Leu Leu Val Leu Leu Cys Leu Pro Ala Val
                20                  25                  30

Trp Gly Asp Ile Gln Met Thr Gln Ser Pro Ser Ser Leu Ser Ala Ser
            35                  40                  45

Val Gly Asp Arg Val Thr Ile Thr Cys Arg Ala Ser Gln Asp Ile Arg
50                  55                  60

Asn Tyr Leu Asn Trp Tyr Gln Gln Lys Pro Gly Lys Ala Pro Lys Leu
65              70                  75                  80

Leu Ile Tyr Tyr Thr Ser Arg Leu Glu Ser Gly Val Pro Ser Arg Phe
                85                  90                  95

Ser Gly Ser Gly Ser Gly Thr Asp Tyr Thr Leu Thr Ile Ser Ser Leu
            100                 105                 110

Gln Pro Glu Asp Phe Ala Thr Tyr Tyr Cys Gln Gln Gly Asn Thr Leu
        115                 120                 125

Pro Trp Thr Phe Gly Gln Gly Thr Lys Val Glu Ile Lys Gly Gly Gly
    130                 135                 140

Gly Ser Gly Gly Gly Gly Ser Gly Gly Gly Gly Ser Glu Val Gln Leu
145                 150                 155                 160

Val Glu Ser Gly Gly Gly Leu Val Gln Pro Gly Gly Ser Leu Arg Leu
                165                 170                 175

Ser Cys Ala Ala Ser Gly Tyr Ser Phe Thr Gly Tyr Thr Met Asn Trp
            180                 185                 190

Val Arg Gln Ala Pro Gly Lys Gly Leu Glu Trp Val Ala Leu Ile Asn
        195                 200                 205

Pro Tyr Lys Gly Val Ser Thr Tyr Asn Gln Lys Phe Lys Asp Arg Phe
    210                 215                 220

Thr Ile Ser Val Asp Lys Ser Lys Asn Thr Ala Tyr Leu Gln Met Asn
225                 230                 235                 240

Ser Leu Arg Ala Glu Asp Thr Ala Val Tyr Tyr Cys Ala Arg Ser Gly
                245                 250                 255

Tyr Tyr Gly Asp Ser Asp Trp Tyr Phe Asp Val Trp Gly Gln Gly Thr
            260                 265                 270

Leu Val Thr Val Ser Ser Glu Pro Lys Ser Cys Asp Lys Thr His Thr
        275                 280                 285

Cys Pro Pro Cys Pro Ala Pro Glu Leu Leu Gly Gly Pro Ser Val Phe
    290                 295                 300

Leu Phe Pro Pro Lys Pro Lys Asp Thr Leu Met Ile Ser Arg Thr Pro
305                 310                 315                 320

Glu Val Thr Cys Val Val Val Asp Val Ser His Glu Asp Pro Glu Val
                325                 330                 335

Lys Phe Asn Trp Tyr Val Asp Gly Val Glu Val His Asn Ala Lys Thr
            340                 345                 350

Lys Pro Arg Glu Glu Gln Tyr Asn Ser Thr Tyr Arg Val Val Ser Val
        355                 360                 365

```
Leu Thr Val Leu His Gln Asp Trp Leu Asn Gly Lys Glu Tyr Lys Cys
    370                 375                 380
Lys Val Ser Asn Lys Ala Leu Pro Ala Pro Ile Glu Lys Thr Ile Ser
385                 390                 395                 400
Lys Ala Lys Gly Gln Pro Arg Glu Pro Gln Val Tyr Thr Leu Pro Pro
                405                 410                 415
Ser Arg Glu Glu Met Thr Lys Asn Gln Val Ser Leu Thr Cys Leu Val
            420                 425                 430
Lys Gly Phe Tyr Pro Ser Asp Ile Ala Val Glu Trp Glu Ser Asn Gly
        435                 440                 445
Gln Pro Glu Asn Asn Tyr Lys Thr Thr Pro Pro Val Leu Asp Ser Asp
450                 455                 460
Gly Ser Phe Phe Leu Tyr Ser Lys Leu Thr Val Asp Lys Ser Arg Trp
465                 470                 475                 480
Gln Gln Gly Asn Val Phe Ser Cys Ser Val Met His Glu Ala Leu His
                485                 490                 495
Asn His Tyr Thr Gln Lys Ser Leu Ser Leu Ser Pro Gly Val Asp Asn
            500                 505                 510
Leu Thr Leu Asp Gly Asn Pro Phe Leu Val Pro Gly Thr Ala Leu Pro
        515                 520                 525
His Glu Gly Ser Met Asn Ser Gly Val Val Pro Ala Cys Ala Arg Ser
530                 535                 540
Thr Leu Ser Val Gly Val Ser Gly Thr Leu Val Leu Leu Gln Gly Ala
545                 550                 555                 560
Arg Gly Phe Ala

<210> SEQ ID NO 288
<211> LENGTH: 280
<212> TYPE: PRT
<213> ORGANISM: Artificial sequence
<220> FEATURE:
<223> OTHER INFORMATION: Synthetic DAFss-CD80ECD-CD16GPI

<400> SEQUENCE: 288

Met Thr Val Ala Arg Pro Ser Val Pro Ala Ala Leu Pro Leu Leu Gly
1               5                   10                  15
Glu Leu Pro Arg Leu Leu Leu Leu Val Leu Leu Cys Leu Pro Ala Val
                20                  25                  30
Trp Gly Val Ile His Val Thr Lys Glu Val Lys Glu Val Ala Thr Leu
            35                  40                  45
Ser Cys Gly His Asn Val Ser Val Glu Glu Leu Ala Gln Thr Arg Ile
        50                  55                  60
Tyr Trp Gln Lys Glu Lys Lys Met Val Leu Thr Met Met Ser Gly Asp
65                  70                  75                  80
Met Asn Ile Trp Pro Glu Tyr Lys Asn Arg Thr Ile Phe Asp Ile Thr
                85                  90                  95
Asn Asn Leu Ser Ile Val Ile Leu Ala Leu Arg Pro Ser Asp Glu Gly
            100                 105                 110
Thr Tyr Glu Cys Val Val Leu Lys Tyr Glu Lys Asp Ala Phe Lys Arg
        115                 120                 125
Glu His Leu Ala Glu Val Thr Leu Ser Val Lys Ala Asp Phe Pro Thr
    130                 135                 140
Pro Ser Ile Ser Asp Phe Glu Ile Pro Thr Ser Asn Ile Arg Arg Ile
145                 150                 155                 160
Ile Cys Ser Thr Ser Gly Gly Phe Pro Glu Pro His Leu Ser Trp Leu
```

```
                      165                 170                 175
Glu Asn Gly Glu Glu Leu Asn Ala Ile Asn Thr Thr Val Ser Gln Asp
                180                 185                 190

Pro Glu Thr Glu Leu Tyr Ala Val Ser Ser Lys Leu Asp Phe Asn Met
            195                 200                 205

Thr Thr Asn His Ser Phe Met Cys Leu Ile Lys Tyr Gly His Leu Arg
        210                 215                 220

Val Asn Gln Thr Phe Asn Trp Asn Thr Thr Lys Gln Glu His Phe Pro
225                 230                 235                 240

Asp Asn Val Ser Thr Ile Ser Ser Phe Ser Pro Pro Gly Tyr Gln Val
                245                 250                 255

Ser Phe Cys Leu Val Met Val Leu Leu Phe Ala Val Asp Thr Gly Leu
            260                 265                 270

Tyr Phe Ser Val Lys Thr Asn Ile
        275                 280

<210> SEQ ID NO 289
<211> LENGTH: 119
<212> TYPE: PRT
<213> ORGANISM: Artificial sequence
<220> FEATURE:
<223> OTHER INFORMATION: Synthetic Target 2 MRB VH

<400> SEQUENCE: 289

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Thr Thr Gly
            20                  25                  30

Glu Tyr Trp Asn Trp Val Arg Gln Ala Arg Gly Gln Arg Leu Glu Trp
        35                  40                  45

Ile Gly Tyr Ile Thr Tyr Asp Gly Ser Lys Asn Tyr Asn Pro Ser Leu
    50                  55                  60

Lys Asn Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ser Arg Phe Glu Gly Val Trp Tyr Gly Leu Asp Tyr Trp Gly Gln Gly
            100                 105                 110

Thr Leu Val Thr Val Ser Ser
        115

<210> SEQ ID NO 290
<211> LENGTH: 111
<212> TYPE: PRT
<213> ORGANISM: Artificial sequence
<220> FEATURE:
<223> OTHER INFORMATION: Synthetic Target 2 MRB VL

<400> SEQUENCE: 290

Ala Ile Gln Leu Thr Gln Ser Pro Ser Ser Leu Ser Ala Ser Val Gly
1               5                   10                  15

Asp Arg Val Thr Ile Thr Cys Arg Ala Ser Glu Ser Val Asp Arg Tyr
            20                  25                  30

Gly Asn Ser Phe Ile His Trp Tyr Gln Gln Lys Pro Gly Lys Ala Pro
        35                  40                  45

Lys Leu Leu Ile Tyr Arg Thr Tyr Asn Leu Glu Ser Gly Ile Pro Ala
    50                  55                  60
```

```
Arg Phe Ser Gly Ser Gly Ser Gly Thr Glu Phe Thr Leu Thr Ile Ser
 65                  70                  75                  80

Ser Leu Gln Ser Glu Asp Phe Ala Val Tyr Tyr Cys Gln Gln Thr Asn
                 85                  90                  95

Glu Asp Pro Trp Thr Phe Gly Gln Gly Thr Lys Val Glu Ile Lys
            100                 105                 110

<210> SEQ ID NO 291
<211> LENGTH: 30
<212> TYPE: PRT
<213> ORGANISM: Artificial sequence
<220> FEATURE:
<223> OTHER INFORMATION: Synthetic Linker2

<400> SEQUENCE: 291

Gly Gly Gly Gly Ser Gly Gly Gly Gly Ser Gly Gly Gly Gly Ser Gly
 1               5                   10                  15

Gly Gly Gly Ser Gly Gly Gly Gly Ser Gly Gly Gly Gly Ser
                20                  25                  30
```